US011883367B2

(12) United States Patent
Wu et al.

(10) Patent No.: US 11,883,367 B2
(45) **Date of Patent: *Jan. 30, 2024**

(54) 6-6 BICYCLIC AROMATIC RING SUBSTITUTED NUCLEOSIDE ANALOGUES FOR USE AS PRMT5 INHIBITORS

(71) Applicant: Janssen Pharmaceutica NV, Beerse (BE)

(72) Inventors: Tongfei Wu, Boortmeerbeek (BE); Dirk Brehmer, Freiburg (BE); Lijs Beke, Antwerp (BE); An Boeckx, Herentals (BE); Gaston Stanislas Marcella Diels, Turnhout (BE); Ronaldus Arnodus Hendrika Joseph Gilissen, Kasterlee (BE); Edward Charles Lawson, Pipersville, PA (US); Vineet Pande, Vosselaar (BE); Marcus Cornelis Bernardus Catharina Paradé, Eindhoven (NL); Wim Bert Griet Schepens, Sint Katelijne Waver (BE); Johannes Wilhelmus John F. Thuring, Antwerp (BE); Marcel Viellevoye, Breda (NL); Weimei Sun, Lower Gwynedd, PA (US); Lieven Meerpoel, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/690,587

(22) Filed: Mar. 9, 2022

(65) Prior Publication Data

US 2023/0071711 A1 Mar. 9, 2023

Related U.S. Application Data

(63) Continuation of application No. 16/825,024, filed on Mar. 20, 2020, now Pat. No. 11,318,157, which is a continuation of application No. 15/755,475, filed as application No. PCT/EP2016/070097 on Aug. 25, 2016, now Pat. No. 10,653,711.

(60) Provisional application No. 62/306,233, filed on Mar. 10, 2016, provisional application No. 62/209,941, filed on Aug. 26, 2015.

(30) Foreign Application Priority Data

Sep. 7, 2015 (EP) .................................... 15184011

(51) Int. Cl.

| | |
|---|---|
| *A01N 43/04* | (2006.01) |
| *A61K 31/70* | (2006.01) |
| *A61K 31/7076* | (2006.01) |
| *A61K 31/519* | (2006.01) |
| *A61K 31/53* | (2006.01) |
| *C07D 471/04* | (2006.01) |
| *A61P 35/00* | (2006.01) |
| *A61K 31/5025* | (2006.01) |

(52) U.S. Cl.

CPC ...... *A61K 31/7076* (2013.01); *A61K 31/5025* (2013.01); *A61K 31/519* (2013.01); *A61K 31/53* (2013.01); *A61P 35/00* (2018.01); *C07D 471/04* (2013.01)

(58) Field of Classification Search

None

See application file for complete search history.

(56) References Cited

U.S. PATENT DOCUMENTS

| | | | |
|---|---|---|---|
| 4,224,438 | A | 9/1980 | Fauland et al. |
| 6,143,749 | A | 11/2000 | Bhagwat et al. |
| 9,856,218 | B2 | 1/2018 | Baiocchi et al. |
| 10,653,711 | B2 | 5/2020 | Wu et al. |
| 11,059,850 | B2 | 7/2021 | Verhoeven et al. |
| 2003/0225205 | A1 | 12/2003 | Epple et al. |
| 2003/0232783 | A1 | 12/2003 | Ibrahim et al. |
| 2004/0043959 | A1 | 3/2004 | Bloom et al. |
| 2005/0209176 | A1 | 9/2005 | Meutermans et al. |
| 2006/0167241 | A1 | 7/2006 | Hayakawa |

(Continued)

FOREIGN PATENT DOCUMENTS

| | | | |
|---|---|---|---|
| JP | 2005-527502 | A | 9/2005 |
| JP | 2006-503020 | A | 1/2006 |

(Continued)

OTHER PUBLICATIONS

Wei, T.Y.W., et al., "Methylosome protein 50 promotes androgen- and estrogen-independent tumorigenesis", Cellular Signaling, (2014), pp. 2940-2950, vol. 26.

(Continued)

*Primary Examiner* — Patrick T Lewis
(74) *Attorney, Agent, or Firm* — BakerHostetler

(57) ABSTRACT

The present invention relates novel 6-6 bicyclic aromatic ring substituted nucleoside analogues of Formula (I)

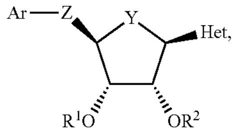

(I)

wherein the variables have the meaning defined in the claims. The compounds according to the present invention are useful as PRMT5 inhibitors. The invention further relates to pharmaceutical compositions comprising said compounds as an active ingredient as well as the use of said compounds as a medicament.

19 Claims, No Drawings

(56) References Cited

U.S. PATENT DOCUMENTS

| | | | |
|---|---|---|---|
| 2008/0132525 | A1 | 6/2008 | Wahhab et al. |
| 2011/0159111 | A1 | 6/2011 | Curry et al. |
| 2012/0035115 | A1 | 2/2012 | Manoharan et al. |
| 2013/0023491 | A1 | 1/2013 | Annes et al. |
| 2013/0310333 | A1 | 11/2013 | Chesworth et al. |
| 2013/0310334 | A1 | 11/2013 | Chesworth et al. |
| 2014/0100184 | A1 | 4/2014 | Song et al. |
| 2014/0213582 | A1 | 7/2014 | Duncan et al. |
| 2014/0221345 | A1 | 8/2014 | Duncan et al. |
| 2014/0228343 | A1 | 8/2014 | Duncan et al. |
| 2014/0329794 | A1 | 11/2014 | Duncan et al. |
| 2016/0009744 | A1 | 1/2016 | Duffey et al. |
| 2016/0244475 | A1 | 8/2016 | Tatlock et al. |
| 2017/0198006 | A1 | 7/2017 | Duncan et al. |
| 2018/0243328 | A1 | 8/2018 | Wu et al. |
| 2019/0263833 | A1 | 8/2019 | Wu et al. |
| 2020/0010881 | A1 | 1/2020 | Brehmer et al. |
| 2020/0360416 | A1 | 11/2020 | Wu et al. |

FOREIGN PATENT DOCUMENTS

| | | | |
|---|---|---|---|
| JP | 2016-505001 | A | 2/2016 |
| TW | I730980 | B | 6/2021 |
| WO | 96/40686 | A1 | 12/1996 |
| WO | 03/39523 | A2 | 5/2003 |
| WO | 03/70739 | | 8/2003 |
| WO | 03/74083 | | 9/2003 |
| WO | 2004/022572 | A1 | 3/2004 |
| WO | 2005/065150 | A2 | 7/2005 |
| WO | 2006/078752 | A2 | 7/2006 |
| WO | 2010/039548 | A2 | 4/2010 |
| WO | 2011/075665 | A2 | 6/2011 |
| WO | 2012/075500 | A2 | 6/2012 |
| WO | 2012/082436 | A2 | 6/2012 |
| WO | 2012/083170 | A1 | 6/2012 |
| WO | 2012/138530 | A1 | 10/2012 |
| WO | 2013/062943 | A1 | 5/2013 |
| WO | 2013/151975 | A1 | 10/2013 |
| WO | 2014/035140 | A2 | 3/2014 |
| WO | 2014/100695 | A1 | 6/2014 |
| WO | 2014/100719 | A2 | 6/2014 |
| WO | 2014/100730 | A1 | 6/2014 |
| WO | 2015/106025 | A1 | 7/2015 |
| WO | 2015/200680 | A2 | 12/2015 |
| WO | 2016/135582 | A1 | 9/2016 |
| WO | 2017/032840 | A1 | 3/2017 |
| WO | 2017/153186 | A1 | 9/2017 |
| WO | 2018/065365 | A1 | 4/2018 |
| WO | 2018/154104 | A1 | 8/2018 |

OTHER PUBLICATIONS

Written Opinion of the International Search Authority relating to International Patent Application No. PCT/EP2017/054324, filed on Feb. 24, 2017. Written Opinion, dated May 2, 2017.

Xiong, et al., Driver Genes as Targets for Lung Cancer Prevention and Treatment Progress in Chemistry, Sep. 9, 2013, vol. 25, pp. 1517-1525.

Zhao, Q., et al., "PRMT5-mediated methylation of histone H4R3 recruits DNMT3A, coupling histone and DNA methylation in gene silencing", Nat Struct Mol Biol, (2009), pp. 304-311, vol. 16, No. 3.

A.J. Herrera et al., "Stereocontrolled photocyclization of 1,2-diketones: application of a 1,3-acetyl group transfer methodology to carbohydrates," Journal of Organic Chemistry, vol. 73, Mar. 28, 2008, pp. 3384-3391.

Alinari et al., "Selective inhibition of progen agrinine methyltransferase 5 blocks initiation and maintenance of B-cell transformation.", Blood, Apr. 16, 2015, pp. 2530-2543, vol. 125(16).

Andreu-Perez et al., "Protein Arginine Methyltransferase 5 Regulates ERK1/2 Signal Transduction Amplitude and Cell Fate Through GRAF.", Sci Signal, 2011, p. ra58, vol. 4(190).

Antonysamy et al., "Crystal structure of the human PRMT5:MEP50 complex.", Proc Natl Acad Sci, USA, 2012, pp. 17960-17965, vol. 109(44).

Barbash, O., et al., "Abstract LB-248: Protein arginine methyltransferase 5 (PRMT5) inhibition as a therapeutic strategy in B-cell lymphoma", Cancer Research, (2015), see Abstract.

Bezzi, M., et al., "Regulation of constitutive and alternative splicing by PRMT5 reveals a role for Mdm4 pre-mRNA in sensing defects in the spliceosomal machinery", Genes & Development, (2013), pp. 1903-1916, vol. 27, No. 17.

Braun, C.J., et al., "Coordinated Splicing of Regulatory Detained Intrans within Oncogenic Transcripts Creates an Exploitable Vulnerability in Malignant Glioma", Cancer Cell, (2017), pp. 411-426, vol. 32, No. 4.

Bundegaard, H., "Design of Prodrugs", Elsevier, New York—Oxford, (1985), pp. 1-92.

Chan-Penebre, E., et al., "A selective inhibitor of PRMT5 with in vivo and in vitro potency in MCL models", Nature Chemical Bioloqv, (2015), pp. 432-437, vol. 11, No. 6.

Colombian office action dated Sep. 12, 2019, relating to co-pending Colombian patent application No. NC2018/0002063.

Crane et al., "Synthesis of Pyrrolo[2,3-d]pyrimidines from Furazano[3,4-d]pyrimidiens via Enolates and Ene Adducts," Journal of Organic Chemistry, 45(19), 3827-3831 (1980).

Deady, L.W., "Ring Nitrogen Oxidation of Amino Substituted Nitrogen Heterocycles with m-Chloroperbenzoic Acid", Synthetic Communications, (1977), pp. 509-514, vol. 7, No. 8.

Dermer, "Another Anniversary for the War on Cancer", Biotechnology, 1994, vol. 12, p. 320.

Devkota, K., et al., "Analogues of the Natural Product Sinefungin as Inhibitors of EHMT1 and EHMT2", ACS Med Chem Lett, (2014), pp. 293-297, vol. 5.

Di Lorenzo, A., et al., "Histone arginine methylation", FEBS Letters, (2011), pp. 2024-2031, vol. 585, No. 13.

European Search Report; EP Patent Application No. EP Patent Application No. 15184011.3; Report: dated Oct. 22, 2015.

Evans, et al., "Pharmacogenomics: Translating Functional Genomics into Rational Therapeutics", Science, 1999, vol. 286, pp. 487-491.

Friesen, W.J., et al., "The Methylosome, a 20S Complex Containing JBP1 and pICln, Produces Dimethylarginine-Modifiied Sm Proteins", Molecular and Cellular Biology, (2001), pp. 8289-8300, vol. 21, No. 24.

Geoghegan, V., et al., "Comprehensive identification of arginine methylation in primary T cells reveals regulatory roles in cell signaling", Nature Communications, (2015), p. 6758, vol. 6.

Graubert, et al., "Recurrent mutations in the U2AF 1 splicing factor in myelodysplastic syndromes", Nature Genetics, Jan. 1, 2012, vol. 44, pp. 53-59.

Gu, Z., et al., "Protein arginine methyltransferase 5 is essential for growth of lung cancer cells", Biochem J., (2012), pp. 235 241, vol. 446, No. 2.

Guo et al., "STING Agonists Induce an Innate Antiviral Immune Response against Hepatitis B Virus", Antimicrobial Agents and Chemotherapy vol. 59, No. 2, Feb. 1, 2015, 1273-1281.

Hsu, J.M., et al., "Crosstalk between Arg 1175 methylation and Tyr 1173 phosphorylation negatively modulates EGFR-mediated ERK activation", Nature Cell Biology, (2011), pp. 174-181, vol. 13, No. 2.

Hu, H., et al., "Small Molecule Inhibitors of Protein Arginine Methyltransferase", Expert Opinion on Investigational Drugs, (2016), pp. 335-358, vol. 25, No. 3.

HUGO Gene Nomenclature Committee (HGNC) reports for the Major Spliceosome found online at https;//www.genenames.org/data/genegroup/#!/group/1518 and accessed Apr. 20, 2021.

International Report on Patentability; International Patent Application No. PCT/EP2016/070097; Report: dated Feb. 27, 2018.

International Search Report relating to International Patent Application No. PCT/EP2016/070097, filed on Aug. 25, 2016. International Search Report: dated Oct. 12, 2016.

International Search Report relating to International Patent Application No. PCT/EP2017/054324, filed on Feb. 24, 2017. International Search Report: dated May 2, 2017.

(56) References Cited

OTHER PUBLICATIONS

International Search Report relating to International Patent Application No. PCT/EP2017/074983, filed on Oct. 2, 2017. International Search Report: dated Nov. 16, 2017.
International Search Report relating to International Patent Application No. PCT/EP2018/054644, filed on Feb. 26, 2018. International Search Report: dated May 3, 2018.
Jansson, M., et al., "Arginine methylation regulates the p53 response", Nature Cell Biology, (2008), pp. 1431-1439, vol. 10, No. 12.
Karkhanis, V., et al., "Versatility of PRMT5-induced methylation in growth control and development", Trends in Biochemical Sciences, (2011), pp. 633-641, vol. 36, No. 12.
Kung, P.P., et al., "Design, synthesis, and biological evaluation of novel human 5'- deoxy-5'-methylthioadenosine phosphorylase (MTAP) substrates", Bioorganic & Medicinal Chemistry Letters, (2005), pp. 2829-2833, vol. 15.
Li, et al., A patent review of arginine methyltransferase inhibitors, Expert Opinion on Therapeutic Patents, 2019, vol. 29, No. 2, pp. 97-114.
March, J., "Advanced Organic Chemistry—Reactions, Mechanisms, and Structure", John Wiley & Sons, Inc., (2002), 4th Edition, A Wiley-Interscience Publication, see Table of Contents.
Matsubara, S., et al., "[2+1] Cycloaddition reaction of bis(iodozincio)methane with 1,2-diketones: face-to-face complex of bis(iodozincio)methane and 1,2-diketones as a reaction intermediate", Tetrahedron, (2002), pp. 8255-8262, vol. 58.
Moukha-Chafiq, 0., et al., "Synthesis and General Biological Activity of a Small Adenosine-5'-(Carboxamide and Sulfanilamide) Library", Nucleosides, Nucleotides and Nucleic Acids, (2014), pp. 709-729, vol. 33, No. 11.
Pal, S., et al., "Low levels of miR-92b/96 induce PRMT5 translation and H3R3 methylation in mantle cell lymphoma", The EMBO Journal, (2007), pp. 3558-3569, vol. 26, No. 15.
Penebre, E., et al., "Identification of a First-in-Class PRMT5 Inhibitor with Potent in Vitro and in Vivo Activity in Preclinical Models of Mantle Cell Lymphoma", Blood, (2014), see Abstract.
Prasad, R.N., et al., "Modification of the 5' Position of Purine Nucleosides. 2. Synthesis and Some Cardiovascular Properties of Adenosine-5'-(N- substituted)carboxamides1,2", J. Med. Chem., (1980), pp. 313-319, vol. 23, No. 3.
Schmidt, R.R., et al., "Synthese 5'-modifizierter Adenosinderivate", Chemische Berichte, (1968), pp. 590-594, vol. 101, No. 2.
Shendure, J., et al., "Next-generation DNA sequencing", Nature Biotechnolgoy, (2008), pp. 1135-1145, vol. 26, No. 10.
Shilo, K., et al., "Cellular localization of protein arginine methyltransferase-5 correlates with grade of lung tumors", Diagnostic Pathology, (2013), pp. 1-9, vol. 8, No. 201.
Stahl, P.H., et al., "Handbook of Pharmaceutical Salts: Properties, Selection, and Use", Journal of Medicinal Chemistry, Book Reviews, (2003), pp. 1277-1278, vol. 46, No. 7.
Stopa, N., et al., "The PRMT5 arginine methyltransferase: many roles in development, cancer and beyond", Cell. Mol. Life Sci., (2015), pp. 2041-2059, vol. 72, No. 11.
Tiwari et al. Synthesis and Anticancer Evaluation of 4'-C-Methyl-2'-Fluoro Arabino Nucleosides, Nucleotides and Nucleic Acids (2009), vol. 28, Nos. 5-7, pp. 657-677.
Vuilhorgne, M., et al., "New Synthetic S-Adenosyl-Homocysteine Analogues with Oncostatic and Antiviral Activity", Heterocylces, 1978, pp. 495-520, vol. 11, XP009112700.
Wang, L., et al., "Protein Arginine Methyltransrerase 5 Suppresses the Transcription of the RB Family of Tumor Suppressors in Leukemia and Lymphoma Cells", Molecular and Cellular Biology, (2008), pp. 6262-6277, vol. 28, No. 20.
Wang, Q., et al., "Identification of a Novel Protein Arginine Methyltransferase 5 Inhibitor in Non-small Cell Lung Cancer by Structure-Based Virtual Screening", Frontiers in Pharmacology, (2018), pp. 1-10, vol. 9, article 173.
Wei, H., et al., "PRMT5 dimethylates R30 of the p65 subunit to activate NF-KB", Proc Natl Acad Sci USA, (2013), pp. 13516-13521, vol. 110, No. 33.
Brand et al., "Synthesis of [n,5]-Spiroketals by Ring Enlargement of Donor-Acceptor-Substituted Cyclopropane Derivatives," JOC, 2009, vol. 74, Issue 22, pp. 8779-8786.
Brehmer et al., "Abstract DDT02-04: A novel PRMT5 inhibitor with potent in vitro and in vivo activity in preclinical lung cancer models", Experimental and Molecular Therapeutics, 2017, AACR Annual Meeting, pp. 1-4.
CAS 1152172-19-4, Dated Jan. 18, 2022.
CAS 1259070-80-8, Dated Jan. 7, 2022.
CAS 33985-40-9, Dated Jan. 12, 2022.
CAS 3680-69-1, Dated Jan. 11, 2022.
CAS 514206-18-9, Dated Jan. 18, 2022.
CAS 54622-95-6, Dated Jan. 14, 2022.
CAS 56613-80-0, Dated Jan. 14, 2022.
CAS 58-61-7, Dated Jan. 11, 2022.
CAS 6991-65-7, Data Feb. 2, 2022.
CAS 78922-04-0, Dated Jan. 11, 2022.
CAS 808744-34-5, Dated Jan. 15, 2022.
CAS 87-42-3, Dated Jan. 11, 2022.
CAS 95408-45-0, Dated Jan. 15, 2022.
Cheson et al., "Clinical Application and Proposal for Modification of the International Working Group (IWG) Response Criteria in Myelodysplasia", Blood, 2006, vol. 108 No. 2, pp. 419-425.
Eisenhauer et al., "New Response Evaluation Criteria in Solid Tumours: Revised RECIST Guideline (Version 1.1).", European Journal of Cancer, 2009, vol. 45, pp. 228-247.
Fitchen, J.H, et al. "Methylthioadenosine phosphorylase deficiency in human leukemias and solid tumors," Cancer research vol. 46, No. 10, Oct. 1986, pp. 5409-5412.
Gerhart et al., "Activation of the p53-MDM4 Regulatory Axis Defines the Anti-Tumour Response to PRMT5 Inhibition Through Its Role in Regulating Cellular Splicing", Scientific Reports, Jun. 2018, vol. 8 No. 1, pp. 1-15, XP055625791.
Guo et al., "Abstract 3905: Translational Efficacy and Safety Modeling and Simulation to Support the Clinical Development of JNJ-64619178, A PRMT5 Inhibitor", Cancer Research, AACR Annual Meeting 2019, vol. 79, Suppl. 13, pp. 1-4.
International Search Report and Written Opinion relating to International Patent Application No. PCT/EP2020/065639, filed Jun. 5, 2020. International Search Report and Written Opinion: dated Aug. 26, 2020.
Lin et al., "Nucleoside Protein Arginine Methyl Transferase 5 (PRMT5) Inhibitors.", Bioorganic & Medicinal Chemistry Letters, 2019, vol. 29 No. 11, pp. 1264-1269, XP055663652.
Millar et al., "Abstract 950: In Vivo Efficacy and Pharmacodynamic Modulation of JNJ-64619178, A Selective PRMT5 Inhibitor, In Human Lung and Hematologic Preclinical Models", Cancer Research Annual Meeting 2019, AACR; Cancer Res 2019, vol. 79, Suppl. 13, Abstract No. 950, pp. 1-4.
Nobori T, et al. "Methylthioadenosine phosphorylase deficiency in human non-small cell lung cancers". Cancer research. vol. 53, No. 5, Mar. 1, 1993, pp. 1098-1101.
Nobori, T, et al. "Genomic cloning of methylthioadenosine phosphorylase: a purine metabolic enzyme deficient in multiple different cancers". Proceedings of the National Academy of Sciences, vol. 93, No. 12, Jun. 11, 1996, pp. 6203-6208.
Nowak et al., "Addition of Difluorocarbene to 4',5'-Unsaturated Nucleosides: Synthesis and Deoxygenation Reactions of Difluorospirocyclopropane Nucleosides," JOC, 2006, vol. 71, pp. 8876-8883.
Ramakrishma et al., "Stereoselective Synthesis of 1,6-Dioxaspirolactones From Spiro-Cyclopropanecarboxylated Sugars: Total Synthesis of Dihydro-Pyrenolide D," RSC Adv., 2015, vol. 5,pp. 8142-8145.
Reagan-Shaw et al., "Dose translation from animal to human studies revisited", The FASEB Journal, 2007, vol. 22, pp. 659-661.
Redlich et al., "Chiral Cyclobutanones by [2+2]-Cycloaddition of Dichloroketene to Carbohydrate Enol Ethers," Angewe Chem., Int. Ed. Engl., 1989, vol. 28, pp. 777-778.
Wilting et al., "Epigenetic Mechanisms in Tumorigenesis, Tumor Cell Heterogeneity and Drug Resistance", Drug Resistance Updates, 2012, vol. 15, pp. 21-38.

(56) References Cited

OTHER PUBLICATIONS

Written Opinion of the International Search Authority relating to International Patent Application No. PCT/EP2016/070097, filed on Aug. 25, 2016. Written Opinion: dated Oct. 12, 2016.
Written Opinion of the International Search Authority relating to International Patent Application No. PCT/EP2018/054644, filed on Feb. 26, 2018. Written Opinion: dated May 3, 2018.
Wu et al., "Abstract 4859: JNJ-64619178, a Selective and Pseudo-Irreversible PRMT5 Inhibitor With Potent Invitro and Invivo Activity, Demonstrated in Several Lung Cancer Models.", Experimental and Molecular Therapeutics, Jul. 2018, pp. 1-4, XP055668420, Retrieved from the Internet: URL:https://www.semanticscholar.org/paper/Abstract-4859:-JNJ-64619178,-a-selective-and-PRMT5-Wu-Millar/a6583b4db0edbaefacf2 888b121f87e020d6889e.
Wuts et al., "Protective Groups in Organic Synthesis," Fourth Edition, Wiley, New York, 2006, pp. 1-1112.

6-6 BICYCLIC AROMATIC RING SUBSTITUTED NUCLEOSIDE ANALOGUES FOR USE AS PRMT5 INHIBITORS

CROSS REFERENCE TO RELATED APPLICATIONS

This application is a continuation of, and claims priority to, U.S. patent application Ser. No. 16/825,024, filed Mar. 20, 2020, which is a continuation U.S. patent application Ser. No. 15/755,475 filed Feb. 26, 2018, now U.S. patent Ser. No. 10/653,711 issued on May 19, 2020, which is a national stage application of International Patent Application No. PCT/EP2016/070097 filed on Aug. 25, 2016, which claims the benefit of U.S. Provisional Patent Application No. 62/306,233 filed on Mar. 10, 2016 and U.S. Provisional Patent Application No. 62/209,941 filed on Aug. 26, 2015, each of which are incorporated herein by reference in their entirety.

FIELD OF THE INVENTION

The present invention relates to novel 6-6 bicyclic aromatic ring substituted nucleoside analogues useful as PRMT5 inhibitors. The invention further relates to pharmaceutical compositions comprising said compounds as an active ingredient as well as the use of said compounds as a medicament.

BACKGROUND OF THE INVENTION

PRMT5, also described as Hsl7, Jbp1, Skb1, Capsuleen or Dart5, is one of the major methyltransferases responsible for mono- and symmetric dimethylation of arginines. Post-translational arginine methylation on histones and non-histone proteins seems to be crucial for a variety of biological processes, like genome organisation, transcription, differentiation, spliceosome function, signal transduction and regulation of cell-cycle progression, stem cells and T-cell fate [Stopa, N. et al., Cell Mol Life Sci, 2015. 72(11): p. 2041-59] [Geoghegan, V. et al., Nat Commun, 2015. 6: p. 6758]. Metazoan PRMT5 forms a functional complex with the methylosome protein 50 (MEP50) also named as Wdr77, androgen receptor coactivator p44 and Valois. Both, elevated PRMT5-MEP50 protein level and cytoplasmic accumulation are implicated in cancer tumorigenesis and have recently been correlated with poor clinical outcome [Shilo, K. et al., Diagn Pathol, 2013. 8: p. 201]. Cellular rescue experiments that addressed both the catalytic and scaffold function of the PRMT5-MEP50 complex, beside comprehensive enzymological studies have substantiate the oncogenic link between protein level, localisation and enzymatic function [Gu, Z. et al., Biochem J, 2012. 446(2): p. 235-41] [Di Lorenzo, A. et. al., FEBS Lett, 2011. 585(13): p. 2024-31] [Chan-Penebre, E. et al., Nat Chem Biol, 2015. 11(6): p. 432-7]. This correlation turns PRMT5 into an essential small molecule drug target against cancer and other diseases [Stopa, N. et al., Cell Mol Life Sci, 2015. 72(11): p. 2041-59].

PRMT5 is a member of the type II PRMT subfamily that utilises S-adenosylmethionine (SAM) to generate symmetric dimethylated arginine on histones and non-histone protein substrates and S-adenosylhomocysteine (SAH). The crystal structure of the human hetereo-octameric complex $(PRMT5)_4(MEP50)_4$ co-crystalised with SAH and a histone H4 peptide substrate illustrated the mechanism of methylation and substrate recognition [Antonysamy, S. et al., Proc Natl Acad Sci USA, 2012. 109(44): p. 17960-5]. The regulation of PRMT5 activity occurs through a vast number of different binding partners, post-translational modification cross talk, miRNAs and subcellular localisation.

Methylation of histones H2A and H4 on Arg3 and histone H3 on Arg8 regulate chromatin organisation for specific repression of gene transcripts that are involved in differentiation, transformation, cell-cycle progression and tumour suppression [Karkhanis, V. et al., Trends Biochem Sci, 2011. 36(12): p. 633-41]. Furthermore, PRMT5-mediated methylation of histone H4 on Arg3 might recruit the DNA-methyltransferase DNMT3A to couple histone and DNA methylation for long-term gene silencing [Zhao, Q. et al., Nat Struct Mol Biol, 2009. 16(3): p. 304-11].

Non-histone methylation can occur either in the cytoplasm or nucleus dependent on the cellular localisation of PRMT5. The methylation of the Sm proteins D1 and D3, which are required for the assembly of the nuclear spliceosome, takes place in the cytoplasm as part of the PRMT5 containing "methylosome" [Friesen, W. J. et al., Mol Cell Biol, 2001. 21(24): p. 8289-300]. Further evidence for PRMT5 involved in splicing has been provided by the conditional PRMT5 knockout in mouse neural stem cells. Cells that lack PRMT5 showed a selective retention of introns and skipping of exons with weak 5' donor sites [Bezzi, M. et al., Genes Dev, 2013. 27(17): p. 1903-16].

In addition to a role in splicing, PRMT5 influences key pathways involved in cell fate and homeostasis by direct methylation of key signalling nodules like p53 [Jansson, M. et al., Nat Cell Biol, 2008. 10(12): p. 1431-9], EGFR [Hsu, J. M. et al., Nat Cell Biol, 2011. 13(2): p. 174-81], CRAF [Andreu-Perez, P. et al., Sci Signal, 2011. 4(190): p. ra58], PI3K/AKT [Wei, T. Y. et al., Cell Signal, 2014. 26(12): p. 2940-50], NFκB [Wei, H. et al., Proc Natl Acad Sci USA, 2013. 110(33): p. 13516-21].

Since PRMT5 is one of the major sym-Arg methyltransferases and involved in a multitude of cellular processes, an increased protein expression appears to be an important factor in its tumourigenicity. Interestingly, the translation of PRMT5 in mantle cell lymphoma (MCL) seems to be regulated by miRNAs. Although MCL cells show less mRNA and a slower transcription rate of PRMT5 than normal B lymphocytes, the PRMT5 level and the methylation of H3R8 and H4R3 are significantly increased [Pal, S. et al., EMBO J, 2007. 26(15): p. 3558-69]. Re-expression of miRNAs that binds the 3'UTR region of PRMT5 decreases PRMT5 protein level [Wang, L. et al., Mol Cell Biol, 2008. 28(20): p. 6262-77]. Strikingly, a prmt5 antisense RNA has been found within the human prmt5 gene that supports the hypothesis of a specific translational regulation rather than high mRNA expression level [Stopa, N. et al., Cell Mol Life Sci, 2015. 72(11): p. 2041-59].

Although PRMT5 is considered as a clinical relevant target, very few selective PRMT5 inhibitors have been published, yet. Very recently, a novel sub-nanomolar potent PRMT5 inhibitor (EPZ015666) with anti-tumour activity in multiple MCL xenograft models has been described to be the first chemical probe suitable for further validation of PRMT5's biology and role in cancer [Chan-Penebre, E. et al., Nat Chem Biol, 2015. 11(6): p. 432-7].

Further development of specific small molecule inhibitors of PRMT5 may lead to novel chemotherapeutic approaches for cancer.

WO2014100695A1 discloses compounds useful for inhibiting PRMT5 activity; Methods of using the compounds for treating PRMT5-mediated disorders are also described.

WO2014100730A1 discloses PRMT5 inhibitors containing a dihydro- or tetrahydroisoquinoline and uses thereof.

Devkota, K. et al., ACS Med Chem Lett, 2014. 5: p. 293-297, describes the synthesis of a series of analogues of the natural product sinefungin and the ability of these analogues to inhibit EHMT1 and EHMT1.

WO2003070739 discloses partial and full agonists of A1 adenosine receptors, their preparation, and their therapeutic use.

WO2012082436 discloses compounds and compositions as modulators of histone methyltransferases, and for treating diseases influenced by modulation of histone methyltransferase activity.

WO2014100719 discloses PRMT5 inhibitors and uses thereof.

WO03074083 discloses combination therapies that selectively kill methylthioadenosine phosphorylase deficient cells. Analogs of MTA are described herein as anti-toxicity agents.

Kung, P.-P. et al., Bioorg Med Chem Lett, 2005. 15: p. 2829-2833, describes the design, synthesis, and biological evaluation of novel human 5'-deoxy-5'-methylthioadenosine phosphorylase (MTAP) substrates.

WO2012075500 discloses 7-deazapurine modulators of histone methyltransferase.

WO2014035140 discloses compounds and compositions for modulating histone methyltransferase activity.

WO2015200680 describes PRMT5 inhibitors and uses thereof.

There is thus a strong need for novel PRMT5 inhibitors thereby opening new avenues for the treatment or prevention of cancer, such as e.g. mantle cell lymphoma. It is accordingly an object of the present invention to provide such compounds.

The compounds of the present invention are structurally different and may have improved properties such as for example improved potency, or improved pharmacokinetics (PK) and oral bioavailability, compared with compounds disclosed in the prior art.

SUMMARY OF THE INVENTION

It has been found that the compounds of the present invention are useful as PRMT5 inhibitors. The compounds according to the invention and compositions thereof, may be useful for the treatment or prevention, in particular for the treatment, of diseases such as a blood disorder, metabolic disorders, autoimmune disorders, cancer, inflammatory diseases, cardiovascular diseases, neurodegenerative diseases, pancreatitis, multiorgan failure, kidney diseases, platelet aggregation, sperm motility, transplantation rejection, graft rejection, lung injuries, and the like.

The present invention concerns novel compounds of Formula (I):

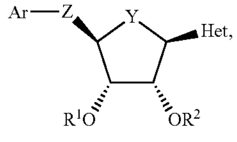

(I)

wherein $R^1$ represents hydrogen or —C(═O)—$C_{1-4}$alkyl;

$R^2$ represents hydrogen or —C(═O)—$C_{1-4}$alkyl;

Y represents —O—, —$CH_2$— or —$CF_2$—;

Z represents —$CH_2$—, —X—$CR^{5a}R^{5b}$—, —$CR^{5c}$═$CR^{5d}$—, —$CR^{5e}R^{5g}$—$CR^{5f}R^{5h}$—, or —C≡C—;

and when Y represents —$CH_2$— or —$CF_2$—, then Z can also represent —O— or —$CR^{5a}R^{5b}$—X—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

$R^{11}$ represents hydrogen, $C_{1-4}$alkyl, or $C_{1-4}$alkyl substituted with one substituent selected from the group consisting of —OH, —O—$C_{1-4}$alkyl, $R^{12}$, —$NH_2$, —NH—$C_{1-4}$alkyl, and —N($C_{1-4}$alkyl)$_2$;

$R^{12}$ represents a 4-, 5-, 6- or 7-membered heterocyclic ring containing one nitrogen atom and optionally one oxygen atom; said 4-, 5-, 6- or 7-membered heterocyclic ring being attached to the remainder of the molecule via a ring nitrogen atom;

Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one, two, three or four substituents each independently selected from the group consisting of halo, —OH, —$NH_2$, —NH—$C_{1-4}$alkyl, —N($C_{1-4}$alkyl)$_2$, —$NHR^{10d}$, —$NR^{10c}R^{10d}$, cyano, —$CF_3$, —C(═O)—$NH_2$, —C(═O)—NH—$C_{1-4}$alkyl, —C(═O)—$C_{1-4}$alkyl, $C_{1-4}$alkyloxy, —C(═O)—O—$C_{1-4}$alkyl, $C_{3-6}$cycloalkyl, —O—$C_{3-6}$cycloalkyl, —NH—$C_{3-6}$cycloalkyl, —N($C_{3-6}$cycloalkyl)$_2$, $C_{2-6}$alkenyl, $C_{1-4}$alkyl substituted with one $C_{1-4}$alkyloxy, and $C_{1-4}$alkyl optionally substituted with one —$NR^{10a}R^{10b}$;

$R^{10a}$ and $R^{10b}$ each independently represent hydrogen or $C_{1-4}$alkyl;

$R^{10c}$ and $R^{10d}$ each independently represent $C_{3-6}$cycloalkyl; $R^{13}$; $R^{14}$; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, $R^{13}$ and $R^{14}$;

$R^{13}$ represents a 4- to 7-membered monocyclic aromatic ring containing one, two or three heteroatoms each independently selected from O, S, S(═O)$_p$ and N; or a 6- to 11-membered bicyclic fused aromatic ring containing one, two or three heteroatoms each independently selected from O, S, S(═O)$_p$ and N;

said 4- to 7-membered monocyclic aromatic ring or 6- to 11-membered bicyclic fused aromatic ring is optionally substituted with one or two substituents selected from the group consisting of $C_{1-4}$alkyl;

p represents 1 or 2;

$R^{14}$ represents phenyl optionally substituted with one, two or three substituents each independently selected from the group consisting of halo;

Het represents a bicyclic aromatic heterocyclic ring system selected from the group consisting of (a-1), (a-2), (a-3), (a-4) and (a-5):

(a-1)

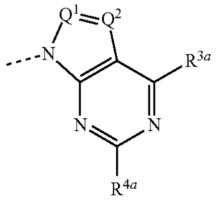

(a-2)

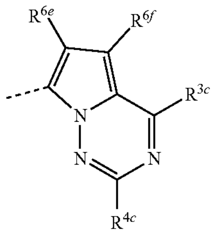

(a-3)

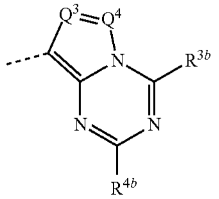

(a-4)

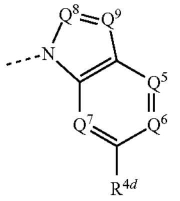

(a-5)

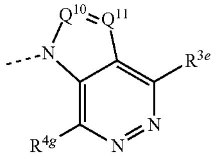

$R^{3a}$, $R^{3b}$, $R^{3c}$, $R^{3d}$ and $R^{3e}$ each independently represent hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl;

$R^{7a}$ represents hydrogen;

$R^{7b}$ represents hydrogen, $C_{3-6}$cycloalkyl, or $C_{1-4}$alkyl;

$R^{4a}$, $R^{4b}$, $R^{4c}$, $R^{4d}$, $R^{4e}$, $R^{4f}$ and $R^{4g}$ each independently represent hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents N or $CR^{6a}$;

$Q^2$ represents N or $CR^{6b}$;

$Q^3$ represents N or $CR^{6c}$;

$Q^4$ represents N or $CR^{6d}$;

provided that maximum one of $Q^3$ and $Q^4$ represents N;

$Q^8$ represents N or $CR^{6g}$;

$Q^9$ represents N or $CR^{6h}$;

$Q^{10}$ represents N or $CR^{6i}$;

$Q^{11}$ represents N or $CR^{6j}$;

$Q^5$ represents $CR^{3d}$; $Q^6$ represents N; and $Q^7$ represents $CR^{4f}$; or $Q^5$ represents $CR^{3d}$; $Q^6$ represents $CR^{4e}$; and $Q^7$ represents N; or $Q^5$ represents N; $Q^6$ represents $CR^{4e}$; and $Q^7$ represents $CR^{4f}$; or $Q^5$ represents N; $Q^6$ represents $CR^{4e}$; and $Q^7$ represents N; or $Q^5$ represents N; $Q^6$ represents N; and $Q^7$ represents $CR^{4f}$; or $Q^5$ represents N; $Q^6$ represents N; and $Q^7$ represents N;

$R^{6a}$, $R^{6b}$, $R^{6c}$, $R^{6d}$, $R^{6e}$, $R^{6f}$, $R^{6g}$, $R^{6h}$, $R^{6i}$ and $R^{6j}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof;

provided that the following compounds, and pharmaceutically acceptable addition salts, and solvates thereof are excluded:

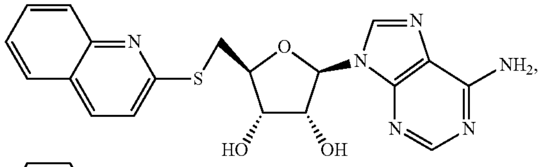

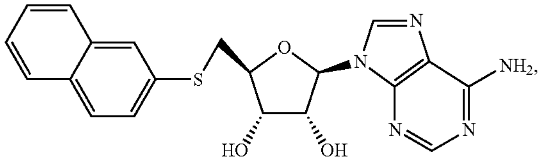

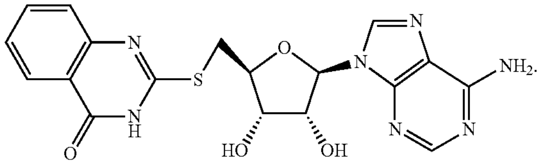

The present invention also concerns methods for the preparation of compounds of the present invention and pharmaceutical compositions comprising them.

The compounds of the present invention were found to inhibit PRMT5 per se or can undergo metabolism to a (more) active form in vivo (prodrugs), and therefore may be useful in the treatment or prevention, in particular in the treatment, of diseases such as a blood disorder, metabolic disorders, autoimmune disorders, cancer, inflammatory diseases, cardiovascular diseases, neurodegenerative diseases, pancreatitis, multiorgan failure, kidney diseases, platelet aggregation, sperm motility, transplantation rejection, graft rejection, lung injuries, and the like.

In view of the aforementioned pharmacology of the compounds of Formula (I) and pharmaceutically acceptable addition salts, and solvates thereof, it follows that they may be suitable for use as a medicament.

In particular the compounds of Formula (I) and pharmaceutically acceptable addition salts, and solvates thereof, may be suitable in the treatment or prevention, in particular in the treatment, of any one of the diseases or conditions mentioned hereinbefore or hereinafter, in particular cancer.

The present invention also concerns the use of compounds of Formula (I) and pharmaceutically acceptable addition salts, and solvates thereof, for the manufacture of a medicament for the inhibition of PRMT5, for the treatment or prevention of any one of the diseases or conditions mentioned hereinbefore or hereinafter, in particular cancer.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

When any variable occurs more than one time in any constituent or in any formula (e.g. Formula (I)), its definition in each occurrence is independent of its definition at every other occurrence.

Whenever the term "substituted" is used in the present invention, it is meant, unless otherwise is indicated or is clear from the context, to indicate that one or more hydrogens, in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

When two or more substituents are present on a moiety they may, unless otherwise is indicated or is clear from the context, replace hydrogens on the same atom or they may replace hydrogen atoms on different atoms in the moiety.

The prefix "$C_{x-y}$" (where x and y are integers) as used herein refers to the number of carbon atoms in a given group. Thus, a $C_{1-4}$alkyl group contains from 1 to 4 carbon atoms, a $C_{1-3}$alkyl group contains from 1 to 3 carbon atoms and so on.

The term "halo" as a group or part of a group is generic for fluoro, chloro, bromo, iodo unless otherwise is indicated or is clear from the context.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain. $C_{1-4}$alkyl includes all linear, or branched alkyl groups with between 1 and 4 carbon atoms, and thus includes methyl, ethyl, n-propyl, i-propyl, 2-methyl-ethyl, butyl and its isomers (e.g. n-butyl, isobutyl and tert-butyl), and the like.

The skilled person will realize that the term '$C_{1-4}$alkoxy' or '$C_{1-4}$alkyloxy' as a group or part of a group refers to a radical having the Formula —$OR^c$ wherein $R^c$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

The term "$C_{2-4}$alkenyl" as used herein as a group or part of a group represents a straight or branched chain hydrocarbon group containing from 2 to 4 carbon atoms and containing a carbon carbon double bond such as, but not limited to, ethenyl, propenyl, butenyl, 1-propen-2-yl, and the like.

The term "$C_{2-6}$alkenyl" as used herein as a group or part of a group represents a straight or branched chain hydrocarbon group containing from 2 to 6 carbon atoms and containing a carbon carbon double bond such as, but not limited to, ethenyl, propenyl, butenyl, pentenyl, 1-propen-2-yl, hexenyl and the like.

The term '$C_{3-6}$cycloalkyl' as used herein as a group or part of a group represents cyclic saturated hydrocarbon radicals having from 3 to 6 carbon atoms such as cyclopropyl, cyclobutyl, cyclopentyl or cyclohexyl.

In case Z is —X—$CR^{5a}R^{5b}$—, it is intended that X is attached to Ar.

In case Z is —$CR^{5c}$═$CR^{5d}$—, it is intended that the C-atom with the $R^{5c}$ substituent is attached to Ar.

In case Z is —$CR^{5e}R^{5g}$—$CR^{5f}R^{5h}$—, it is intended that the C-atom with the $R^{5e}$ and $R^{5g}$ substituents is attached to Ar.

In case Z is —$CR^{5a}R^{5b}$—X—, it is intended that the C-atom with the $R^{5a}$ and $R^{5b}$ substituents is attached to Ar.

The skilled person will realize that the 4-, 5-, 6- or 7-membered heterocyclic ring being attached to the remainder of the molecule via a ring nitrogen atom (in the definition of $R^{12}$) particularly is a saturated ring. Non-limiting examples of $R^{12}$ are 1-piperidinyl, 1-pyrrolidinyl, 1-morpholinyl, 1-azetidinyl, and the like.

It will be clear for the skilled person that, unless otherwise is indicated or is clear from the context, a substituent on a 4- to 7-membered monocyclic aromatic ring containing one, two or three heteroatoms (as in the definition of $R^{13}$) (non-limiting examples are pyrrolyl, pyridinyl, furanyl, and the like), may replace any hydrogen atom on a ring carbon atom or where possible on a ring nitrogen atom (in which case a hydrogen on a nitrogen atom may be replaced by a substituent). It will be clear for the skilled person that the same is applicable to the 6- to 11-membered bicyclic fused aromatic ring containing one, two or three heteroatoms (as in the definition of $R^{13}$) (non-limiting examples are indolyl, quinolinyl, and the like).

A 4- to 7-membered monocyclic aromatic ring containing one, two or three heteroatoms (as in the definition of $R^{13}$), may be attached to the remainder of the molecule of Formula (I) through any available ring carbon or nitrogen atom as appropriate, if not otherwise specified. It will be clear for the skilled person that the same is applicable to the 6- to 11-membered bicyclic fused aromatic ring containing one, two or three heteroatoms (as in the definition of $R^{13}$).

In case a nitrogen atom replaces one of the two fused carbon atoms in the Ar group, a carbonyl group is present in said bicyclic aromatic ring system as exemplified by the structure shown below:

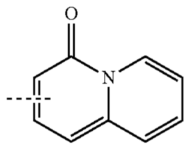

which is optionally substituted according to any of the embodiments. It will be clear this example is non-limiting.

Other, non-limiting, examples of the Ar group being a 10-membered bicyclic aromatic ring system consisting of two fused 6-membered rings, wherein optionally 1 or 2 ring carbon atoms are replaced by a nitrogen atom, are shown below:

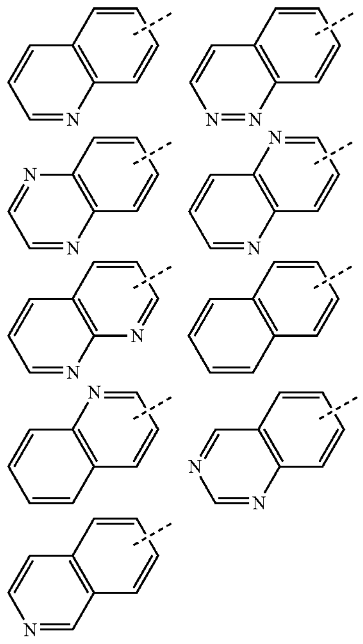

each of which are optionally substituted according to any of the embodiments.

The skilled person will understand that the 10 members of the 10-membered Ar group (the 10-membered bicyclic aromatic ring system consisting of two fused 6-membered rings, wherein optionally 1 or 2 ring carbon atoms are replaced by a nitrogen atom), are 10 carbon atoms, 9 carbon atoms and 1 nitrogen atom, or 8 carbon atoms and 2 nitrogen atoms. Ar is optionally substituted according to any of the embodiments.

Whenever substituents are represented by chemical structure, "---" represents the bond of attachment to the remainder of the molecule of Formula (I). Lines drawn from substituents into ring systems indicate that the bond may be attached to any of the suitable ring atoms.

For example

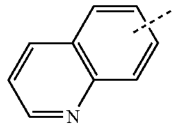

covers any one of the following ring systems:

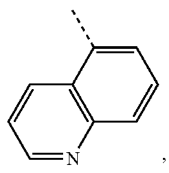 , 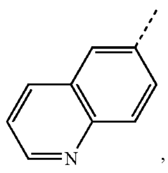 ,

-continued

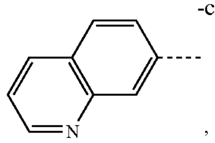 , and 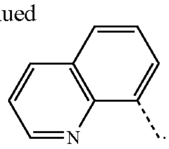 .

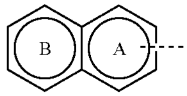

is an alternative representation for

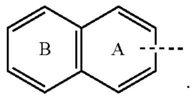 .

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compounds of the (present) invention" as used herein, is meant to include the compounds of Formula (I) and pharmaceutically acceptable addition salts, and solvates thereof.

Some of the compounds of Formula (I) may also exist in their tautomeric form. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganisation of some of the bonding electrons.

Such forms in so far as they may exist, although not explicitly indicated in the above Formula (I), are intended to be included within the scope of the present invention.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers. Where the stereochemistry of any particular chiral atom is not specified in the structures shown herein, then all stereoisomers are contemplated and included as the compounds of the invention, either as a pure stereoisomer or as a mixture of two or more stereoisomers.

Hereinbefore and hereinafter, the term "compound of Formula (I)" is meant to include the stereoisomers thereof and the tautomeric forms thereof. However where stereochemistry, as mentioned in the previous paragraph, is specified by bonds which are shown as solid wedged or hashed wedged bonds, or are otherwise indicated as having a particular configuration (e.g. R, S), then that stereoisomer is so specified and defined. It will be clear this also applies to subgroups of Formula (I).

It follows that a single compound may, where possible, exist in both stereoisomeric and tautomeric form.

The terms "stereoisomers", "stereoisomeric forms" or "stereochemically isomeric forms" hereinbefore or hereinafter are used interchangeably.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

For therapeutic use, salts of the compounds of Formula (I) and solvates thereof, are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

Pharmaceutically-acceptable salts include acid addition salts and base addition salts. Such salts may be formed by conventional means, for example by reaction of a free acid or a free base form with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable addition salts as mentioned hereinabove or hereinafter are meant to comprise the therapeutically active non-toxic acid and base addition salt forms which the compounds of Formula (I) and solvates thereof, are able to form.

Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine addition salt forms by treatment with appropriate organic and inorganic bases.

Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

For the purposes of this invention prodrugs are also included within the scope of the invention.

The term "prodrug" of a relevant compound of the invention includes any compound that, following oral or parenteral administration, in particular oral administration, is metabolised in vivo to a form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration, in particular intravenous (IV), intramuscular (IM), and subcutaneous (SC) injection. Prodrugs may be prepared by modifying functional groups present on the compound in such a way that the modifications are cleaved, in vivo when such prodrug is administered to a mammalian subject. The modifications typically are achieved by synthesising the parent compound with a prodrug substituent. In general, prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively; in particular wherein a hydroxyl group in a compound of the invention is bonded to any group (e.g. —C(═O)—$C_{1-4}$alkyl) that may be cleaved in vivo to regenerate the free hydroxyl. Within the context of this invention, prodrugs in particular are compounds of Formula (I) or subgroups thereof wherein $R^1$ and/or $R^2$ represent —C(═O)—$C_{1-4}$alkyl.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. 1-92, Elesevier, New York-Oxford (1985).

The term solvate comprises the hydrates and solvent addition forms which the compounds of Formula (I) are able to form, as well as pharmaceutically acceptable addition salts thereof. Examples of such forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature).

All isotopes and isotopic mixtures of any particular atom or element as specified herein are contemplated within the scope of the compounds of the invention, either naturally occurring or synthetically produced, either with natural abundance or in an isotopically enriched form. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{2}H$, $^{3}H$, $^{11}C$ and $^{18}F$. More preferably, the radioactive isotope is $^{2}H$. In particular, deuterated compounds are intended to be included within the scope of the present invention.

Certain isotopically-labeled compounds of the present invention (e.g., those labeled with $^{3}H$ and $^{14}C$) are useful in compound and for substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$ may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy.

In all embodiments below, the following compounds, and pharmaceutically acceptable addition salts, and solvates thereof are excluded:

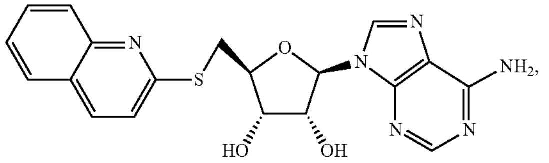

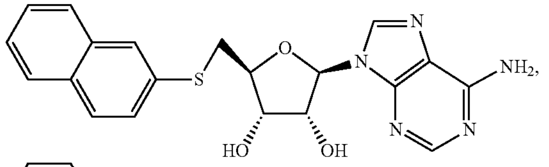

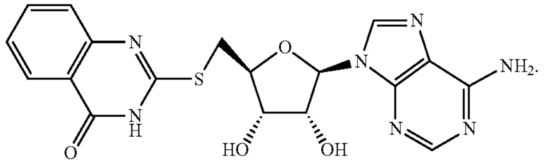

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

Y represents —O—, —$CH_2$— or —$CF_2$—;

Z represents —$CH_2$—, —X—$CR^{5a}R^{5b}$—, —$CR^{5c}$═$CR^{5d}$—, —$CR^{5e}R^{5g}$—$CR^{5f}R^{5h}$—, or —C≡C—;

and when Y represents —$CH_2$— or —$CF_2$—, then Z can also represent —O— or —$CR^{5a}R^{5b}$—X—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

$R^{11}$ represents hydrogen or $C_{1-4}$alkyl;

Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one, two, three or four substituents each independently selected from the group consisting of halo, —OH, —$NH_2$, —NH—$C_{1-4}$alkyl, —N($C_{1-4}$alkyl)$_2$, —$NHR^{10d}$, —$NR^{10c}R^{10d}$, cyano, —$CF_3$, —C(═O)—$NH_2$, —C(═O)—NH—$C_{1-4}$alkyl, —C(═O)—$C_{1-4}$alkyl, $C_{1-4}$alkyloxy, —C(═O)—O—$C_{1-4}$alkyl, $C_{3-6}$cycloalkyl, —O—$C_{3-6}$cycloalkyl, —NH—$C_{3-6}$cycloalkyl, —N($C_{3-6}$cycloalkyl)$_2$, $C_{2-6}$alkenyl, $C_{1-4}$alkyl substituted with one $C_{1-4}$alkyloxy, and $C_{1-4}$alkyl optionally substituted with one —$NR^{10a}R^{10b}$;

$R^{10a}$ and $R^{10b}$ each independently represent hydrogen or $C_{1-4}$alkyl;

$R^{10c}$ and $R^{10d}$ each independently represent $C_{3-6}$cycloalkyl; $R^{14}$; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, and $R^{14}$;

$R^{14}$ represents phenyl optionally substituted with one, two or three substituents each independently selected from the group consisting of halo;

Het represents a bicyclic aromatic heterocyclic ring system selected from the group consisting of (a-1), (a-2), (a-3), (a-4) and (a-5):

(a-1)

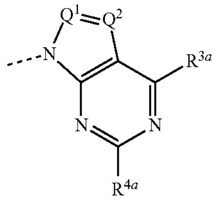

(a-2)

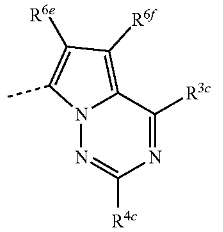

(a-3)

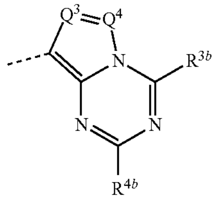

(a-4)

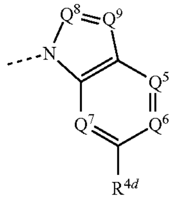

(a-5)

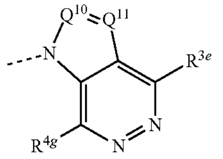

$R^{3a}$, $R^{3b}$, $R^{3c}$, $R^{3d}$ and $R^{3e}$ each independently represent hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl;

$R^{7a}$ represents hydrogen;

$R^{7b}$ represents hydrogen, $C_{3-6}$cycloalkyl, or $C_{1-4}$alkyl;

$R^{4a}$, $R^{4b}$, $R^{4c}$, $R^{4d}$, $R^{4e}$, $R^{4f}$ and $R^{4g}$ each independently represent hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents N or $CR^{6a}$;

$Q^2$ represents N or $CR^{6b}$;

$Q^3$ represents N or $CR^{6c}$;

$Q^4$ represents N or $CR^{6d}$;

provided that maximum one of $Q^3$ and $Q^4$ represents N;

$Q^8$ represents N or $CR^{6g}$;

$Q^9$ represents N or $CR^{6h}$;

$Q^{10}$ represents N or $CR^{6i}$;

$Q^{11}$ represents N or $CR^{6j}$;

$Q^5$ represents $CR^{3d}$; $Q^6$ represents N; and $Q^7$ represents $CR^{4f}$; or $Q^5$ represents $CR^{3d}$; $Q^6$ represents $CR^{4e}$; and $Q^7$ represents N; or $Q^5$ represents N; $Q^6$ represents $CR^{4e}$; and $Q^7$ represents $CR^{4f}$; or $Q^5$ represents N; $Q^6$ represents $CR^{4e}$; and $Q^7$ represents N; or $Q^5$ represents N; $Q^6$ represents N; and $Q^7$ represents $CR^{4f}$; or $Q^5$ represents N; $Q^6$ represents N; and $Q^7$ represents N;

$R^{6a}$, $R^{6b}$, $R^{6c}$, $R^{6d}$, $R^{6e}$, $R^{6f}$, $R^{6g}$, $R^{6h}$, $R^{6i}$ and $R^{6j}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

Y represents —O—, —$CH_2$— or —$CF_2$—;

Z represents —$CH_2$—, —X—$CR^{5a}R^{5b}$—, —$CR^{5c}$═$CR^{5d}$—, —$CR^{5e}R^{5g}$—$CR^{5f}R^{5h}$—, or —C≡C—;

and when Y represents —$CH_2$— or —$CF_2$—, then Z can also represent —O— or —$CR^{5a}R^{5b}$—X—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

$R^{11}$ represents hydrogen, $C_{1-4}$alkyl, or $C_{1-4}$alkyl substituted with one substituent selected from the group consisting of —OH, —O—$C_{1-4}$alkyl, $R^{12}$, —$NH_2$, —NH—$C_{1-4}$alkyl, and —N($C_{1-4}$alkyl)$_2$;

$R^{12}$ represents a 4-, 5-, 6- or 7-membered heterocyclic ring containing one nitrogen atom and optionally one oxygen atom; said 4-, 5-, 6- or 7-membered heterocyclic ring being attached to the remainder of the molecule via a ring nitrogen atom;

Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one, two, three or four substituents each independently selected from the group consisting of halo, —OH, —$NH_2$, —NH—$C_{1-4}$alkyl, —N($C_{1-4}$alkyl)$_2$, —$NHR^{10d}$, —$NR^{10c}R^{10d}$, cyano, —$CF_3$, —C(═O)—$NH_2$, —C(═O)—NH—$C_{1-4}$alkyl, —C(═O)—$C_{1-4}$alkyl, $C_{1-4}$alkyloxy, —C(═O)—O—$C_{1-4}$alkyl, $C_{3-6}$cycloalkyl, —O—$C_{3-6}$cycloalkyl, —NH—$C_{3-6}$cycloalkyl, —N($C_{3-6}$cycloalkyl)$_2$, $C_{2-6}$alkenyl, $C_{1-4}$alkyl substituted with one $C_{1-4}$alkyloxy, and $C_{1-4}$alkyl optionally substituted with one —$NR^{10a}R^{10b}$;

$R^{10a}$ and $R^{10b}$ each independently represent hydrogen or $C_{1-4}$alkyl;

$R^{10c}$ and $R^{10d}$ each independently represent $C_{3-6}$cycloalkyl; $R^{13}$; $R^{14}$; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, $R^{13}$ and $R^{14}$;

$R^{13}$ represents a 4- to 7-membered monocyclic aromatic ring containing one, two or three heteroatoms each independently selected from O, S, S(═O)$_p$ and N; or a 6- to 11-membered bicyclic fused aromatic ring containing one, two or three heteroatoms each independently selected from O, S, S(═O)$_p$ and N;

said 4- to 7-membered monocyclic aromatic ring or 6- to 11-membered bicyclic fused aromatic ring is optionally substituted with one or two substituents selected from the group consisting of $C_{1-4}$alkyl;

p represents 1 or 2;

$R^{14}$ represents phenyl optionally substituted with one, two or three substituents each independently selected from the group consisting of halo;

Het represents a bicyclic aromatic heterocyclic ring system selected from the group consisting of (a-1), (a-2), (a-3), (a-4) and (a-5):

(a-1)

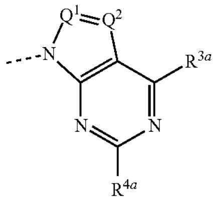

(a-2)

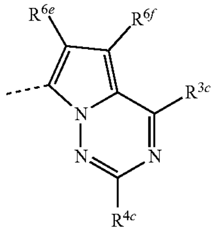

(a-3)

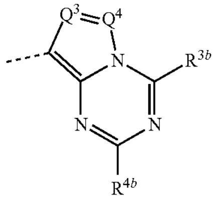

-continued (a-4)

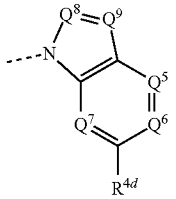

(a-5)

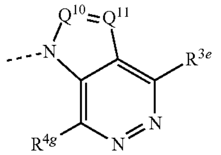

$R^{3a}$, $R^{3b}$, $R^{3c}$, $R^{3d}$ and $R^{3e}$ each independently represent hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl;

$R^{7a}$ represents hydrogen;

$R^{7b}$ represents hydrogen, $C_{3-6}$cycloalkyl, or $C_{1-4}$alkyl;

$R^{4a}$, $R^{4b}$, $R^{4c}$, $R^{4d}$, $R^{4e}$, $R^{4f}$ and $R^{4g}$ each independently represent hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents $CR^{6a}$;

$Q^2$ represents $CR^{6b}$;

$Q^3$ represents N or $CR^{6c}$;

$Q^4$ represents N or $CR^{6d}$;

provided that maximum one of $Q^3$ and $Q^4$ represents N;

$Q^8$ represents N or $CR^{6g}$;

$Q^9$ represents N or $CR^{6h}$;

$Q^{10}$ represents N or $CR^{6i}$;

$Q^{11}$ represents N or $CR^{6j}$;

$Q^5$ represents $CR^{3d}$; $Q^6$ represents N; and $Q^7$ represents $CR^{4f}$; or $Q^5$ represents $CR^{3d}$; $Q^6$ represents $CR^{4e}$; and $Q^7$ represents N; or $Q^5$ represents N; $Q^6$ represents $CR^{4e}$; and $Q^7$ represents $CR^{4f}$; or $Q^5$ represents N; $Q^6$ represents $CR^{4e}$; and $Q^7$ represents N; or $Q^5$ represents N; $Q^6$ represents N; and $Q^7$ represents $CR^{4f}$; or $Q^5$ represents N; $Q^6$ represents N; and $Q^7$ represents N;

$R^{6a}$, $R^{6b}$, $R^{6c}$, $R^{6d}$, $R^{6e}$, $R^{6f}$, $R^{6g}$, $R^{6h}$, $R^{6i}$ and $R^{6j}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

Y represents —O—, —$CH_2$— or —$CF_2$—;

Z represents —$CH_2$—, —X—$CR^{5a}R^{5b}$—, —$CR^{5c}$═$CR^{5d}$—, —$CR^{5e}R^{5g}$—$CR^{5f}R^{5h}$—, or —C≡C—;

and when Y represents —$CH_2$— or —$CF_2$—, then Z can also represent —O— or —$CR^{5a}R^{5b}$—X—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

$R^{11}$ represents hydrogen, $C_{1-4}$alkyl, or $C_{1-4}$alkyl substituted with one substituent selected from the group consisting of —OH, —O—$C_{1-4}$alkyl, $R^{12}$, —$NH_2$, —NH—$C_{1-4}$alkyl, and —N($C_{1-4}$alkyl)$_2$;

$R^{12}$ represents a 4-, 5-, 6- or 7-membered heterocyclic ring containing one nitrogen atom and optionally one oxygen atom; said 4-, 5-, 6- or 7-membered heterocyclic ring being attached to the remainder of the molecule via a ring nitrogen atom;

Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one, two, three or four substituents each independently selected from the group consisting of halo, —OH, —$NH_2$, —NH—$C_{1-4}$alkyl, —N($C_{1-4}$alkyl)$_2$, —$NHR^{10d}$, —$NR^{10c}R^{10d}$, cyano, —$CF_3$, —C(═O)—$NH_2$, —C(═O)—NH—$C_{1-4}$alkyl, —C(═O)—$C_{1-4}$alkyl, $C_{1-4}$alkyloxy, —C(═O)—O—$C_{1-4}$alkyl, $C_{3-6}$cycloalkyl, $C_{2-6}$alkenyl, $C_{1-4}$alkyl substituted with one $C_{1-4}$alkyloxy, and $C_{1-4}$alkyl optionally substituted with one —$NR^{10a}R^{10b}$;

$R^{10a}$ and $R^{10b}$ each independently represent hydrogen or $C_{1-4}$alkyl;

$R^{10c}$ and $R^{10d}$ each independently represent $C_{3-6}$cycloalkyl; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, $R^3$ and $R^{14}$;

$R^{13}$ represents a 4- to 7-membered monocyclic aromatic ring containing one, two or three heteroatoms each independently selected from O, S, S(═O)$_p$ and N; or a 6- to 11-membered bicyclic fused aromatic ring containing one, two or three heteroatoms each independently selected from O, S, S(═O)$_p$ and N;

said 4- to 7-membered monocyclic aromatic ring or 6- to 11-membered bicyclic fused aromatic ring is optionally substituted with one or two substituents selected from the group consisting of $C_{1-4}$alkyl;

p represents 1 or 2;

$R^{14}$ represents phenyl optionally substituted with one, two or three substituents each independently selected from the group consisting of halo;

Het represents a bicyclic aromatic heterocyclic ring system selected from the group consisting of (a-1), (a-2) and (a-3):

(a-1)

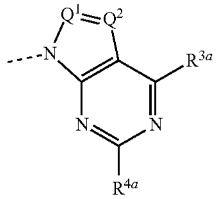

-continued (a-2)

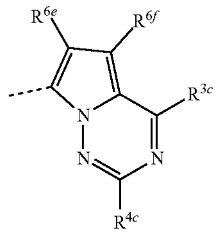

(a-3)

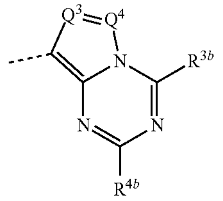

$R^{3a}$, $R^{3b}$ and $R^{3c}$ each independently represent hydrogen, halo, —$NR^{7a}R^{7b}$, $C_{1-4}$alkyl, or —O—$C_{1-4}$alkyl;

$R^{7a}$ represents hydrogen;

$R^{7b}$ represents hydrogen or $C_{1-4}$alkyl;

$R^{4a}$, $R^{4b}$ and $R^{4c}$ each independently represent hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents N or $CR^{6a}$;

$Q^2$ represents N or $CR^{6b}$;

$Q^3$ represents N or $CR^{6c}$;

$Q^4$ represents N or $CR^{6d}$;

provided that maximum one of $Q^3$ and $Q^4$ represents N;

$R^{6a}$, $R^{6b}$, $R^{6c}$, $R^{6d}$, $R^{6e}$ and $R^{6f}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

Y represents —O—, —$CH_2$— or —$CF_2$—;

Z represents —$CH_2$—, —X—$CR^{5a}R^{5b}$—, —$CR^{5c}$═$CR^{5d}$—, —$CR^{5e}R^{5g}$—$CR^{5f}R^{5h}$—, or —C≡C—;

and when Y represents —$CH_2$— or —$CF_2$—, then Z can also represent —O— or —$CR^{5a}R^{5b}$—X—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

$R^{11}$ represents hydrogen, $C_{1-4}$alkyl, or $C_{1-4}$alkyl substituted with one substituent selected from the group consisting of —OH, —O—$C_{1-4}$alkyl, $R^{12}$, —$NH_2$, —NH—$C_{1-4}$alkyl, and —N($C_{1-4}$alkyl)$_2$;

$R^{12}$ represents a 4-, 5-, 6- or 7-membered heterocyclic ring containing one nitrogen atom and optionally one oxygen atom; said 4-, 5-, 6- or 7-membered heterocyclic ring being attached to the remainder of the molecule via a ring nitrogen atom;

Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one, two, three or four substituents each independently selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, —C(═O)—$C_{1-4}$alkyl, $C_{1-4}$alkyloxy, and $C_{1-4}$alkyl optionally substituted with one —$NR^{10a}R^{10b}$;

$R^{10a}$ and $R^{10b}$ each independently represent hydrogen or $C_{1-4}$alkyl;

Het represents a bicyclic aromatic heterocyclic ring system selected from the group consisting of (a-1), (a-2) and (a-3):

(a-1)

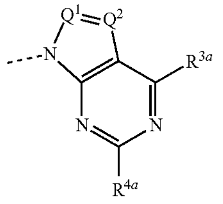

(a-2)

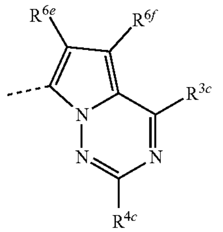

(a-3)

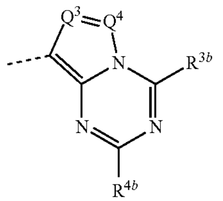

$R^{3a}$, $R^{3b}$ and $R^{3c}$ each independently represent hydrogen, halo, —$NR^{7a}R^{7b}$, or —O—$C_{1-4}$alkyl;

$R^{7a}$ represents hydrogen;

$R^{7b}$ represents hydrogen or $C_{1-4}$alkyl;

$R^{4a}$, $R^{4b}$ and $R^{4c}$ each independently represent hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents N or $CR^{6a}$;

$Q^2$ represents N or $CR^{6b}$;

$Q^3$ represents N or $CR^{6c}$;

$Q^4$ represents N or $CR^{6d}$;

provided that maximum one of $Q^3$ and $Q^4$ represents N;

$R^{6a}$, $R^{6b}$, $R^{6c}$, $R^{6d}$, $R^{6e}$ and $R^{6f}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

Y represents —O—, —$CH_2$— or —$CF_2$—;

Z represents —$CH_2$—, —X—$CR^{5a}R^{5b}$—, —$CR^{5c}$═$CR^{5d}$—, —$CR^{5e}R^{5g}$—$CR^{5f}R^{5h}$—, or —C≡C—;

and when Y represents —$CH_2$— or —$CF_2$—, then Z can also represent —O— or —$CR^{5a}R^{5b}$—X—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

$R^{11}$ represents hydrogen, $C_{1-4}$alkyl, or $C_{1-4}$alkyl substituted with one substituent selected from the group consisting of —OH, —O—$C_{1-4}$alkyl, $R^{12}$, —$NH_2$, —NH—$C_{1-4}$alkyl, and —N($C_{1-4}$alkyl)$_2$;

$R^{12}$ represents a 4-, 5-, 6- or 7-membered heterocyclic ring containing one nitrogen atom and optionally one oxygen atom; said 4-, 5-, 6- or 7-membered heterocyclic ring being attached to the remainder of the molecule via a ring nitrogen atom;

Ar represents a 10-membered bicyclic aromatic ring system consisting of two fused 6-membered rings,

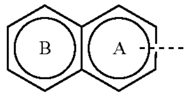

wherein at least 1 ring carbon atom of ring B is replaced by a nitrogen atom;

wherein optionally 1 additional ring carbon atom of ring A or ring B is replaced by a nitrogen atom; provided that when a nitrogen atom replaces one of the two fused carbon atoms, a carbonyl group is present in said bicyclic aromatic ring system;

Ar is optionally substituted with one, two, three or four substituents each independently selected from the group consisting of halo, —OH, —$NH_2$, —NH—$C_{1-4}$alkyl, —N($C_{1-4}$alkyl)$_2$, —$NHR^{10d}$, —$NR^{10c}R^{10d}$, cyano, —$CF_3$, —C(═O)—$NH_2$, —C(═O)—NH—$C_{1-4}$alkyl, —C(═O)—$C_{1-4}$alkyl, $C_{1-4}$alkyloxy, —C(═O)—O—$C_{1-4}$alkyl, $C_{3-6}$cycloalkyl, —O—$C_{3-6}$cycloalkyl, —NH—$C_{3-6}$cycloalkyl, —N($C_{3-6}$cycloalkyl)$_2$, $C_{2-6}$alkenyl, $C_{1-4}$alkyl substituted with one $C_{1-4}$alkyloxy, and $C_{1-4}$alkyl optionally substituted with one —$NR^{10a}R^{10b}$;

$R^{10a}$ and $R^{10b}$ each independently represent hydrogen or $C_{1-4}$alkyl;

$R^{10c}$ and $R^{10d}$ each independently represent $C_{3-6}$cycloalkyl; $R^{13}$; $R^{14}$; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, $R^{13}$ and $R^{14}$;

$R^{13}$ represents a 4- to 7-membered monocyclic aromatic ring containing one, two or three heteroatoms each independently selected from O, S, S(═O)$_p$ and N; or a 6- to 11-membered bicyclic fused aromatic ring containing one, two or three heteroatoms each independently selected from O, S, $S(=O)_p$ and N;

said 4- to 7-membered monocyclic aromatic ring or 6- to 11-membered bicyclic fused aromatic ring is optionally substituted with one or two substituents selected from the group consisting of $C_{1-4}$alkyl;

p represents 1 or 2;

$R^{14}$ represents phenyl optionally substituted with one, two or three substituents each independently selected from the group consisting of halo;

Het represents a bicyclic aromatic heterocyclic ring system selected from the group consisting of (a-1), (a-2), (a-3), (a-4) and (a-5):

(a-1)

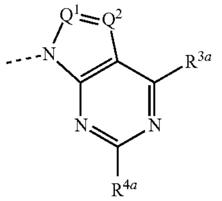

(a-2)

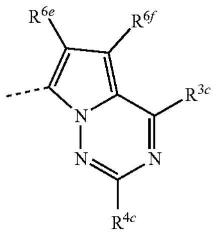

(a-3)

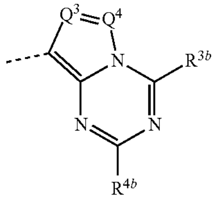

(a-4)

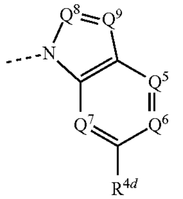

(a-5)

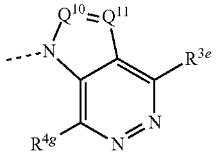

$R^{3a}$, $R^{3b}$, $R^{3c}$, $R^{3d}$ and $R^{3e}$ each independently represent hydrogen, halo, $—NR^{7a}R^{7b}$, $C_{1-4}$alkyl, $C_{2-4}$alkenyl, $C_{3-6}$cycloalkyl, —OH, or $—O—C_{1-4}$alkyl;

$R^{7a}$ represents hydrogen;

$R^{7b}$ represents hydrogen, $C_{3-6}$cycloalkyl, or $C_{1-4}$alkyl;

$R^{4a}$, $R^{4b}$, $R^{4c}$, $R^{4d}$, $R^{4e}$, $R^{4f}$ and $R^{4g}$ each independently represent hydrogen, halo, $—NR^{8a}R^{8b}$, or $C_{1-4}$alkyl;

$R^{8a}$ and $R^{8b}$ each independently represent hydrogen or $C_{1-4}$alkyl;

$Q^1$ represents N or $CR^{6a}$;

$Q^2$ represents N or $CR^{6b}$;

$Q^3$ represents N or $CR^{6c}$;

$Q^4$ represents N or $CR^{6d}$;

provided that maximum one of $Q^3$ and $Q^4$ represents N;

$Q^8$ represents N or $CR^{6g}$;

$Q^9$ represents N or $CR^{6h}$;

$Q^{10}$ represents N or $CR^{6i}$;

$Q^{11}$ represents N or $CR^{6j}$;

$Q^5$ represents $CR^{3d}$; $Q^6$ represents N; and $Q^7$ represents $CR^{4f}$; or $Q^5$ represents $CR^{3d}$; $Q^6$ represents $CR^{4e}$; and $Q^7$ represents N; or $Q^5$ represents N; $Q^6$ represents $CR^{4e}$; and $Q^7$ represents $CR^{4f}$; or $Q^5$ represents N; $Q^6$ represents $CR^{4e}$; and $Q^7$ represents N; or $Q^5$ represents N; $Q^6$ represents N; and $Q^7$ represents $CR^{4f}$; or $Q^5$ represents N; $Q^6$ represents N; and $Q^7$ represents N;

$R^{6a}$, $R^{6b}$, $R^{6c}$, $R^{6d}$, $R^{6e}$, $R^{6f}$, $R^{6e}$, $R^{6f}$, $R^{6g}$, $R^{6h}$, $R^{6i}$ and $R^{6j}$ each independently represent hydrogen, halogen, $C_{1-4}$alkyl, $—NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen;

$R^2$ represents hydrogen;

Y represents —O—, $—CH_2—$ or $—CF_2—$;

Z represents $—CH_2—$, $—X—CR^{5a}R^{5b}—$, $—CR^{5c}=CR^{5d}—$, $—CR^{5e}R^{5g}—CR^{5f}R^{5h}—$, or —C≡C—;

and when Y represents $—CH_2—$ or $—CF_2—$, then Z can also represent —O— or $—CR^{5a}R^{5b}—X—$;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or $—NR^{11}—$;

$R^{11}$ represents hydrogen, $C_{1-4}$alkyl, or $C_{1-4}$alkyl substituted with one substituent selected from the group consisting of —OH, $—O—C_{1-4}$alkyl, $R^{12}$, $—NH_2$, $—NH—C_{1-4}$alkyl, and $—N(C_{1-4}alkyl)_2$;

$R^{12}$ represents a 4-, 5-, 6- or 7-membered heterocyclic ring containing one nitrogen atom and optionally one oxygen atom; said 4-, 5-, 6- or 7-membered heterocyclic ring being attached to the remainder of the molecule via a ring nitrogen atom;

Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one, two, three or four substituents each independently selected from the group consisting of halo, —OH, $—NH_2$, $—NH—C_{1-4}$alkyl, $—N(C_{1-4}alkyl)_2$, $—NHR^{10d}$, $—NR^{10c}R^{10d}$, cyano, $—CF_3$, $—C(=O)—NH_2$, $—C(=O)—NH—C_{1-4}$alkyl, $—C(=O)—C_{1-4}$alkyl, $C_{1-4}$alkyloxy, $—C(=O)—O—C_{1-4}$alkyl, $C_{3-6}$cycloalkyl, $—O—C_{3-6}$cycloalkyl, $—NH—C_{3-6}$cycloalkyl, $—N(C_{3-6}$cycloalkyl)$_2$, $C_{2\text{-}6}$alkenyl, $C_{1\text{-}4}$alkyl substituted with one $C_{1\text{-}4}$alkyloxy, and $C_{1\text{-}4}$alkyl optionally substituted with one —$NR^{10a}R^{10b}$;

$R^{10a}$ and $R^{10b}$ each independently represent hydrogen or $C_{1\text{-}4}$alkyl;

$R^{10c}$ and $R^{10d}$ each independently represent $C_{3\text{-}6}$cycloalkyl; $R^{13}$; $R^{14}$; $C_{3\text{-}6}$cycloalkyl substituted with one, two or three substituents each independently selected from the group consisting of halo, —OH and —O—$C_{1\text{-}4}$alkyl; $C_{1\text{-}4}$alkyl substituted with one, two or three substituents each independently selected from the group consisting of halo, —OH and —O—$C_{1\text{-}4}$alkyl; or $C_{1\text{-}4}$alkyl substituted with one substituent selected from the group consisting of $C_{3\text{-}6}$cycloalkyl, $R^{13}$ and $R^{14}$;

$R^{13}$ represents a 4- to 7-membered monocyclic aromatic ring containing one, two or three heteroatoms each independently selected from O, S, S(=O)$_p$ and N; or a 6- to 11-membered bicyclic fused aromatic ring containing one, two or three heteroatoms each independently selected from O, S, S(=O)$_p$ and N;

said 4- to 7-membered monocyclic aromatic ring or 6- to 11-membered bicyclic fused aromatic ring is optionally substituted with one or two substituents selected from the group consisting of $C_{1\text{-}4}$alkyl;

p represents 1 or 2;

$R^{14}$ represents phenyl optionally substituted with one, two or three substituents each independently selected from the group consisting of halo;

Het represents a bicyclic aromatic heterocyclic ring system selected from the group consisting of (a-1), (a-2), (a-3), (a-4) and (a-5):

(a-1)

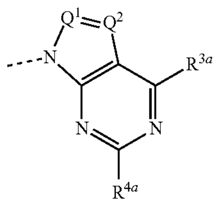

(a-2)

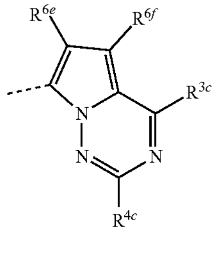

(a-3)

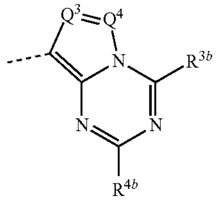

-continued (a-4)

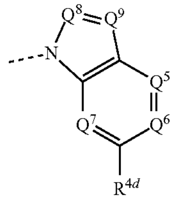

(a-5)

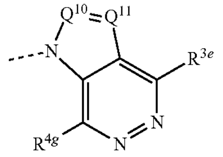

$R^{3a}$, $R^{3b}$, $R^{3c}$, $R^{3d}$ and $R^{3e}$ each independently represent hydrogen, halo, —$NR^{7a}R^{7b}$, $C_{1\text{-}4}$alkyl, $C_{2\text{-}4}$alkenyl, $C_{3\text{-}6}$cycloalkyl, —OH, or —O—$C_{1\text{-}4}$alkyl;

$R^{7a}$ represents hydrogen;

$R^{7b}$ represents hydrogen, $C_{3\text{-}6}$cycloalkyl, or $C_{1\text{-}4}$alkyl;

$R^{4a}$, $R^{4b}$, $R^{4c}$, $R^{4d}$, $R^{4e}$, $R^{4f}$ and $R^{4g}$ each independently represent hydrogen, halo, —$NR^{8a}R^{8b}$, or $C_{1\text{-}4}$alkyl;

$R^{8a}$ and $R^{8b}$ each independently represent hydrogen or $C_{1\text{-}4}$alkyl;

$Q^1$ represents N or $CR^{6a}$;

$Q^2$ represents N or $CR^{6b}$;

$Q^3$ represents N or $CR^{6c}$;

$Q^4$ represents N or $CR^{6d}$;

provided that maximum one of $Q^3$ and $Q^4$ represents N;

$Q^8$ represents N or $CR^{6g}$;

$Q^9$ represents N or $CR^{6h}$;

$Q^{10}$ represents N or $CR^{6i}$;

$Q^{11}$ represents N or $CR^{6j}$;

$Q^5$ represents $CR^{3d}$; $Q^6$ represents N; and $Q^7$ represents $CR^{4f}$; or $Q^5$ represents $CR^{3d}$; $Q^6$ represents $CR^{4e}$; and $Q^7$ represents N; or $Q^5$ represents N; $Q^6$ represents $CR^{4e}$; and $Q^7$ represents $CR^{4f}$; or $Q^5$ represents N; $Q^6$ represents $CR^{4e}$; and $Q^7$ represents N; or $Q^5$ represents N; $Q^6$ represents N; and $Q^7$ represents $CR^{4f}$; or $Q^5$ represents N; $Q^6$ represents N; and $Q^7$ represents N;

$R^{6a}$, $R^{6b}$, $R^{6c}$, $R^{6d}$, $R^{6e}$, $R^{6f}$, $R^{6g}$, $R^{6h}$, $R^{6i}$ and $R^{6j}$ each independently represent hydrogen, halogen, $C_{1\text{-}4}$alkyl, —$NR^{9a}R^{9b}$, or $C_{1\text{-}4}$alkyl substituted with one, two or three halo atoms;

$R^{9a}$ and $R^{9b}$ each independently represent hydrogen or $C_{1\text{-}4}$alkyl;

and pharmaceutically acceptable addition salts, and solvates thereof.

In an embodiment, the present invention concerns novel compounds of Formula (I), wherein $R^1$ represents hydrogen;

$R^2$ represents hydrogen;

Y represents —O—, —$CH_2$— or —$CF_2$—;

Z represents —$CH_2$—, —X—$CR^{5a}R^{5b}$—, —$CR^{5c}$=$CR^{5d}$—, —$CR^{5e}R^{5g}$—$CR^{5f}R^{5h}$—, or —C≡C—;

and when Y represents —$CH_2$— or —$CF_2$—, then Z can also represent —O— or —$CR^{5a}R^{5b}$—X—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

$R^{11}$ represents hydrogen, $C_{1-4}$alkyl, or $C_{1-4}$alkyl substituted with one substituent selected from the group consisting of —OH, —O—$C_{1-4}$alkyl, $R^{12}$, —$NH_2$, —NH—$C_{1-4}$alkyl, and —N($C_{1-4}$alkyl)$_2$;

$R^{12}$ represents a 4-, 5-, 6- or 7-membered heterocyclic ring containing one nitrogen atom and optionally one oxygen atom; said 4-, 5-, 6- or 7-membered heterocyclic ring being attached to the remainder of the molecule via a ring nitrogen atom;

Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one, two, three or four substituents each independently selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, —C(═O)—$C_{1-4}$alkyl, $C_{1-4}$alkyloxy, and $C_{1-4}$alkyl optionally substituted with one —$NR^{10a}R^{10b}$;

$R^{10a}$ and $R^{10b}$ each independently represent hydrogen or $C_{1-4}$alkyl;

Het represents a bicyclic aromatic heterocyclic ring system selected from the group consisting of (a-1), (a-2) and (a-3);

$R^{3a}$, $R^{3b}$ and $R^{3c}$ each independently represent hydrogen, halo, —$NR^{7a}R^{7b}$, or —O—$C_{1-4}$alkyl;

$R^{7a}$ represents hydrogen;

$R^{7b}$ represents hydrogen or $C_{1-4}$alkyl;

$R^{4a}$, $R^{4b}$ and $R^{4c}$ each independently represent hydrogen, halo, —$NR^{8a}R^{8b}$, $C_{1-4}$alkyl;

$R^{8a}$ and $R^{8b}$ each independently represent hydrogen or $C_{1-4}$alkyl;

$Q^1$ represents N or $CR^{6a}$;

$Q^2$ represents N or $CR^{6b}$;

$Q^3$ represents N or $CR^{6c}$;

$Q^4$ represents N or $CR^{6d}$;

provided that maximum one of $Q^3$ and $Q^4$ represents N;

$R^{6a}$, $R^{6b}$, $R^{6c}$, $R^{6d}$, $R^{6e}$ and $R^{6f}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

Y represents —O—, —$CH_2$— or —$CF_2$—;

Z represents —$CH_2$—, —X—$CR^{5a}R^{5b}$—, —$CR^{5c}$═$CR^{5d}$—, —$CR^{5e}R^{5g}$—$CR^{5f}R^{5h}$—, or —C≡C—;

and when Y represents —$CH_2$— or —$CF_2$—, then Z can also represent —O— or —$CR^{5a}R^{5b}$—X—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

$R^{11}$ represents hydrogen, $C_{1-4}$alkyl, or $C_{1-4}$alkyl substituted with one substituent selected from the group consisting of —OH, —O—$C_{1-4}$alkyl, $R^{12}$, —$NH_2$, —NH—$C_{1-4}$alkyl, and —N($C_{1-4}$alkyl)$_2$;

$R^{12}$ represents a 4-, 5-, 6- or 7-membered heterocyclic ring containing one nitrogen atom and optionally one oxygen atom; said 4-, 5-, 6- or 7-membered heterocyclic ring being attached to the remainder of the molecule via a ring nitrogen atom;

Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one, two, three or four substituents each independently selected from the group consisting of halo, —OH, —$NH_2$, —NH—$C_{1-4}$alkyl, —N($C_{1-4}$alkyl)$_2$, —$NHR^{10d}$, —$NR^{10c}R^{10d}$, cyano, —$CF_3$, —C(═O)—$NH_2$, —C(═O)—NH—$C_{1-4}$alkyl, —C(═O)—$C_{1-4}$alkyl, $C_{1-4}$alkyloxy, —C(═O)—O—$C_{1-4}$alkyl, $C_{3-6}$cycloalkyl, —O—$C_{3-6}$cycloalkyl, —NH—$C_{3-6}$cycloalkyl, —N($C_{3-6}$cycloalkyl)$_2$, $C_{2-6}$alkenyl, $C_{1-4}$alkyl substituted with one $C_{1-4}$alkyloxy, and $C_{1-4}$alkyl optionally substituted with one —$NR^{10a}R^{10b}$;

$R^{10a}$ and $R^{10b}$ each independently represent hydrogen or $C_{1-4}$alkyl;

$R^{10c}$ and $R^{10d}$ each independently represent $C_{3-6}$cycloalkyl; $R^{13}$; $R^{14}$; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, $R^{13}$ and $R^{14}$;

$R^{13}$ represents a 4- to 7-membered monocyclic aromatic ring containing one, two or three heteroatoms each independently selected from O, S, S(═O)$_p$ and N; or a 6- to 11-membered bicyclic fused aromatic ring containing one, two or three heteroatoms each independently selected from O, S, S(═O)$_p$ and N;

said 4- to 7-membered monocyclic aromatic ring or 6- to 11-membered bicyclic fused aromatic ring is optionally substituted with one or two substituents selected from the group consisting of $C_{1-4}$alkyl;

p represents 1 or 2;

$R^{14}$ represents phenyl optionally substituted with one, two or three substituents each independently selected from the group consisting of halo;

Het represents a bicyclic aromatic heterocyclic ring system selected from the group consisting of (a-1);

$R^{3a}$ represents hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl;

$R^{7a}$ represents hydrogen;

$R^{7b}$ represents hydrogen, $C_{3-6}$cycloalkyl, or $C_{1-4}$alkyl;

$R^{4a}$ represents hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents N or $CR^{6a}$;

$Q^2$ represents N or $CR^{6b}$;

in particular $Q^1$ and $Q^2$ represent CH;

$R^{6a}$ and $R^{6b}$, each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

Y represents —O—, —$CH_2$— or —$CF_2$—;

Z represents —$CH_2$—, —X—$CR^{5a}R^{5b}$—, —$CR^{5c}$═$CR^{5d}$—, —$CR^{5e}R^{5g}$—$CR^{5f}R^{5h}$—, or —C≡C—;

and when Y represents —$CH_2$— or —$CF_2$—, then Z can also represent —O— or —$CR^{5a}R^{5b}$—X—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

$R^{11}$ represents hydrogen, $C_{1-4}$alkyl, or $C_{1-4}$alkyl substituted with one substituent selected from the group consisting of —OH, —O—$C_{1-4}$alkyl, $R^{12}$, —$NH_2$, —NH—$C_{1-4}$alkyl, and —N($C_{1-4}$alkyl)$_2$;

$R^{12}$ represents a 4-, 5-, 6- or 7-membered heterocyclic ring containing one nitrogen atom and optionally one oxygen atom; said 4-, 5-, 6- or 7-membered heterocyclic ring being attached to the remainder of the molecule via a ring nitrogen atom;

Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one, two, three or four substituents each independently selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, —C(═O)—$C_{1-4}$alkyl, $C_{1-4}$alkyloxy, and $C_{1-4}$alkyl optionally substituted with one —$NR^{10a}R^{10b}$;

$R^{10a}$ and $R^{10b}$ each independently represent hydrogen or $C_{1-4}$alkyl;

Het represents a bicyclic aromatic heterocyclic ring system selected from the group consisting of (a-1);

$R^{3a}$ represents hydrogen, halo, —$NR^{7a}R^{7b}$, or —O—$C_{1-4}$alkyl;

$R^{7a}$ represents hydrogen;

$R^{7b}$ represents hydrogen or $C_{1-4}$alkyl;

$R^{4a}$ represents hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents N or $CR^{6a}$;

$Q^2$ represents N or $CR^{6b}$;

in particular $Q^1$ and $Q^2$ represent CH;

$R^{6a}$ and $R^{6b}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

Y represents —O— or —$CH_2$—;

Z represents —$CH_2$—, —X—$CR^{5a}R^{5b}$—, —$CR^{5c}$═$CR^{5d}$—, —$CR^{5e}R^{5g}$—$CR^{5f}R^{5h}$—, or —C≡C—;

and when Y represents —$CH_2$—, then Z can also represent —$CR^{5a}R^{5b}$—X—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

$R^{11}$ represents hydrogen or $C_{1-4}$alkyl;

Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one, two, three or four substituents each independently selected from the group consisting of halo, —OH, —$NH_2$, —NH—$C_{1-4}$alkyl, —N($C_{1-4}$alkyl)$_2$, —$NHR^{10d}$, cyano, —$CF_3$, —C(═O)—$NH_2$, —C(═O)—NH—$C_{1-4}$alkyl, $C_{1-4}$alkyloxy, —C(═O)—O—$C_{1-4}$alkyl, $C_{3-6}$cycloalkyl, $C_{2-6}$alkenyl, $C_{1-4}$alkyl substituted with one $C_{1-4}$alkyloxy, and $C_{1-4}$alkyl optionally substituted with one —$NR^{10a}R^{10b}$;

$R^{10a}$ and $R^{10b}$ represent $C_{1-4}$alkyl;

$R^{10d}$ represents $C_{3-6}$cycloalkyl; $R^{14}$; $C_{1-4}$alkyl substituted with one, two or three halo substituents; or $C_{1-4}$alkyl substituted with one substituent selected from the group consisting of $C_{3-6}$cycloalkyl, and $R^{14}$;

$R^{14}$ represents phenyl optionally substituted with one, two or three substituents each independently selected from the group consisting of halo;

Het represents a bicyclic aromatic heterocyclic ring system selected from the group consisting of (a-1), (a-2) and (a-4);

$R^{3a}$, $R^{3b}$, $R^{3c}$ and $R^{3d}$ each independently represent hydrogen, halo, —$NR^{7a}R^{7b}$, $C_{2-4}$alkenyl, $C_{3-6}$cycloalkyl, —OH, or —O—$C_{1-4}$alkyl;

$R^{7a}$ represents hydrogen;

$R^{7b}$ represents hydrogen, $C_{3-6}$cycloalkyl, or $C_{1-4}$alkyl;

$R^{4a}$, $R^{4b}$, $R^{4c}$, $R^{4d}$, $R^{4e}$ and $R^{4f}$ each independently represent hydrogen, halo, —$NR^{8a}R^{8b}$, or $C_{1-4}$alkyl;

$R^{8a}$ and $R^{8b}$ each independently represent hydrogen;

$Q^1$ represents $CR^{6a}$;

$Q^2$ represents $CR^{6b}$;

$Q^8$ represents $CR^{6g}$;

$Q^9$ represents $CR^{6h}$;

$Q^5$ represents $CR^{3d}$; $Q^6$ represents N; and $Q^7$ represents $CR^{4f}$; or $Q^5$ represents $CR^{3d}$; $Q^6$ represents $CR^{4e}$; and $Q^7$ represents N; or $Q^5$ represents N; $Q^6$ represents $CR^{4e}$; and $Q^7$ represents $CR^{4f}$; or $Q^5$ represents N; $Q^6$ represents $CR^{4e}$; and $Q^7$ represents N;

$R^{6a}$, $R^{6b}$, $R^{6c}$, $R^{6d}$, $R^{6e}$, $R^{6f}$, $R^{6g}$ and $R^{6h}$ each independently represent hydrogen, halogen, or $C_{1-4}$alkyl;

and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

Y represents —O—, or —$CH_2$—;

Z represents —$CH_2$—, —X—$CR^{5a}R^{5b}$—, —$CR^{5c}$═$CR^{5d}$—, —$CR^{5e}R^{5g}$—$CR^{5f}R^{5h}$—, or —C≡C—;

and when Y represents —$CH_2$—, then Z can also represent —O— or —$CR^{5a}R^{5b}$—X—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

represents hydrogen or $C_{1-4}$alkyl;

Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one, two, three or four substituents each independently selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, —C(═O)—$C_{1-4}$alkyl, $C_{1-4}$alkyloxy, and $C_{1-4}$alkyl optionally substituted with one —$NR^{10a}R^{10b}$;

$R^{10a}$ and $R^{10b}$ each independently represent hydrogen or $C_{1-4}$alkyl;

Het represents a bicyclic aromatic heterocyclic ring system selected from the group consisting of (a-1), (a-2) and (a-3);

$R^{3a}$, $R^{3b}$ and $R^{3c}$ each independently represent hydrogen, halo, —$NR^{7a}R^{7b}$, or —O—$C_{1-4}$alkyl;

$R^{7a}$ represents hydrogen;

$R^{7b}$ represents hydrogen or $C_{1-4}$alkyl;

$R^{4a}$, $R^{4b}$, $R^{4c}$ each independently represent hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents $CR^{6a}$;

$Q^2$ represents $CR^{6b}$;

$Q^3$ represents $CR^{6c}$;

$Q^4$ represents $CR^{6d}$;

$R^{6a}$, $R^{6b}$, $R^{6c}$, $R^{6d}$, $R^{6e}$ and $R^{6f}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

Y represents —O—, or —$CH_2$—;

Z represents —$CH_2$—, —X—$CR^{5a}R^{5b}$—, —$CR^{5c}$═$CR^{5d}$—, —$CR^{5e}R^{5g}$—$CR^{5f}R^{5h}$—, or —C≡C—;

and when Y represents —$CH_2$—, then Z can also represent —O— or —$CR^{5a}R^{5b}$—X—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

$R^{11}$ represents hydrogen or $C_{1-4}$alkyl;

Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one substituent selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, —C(═O)—$C_{1-4}$alkyl, $C_{1-4}$alkyloxy, and $C_{1-4}$alkyl optionally substituted with one —$NR^{10a}R^{10b}$;

$R^{10a}$ and $R^{10b}$ each independently represent hydrogen or $C_{1-4}$alkyl;

Het represents a bicyclic aromatic heterocyclic ring system selected from the group consisting of (a-1), (a-2) and (a-3);

$R^{3a}$, $R^{3b}$ and $R^{3c}$ represent —$NR^{7a}R^{7b}$;

$R^{7a}$ represents hydrogen;

$R^{7b}$ represents hydrogen;

$R^{4a}$, $R^{4b}$ and $R^{4c}$ each independently represent hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents $CR^{6a}$;

$Q^2$ represents $CR^{6b}$;

$Q^3$ represents $CR^{6c}$;

$Q^4$ represents $CR^{6d}$;

$R^{6a}$, $R^{6b}$, $R^{6c}$, $R^{6d}$, $R^{6e}$ and $R^{6f}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl; in particular $R^1$ and $R^2$ represent hydrogen;

Y represents —O— or —$CH_2$—;

Z represents —$CH_2$—, —X—$CR^{5a}R^{5b}$—, —$CR^{5c}$═$CR^{5d}$—, —$CR^{5e}R^{5g}$—$CR^{5f}R^{5h}$—, or —C≡C—;

and when Y represents —$CH_2$—, then Z can also represent —$CR^{5a}R^{5b}$—X—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

$R^{11}$ represents hydrogen or $C_{1-4}$alkyl;

Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one, two or three substituents each independently selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, $C_{1-4}$alkyloxy, and $C_{1-4}$alkyl;

Het represents a bicyclic aromatic heterocyclic ring system selected from the group consisting of (a-1) and (a-2);

$R^{3a}$ and $R^{3c}$ each independently represent halo, —$NR^{7a}R^{7b}$, or —O—$C_{1-4}$alkyl;

$R^{7a}$ represents hydrogen;

$R^{7b}$ represents hydrogen;

$R^{4a}$, and $R^{4c}$ each independently represent hydrogen, halo, or $C_{1-4}$alkyl;

$Q^1$ represents $CR^{6a}$;

$Q^2$ represents $CR^{6b}$;

$R^{6a}$, $R^{6b}$, $R^{6e}$ and $R^{6f}$ each independently represent hydrogen, halogen, or $C_{1-4}$alkyl;

and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl; in particular $R^1$ and $R^2$ represent hydrogen;

Y represents —O— or —$CH_2$—;

Z represents —$CH_2$—, —X—$CR^{5a}R^{5b}$—, —$CR^{5c}$═$CR^{5d}$—, —$CR^{5e}R^{5g}$—$CR^{5f}R^{5h}$—, or —C≡C—;

and when Y represents —$CH_2$—, then Z can also represent —$CR^{5a}R^{5b}$—X—;

$R^{5a}$, $R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

$R^{11}$ represents hydrogen or $C_{1-4}$alkyl;

Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one, two or three substituents each independently selected from the group consisting of halo, —OH, —$NH_2$, —NH—$C_{1-4}$alkyl, —N($C_{1-4}$alkyl)$_2$, —$NHR^{10d}$, cyano, —$CF_3$, —C(═O)—NH—$C_{1-4}$alkyl, $C_{1-4}$alkyloxy, and $C_{1-4}$alkyl;

$R^{10d}$ represents $C_{1-4}$alkyl substituted with one, two or three halo substituents; or $C_{1-4}$alkyl substituted with one $C_{3-6}$cycloalkyl;

Het represents a bicyclic aromatic heterocyclic ring system selected from the group consisting of (a-1) and (a-2);

$R^{3a}$ and $R^{3c}$ each independently represent hydrogen, halo, —$NR^{7a}R^{7b}$, or —O—$C_{1-4}$alkyl;

$R^{7a}$ represents hydrogen;

$R^{7b}$ represents hydrogen or $C_{1-4}$alkyl;

$R^{4a}$, and $R^{4c}$ each independently represent hydrogen, halo, or $C_{1-4}$alkyl;

$Q^1$ represents $CR^{6a}$;

$Q^2$ represents $CR^{6b}$;

$R^{6a}$, $R^{6b}$, $R^{6e}$ and $R^{6f}$ each independently represent hydrogen, halogen, or $C_{1-4}$alkyl;

and pharmaceutically acceptable addition salts, and solvates thereof.

Another embodiment of the present invention relates to those compounds of Formula (I), and pharmaceutically acceptable addition salts, and solvates thereof, or any subgroup thereof as mentioned in any of the other embodiments, wherein one or more of the following restrictions apply:

(i) $R^1$ and $R^2$ represent hydrogen;

(ii) Y represents —O— or —$CH_2$—; in particular Y represents —O—;

(iii) Z represents —$CH_2$—, —X—$CR^{5a}R^{5b}$—, —$CR^{5c}$═$CR^{5d}$—, —$CR^{5e}R^{5g}$—$CR^{5f}R^{5h}$—, or —C≡C—; and when Y represents —$CH_2$—, then Z can also represent —$CR^{5a}R^{5b}$—X—;

(iv) $R^{5a}$, $R^{5b}$, $R^{5c}$, $R^{5d}$, $R^{5e}$, $R^{5f}$, $R^{5g}$, and $R^{5h}$ represent hydrogen;

(v) X represents —O—;

(vi) $R^{11}$ represents hydrogen or $C_{1-4}$alkyl;

(vii) Ar is optionally substituted with one, two or three substituents, in particular one substituent, each independently selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, $C_{1-4}$alkyloxy, and $C_{1-4}$alkyl;

(viii) Het represents a bicyclic aromatic heterocyclic ring system selected from the group consisting of (a-1) and (a-2);

(ix) $R^{3a}$ and $R^{3c}$ each independently represent halo, —$NR^{7a}R^{7b}$, or —O—$C_{1-4}$alkyl;

(x) $R^{7a}$ and $R^{7b}$ represent hydrogen;

(xi) $R^{4a}$, and $R^{4c}$ each independently represent hydrogen, halo, or $C_{1-4}$alkyl;

(xii) $Q^1$ represents $CR^{6a}$;

(xiii) $Q^2$ represents $CR^{6b}$;

(xiv) $R^{6a}$, $R^{6b}$, $R^{6e}$ and $R^{6f}$ each independently represent hydrogen, halogen, or $C_{1-4}$alkyl.

In an embodiment, the present invention concerns novel compounds of Formula (I), wherein $R^1$ represents hydrogen;

$R^2$ represents hydrogen;

Y represents —O— or —$CH_2$—;

Z represents —X—$CR^{5a}R^{5b}$— or —$CR^{5e}R^{5g}$—$CR^{5f}R^{5h}$—;

and when Y represents —$CH_2$—, then Z can also represent —$CR^{5a}R^{5b}$—X—;

$R^{5a}$, $R^{5b}$, $R^{5e}$, $R^{5f}$, $R^{5g}$, and $R^{5h}$ represent hydrogen;

X represents —O—;

Ar represents

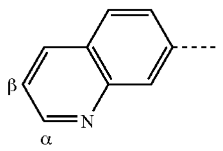

wherein Ar is optionally substituted in the position indicated by α with a substituent selected from the group consisting of —$NH_2$, —NH—$C_{1-4}$alkyl, and —$NHR^{10d}$; and wherein Ar is optionally substituted in the position indicated by β with a substituent selected from the group consisting of halo and $CF_3$;

provided however that Ar is substituted in at least one of the positions indicated by α or β;

$R^{10d}$ represents $C_{3-6}$cycloalkyl; $C_{1-4}$alkyl substituted with one, two or three halo substituents; or $C_{1-4}$alkyl substituted with one $C_{3-6}$cycloalkyl substituent;

Het represents a bicyclic aromatic heterocyclic ring system selected from the group consisting of (a-1) and (a-4);

$R^{3a}$ and $R^{3d}$ each independently represent hydrogen, halo, —$NR^{7a}R^{7b}$, $C_{1-4}$alkyl, or —O—$C_{1-4}$alkyl;

$R^{7a}$ represents hydrogen;

$R^{7b}$ represents hydrogen or $C_{1-4}$alkyl;

$R^{4a}$, $R^{4d}$ and $R^{4f}$ each independently represent hydrogen or halo;

$Q^1$ represents $CR^{6a}$;

$Q^2$ represents $CR^{6b}$;

$Q^8$ represents $CR^{6g}$;

$Q^9$ represents $CR^{6h}$;

$Q^5$ represents $CR^{3d}$; $Q^6$ represents N; and $Q^7$ represents $CR^{4f}$;

$R^{6a}$, $R^{6b}$, $R^{6g}$, and $R^{6h}$ represent hydrogen;

and pharmaceutically acceptable addition salts, and solvates thereof.

Another embodiment of the present invention relates to those compounds of Formula (I), and pharmaceutically acceptable addition salts, and solvates thereof, or any subgroup thereof as mentioned in any of the other embodiments, wherein one or more of the following restrictions apply:

(i) $R^1$ and $R^2$ represent hydrogen;

(ii) Y represents —O— or —$CH_2$—;

(iii) Z represents —X—$CR^{5a}R^{5b}$— or —$CR^{5e}R^{5g}$—$CR^{5f}R^{5h}$—;

and when Y represents —$CH_2$—, then Z can also represent —$CR^{5a}R^{5b}$—X—;

(iv) $R^{5a}$, $R^{5b}$, $R^{5e}$, $R^{5f}$, $R^{5g}$, and $R^{5h}$ represent hydrogen;

(v) X represents —O—;

(vi) Ar represents

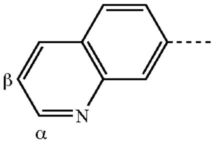

wherein Ar is optionally substituted in the position indicated by α with a substituent selected from the group consisting of —$NH_2$, —NH—$C_{1-4}$alkyl, and —$NHR^{10d}$; and wherein Ar is optionally substituted in the position indicated by β with a substituent selected from the group consisting of halo and $CF_3$;

provided however that Ar is substituted in at least one of the positions indicated by α or β;

(vii) $R^{10d}$ represents $C_{3-6}$cycloalkyl; $C_{1-4}$alkyl substituted with one, two or three halo substituents; or $C_{1-4}$alkyl substituted with one $C_{3-6}$cycloalkyl substituent;

(viii) Het represents a bicyclic aromatic heterocyclic ring system selected from the group consisting of (a-1) and (a-4);

(ix) $R^{3a}$ and $R^{3d}$ each independently represent hydrogen, halo, —$NR^{7a}R^{7b}$, $C_{1-4}$alkyl, or —O—$C_{1-4}$alkyl;

(x) $R^{7a}$ represents hydrogen;

(xi) $R^{7b}$ represents hydrogen or $C_{1-4}$alkyl;

(xii) $R^{4a}$, $R^{4d}$ and $R^{4f}$ each independently represent hydrogen or halo;

(xiii) $Q^1$ represents $CR^{6a}$;

(xiv) $Q^2$ represents $CR^{6b}$;

(xv) $Q^8$ represents $CR^{6g}$;

(xvi) $Q^9$ represents $CR^{6h}$;

(xvii) $Q^5$ represents $CR^{3d}$; $Q^6$ represents N; and $Q^7$ represents $CR^{4f}$;

(xviii) $R^{6a}$, $R^{6b}$, $R^{6g}$, and $R^{6h}$ represent hydrogen.

In an embodiment, the present invention concerns novel compounds of Formula (I), wherein $R^1$ represents hydrogen;

$R^2$ represents hydrogen;

Y represents —O— or —$CH_2$—;

Z represents —X—$CR^{5a}R^{5b}$— or —$CR^{5e}R^{5g}$—$CR^{5f}R^{5h}$—;

and when Y represents —$CH_2$—, then Z can also represent —$CR^{5a}R^{5b}$—X—;

$R^{5a}$, $R^{5b}$, $R^{5e}$, $R^{5f}$, $R^{5g}$, and $R^{5h}$ represent hydrogen;

X represents —O—;

Ar represents

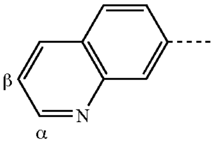

wherein Ar is optionally substituted in the position indicated by α with a substituent selected from the group consisting of —$NH_2$, —NH—$C_{1-4}$alkyl, and —$NHR^{10d}$; and wherein Ar is optionally substituted in the position indicated by β with a substituent selected from the group consisting of halo and $CF_3$;

provided however that Ar is substituted in at least one of the positions indicated by α or β;

$R^{10d}$ represents $C_{3-6}$cycloalkyl; $C_{1-4}$alkyl substituted with one, two or three halo substituents; or $C_{1-4}$alkyl substituted with one $C_{3-6}$cycloalkyl substituent;

Het represents a bicyclic aromatic heterocyclic ring system selected from the group consisting of (a-1);

$R^{3a}$ represents hydrogen, halo, —$NR^{7a}R^{7b}$, $C_{1-4}$alkyl, or —O—$C_{1-4}$alkyl;

$R^{7a}$ represents hydrogen;

$R^{7b}$ represents hydrogen or $C_{1-4}$alkyl;

$R^{4a}$ represents hydrogen or halo;

$Q^1$ represents $CR^{6a}$;

$Q^2$ represents $CR^{6b}$;

$R^{6a}$ and $R^{6b}$ represent hydrogen;

and pharmaceutically acceptable addition salts, and solvates thereof.

In an embodiment, the present invention concerns novel compounds of Formula (I), wherein $R^1$ represents hydrogen;

$R^2$ represents hydrogen;

Y represents —O— or —$CH_2$—;

Z represents —X—$CR^{5a}R^{5b}$— or —$CR^{5e}R^{5g}$—$CR^{5f}R^{5h}$—;

$R^{5a}$, $R^{5b}$, $R^{5e}$, $R^{5f}$, $R^{5g}$, and $R^{5h}$ represent hydrogen;

X represents —O—;

Ar represents

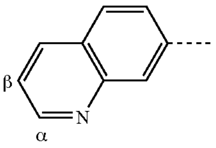

wherein Ar is optionally substituted in the position indicated by α with a substituent selected from the group consisting of —$NH_2$, —NH—$C_{1-4}$alkyl, and —$NHR^{10d}$; and wherein Ar is optionally substituted in the position indicated by β with a substituent selected from the group consisting of halo and $CF_3$;

provided however that Ar is substituted in at least one of the positions indicated by α or β;

$R^{10d}$ represents $C_{3-6}$cycloalkyl; $C_{1-4}$alkyl substituted with one, two or three halo substituents; or $C_{1-4}$alkyl substituted with one $C_{3-6}$cycloalkyl substituent;

Het represents a bicyclic aromatic heterocyclic ring system selected from the group consisting of (a-1);

$R^{3a}$ represents hydrogen, halo, —$NR^{7a}R^{7b}$, $C_{1-4}$alkyl, or —O—$C_{1-4}$alkyl;

$R^{7a}$ represents hydrogen;

$R^{7b}$ represents hydrogen or $C_{1-4}$alkyl;

$R^{4a}$ represents hydrogen or halo;

$Q^1$ represents $CR^{6a}$;

$Q^2$ represents $CR^{6b}$;

$R^{6a}$ and $R^{6b}$ represent hydrogen;

and pharmaceutically acceptable addition salts, and solvates thereof.

In an embodiment, the present invention concerns novel compounds of Formula (I), wherein $R^1$ represents hydrogen;

$R^2$ represents hydrogen;

Y represents —O— or —$CH_2$—;

Z represents —X—$CR^{5a}R^{5b}$— or —$CR^{5e}R^{5g}$—$CR^{5f}R^{5h}$—;

and when Y represents —$CH_2$—, then Z can also represent —$CR^{5a}R^{5b}$—X—;

$R^{5a}$, $R^{5b}$, $R^{5e}$, $R^{5f}$, $R^{5g}$, and $R^{5h}$ represent hydrogen;

X represents —O—;

Ar represents

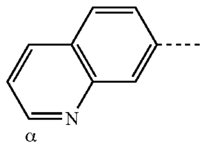

wherein Ar is substituted in the position indicated by α with a substituent selected from the group consisting of —$NH_2$, —NH—$C_{1-4}$alkyl, and —$NHR^{10d}$;

$R^{10d}$ represents $C_{3-6}$cycloalkyl; or $C_{1-4}$alkyl substituted with one substituent selected from the group consisting of $C_{3-6}$cycloalkyl, and $R^{14}$;

$R^{14}$ represents phenyl optionally substituted with one, two or three substituents each independently selected from the group consisting of halo;

Het represents the bicyclic aromatic heterocyclic ring system (a-1);

$R^{3a}$ represents hydrogen, halo, —$NR^{7a}R^{7b}$, or $C_{1-4}$alkyl;

$R^{7a}$ represents hydrogen;

$R^{7b}$ represents hydrogen or $C_{1-4}$alkyl;

$R^{4a}$ represents hydrogen;

$Q^1$ represents $CR^{6a}$;

$Q^2$ represents $CR^{6b}$;

$R^{6a}$ and $R^{6b}$ represent hydrogen;

and pharmaceutically acceptable addition salts, and solvates thereof.

In an embodiment, the present invention concerns novel compounds of Formula (I), wherein $R^1$ represents hydrogen;

$R^2$ represents hydrogen;

Y represents —O— or —$CH_2$—;

Z represents —X—$CR^{5a}R^{5b}$— or —$CR^{5e}R^{5g}$—$CR^{5f}R^{5h}$—;

and when Y represents —$CH_2$—, then Z can also represent —$CR^{5a}R^{5b}$—X—;

$R^{5a}$, $R^{5b}$, $R^{5e}$, $R^{5f}$, $R^{5g}$, and $R^{5h}$ represent hydrogen;

X represents —O—;

Ar represents

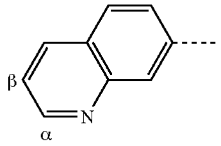

wherein Ar is optionally substituted in the position indicated by α with —$NH_2$; and wherein Ar is substituted in the position indicated by β with a substituent selected from the group consisting of halo and $CF_3$;

Het represents the bicyclic aromatic heterocyclic ring system (a-1);

$R^{3a}$ represents hydrogen, halo, —$NR^{7a}R^{7b}$, or $C_{1-4}$alkyl;

$R^{7a}$ represents hydrogen;

$R^{7b}$ represents hydrogen or $C_{1-4}$alkyl;

$R^{4a}$ represents hydrogen;

$Q^1$ represents $CR^{6a}$;

$Q^2$ represents $CR^{6b}$;

$R^{6a}$ and $R^{6b}$ represent hydrogen;

and pharmaceutically acceptable addition salts, and solvates thereof.

In an embodiment, the present invention concerns novel compounds of Formula (I), wherein $R^1$ represents hydrogen;

$R^2$ represents hydrogen;

Y represents —O— or —$CH_2$—;

Z represents —X—$CR^{5a}R^{5b}$— or —$CR^{5e}R^{5g}$—$CR^{5f}R^{5h}$—;

and when Y represents —$CH_2$—, then Z can also represent —$CR^{5a}R^{5b}$—X—;

$R^{5a}$, $R^{5b}$, $R^{5e}$, $R^{5f}$, $R^{5g}$, and $R^{5h}$ represent hydrogen;

X represents —O—;

Ar represents

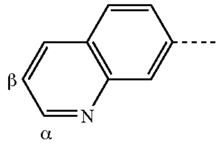

wherein Ar is substituted in the position indicated by α with —$NH_2$; and wherein Ar is substituted in the position indicated by β with a substituent selected from the group consisting of halo and $CF_3$;

Het represents the bicyclic aromatic heterocyclic ring system (a-1);

$R^{3a}$ represents hydrogen, halo, —$NR^{7a}R^{7b}$, or $C_{1-4}$alkyl;

$R^{7a}$ represents hydrogen;

$R^{7b}$ represents hydrogen or $C_{1-4}$alkyl;

$R^{4a}$ represents hydrogen;

$Q^1$ represents $CR^{6a}$;

$Q^2$ represents $CR^{6b}$;

$R^{6a}$ and $R^{6b}$ represent hydrogen;

and pharmaceutically acceptable addition salts, and solvates thereof.

In an embodiment, the present invention concerns novel compounds of Formula (I), wherein $R^1$ represents hydrogen;

$R^2$ represents hydrogen;

Y represents —O— or —$CH_2$—;

Z represents —X—$CR^{5a}R^{5b}$— or —$CR^{5e}R^{5g}$—$CR^{5f}R^{5h}$—;

and when Y represents —$CH_2$—, then Z can also represent —$CR^{5a}R^{5b}$—X—;

$R^{5a}$, $R^{5b}$, $R^{5e}$, $R^{5f}$, $R^{5g}$, and $R^{5h}$ represent hydrogen;

X represents —O—;

Ar represents

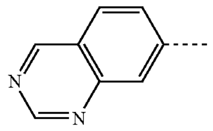

Het represents the bicyclic aromatic heterocyclic ring system (a-1);

$R^{3a}$ represents hydrogen, halo, —$NR^{7a}R^{7b}$, or $C_{1-4}$alkyl;

$R^{7a}$ represents hydrogen;

$R^{7b}$ represents hydrogen or $C_{1-4}$alkyl;

$R^{4a}$ represents hydrogen;

$Q^1$ represents $CR^{6a}$;

$Q^2$ represents $CR^{6b}$;

$R^{6a}$ and $R^{6b}$ represent hydrogen;

and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

in particular $R^1$ and $R^2$ represent hydrogen;

Y represents —$CH_2$— or —O—;

Z represents —X—$CR^{5a}R^{5b}$— or —$CH_2CH_2$—;

$R^{5a}$ and $R^{5b}$ each independently represent hydrogen or $C_{1-4}$alkyl;

X represents —O—, —S—, or —$NR^{11}$—;

$R^{11}$ represents hydrogen;

Ar represents a 10-membered bicyclic aromatic ring system consisting of two fused 6-membered rings, wherein 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one or two substituents each independently selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, —C(═O)—$C_{1-4}$alkyl, $C_{1-4}$alkyloxy, and $C_{1-4}$alkyl optionally substituted with one —$NR^{10a}R^{10b}$;

$R^{10a}$ and $R^{10b}$ each independently represent hydrogen or $C_{1-4}$alkyl;

Het represents a bicyclic aromatic heterocyclic ring system selected from the group consisting of (a-1);

$R^{3a}$ represents hydrogen, halo, —$NR^{7a}R^{7b}$, or —O—$C_{1-4}$alkyl;

$R^{7a}$ represents hydrogen;

$R^{7b}$ represents hydrogen;

$R^{4a}$ represents hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents $CR^{6a}$;

$Q^2$ represents $CR^{6b}$;

$R^{6a}$ and $R^{6b}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen;

$R^2$ represents hydrogen;

Y represents —$CH_2$—;

Z represents —$CR^{5e}R^{5g}$—$CR^{5f}R^{5h}$—;

$R^{5e}$, $R^{5f}$, $R^{5g}$, and $R^{5h}$ represent hydrogen;

Ar represents any one of the following 10-membered bicyclic aromatic ring systems:

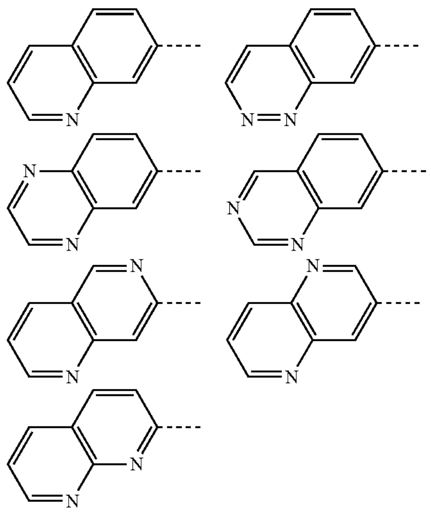

Ar is optionally substituted with one, two, three or four substituents each independently selected from the group consisting of halo, —$NH_2$, —NH—$C_{1-4}$alkyl, —N($C_{1-4}$alkyl)$_2$, —$NHR^{10d}$, —$NR^{10c}R^{10d}$;

$R^{10c}$ and $R^{10d}$ each independently represent $C_{3-6}$cycloalkyl; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one $C_{3-6}$cycloalkyl substituent;

Het represents a bicyclic aromatic heterocyclic ring system selected from the group consisting of (a-1);

$R^{3a}$ represents hydrogen, —$NR^{7a}R^{7b}$, or —O—$C_{1-4}$alkyl;

$R^{7a}$ represents hydrogen;

$R^{7b}$ represents hydrogen or $C_{1-4}$alkyl;

$R^{4a}$ represents hydrogen;

$Q^1$ represents $CR^{6a}$;

$Q^2$ represents $CR^{6b}$;

$R^{6a}$ and $R^{6b}$ represent hydrogen;

and pharmaceutically acceptable addition salts, and solvates thereof.

In an embodiment, the present invention concerns novel compounds of Formula (I), wherein $R^1$ represents hydrogen;

$R^2$ represents hydrogen;

Y represents —$CH_2$—;

Z represents —$CR^{5e}R^{5g}$—$CR^{5f}R^{5h}$—;

$R^{5e}$, $R^{5f}$, $R^{5g}$, and $R^{5h}$ represent hydrogen;

Ar represents

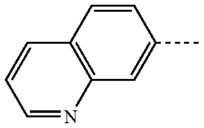

Ar is optionally substituted with one, two, three or four substituents each independently selected from the group consisting of halo, —$NH_2$, —NH—$C_{1-4}$alkyl, —N($C_{1-4}$alkyl)$_2$, —$NHR^{10d}$;

$R^{10d}$ represents $C_{1-4}$alkyl substituted with one, two or three halo substituents; or $C_{1-4}$alkyl substituted with one $C_{3-6}$cycloalkyl substituent;

Het represents a bicyclic aromatic heterocyclic ring system selected from the group consisting of (a-1);

$R^{3a}$ represents hydrogen, —$NR^{7a}R^{7b}$, or —O—$C_{1-4}$alkyl;

$R^{7a}$ represents hydrogen;

$R^{7b}$ represents hydrogen or $C_{1-4}$alkyl;

$R^{4a}$ represents hydrogen;

$Q^1$ represents $CR^{6a}$;

$Q^2$ represents $CR^{6b}$;

$R^{6a}$ and $R^{6b}$ represent hydrogen;

and pharmaceutically acceptable addition salts, and solvates thereof.

Another embodiment of the present invention relates to those compounds of Formula (I), and pharmaceutically acceptable addition salts, and solvates thereof, or any subgroup thereof as mentioned in any of the other embodiments, wherein one or more of the following restrictions apply:

(i) $R^1$ represents hydrogen;

$R^2$ represents hydrogen;

(ii) Y represents —$CH_2$—;

(iii) Z represents —$CR^{5e}R^{5g}$—$CR^{5f}R^{5h}$—;

(iv) $R^{5e}$, $R^{5f}$, $R^{5g}$, and $R^{5h}$ represent hydrogen;

(v) Ar represents

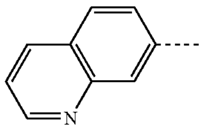

Ar is optionally substituted with one, two, three or four substituents each independently selected from the group consisting of halo, —$NH_2$, —NH—$C_{1-4}$alkyl, —N($C_{1-4}$alkyl)$_2$, —$NHR^{10d}$;

(vi) $R^{10d}$ represents $C_{1-4}$alkyl substituted with one, two or three halo substituents; or $C_{1-4}$alkyl substituted with one $C_{3-6}$cycloalkyl substituent;

(vii) Het represents a bicyclic aromatic heterocyclic ring system selected from the group consisting of (a-1);

(viii) $R^{3a}$ represents hydrogen, —$NR^{7a}R^{7b}$, or —O—$C_{1-4}$alkyl;

(ix) $R^{7a}$ represents hydrogen;

$R^{7b}$ represents hydrogen or $C_{1-4}$alkyl;

(x) $R^{4a}$ represents hydrogen;

(xi) $Q^1$ represents $CR^{6a}$;

$Q^2$ represents $CR^{6b}$;

(xii) $R^{6a}$ and $R^{6b}$ represent hydrogen.

Another embodiment of the present invention relates to those compounds of Formula (I), and pharmaceutically acceptable addition salts, and solvates thereof, or any subgroup thereof as mentioned in any of the other embodiments, wherein one or more of the following restrictions apply:

(i) $R^1$ represents hydrogen or —C(=O)—$C_{1-4}$alkyl;

$R^2$ represents hydrogen or —C(=O)—$C_{1-4}$alkyl;

in particular $R^1$ and $R^2$ represent hydrogen;

(ii) Y represents —$CH_2$— or —O—;

(iii) Z represents —X—$CR^{5a}R^{5b}$— or —$CH_2CH_2$—;

(iv) $R^{5a}$ and $R^{5b}$ each independently represent hydrogen or $C_{1-4}$alkyl;

(v) X represents —O—, —S—, or —$NR^{11}$—;

(vi) $R^{11}$ represents hydrogen;

(vii) Ar is optionally substituted with one or two substituents each independently selected from the group consisting of halo, —OH, —$NH_2$, —NH—$C_{1-4}$alkyl, —N($C_{1-4}$alkyl)$_2$, cyano, —$CF_3$, —C(=O)—NH—$C_{1-4}$alkyl, —C(=O)—$C_{1-4}$alkyl, $C_{1-4}$alkyloxy, and $C_{1-4}$alkyl optionally substituted with one —$NR^{10a}R^{10b}$;

(viii) $R^{10a}$ and $R^{10b}$ each independently represent hydrogen or $C_{1-4}$alkyl;

(ix) Het represents a bicyclic aromatic heterocyclic ring system selected from the group consisting of (a-1);

(x) $R^{3a}$ represents hydrogen, halo, —$NR^{7a}R^{7b}$, or —O—$C_{1-4}$alkyl;

(xi) $R^{7a}$ represents hydrogen;

$R^{7b}$ represents hydrogen;

(xii) $R^{4a}$ represents hydrogen, halo, —$NR^{8a}R^{8b}$, or $C_{1-4}$alkyl;

(xiii) $R^{8a}$ and $R^{8b}$ each independently represent hydrogen or $C_{1-4}$alkyl;

(xiv) $Q^1$ represents $CR^{6a}$;

(xv) $Q^2$ represents $CR^{6b}$;

(xvi) $R^{6a}$ and $R^{6b}$ each independently represent hydrogen, halogen, $C_{1-4}$alkyl, —$NR^{9a}R^{9b}$, or $C_{1-4}$alkyl substituted with one, two or three halo atoms;

(xvii) $R^{9a}$ and $R^{9b}$ each independently represent hydrogen or $C_{1-4}$alkyl.

In an embodiment, the present invention concerns novel compounds of Formula (I), wherein $R^1$ represents hydrogen or —C(=O)—$C_{1-4}$alkyl;

$R^2$ represents hydrogen or —C(=O)—$C_{1-4}$alkyl;

in particular $R^1$ and $R^2$ represent hydrogen;

Y represents —O—;

Z represents —X—$CR^{5a}R^{5b}$—;

$R^{5a}$ and $R^{5b}$ each independently represent hydrogen or $C_{1-4}$alkyl;

X represents —O—, —S—, or —$NR^{11}$—;

$R^{11}$ represents hydrogen;

Ar represents a 10-membered bicyclic aromatic ring system consisting of two fused 6-membered rings, wherein 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one or two substituents each independently selected from the group consisting of halo, —OH, —$NH_2$, —NH—$C_{1-4}$alkyl, —N($C_{1-4}$alkyl)$_2$, cyano, —$CF_3$, —C(=O)—NH—

$C_{1-4}$alkyl, —C(═O)—$C_{1-4}$alkyl, $C_{1-4}$alkyloxy, and $C_{1-4}$alkyl optionally substituted with one —$NR^{10a}R^{10b}$;

$R^{10a}$ and $R^{10b}$ each independently represent hydrogen or $C_{1-4}$alkyl;

Het represents a bicyclic aromatic heterocyclic ring system selected from the group consisting of (a-1);

$R^{3a}$ represents hydrogen, halo, —$NR^{7a}R^{7b}$, or —O—$C_{1-4}$alkyl;

$R^{7a}$ represents hydrogen;

$R^{7b}$ represents hydrogen;

$R^{4a}$ represents hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents $CR^{6a}$;

$Q^2$ represents $CR^{6b}$;

$R^{6a}$ and $R^{6b}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

Another embodiment of the present invention relates to those compounds of Formula (I), and pharmaceutically acceptable addition salts, and solvates thereof, or any subgroup thereof as mentioned in any of the other embodiments, wherein one or more of the following restrictions apply:

(i) $R^1$ represents hydrogen or —C(═O)—$C_{1-4}$alkyl;

$R^2$ represents hydrogen or —C(═O)—$C_{1-4}$alkyl;

in particular $R^1$ and $R^2$ represent hydrogen;

(ii) Y represents —O—;

(iii) Z represents —X—$CR^{5a}R^{5b}$—;

(iv) $R^{5a}$ and $R^{5b}$ each independently represent hydrogen or $C_{1-4}$alkyl;

(v) X represents —O—, —S—, or —$NR^{11}$—;

(vi) $R^{11}$ represents hydrogen;

(vii) Ar is optionally substituted with one or two substituents each independently selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, —C(═O)—$C_{1-4}$alkyl, $C_{1-4}$alkyloxy, and $C_{1-4}$alkyl optionally substituted with one —$NR^{10a}R^{10b}$;

(viii) $R^{10a}$ and $R^{10b}$ each independently represent hydrogen or $C_{1-4}$alkyl;

(ix) Het represents a bicyclic aromatic heterocyclic ring system selected from the group consisting of (a-1);

(x) $R^{3a}$ represents hydrogen, halo, —$NR^{7a}R^{7b}$, or —O—$C_{1-4}$alkyl;

(xi) $R^{7a}$ represents hydrogen;

$R^{7b}$ represents hydrogen;

(xii) $R^{4a}$ represents hydrogen, halo, —$NR^{8a}R^{8b}$, or $C_{1-4}$alkyl;

(xiii) $R^{8a}$ and $R^{8b}$ each independently represent hydrogen or $C_{1-4}$alkyl;

(xiv) $Q^1$ represents $CR^{6a}$;

(xv) $Q^2$ represents $CR^{6b}$;

(xvi) $R^{6a}$ and $R^{6b}$ each independently represent hydrogen, halogen, $C_{1-4}$alkyl, —$NR^{9a}R^{9b}$, or $C_{1-4}$alkyl substituted with one, two or three halo atoms;

(xvii) $R^{9a}$ and $R^{9b}$ each independently represent hydrogen or $C_{1-4}$alkyl.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

in particular $R^1$ and $R^2$ represent hydrogen;

Y represents —$CH_2$— or —O—;

Z represents —X—$CR^{5a}R^{5b}$— or —$CH_2CH_2$—

$R^{5a}$ and $R^{5b}$ each independently represent hydrogen or $C_{1-4}$alkyl;

X represents —O—, —S—, or —$NR^{11}$—;

$R^{11}$ represents hydrogen;

Ar represents

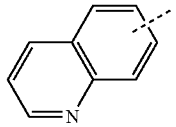

;

in particular Ar represents

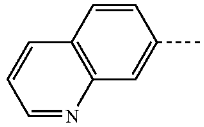

;

Ar is optionally substituted with one or two substituents each independently selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, —C(═O)—$C_{1-4}$alkyl, $C_{1-4}$alkyloxy, and $C_{1-4}$alkyl optionally substituted with one —$NR^{10a}R^{10b}$;

$R^{10a}$ and $R^{10b}$ each independently represent hydrogen or $C_{1-4}$alkyl;

Het represents a bicyclic aromatic heterocyclic ring system selected from the group consisting of (a-1);

$R^{3a}$ represents hydrogen, halo, —$NR^{7a}R^{7b}$, or —O—$C_{1-4}$alkyl;

$R^{7a}$ represents hydrogen;

$R^{7b}$ represents hydrogen;

$R^{4a}$ represents hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents $CR^{6a}$;

$Q^2$ represents $CR^{6b}$;

$R^{6a}$ and $R^{6b}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

in particular $R^1$ and $R^2$ represent hydrogen;

Y represents —O—;

Z represents —X—$CR^{5a}R^{5b}$—;

$R^{5a}$ and $R^{5b}$ each independently represent hydrogen or $C_{1-4}$alkyl;

X represents —O—, —S—, or —$NR^{11}$—;

$R^{11}$ represents hydrogen;

Ar represents

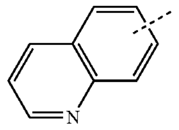

;

in particular Ar represents

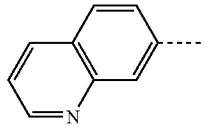

;

Ar is optionally substituted with one or two substituents each independently selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, —C(═O)—$C_{1-4}$alkyl, $C_{1-4}$alkyloxy, and $C_{1-4}$alkyl optionally substituted with one —$NR^{10a}R^{10b}$;

$R^{10a}$ and $R^{10b}$ each independently represent hydrogen or $C_{1-4}$alkyl;

Het represents a bicyclic aromatic heterocyclic ring system selected from the group consisting of (a-1);

$R^{3a}$ represents hydrogen, halo, —$NR^{7a}R^{7b}$, or —O—$C_{1-4}$alkyl;

$R^{7a}$ represents hydrogen;

$R^{7b}$ represents hydrogen;

$R^{4a}$ represents hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents $CR^{6a}$;

$Q^2$ represents $CR^{6b}$;

$R^{6a}$ and $R^{6b}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl;

and pharmaceutically acceptable addition salts, and solvates thereof.

Another embodiment of the present invention relates to those compounds of Formula (I), and pharmaceutically acceptable addition salts, and solvates thereof, or any subgroup thereof as mentioned in any of the other embodiments, wherein one or more of the following restrictions apply:

(i) $R^1$ represents hydrogen or —C(═O)—$C_{1-4}$alkyl;

$R^2$ represents hydrogen or —C(═O)—$C_{1-4}$alkyl;

in particular $R^1$ and $R^2$ represent hydrogen;

(ii) Y represents —O—;

(iii) Z represents —X—$CR^{5a}R^{5b}$—;

(iv) $R^{5a}$ and $R^{5b}$ each independently represent hydrogen or $C_{1-4}$alkyl;

(v) X represents —O—, —S—, or —$NR^{11}$—;

(vi) $R^{11}$ represents hydrogen;

(vii) Ar represents

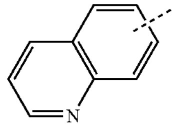

;

in particular Ar represents

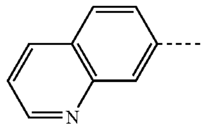

;

(viii) Ar is optionally substituted with one or two substituents each independently selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, —C(═O)—$C_{1-4}$alkyl, $C_{1-4}$alkyloxy, and $C_{1-4}$alkyl optionally substituted with one —$NR^{10a}R^{10b}$;

(ix) $R^{10a}$ and $R^{10b}$ each independently represent hydrogen or $C_{1-4}$alkyl;

(x) Het represents a bicyclic aromatic heterocyclic ring system selected from the group consisting of (a-1);

(xi) $R^{3a}$ represents hydrogen, halo, —$NR^{7a}R^{7b}$, or —O—$C_{1-4}$alkyl;

(xii) $R^{7a}$ represents hydrogen;

$R^{7b}$ represents hydrogen;

(xiii) $R^{4a}$ represents hydrogen, halo, —$NR^{8a}R^{8b}$, or $C_{1-4}$alkyl;

(xiv) $R^{8a}$ and $R^{8b}$ each independently represent hydrogen or $C_{1-4}$alkyl;

(xv) $Q^1$ represents $CR^{6a}$;

(xvi) $Q^2$ represents $CR^{6b}$;

(xvii) $R^{6a}$ and $R^{6b}$ each independently represent hydrogen, halogen, $C_{1-4}$alkyl, —$NR^{9a}R^{9b}$, or $C_{1-4}$alkyl substituted with one, two or three halo atoms;

(xviii) $R^{9a}$ and $R^{9b}$ each independently represent hydrogen or $C_{1-4}$alkyl.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

in particular $R^1$ and $R^2$ represent hydrogen;

Y represents —O— or —$CH_2$—; Z represents —X—$CR^{5a}R^{5b}$— or —$CH_2CH_2$—;

$R^{5a}$ and $R^{5b}$ represent hydrogen; X represents —O—;

$R^{11}$ represents hydrogen;

Ar represents

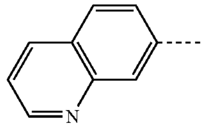

;

Ar is optionally substituted with one or two substituents each independently selected from the group consisting of halo, —OH, —$NH_2$, —NH—$C_{1-4}$alkyl, —N($C_{1-4}$alkyl)$_2$, cyano, and —$CF_3$;

Het represents a bicyclic aromatic heterocyclic ring system selected from the group consisting of (a-1);

$R^{3a}$ represents —$NR^{7a}R^{7b}$;

$R^{7a}$ represents hydrogen;

$R^{7b}$ represents hydrogen;

$R^{4a}$ represents hydrogen;

$Q^1$ represents $CR^{6a}$; $Q^2$ represents $CR^{6b}$; $R^{6a}$ and $R^{6b}$ represent hydrogen;

and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

in particular $R^1$ and $R^2$ represent hydrogen;

Y represents —O— or —$CH_2$—; Z represents —X—$CR^{5a}R^{5b}$— or —$CH_2CH_2$—;

$R^{5a}$ and $R^{5b}$ represent hydrogen; X represents —O—;

$R^{11}$ represents hydrogen;

Ar represents

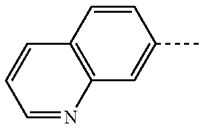

;

Ar is optionally substituted with one substituent selected from the group consisting of halo, —OH, —$NH_2$, —NH—$C_{1-4}$alkyl, —N($C_{1-4}$alkyl)$_2$, cyano, and —$CF_3$;

Het represents a bicyclic aromatic heterocyclic ring system selected from the group consisting of (a-1);

$R^{3a}$ represents —$NR^{7a}R^{7b}$;

$R^{7a}$ represents hydrogen;

$R^{7b}$ represents hydrogen;

$R^{4a}$ represents hydrogen;

$Q^1$ represents $CR^{6a}$; $Q^2$ represents $CR^{6b}$; $R^{6a}$ and $R^{6b}$ represent hydrogen;

and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

in particular $R^1$ and $R^2$ represent hydrogen;

Y represents —O—; Z represents —X—$CR^{5a}R^{5b}$—;

$R^{5a}$ and $R^{5b}$ represent hydrogen; X represents —O—;

$R^{11}$ represents hydrogen;

Ar represents

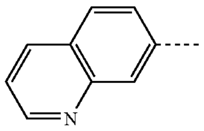

;

Ar is optionally substituted with one or two substituents each independently selected from the group consisting of halo, —OH, —$NH_2$, —NH—$C_{1-4}$alkyl, —N($C_{1-4}$alkyl)$_2$, cyano, and —$CF_3$;

Het represents a bicyclic aromatic heterocyclic ring system selected from the group consisting of (a-1);

$R^{3a}$ represents —$NR^{7a}R^{7b}$;

$R^{7a}$ represents hydrogen;

$R^{7b}$ represents hydrogen;

$R^{4a}$ represents hydrogen;

$Q^1$ represents $CR^{6a}$; $Q^2$ represents $CR^{6b}$; $R^{6a}$ and $R^{6b}$ represent hydrogen;

and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

in particular $R^1$ and $R^2$ represent hydrogen;

Y represents —O—; Z represents —X—$CR^{5a}R^{5b}$—;

$R^{5a}$ and $R^{5b}$ represent hydrogen; X represents —O—;

$R^{11}$ represents hydrogen;

Ar represents

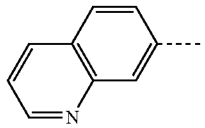

;

Ar is optionally substituted with one substituent selected from the group consisting of halo, —OH, —$NH_2$, —NH—$C_{1-4}$alkyl, —N($C_{1-4}$alkyl)$_2$, cyano, and —$CF_3$;

Het represents a bicyclic aromatic heterocyclic ring system selected from the group consisting of (a-1);

$R^{3a}$ represents —$NR^{7a}R^{7b}$;

$R^{7a}$ represents hydrogen;

$R^{7b}$ represents hydrogen;

$R^{4a}$ represents hydrogen;

$Q^1$ represents $CR^{6a}$; $Q^2$ represents $CR^{6b}$; $R^{6a}$ and $R^{6b}$ represent hydrogen; and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

in particular $R^1$ and $R^2$ represent hydrogen;

Y represents —O— or —$CH_2$—; Z represents —X—$CR^{5a}R^{5b}$— or —$CH_2CH_2$—;

$R^{5a}$ and $R^{5b}$ represent hydrogen; X represents —O—;

$R^{11}$ represents hydrogen;

Ar represents

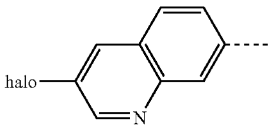

;

Het represents a bicyclic aromatic heterocyclic ring system selected from the group consisting of (a-1);

$R^{3a}$ represents —$NR^{7a}R^{7b}$;

$R^{7a}$ represents hydrogen;

$R^{7b}$ represents hydrogen;

$R^{4a}$ represents hydrogen;

$Q^1$ represents $CR^{6a}$; $Q^2$ represents $CR^{6b}$; $R^{6a}$ and $R^{6b}$ represent hydrogen;

and pharmaceutically acceptable addition salts, and solvates thereof.

In an embodiment, the present invention concerns novel compounds of Formula (I), wherein $R^1$ represents hydrogen or —C(═O)—$C_{1-4}$alkyl;

$R^2$ represents hydrogen or —C(═O)—$C_{1-4}$alkyl;

in particular $R^1$ and $R^2$ represent hydrogen;

Y represents —O—; Z represents —X—$CR^{5a}R^{5b}$—;

$R^{5a}$ and $R^{5b}$ represent hydrogen; X represents —O—;

$R^{11}$ represents hydrogen;

Ar represents

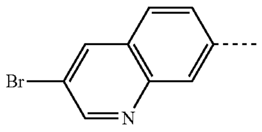
;

Het represents a bicyclic aromatic heterocyclic ring system selected from the group consisting of (a-1);

$R^{3a}$ represents —$NR^{7a}R^{7b}$;

$R^{7a}$ represents hydrogen;

$R^{7b}$ represents hydrogen;

$R^{4a}$ represents hydrogen;

$Q^1$ represents $CR^{6a}$; $Q^2$ represents $CR^{6b}$; $R^{6a}$ and $R^{6b}$ represent hydrogen;

and pharmaceutically acceptable addition salts, and solvates thereof.

Another embodiment of the present invention relates to those compounds of Formula (I), and pharmaceutically acceptable addition salts, and solvates thereof, or any subgroup thereof as mentioned in any of the other embodiments, wherein one or more of the following restrictions apply:

(i) $R^1$ represents hydrogen or —C(═O)—$C_{1-4}$alkyl;

$R^2$ represents hydrogen or —C(═O)—$C_{1-4}$alkyl;

in particular $R^1$ and $R^2$ represent hydrogen;

(ii) Y represents —O—;

(iii) Z represents —X—$CR^{5a}R^{5b}$—;

(iv) $R^{5a}$ and $R^{5b}$ represent hydrogen;

(v) X represents —O—;

(vi) $R^{11}$ represents hydrogen;

(vii) Ar represents

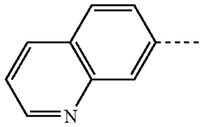
;

Ar is optionally substituted with one or two substituents each independently selected from the group consisting of halo, —OH, —$NH_2$, —NH—$C_{1-4}$alkyl, —N($C_{1-4}$alkyl)$_2$, cyano, and —$CF_3$; in particular Ar is optionally substituted with one substituent selected from the group consisting of halo, —OH, —$NH_2$, —NH—$C_{1-4}$alkyl, —N($C_{1-4}$alkyl)$_2$, cyano, and —$CF_3$;

more in particular Ar represents

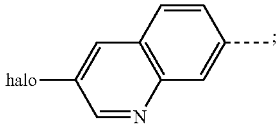
;

even more in particular Ar represents

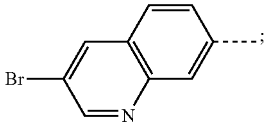
;

(ix) Het represents a bicyclic aromatic heterocyclic ring system selected from the group consisting of (a-1);

(x) $R^{3a}$ represents —$NR^{7a}R^{7b}$;

(xi) $R^{7a}$ represents hydrogen;

$R^{7b}$ represents hydrogen;

(xii) $R^{4a}$ represents hydrogen;

(xiii) $Q^1$ represents $CR^{6a}$;

(xiv) $Q^2$ represents $CR^{6b}$;

(xv) $R^{6a}$ and $R^{6b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein $R^1$ and $R^2$ represent hydrogen.

In an embodiment, the present invention relates to those compounds of Formula (I) and pharmaceutically acceptable addition salts, and solvates thereof, or any subgroup thereof as mentioned in any of the other embodiments, wherein $R^1$ represents —C(═O)—$C_{1-4}$alkyl; $R^2$ represents —C(═O)—$C_{1-4}$alkyl.

In an embodiment, the present invention relates to those compounds of Formula (I) and pharmaceutically acceptable addition salts, and solvates thereof, or any subgroup thereof as mentioned in any of the other embodiments, wherein $R^1$ and $R^2$ represent hydrogen;

Het represents (a-1);

$Q^1$ represents CH; $Q^2$ represents CH; and

Ar represents

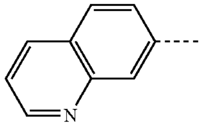

optionally substituted according to any of the other embodiments.

In an embodiment, the present invention relates to those compounds of Formula (I) and pharmaceutically acceptable addition salts, and solvates thereof, or any subgroup thereof as mentioned in any of the other embodiments, wherein $R^1$ and $R^2$ represent hydrogen;

Het represents (a-1);

$Q^1$ represents CH; $Q^2$ represents CH; and

Ar represents

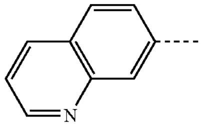

wherein Ar is substituted with one, two, three or four substituents each independently selected from the group consisting of halo, —$NH_2$, —NH—$C_{1-4}$alkyl, —N($C_{1-4}$alkyl)$_2$, —$NHR^{10d}$, —$NR^{10c}R^{10d}$;

$R^{10c}$ and $R^{10d}$ each independently represent $C_{1-4}$alkyl substituted with one, two or three halo substituents; or $C_{1-4}$alkyl substituted with one $C_{3-6}$cycloalkyl substituent.

In an embodiment, the present invention relates to those compounds of Formula (I) and pharmaceutically acceptable addition salts, and solvates thereof, or any subgroup thereof as mentioned in any of the other embodiments, wherein Y represents —O—.

In an embodiment, the present invention relates to those compounds of Formula (I) and pharmaceutically acceptable addition salts, and solvates thereof, or any subgroup thereof as mentioned in any of the other embodiments, wherein Y represents —$CH_2$— or —$CF_2$—; in particular wherein Y represents —$CH_2$—.

In an embodiment, the present invention relates to those compounds of Formula (I) and pharmaceutically acceptable addition salts, and solvates thereof, or any subgroup thereof as mentioned in any of the other embodiments, wherein maximum one of $Q^1$ and $Q^2$ represents N.

In an embodiment, the present invention relates to those compounds of Formula (I) and pharmaceutically acceptable addition salts, and solvates thereof, or any subgroup thereof as mentioned in any of the other embodiments, wherein $Q^1$ represents $CR^{6a}$; and $Q^2$ represents $CR^{6b}$; in particular wherein $Q^1$ represents CH; and $Q^2$ represents CH.

In an embodiment, the present invention relates to those compounds of Formula (I) and pharmaceutically acceptable addition salts, and solvates thereof, or any subgroup thereof as mentioned in any of the other embodiments, wherein Het represents (a-1); $Q^1$ represents $CR^{6a}$; and $Q^2$ represents $CR^{6b}$; in particular wherein $Q^1$ represents CH; and $Q^2$ represents CH.

In an embodiment, the present invention relates to those compounds of Formula (I) and pharmaceutically acceptable addition salts, and solvates thereof, or any subgroup thereof as mentioned in any of the other embodiments, wherein $Q^5$ represents $CR^{3d}$; $Q^6$ represents N; and $Q^7$ represents $CR^{4f}$; or $Q^5$ represents $CR^{3d}$; $Q^6$ represents $CR^{4e}$; and $Q^7$ represents N; or $Q^5$ represents N; $Q^6$ represents $CR^{4e}$; and $Q^7$ represents $CR^{4f}$; or $Q^5$ represents N; $Q^6$ represents $CR^{4e}$; and $Q^7$ represents N.

In an embodiment, the present invention relates to those compounds of Formula (I) and pharmaceutically acceptable addition salts, and solvates thereof, or any subgroup thereof as mentioned in any of the other embodiments, wherein Het represents a bicyclic aromatic heterocyclic ring system selected from the group consisting of (a-1), (a-2) and (a-4).

In an embodiment, the present invention relates to those compounds of Formula (I) and pharmaceutically acceptable addition salts, and solvates thereof, or any subgroup thereof as mentioned in any of the other embodiments, wherein $R^1$ and $R^2$ represent hydrogen; and Y represents —O—.

In an embodiment, the present invention relates to those compounds of Formula (I) and pharmaceutically acceptable addition salts, and solvates thereof, or any subgroup thereof as mentioned in any of the other embodiments, wherein Het represents a bicyclic aromatic heterocyclic ring system selected from the group consisting of (a-1), (a-2) and (a-3).

In an embodiment, the present invention relates to those compounds of Formula (I) and pharmaceutically acceptable addition salts, and solvates thereof, or any subgroup thereof as mentioned in any of the other embodiments, wherein Het represents a bicyclic aromatic heterocyclic ring system selected from the group consisting of (a-1) and (a-2).

In an embodiment, the present invention relates to those compounds of Formula (I) and pharmaceutically acceptable addition salts, and solvates thereof, or any subgroup thereof as mentioned in any of the other embodiments, wherein Het represents a bicyclic aromatic heterocyclic ring system selected from the group consisting of (a-1) and (a-4).

In an embodiment, the present invention relates to those compounds of Formula (I) and pharmaceutically acceptable addition salts, and solvates thereof, or any subgroup thereof as mentioned in any of the other embodiments, wherein Het represents a bicyclic aromatic heterocyclic ring system of Formula (a-1).

In an embodiment, the present invention relates to those compounds of Formula (I) and pharmaceutically acceptable addition salts, and solvates thereof, or any subgroup thereof as mentioned in any of the other embodiments, wherein $R^1$ and $R^2$ represent hydrogen; Y represents —O—; and Het represents a bicyclic aromatic heterocyclic ring system of Formula (a-1).

In an embodiment, the present invention relates to those compounds of Formula (I) and pharmaceutically acceptable addition salts, and solvates thereof, or any subgroup thereof as mentioned in any of the other embodiments, wherein Ar represents an optionally substituted 10-membered bicyclic aromatic ring system consisting of two fused 6-membered rings, wherein 1 or 2 ring carbon atoms are replaced by a nitrogen atom; provided that the nitrogen atom does not replace one of the two fused carbon atoms.

In an embodiment, the present invention relates to those compounds of Formula (I) and pharmaceutically acceptable addition salts, and solvates thereof, or any subgroup thereof as mentioned in any of the other embodiments, wherein Ar is optionally substituted with one or two substituents according to any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar is optionally substituted with one substituent according to any of the other embodiments.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3c}$, $R^{3b}$ represent hydrogen; and $R^{4a}$, $R^{4c}$, $R^{4b}$ represent hydrogen, halo, or $C_{1-4}$alkyl; in particular $R^{4a}$, $R^{4c}$, $R^{4b}$ represent halo, or $C_{1-4}$alkyl.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3c}$, $R^{3b}$, $R^{3d}$ and $R^{3e}$ represent hydrogen; and $R^{4a}$, $R^{4c}$, $R^{4b}$, $R^{4d}$, $R^{4e}$, $R^{4f}$ and $R^{4g}$ represent hydrogen, halo, or $C_{1-4}$alkyl; in particular $R^{4a}$, $R^{4c}$, $R^{4b}$, $R^{4d}$, $R^{4e}$, $R^{4f}$ and $R^{4g}$ represent halo, or $C_{1-4}$alkyl.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3c}$, $R^{3b}$ represent hydrogen, halo, —$NR^{7a}R^{7b}$, or —O—$C_{1-4}$alkyl; in particular $R^{3a}$, $R^{3c}$, $R^{3b}$ represent halo, —$NR^{7a}R^{7b}$, or —O—$C_{1-4}$alkyl;

$R^{4a}$, $R^{4c}$, $R^{b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3c}$, $R^{3b}$, $R^{3d}$ and $R^{3e}$ represent hydrogen, halo, —$NR^{7a}R^{7b}$, or —O—$C_{1-4}$alkyl; in particular $R^{3a}$, $R^{3c}$, $R^{3b}$, $R^{3d}$ and $R^{3e}$ represent halo, —$NR^{7a}R^{7b}$, or —O—$C_{1-4}$alkyl;

$R^{4a}$, $R^{4c}$, $R^{4b}$, $R^{4d}$, $R^{4e}$, $R^{4f}$ and $R^{4g}$ represent hydrogen.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3c}$, $R^{3b}$ represent hydrogen, when $R^{4a}$, $R^{4c}$, $R^{4b}$ are different from hydrogen.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3c}$, $R^{3b}$, $R^{3d}$, $R^{3e}$ represent hydrogen, when $R^{4a}$, $R^{4c}$, $R^{4b}$, $R^{4d}$, $R^{4e}$, $R^{4f}$, $R^{4g}$ are different from hydrogen.

In an embodiment, the present invention relates to those compounds of Formula (I) and pharmaceutically acceptable addition salts, and solvates thereof, or any subgroup thereof as mentioned in any of the other embodiments, wherein $R^{4a}$, $R^{4c}$, $R^{4b}$ represent hydrogen, when $R^{3a}$, $R^{3c}$, $R^{3b}$ are different from hydrogen.

In an embodiment, the present invention relates to those compounds of Formula (I) and pharmaceutically acceptable addition salts, and solvates thereof, or any subgroup thereof as mentioned in any of the other embodiments, wherein $R^{4a}$, $R^{4c}$, $R^{4b}$, $R^{4d}$, $R^{4e}$, $R^{4f}$, $R^{4g}$ represent hydrogen, when $R^{3a}$, $R^{3c}$, $R^{3b}$, $R^{3d}$, $R^{3e}$ are different from hydrogen.

In an embodiment, the present invention relates to those compounds of Formula (I) and pharmaceutically acceptable addition salts, and solvates thereof, or any subgroup thereof as mentioned in any of the other embodiments, wherein Ar represents a 10-membered bicyclic aromatic ring system consisting of two fused 6-membered rings,

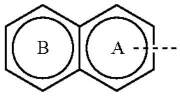

wherein at least 1 ring carbon atom of ring B is replaced by a nitrogen atom;

wherein optionally 1 additional ring carbon atom of ring A or ring B is replaced by a nitrogen atom; provided that when a nitrogen atom replaces one of the two fused carbon atoms, a carbonyl group is present in said bicyclic aromatic ring system;

Ar is optionally substituted according to any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar represents a 10-membered bicyclic aromatic ring system consisting of two fused 6-membered rings,

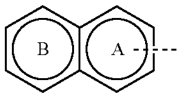

wherein at least 1 ring carbon atom of ring B is replaced by a nitrogen atom;

wherein optionally 1 additional ring carbon atom of ring A or ring B is replaced by a nitrogen atom; provided that when a nitrogen atom replaces one of the two fused carbon atoms, a carbonyl group is present in said bicyclic aromatic ring system;

Ar is optionally substituted with one, two, three or four substituents each independently selected from the group consisting of halo, —OH, —$NH_2$, —NH—$C_{1-4}$alkyl, —$N(C_{1-4}alkyl)_2$, —$NHR^{10d}$, —$NR^{10c}R^{10d}$, cyano, —$CF_3$, —C(═O)—$NH_2$, —C(═O)—NH—$C_{1-4}$alkyl, —C(═O)—$C_{1-4}$alkyl, $C_{1-4}$alkyloxy, —C(═O)—O—$C_{1-4}$alkyl, $C_{3-6}$cycloalkyl, $C_{2-6}$alkenyl, $C_{1-4}$alkyl substituted with one $C_{1-4}$alkyloxy, and $C_{1-4}$alkyl optionally substituted with one —$NR^{10}R^{10b}$;

in particular Ar is optionally substituted with one, two, three or four substituents each independently selected from the group consisting of halo, —OH, —$NH_2$, —NH—$C_{1-4}$alkyl, —$N(C_{1-4}alkyl)_2$, cyano, —$CF_3$, —C(═O)—NH—$C_{1-4}$alkyl, —C(═O)—$C_{1-4}$alkyl, $C_{1-4}$alkyloxy, and $C_{1-4}$alkyl optionally substituted with one —$NR^{10a}R^{10b}$.

In an embodiment, the present invention relates to those compounds of Formula (I) and pharmaceutically acceptable addition salts, and solvates thereof, or any subgroup thereof as mentioned in any of the other embodiments, wherein Ar represents a 10-membered bicyclic aromatic ring system consisting of two fused 6-membered rings with the following structure,

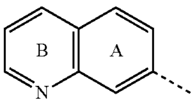

wherein optionally 1 additional ring carbon atom of ring A or ring B is replaced by a nitrogen atom; provided that when a nitrogen atom replaces one of the two fused carbon atoms, a carbonyl group is present in said bicyclic aromatic ring system;

Ar is optionally substituted according to any of the other embodiments.

It will be clear that

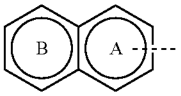

covers any one of the following ring systems:

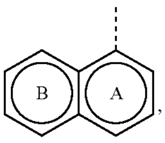, 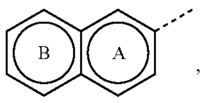,

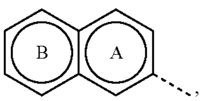, and 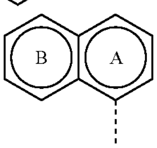.

In an embodiment, the present invention relates to those compounds of Formula (I) and pharmaceutically acceptable addition salts, and solvates thereof, or any subgroup thereof as mentioned in any of the other embodiments, wherein Ar is selected from the group consisting of:

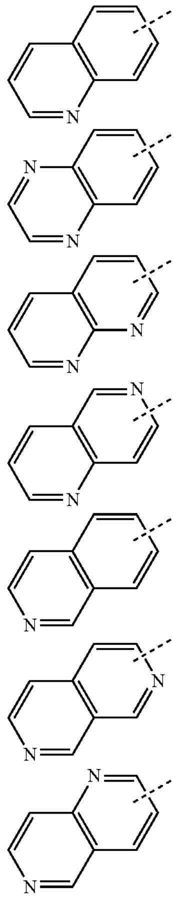

wherein each Ar is optionally substituted according to any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar is selected from the group consisting of:

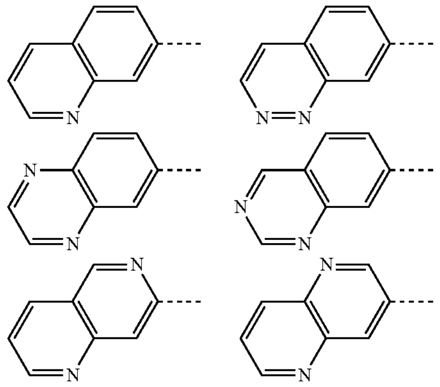

-continued

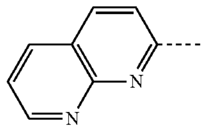

wherein each Ar is optionally substituted according to any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar is selected from the group consisting of:

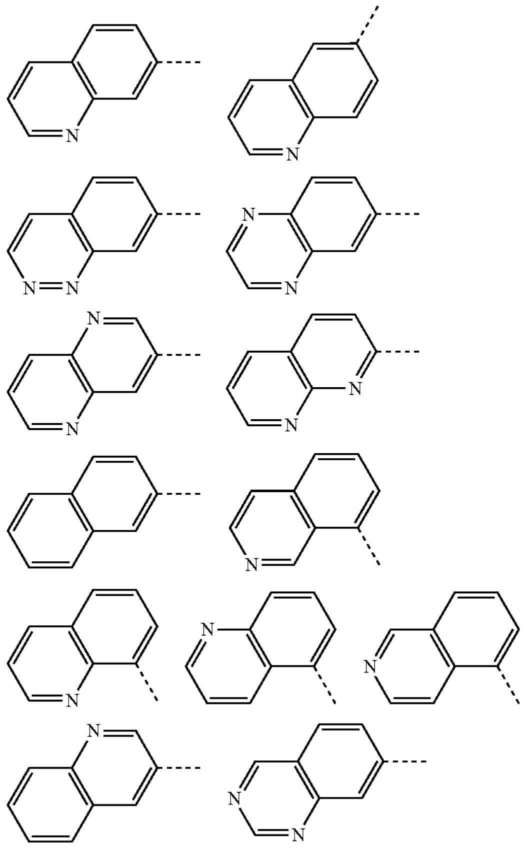

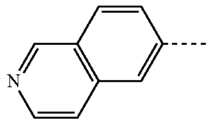

wherein each Ar is optionally substituted according to any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar is selected from the group consisting of:

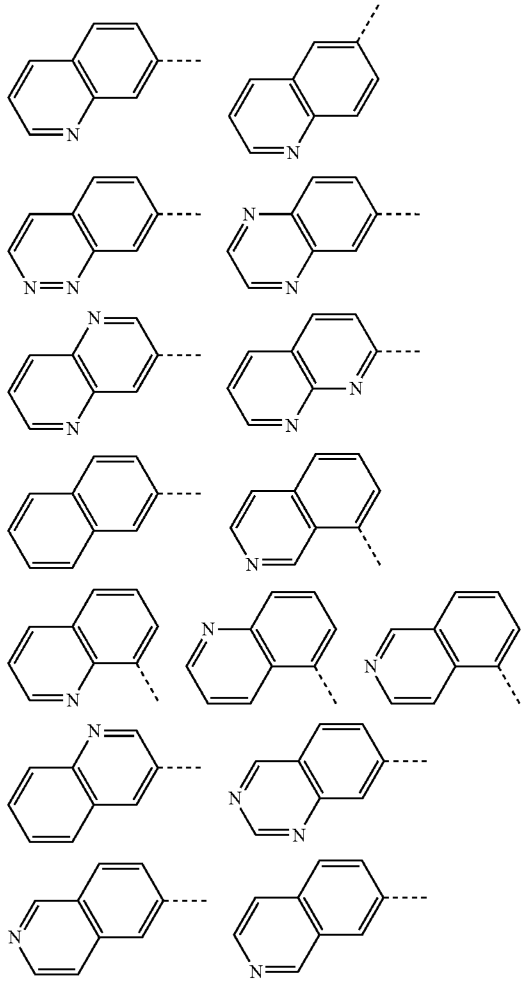

wherein each Ar is optionally substituted according to any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar is selected from the group consisting of:

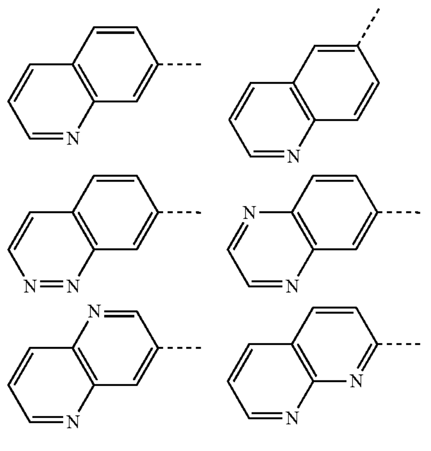

-continued

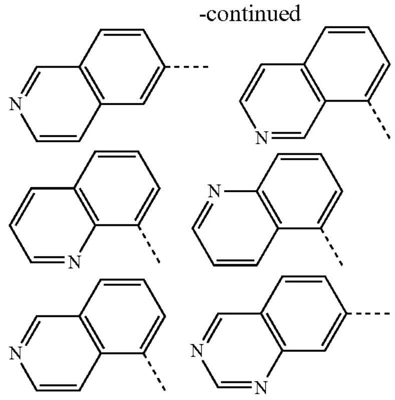

wherein each Ar is optionally substituted according to any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar is

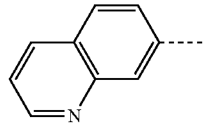

wherein Ar is optionally substituted according to any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar is other than

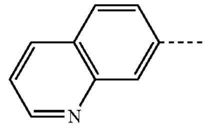

wherein Ar is optionally substituted according to any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar represents

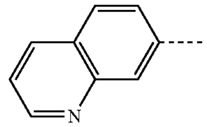

wherein Ar is substituted with one, two, three or four substituents each independently selected from the group consisting of halo, —$NH_2$, —NH—$C_{1-4}$alkyl, —$N(C_{1-4}alkyl)_2$, —$NHR^{10d}$, —$NR^{10c}R^{10d}$.

In an embodiment, the present invention relates to those compounds of Formula (I) and pharmaceutically acceptable addition salts, and solvates thereof, or any subgroup thereof as mentioned in any of the other embodiments, wherein Ar represents

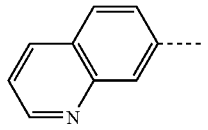

wherein Ar is substituted with one substituent selected from the group consisting of —$NH_2$, —NH—$C_{1-4}$alkyl, —N($C_{1-4}$alkyl)$_2$, —$NHR^{10d}$, —$NR^{10c}R^{10d}$; and optionally substituted with a halo substituent;

$R^{10c}$ and $R^{10d}$ each independently represent $C_{1-4}$alkyl substituted with one, two or three halo substituents; or $C_{1-4}$alkyl substituted with one $C_{3-6}$cycloalkyl substituent.

In an embodiment, the present invention relates to those compounds of Formula (I) and pharmaceutically acceptable addition salts, and solvates thereof, or any subgroup thereof as mentioned in any of the other embodiments, wherein Ar represents

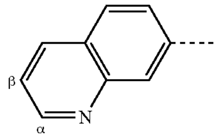

wherein Ar is substituted in the position indicated by α with a substituent selected from the group consisting of —$NH_2$, —NH—$C_{1-4}$alkyl, —N($C_{1-4}$alkyl)$_2$, —$NHR^{10d}$, —$NR^{10c}R^{10d}$; and wherein Ar is optionally substituted in the position indicated by β with a halo substituent.

In an embodiment, the present invention relates to those compounds of Formula (I) and pharmaceutically acceptable addition salts, and solvates thereof, or any subgroup thereof as mentioned in any of the other embodiments, wherein Ar represents

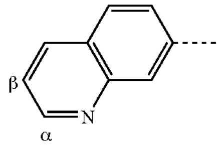

wherein Ar is substituted in the position indicated by α with a substituent selected from the group consisting of —$NH_2$, —NH—$C_{1-4}$alkyl, —N($C_{1-4}$alkyl)$_2$, —$NHR^{10d}$, —$NR^{10c}R^{10d}$; and wherein Ar is optionally substituted in the position indicated by β with a halo substituent;

$R^{10c}$ and $R^{10d}$ each independently represent $C_{1-4}$alkyl substituted with one, two or three halo substituents; or $C_{1-4}$alkyl substituted with one $C_{3-6}$cycloalkyl substituent.

In an embodiment, the present invention relates to those compounds of Formula (I) and pharmaceutically acceptable addition salts, and solvates thereof, or any subgroup thereof as mentioned in any of the other embodiments, wherein Ar represents

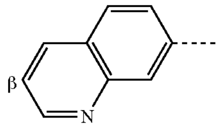

wherein Ar is substituted in the position indicated by β with a halo substituent; in particular chloro or bromo; more in particular bromo.

In an embodiment, the present invention relates to those compounds of Formula (I) and pharmaceutically acceptable addition salts, and solvates thereof, or any subgroup thereof as mentioned in any of the other embodiments, wherein Het represent (a-1); $Q^1$ represents $CR^{6a}$; $Q^2$ represents $CR^{6b}$; and Ar represents

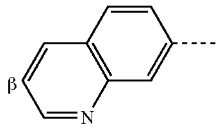

wherein Ar is substituted in the position indicated by β with a halo substituent; in particular chloro or bromo; more in particular bromo.

In an embodiment, the present invention relates to those compounds of Formula (I) and pharmaceutically acceptable addition salts, and solvates thereof, or any subgroup thereof as mentioned in any of the other embodiments, wherein Ar is substituted with one substituent selected from the group consisting of —$NH_2$, —NH—$C_{1-4}$alkyl, —N($C_{1-4}$alkyl)$_2$, —$NHR^{10d}$, —$NR^{10c}R^{10d}$; and wherein Ar is optionally substituted with another substituent selected from the list of substituents on Ar in any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar represents

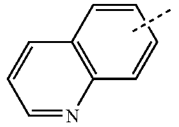

optionally substituted according to any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar represents

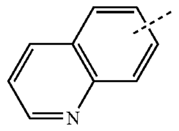

optionally substituted with one, two or three substituents each independently selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, $C_{1-4}$alkyloxy, and $C_{1-4}$alkyl;

in particular optionally substituted with one, two or three substituents each independently selected from the group consisting of halo, —$NH_2$, cyano, —$CF_3$, $C_{1-4}$alkyloxy, and $C_{1-4}$alkyl;

more in particular optionally substituted with one, two or three substituents each independently selected from the group consisting of halo, or —$CF_3$;

more in particular optionally substituted with one or two halo substituents;

more in particular substituted with one or two halo substituents;

even more in particular substituted with one halo substituent;

most in particular substituted with one chloro substituent.

In an embodiment, the present invention relates to those compounds of Formula (I) and pharmaceutically acceptable addition salts, and solvates thereof, or any subgroup thereof as mentioned in any of the other embodiments, wherein Ar represents

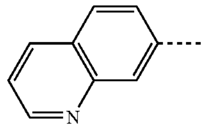

optionally substituted according to any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar represents

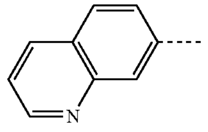

optionally substituted with one, two or three substituents each independently selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, $C_{1-4}$alkyloxy, and $C_{1-4}$alkyl;

in particular optionally substituted with one, two or three substituents each independently selected from the group consisting of halo, —$NH_2$, cyano, —$CF_3$, $C_{1-4}$alkyloxy, and $C_{1-4}$alkyl;

more in particular optionally substituted with one, two or three substituents each independently selected from the group consisting of halo, or —$CF_3$;

more in particular optionally substituted with one or two halo substituents;

more in particular substituted with one or two halo substituents;

even more in particular substituted with one halo substituent;

most in particular substituted with one chloro substituent.

In an embodiment, the present invention relates to those compounds of Formula (I) and pharmaceutically acceptable addition salts, and solvates thereof, or any subgroup thereof as mentioned in any of the other embodiments, wherein Het represents (a-1); and Ar represents

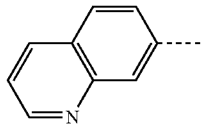

optionally substituted with one, two or three substituents each independently selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, $C_{1-4}$alkyloxy, and $C_{1-4}$alkyl;

in particular optionally substituted with one, two or three substituents each independently selected from the group consisting of halo, —$NH_2$, cyano, —$CF_3$, $C_{1-4}$alkyloxy, and $C_{1-4}$alkyl;

more in particular optionally substituted with one, two or three substituents each independently selected from the group consisting of halo, or —$CF_3$;

more in particular optionally substituted with one or two halo substituents;

more in particular substituted with one or two halo substituents;

even more in particular substituted with one halo substituent;

most in particular substituted with one chloro substituent.

In an embodiment, the present invention relates to those compounds of Formula (I) and pharmaceutically acceptable addition salts, and solvates thereof, or any subgroup thereof as mentioned in any of the other embodiments, wherein Het represents (a-1); and Ar represents

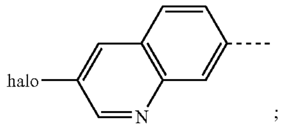

;

in particular Ar represents

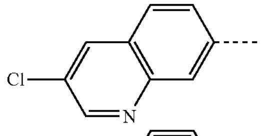

or

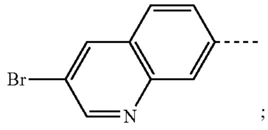

;

more in particular Ar represents

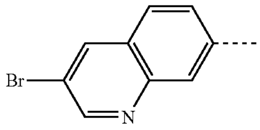

.

In an embodiment, the present invention relates to those compounds of Formula (I) and pharmaceutically acceptable addition salts, and solvates thereof, or any subgroup thereof as mentioned in any of the other embodiments, wherein Ar represents

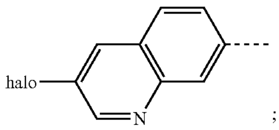

;

in particular Ar represents

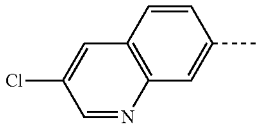

or

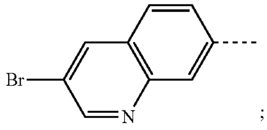

;

more in particular Ar represents

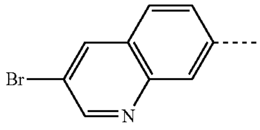

.

In an embodiment, the present invention relates to those compounds of Formula (I) and pharmaceutically acceptable addition salts, and solvates thereof, or any subgroup thereof as mentioned in any of the other embodiments, wherein $R^{5b}$, $R^{5g}$ and $R^{5h}$ represent hydrogen.

In an embodiment, the present invention relates to those compounds of Formula (I) and pharmaceutically acceptable addition salts, and solvates thereof, or any subgroup thereof as mentioned in any of the other embodiments, wherein $Q^1$ represents $CR^{6a}$; and $Q^2$ represents $CR^{6b}$.

In an embodiment, the present invention relates to those compounds of Formula (I) and pharmaceutically acceptable addition salts, and solvates thereof, or any subgroup thereof as mentioned in any of the other embodiments, wherein X represents —O—; $Q^1$ represents $CR^{6a}$; and $Q^2$ represents $CR^{6b}$.

In an embodiment, the present invention relates to those compounds of Formula (I) and pharmaceutically acceptable addition salts, and solvates thereof, or any subgroup thereof as mentioned in any of the other embodiments, wherein X represents —O—; $Q^1$ represents CH; and $Q^2$ represents $CR^{H}$.

In an embodiment, the present invention relates to those compounds of Formula (I) and pharmaceutically acceptable addition salts, and solvates thereof, or any subgroup thereof as mentioned in any of the other embodiments, wherein $R^{5b}$, $R^{5g}$ and $R^{5h}$ represent hydrogen;

Y represents —$CH_2$— or —$CF_2$—; in particular Y represents —$CH_2$—; and

Het represents (a-1);

$Q^1$ represents $CR^{6a}$; and $Q^2$ represents $CR^{6b}$; in particular wherein $Q^1$ represents CH; and $Q^2$ represents CH.

In an embodiment, the present invention relates to those compounds of Formula (I) and pharmaceutically acceptable addition salts, and solvates thereof, or any subgroup thereof as mentioned in any of the other embodiments, wherein $R^{5b}$, $R^{5g}$ and $R^{5h}$ represent hydrogen; Y represents —O—; and Het represents (a-1);

$Q^1$ represents $CR^{6a}$; and $Q^2$ represents $CR^{6b}$; in particular wherein $Q^1$ represents CH; and $Q^2$ represents CH.

In an embodiment, the present invention relates to those compounds of Formula (I) and pharmaceutically acceptable addition salts, and solvates thereof, or any subgroup thereof as mentioned in any of the other embodiments, wherein $Q^2$ represents $CR^{6b}$.

In an embodiment, the present invention relates to those compounds of Formula (I) and pharmaceutically acceptable addition salts, and solvates thereof, or any subgroup thereof as mentioned in any of the other embodiments, wherein Z represents —X—$CR^{5a}R^{5b}$—.

In an embodiment, the present invention relates to those compounds of Formula (I) and pharmaceutically acceptable addition salts, and solvates thereof, or any subgroup thereof as mentioned in any of the other embodiments, wherein Z represents —O—$CH_2$—.

In an embodiment, the present invention relates to those compounds of Formula (I) and pharmaceutically acceptable addition salts, and solvates thereof, or any subgroup thereof as mentioned in any of the other embodiments, wherein Z represents —X—$CR^{5a}R^{5b}$—; X represents —O—; and $R^{5a}$ and $R^{5b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein X represents —O— or —$NR^{11}$—; in particular X represents —O—.

In an embodiment, the present invention relates to those compounds of Formula (I) and pharmaceutically acceptable addition salts, and solvates thereof, or any subgroup thereof as mentioned in any of the other embodiments, wherein $R^{7a}$ and $R^{7b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein Het represents (a-1); $R^{3a}$ represents —$NR^{7a}R^{7b}$; and $R^{7a}$ and $R^{7b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one substituent selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, —C(═O)—$C_{1-4}$alkyl, $C_{1-4}$alkyloxy, and $C_{1-4}$alkyl optionally substituted with one —$NR^{10a}R^{10b}$;

$R^{3a}$, $R^{3b}$ and $R^{3c}$ represent —$NR^{7a}R^{7b}$; and $R^{7a}$ and $R^{7b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one substituent selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, —C(═O)—$C_{1-4}$alkyl, $C_{1-4}$alkyloxy, and $C_{1-4}$alkyl optionally substituted with one —$NR^{10a}R^{10b}$;

$R^{3a}$, $R^{3c}$, $R^{3b}$, $R^{3d}$ and $R^{3e}$ represent —$NR^{7a}R^{7b}$; and $R^{7a}$ and $R^{7b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3b}$ and $R^{3c}$ represent other than halo.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3c}$, $R^{3b}$, $R^{3d}$ and $R^{3e}$ represent other than halo.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3b}$ and $R^{3c}$ represent —$NR^{7a}R^{7b}$;

$R^{7a}$ represents hydrogen;

$R^{7b}$ represents hydrogen.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3b}$ and $R^{3c}$ represent —$NH_2$.

In an embodiment, the present invention relates to those compounds of Formula (I) and pharmaceutically acceptable addition salts, and solvates thereof, or any subgroup thereof as mentioned in any of the other embodiments, wherein Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is optionally substituted with one substituent selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, —C(═O)—$C_{1-4}$alkyl, $C_{1-4}$alkyloxy, and $C_{1-4}$alkyl optionally substituted with one —$NR^{10a}R^{10b}$;

Het represents (a-1); $R^{3a}$ represents —$NR^{7a}R^{7b}$; and $R^{7a}$ and $R^{7b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein Ar represents a 10-membered bicyclic aromatic ring system consisting of two fused 6-membered rings, wherein optionally 1 or 2 ring carbon atoms are replaced by a nitrogen atom; provided that when the nitrogen atom replaces one of the two fused carbon atoms, a carbonyl group is present in said bicyclic aromatic ring system;

Ar is substituted with one substituent selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, —C(═O)—$C_{1-4}$alkyl, $C_{1-4}$alkyloxy, and $C_{1-4}$alkyl optionally substituted with one —$NR^{10a}R^{10b}$;

Het represents (a-1); $R^{3a}$ represents —$NR^{7a}R^{7b}$; and $R^{7a}$ and $R^{7b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein Ar represents

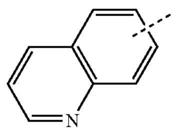

optionally substituted with one substituent selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, $C_{1-4}$alkyloxy, and $C_{1-4}$alkyl;

in particular optionally substituted with one substituent selected from the group consisting of halo, —$NH_2$, —NH—$C_{1-4}$alkyl, cyano, —$CF_3$, $C_{1-4}$alkyloxy, and $C_{1-4}$alkyl;

more in particular optionally substituted with one substituent selected from the group consisting of halo, and —$CF_3$;

more in particular optionally substituted with one halo substituent;

more in particular substituted with one halo substituent;

even more in particular substituted with one chloro substituent.

In an embodiment, the present invention relates to those compounds of Formula (I) and pharmaceutically acceptable addition salts, and solvates thereof, or any subgroup thereof as mentioned in any of the other embodiments, wherein Ar is selected from the group consisting of:

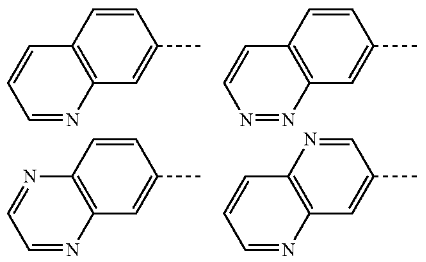

-continued

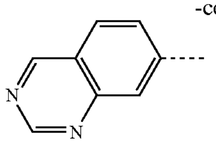

wherein each Ar is optionally substituted according to any of the other embodiments; in particular wherein Ar is optionally substituted with one substituent as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar is selected from the group consisting of:

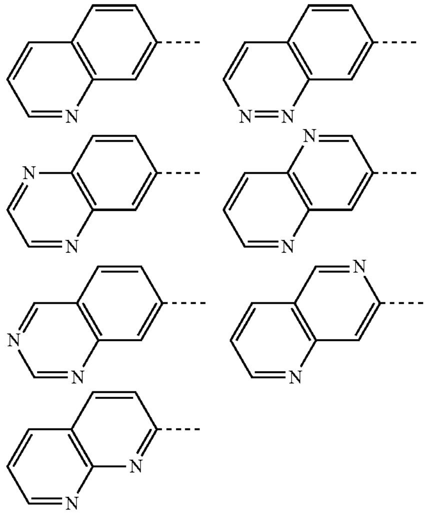

wherein each Ar is optionally substituted according to any of the other embodiments; in particular wherein Ar is optionally substituted with one substituent as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar is selected from the group consisting of:

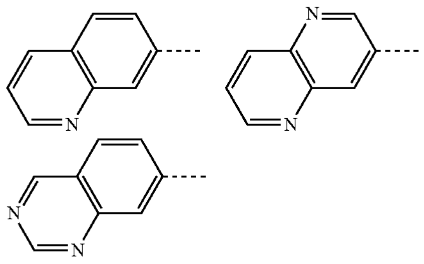

wherein each Ar is optionally substituted according to any of the other embodiments; in particular wherein Ar is optionally substituted with one substituent as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar is selected from the group consisting of:

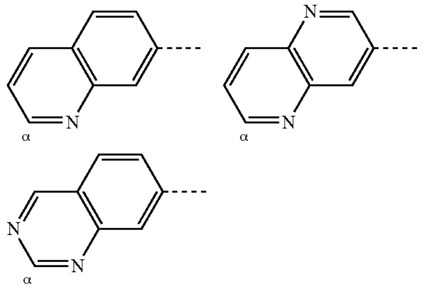

wherein each Ar is optionally substituted in position α with a substituent selected from the group consisting of —$NH_2$, —NH—$C_{1-4}$alkyl, —N($C_{1-4}$alkyl)$_2$, —$NHR^{10d}$, and —$NR^{10c}R^{10d}$;

$R^{10c}$ and $R^{10d}$ each independently represent $C_{3-6}$cycloalkyl; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, $R^{13}$ and $R^{14}$;

$R^{13}$ represents a 4- to 7-membered monocyclic aromatic ring containing one, two or three heteroatoms each independently selected from O, S, S(=O)$_p$ and N; or a 6- to 11-membered bicyclic fused aromatic ring containing one, two or three heteroatoms each independently selected from O, S, S(=O)$_p$ and N;

said 4- to 7-membered monocyclic aromatic ring or 6- to 11-membered bicyclic fused aromatic ring is optionally substituted with one or two substituents selected from the group consisting of $C_{1-4}$alkyl;

p represents 1 or 2;

$R^{14}$ represents phenyl optionally substituted with one, two or three substituents each independently selected from the group consisting of halo.

In an embodiment, the present invention relates to those compounds of Formula (I) and pharmaceutically acceptable addition salts, and solvates thereof, or any subgroup thereof as mentioned in any of the other embodiments, wherein Ar is selected from the group consisting of:

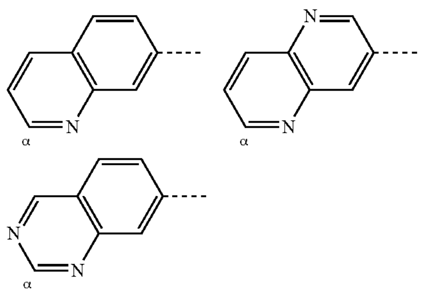

wherein each Ar is optionally substituted in position α with a substituent selected from the group consisting of $-NH_2$, $-NH-C_{1-4}alkyl$, $-N(C_{1-4}alkyl)_2$, $-NHR^{10d}$, and $-NR^{10c}R^{10d}$;

and wherein Ar is optionally substituted in another position with a halo substituent.

In an embodiment, the present invention relates to those compounds of Formula (I) and pharmaceutically acceptable addition salts, and solvates thereof, or any subgroup thereof as mentioned in any of the other embodiments, wherein Ar is selected from the group consisting of:

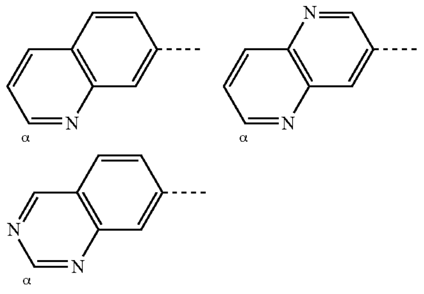

wherein each Ar is substituted in position α with a substituent selected from the group consisting of $-NH_2$, $-NH-C_{1-4}alkyl$, $-N(C_{1-4}alkyl)_2$, $-NHR^{10d}$, and $-NR^{10c}R^{10d}$;

and wherein Ar is optionally substituted in another position with a halo substituent.

In an embodiment, the present invention relates to those compounds of Formula (I) and pharmaceutically acceptable addition salts, and solvates thereof, or any subgroup thereof as mentioned in any of the other embodiments, wherein Ar represents a 10-membered bicyclic aromatic ring system consisting of two fused 6-membered rings, wherein 1 or 2 ring carbon atoms are replaced by a nitrogen atom; provided that when the nitrogen atom replaces one of the two fused carbon atoms, a carbonyl group is present in said bicyclic aromatic ring system;

wherein each Ar is optionally substituted according to any of the other embodiments; in particular wherein Ar is optionally substituted with one substituent as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar is optionally substituted with one substituent as defined in any of the other embodiments.

In an embodiment, the present invention relates to those compounds of Formula (I) and pharmaceutically acceptable addition salts, and solvates thereof, or any subgroup thereof as mentioned in any of the other embodiments, wherein Ar is optionally substituted with one, two, three or four substituents each independently selected from the group consisting of halo, $-OH$, $-NH_2$, $-NH-C_{1-4}alkyl$, $-N(C_{1-4}alkyl)_2$, $-NHR^{10d}$, $-NR^{10c}R^{10d}$, cyano, $-CF_3$, $-C(=O)-NH_2$, $-C(=O)-NH-C_{1-4}alkyl$, $-C(=O)-C_{1-4}alkyl$, $C_{1-4}alkyloxy$, $-C(=O)-O-C_{1-4}alkyl$, $C_{2-6}alkenyl$, $C_{1-4}alkyl$ substituted with one $C_{1-4}alkyloxy$, and $C_{1-4}alkyl$ optionally substituted with one $-NR^{10a}R^{10b}$.

In an embodiment, the present invention relates to those compounds of Formula (I) and pharmaceutically acceptable addition salts, and solvates thereof, or any subgroup thereof as mentioned in any of the other embodiments, wherein Ar represents

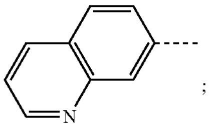

;

Ar is optionally substituted with one substituent selected from the group consisting of halo, $-OH$, $-NH_2$, $-NH-C_{1-4}alkyl$, $-N(C_{1-4}alkyl)_2$, cyano, and $-CF_3$; more in particular Ar represents

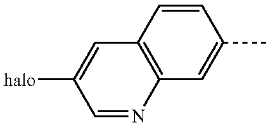

;

even more in particular Ar represents

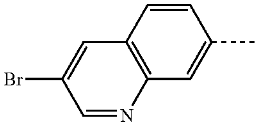

.

In an embodiment, the present invention relates to those compounds of Formula (I) and pharmaceutically acceptable addition salts, and solvates thereof, or any subgroup thereof as mentioned in any of the other embodiments, wherein Ar represents

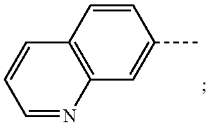

;

Ar is substituted with one substituent selected from the group consisting of halo, $-OH$, $-NH_2$, $-NH-C_{1-4}alkyl$, $-N(C_{1-4}alkyl)_2$, cyano, and $-CF_3$; more in particular Ar represents

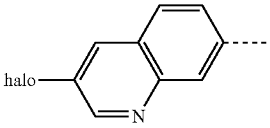

;

even more in particular Ar represents

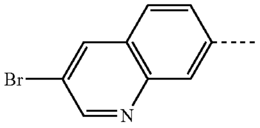

;

Het represents (a-1); $R^{3a}$ represents $-NR^{7a}R^{7b}$; and $R^{7a}$ and $R^{7b}$ represent hydrogen.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to compounds of Formula (I-a1):

(I-a1)

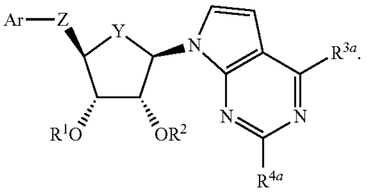

It will be clear that all variables in the structure of Formula (I-a1), may be defined as defined for the compounds of Formula (I) or any subgroup thereof as mentioned in any of the other embodiments.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to compounds of Formula (I-a1):

(I-a1)

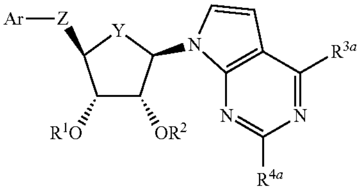

wherein $R^{3a}$ represents —$NH_2$; and $R^{4a}$ represents hydrogen.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to compounds of Formula (I-a1):

(I-a1)

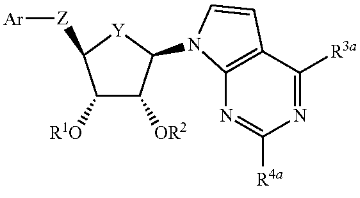

wherein $R^{3a}$ represents —$NH_2$; $R^{4a}$ represents hydrogen; and

Ar represents

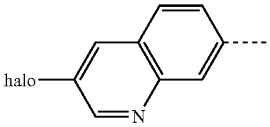

;

more in particular Ar represents

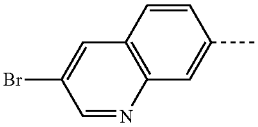

.

In an embodiment, the present invention relates to those compounds of Formula (I) and pharmaceutically acceptable addition salts, and solvates thereof, or any subgroup thereof as mentioned in any of the other embodiments, wherein the compounds of Formula (I) are restricted to compounds of Formula (I-a1):

(I-a1)

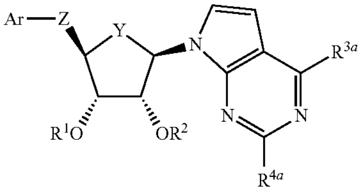

wherein $R^1$ and $R^2$ represent hydrogen;

$R^{3a}$ represents hydrogen, —$NR^{7a}R^{7b}$, or —$OC_{1-4}$alkyl;

$R^{4a}$ represents hydrogen; and

Ar represents

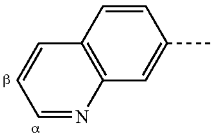

wherein Ar is substituted in the position indicated by α with a substituent selected from the group consisting of —$NH_2$, —NH—$C_{1-4}$alkyl, —N($C_{1-4}$alkyl)$_2$, —$NHR^{10d}$, —$NR^{10c}R^{10d}$; and wherein Ar is optionally substituted in the position indicated by β with a halo substituent;

$R^{10c}$ and $R^{10d}$ each independently represent $C_{1-4}$alkyl substituted with one, two or three halo substituents; or $C_{1-4}$alkyl substituted with one $C_{3-6}$cycloalkyl substituent.

In an embodiment, the present invention concerns novel compounds of Formula (I-a1)

(I-a1)

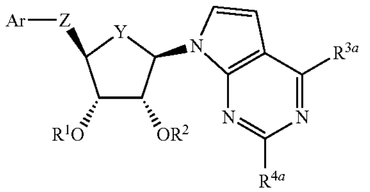

wherein $R^1$ and $R^2$ represent hydrogen;

$R^{3a}$ represents hydrogen, —$NR^{7a}R^{7b}$, or —$OC_{1-4}$alkyl;

$R^{7a}$ represents hydrogen;

$R^{7b}$ represents hydrogen or $C_{1-4}$alkyl;

Z represents —$CH_2CH_2$—;

Y represents —O—, —$CH_2$— or —$CF_2$—; in particular —$CH_2$—;

$R^{4a}$ represents hydrogen; and

Ar represents

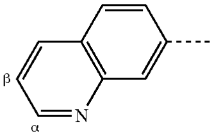

wherein Ar is substituted in the position indicated by α with a substituent selected from the group consisting of —$NH_2$, —NH—$C_{1-4}$alkyl, —$N(C_{1-4}alkyl)_2$, —$NHR^{10d}$, —$NR^{10c}R^{10d}$; and wherein Ar is optionally substituted in the position indicated by β with a halo substituent;

$R^{10c}$ and $R^{10d}$ each independently represent $C_{1-4}$alkyl substituted with one, two or three halo substituents; or $C_{1-4}$alkyl substituted with one $C_{3-6}$cycloalkyl substituent;

and pharmaceutically acceptable addition salts, and solvates thereof.

In an embodiment, the present invention concerns novel compounds of Formula (I-a1)

(I-a1)

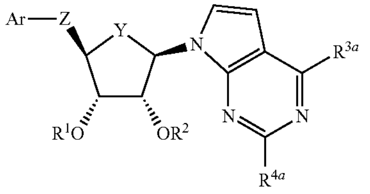

wherein $R^1$ and $R^2$ represent hydrogen;

$R^{3a}$ represents hydrogen, —$NR^{7a}R^{7b}$, or —$OC_{1-4}$alkyl;

$R^{7a}$ represents hydrogen;

$R^{7b}$ represents hydrogen or $C_{1-4}$alkyl;

Z represents —X—$CR^{5a}R^{5b}$— or —$CH_2CH_2$—;

$R^{5a}$ and $R^{5b}$ represent hydrogen; X represents —O—;

Y represents —O—, —$CH_2$— or —$CF_2$—; in particular —$CH_2$—;

$R^{4a}$ represents hydrogen; and

Ar represents

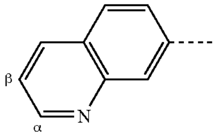

wherein Ar is optionally substituted in the position indicated by α with a substituent selected from the group consisting of —$NH_2$, —NH—$C_{1-4}$alkyl, —$N(C_{1-4}alkyl)_2$, —$NHR^{10d}$, —$NR^{10c}R^{10d}$; and wherein Ar is optionally substituted in the position indicated by β with a halo substituent;

$R^{10c}$ and $R^{10d}$ each independently represent $C_{1-4}$alkyl substituted with one, two or three halo substituents; or $C_{1-4}$alkyl substituted with one $C_{3-6}$cycloalkyl substituent;

and pharmaceutically acceptable addition salts, and solvates thereof.

In an embodiment, the present invention concerns novel compounds of Formula (I-a1)

(I-a1)

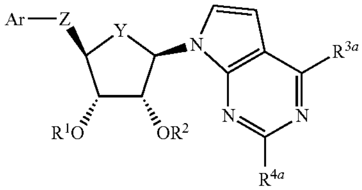

wherein $R^1$ and $R^2$ represent hydrogen;

$R^{3a}$ represents —$NR^{7a}R^{7b}$;

$R^{7a}$ represents hydrogen;

$R^{7b}$ represents hydrogen;

Z represents —X—$CR^{5a}R^{5b}$— or —$CH_2CH_2$—;

$R^{5a}$ and $R^{5b}$ represent hydrogen; X represents —O—;

Y represents —O— or —$CH_2$—;

$R^{4a}$ represents hydrogen; and

Ar represents

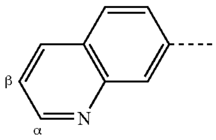

wherein Ar is optionally substituted in the position indicated by α with —$NH_2$; and wherein Ar is substituted in the position indicated by β with a halo substituent, in particular Br;

and pharmaceutically acceptable addition salts, and solvates thereof.

In an embodiment, the present invention relates to those compounds of Formula (I) and pharmaceutically acceptable addition salts, and solvates thereof, or any subgroup thereof as mentioned in any of the other embodiments, wherein Z represents —X—$CR^{5a}R^{5b}$— or —$CH_2CH_2$—.

In an embodiment, the present invention relates to those compounds of Formula (I) and pharmaceutically acceptable addition salts, and solvates thereof, or any subgroup thereof as mentioned in any of the other embodiments, wherein Z represents —X—$CR^{5a}R^{5b}$— or —$CH_2CH_2$—;

$R^{5a}$ and $R^{5b}$ represent hydrogen;

X represents —O—.

In an embodiment, the present invention relates to those compounds of Formula (I) and pharmaceutically acceptable addition salts, and solvates thereof, or any subgroup thereof as mentioned in any of the other embodiments, wherein Z represents —X—$CR^{5a}R^{5b}$— or —$CH_2CH_2$—;

$R^{5a}$ and $R^{5b}$ represent hydrogen;

X represents —O—;

Het represents (a-1).

In an embodiment, the present invention relates to those compounds of Formula (I) and pharmaceutically acceptable addition salts, and solvates thereof, or any subgroup thereof as mentioned in any of the other embodiments, wherein Z represents —X—$CR^{5a}R^{5b}$— or —$CH_2CH_2$—;

$R^{5a}$ and $R^{5b}$ represent hydrogen;

X represents —O—;

Het represents (a-1);

$R^{3a}$ represents —$NR^{7a}R^{7b}$;

$R^{7a}$ represents hydrogen;

$R^{7b}$ represents hydrogen.

In an embodiment, the present invention relates to those compounds of Formula (I) and pharmaceutically acceptable addition salts, and solvates thereof, or any subgroup thereof as mentioned in any of the other embodiments, wherein X represents —O—.

In an embodiment, the present invention relates to those compounds of Formula (I) and pharmaceutically acceptable addition salts, and solvates thereof, or any subgroup thereof as mentioned in any of the other embodiments, wherein Z represents —X—$CR^{5a}R^{5b}$— or —$CH_2CH_2$—;

$R^{5a}$ and $R^{5b}$ represent hydrogen;

X represents —O—;

Ar represents

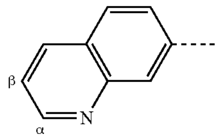

wherein Ar is optionally substituted in the position indicated by α with a substituent selected from the group consisting of —$NH_2$, —NH—$C_{1-4}$alkyl, and —$NHR^{10d}$; and wherein Ar is optionally substituted in the position indicated by β with a substituent selected from the group consisting of halo and $CF_3$;

provided however that Ar is substituted in at least one of the positions indicated by α or β;

Het represents (a-1), $R^{3a}$ represents —$NR^{7a}R^{7b}$;

$R^{7a}$ represents hydrogen;

$R^{7b}$ represents hydrogen.

In an embodiment, the present invention relates to those compounds of Formula (I) and pharmaceutically acceptable addition salts, and solvates thereof, or any subgroup thereof as mentioned in any of the other embodiments, wherein Het represents (a-1);

$R^{3a}$ represents —$NR^{7a}R^{7b}$;

$R^{7a}$ represents hydrogen;

$R^{7b}$ represents hydrogen.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3b}$, $R^{3c}$, $R^{3d}$ and $R^{3e}$ represent —$NR^{7a}R^{7b}$;

$R^{7a}$ represents hydrogen;

$R^{7b}$ represents hydrogen, $C_{3-6}$cycloalkyl, or $C_{1-4}$alkyl.

In an embodiment, the present invention relates to those compounds of Formula (I) and pharmaceutically acceptable addition salts, and solvates thereof, or any subgroup thereof as mentioned in any of the other embodiments, wherein $R^{3a}$, $R^{3b}$, $R^{3c}$, $R^{3d}$ and $R^{3e}$ represent —$NR^{7a}R^{7b}$;

$R^{7a}$ represents hydrogen;

$R^{7b}$ represents hydrogen.

In an embodiment, the present invention relates to those compounds of Formula (I) and pharmaceutically acceptable addition salts, and solvates thereof, or any subgroup thereof as mentioned in any of the other embodiments, wherein $R^{11}$ represents hydrogen, $C_{1-4}$alkyl, or $C_{1-4}$alkyl substituted with one substituent selected from the group consisting of —OH, —O—$C_{1-4}$alkyl, —$NH_2$, —NH—$C_{1-4}$alkyl, and —N($C_{1-4}$alkyl)$_2$; and $R^{10c}$ and $R^{10d}$ each independently represent $C_{3-6}$cycloalkyl; $R^{14}$; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, and $R^{14}$.

In an embodiment, the present invention relates to those compounds of Formula (I) and pharmaceutically acceptable addition salts, and solvates thereof, or any subgroup thereof as mentioned in any of the other embodiments, wherein Y represents —$CH_2$—; and Z represents —$CH_2CH_2$—.

In an embodiment, the present invention relates to a subgroup of Formula (I) as defined in the general reaction schemes.

In an embodiment the compound of Formula (I) is selected from the group consisting of compounds 2 and 58.

In an embodiment the compound of Formula (I) is selected from the group consisting of compounds 2 and 80.

In an embodiment the compound of Formula (I) is selected from the group consisting of compounds 74, 75, 76, 77, 78, 79, 80 and 81.

In an embodiment the compound of Formula (I) is selected from the group consisting of compounds 2, 58, 74, 75, 76, 77, 78, 79, 80, 81, 154, 159, 235, 240 and 247.

In an embodiment the compound of Formula (I) is selected from the group consisting of compounds 2 and 58, and pharmaceutically acceptable addition salts, and solvates thereof.

In an embodiment the compound of Formula (I) is selected from the group consisting of compounds 2 and 80, and pharmaceutically acceptable addition salts, and solvates thereof.

In an embodiment the compound of Formula (I) is selected from the group consisting of compounds 74, 75, 76, 77, 78, 79, 80 and 81, and pharmaceutically acceptable addition salts, and solvates thereof.

In an embodiment the compound of Formula (I) is selected from the group consisting of compounds 2, 58, 74, 75, 76, 77, 78, 79, 80, 81, 154, 159, 235, 240 and 247 and pharmaceutically acceptable addition salts, and solvates thereof.

In an embodiment the compound of Formula (I) is selected from the group consisting of any of the exemplified compounds, and the free bases, the pharmaceutically acceptable addition salts, and the solvates thereof.

All possible combinations of the above-indicated embodiments are considered to be embraced within the scope of this invention.

Methods for the Preparation

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The skilled person will realize that in the reactions described in the Schemes, it may be necessary to protect reactive functional groups, for example hydroxy, amino, or carboxy groups, where these are desired in the final product, to avoid their unwanted participation in the reactions. Conventional protecting groups can be used in accordance with standard practice. This is illustrated in the specific examples.

The skilled person will realize that in the reactions described in the Schemes, it may be advisable or necessary to perform the reaction under an inert atmosphere, such as for example under $N_2$-gas atmosphere, for example when NaH is used in the reaction.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of Formula (I).

The skilled person will realize that intermediates and compounds shown in the schemes below may be further functionalized according to methods well-known by the person skilled in the art.

The skilled person will realize that more Compounds of Formula (I) can be prepared by using similar synthetic protocols as described in the Schemes below.

In case one of the starting materials is available as a salt form, the skilled person will realize that it may be necessary to first treat the salt with a base, such as for example N,N-diisopropylethylamine (DIPEA).

All variables are defined as mentioned hereabove unless otherwise is indicated or is clear from the context.

The skilled person will understand that analogous chemistry as described in Schemes 1 to 9, may also be applied to make compounds of Formula (I) wherein Het represents a bicyclic aromatic heterocyclic rings system (a-4) or (a-5). Some typical examples are illustrated in the specific examples. In addition, this information may be combined with standard synthetic processes commonly used by those skilled in the art of organic chemistry to obtain more compounds of Formula (I) wherein Het represents (a-4) or (a-5).

In general, compounds of Formula (I) can be prepared according to Scheme 1:

General scheme 1

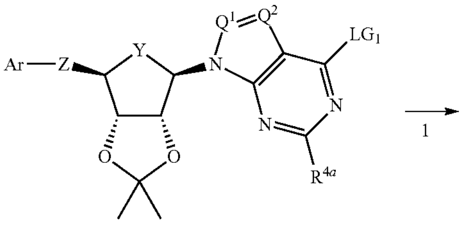

Int. II

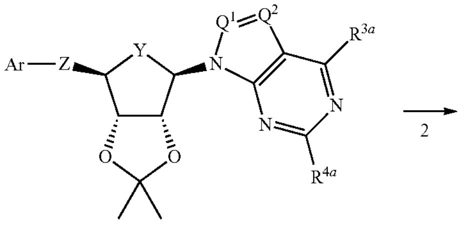

Int. III

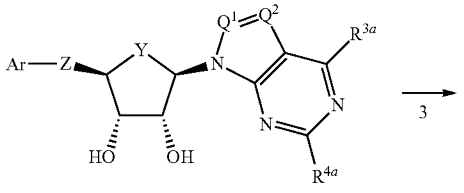

I-a

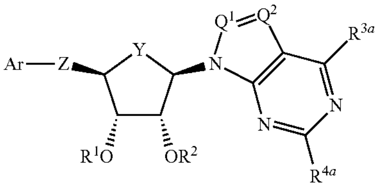

I-b

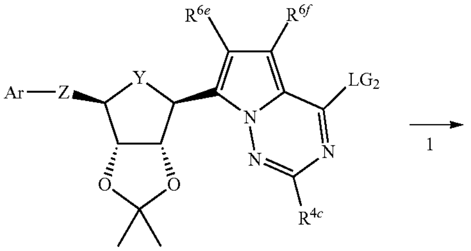

Int. IV

-continued

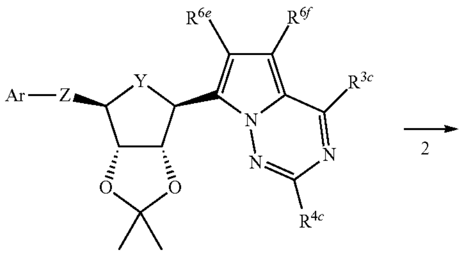

Int. V

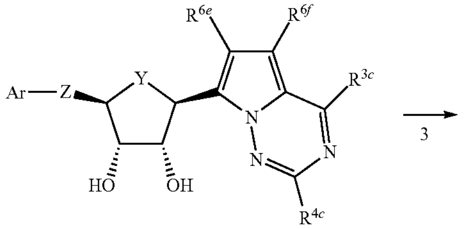

I-c

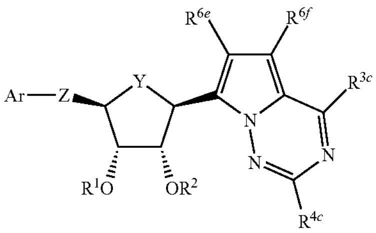

I-d

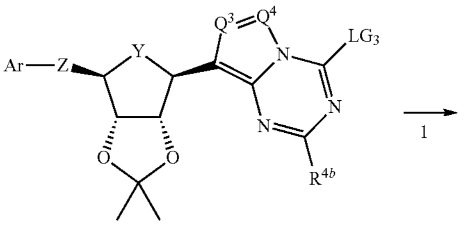

Int. VI

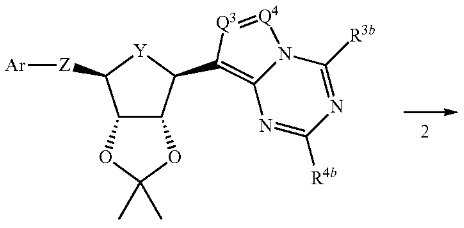

Int. VII

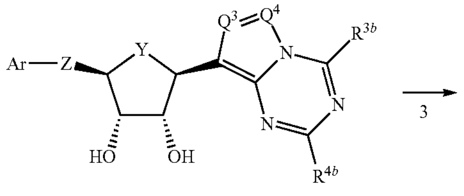

I-e

-continued

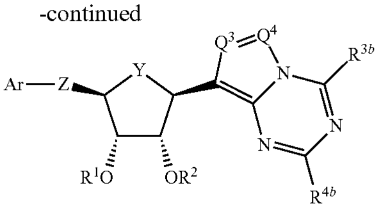

I-f

In scheme 1, '$LG_1$' is defined as a suitable leaving group such as for example halogen; '$LG_2$' is defined as a suitable leaving group such as for example halogen or —$SCH_3$. '$LG_3$' is defined as a leaving group such as halogen and —$SCH_3$. All other variables in Scheme 1 are defined according to the scope of the present invention.

In scheme 1, the following reaction conditions typically apply:

1: Different sets of reaction conditions dependent on the definition of $R^{3a}$, $R^{3b}$ or $R^{3c}$:

1a: When $R^{3a}$, $R^{3b}$ or $R^{3c}$ is halogen, step 1 can be skipped.

1b: When $R^{3a}$, $R^{3b}$ or $R^{3c}$ is $NR^{7a}R^{7b}$, in the presence of a suitable amine of formula $HNR^{7a}R^{7b}$, with a suitable solvent such as for example, $H_2O$, MeOH, or EtOH, at a suitable temperature such as for example between 100-130° C. typical under microwave conditions or using an autoclave vessel for heating.

1c: When $R^{3a}$, $R^{3b}$ or $R^{3c}$ is —O—$C_{1-4}$alkyl, in the presence of a suitable HO—$C_{1-4}$alkyl, with a suitable base such as for example NaH, potassium tert-butoxide (tBuOK) in a suitable solvent such as for example tetrahydrofuran (THF) at a suitable temperature. Alternatively in the presence of the suitable HO—$C_{1-4}$alkyl as solvent with a suitable acid such as for example HCl.

1d: When $R^{3a}$, $R^{3b}$ or $R^{3c}$ is hydrogen, under hydrogenation conditions: $H_2$-gas atmosphere in the presence of a catalyst such as for example Raney Ni, Pd/C (for example 5 wt % or 10 wt %) or Pt/C (for example 5 wt %) in a suitable solvent such as for example methanol (MeOH), ethanol (EtOH) or THF;

1e: When $R^{3a}$, $R^{3b}$ or $R^{3c}$ is $C_{1-4}$alkyl, in the presence of a suitable boronic acid or ester such as for example methylboronic acid with a suitable catalyst such as for example 1,1'-bis(diphenylphosphino)ferrocene and with a suitable base such as for example $K_3PO_4$ in a in a suitable solvent mixture such as for example dioxane/$H_2O$ ratio 5 to 1 at a suitable temperature such as for example 100° C.;

2: in the presence of a suitable acid, such as for example 4M HCl in dioxane or 4M HCl in MeOH, with a suitable solvent such as for example MeOH at a suitable temperature such as for example room temperature; or alternatively in the presence of a suitable acid such as for example trifluoroacetic acid (TFA) in dichloromethane (DCM) at a suitable temperature, or acetic acid in THF and water at a suitable temperature such as for example room temperature.

3: in the presence of suitable acid anhydride of formula $(C_{1-4}alkylC{=}O)_2O$ with a suitable solvent such as pyridine at a suitable temperature. When $R^{3a}$, $R^{3b}$ or $R^{3c}$ is $NH_2$, $(C_{1-4}alkylC{=}O)_2O$ can react with the $NH_2$ to obtain the $N(C_{1-4}alkylC{=}O)_2$ intermediate. Such an intermediate can be converted to the targeted product in a suitable solvent such as for example MeOH at a suitable temperature such as for example 100-130° C.

under microwave conditions or using an autoclave vessel for heating. The reaction may benefit from the presence of an acid, such as HCl or $C_{1-4}$ alkyl$CO_2H$.

The starting materials in scheme 1 are commercially available or can be prepared by standard means obvious to those skilled in the art or as described in following general schemes.

General scheme 2a

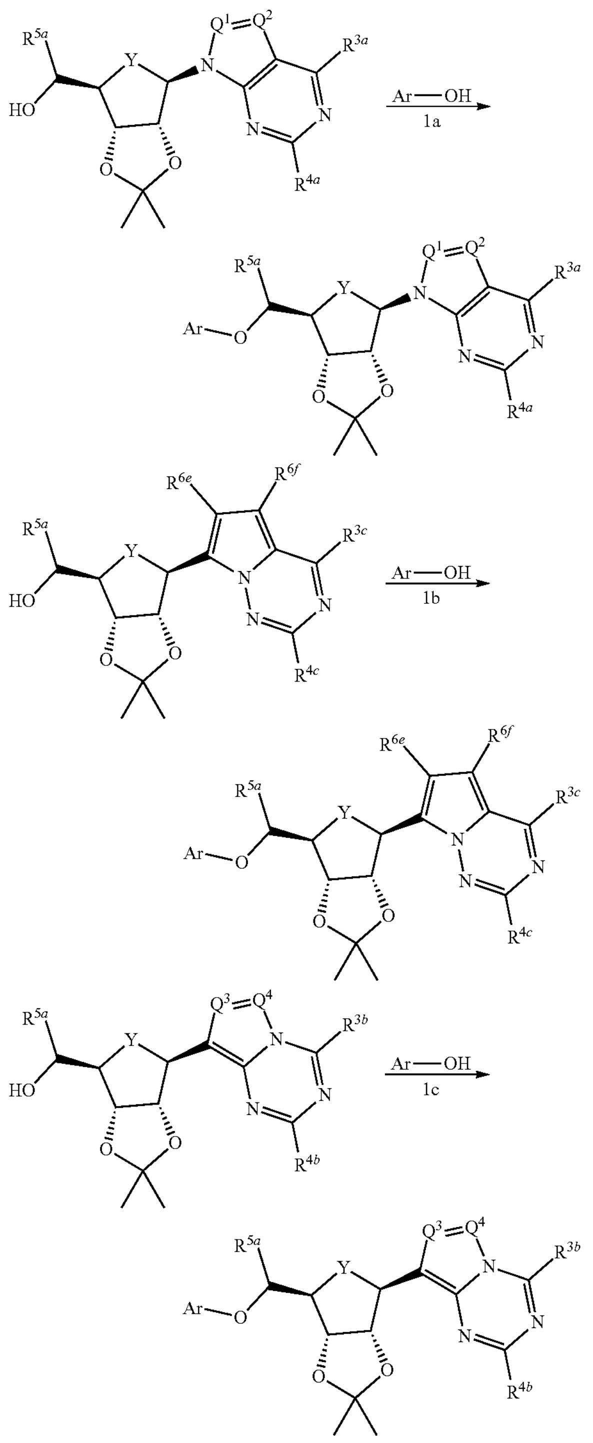

In general, intermediates of Formula III, V and VII wherein Z represents —O—$CHR^{5a}$— can be prepared according to Scheme 2a. All other variables in Scheme 2a are defined according to the scope of the present invention. The skilled person will realize a suitable protection group is needed when $R^{3a}$, $R^{3b}$ or $R^{3c}$ is —$NH_2$ or —$NHR^{7b}$;

In scheme 2a, the following reaction conditions apply:

1: The Mitsunobu reaction:

1a: In the presence of $PPh_3$-Polymer supported, diisopropyl azodicarboxylate (DIAD) or diethyl azodicarboxylate (DEAD) or Bis(1,1-dimethylethyl)-azodicarboxylate (DBAD) in a suitable solvent such as for example anhydrous THF at a suitable temperature such as for example room temperature.

1b: In the presence of triphenylphosphine ($PPh_3$), DIAD or DEAD in a suitable solvent such as for example anhydrous THF at a suitable temperature such as for example room temperature.

1c: In the presence of cyanomethylenetributylphosphorane (CMBP) or cyanomethylenetrimethylphosphorane (CMMP), in a suitable solvent such as for example anhydrous toluene at a suitable temperature such as for example 80° C.

The starting materials in scheme 2a are commercially available or can be prepared by standard means obvious to those skilled in the art or as described in following general schemes. The skilled person will realize that when $R^5$ is $C_{1-4}$alkyl, the different isomers can be separated from each other by using Reversed-Phase High-Performance Liquid Chromatography (RP-HPLC) or Supercritical Fluid Chromatography (SFC).

General scheme 2b

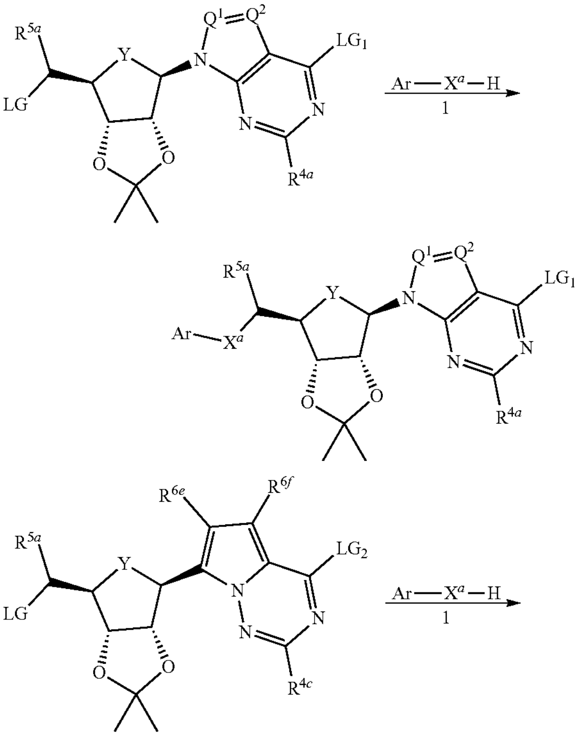

-continued

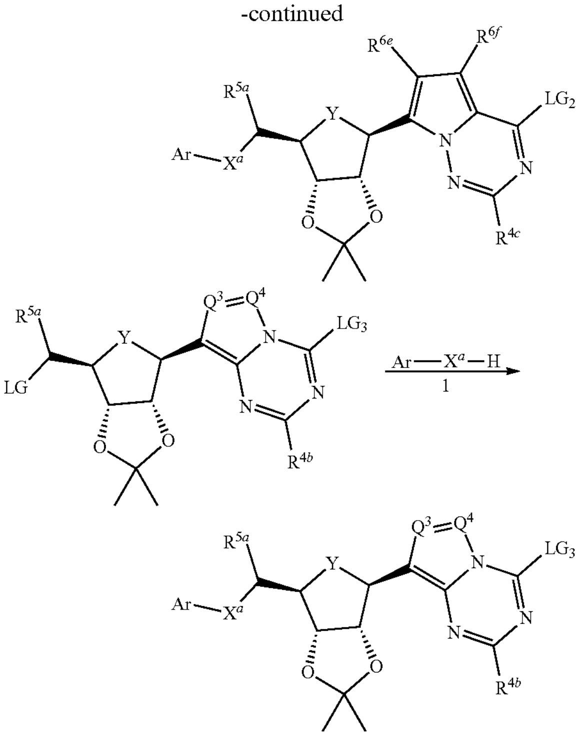

Int. VI

Intermediates of Formula II, IV and VI wherein Z represents —$X^a$—$CHR^{5a}$— can be prepared according to Scheme 2b. In scheme 2b, 'X' is defined as O or S; 'LG' is defined as a leaving group such as for example halogen, mesylate (MsO) and tosylate (TosO), preferably TosO. '$LG_1$' is defined as leaving group such as for example halogen; '$LG_2$' is defined as a leaving group such as for example halogen or —$SCH_3$. '$LG_3$' is defined as a leaving group such as for example halogen or —$SCH_3$. All other variables in Scheme 2b are defined according to the scope of the present invention.

In scheme 2b, the following reaction conditions apply:

1: in the presence of a base such as for example $K_2CO_3$, trietylamine ($Et_3N$) or DIPEA, in a suitable solvent such as $CH_3CN$, DCM or N,N-dimethylacetamide (DMA).

The starting materials in scheme 2b are commercially available or can be prepared by standard means obvious to those skilled in the art or as described in following general schemes. The skilled person will realize that when $R^{5a}$ is $C_{1-4}$alkyl, the different isomers can be separated from each other by using Reversed-Phase High-Performance Liquid Chromatography (RP-HPLC) or Supercritical Fluid Chromatography (SFC).

General scheme 2c

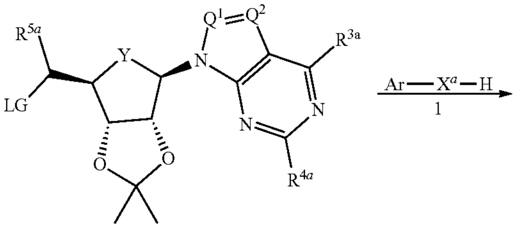

-continued

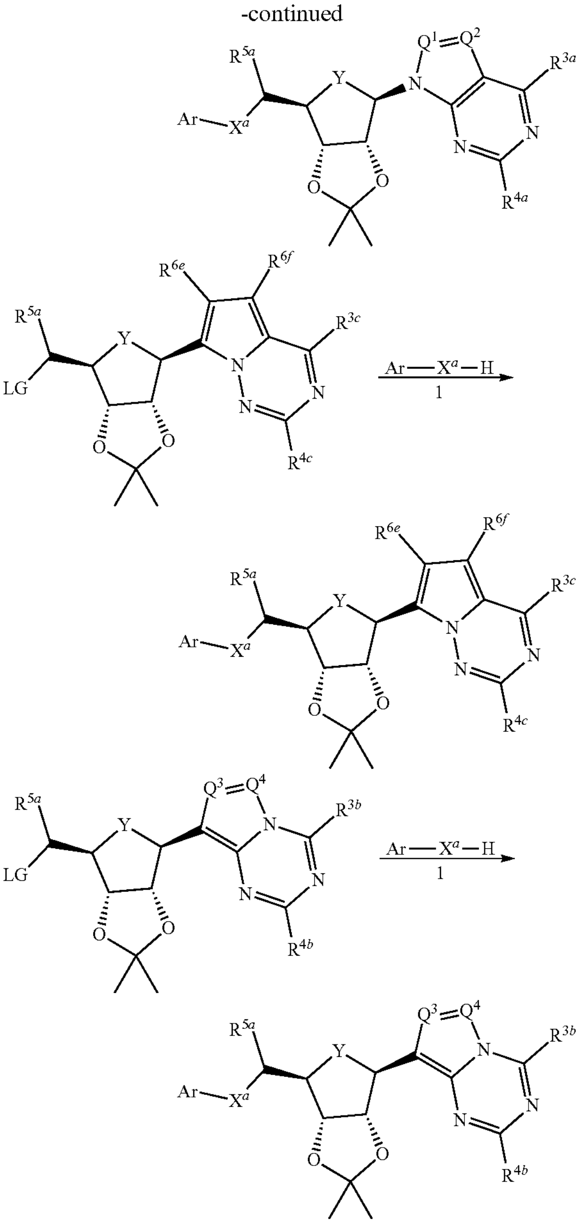

Intermediates III, V and VII wherein Z represents —$X^a$—$CHR^{5a}$— can be prepared according to Scheme 2c. In scheme 2c, 'X' is defined as O or S. 'LG' is defined as a leaving group such as for example halogen, MsO or TosO, preferably TosO. All other variables in Scheme 2c are defined according to the scope of the present invention. The skilled person will realize that a suitable protection group is needed when $R^{3a}$, $R^{3b}$ or $R^{3c}$ is —$NH_2$ or —$NHR^{7b}$.

In scheme 2c, the following reaction conditions apply:

1: in the presence of a base such as for example $K_2CO_3$, $Et_3N$ or DIPEA, in a suitable solvent such as $CH_3CN$, DCM or N,N-dimethylacetamide (DMA).

The starting materials in scheme 2c are commercially available or can be prepared by standard means obvious to those skilled in the art or as described in following general schemes. The skilled person will realize that when $R^5$ is $C_{1-4}$alkyl, the different isomers can be separated from each other by using Reversed-Phase High-Performance Liquid Chromatography (RP-HPLC) or Supercritical Fluid Chromatography (SFC).

General scheme 3

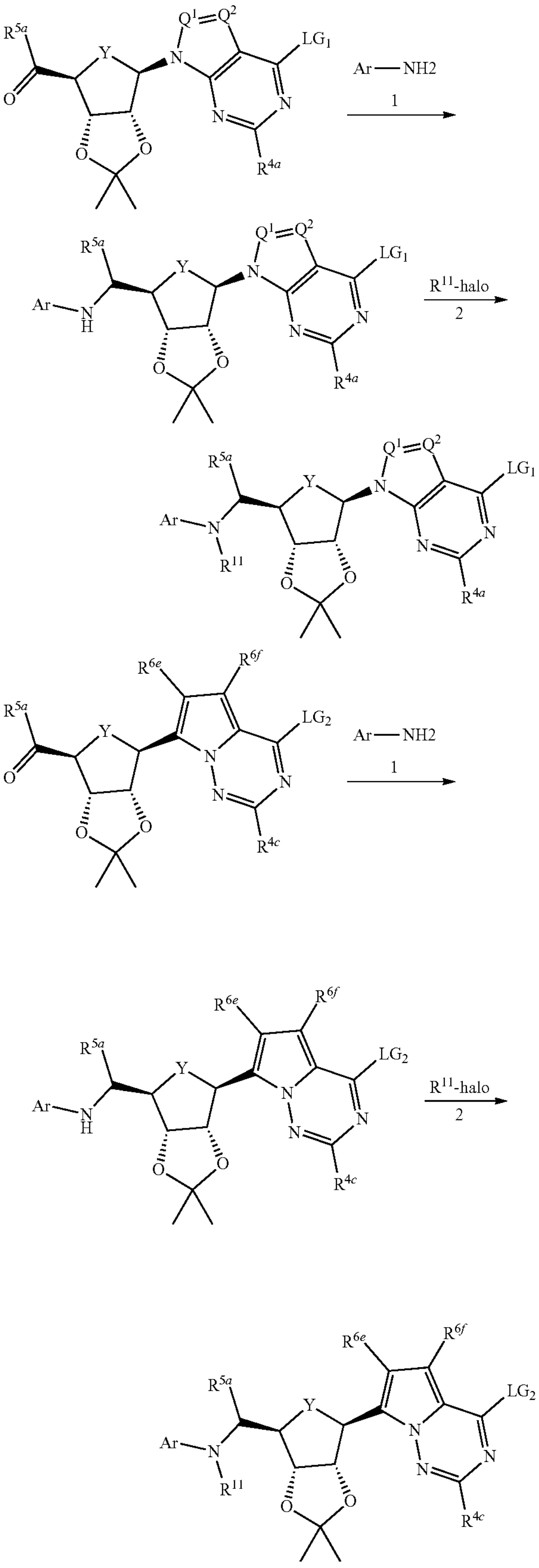

-continued

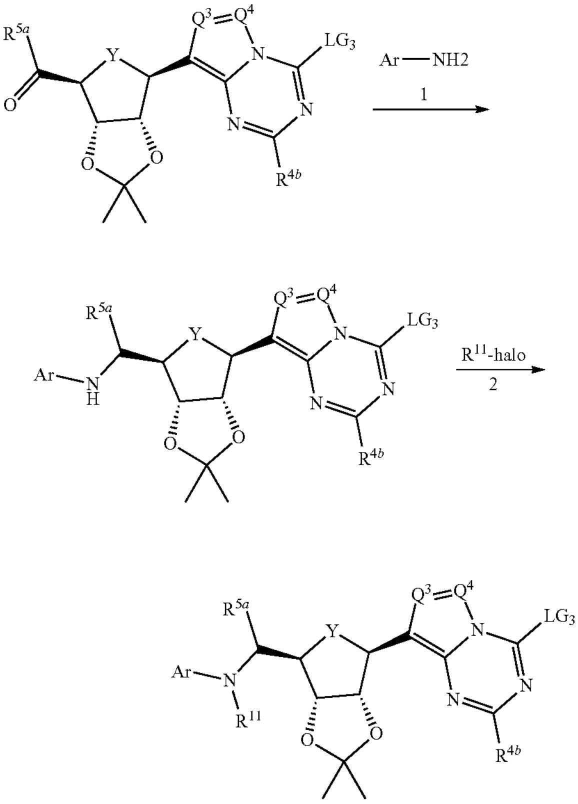

In general, intermediates wherein Z represents —X—$CHR^{5a}$—; and wherein X represents —NH— or —$NR^{11}$— can be prepared according to Scheme 3. In scheme 3, '$LG_1$' is defined as a leaving group such as for example halogen; '$LG_2$' is defined as a leaving group such as for example halogen or —$SCH_3$. '$LG_3$' is defined as a leaving group such as for example halogen or —$SCH_3$. All other variables in Scheme 3 are defined according to the scope of the present invention.

In scheme 3, the following reaction conditions apply:

1: in the presence of a suitable reduction reagent such as for example sodium triacetoxyborohydride (NaBH$(AcO)_3$) together with a suitable solvent such as for example DCM at a suitable temperature such as for example room temperature; or alternatively $NaBH_3CN$ together with a suitable solvent such as for example MeOH at a suitable temperature such as for example between room temperature and 50° C.

2: in the presence of a suitable base such as for example NaH together with a suitable solvent such as for example anhydrous THF, N,N-dimethylformamide (DMF), DMA at a suitable temperature such as for example between room temperature and 50° C.

The starting materials in scheme 3 are commercially available or can be prepared by standard means obvious to those skilled in the art or as described in the specific experimental part. The skilled person will realize that when $R^{5a}$ is $C_{1-4}$alkyl, the different isomers can be separated from each other by using Reversed-Phase High-Performance Liquid Chromatography (RP-HPLC) or Supercritical Fluid Chromatography (SFC).

General scheme 4

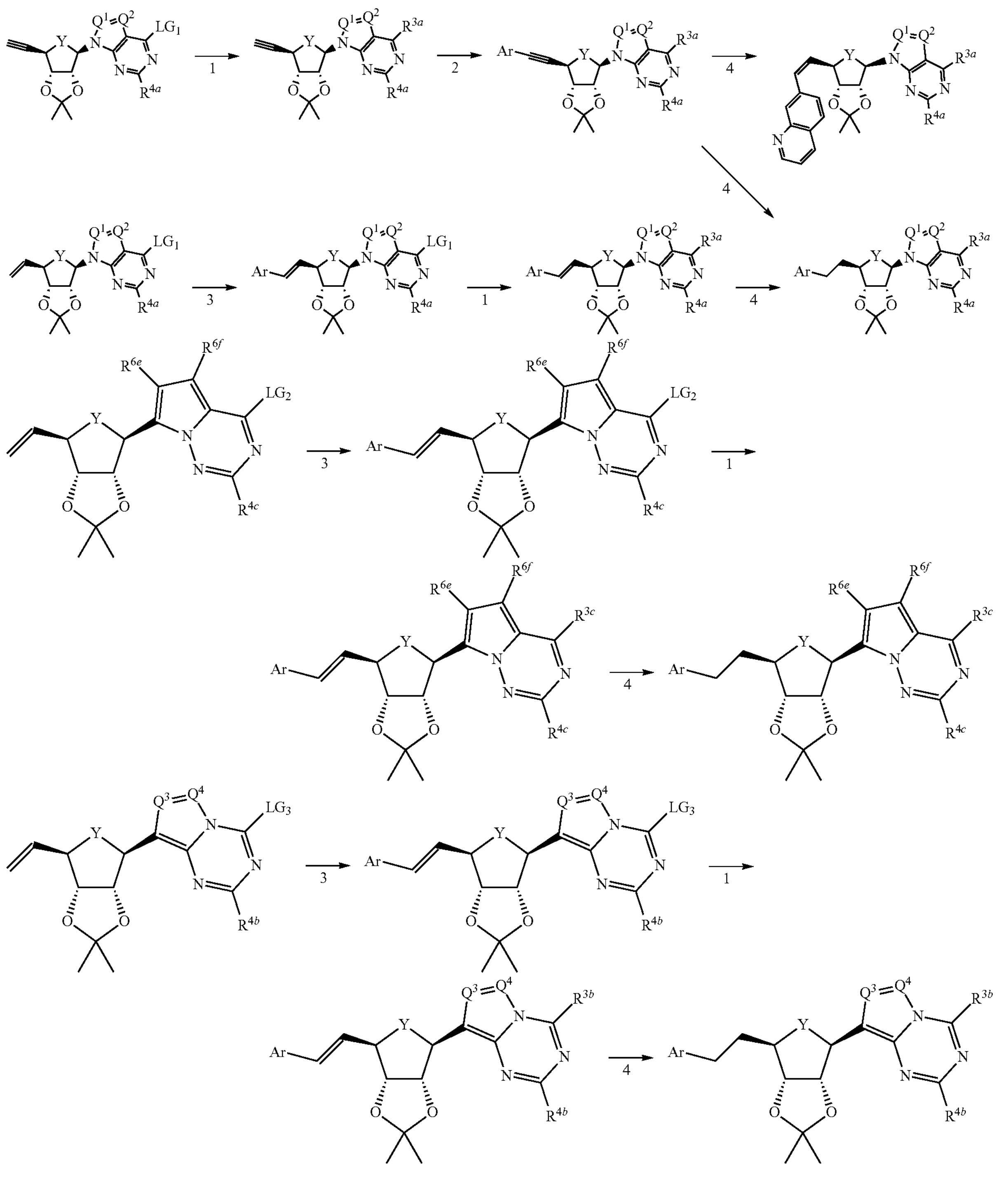

In general, intermediates wherein Z represents —CH≡CH—, or —$CH_2$—$CH_2$— can be prepared according to Scheme 4. In scheme 4, '$LG_1$' is defined as a leaving group such as for example halogen; '$LG_2$' is defined as a leaving group such as for example halogen or —$SCH_3$. '$LG_3$' is defined as leaving group such as for example halogen or —$SCH_3$. All other variables in Scheme 4 are defined according to the scope of the present invention.

In scheme 4, the following reaction conditions apply:

1: In the presence of suitable amine, such as HNR'R" or NaOR', with a suitable solvent such as for example $H_2O$, MeOH, or EtOH at a suitable temperature such as for example between 100-130° C. under microwave condition or using an autoclave vessel for heating.

2: In the presence of suitable catalyst, such as bis(triphenylphosphine)palladium(II) dichloride and copper(I) iodide in a suitable solvent, such as 2-methyltetrahydrofuran with a suitable base, such as for example triethylamine at a suitable temperature, such as for example 80° C.

3: in the presence of a suitable salt, such as for example tetraethylammonium chloride ($Et_4NCl$), in a suitable solvent, such as for example DMF, with a suitable base such as for example DIPEA and a palladium catalyst, such as for example $Pd(OAc)_2$ (palladium(II) acetate) at suitable temperature such as for example 100° C.

4: in the presence of a $H_2$-gas atmosphere and a catalyst such as for example Pd/C (for example 5 wt % or 10 wt %) in a suitable solvent such as for example MeOH.

The starting materials in scheme 4 are commercially available or can be prepared by standard means obvious to those skilled in the art or as described in the specific experimental part.

General scheme 5

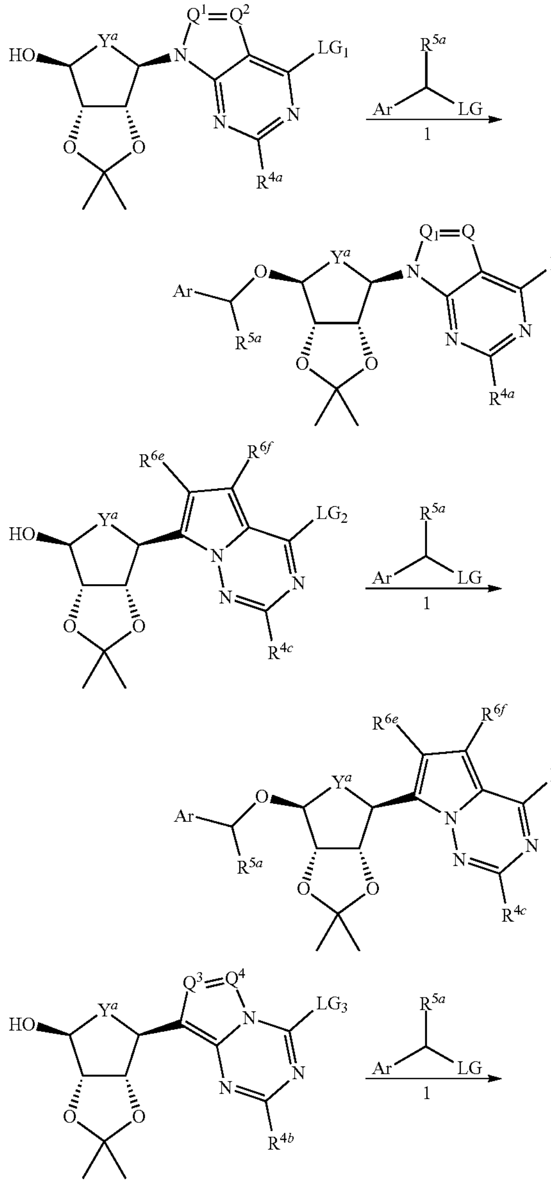

-continued

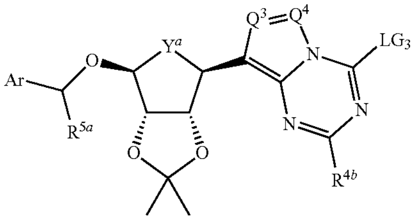

In general, intermediates wherein Y represents $CH_2$ or $CF_2$, hereby named $Y^a$, and wherein Z represents —$CH_2O$— can be prepared according to Scheme 5.

In scheme 5, '$LD_1$' is defined as a leaving group such as for example halogen; '$LG_2$' is defined as a leaving group such as for example halogen or —$SCH_3$. '$LG_3$' is defined as leaving group such as halogen or —$SCH_3$. All other variables in Scheme 5 are defined according to the scope of the present invention.

In scheme 5, the following reaction conditions apply:

1: in the presence of a base such as for example $K_2CO_3$, $Et_3N$ or DIPEA, in a suitable solvent such as $CH_3CN$, DCM or N,N-dimethylacetamide (DMA).

General scheme 6

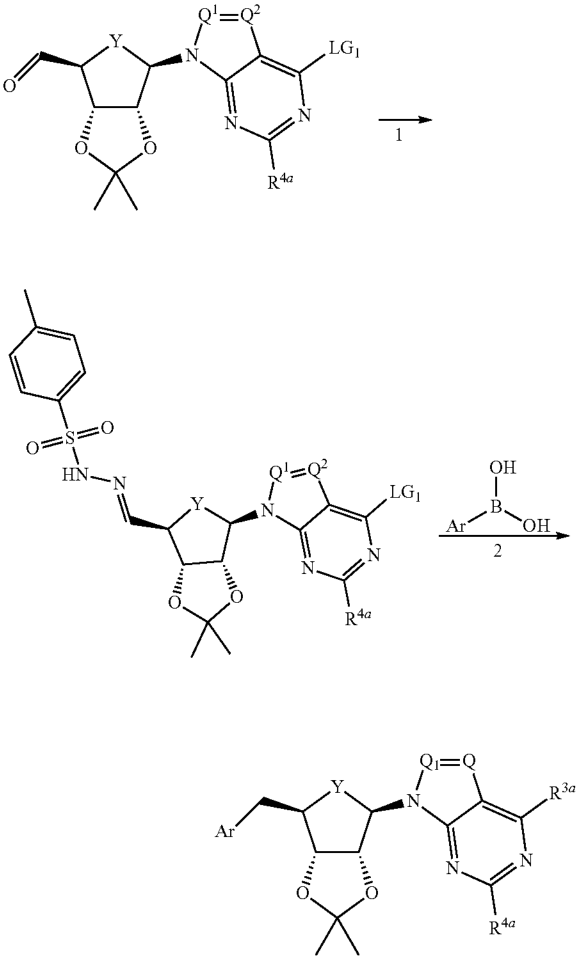

-continued

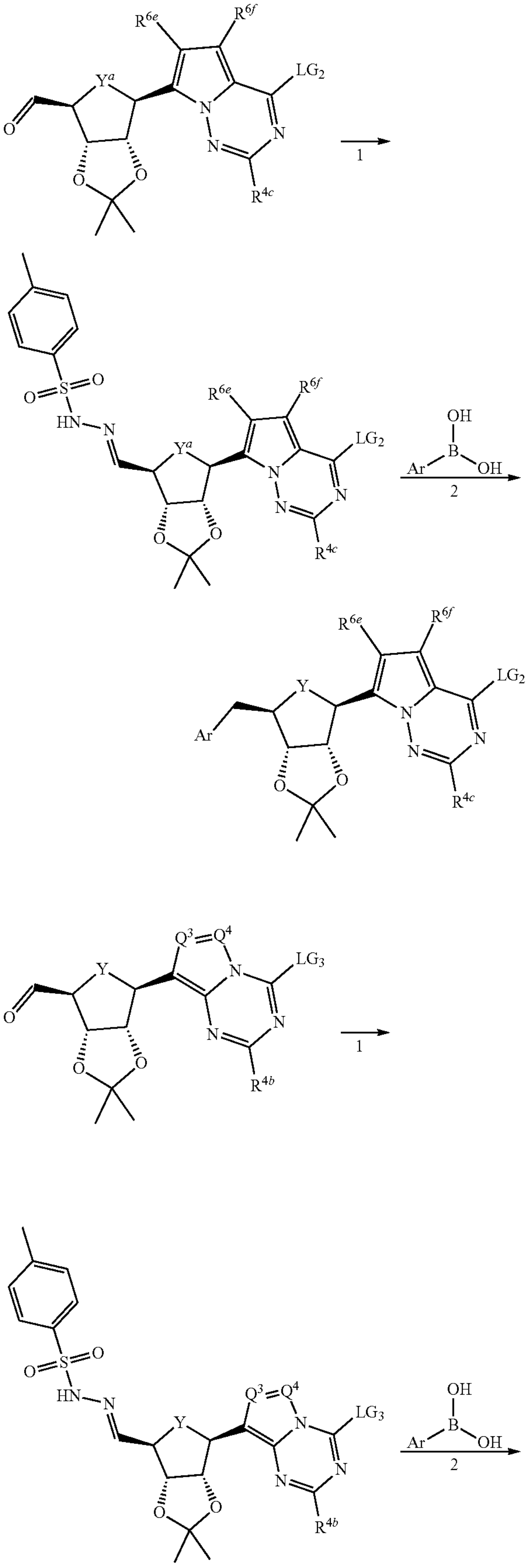

-continued

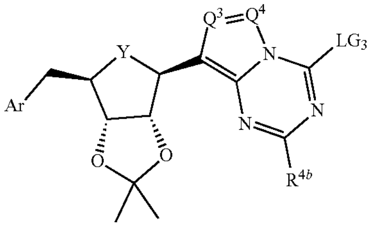

In general, intermediates wherein Z represents —$CH_2$— can be prepared according to Scheme 6. In scheme 6, '$LG_1$' is defined as a leaving group such as for example halogen; '$LG_2$' is defined as a leaving group such for example halogen or —$SCH_3$. '$LG_3$' is defined as a leaving group such as for example halogen or —$SCH_3$. All other variables in Scheme 6 are defined according to the scope of the present invention.

In scheme 6, the following reaction conditions apply:

1: In the presence of tosylhydrazide, with a suitable solvent such as for example, MeOH, EtOH, or DCM at a suitable temperature such as room temperature.

2: In the presence of Boronic acids, with suitable base such as $K_2CO_3$, $Na_2CO_3$, $Cs_2CO_3$, with a suitable solvent such as for example, 1,4-dioxane at a suitable temperature such 90° C.

The starting materials in scheme 6 are commercially available or can be prepared by standard means obvious to those skilled in the art or as described in the specific experimental part.

General scheme 7

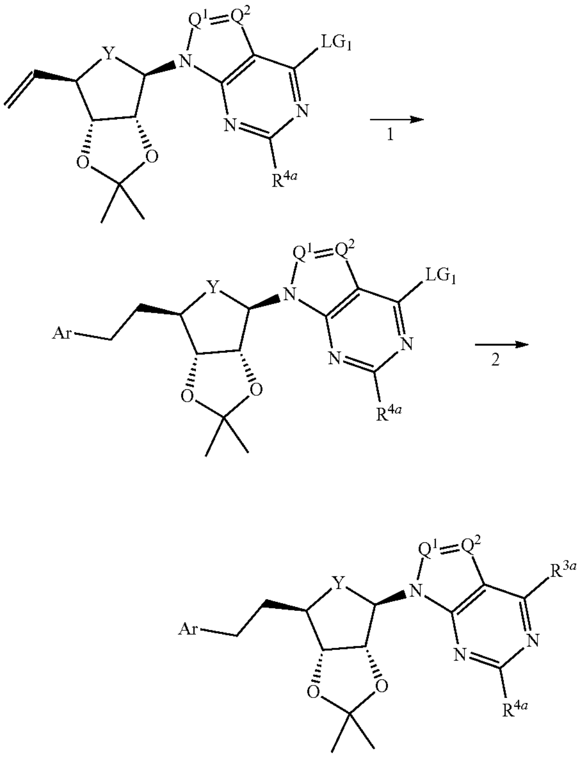

-continued

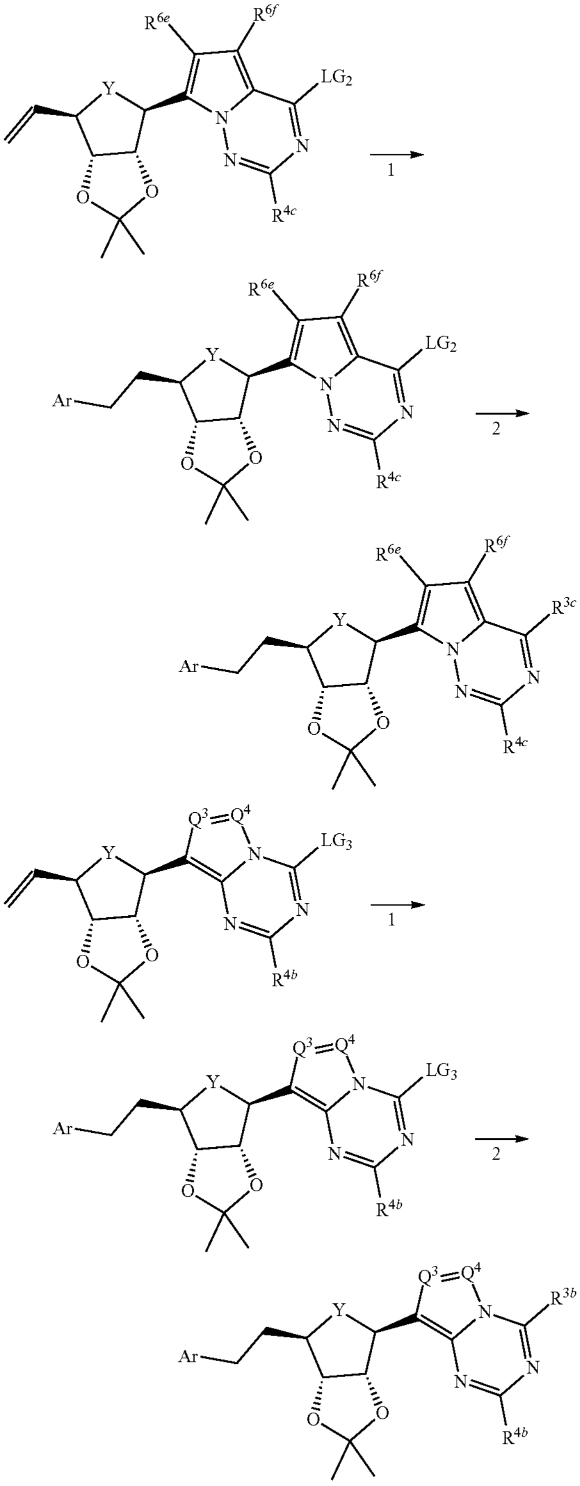

In general, intermediates wherein Z represents —$CH_2$—$CH_2$— can be prepared according to Scheme 7. In scheme 7, '$LG_1$' is defined as a leaving group such as for example halogen; '$LG_2$' is defined as a leaving group such as for example halogen or —$SCH_3$. '$LG_3$' is defined as leaving group such as for example halogen or —$SCH_3$. All other variables in Scheme 7 are defined according to the scope of the present invention.

In scheme 7, the following reaction conditions typically apply:

1: In a first step in the presence of an alkene precursor and a 9-Borabicyclo(3.3.1)nonane (9-BBN) solution 0.5 M in THF under nitrogen atmosphere at a temperature between room temperature and reflux and a reaction time between 1 to 3 hours. In a second step in the presence of, for example, a suitable Ar-bromide or Ar-iodide and a suitable catalyst as for example 1,1'-bis(diphenylphosphino)ferrocene]dichloropalladium (II) and in the presence of a suitable base as for example potassium phosphate tribasic in a suitable solvent mixture as for example THF and water at a suitable temperature between 50° C. and reflux and a suitable reaction time between 1 and 3 hours.

2: Different sets of reaction conditions dependent on the definition of $R^{3a}$, $R^{3b}$ or $R^{3c}$:

2a: When $R^{3a}$, $R^{3b}$ or $R^{3c}$ is halogen, step 1 can be skipped.

2b: When $R^{3a}$, $R^{3b}$ or $R^{3c}$ is $NR^{7a}R^{7b}$, in the presence of a suitable amine of formula $HNR^{7a}R^{7b}$, with a suitable solvent such as for example, $H_2O$, MeOH, or EtOH, at a suitable temperature such as for example between 100-130° C. typical under microwave conditions or using an autoclave vessel for heating.

2c: When $R^{3a}$, $R^{3b}$ or $R^{3c}$ is —O—$C_{1-4}$alkyl, in the presence of a suitable HO—$C_{1-4}$alkyl, with a suitable base such as for example NaH, potassium tert-butoxide (tBuOK) in a suitable solvent such as for example tetrahydrofuran (THF) at a suitable temperature. Alternatively in the presence of the suitable HO—$C_{1-4}$alkyl as solvent with a suitable acid such as for example HCl.

2d: When $R^{3a}$, $R^{3b}$ or $R^{3c}$ is hydrogen, under hydrogenation conditions: $H_2$-gas atmosphere in the presence of a catalyst such as for example Raney Ni, Pd/C (for example 5 wt % or 10 wt %) or Pt/C (for example 5 wt %) in a suitable solvent such as for example methanol (MeOH), ethanol (EtOH) or THF;

2e: When $R^{3a}$, $R^{3b}$ or $R^{3c}$ is $C_{1-4}$alkyl, in the presence of a suitable boronic acid or ester such as for example methylboronic acid with a suitable catalyst such as for example 1,1'-bis(diphenylphosphino)ferrocene and with a suitable base such as for example $K_3PO_4$ in a in a suitable solvent mixture such as for example dioxane/$H_2O$ ratio 5 to 1 at a suitable temperature such as for example 100° C.

The starting materials in scheme 7 are commercially available or can be prepared by standard means obvious to those skilled in the art or as described in the specific experimental part.

General scheme 8

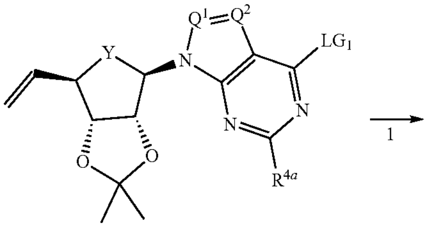

-continued

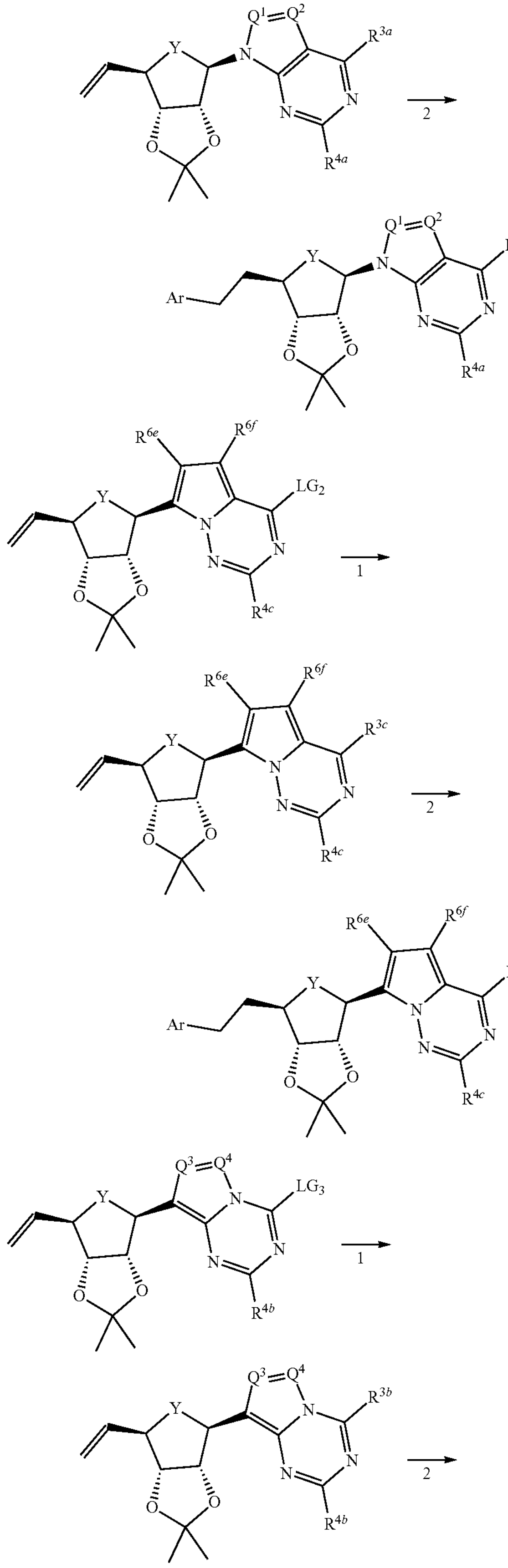

-continued

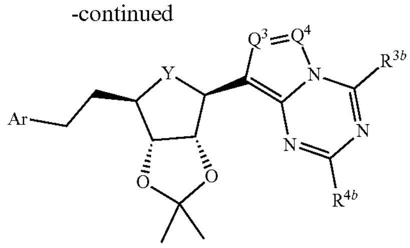

In general, intermediates wherein Z represents —$CH_2$—$CH_2$— can be prepared according to Scheme 8. In scheme 8, '$LG_1$' is defined as a leaving group such as for example halogen; '$LG_2$' is defined as a leaving group such as for example halogen or —$SCH_3$. '$LG_3$' is defined as leaving group such as for example halogen or —$SCH_3$. All other variables in Scheme 8 are defined according to the scope of the present invention.

In scheme 8, the following reaction conditions typically apply:

1: Different sets of reaction conditions dependent on the definition of $R^{3a}$, $R^{3b}$ or $R^{3c}$:

1a: When $R^{3a}$, $R^{3b}$ or $R^{3c}$ is halogen, step 1 can be skipped.

1b: When $R^{3a}$, $R^{3b}$ or $R^{3c}$ is $NR^{7a}R^{7b}$, in the presence of a suitable amine of formula $HNR^{7a}R^{7b}$, with a suitable solvent such as for example, $H_2O$, MeOH, or EtOH, at a suitable temperature such as for example between 100-130° C. typical under microwave conditions or using an autoclave vessel for heating.

1c: When $R^{3a}$, $R^{3b}$ or $R^{3c}$ is —O—$C_{1-4}$alkyl, in the presence of a suitable HO—$C_{1-4}$alkyl, with a suitable base such as for example NaH, potassium tert-butoxide (tBuOK) in a suitable solvent such as for example tetrahydrofuran (THE) at a suitable temperature. Alternatively in the presence of the suitable HO—$C_{1-4}$alkyl as solvent with a suitable acid such as for example HCl.

1d: When $R^{3a}$, $R^{3b}$ or $R^{3c}$ is hydrogen, under hydrogenation conditions: $H_2$-gas atmosphere in the presence of a catalyst such as for example Raney Ni, Pd/C (for example 5 wt % or 10 wt %) or Pt/C (for example 5 wt %) in a suitable solvent such as for example methanol (MeOH), ethanol (EtOH) or THF;

1e: When $R^{3a}$, $R^{3b}$ or $R^{3c}$ is $C_{1-4}$alkyl, in the presence of a suitable boronic acid or ester such as for example methylboronic acid with a suitable catalyst such as for example 1,1'-bis(diphenylphosphino)ferrocene and with a suitable base such as for example $K_3PO_4$ in a in a suitable solvent mixture such as for example dioxane/$H_2O$ ratio 5 to 1 at a suitable temperature such as for example 100° C.;

2: In a first step in the presence of an alkene precursor and a 9-BBN solution 0.5 M in THF under nitrogen atmosphere at a temperature between room temperature and reflux and a reaction time between 1 to 3 hours. In a second step in the presence of suitable (het)arylbromide or (het)aryliodide and a suitable catalyst as for example 1,1'-bis(diphenylphosphino)ferrocene]dichloropalladium(II) and in the presence of a suitable base as for example potassium phosphate tribasic in a suitable solvent mixture as for example THF and water at a suitable temperature between 50° C. and reflux and a suitable reaction time between 1 and 3 hours.

The starting materials in scheme 8 are commercially available or can be prepared by standard means obvious to those skilled in the art or as described in the specific experimental part.

General scheme 9

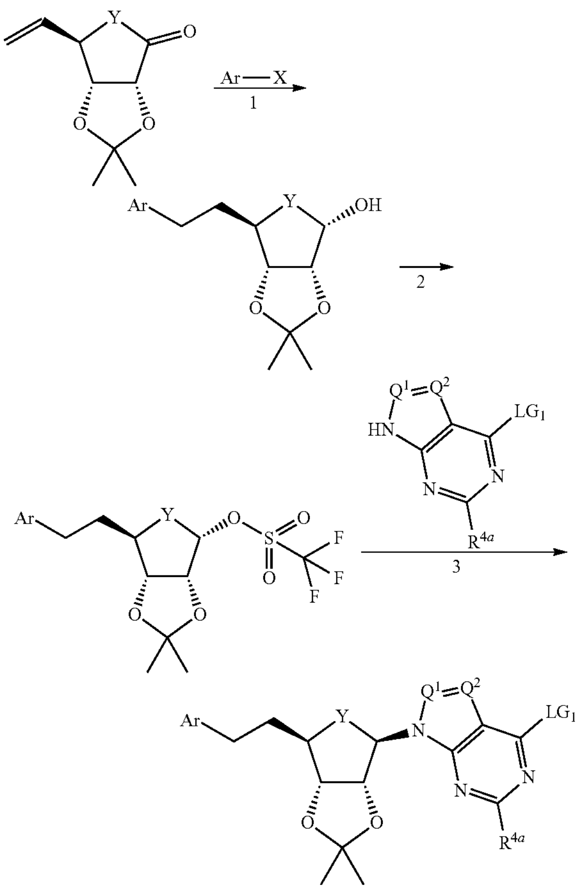

In general, intermediates as shown in Scheme 9 wherein Z represents —$CH_2$—$CH_2$— can be prepared according to Scheme 9. In scheme 9, '$LG_1$' is defined as a leaving group such as for example halogen. All other variables in Scheme 9 are defined according to the scope of the present invention 1: In a first step in the presence of an alkene precursor and a 9-BBN solution 0.5 M in THF under nitrogen atmosphere at a temperature between room temperature and reflux and a reaction time between 1 to 3 hours. In a second step in the presence of, for example, a suitable Ar-bromide or Ar-iodide (X being Br or I respectively) and a suitable catalyst as for example 1,1'-bis(diphenylphosphino)ferrocene]dichloropalladium(II) and in the presence of a suitable base as for example potassium phosphate tribasic in a suitable solvent mixture as for example THF and water at a suitable temperature between 50° C. and reflux and a suitable reaction time between 1 and 3 hours.

2: In the presence of triflic anhydride and a suitable base as for example pyridine in a suitable solvent as for example DCM at a suitable temperature as for example 0° C. under an inert atmosphere of Na gas.

3: In the presence of a suitable base as for example $Cs_2CO_3$ in a suitable solvent as for example DMF at a suitable temperature as for example room temperature under an inert atmosphere of Na gas.

The starting materials in scheme 9 are commercially available or can be prepared by standard means obvious to those skilled in the art or as described in the specific experimental part.

In all these preparations, the reaction products may be isolated from the reaction medium and, if necessary, further purified according to methodologies generally known in the art such as, for example, extraction, crystallization, trituration and chromatography.

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

Pharmacology

It has been found that the compounds of the present invention inhibit PRMT5 activity.

In particular compounds of the present invention bind to the PRMT5 enzyme, and competitively with natural substrate SAM (S-adenosyl-L-methionine), to inhibit such enzyme.

It is therefore anticipated that the compounds according to the present invention or pharmaceutical compositions thereof may be useful for treating or preventing, in particular treating, of diseases such as a blood disorder, metabolic disorders, autoimmune disorders, cancer, inflammatory diseases, cardiovascular diseases, neurodegenerative diseases, pancreatitis, multiorgan failure, kidney diseases, platelet aggregation, sperm motility, transplantation rejection, graft rejection, lung injuries and the like.

In particular the compounds according to the present invention or pharmaceutical compositions thereof may be useful for treating or preventing, in particular treating, of diseases such as allergy, asthma, hematopoietic cancer, lung cancer, prostate cancer, melanoma, metabolic disorder, diabetes, obesity, blood disorder, sickle cell anemia, and the like.

The compounds according to the present invention or pharmaceutical compositions thereof may be useful for treating or preventing, in particular treating, of diseases such as a proliferative disorder, such as an autoimmune disease, cancer, a benign neoplasm, or an inflammatory disease.

The compounds according to the present invention or pharmaceutical compositions thereof may be useful for treating or preventing, in particular treating, of diseases such as a metabolic disorder comprising diabetes, obesity; a proliferative disorder comprising cancer, hematopoietic cancer, lung cancer, prostate cancer, melanoma, or pancreatic cancer; blood disorder; hemoglobinopathy; sickle cell anemia; β-thalessemia, an inflammatory disease, and autoimmune disease e.g. rheumatoid arthritis, systemic lupus erythematosus, Sjogren's syndrome, diarrhea, gastroesophageal reflux disease, and the like.

In some embodiments, the inhibition of PRMT5 by a provided compound may be useful in treating or preventing, in particular treating, the following non-limiting list of cancers: breast cancer, lung cancer, esophageal cancer, bladder cancer, hematopoietic cancer, lymphoma, medulloblastoma, rectum adenocarcinoma, colon adenocarcinoma, gastric cancer, pancreatic cancer, liver cancer, adenoid cystic carcinoma, lung adenocarcinoma, head and neck squamous cell carcinoma, brain tumors, hepatocellular carcinoma, renal cell carcinoma, melanoma, oligodendroglioma, ovarian clear cell carcinoma, and ovarian serous cystadenoma.

Examples of metabolic disorders which may be treated or prevented, in particular treated, include, but are not limited to, diabetes or obesity.

Examples of blood disorders which may be treated or prevented, in particular treated, include, but are not limited to, hemoglobinopathy, such as sickle cell disease or β-thalassemia.

Examples of cancers which may be treated or prevented, in particular treated, include, but are not limited to, acoustic neuroma, adenocarcinoma, adrenal gland cancer, anal cancer, angiosarcoma (e.g., lymphangio sarcoma, lymphangioendothelio sarcoma, hemangio sarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), chordoma, choriocarcinoma, craniopharyngioma, colorectal cancer (e.g., colon cancer, rectal cancer, colorectal adenocarcinoma), epithelial carcinoma, ependymoma, endothelio sarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., pharyngeal cancer, laryngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macro globulinemia"), immunoblastic large cell lymphoma, hairy cell leukemia (HCL), precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, non-small cell lung cancer (NSCLC), squamous lung cancer (SLC), adenocarcinoma of the lung, Lewis lung carcinoma, lung neuroendocrine tumors: typical carcinoid, atypical carcinoid, small cell lung cancer (SCLC), and large cell neuroendocrine carcinoma), leiomyosarcoma (LMS), mastocytosis (e.g., systemic mastocytosis), myelodysplastic syndromes (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer, and vulvar cancer (e.g. Paget's disease of the vulva).

Examples of neurodegenerative diseases which may be treated or prevented, in particular treated, include, but are not limited to, motor neurone disease, progressive supranuclear palsy, corticobasal degeneration, Pick's disease, Alzheimer's disease, AIDS-related dementia, Parkinson's disease, amyotropic lateral sclerosis, retinitis pigmentosa, spinal muscular atropy, and cerebellar degeneration.

Examples of cardiovascular diseases which may be treated or prevented, in particular treated, include, but are not limited to, cardiac hypertrophy, restenosis, atherosclerosis, and glomerulonephritis.

Examples of inflammatory diseases which may be treated or prevented, in particular treated, include, but are not limited to, inflammation associated with acne, anemia (e.g., aplastic anemia, haemolytic autoimmune anaemia), rhinitis, asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), upper respiratory tract disease, ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, diverticulitis, cermatomyositis, diabetes (e.g., type I diabetes mellitus, type 2 diabetes mellitus), a skin condition (e.g., psoriasis, eczema, eczema hypersensitivity reactions, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, morphea, myeasthenia gravis, myocardial ischemic, multiple sclerosis, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis.

In particular the inflammatory disease is an acute inflammatory disease (e.g., for example, inflammation resulting from infection). in particular the inflammatory disease is a chronic inflammatory disease (e.g., conditions resulting from asthma, arthritis and inflammatory bowel disease). The compounds may also be useful in treating inflammation associated with trauma and non-inflammatory myalgia. The compounds may also be useful in treating inflammation associated with cancer.

Examples of autoimmune diseases which may be treated or prevented, in particular treated, include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, amyotrophic lateral sclerosis, amylosis, multiple sclerosis, acute painful shoulder, psoriatic, and juvenile arthritis), asthma, atherosclerosis, osteoporosis, bronchitis, tendonitis, bursitis, skin condition (e.g., psoriasis, eczema, eczema hypersensitivity reactions, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In a particular embodiment, a provided compound may be useful in somatic cell reprogramming, such as reprogramming somatic cells into stem cells. In a particular embodiment, a provided compound may be useful in germ cell development, and are thus envisioned useful in the areas of reproductive technology and regenerative medicine.

Other diseases which may be treated or prevented, in particular treated, include, but are not limited to, ischemic injury associated myocardial infarctions, immunological diseases, stroke, arrhythmia, toxin-induced or alcohol related liver diseases, aspirin-sensitive rhinosinusitis, cystic fibrosis, cancer pain, and haematological diseases, for example chronic anemia and aplastic anemia.

The compounds of the present invention may also have therapeutic applications in sensitising tumour cells for radiotherapy and chemotherapy.

Hence the compounds of the present invention may be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

The compounds of the present invention might also reduce the risk of cancer recurrence.

The invention relates to compounds of Formula (I) and pharmaceutically acceptable addition salts, and solvates thereof, for use as a medicament.

The invention relates to compounds of Formula (I) and pharmaceutically acceptable addition salts, and solvates thereof, for use in the inhibition of PRMT5 activity.

The compounds of the present invention can be "anti-cancer agents", which term also encompasses "anti-tumor cell growth agents" and "anti-neoplastic agents".

The invention relates to compounds of Formula (I) and pharmaceutically acceptable addition salts, and solvates thereof, for use in the treatment of diseases mentioned above.

The invention relates to compounds of Formula (I) and pharmaceutically acceptable addition salts, and solvates thereof, for the treatment or prevention, in particular for the treatment, of said diseases.

The invention relates to compounds of Formula (I) and pharmaceutically acceptable addition salts, and solvates thereof, for the treatment or prevention, in particular in the treatment, of PRMT5 mediated diseases or conditions.

The invention relates to compounds of Formula (I) and pharmaceutically acceptable addition salts, and solvates thereof, for the manufacture of a medicament.

The invention relates to compounds of Formula (I) and pharmaceutically acceptable addition salts, and solvates thereof, for the manufacture of a medicament for the inhibition of PRMT5.

The invention relates to compounds of Formula (I) and pharmaceutically acceptable addition salts, and solvates thereof, for the manufacture of a medicament for the treatment or prevention, in particular for the treatment, of any one of the disease conditions mentioned hereinbefore.

The invention relates to compounds of Formula (I) and pharmaceutically acceptable addition salts, and solvates thereof, for the manufacture of a medicament for the treatment of any one of the disease conditions mentioned hereinbefore.

The invention relates to compounds of Formula (I) and pharmaceutically acceptable addition salts, and solvates thereof, can be administered to mammals, preferably humans, for the treatment or prevention of any one of the diseases mentioned hereinbefore.

In view of the utility of the compounds of Formula (I) and pharmaceutically acceptable addition salts, and solvates thereof, there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I) or a pharmaceutically acceptable addition salt, or a solvate thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. A particular effective therapeutic daily amount might be from about 0.01 to 1.00 g twice a day (BID), more in particular 0.30 to 0.85 g BID; even more in particular 0.40 g BID. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent cancer or cancer-related conditions, may be administered alone or in combination with one or more additional therapeutic agents. Combination therapy includes administration of a single pharmaceutical dosage formulation which contains a compound of Formula (I), a pharmaceutically acceptable addition salt, or a solvate thereof, and one or more additional therapeutic agents, as well as administration of the compound of Formula (I), a pharmaceutically acceptable addition salt, or a solvate thereof, and each additional therapeutic agents in its own separate pharmaceutical dosage formulation. For example, a compound of Formula (I), a pharmaceutically acceptable addition salt, or a solvate thereof, and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition and, as active ingredient, a therapeutically effective amount of a compound of Formula (I), a pharmaceutically acceptable addition salt, or a solvate thereof.

Accordingly, the present invention further provides a pharmaceutical composition comprising a pharmaceutically acceptable carrier and, as active ingredient, a therapeutically effective amount of a compound of Formula (I), a pharmaceutically acceptable addition salt, or a solvate thereof.

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds of Formula (I) and pharmaceutically acceptable addition salts, and solvates thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing a compound of Formula (I), a pharmaceutically acceptable addition salt, or a solvate thereof, may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the compounds of Formula (I) and pharmaceutically acceptable addition salts, and solvates thereof, in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), a pharmaceutically acceptable addition salt, or a solvate thereof, and from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anticancer agent is envisaged, especially for use as a medicine, more specifically for use in the treatment of cancer or related diseases.

For the treatment of the above conditions, the compounds of the invention may be advantageously employed in combination with antibody based immune cell redirection, for example T-cell/neutrophil redirection. This can be achieved for example by the use of bispecific monoclonal antibodies or artificial T-cell receptors.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

- platinum coordination compounds for example cisplatin optionally combined with amifostine, carboplatin or oxaliplatin;
- taxane compounds for example paclitaxel, paclitaxel protein bound particles (Abraxane™) or docetaxel;
- topoisomerase I inhibitors such as camptothecin compounds for example irinotecan, SN-38, topotecan, topotecan hcl;
- topoisomerase II inhibitors such as anti-tumour epipodophyllotoxins or podophyllotoxin derivatives for example etoposide, etoposide phosphate or teniposide;
- anti-tumour vinca alkaloids for example vinblastine, vincristine or vinorelbine;
- anti-tumour nucleoside derivatives for example 5-fluorouracil, leucovorin, gemcitabine, gemcitabine hcl, capecitabine, cladribine, fludarabine, nelarabine;
- alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetrocarcin derivatives for example tetrocarcin A;

glucocorticoids for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, carminomycin, daunomycin, levamisole, plicamycin, mithramycin;

antimetabolites for example clofarabine, aminopterin, cytosine arabinoside or methotrexate, azacitidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

farnesyltransferase inhibitors for example tipifarnib;

histone deacetylase (HDAC) inhibitors for example sodium butyrate, suberoylanilide hydroxamic acid (SAHA), depsipeptide (FR 901228), NVP-LAQ824, R306465, JNJ-26481585, trichostatin A, vorinostat;

Inhibitors of the ubiquitin-proteasome pathway for example PS-341, MLN .41 or bortezomib;

Yondelis;

Telomerase inhibitors for example telomestatin;

Matrix metalloproteinase inhibitors for example batimastat, marimastat, prinostat or metastat.

Recombinant interleukins for example aldesleukin, denileukin diftitox, interferon alfa 2a, interferon alfa 2b, peginterferon alfa 2b MAPK inhibitors Retinoids for example alitretinoin, bexarotene, tretinoin Arsenic trioxide Asparaginase Steroids for example dromostanolone propionate, megestrol acetate, nandrolone (decanoate, phenpropionate), dexamethasone Gonadotropin releasing hormone agonists or antagonists for example abarelix, goserelin acetate, histrelin acetate, leuprolide acetate Thalidomide, lenalidomide Mercaptopurine, mitotane, pamidronate, pegademase, pegaspargase, rasburicase BH3 mimetics for example ABT-737

MEK inhibitors for example PD98059, AZD6244, CI-1040 colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin a steroidal cytochrome P450 17alpha-hydroxylase-17,20-lyase inhibitor (CYP17), e.g. abiraterone, abiraterone acetate Glycolysis inhibitors, such as 2-deoxyglucose mTOR inhibitors such as rapamycins and rapalogs, and mTOR kinase inhibitors PI3K inhibitors and dual mTOR/PI3K inhibitors autophagy inhibitors, such as chloroquine and hydroxychloroquine antibodies that re-activate the immune response to tumors, for example nivolumab (anti-PD-1), lambrolizumab (anti-PD-1), ipilimumab (anti-CTLA4), and MPDL3280A (anti-PD-L1).

The present invention further relates to a product containing as first active ingredient a compound according to the invention and as further active ingredient one or more anticancer agents, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for cartnustine in a dosage of about 150 to 200 $mg/m^2$, and for lomustine in a dosage of about 100 to 150 $mg/m^2$ per course of treatment.

The anti-tumour anthracycline derivative is advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter ($mg/m^2$) of body surface area, or as known in the art, if different. Trastuzumab is advantageously administered in a dosage of 1 to 5 mg per square meter ($mg/m^2$) of body surface area, particularly 2 to 4 $mg/m^2$ per course of treatment.

These dosages may be administered for example once, twice or more per course of treatment, which may be repeated for example every 7, 14, 21 or 28 days.

The following examples illustrate the present invention. In case no specific stereochemistry is indicated for a stereocenter of a compound, this means that a mixture of the R and the S enantiomers was obtained. In case more than 1 stereocenter is present in a structure, each stereocenter for which no specific stereochemistry is indicated was obtained as a mixture of R and S.

The skilled person will realize that typically after a column purification, the desired fractions were collected and the solvent was evaporated to obtain the desired compound or intermediate.

EXAMPLES

Hereinafter, the term "rt", "r.t." or "RT" means room temperature; "Me" means methyl;

"MeOH" means methanol; "Et" means ethyl; "EtOH" means ethanol; "NaH" means sodium hydride; "DEAD" means diethyl azodicarboxylate; "HMPT" means hexamethylphosphorous triamide; "$Boc_2O$" means tert-butoxycarbonyl anhydride;

"$Bu^tONO$" means tert-butyl nitrite; "TosOH" means 4-methylbenzenesulfonic acid;

"TosCl" means 4-methylbenzenesulfonyl chloride (also p-toluenesulfonyl chloride);

"CMBP" means cyanomethylenetributylphosphorane; "DBAD" means di-tert-butyl azodicarboxylate; "LAH" means lithium aluminum hydride; "$NaBH(AcO)_3$" or "$NaBH(OAc)_3$" means sodium triacetoxyborohydride; "EtOAc" means ethyl acetate;

"TEA" or "$Et_3N$" means triethylamine; "DCM" means dichloromethane; "q.s." means quantum sufficit; "Int." Means intermediate; "MeCN" or "ACN" means acetonitrile;

"DMF" means N,N-dimethyl formamide; "DMA" means N,N-dimethylacetamide;

"DMF-DMA" means N,N-Dimethylformamide dimethyl acetal; "$Pd(dppf)Cl_2$" means [1,1'-Bis(diphenylphosphino)ferrocene]dichloropalladium(II); "THF" means tetrahydrofuran; "$C_{34}H_{28}FeP_2{\cdot}Cl_2Pd$" means [1,1'-bis(diphenylphosphino)ferrocene] dichloropalladium(ii); "i-PrOH" or "iPrOH" means 2-propanol; "LC" means liquid chromatography; "LCMS" means Liquid Chromatography/Mass spectrometry;

"HPLC" means high-performance liquid chromatography; "int." means intermediate;

"prep-HPLC" means preparative high-performance liquid chromatography; "m-CPBA" means meta-Chloroperoxybenzoic acid; "TFA" means trifluoroacetic acid; "m.p." means melting point; "RP" means reversed phase; "min" means minute(s); "h" means hour(s); "PE" means petroleum ether; "v/v" means volume per volume; "Celite®" means diatomaceous earth; "DMSO" means dimethyl sulfoxide; "SFC" means Supercritical Fluid Chromatography; "DIPE" means diisopropyl ether; "dppf" or "DPPF" means 1,1'-Bis(diphenylphosphino)ferrocene; "DIPEA" or "DIEA" means N,N-diisopropylethylamine; "$PPh_3$" means triphenylphosphine; "$Et_2O$" means diethyl ether; "Pd/C" means palladium on carbon; "Pt/C" means platina on carbon;

"$Pd(OH)_2/C$" means palladium hydroxide on carbon; "CPME" means cyclopentyl methyl ether; "$Pd_2(dba)_3$ means Tris(dibenzylideneacetone)dipalladium; "DIAD" means diisopropyl azodicarboxylate; "$TMSCF_3$" means trimethyl (trifluoromethyl)silane; "TBAF" means tetrabutylammonium fluoride; "psi" means pound-force per square inch; "$Et_4NCl$" means tetraethylammonium chloride;

"eq." means equivalent(s); "$Pd(OAc)_2$" means palladium (II) acetate; "AcOH" means acetic acid; "DMAP" means 4-(dimethylamino)pyridine; "t-BuOK", "$^t$BuOK" or "KOtBu" means potassium tert-butoxide; "Dess-Martin periodinane" means 1,1,1-Triacetoxy-1,1-dihydro-1,2-benziodoxol-3(1H)-one; "TBDMSCl" means tert-Butyldimethylsilyl chloride; "$PPh_3$-polymer" or "$PPh_3$-pol" means triphenylphosphine polymer bound; "$Ph_3PCH_3Br$" means methyltriphenylphosphonium bromide; "Bn" means benzyl; "Bz" means benzoyl; "p-TSA" means 4-methylbenzenesulfonic acid;

"$BF_3 \cdot Et_2O$" means Boron Trifluoride-Ethyl Ether Complex; "9-BBN" means 9-Borabicyclo[3.3.1]nonane; "Pd-118" means Dichloro[1,1'-bis(di-tert-butylphosphino)ferrocene]palladium(II); and "TLC" means thin layer chromatography;

"prep-TLC" means preparative TLC;

"$p\text{-}MeC_6H_4SO_3H \cdot H_2O$" means para toluenesulfonic acid hydrate; "PMB" means para methoxybenzyl; "KOAc" means potassium acetate; "PTSA" para toluenesulfonic acid;

"MTBE" means methyl tert. butyl ether; $Rh(acac)(eth)_2$" means Acetylacetonatobis(ethylene)rhodium(I); "(S)-MonoPhos" means (S)—N,N-dimethyldinaphtho[2,1-D:1',2'-F][1,3,2]dioxaphosphepin-4-amine; "$Tf_2O$" means triflic anhydride; "MeI" means methyliodide; "$Me_2NH$" means dimethylamine;

"$Me_2 \cdot NH \cdot HCl$" means dimethylamine hydrochloric acid; "$Me_4NCl$" means tetramethylammonium chloride; "MeONa" means sodium methoxide; "Ts" means tosyl; "MsCl" means mesylchloride; "DIBAH" means Diisobutylaluminium hydride;

"TBDMS" means tertButyl dimethylsilyl; "Pd(dppf) $Cl_2 \cdot CH_2Cl_2$" means [1,1'-Bis(diphenylphosphino)ferrocene] dichloropalladium(II), complex with dichloromethane; "PPA" means polyphosphoric acid; "$NH_2Bn$" means benzylamine;

"$Pd(PPh_3)_2Cl_2$" means Dichlorobis(triphenylphosphine) palladium(II).

Intermediates containing a double bond with substituents which may be in the E or the Z configuration are show in one particular configuration in the experimental part below. However, unless explicitly indicated by (E) or (Z), it is unknown if these intermediates were obtained in the E or Z configuration or as a mixture of both configurations. For example intermediates 24-26, 29-31, 72-76, and intermediates 79-88 might be in the E or Z configuration or might be mixtures thereof.

For example Intermediates 44, 97-100, 136-138, 150 and compounds 55, 57, 57a and 61 were obtained in the E configuration and are explicitly indicated as such (E) in the experimental part below.

For intermediates that were used in a next reaction step as a crude or as a partially purified intermediate, estimated mol amounts (in some cases indicated by ≈) are indicated in the reaction protocols described below, or alternatively theoretical mol amounts are indicated.

A. Preparation of Intermediates

Example A1

Preparation of Intermediate 1

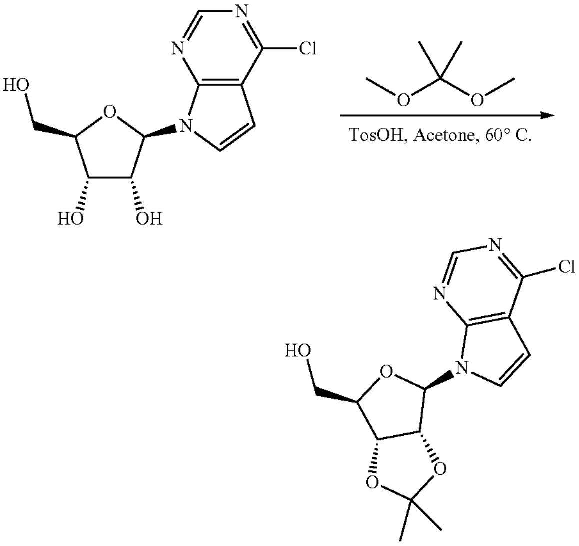

intermediate 1

To a mixture of 6-chloro-7-deazapurinebeta-d-riboside (25.0 g, 87.5 mmol) in acetone (330 mL) was added 2,2-dimethoxypropane (18.2 g, 175 mmol) and 4-methylbenzenesulfonic acid (TosOH) (1.51 g, 8.75 mmol) in one portion at 25° C. under $N_2$. The mixture was stirred at 60° C. for 2 hours. The mixture was cooled to 25° C. The reaction was quenched by adding saturated $NaHCO_3$ (100 mL) slowly and then extracted with ethyl acetate (125 mL×5). The combined organic phase was washed with saturated brine (120 mL), dried with anhydrous $MgSO_4$, filtered and concentrated in vacuum. The residue was purified by silica gel chromatography (gradient elution: DCM/Ethyl acetate from 1:0 to 2:1) to afford crude intermediate 1 (38.0 g) as light yellow gum.

Example A2

Preparation of Intermediate 3

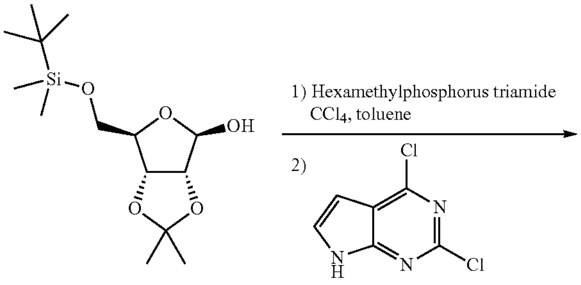

intermediate 2

Tris(3,6-dioxaheptyl)amine,
KOH, toluene

-continued

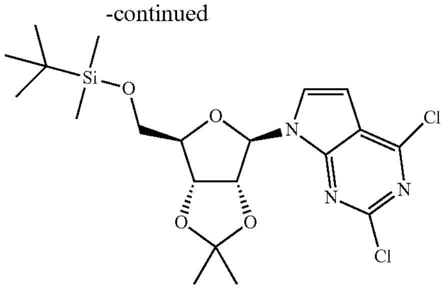

intermediate 3

To a solution of 5-O-tert-Butyldimethylsilyl-2,3-o-isopropylidene-D-ribofuranose (intermediate 2) (24.3 g, 79.8 mmol) in $CCl_4$ (12.8 mL, 133 mmol) and toluene (200 ml) was added dropwise HMPT at −50° C. over 30 minutes. After the mixture was stirred at −50° C. for 2 hours, the reaction mixture was quickly washed with ice cold brine (30 mL), dried over anhydrous $Na_2SO_4$ and added immediately to a heavily stirred mixture of powdered KOH (6.5 g, 117 mmol), 2,4-dichloro-7h-pyrrolopyrimidine (10.0 g, 53 mmol), tris(3,6-dioxaheptyl)amine (8.27 mL, 26.6 mmol) and toluene (200 ml). The mixture was stirred at room temperature for 48 hours. Then the solvent was concentrated in vacuum. The residue was treated with 250 ml $NH_4Cl$ solution and extracted with ethyl acetate (300 ml×2). The organic layers were combined and dried with $Na_2SO_4$, filtered and the filtrate was concentrated in vacuum. The residue was purified by column chromatography over silica gel (gradient elution: petroleum ether/ethyl acetate from 25:1 to 15:1). The product fractions were collected and the solvent was evaporated to give the desired intermediate 3 (6.50 g, crude)

Below intermediates were prepared by an analogous reaction protocol as was used for the preparation of intermediate 3 using the appropriate starting materials (Table 1).

TABLE 1

| Int. | Structure | Starting materials |
|---|---|---|
| 4 | 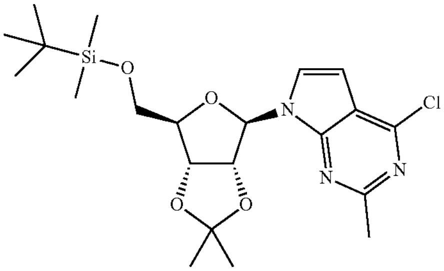 [SMILES: Cc1nc(Cl)c2ccn([C@@H]3O[C@H](CO[Si](C)(C)C(C)(C)C)[C@H]4OC(C)(C)O[C@H]43)c2n1] | Intermediate 2 and 4-chloro-2-methyl-7H-pyrrolo[2,3-d]pyrimidine |
| 5 | 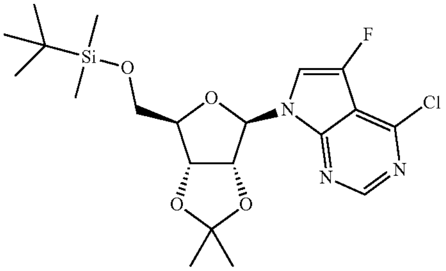 [SMILES: CC1(C)O[C@@H]2[C@H](O1)[C@@H](CO[Si](C)(C)C(C)(C)C)O[C@H]2n1cc(F)c2c(Cl)ncnc21] | Intermediate 2 and 4-Chloro-5-fluoro-7H-pyrrolo[2,3-d]-pyrimidine |
| 185 | 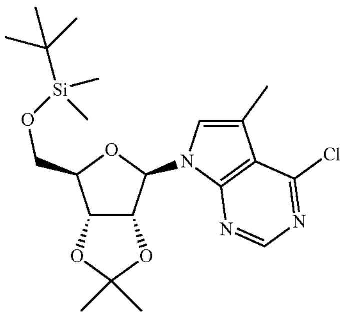 [SMILES: Cc1cn([C@@H]2O[C@H](CO[Si](C)(C)C(C)(C)C)[C@H]3OC(C)(C)O[C@H]32)c2ncnc(Cl)c12] | Intermediate 2 and 4-Chloro-5-methyl-7H-pyrrolo[2,3-d]-pyrimidine |

TABLE 1-continued

| Int. | Structure | Starting materials |
|---|---|---|
| 189 | 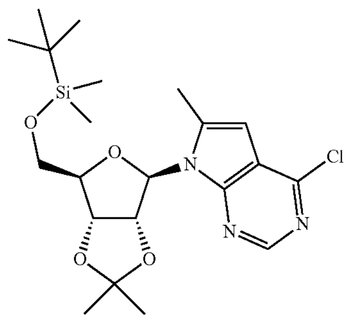 [SMILES: Cc1cc2c(Cl)ncnc2n1[C@@H]1O[C@H](CO[Si](C)(C)C(C)(C)C)[C@H]2OC(C)(C)O[C@H]21] | Intermediate 2 and 4-Chloro-6-methyl-7H-pyrrolo[2,3-d]-pyrimidine |
| 282 | 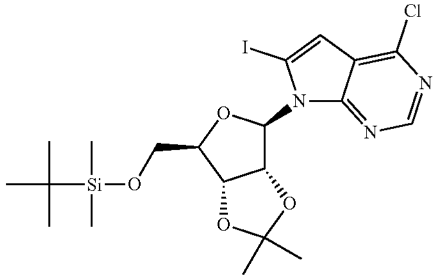 [SMILES: CC1(C)O[C@@H]2[C@H](O1)[C@@H](CO[Si](C)(C)C(C)(C)C)O[C@H]2n1c(I)cc2c(Cl)ncnc21] | Intermediate 2 and 4-Chloro-6-Iodo-7H-pyrrolo[2,3-d]-pyrimidine |

Example A3

Preparation of Intermediate 6

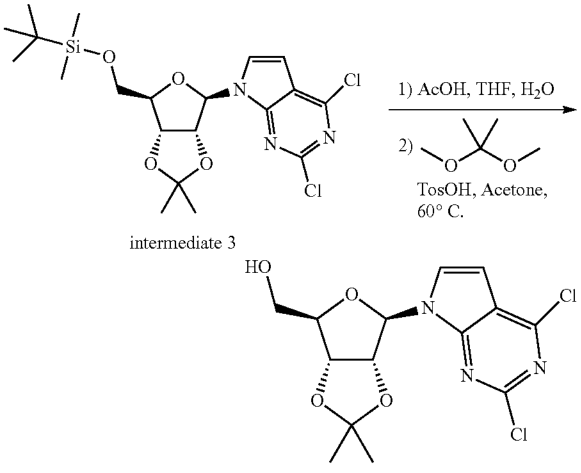

intermediate 3 intermediate 6

Intermediate 3 (7.00 g, 14.8 mmol) was dissolved into the solvent mixture of acetic acid, water and THF with ratio as 13:7:3 (100 mL). The reaction mixture was stirred at room temperature for 12 hours. The solvent was removed under reduced pressure at 60° C., afforded 6.8 g of crude intermediate 6 together with byproduct. To the solution of the above crude product in acetone (50 mL) was added 2,2-dimethoxypropane (5 mL, 42 mmol) and 4-methylbenzenesulfonic acid mono hydrate (13 mg, 0.07 mmol) at room temperature under $N_2$. The mixture was stirred at 60° C. for 2 hours. The solvent was removed under reduced pressure below 30° C. The residue was purified by column chromatography (gradient elution: EtOAc/petroleum ether from 1/10 to 1/3) on silica gel to afford the desired intermediate 6 (3.02 g, 34% yield).

Example A4

Preparation of Intermediate 7

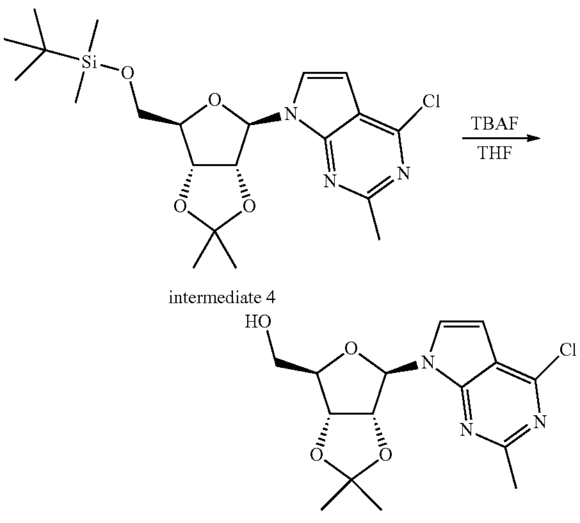

intermediate 4 intermediate 7

To a solution of intermediate 4 (9.50 g, 20.9 mmol) in THF (82 mL) was added 1M TBAF solution in THF (41.8 mL, 41.8 mmol) at room temperature. The reaction mixture was stirred at room temperature for 3 hours. The mixture was evaporated to dryness. The residue was taken up into water and extracted with DCM (150 ml×2). The organic layers were dried ($Na_2SO_4$), filtered and the filtrate was concentrated in vacuum. The residue was purified by column chromatography over silica gel (gradient elution: petroleum ether/ethyl acetate from 10/1 to 4/1) to give the desired intermediate 7 (3.68 g, 88% yield)

Below intermediate was prepared by an analogous reaction protocol as was used for the preparation of intermediate 7 using the appropriate starting materials (Table 2).

TABLE 2

| Int. | Structure | Starting material |
|---|---|---|
| 8 | 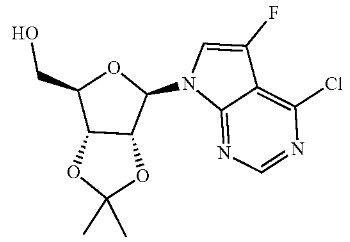 [SMILES: CC1(C)O[C@@H]2[C@H](O1)[C@@H](CO)O[C@H]2n1cc(F)c2c(Cl)ncnc21] | Intermediate 5 |
| 186 | 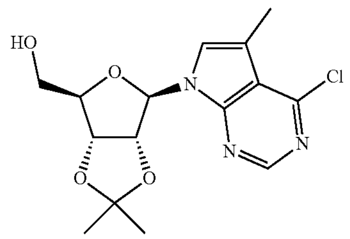 [SMILES: Cc1cn([C@@H]2O[C@H](CO)[C@H]3OC(C)(C)O[C@H]32)c2ncnc(Cl)c12] | Intermediate 185 |
| 190 | 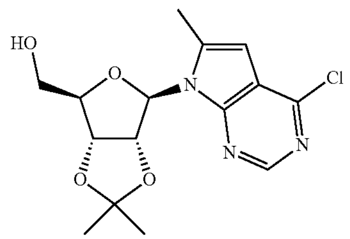 [SMILES: Cc1cc2c(Cl)ncnc2n1[C@@H]1O[C@H](CO)[C@H]2OC(C)(C)O[C@H]21] | Intermediate 189 |

Example A5

Preparation of Intermediate 10

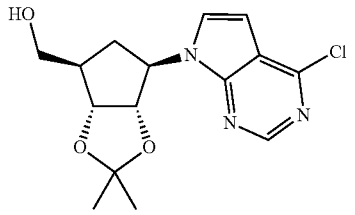

intermediate 10

Step a)

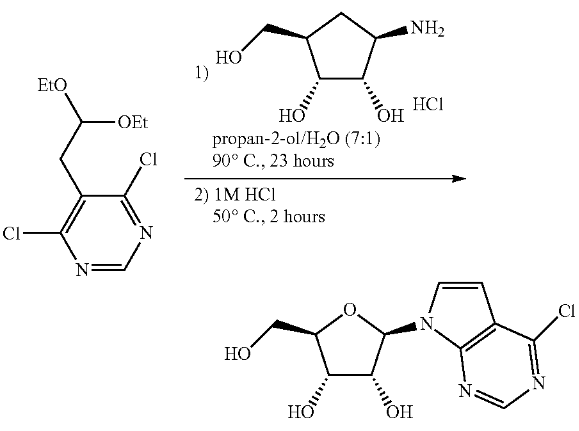

intermediate 9

To a mixture of 4,6-dichloro-5-(2,2-diethoxyethyl)pyrimidine (14.0 g, 52, 8 mmol) and (1R,2S,3R,5R)-3-amino-5-(hydroxymethyl)cyclopentane-1,2-diol hydrochloride (10.7 g, 58.1 mmol) in propan-2-ol/$H_2O$ (208 mL, 7:1), was added $Et_3N$ (13.4 g, 132 mmol) in one portion at 25° C. under $N_2$. The mixture was stirred at 90° C. for 23 hours. The mixture was cooled to 50° C. and 4M HCl (24 mL, 106 mmol) was added slowly. The residue was then stirred at 50° C. for 2 hours. The reaction mixture was cooled to 25° C. and $NaHCO_3$ (14 g, 100 mmol) was added slowly. Ethyl acetate (230 mL) was added, followed by the addition of a half-saturated $NaHCO_3$ solution (q.s.). The organic phase was isolated and the aqueous phase was extracted with ethyl acetate (230 mL×2). The combined organic phase was dried with anhydrous $MgSO_4$, filtered and concentrated in vacuum to afford intermediate 9 as yellow solid (17.4 g, quantitative yield in 2 steps). The crude product was directly used as such in the next reaction step without further purification.

Step b)

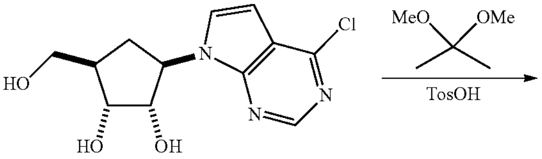

Intemediate 9

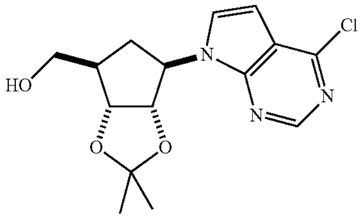

Intemediate 10

To a mixture of intermediate 9 (17.4 g, ≈52.7 mmol) in acetone (250 mL) was added 2,2-dimethoxypropane (11.0 g, 105 mmol) and TsOH·$H_2O$ (908 mg, 5.27 mmol) in one portion at 25° C. under $N_2$. The mixture was stirred at 60° C. for 2 hours. The mixture was cooled to 25° C. and the solution was concentrated in vacuum, quenched by saturated $NaHCO_3$ (100 mL) slowly and then extracted with ethyl acetate (100 mL×3). The combined organic phase was washed with saturated brine (100 mL), dried with anhydrous $MgSO_4$, filtered and concentrated in vacuum. The residue was purified by flash chromatography on silica gel (gradient elution: DCM/Ethyl acetate from 1/0 to 2/1) to afford intermediate 10 as light yellow gum (15.5 g, 89% yield).

Example A6

Preparation of Intermediate 14 intermediate 14

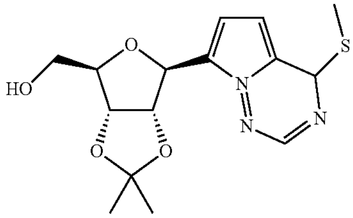

Step a)

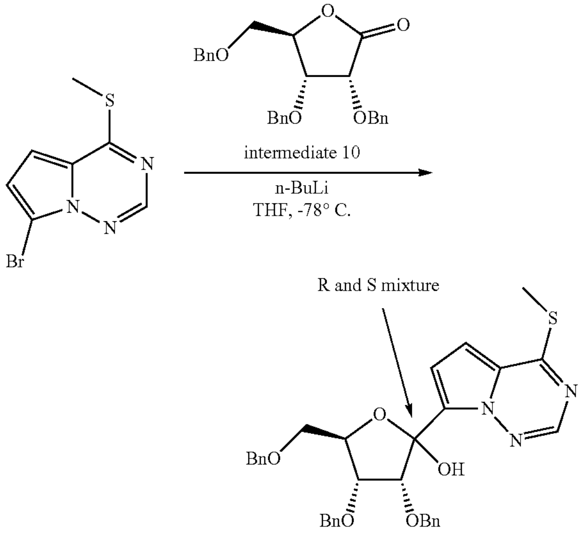

intermediate 11

An oven-dried flask was charged with 7-bromo-4-(methylthio)pyrrolo[2,1-f][1,2,4]triazine (45.0 g, 184 mmol) and dry THF (1.20 L) under $N_2$. The yellow solution was cooled to −78° C., and a yellow suspension was formed. n-BuLi (2.5 M, 79.6 mL) was added dropwise to the reaction mixture over period of 25 minutes at −78° C. The reaction mixture was stirred at −78° C. for 1 hour and a yellow-brown solution formed. A pre-cooled solution of intermediate 10 (84.0 g, 201 mmol) in dry THF (800 mL) in another flask (−78° C.) was added to the solution under $N_2$. The resulting red-brown solution was stirred at −78° C. for 1.5 h. 2 batches were carried out in parallel. The reaction was quenched by addition of a saturated $NH_4Cl$ aqueous solution (300 mL) at −78° C., and subsequently the mixture was warmed to 10° C. The mixture was extracted with ethyl acetate (500 mL×3). The combined organic layers were washed with brine, dried over $MgSO_4$, filtered and concentrated under reduced pressure. The residue was load on silica gel then purified by column chromatography ($SiO_2$, gradient elution: Petroleum ether/Ethyl acetate from 10/1 to 3:1) to afford intermediate 11 (149 g, 56% yield) as an orange gum.

Step b)

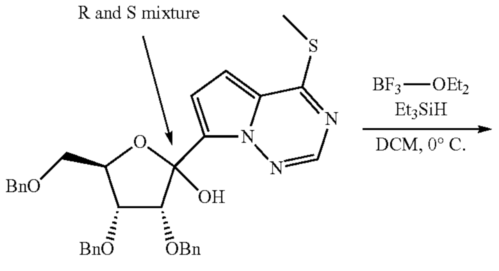

intermediate 11

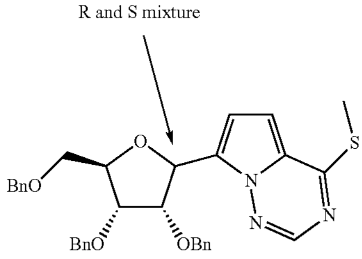

intermediate 12

To a stirred solution of intermediate 11 (74.0 g, 127 mmol) and triethylsilane (59.9 g, 515 mmol) in DCM (1.80 L) was added $BF_3{\cdot}Et_2O$ (90.9 g, 640 mmol) dropwise at −30~−20° C. 2 batches were carried out in parallel. The resulting orange solution was stirred between −30 and −20° C. for 4.5 hours. The reaction mixture was carefully poured into a saturated $NaHCO_3$ aqueous solution (2.5 L) with vigorous stirring (gas evolution). The mixture was stirred for 2 hours. The organic layer was separated and the aqueous phase was extracted with DCM (200 mL×3). The combined organic layers were washed with brine (500 mL×2), dried over $MgSO_4$, filtered and concentrated under reduced pressure. The residue was purified by column chromatography (silica gel, gradient elution: petroleum ether:ethyl acetate: from 12:1 to 8:1), affording intermediate 12 as a light yellow gum (125.7 g, 83% yield,)

Step c)

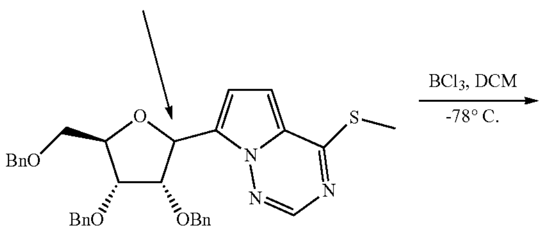

intermediate 12

-continued

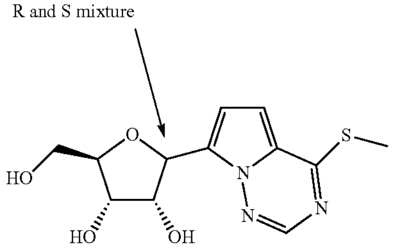

intermediate 13

1M $BCl_3$ in $CH_2Cl_2$ (860 mL, 860 mmol) was added dropwise at −78° C. to a stirred solution of intermediate 12 (75.0 g, 132 mmol) in DCM (1.20 L) dropwise over period of 2.5 hour under $N_2$. The mixture was stirred at −78° C. for 1 hour. The reaction mixture was slowly warmed to −40° C. The reaction mixture was poured into MeOH (2.5 L, 20° C.) with stirring. The resulting red solution was stirred for 3 hours. Water (250 mL) was added into the mixture and left at 20° C. for 16 h. The solution was portion wise poured onto solid $NaHCO_3$ (500 g) carefully with vigorous stirring (gas evolution, the color of mixture was turned from orange-red to yellow). The resulting suspension was filtered and the filtrate was concentrated under reduced pressure. The residue was dispensed in iPrOH/$CH_2Cl_2$ (1:3, 1 L) then filtered (to remove some inorganic salt) and the filtrate was concentrated under reduced pressure. The residue was triturated with petroleum ether (500 mL×3) to afford crude intermediate 13 (402 g, crude) as an orange solid, which used in the next reaction step without further purification.

Step d)

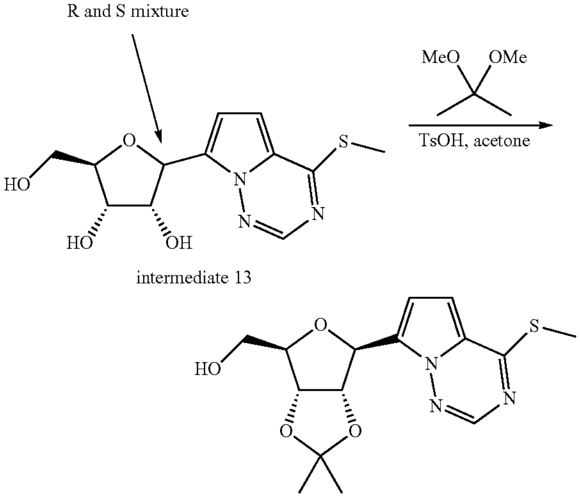

intermediate 13 intermediate 14

To a suspension of intermediate 13 (40.2 g, crude) and 2,2-dimethoxypropane (34 mL, 277 mmol) in acetone (600 mL) was added TsOH·$H_2O$ (5.92 g, 31.10 mmol, 0.23 eq) at 25° C. (pH=2). The resulting mixture was heated at 60° C. for 2 hours. After being cooled to 25° C., the reaction mixture was concentrated under reduced pressure. The residue was partitioned between ethyl acetate (500 mL) and saturated aqueous $NaHCO_3$ solution (500 mL). The layers were separated and the aqueous phase was extracted with ethyl acetate (200 mL×3). The combined organic layers were washed with brine (100 mL), dried over $MgSO_4$, filtered and concentrated under reduced pressure. The residue was purified by column chromatography (silica gel, gradient elution: $CH_2Cl_2$/Ethyl acetate from 10/1 to 6/1). The fractions containing desired intermediate 14 were combined and concentrated under reduced pressure. The residue (28 g, about 80% purity) was purified again by column chromatography (silica gel, gradient elution: Petroleum ether/Ethyl acetate: from 20/1 to 4/1). The desired fractions were combined and concentrated under reduced pressure. The residue was diluted with $CH_2Cl_2$ (15 mL) then petroleum ether/ethyl acetate (4:1, 200 mL) was added. The mixture was concentrated to about 150 mL and solids were precipitated. The slurry was diluted with petroleum ether to about 400 mL and stirred for 16 hours at 20° C. The mixture was filtered and the solid was rinsed with petroleum ether/ethyl acetate (20/1, 100 mL). The solids were collected and dried under high vacuum to afford pure intermediate 14 as white solid (18.6 g, 42% yield for 2 steps).

Example A7

Preparation of Intermediate 15

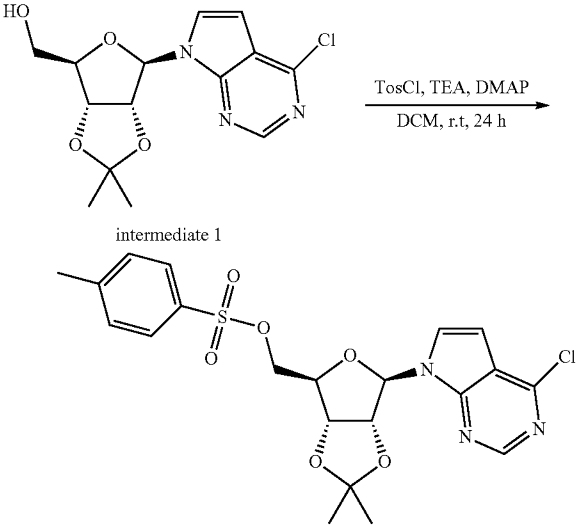

intermediate 1 intermediate 15

The intermediate 1 (10.0 g, ≈28.6 mmol), TEA (12 mL, 85.7 mmol) and DMAP (0.70 g, 5.71 mmol) were dissolved in $CH_2Cl_2$ (100 mL). p-toluenesulfonyl chloride (10.9 g, 57.1 mmol) was added at 0° C. The mixture was stirred at room temperature overnight. Water (100 mL) was added to the above solution. The aqueous layer was extracted with DCM (100 mL×3). The combined organic layer was dried over $Na_2SO_4$ and concentrated to dryness. The residue was purified by flash column (gradient elution: petroleum ether/EtOAc from 1/0 to 3/1). The product fractions were collected and the solvent was evaporated to give intermediate 15 as yellow oil (14.5 g, 97% yield).

Below intermediates were prepared by an analogous reaction protocol as was used for the preparation of intermediate 15 using the appropriate starting materials (Table 3).

TABLE 3

| Int. | structure | Starting material |
| --- | --- | --- |
| 16 | 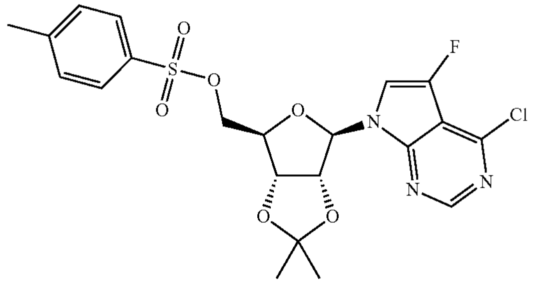 [SMILES: Cc1ccc(S(=O)(=O)OC[C@H]2O[C@@H](n3cc(F)c4c(Cl)ncnc43)[C@@H]3OC(C)(C)O[C@@H]32)cc1] | Intermediate 8 |
| 17 | 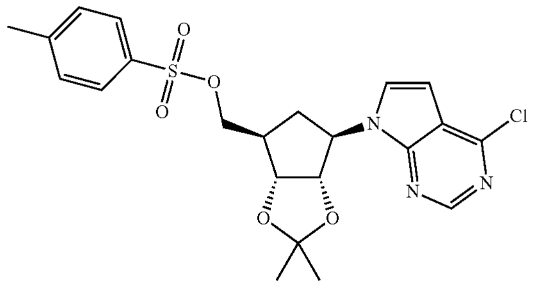 [SMILES: Cc1ccc(S(=O)(=O)OC[C@H]2C[C@@H](n3ccc4c(Cl)ncnc43)[C@@H]3OC(C)(C)O[C@H]23)cc1] | Intermediate 10 |

Example A8

Preparation of Intermediate 18

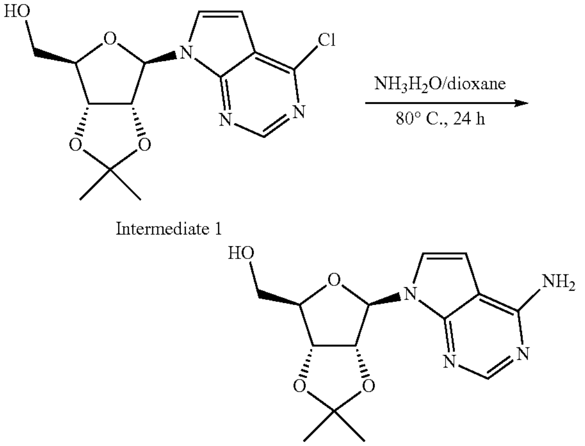

Intermediate 18

Intermediate 1 (100.0 g, theoretically 307 mmol) was dissolved in 400 mL of 1,4-dioxane. Then 400 mL of Ammonia water (28-30% $NH_3$ basis) was added. The mixture was stirred in a sealed tube at 100° C. for 20 hours. The mixture was cooled to room temperature. The reaction mixture was evaporated in vacuum to remove half of the solvent. Water (200 mL) was added and extracted with EtOAc (500 mL×3). The combined organic layers were washed with brine (200 ml×2), dried and concentrated to give intermediate 18 as white solid (93 g, 93% yield).

Below intermediates were prepared by an analogous reaction protocol as was used for the preparation of intermediate 18 using the appropriate starting materials (Table 4).

TABLE 4

| Intermediates | structure | Starting material |
| --- | --- | --- |
| 19 | 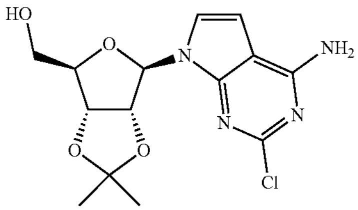 [SMILES: CC1(C)O[C@@H]2[C@H](O1)[C@@H](CO)O[C@H]2n1ccc2c(N)nc(Cl)nc21] | Intermediate 6 |

TABLE 4-continued

| Intermediates | structure | Starting material |
| --- | --- | --- |
| 20 | 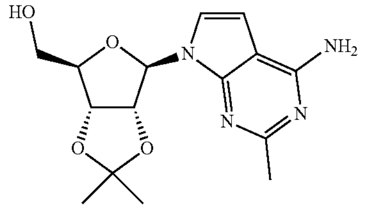 [SMILES: Cc1nc(N)c2ccn([C@@H]3O[C@H](CO)[C@H]4OC(C)(C)O[C@H]43)c2n1] | Intermediate 7 |
| 283 | 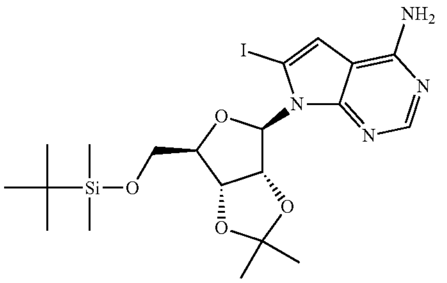 [SMILES: CC1(C)O[C@@H]2[C@H](O1)[C@@H](CO[Si](C)(C)C(C)(C)C)O[C@H]2n1c(I)cc2c(N)ncnc21] | Intermediate 282 |
| 502 | 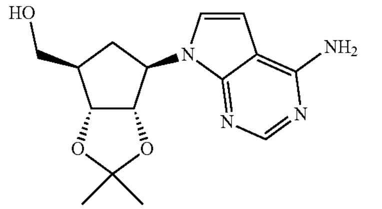 [SMILES: CC1(C)O[C@@H]2[C@@H](CO)C[C@@H](n3ccc4c(N)ncnc43)[C@@H]2O1] | Intermediate 10 |

Example A9

Preparation of Intermediate 23 intermediate 23

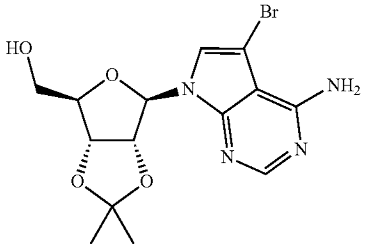

Step a:

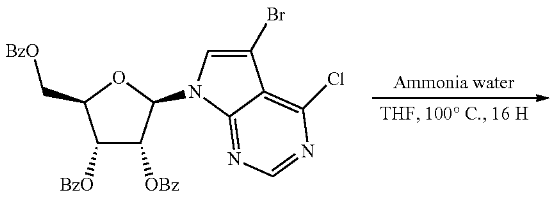

intermediate 21

-continued

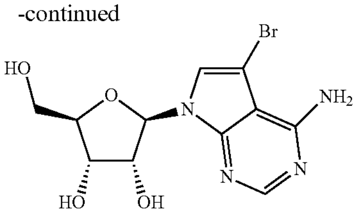

intermediate 22

To a solution of intermediate 21 (6.6 g, 9.75 mmol) in THF (130 mL) was added ammonia (28% in $H_2O$, 65 mL) at room temperature. The reaction mixture was stirred at 100° C. (using an autoclave) for 16 hours. The reaction mixture cooled to room temperature and evaporated to dryness under reduced pressure. The residue was taken up into water (100 mL) and DCM (100 mL) and stirred for 1 hour. The layers were separated and the water layer was washed again with DCM (100 mL) to remove impurities. The water layer was filtered and the filtrate was evaporated to dryness. The residue was purified on flash chromatography on silica (gradient eluention: DCM/MeOH from 95:5 to 90:10). The desired fractions were collected and the solvent was evaporated, yielding intermediate 22 (3.4 g, crude). The crude product was directly used for the next reaction step without further purification.

Step b:

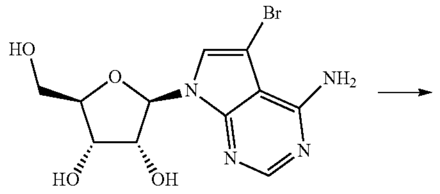

intermediate 22

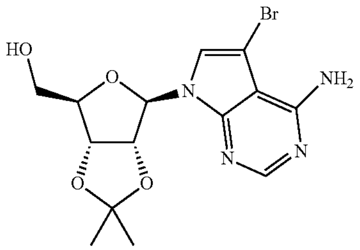

intermediate 23

To a mixture of intermediate 22 (1.0 g, crude) in acetone (32 mL) was added 2,2-dimethoxypropane (1.78 mL g, 14.5 mmol) and 4-methylbenzenesulfonic acid (0.61 g, 3.19 mmol) in one portion at room temperature. The mixture was stirred at 60° C. for 3 hours. The mixture was cooled to room temperature and quenched by adding saturated $NaHCO_3$ (10 mL) slowly and then extracted with ethyl acetate (50 mL×5). The combined organic phase was washed with saturated brine (120 mL), dried with $MgSO_4$, filtered and concentrated in vacuum, offered intermediate 23 (0.80 g, crude). The crude product was directly used for the next reaction step without further purification.

Example A10

Preparation of Intermediate 24

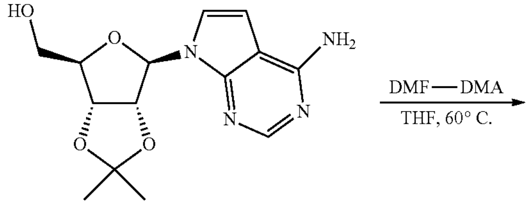

intermediate 18

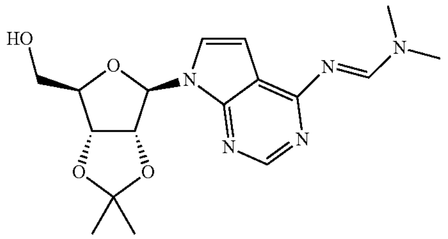

intermediate 24

Intermediate 18 (10.0 g, 32.6 mmol) was dissolved in THF (200 ml). Then Dimethylformamide Dimethylacetal (DMF-DMA) (5.84 g, 49.0 mmol) was added. The mixture was stirred at 60° C. for 24 hours. The mixture was cooled to room temperature and the solvent was concentrated in vacuum. The residue was triturated with EtOAc (200 mL) and water (100 mL). The organic layer was separated, the aqueous was extracted with EtOAc (200 mL×1), the combined organic layer was washed by brine (50 mL), dried over anhydrous $Na_2SO_4$, filtration and concentration to afford the desired intermediate 24 as a yellow solid (10.5 g, 85% yield)

Below intermediates were prepared by an analogous reaction protocol as was used for the preparation of intermediate 24 using the appropriate starting materials (Table 5).

TABLE 5

| Intermediates | structure | Starting material |
|---|---|---|
| 25 | 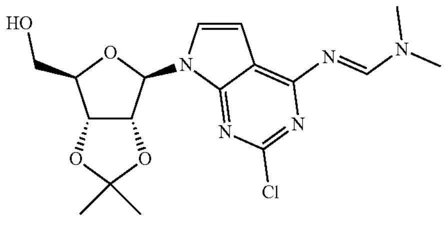 [SMILES: CN(C)/C=N/c1nc(Cl)nc2c1ccn2[C@@H]1O[C@H](CO)[C@H]2OC(C)(C)O[C@H]21] | Intermediate 19 |
| 26 | 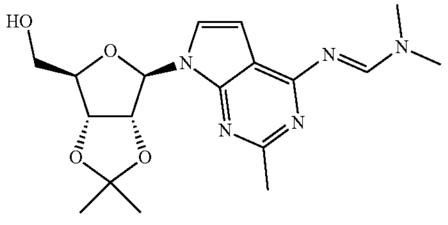 [SMILES: Cc1nc(/N=C/N(C)C)c2ccn([C@@H]3O[C@H](CO)[C@H]4OC(C)(C)O[C@H]43)c2n1] | Intermediate 20 |

TABLE 5-continued

| Intermediates | structure | Starting material |
|---|---|---|
| 503 | 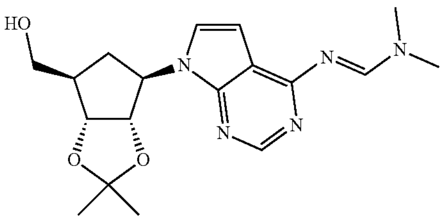 [SMILES: CN(C)/C=N/c1ncnc2c1ccn2[C@@H]1C[C@H](CO)[C@H]2OC(C)(C)O[C@H]21] | Intermediate 502 |

Example A 11 intermediate 28

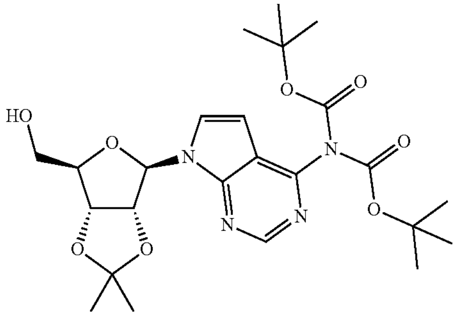

Step a:

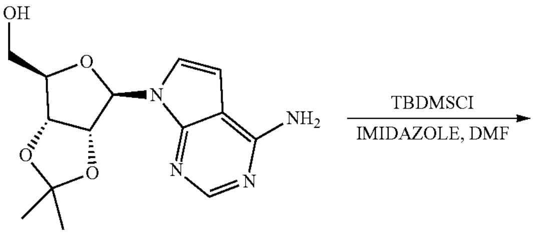

Intermediate 18

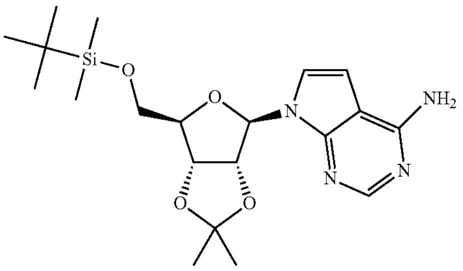

Intermediate 27

To the mixture of intermediate 18 (88.0 g, 287 mmol) and imidazole (39.1 g, 575 mmol) in DMF (300.0 mL) was added TBDMSCl (52.0 g, 345 mmol) in one portion at 0° C. under $N_2$. The reaction mixture was stirred overnight at room temperature. Subsequently, water (500 ml) was added and the mixture was extracted with EtOAc (800 mL×3). The organic layer was washed with brine (500 mL). Then the organic phase was dried with anhydrous $Na_2SO_4$, filtered, and the organic phase was concentrated under vacuum to give the crude product. The crude product was purified by column chromatography over silica gel (gradiente elution: petroleum ether/ethyl acetate 1:1). The desired fraction was concentrated to give the intermediate 27 as oil (120 g, 96% yield).

Step b:

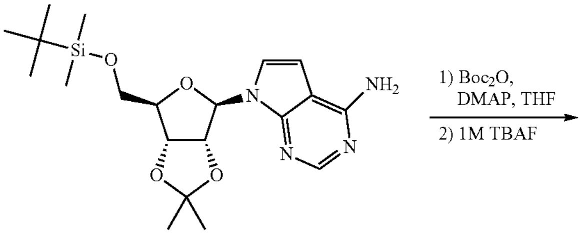

Intermediate 27

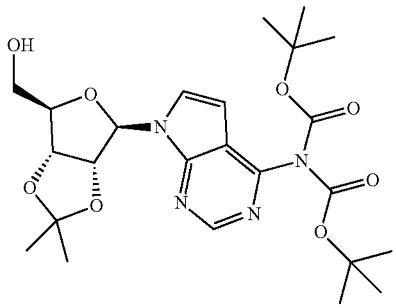

Intermediate 28

To the solution of intermediate 27 (12.4 g, ≈24.4 mmol) and DMAP (0.30 g, 2.44 mmol) in THF (50 mL) was added $(Boc)_2O$ (13.3 g, 61.0 mmol) dropwise at room temperature. The reaction mixture was stirred at room temperature for 3 hours. Then 1 M TBAF solution in THF (24.4 mL, 24.4 mL) was added dropwise. The reaction mixture was stirred at rt for 18 hours. The reaction mixture was poured into 250 ml of water and extracted with ethylacetate (250 mL×2). The organic layer was washed (water) and brine, dried with $Na_2SO_4$, and concentrated to be dry. The residue was purified by flash chromatography (elution: ethylacetate/heptane=50/50). The desired fraction was collected and the residue was stirred in heptane. The solid product is filtered off and dried at rt under reduced pressure, yielding intermediate 28 (10.2 g, 83% yield) as solid product.

Below intermediates were prepared by an analogous reaction protocol as was used for the preparation of intermediate 28 using the appropriate starting materials (Table 23).

-continued

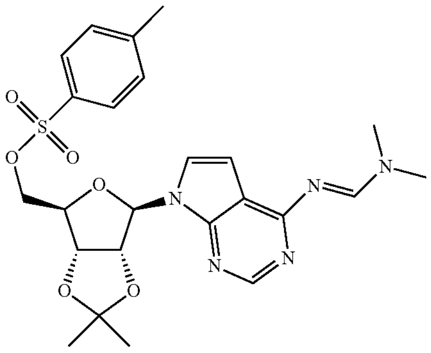

intermediate 29

TABLE 23

| Intermediates | structure | Starting material |
|---|---|---|
| 284 | 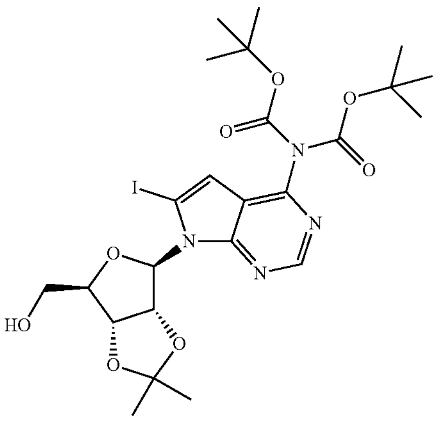 [SMILES: CC(C)(C)OC(=O)N(C(=O)OC(C)(C)C)c1ncnc2c1cc(I)n2[C@@H]1O[C@H](CO)[C@H]2OC(C)(C)O[C@H]21] | Intermediate 283 |

Example A12

Preparation of Intermediate 29

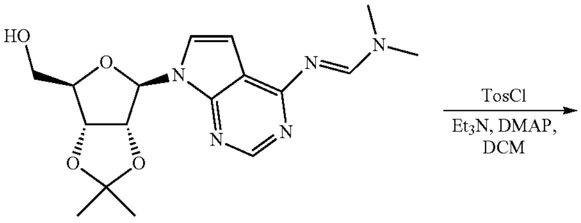

intermediate 24

To a reaction mixture of intermediate 24 (15.0 g, 41.7 mmol), $Et_3N$ (11.6 mL, 83.3 mmol) and DMAP (509 mg, 4.17 mmol) in DCM (200 mL) was added p-Toluenesulfonyl chloride (8.74 g, 45.9 mmol) at room temperature. The reaction mixture was stirred at room temperature for 3 hours. Water (100 mL) was added into the reaction mixture, the organic layer was separated, and the aqueous layer was extracted with EtOAc (100 mL×2). The combined organic layers were washed with brine (100 mL), dried over anhydrous $Na_2SO_4$, filtered and concentrated to yield the crude intermediate 29 as a brown solid, which was used in the next reaction step without further purification.

Below intermediates were prepared by an analogous reaction protocol as was used for the preparation of intermediate 29 using the appropriate starting materials (Table 6)

TABLE 6
| Int. | structure | Starting material |
| --- | --- | --- |
| 30 | 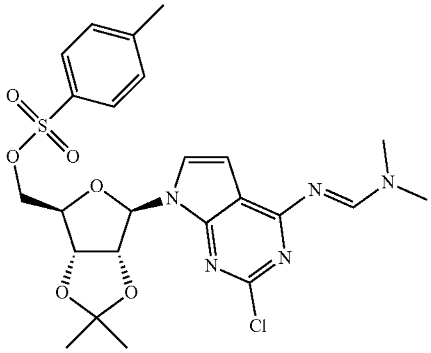 [SMILES: Cc1ccc(S(=O)(=O)OC[C@H]2O[C@@H](n3ccc4c(/N=C/N(C)C)nc(Cl)nc43)[C@@H]3OC(C)(C)O[C@@H]32)cc1] | Intermediate 25 |
| 31 | 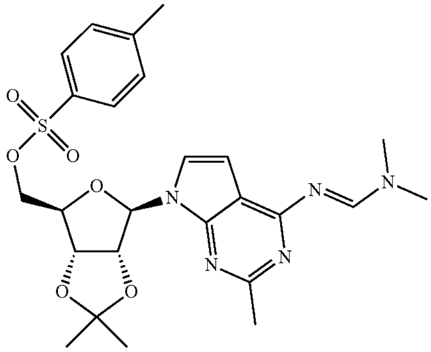 [SMILES: Cc1ccc(S(=O)(=O)OC[C@H]2O[C@@H](n3ccc4c(/N=C/N(C)C)nc(C)nc43)[C@@H]3OC(C)(C)O[C@@H]32)cc1] | Intermediate 26 |
| 32 | 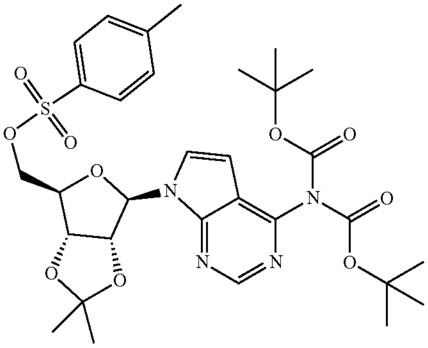 [SMILES: Cc1ccc(S(=O)(=O)OC[C@H]2O[C@@H](n3ccc4c(N(C(=O)OC(C)(C)C)C(=O)OC(C)(C)C)ncnc43)[C@@H]3OC(C)(C)O[C@@H]32)cc1] | Intermediate 28 |
| 285 | 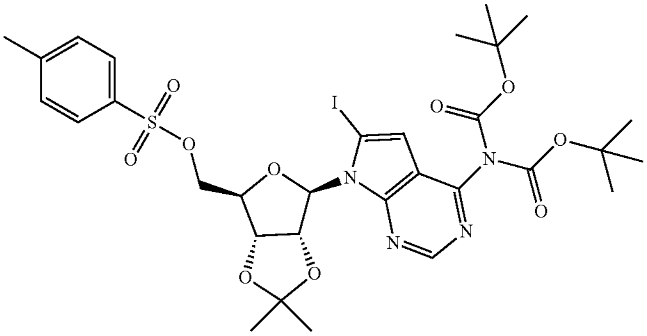 [SMILES: Cc1ccc(S(=O)(=O)OC[C@H]2O[C@@H](n3c(I)cc4c(N(C(=O)OC(C)(C)C)C(=O)OC(C)(C)C)ncnc43)[C@@H]3OC(C)(C)O[C@@H]32)cc1] | Intermediate 284 |

Example A12b

Preparation of Intermediate 32

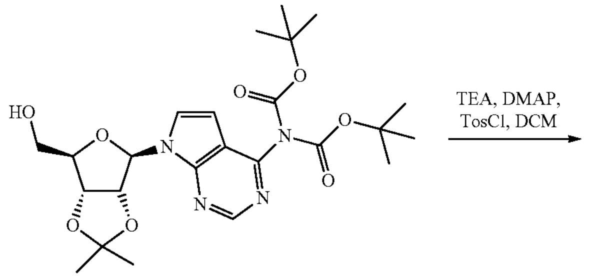

intermediate 28

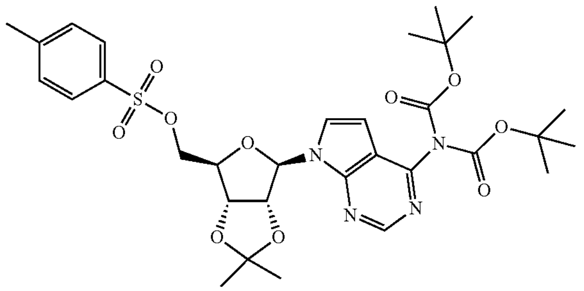

intermediate 32

Intermediate 28 (4.5 g, 8.89 mmol), TEA (2.70 g, 26.6 mmol), DMAP (0.54 g, 4.4 mmol) and DCM (40 ml) were stirred on an ice bath. p-Toluenesulfonyl chloride (3.39 g, 17.8 mmol) was added dropwise. The mixture was stirred at room temperature for 5 hours. The reaction mixture was poured into water and was extracted with DCM. The organic layer was evaporated and purified with flash chromatography on silica (eluent: DCM 98% MeOH 2%) to give intermediate 32 (5.6 g, 95% yield).

Example A13

Preparation of Intermediate 33

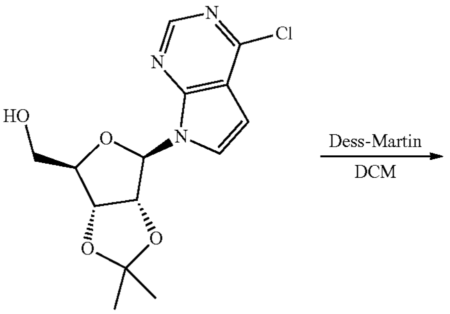

intermediate 1

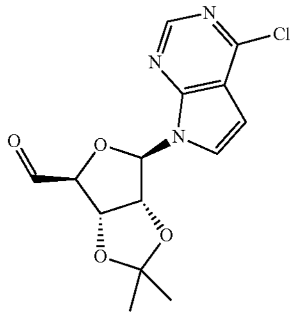

intermediate 33

To a mixture of intermediate 1 (2.00 g, theoretically 6.18 mmol) in DCM (40 mL) was added Dess-Martin periodinane (5.24 g, 12.36 mmol) in one portion at 0° C. under $N_2$. The mixture was stirred at 0° C. for 3 hours. To the mixture was added $Na_2S_2O_3$ (4 g) in saturated $NaHCO_3$ (20 mL) and stirred for 10 min. The aqueous phase was extracted with DCM (20 mL×3). The combined organic phase was washed with saturated brine (20 mL×2), dried with anhydrous $MgSO_4$, filtered and concentrated in vacuum to afford intermediate 33 (1.80 g, crude) as light yellow gum. The crude product was directly used for the next reaction step without further purification.

Below intermediates were prepared by an analogous reaction protocol as was used for the preparation of intermediate 33 using the appropriate starting materials (Table 7).

TABLE 7

| Int. | structure | Starting material |
|---|---|---|
| 34 | 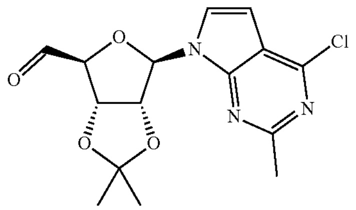 [SMILES: Cc1nc(Cl)c2ccn([C@@H]3O[C@H](C=O)[C@H]4OC(C)(C)O[C@H]43)c2n1] | intermediate 7 |

TABLE 7-continued

| Int. | structure | Starting material |
|---|---|---|
| 35 | 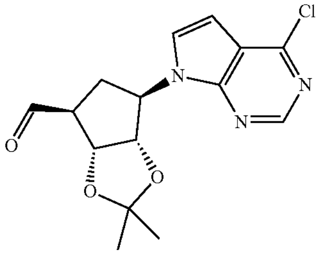 [SMILES: CC1(C)O[C@@H]2[C@H](O1)[C@@H](C=O)C[C@H]2n1ccc2c(Cl)ncnc21] | intermediate 10 |
| 36 | 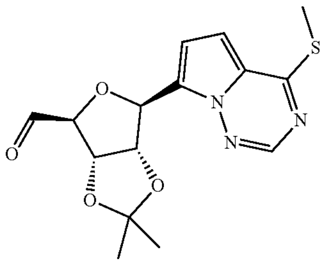 [SMILES: CSc1ncnn2c([C@@H]3O[C@H](C=O)[C@H]4OC(C)(C)O[C@H]43)ccc12] | intermediate 14 |
| 512 | 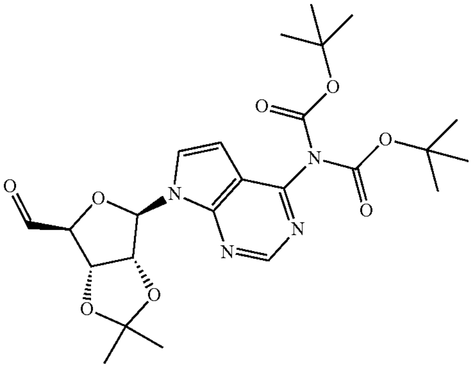 [SMILES: CC(C)(C)OC(=O)N(C(=O)OC(C)(C)C)c1ncnc2c1ccn2[C@@H]1O[C@H](C=O)[C@H]2OC(C)(C)O[C@H]21] | intermediate 28 |

Example A14

Preparation of Intermediate 37

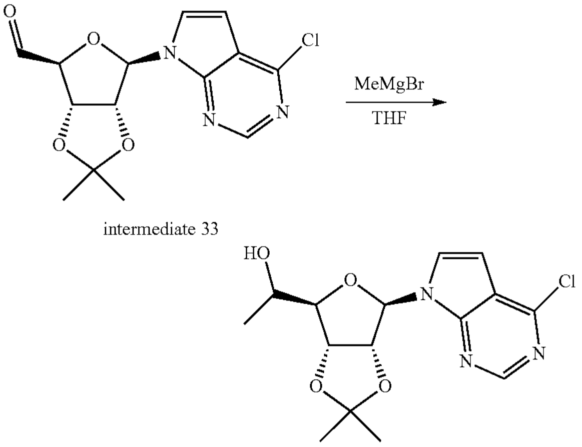

intermediate 33 intermediate 37

To a solution of intermediate 33 (6.5 g, crude, ≈15.46 mmol) in THF (200 mL) was added dropwise MeMgBr (1M, 18.55 ml, 18.55 mmol) at −78° C. under $N_2$. The mixture was stirred overnight at room temperature under $N_2$. The reaction mixture was concentrated under vacuum to give crude product as a yellow solid. The crude product was purified by column chromatography (gradient elution: petroleum ether/EtOAc from 40:1 to 10:1). The desired fractions were collected and the solvent was evaporated to give Intermediate 37 as light yellow oil (700 mg crude; and 3 g crude with more impurities).

Example A15

Preparation of Intermediate 38
Method 1

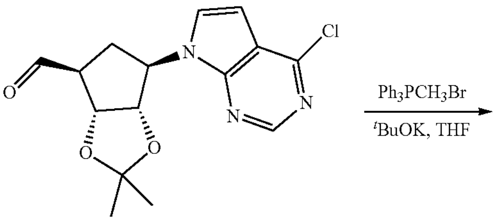

Intermediate 35

-continued

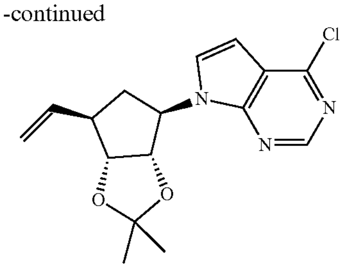

Intermediate 38

To a mixture of methyltriphenylphosphonium bromide (4.87 g, 13.62 mmol) in THF (500 mL) was added t-BuOK (11.4 mL, 1 M in THF, 1.27 g, 11.35 mmol,) dropwise at 0° C. under $N_2$. The suspension was turned to bright yellow and stirred at 0° C. for 0.5 h and then warmed to 25° C. for 0.5 h. The mixture was cooled to −40° C. The solution of Intermediate 35 (1.46 g, theoretically 4.54 mmol) in THF (130.0 mL) was added drop-wise and then stirred at −20° C. for 1 h, after this, the mixture was warmed to 25° C. for 2 h. To the mixture was added saturated $NH_4Cl$ (300 ml) and stirred for 10 min. Layers were separated and the aqueous phase was extracted with DCM (300 mL×2). The combined organic phase was washed with saturated brine (500 mL), dried with anhydrous $MgSO_4$, filtered and concentrated in vacuum. The residue was purified by silica gel chromatography (ISCO®; 80 g SepaFlash® Silica Flash Column, Gradient eluention: From 0 to 15% of Ethyl acetate/Petroleum ether). The desired fractions were collected and the solvent was evaporated. Intermediate 38 was obtained as off-white solid (530 mg, 36% yield).

Below intermediates were prepared by an analogous reaction protocol as was used for the preparation of intermediate 38 (Method 1) using the appropriate starting materials (Table 8).

TABLE 8

| Int. | structure | Starting material |
|---|---|---|
| 39 | 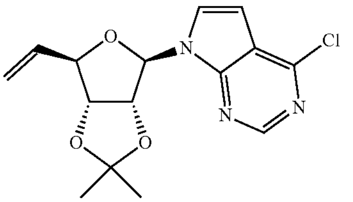 [SMILES: C=C[C@H]1O[C@@H](n2ccc3c(Cl)ncnc32)[C@@H]2OC(C)(C)O[C@@H]21] | Intermediate 33 |
| 40 | 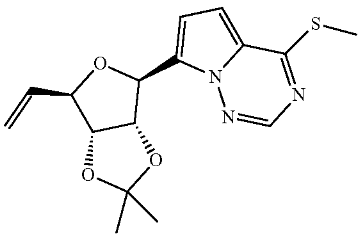 [SMILES: C=C[C@H]1O[C@@H](c2ccc3c(SC)ncnn23)[C@@H]2OC(C)(C)O[C@@H]21] | Intermediate 36 |
| 513 | 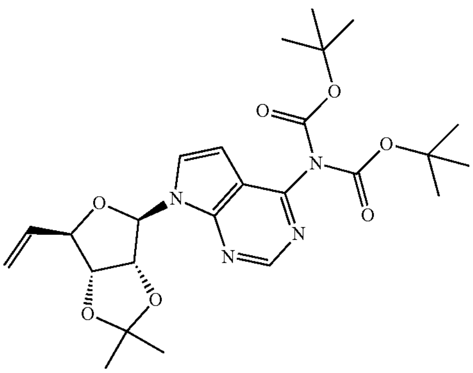 [SMILES: C=C[C@H]1O[C@@H](n2ccc3c(N(C(=O)OC(C)(C)C)C(=O)OC(C)(C)C)ncnc32)[C@@H]2OC(C)(C)O[C@@H]21] | Intermediate 512 |

Method 2

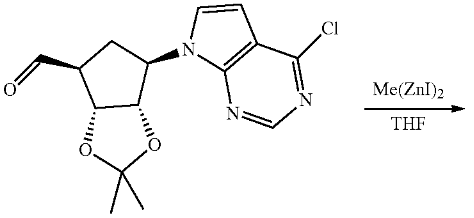

Intermediate 35

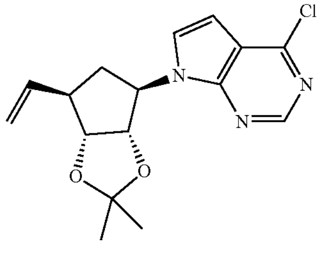

Intermediate 38

A solution of Intermediate 35 (10.0 g, theoretically 31.1 mmol) in THF (100 mL) was added drop-wise under $N_2$ over a period of 30 minutes to a bis(iodozincio)methane solution in THF (180 mL, 0.31 M, 55.9 mmol, prepared according to the procedure described in *Tetrahedron* 2002, 58, 8255-8262), stirring was continued until complete conversion (approximately 2 hours). The reaction mixture was quenched by the slow addition of a saturated aqueous $NH_4Cl$ solution, during which salt formation was observed. Prior to extraction (EtOAc, 2×200 mL), the salts were dissolved again by the addition of an aqueous ammonia solution (25%). The combined organic phases were washed with an aqueous sodium bisulfite solution and brine, dried with anhydrous $MgSO_4$, filtered and concentrated in vacuum. The residue was purified by silica gel chromatography (eluent: dichloromethane/EtOAc 95/5) to provide Intermediate 38 as an off-white solid (6.9 g, 66%).

Method 3

Step 1

Preparation of Intermediate 408

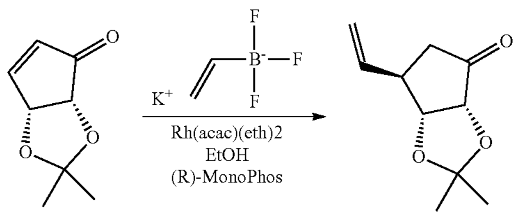

Intermediate 408

Acetylacetonatobis(ethylene)rhodium(I) (0.837 g, 3.24 mmol) and (R)—N,N-dimethyldinaphtho[2,1-D:1',2'-F][1,3,2]dioxaphosphepin-4-amine (2.91 g, 8.11 mmol) were dissolved in EtOH (625 mL) under nitrogen atmosphere. The mixture was stirred at room temperature and flushed through with nitrogen gas for 15 minutes. Then (−)-(3AR,6AR)-3A,6A-dihydro-2,2-dimethyl-4H-cyclopenta-1,3-dioxol-4-one (25 g, 162.16 mmol) and potassium vinyltrifluoroborate (45.73 g, 324.33 mmol) were added and then the reaction mixture was stirred and refluxed for 4 hours. The reaction mixture (suspension) was cooled down to room temperature. The precipitate was filtered off over a pad of Celite and washed with ethanol. The solvents of the filtrate were evaporated. 1 L heptane was added to the residue. The resulting suspension was filtered off over a pad of Celite and washed with heptanes resulting in a dark brown solid residue. The filtrate was washed three times with 300 mL $NH_4OH$, washed with brine, dried with $MgSO_4$, filtered and the solvents of the filtrate evaporated yielding intermediate 408 (16.18 g, 51% yield).

Step 2

Preparation of Intermediate 409

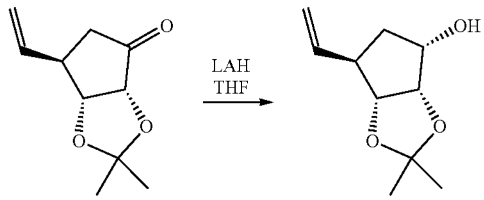

Intermediate 408 Intermediate 409

A solution of intermediate 408 (16.18 g, 82.58 mmol) in THF (200 mL) was added dropwise to a stirred solution of lithium aluminum hydride 1M in THF (24.78 mL, 1 M, 24.78 mmol) in THF (400 mL) at −78° C. under nitrogen atmosphere. The reaction mixture was stirred at −78° C. under nitrogen atmosphere for 30 minutes. The reaction was quenched by the dropwise addition of acetone (6.1 mL) followed by 50 mL water at −78° C. After addition the reaction mixture was allowed to warm up to room temperature and then 400 mL EtOAc was added. The mixture was shaken vigorously. The organic layer was separated, washed three times with water, washed with brine, dried with $MgSO_4$, filtered and the solvents of the filtrate evaporated. The residue was dissolved in ethylacetate and purified over a $SiO_2$ column, type Grace Reveleris SRC, 80 g, Si 40, on an Armen Spot II Ultimate purification system using ethyl acetate and heptane as eluent in a gradient starting from 100% heptanes and ending with 50% heptane and 50% ethyl acetate. The fractions containing product were combined and the solvents were evaporated yielding intermediate 409 (10.77 g, 71% yield).

Step 3

Preparation of Intermediate 410

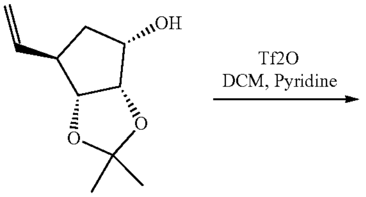

Intermediate 409

-continued

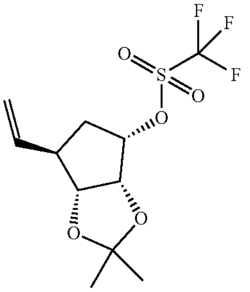

Intermediate 410

A solution of $Tf_2O$ (13.31 mL, 1.71 g/mL, 80.93 mmol) in DCM, anhydrous (60 ml) was added dropwise to a mixture of intermediate 409 (9.94 g, 53.95 mmol) and pyridine, anhydrous (85 mL) in DCM, anhydrous (140 mL) at 0° C. The reaction mixture was stirred for 30 minutes and then 75 mL cold water was added. The layers were separated and the organic layer was washed three times with 75 mL water, dried with $MgSO_4$, filtered and the solvents evaporated and co-evaporated with 200 mL toluene. The residue was dissolved in heptane and ethyl acetate and purified over a Sift column, type Grace Reveleris SRC, 40 g, Si 40, on an Armen Spot II Ultimate purification system using ethyl acetate and heptane as eluent in a gradient starting from 100% heptane and ending with 50% heptane and 50% ethyl acetate. The fractions containing product were combined and the solvents were evaporated yielding intermediate 410 (13.0 g, 67% yield).

Step 4

Preparation of Intermediate 411

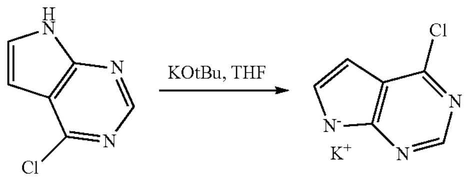

Intermediate 411

A mixture of 4-chloro-7H-pyrrolo[2,3-D]pyrimidine (100 g, 651 mmol) and KOtBu (73.07 g, 651 mmol) in THF (1 L) was stirred at room temperature for 45 minutes until a clear solution was obtained. The solvents were evaporated. The residue was triturated in DIPE. The white solids were filtered off and dried in vacuo at 30° C. yielding intermediate 411 (112.6 g, 90% yield).

Step 5
Preparation of Intermediate 38

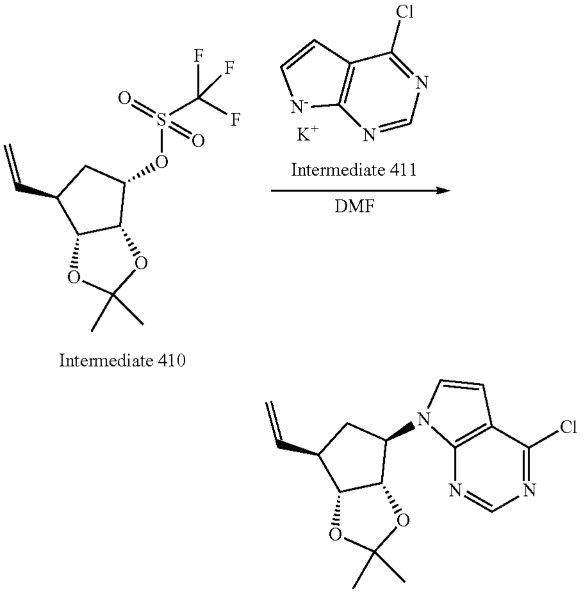

Intermediate 410

Intermediate 38

A solution of intermediate 410 (13 g, 41.1 mmol) in DMF (50 mL) was added dropwise to a stirred solution of intermediate 411 (7.88 g, 41.1 mmol) in DMF (150 mL) at 0° C. After addition the reaction mixture was allowed to warm up to room temperature and was then stirred for 18 hours. Another amount of intermediate 411 (1.57 g, 8.22 mmol) was added. The reaction mixture was stirred at room temperature for 2 hours. The reaction mixture was poured out into a beaker with ice and water (~0.5 L). The resulting suspension was stirred for 2 hours and then filtered off. The residue was washed three times with water and then dried in vacuo at 50° C. yielding intermediate 38 as a white solid (8.75 g, 65% yield).

Example A 54

Preparation of Intermediate 433

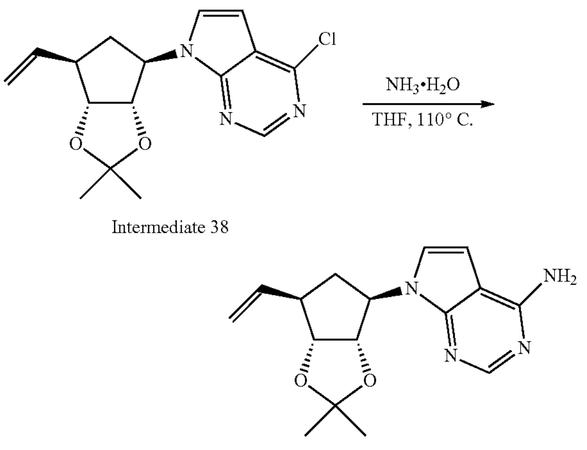

Intermediate 38

Intermediate 433

A solution of intermediate 38 (18.3 g, 57.22 mmol) in a mixture of aqueous ammonia (25%, 100 ml) and THF (100 ml) was heated in a sealed metal pressure vessel at 110° C. until complete conversion (~16 h). The reaction mixture was allowed to cool to room temperature, after which ethyl acetate and brine were added. Both layers were separated, the water layer was extracted once with ethyl acetate. The combined organic phases were washed with brine, dried with anhydrous $MgSO_4$, filtered and concentrated in vacuum to give Intermediate 433 as a light yellow solid (17.2 g, 100%), which was used in the next reaction step without further purification.

Below intermediates were prepared by an analogous reaction protocol as was used for the preparation of intermediate 433 using the appropriate starting materials (Table 24

TABLE 24

| Int. | structure | Starting materials |
|---|---|---|
| 487 | 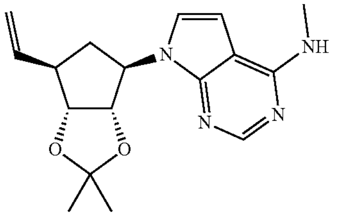 [SMILES: C=C[C@H]1C[C@@H](n2ccc3c(NC)ncnc32)[C@@H]2OC(C)(C)O[C@@H]21] | Intermediate 38 methylamine |
| 490 | 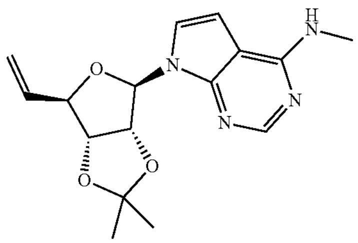 [SMILES: C=C[C@H]1O[C@@H](n2ccc3c(NC)ncnc32)[C@@H]2OC(C)(C)O[C@@H]21] | Intermediate 39 methylamine |

Example A16

Preparation of Intermediate 41

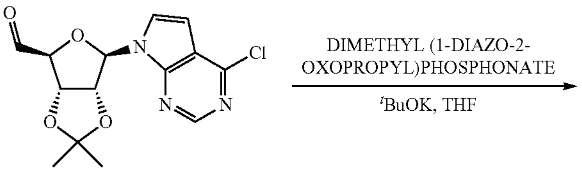

intermediate 33

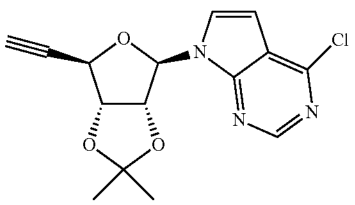

intermediate 41

To a solution of potassium tert-butoxide (1.28 g; 11.4 mmol) in THF (30 mL) at −78° C. was added a solution of dimethyl (1-diazo-2-oxopropyl)phosphonate (1.72 g; 11.4 mmol) in THF (5 mL). The solution was stirred for 5 min and then the solution of intermediate 33 (1.90 g; theoretically 5.87 mmol) in THF (20 mL) was added. The solution was allowed to warm to room temperature and stirred at room temperature for 15 minutes. Water and EtOAc were added, the organic layer was separated, dried over MgSO4, filtered and evaporated in vacuo. The residues were purified by preparative LC (Irregular SiOH 15-40 μm, 80 g Grace, DCM loading, mobile phase gradient elution:heptane: 10% MeOH in EtOAc from 90:10, to 70:30). The desired fractions were collected and the solvent was evaporated to yield intermediate 41 as a colorless oil (1.08 g, 58% yield).

Example A17

Preparation of Intermediate 43

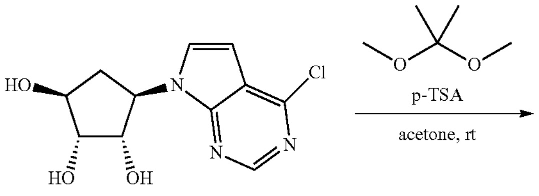

intermediate 42

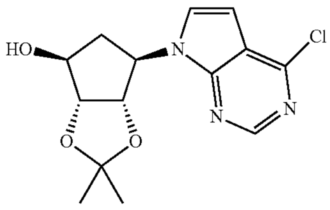

intermediate 43

To a solution of intermediate 42 (9.2 g, 34.114 mmol) in acetone (100 mL) was added 2,2-dimethoxypropane (7.1 g, 68.118 mmol) and p-TSA (1.8 g, 10.184 mmol). The reaction mixture was stirred overnight at room temperature. The reaction mixture was treated with aqueous $NaHCO_3$ (PH to 7-8), then concentrated under reduced pressure. The resulting residue was diluted with water (100 mL) and extracted with ethyl acetate (100 mL×3). The organic layer was dried and concentrated under reduced pressure.

The crude product was purified by silica gel chromatography (gradient elution: petroleum ether/ethyl acetate from 8/1 to 2/1). The desired fractions were collected and the solvent was evaporated to afford the intermediate 43 as a pale yellow solid (9.5 g, 90% yield).

Example A18

Preparation of Intermediate 44

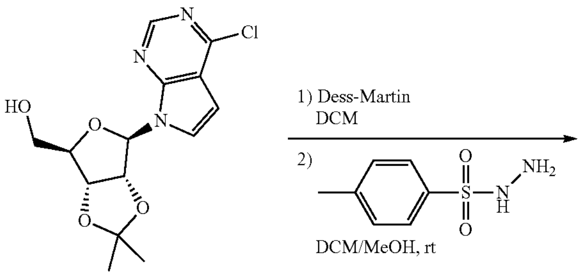

intermediate 1

-continued

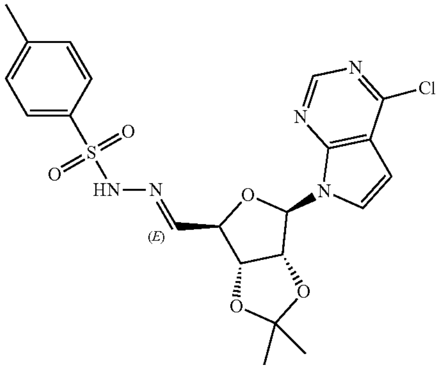

intermediate 44
(70% over two steps)

A solution of intermediate 1 (2.00 g, theoretically 6.18 mmol) in DCM (30.00 mL) was added dropwise to a suspension of Dess-Martin periodinane (3.14 g, 7.41 mmol) in DCM (30.00 mL) at 0° C. under $N_2$. The reaction mixture was allowed to warm to room temperature and stirred until oxidation was finished (2 hours). Subsequently, MeOH (60 mL) and tosylhydrazide (1.50 g, 8.03 mmol) were added and stirring was continued for 3 hours. Water and ethyl acetate were added to the reaction mixture, the organic phase was separated and washed with saturated $Na_2CO_3$, dried with anhydrous $MgSO_4$, filtered and concentrated in vacuum. The crude product was purified by silica gel column chromatography (gradient elution: dichloromethane/methanol from 100:0 to 98.5:1.5). The desired fractions were collected and the solvent was evaporated to yield intermediate 44 as a white powder (2.60 g, 70% yield; (E)).

Below intermediates were prepared by an analogous reaction protocol as was used for the preparation of intermediate 44 using the appropriate starting materials (Table 25

TABLE 25

| Int. | Structure | Starting materials |
|---|---|---|
| 207 | 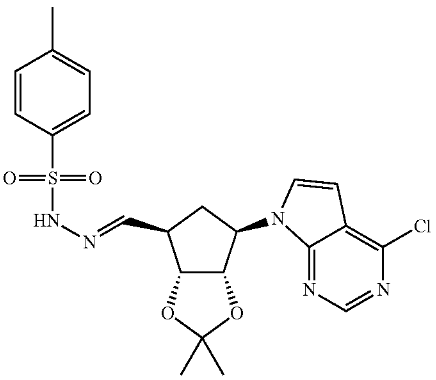 [SMILES: Cc1ccc(S(=O)(=O)N/N=C/[C@H]2C[C@@H](n3ccc4c(Cl)ncnc43)[C@@H]3OC(C)(C)O[C@@H]32)cc1] | Intermediate 10 |

Example A 55

Preparation of Intermediate 224

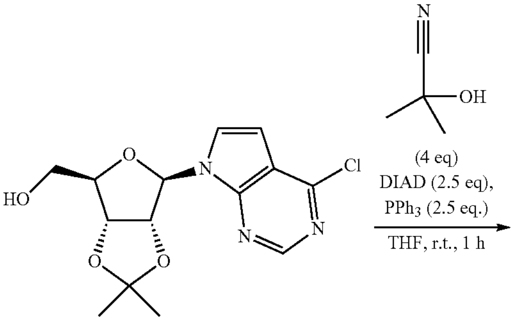

intermediate 2

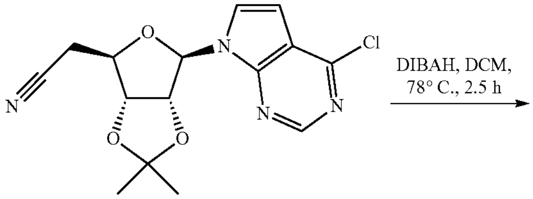

intermediate 222

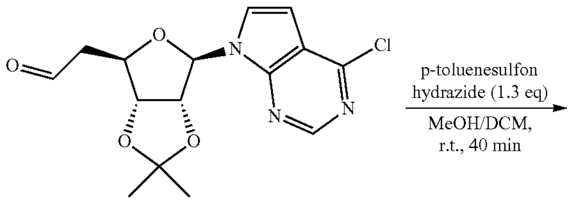

intermediate 223

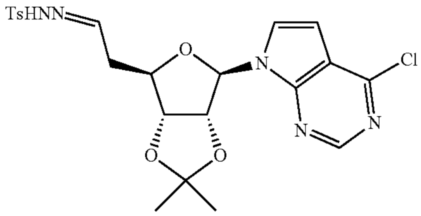

intermediate 224

Step 1:

Preparation of intermediate 222

DIAD (7.6 mL, 38.4 mmol, 2.5 eq) was added to a solution of intermediate 2 (5.0 g, 15.3 mmol, 1.0 eq), triphenylphosphine (10.0 g, 38.4 mmol, 2.5 eq) and acetone cyanohydrin (5.6 mL, 61.4 mmol, 4.0 eq) in anhydrous THF (75 mL) at r.t. The reaction mixture was stirred for 1 hour and then concentrated in vacuo. The crude product was purified by normal phase flash chromatography using heptane and DCM as eluent ($SiO_2$ column, gradient: 50% to 100% DCM isocratic 100% DCM) and then followed by a preparative reversed phase flash chromatography using acetonitrile and water with 0.2% $NH_4HCO_3$ as eluent to afford intermediate 222 as white solid product (2.8 g, 8.5 mmol, yield 55%)

Step 2:

Preparation of Intermediate 223 and Intermediate 224

A solution of intermediate 222 (1.54 g, 4.6 mmol, 1 eq) in anhydrous DCM was dried overnight over molecular sieves and filtered. The filtrate was cooled to −78° C. and then 1M DIBAH in DCM (4.6 mL, 4.6 mmol, 1 eq) was added dropwise. The reaction mixture was stirred for 1 hour at −78° C., then extra 1M DIBAH in DCM (0.46 mL, 0.46 mmol, 0.1 eq) was added and stirred for another 1.5 hours, then quenched with sodium acetate (4.2 g, 51.2 mmol, 11.1 eq) and acetic acid (4.2 mL, 73.4 mL, 16.0 eq) in a mixture of water/THF (57 mL/12 mL). After the quench, the cooling bath was removed and the mixture was stirred until all ice was melted. The layers were separated and then the aqueous phase was extracted twice with DCM (30 mL). The organic phases were combined, washed twice with brine, dried over $MgSO_4$ and filtered. To the obtained filtrate containing intermediate 223 was added MeOH (50 mL), p-toluenesulfonyl hydrazide (1.1 g, 6.0 mmol, 3 eq) and then stirred at r.t. for 40 minutes The reaction mixture was washed three times with sat. $NaHCO_3$, twice with brine, dried over $MgSO_4$, filtered and concentrated in vacuo. The crude product was purified by normal phase flash chromatography using heptane and EtOAc as eluent (gradient: 40% to 60% EtOAc to afford the crude product The mixture was further purified by normal phase flash chromatography using EtOAc and heptane as eluent ($SiO_2$ column, gradient: 40% to 60% EtOAc) to afford intermediate 224 (0.5 g, 0.6 mmol, yield: 14%).

Example A19

Preparation of Intermediate 45

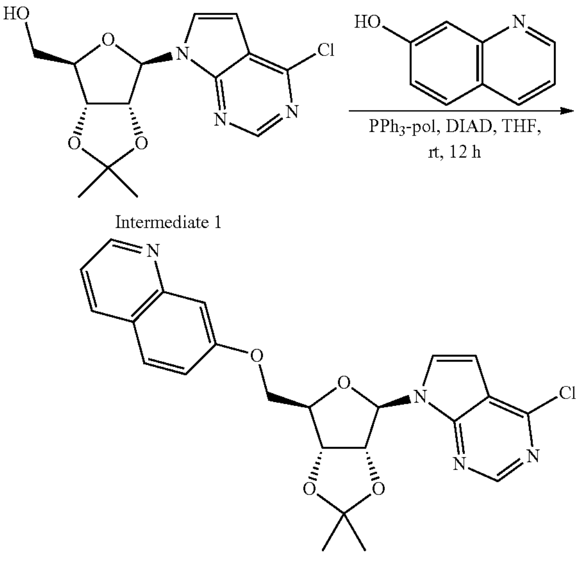

Intermediate 1

Intermediate 45

Intermediate 1 (300 mg, theoretically 0.921 mmol), 7-Quinolinol (160 mg, 1.11 mmol) and polymer-bounded Triphenylphosphine (~3 mmol/g triphenylphosphine loading, 0.8 g, 2.4 mmol) were stirred in anhydrous THF (12 mL) under $N_2$. Subsequently, DIAD (0.465 g, 2.30 mmol) was added dropwise at 0° C. The mixture was stirred at room temperature for 12 hours under $N_2$. The reaction mixture was filtered over a pad of diatomaceous earth. The residue was washed with MeOH. The filtrate was concentrated in vacuum. The residue was purified by column chromatography over silica gel (eluent: petroleum ether/ethyl acetate from 10/1 to 3/1). The desired fractions were collected and the solvent was evaporated to give the crude intermediate 45 as oil (342 mg).

Below intermediates were prepared by an analogous reaction protocol as was used for the preparation of intermediate 45 using the appropriate starting materials (Table 9).

TABLE 9

| Int. | Structure | Starting materials |
|---|---|---|
| 46 | 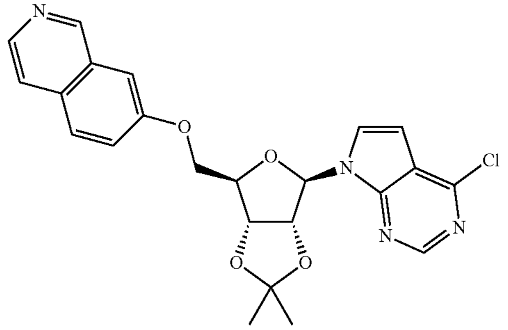 [SMILES: CC1(C)O[C@@H]2[C@H](O1)[C@@H](COc1ccc3ccncc3c1)O[C@H]2n1ccc2c(Cl)ncnc21] | a) Intermediate 1<br>b) 7-isoquinolinol |

TABLE 9-continued
| Int. | Structure | Starting materials |
| --- | --- | --- |
| 47 | 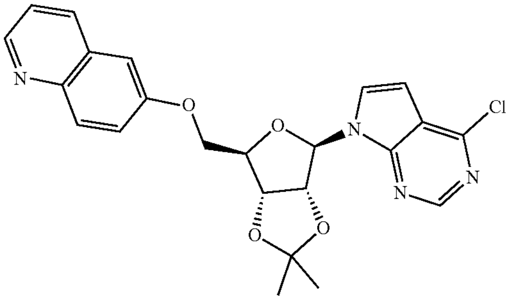 [SMILES: CC1(C)O[C@@H]2[C@H](O1)[C@@H](COc1ccc3ncccc3c1)O[C@H]2n1ccc2c(Cl)ncnc21] | a) Intermediate 1<br>b) 6-hydroxyquinoline |
| 48 | 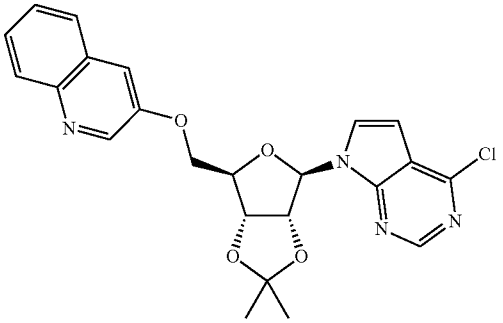 [SMILES: CC1(C)O[C@@H]2[C@H](O1)[C@@H](COc1cnc3ccccc3c1)O[C@H]2n1ccc2c(Cl)ncnc21] | a) Intermediate 1<br>b) 3-hydroxyquinoline |
| 49 | 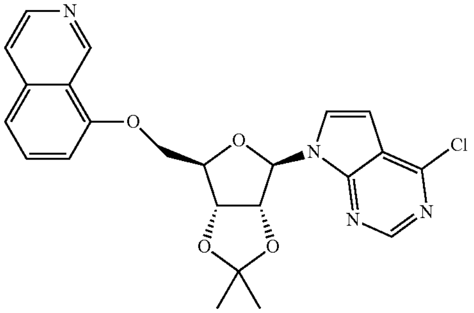 [SMILES: CC1(C)O[C@@H]2[C@H](O1)[C@@H](COc1cccc3ccncc13)O[C@H]2n1ccc2c(Cl)ncnc21] | a) Intermediate 1<br>b) 8-hydroxyisoquinoline |
| 50 | 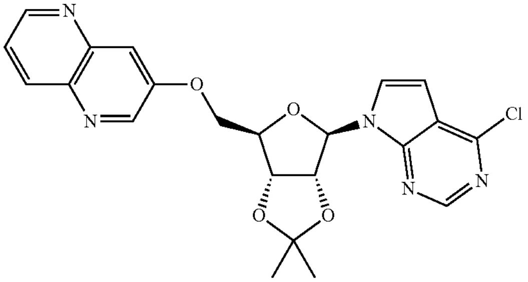 [SMILES: CC1(C)O[C@@H]2[C@H](O1)[C@@H](COc1cnc3cccnc3c1)O[C@H]2n1ccc2c(Cl)ncnc21] | a) Intermediate 1<br>b) 1,5-naphthyridin-3-ol |
| 51 | 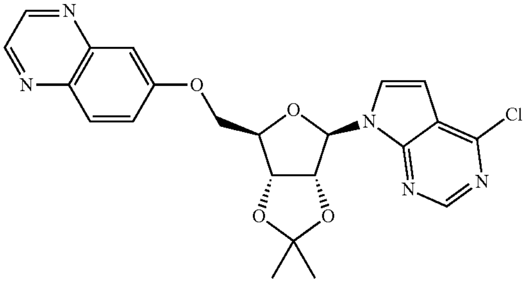 [SMILES: CC1(C)O[C@@H]2[C@H](O1)[C@@H](COc1ccc3nccnc3c1)O[C@H]2n1ccc2c(Cl)ncnc21] | a) Intermediate 1<br>b) 6-quinoxalinol |

TABLE 9-continued
| Int. | Structure | Starting materials |
|---|---|---|
| 52 | 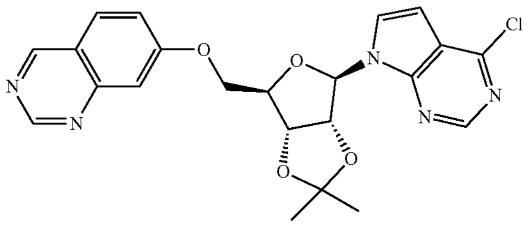 [SMILES: CC1(C)O[C@@H]2[C@H](O1)[C@@H](COc1ccc3cncnc3c1)O[C@H]2n1ccc2c(Cl)ncnc21] | a) Intermediate 1<br>b) Quinazolin-7-ol |
| 53 | 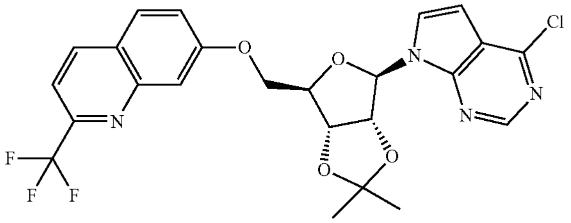 [SMILES: CC1(C)O[C@@H]2[C@H](O1)[C@@H](COc1ccc3ccc(C(F)(F)F)nc3c1)O[C@H]2n1ccc2c(Cl)ncnc21] | a) Intermediate 1<br>b) 2-(trifluoromethyl)-quinolin-7-ol |
| 54 | 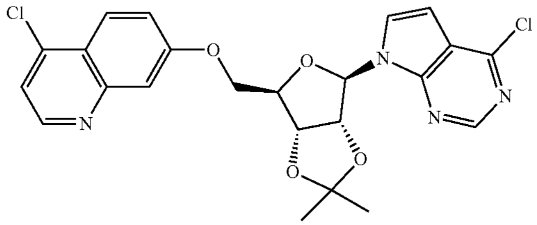 [SMILES: CC1(C)O[C@@H]2[C@H](O1)[C@@H](COc1ccc3c(Cl)ccnc3c1)O[C@H]2n1ccc2c(Cl)ncnc21] | a) Intermediate 1<br>b) 4-chloro-7-hydroxyquinoline |
| 55 | 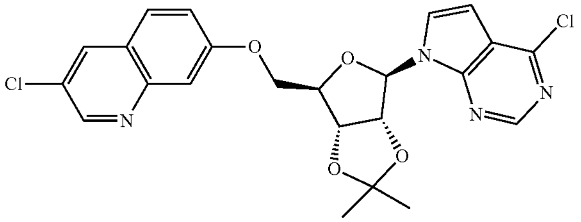 [SMILES: CC1(C)O[C@@H]2[C@H](O1)[C@@H](COc1ccc3cc(Cl)cnc3c1)O[C@H]2n1ccc2c(Cl)ncnc21] | a) Intermediate 1<br>b) 3-chloroquinolin-7-ol |
| 56 | 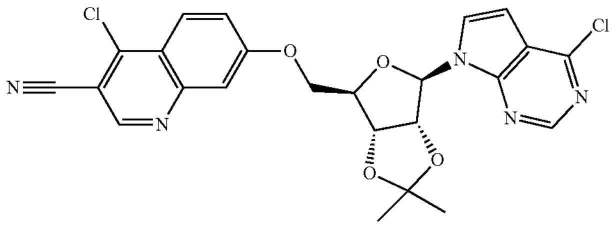 [SMILES: CC1(C)O[C@@H]2[C@H](O1)[C@@H](COc1ccc3c(Cl)c(C#N)cnc3c1)O[C@H]2n1ccc2c(Cl)ncnc21] | a) Intermediate 1<br>b) 4-chloro-7-hydroxy-quinoline-3-carbonitrile |
| 57 | 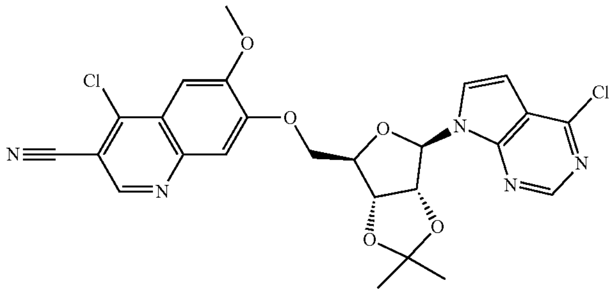 [SMILES: COc1cc2c(Cl)c(C#N)cnc2cc1OC[C@H]1O[C@@H](n2ccc3c(Cl)ncnc32)[C@@H]2OC(C)(C)O[C@@H]21] | a) Intermediate 1<br>b) 4-chloro-7-hydroxy-6-methoxyquinoline-3-carbonitrile |

TABLE 9-continued
| Int. | Structure | Starting materials |
|---|---|---|
| 58 | 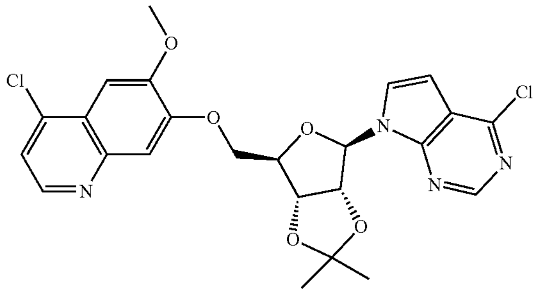 [SMILES: COc1cc2c(Cl)ccnc2cc1OC[C@H]1O[C@@H](n2ccc3c(Cl)ncnc32)[C@@H]2OC(C)(C)O[C@@H]21] | a) Intermediate 1<br>b) 4-chloro-6-methoxyquinoline-7-ol |
| 59 | 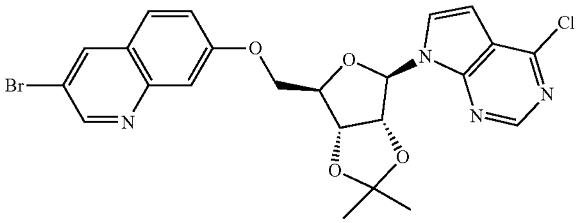 | a) Intermediate 1<br>b) 3-bromoquinolin-7-ol |
| 60 | 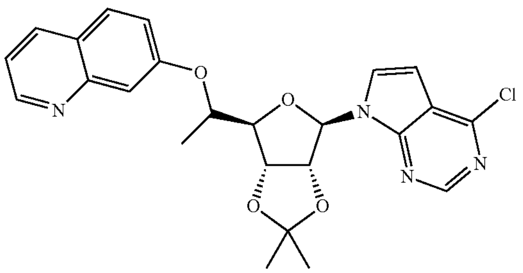 [SMILES: CC(Oc1ccc2cccnc2c1)[C@H]1O[C@@H](n2ccc3c(Cl)ncnc32)[C@@H]2OC(C)(C)O[C@@H]21] | a) Intermediate 34<br>b) 7-quinolinol |
| 187 | 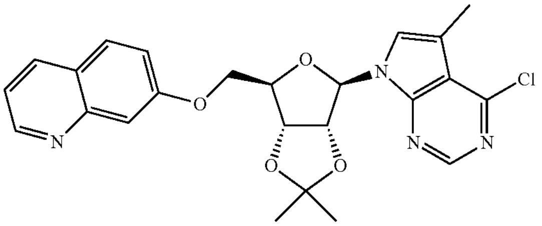 [SMILES: Cc1cn([C@@H]2O[C@H](COc3ccc4cccnc4c3)[C@H]3OC(C)(C)O[C@H]32)c2ncnc(Cl)c12] | a) Intermediate 186<br>b) 7-quinolinol |

TABLE 9-continued

| Int. | Structure | Starting materials |
|---|---|---|
| 191 | 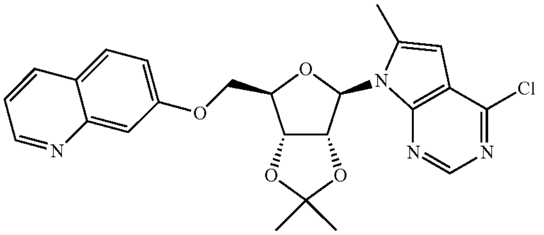 [SMILES: Cc1cc2c(Cl)ncnc2n1[C@@H]1O[C@H](COc2ccc3cccnc3c2)[C@H]2OC(C)(C)O[C@H]21] | a) Intermediate 190<br>b) 7-quinolinol |
| 233 | 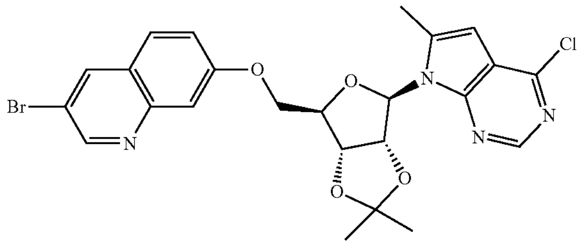 [SMILES: Cc1cc2c(Cl)ncnc2n1[C@@H]1O[C@H](COc2ccc3cc(Br)cnc3c2)[C@H]2OC(C)(C)O[C@H]21] | a) Intermediate 190<br>b) 3-bromoquinolin-7-ol |

Example A19b

Preparation of Intermediate 59

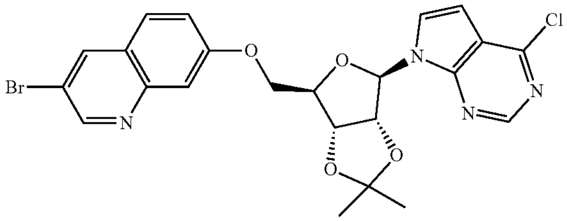 [SMILES: CC1(C)O[C@@H]2[C@H](O1)[C@@H](COc1ccc3cc(Br)cnc3c1)O[C@H]2n1ccc2c(Cl)ncnc21]

Diisopropyl azodicarboxylate (0.221 mL, 1.125 mmol) was added dropwise to a stirred suspension of intermediate 1 (0.27 g, 0.80 mmol), 3-bromoquinolin-7-ol (0.18 g, 0.80 mmol) and triphenylphosphine resin (0.375 g, 3 mmol/g, 1.125 mmol) in THF (8 ml) at room temperature. After addition the reaction mixture was stirred for 18 hours. The reaction mixture was filtered over a pad of Dicalite®. The residue was washed with methanol. The solvents of the filtrate were evaporated. The residue was used as such in the next step.

Example A20

Preparation of Intermediate 61

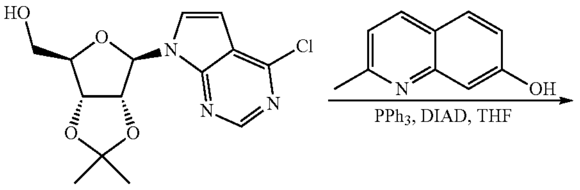

intermediate 1

-continued

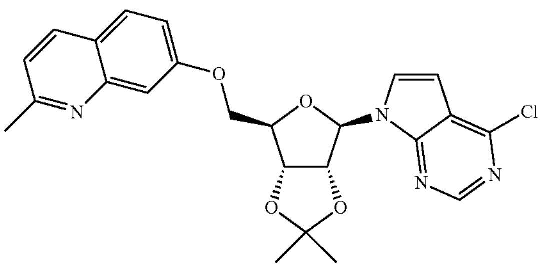

intermediate 61

The mixture of intermediate 1 (2.46 g, theoretically 7.54 mmol), 2-methylquinolin-7-ol (1.2 g, 7.54 mmol) and $PPh_3$ (5.93 g, 22.6 mmol) in dry THF (40 ml) was stirred at room temperature under $N_2$. DIAD (4.57 g, 22.6 mmol) was added dropwise. The reaction mixture was stirred overnight at room temperature. Water (80 mL) was added to the mixture, extracted with EtOAc (100 mL×3). The combined organic layers were washed by brine (100 mL), dried over anhydrous $Na_2SO_4$, filtered and concentrated under vacuum. The residue was purified by column chromatography (gradient elution: EtOAc/Petroleum ether from 1:20 to 1:1). The desired fractions were collected and the solvent was evaporated to yield intermediate 61 (3.0 g, crude). The crude intermediate 61 was used for the next reaction step without further purification.

Below intermediates were prepared by an analogous reaction protocol as was used for the preparation of intermediate 61 using the appropriate starting materials (Table 10).

TABLE 10
| Int. | Structure | Starting materials |
| --- | --- | --- |
| 62 | 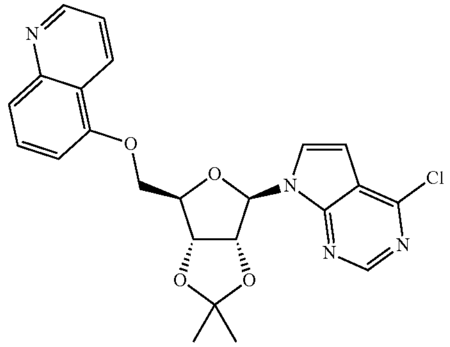 [SMILES: CC1(C)O[C@@H]2[C@H](O1)[C@@H](COc1cccc3ncccc13)O[C@H]2n1ccc2c(Cl)ncnc21] | a) Intermediate 1<br>b) 5-Quinolinol |
| 63 | 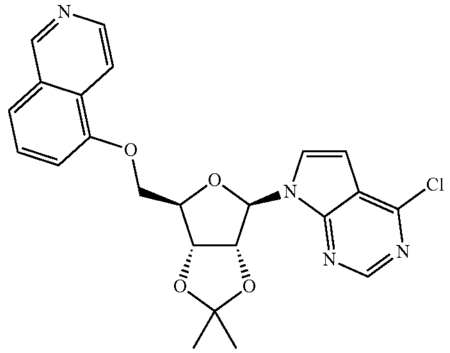 [SMILES: CC1(C)O[C@@H]2[C@H](O1)[C@@H](COc1cccc3cnccc13)O[C@H]2n1ccc2c(Cl)ncnc21] | a) Intermediate 1<br>b) 5-Isoquinolinol |
| 64 | 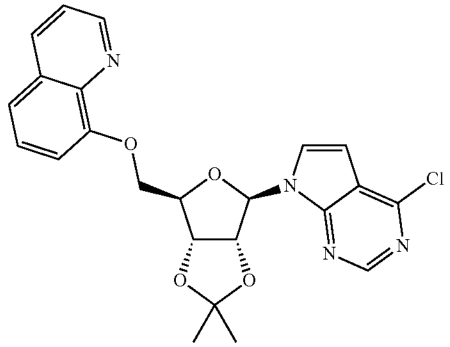 [SMILES: CC1(C)O[C@@H]2[C@H](O1)[C@@H](COc1cccc3cccnc13)O[C@H]2n1ccc2c(Cl)ncnc21] | a) Intermediate 1<br>b) 8-Quinolinol |
| 65 | 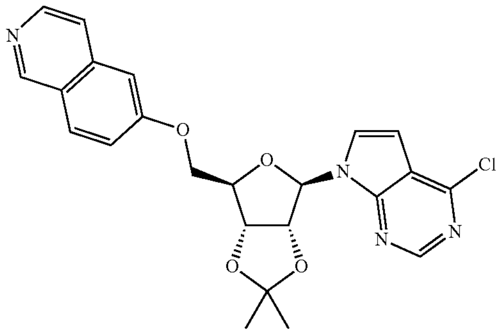 [SMILES: CC1(C)O[C@@H]2[C@H](O1)[C@@H](COc1ccc3cnccc3c1)O[C@H]2n1ccc2c(Cl)ncnc21] | a) Intermediate 1<br>b) 6-Isoquinolinol |

TABLE 10-continued
| Int. | Structure | Starting materials |
|---|---|---|
| 66 | 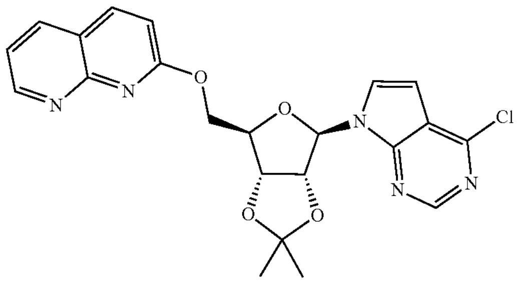 [SMILES: CC1(C)O[C@@H]2[C@H](O1)[C@@H](COc1ccc3cccnc3n1)O[C@H]2n1ccc2c(Cl)ncnc21] | a) Intermediate 1<br>b) 1,8-naphthyridin-2-ol |
| 67 | 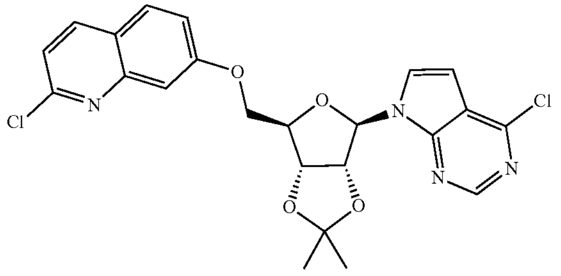 [SMILES: CC1(C)O[C@@H]2[C@H](O1)[C@@H](COc1ccc3ccc(Cl)nc3c1)O[C@H]2n1ccc2c(Cl)ncnc21] | a) Intermediate 1<br>b) 2-chloroquinolin-7-ol |
| 68 | 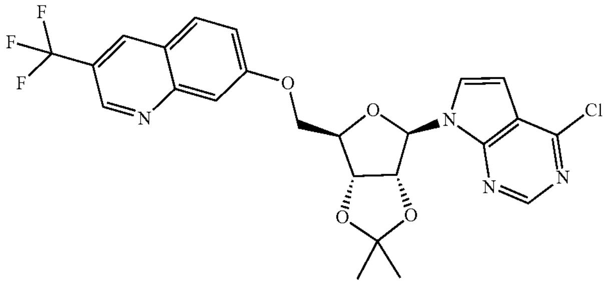 [SMILES: CC1(C)O[C@@H]2[C@H](O1)[C@@H](COc1ccc3cc(C(F)(F)F)cnc3c1)O[C@H]2n1ccc2c(Cl)ncnc21] | a) Intermediate 1<br>b) 3-(trifluoromethy)quinolin-7-ol |
| 69 | 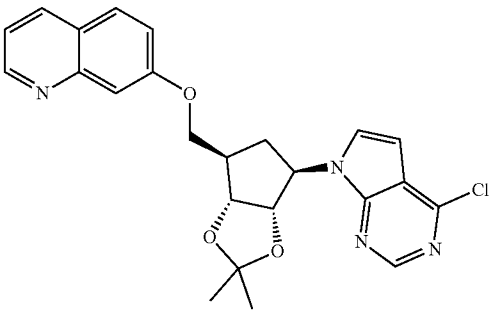 [SMILES: CC1(C)O[C@@H]2[C@@H](COc3ccc4cccnc4c3)C[C@@H](n3ccc4c(Cl)ncnc43)[C@@H]2O1] | a) Intermediate 10<br>b) 7-Quinolinol |
| 70 | 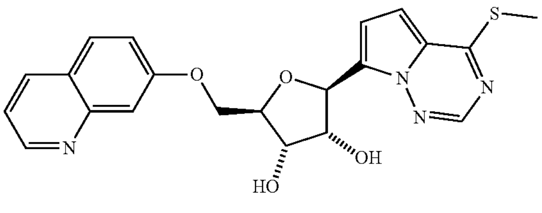 [SMILES: CSc1ncnn2c([C@@H]3O[C@H](COc4ccc5cccnc5c4)[C@@H](O)[C@H]3O)ccc12] | a) Intermediate 14<br>b) 7-Quinolinol |

TABLE 10-continued

| Int. | Structure | Starting materials |
|---|---|---|
| 515 | 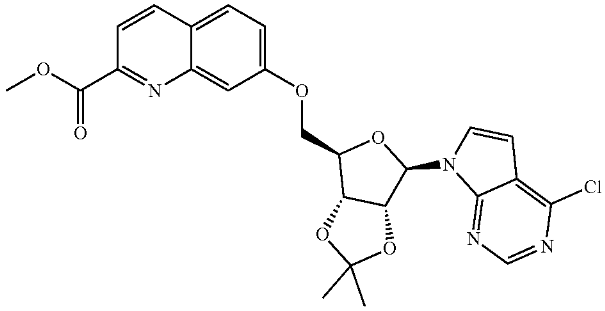 [SMILES: COC(=O)c1ccc2ccc(OC[C@H]3O[C@@H](n4ccc5c(Cl)ncnc54)[C@@H]4OC(C)(C)O[C@@H]43)cc2n1] | a) Intermediate 1<br>b) 2-Quinolinecarboxylic acid, 7-hydroxy-, methyl ester |

Example A21

Preparation of Intermediate 71

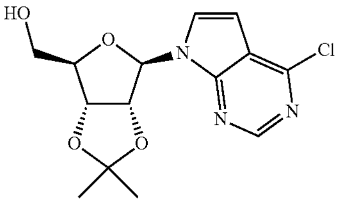

intermediate 1

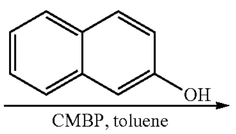

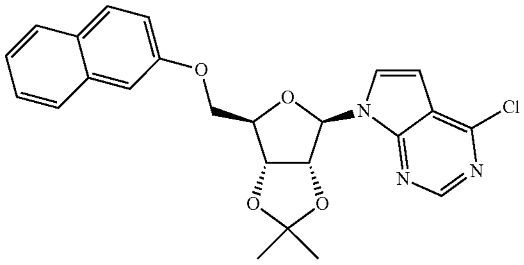

intermediate 71

To a solution of intermediate 1 (1.00 g, ≈2.92 mmol) and 2-naphthol (463 mg, 3.21 mmol) in toluene (30 mL) was added CMBP (1.15 mL, 4.38 mmol), The solution was heated at 80° C. for 18 hours and was then cooled down to room temperature. The reaction mixture was evaporated in vacuo. The residues were purified by preparative LC (Irregular SiOH 15-40 μm, 120 g Grace, DCM deposit, mobile phase gradient: heptane/EtOAc from 80/20 to 70/30) to give intermediate 71 as a colourless gum (1.00 g, 76% yield).

Example A22

Preparation of Intermediate 72

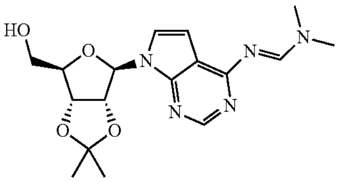

intermediate 24

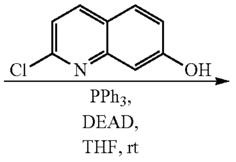

-continued

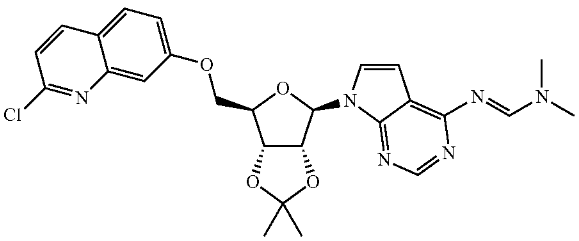

intermediate 72

A mixture of $PPh_3$ (9.07 g, 34.6 mmol) and DEAD (4.82 g, 27.7 mmol) in THF (100 mL) was stirred at room temperature for 10 min. Then Intermediate 24 (5.0 g, theoretically 13.8 mmol) was added, followed by 2-chloroquinolin-7-ol (2.98 g, 16.6 mmol). The resulting mixture was stirred at room temperature overnight. Subsequently, the mixture was diluted with EtOAc (100 mL), washed with water and brine. The organic phase was dried over $Na_2SO_4$, filtered and concentrated. The residue was purified by chromatography (elution: Petroleum ether/EtOAc=5/95). The desired fractions were collected and concentrated to give Intermediate 72 as solid (6.0 g, 83% yield).

Example A23

Preparation of Intermediate 73

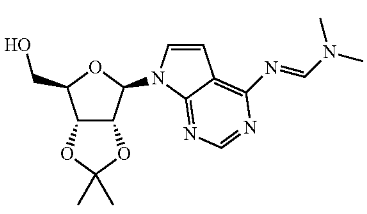

intermediate 24

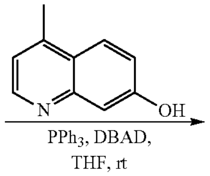

-continued

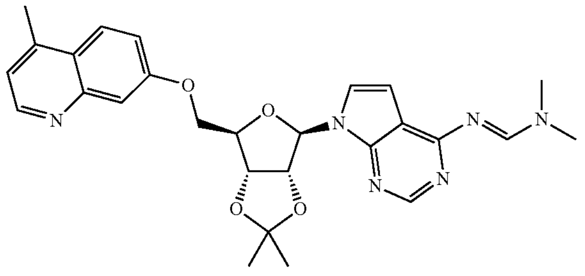

intermediate 73

To a solution of intermediate 24 (700 mg, theoretically 1.94 mmol) and 4-methylquinolin-7-ol (370 mg, 2.32 mmol) in THF (20 mL) were added triphenylphosine (624 mg, 2.71 mmol) and DBAD (711 mg, 2.71 mmol). The mixture was stirred overnight at room temperature and was then evaporated in vacuo. The crude was purified by preparative LC (irregular SiOH, 15-40 μm, 50 g, Merck, dry loading (Celite®) mobile phase gradient: from Heptane 80%, EtOAc 18%, MeOH 2% to Heptane 10%, EtOAc 81%, MeOH 9%) to give intermediate 73 as an off-white foam (697 mg, 67% yield).

Below intermediates were prepared by an analogous reaction protocol as was used for the preparation of intermediate 73 using the appropriate starting materials (Table 12).

TABLE 12

| Int. | Structure | Starting materials |
|---|---|---|
| 74 | 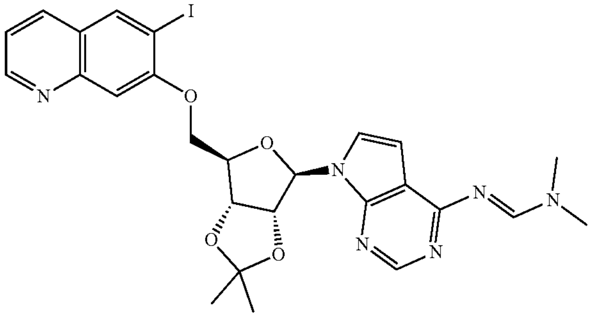 [SMILES: CN(C)/C=N/c1ncnc2c1ccn2[C@@H]1O[C@H](COc2cc3ncccc3cc2I)[C@H]2OC(C)(C)O[C@H]21] | a) Intermediate 24<br>b) 6-iodoquinolin-7-ol |
| 75 | 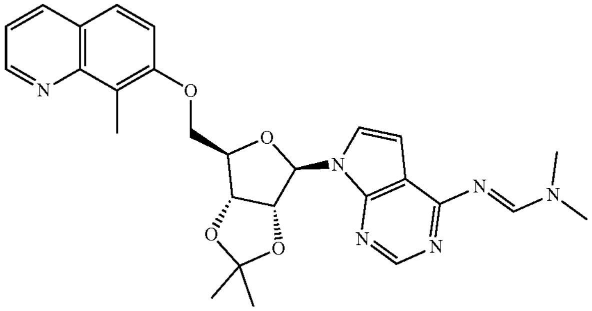 [SMILES: CN(C)/C=N/c1ncnc2c1ccn2[C@@H]1O[C@H](COc2ccc3cccnc3c2I)[C@H]2OC(C)(C)O[C@H]21] | a) Intermediate 24<br>b) 8-methylQuinolin-7-ol |
| 76 | 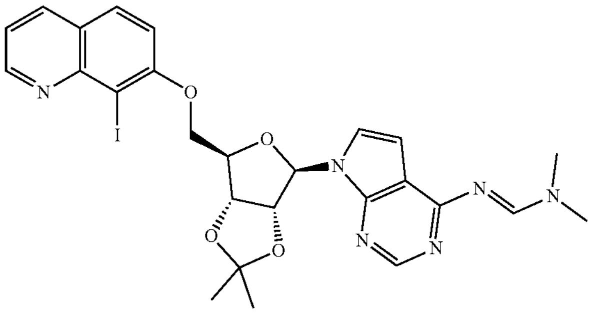 | a) Intermediate 24<br>b) 8-iodoquinolin-7-ol |

TABLE 12-continued
| Int. | Structure | Starting materials |
| --- | --- | --- |
| 504 | 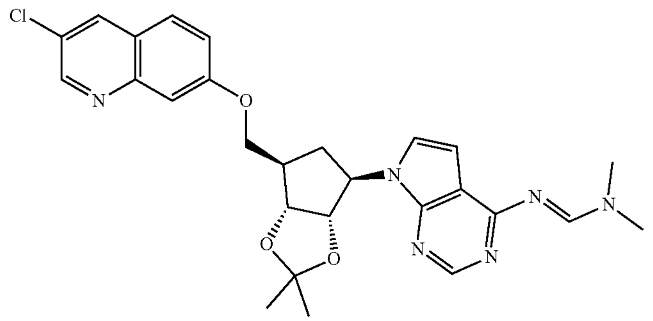 [SMILES: CN(C)/C=N/c1ncnc2c1ccn2[C@@H]1C[C@H](COc2ccc3cc(Cl)cnc3c2)[C@H]2OC(C)(C)O[C@H]21] | a) Intermediate 503<br>b) 3-chloroquinolin-7-ol |
| 517 | 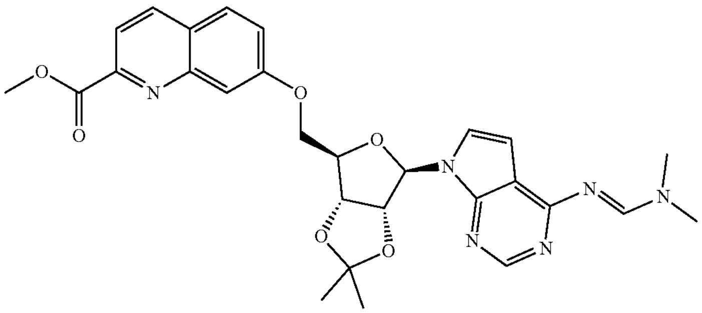 | a) intermediate 24<br>b) 2-Quinolinecarboxylic acid, 7-hydroxy-, methyl ester |
Example A24
Preparation of Intermediate 77
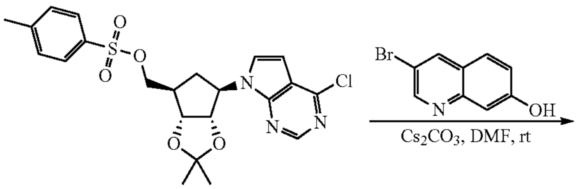
intermediate 17
-continued
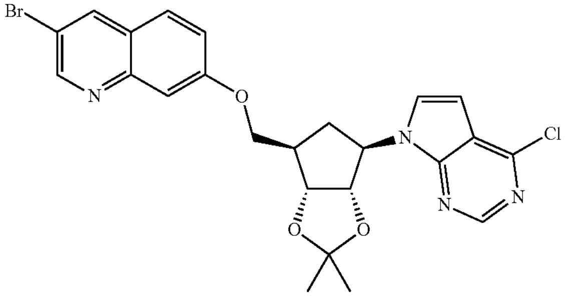
intermediate 77

Cesium Carbonate (2.18 g, 6.70 mmol) was added to a solution of intermediate 17 (1.15 g, ≈2.23 mmol) and 3-bromoquinolin-7-ol (0.5 g, 2.23 mmol) in DMF (25 mL). The mixture was stirred overnight at room temperature. The reaction mixture was treated with $H_2O$ (100 ml) and filtrated. The resulting residue was washed with $H_2O$ (30 mL) and dried under reduced pressure to obtain desired crude intermediate 77 as a pale yellow solid (1.1 g).

Below intermediates were prepared by an analogous reaction protocol as was used for the preparation of intermediate 77 using the appropriate starting materials (Table 13).

TABLE 13

| Int. | Structure | Starting materials |
|---|---|---|
| 78 | 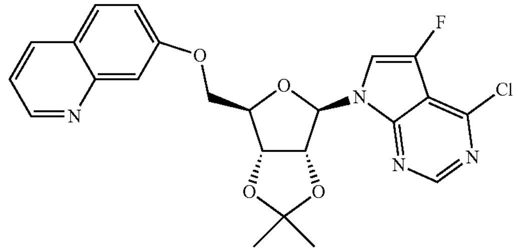 [SMILES: CC1(C)O[C@@H]2[C@H](O1)[C@@H](COc1ccc3cccnc3c1)O[C@H]2n1cc(F)c2c(Cl)ncnc21] | a) Intermediate 16<br>b) 7-Quinolinol |
| 262 | 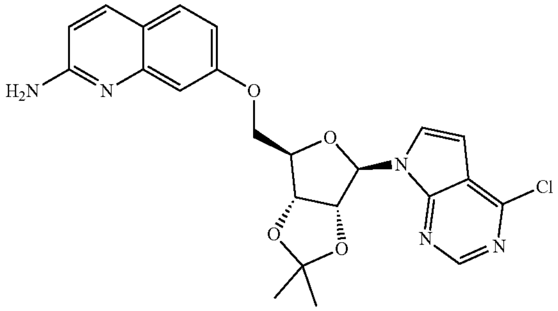 [SMILES: CC1(C)O[C@@H]2[C@H](O1)[C@@H](COc1ccc3ccc(N)nc3c1)O[C@H]2n1ccc2c(Cl)ncnc21] | a) Intermediate 15<br>b) 2-amino-7-hydroxy quinoline |
| 264 | 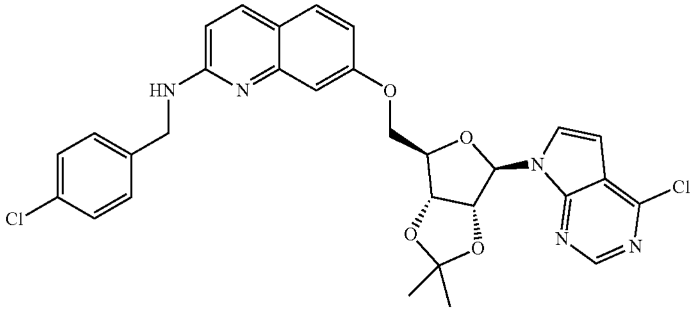 [SMILES: CC1(C)O[C@@H]2[C@H](O1)[C@@H](COc1ccc3ccc(NCc4ccc(Cl)cc4)nc3c1)O[C@H]2n1ccc2c(Cl)ncnc21] | a) Intermediate 15<br>b) Intermediate 263 |
| 270 | 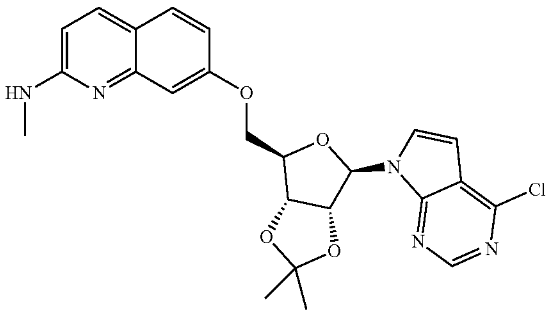 [SMILES: CNc1ccc2ccc(OC[C@H]3O[C@@H](n4ccc5c(Cl)ncnc54)[C@@H]4OC(C)(C)O[C@@H]43)cc2n1] | a) Intermediate 15<br>b) 2-Quinolinamine, 7-hydroxy-N-methyl- |

TABLE 13-continued
| Int. | Structure | Starting materials |
|---|---|---|
| 275 | 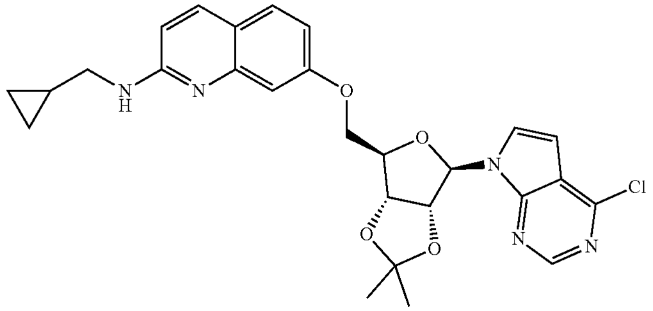 [SMILES: CC1(C)O[C@@H]2[C@H](O1)[C@@H](COc1ccc3ccc(NCC4CC4)nc3c1)O[C@H]2n1ccc2c(Cl)ncnc21] | a) Intermediate 15<br>b) Intermediate 274 |
| 461 | 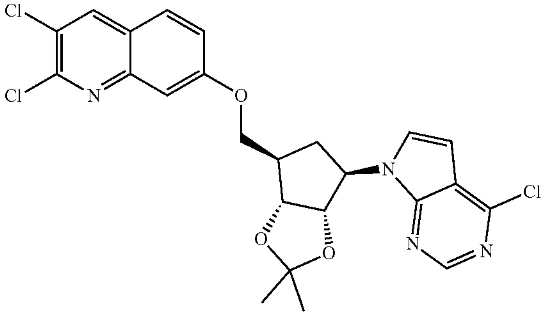 [SMILES: CC1(C)O[C@@H]2[C@@H](COc3ccc4cc(Cl)c(Cl)nc4c3)C[C@@H](n3ccc4c(Cl)ncnc43)[C@@H]2O1] | a) Intermediate 17<br>b) 7-Quinolinol, 2,3-dichloro- |
| 463 | 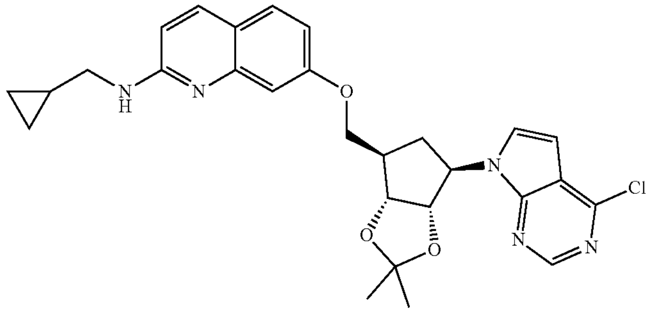 [SMILES: CC1(C)O[C@@H]2[C@@H](COc3ccc4ccc(NCC5CC5)nc4c3)C[C@@H](n3ccc4c(Cl)ncnc43)[C@@H]2O1] | a) Intermediate 17<br>b) Intermediate 274 |
| 466 | 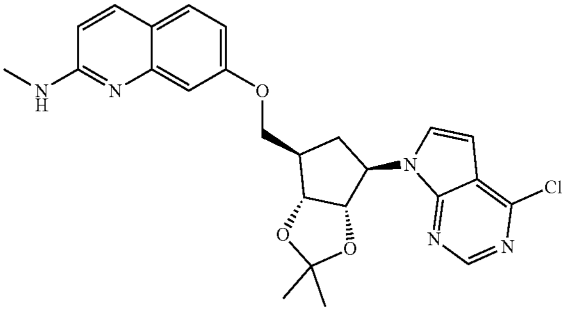 [SMILES: CNc1ccc2ccc(OC[C@H]3C[C@@H](n4ccc5c(Cl)ncnc54)[C@@H]4OC(C)(C)O[C@H]34)cc2n1] | a) Intermediate 17<br>b) 2-Quinolinamine, 7-hydroxy-N-methyl- |
| 469 | 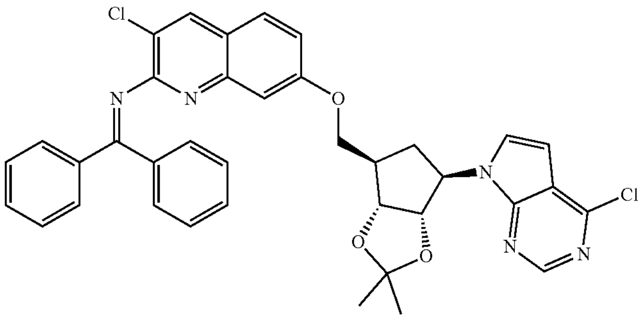 [SMILES: CC1(C)O[C@@H]2[C@@H](COc3ccc4cc(Cl)c(N=C(c5ccccc5)c5ccccc5)nc4c3)C[C@@H](n3ccc4c(Cl)ncnc43)[C@@H]2O1] | a) Intermediate 17<br>b) Intermediate 468 |

TABLE 13-continued

| Int. | Structure | Starting materials |
|---|---|---|
| 478 | 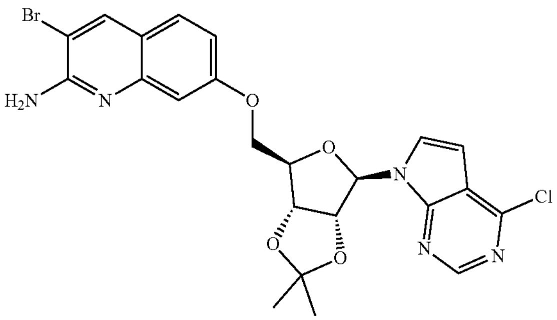 [SMILES: CC1(C)O[C@@H]2[C@H](O1)[C@@H](COc1ccc3cc(Br)c(N)nc3c1)O[C@H]2n1ccc2c(Cl)ncnc21] | a) Intermediate 15<br>b) Intermediate 477 |
| 484 | 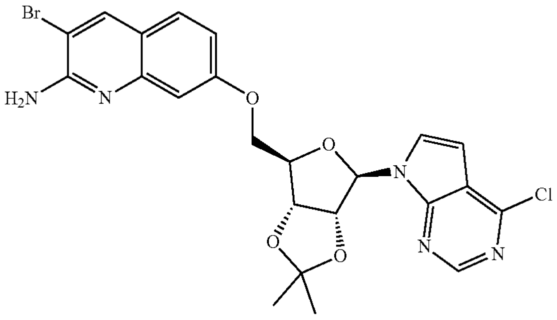 [SMILES: CC1(C)O[C@@H]2[C@H](O1)[C@@H](COc1ccc3cc(Br)c(N)nc3c1)O[C@H]2n1ccc2c(Cl)ncnc21] | a) Intermediate 17<br>b) Intermediate |

Example A25

Preparation of Intermediate 79

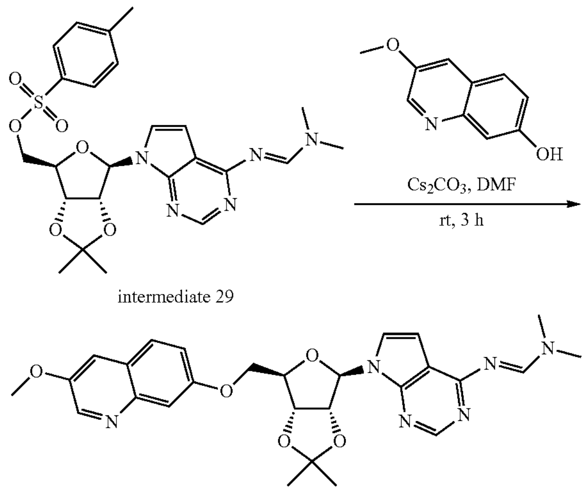

intermediate 29 intermediate 79

To a solution of intermediate 29 (500 mg, crude, ≈0.67 mmol) in DMF (20 mL) were added 3-methoxyquinolin-7-ol (187 mg, 0.80 mmol) and $Cs_2O_3$ (652 mg, 2.0 mmol). The reaction mixture was stirred at room temperature for 12 hours. The mixture was quenched with water (80 ml) and extracted with DCM (50 ml×3). The organic layers were dried ($Na_2SO_4$), filtered and the solvent was concentrated in vacuum to give the crude intermediate 79 as a yellow oil (650 mg).

Below intermediates were prepared by an analogous reaction protocol as was used for the preparation of intermediate 79 using the appropriate starting materials (Table 14).

TABLE 14
| Int. | structure | Starting materials |
| --- | --- | --- |
| 80 | 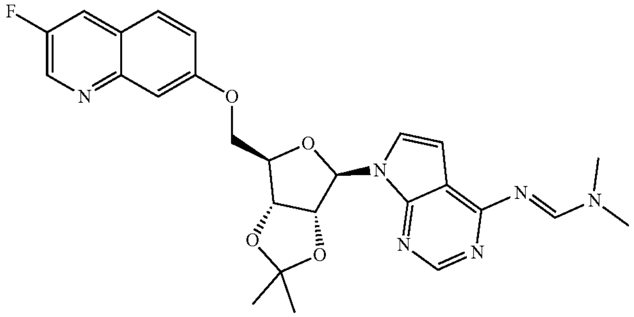 [SMILES: CN(C)/C=N/c1ncnc2c1ccn2[C@@H]1O[C@H](COc2ccc3cc(F)cnc3c2)[C@H]2OC(C)(C)O[C@H]21] | a) Intermediate 29<br>b) 3-fluoroquinolin-7-ol |
| 81 | 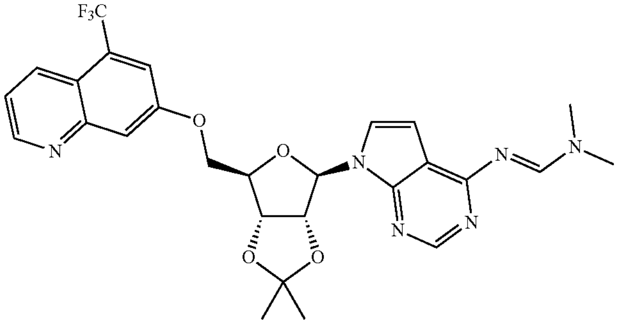 [SMILES: CN(C)/C=N/c1ncnc2c1ccn2[C@@H]1O[C@H](COc2cc(C(F)(F)F)c3cccnc3c2)[C@H]2OC(C)(C)O[C@H]21] | a) Intermediate 29<br>b) 5-(trifluoromethyl)quinolin-7-ol |
| 82 | 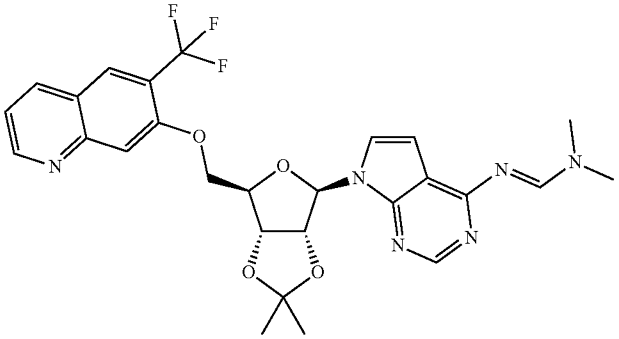 [SMILES: CN(C)/C=N/c1ncnc2c1ccn2[C@@H]1O[C@H](COc2cc3ncccc3cc2C(F)(F)F)[C@H]2OC(C)(C)O[C@H]21] | a) Intermediate 29<br>b) 6-(trifluoromethyl)quinolin-7-ol |
| 83 | 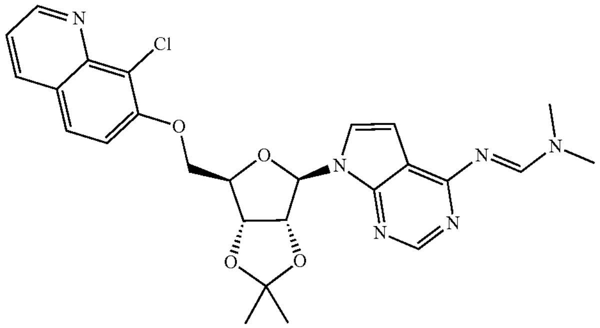 [SMILES: CN(C)/C=N/c1ncnc2c1ccn2[C@@H]1O[C@H](COc2ccc3cccnc3c2Cl)[C@H]2OC(C)(C)O[C@H]21] | a) Intermediate 29<br>b) 8-chloroquinolin-7-ol |

TABLE 14-continued
| Int. | structure | Starting materials |
| --- | --- | --- |
| 84 | 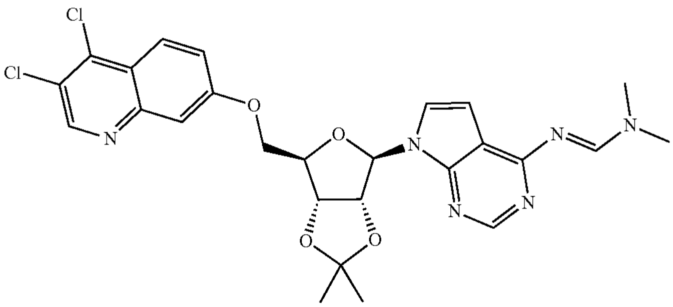 [SMILES: CN(C)/C=N/c1ncnc2c1ccn2[C@@H]1O[C@H](COc2ccc3c(Cl)c(Cl)cnc3c2)[C@H]2OC(C)(C)O[C@H]21] | a) Intermediate 29<br>b) 3,4-dichloroquinolin-7-ol (which was Prepared from 3,4-dichloro-7-methoxyquinoline) |
| 85 | 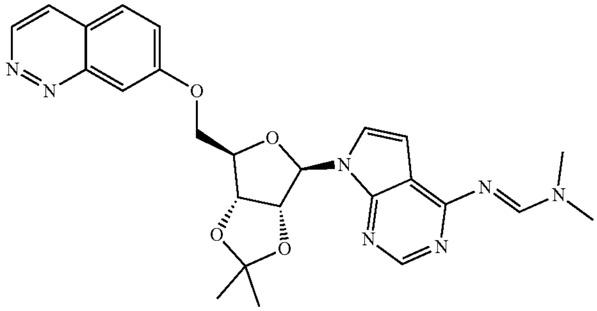 [SMILES: CN(C)/C=N/c1ncnc2c1ccn2[C@@H]1O[C@H](COc2ccc3ccnnc3c2)[C@H]2OC(C)(C)O[C@H]21] | a) Intermediate 29<br>b) 7-cinnolinol |
| 86 | 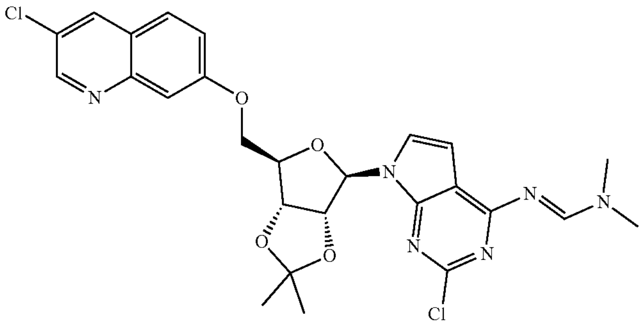 | a) Intermediate 30<br>b) 3-chloroquinolin-7-ol |
| 87 | 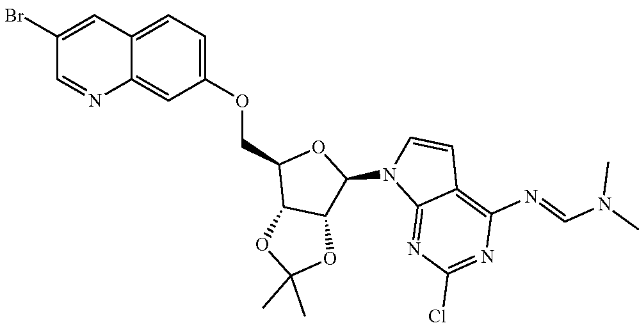 [SMILES: CN(C)/C=N/c1nc(Cl)nc2c1ccn2[C@@H]1O[C@H](COc2ccc3cc(Cl)cnc3c2)[C@H]2OC(C)(C)O[C@H]21] | a) Intermediate 30<br>b) 3-bromoquinolin-7-ol |

TABLE 14-continued

| Int. | structure | Starting materials |
| --- | --- | --- |
| 88 | 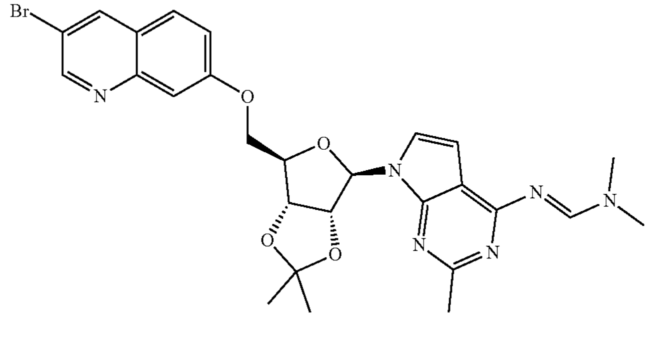 [SMILES: Cc1nc(/N=C/N(C)C)c2ccn([C@@H]3O[C@H](COc4ccc5cc(Br)cnc5c4)[C@H]4OC(C)(C)O[C@H]43)c2n1] | a) Intermediate 31<br>b) 3-bromoquinolin-7-ol |
| 199 | 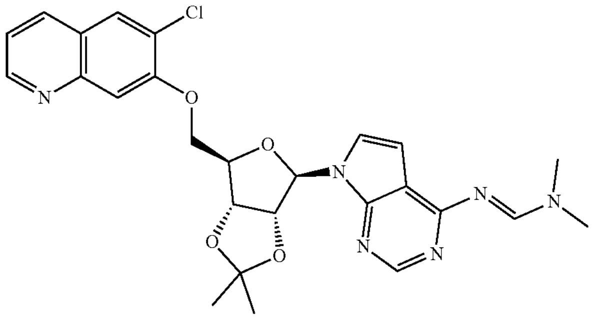 [SMILES: CN(C)/C=N/c1ncnc2c1ccn2[C@@H]1O[C@H](COc2cc3ncccc3cc2Cl)[C@H]2OC(C)(C)O[C@H]21] | a) Intermediate 29<br>b) 7-Quinolinol, 6-chloro |

Example A26

Preparation of Intermediate 89

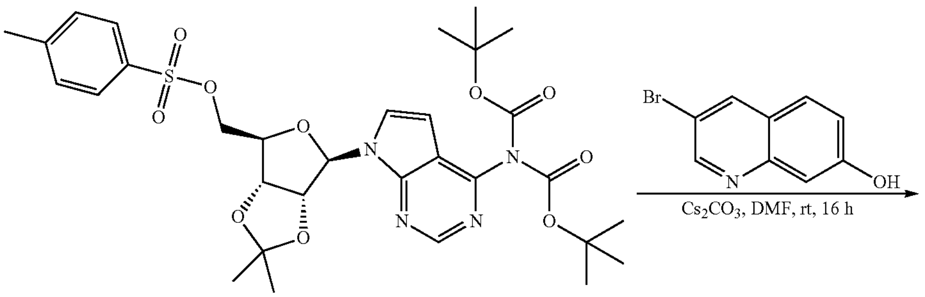

Intermediate 32

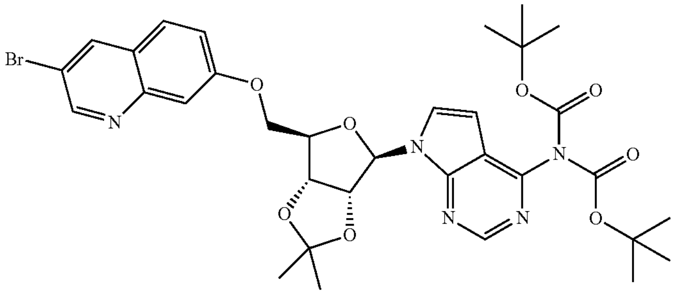

Intermediate 89

Intermediate 32 (48.3 g, ≈67.99 mmol) was dissolved in 400 ml of DMF. 7-Br-quinolin-7-ol (16.03 g, ≈67.98 mmol) and $Cs_2CO_3$ (44.33 g, 135.97 mmol) were added into the reaction mixture and the mixture was stirred at room temperature 16 hours. The reaction mixture was poured into 1000 ml of cold water and extracted by EtOAc (2×600 mL). The organic layer was washed with water (300 mL×2), dried with anhydrous $Na_2SO_4$, filtered and the solvent was concentrated in vacuum to give the crude intermediate 89 (52 g) as an oil which was used in the next step without further purification.

Below intermediates were prepared by an analogous reaction protocol as was used for the preparation of intermediate 89 using the appropriate starting materials (Table 26

TABLE 26

| Int. | structure | Starting materials |
|---|---|---|
| 201 | 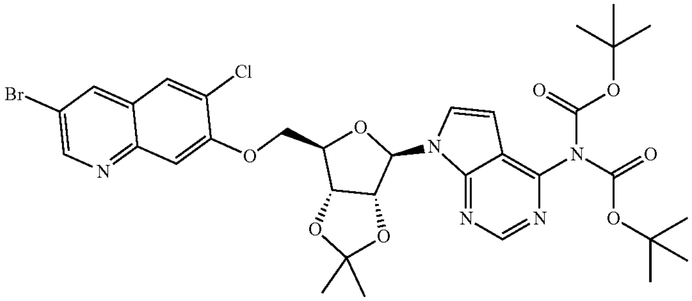 [SMILES: CC(C)(C)OC(=O)N(C(=O)OC(C)(C)C)c1ncnc2c1ccn2[C@@H]1O[C@H](COc2cc3ncc(Br)cc3cc2Cl)[C@H]2OC(C)(C)O[C@H]21] | a) Intermediate 32<br>b) Intermediate 200 |
| 206 | 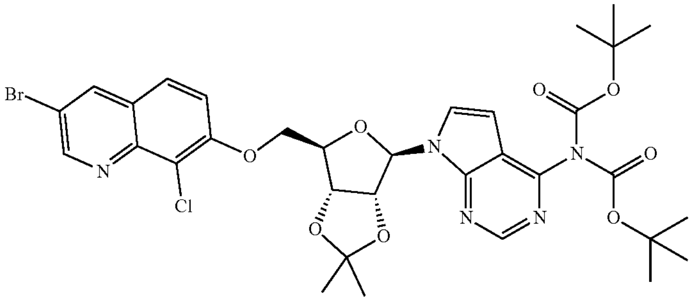 [SMILES: CC(C)(C)OC(=O)N(C(=O)OC(C)(C)C)c1ncnc2c1ccn2[C@@H]1O[C@H](COc2ccc3cc(Br)cnc3c2Cl)[C@H]2OC(C)(C)O[C@H]21] | a) Intermediate 32<br>b) Intermediate 205 |
| 211 | 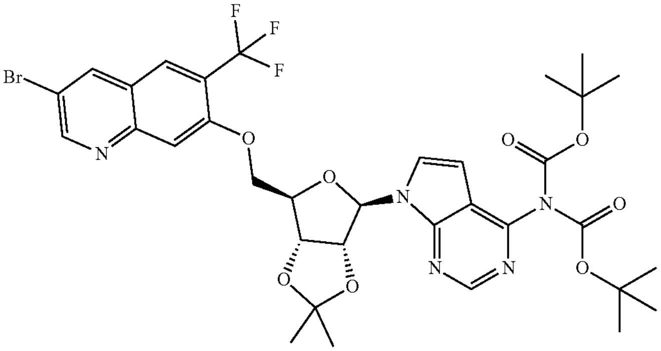 [SMILES: CC(C)(C)OC(=O)N(C(=O)OC(C)(C)C)c1ncnc2c1ccn2[C@@H]1O[C@H](COc2cc3ncc(Br)cc3cc2C(F)(F)F)[C@H]2OC(C)(C)O[C@H]21] | a) Intermediate 32<br>b) Intermediate 210 |
| 213 | 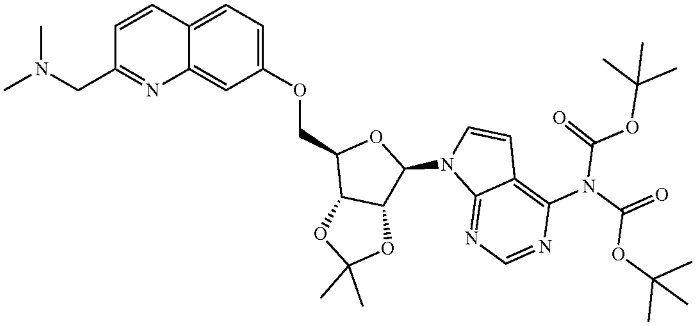 [SMILES: CN(C)Cc1ccc2ccc(OC[C@H]3O[C@@H](n4ccc5c(N(C(=O)OC(C)(C)C)C(=O)OC(C)(C)C)ncnc54)[C@@H]4OC(C)(C)O[C@@H]43)cc2n1] | a) Intermediate 32<br>b) Intermediate 212 |

TABLE 26-continued
| Int. | structure | Starting materials |
| --- | --- | --- |
| 215 | 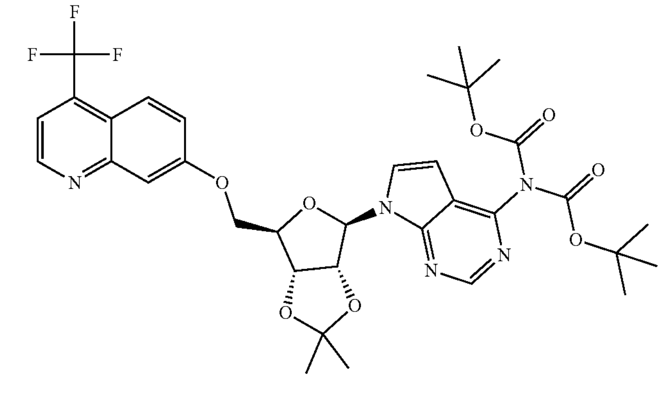 [SMILES: CC(C)(C)OC(=O)N(C(=O)OC(C)(C)C)c1ncnc2c1ccn2[C@@H]1O[C@H](COc2ccc3c(C(F)(F)F)ccnc3c2)[C@H]2OC(C)(C)O[C@H]21] | a) Intermediate 32<br>b) 7-Quinolinol, 4-(trifluoromethyl)- |
| 217 | 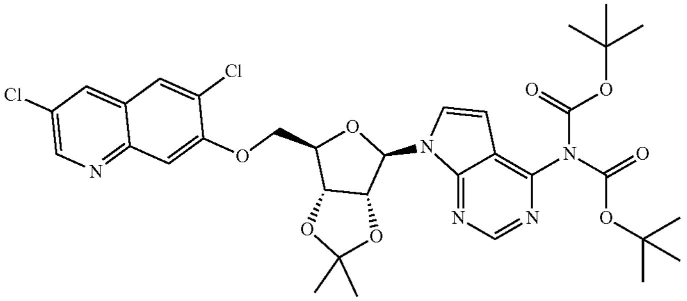 [SMILES: CC(C)(C)OC(=O)N(C(=O)OC(C)(C)C)c1ncnc2c1ccn2[C@@H]1O[C@H](COc2cc3ncc(Cl)cc3cc2Cl)[C@H]2OC(C)(C)O[C@H]21] | a) Intermediate 32<br>b) Intermediate 216 |
| 219 | 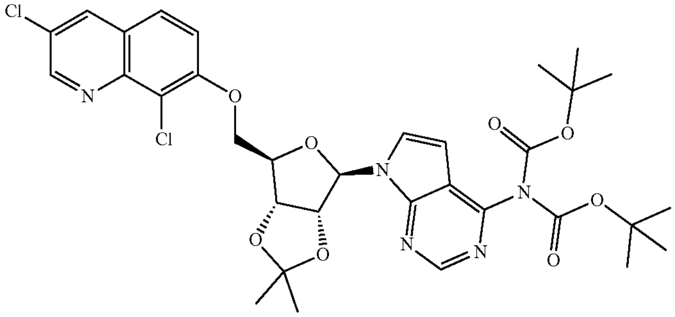 [SMILES: CC(C)(C)OC(=O)N(C(=O)OC(C)(C)C)c1ncnc2c1ccn2[C@@H]1O[C@H](COc2ccc3cc(Cl)cnc3c2Cl)[C@H]2OC(C)(C)O[C@H]21] | a) Intermediate 32<br>b) Intermediate 218 |
| 221 | 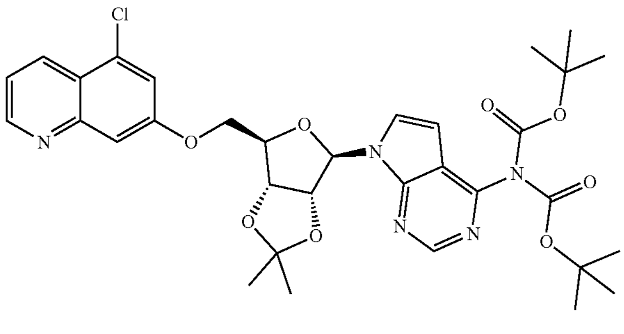 [SMILES: CC(C)(C)OC(=O)N(C(=O)OC(C)(C)C)c1ncnc2c1ccn2[C@@H]1O[C@H](COc2cc(Cl)c3cccnc3c2)[C@H]2OC(C)(C)O[C@H]21] | a) Intermediate 32<br>b) Intermediate 220a |

TABLE 26-continued
| Int. | structure | Starting materials |
|---|---|---|
| 227 | 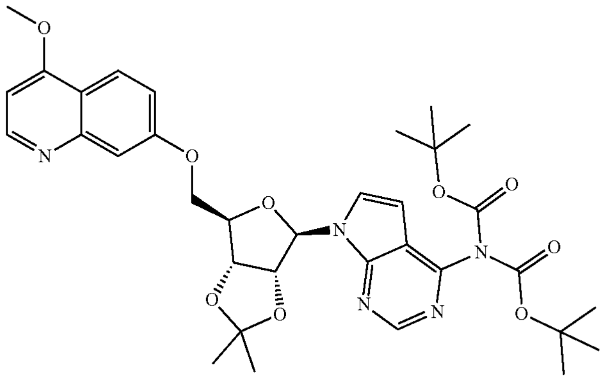 [SMILES: COc1ccnc2cc(OC[C@H]3O[C@@H](n4ccc5c(N(C(=O)OC(C)(C)C)C(=O)OC(C)(C)C)ncnc54)[C@@H]4OC(C)(C)O[C@@H]43)ccc12] | a) Intermediate 32<br>b) 7-Quinolinol, 4-methoxy- |
| 228 | 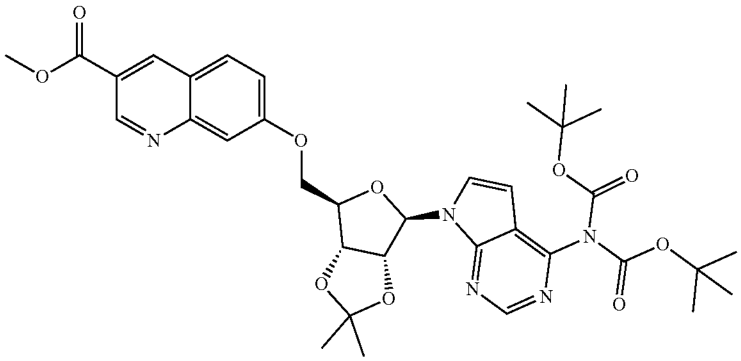 [SMILES: COC(=O)c1cnc2cc(OC[C@H]3O[C@@H](n4ccc5c(N(C(=O)OC(C)(C)C)C(=O)OC(C)(C)C)ncnc54)[C@@H]4OC(C)(C)O[C@@H]43)ccc2c1] | a) Intermediate 32<br>b) 3-Quinolinecarboxylic acid, 7-hydroxy-, methyl ester |
| 230 | 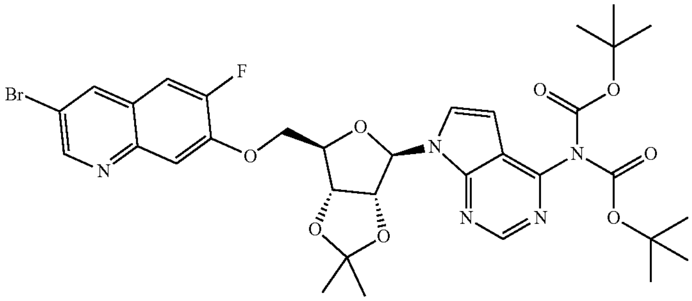 [SMILES: CC(C)(C)OC(=O)N(C(=O)OC(C)(C)C)c1ncnc2c1ccn2[C@@H]1O[C@H](COc2cc3ncc(Br)cc3cc2F)[C@H]2OC(C)(C)O[C@H]21] | a) Intermediate 32<br>b) Intermediate 229 |
| 232 | 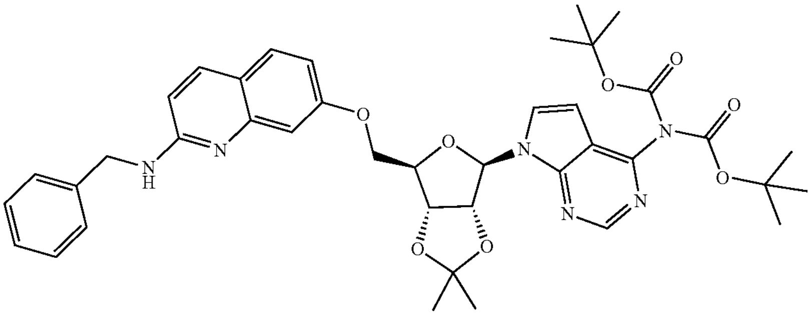 [SMILES: CC(C)(C)OC(=O)N(C(=O)OC(C)(C)C)c1ncnc2c1ccn2[C@@H]1O[C@H](COc2ccc3ccc(NCc4ccccc4)nc3c2)[C@H]2OC(C)(C)O[C@H]21] | a) Intermediate 32<br>b) Intermediate 231 |

TABLE 26-continued
| Int. | structure | Starting materials |
| --- | --- | --- |
| 236 | 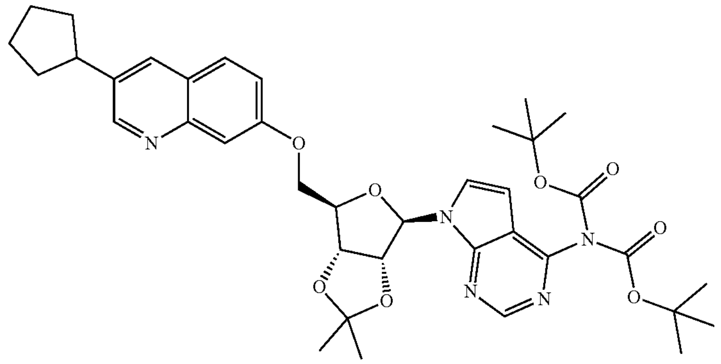 [SMILES: CC(C)(C)OC(=O)N(C(=O)OC(C)(C)C)c1ncnc2c1ccn2[C@@H]1O[C@H](COc2ccc3cc(C4CCCC4)cnc3c2)[C@H]2OC(C)(C)O[C@H]21] | a) Intermediate 32<br>b) Intermediate 235 |
| 241 | 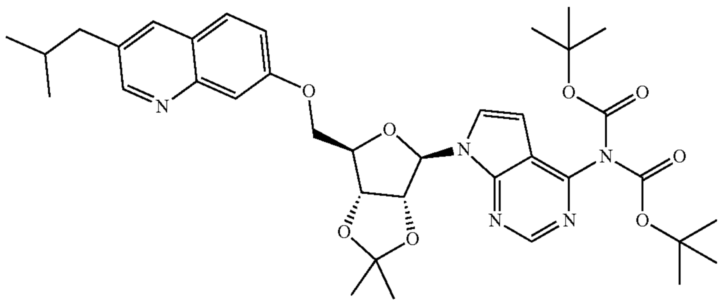 [SMILES: CC(C)Cc1cnc2cc(OC[C@H]3O[C@@H](n4ccc5c(N(C(=O)OC(C)(C)C)C(=O)OC(C)(C)C)ncnc54)[C@@H]4OC(C)(C)O[C@@H]43)ccc2c1] | a) Intermediate 32<br>b) Intermediate 240 |
| 247 | 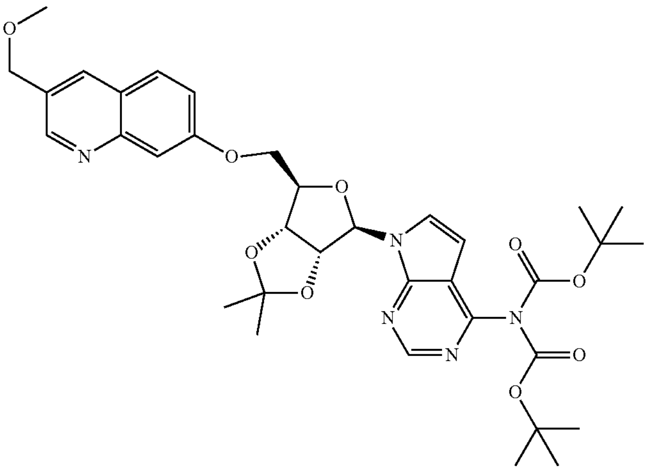 [SMILES: COCc1cnc2cc(OC[C@H]3O[C@@H](n4ccc5c(N(C(=O)OC(C)(C)C)C(=O)OC(C)(C)C)ncnc54)[C@@H]4OC(C)(C)O[C@@H]43)ccc2c1] | a) Intermediate 32<br>b) Intermediate 246 |
| 279 | 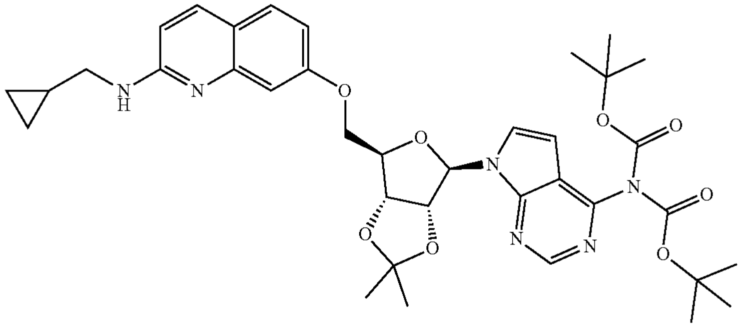 [SMILES: CC(C)(C)OC(=O)N(C(=O)OC(C)(C)C)c1ncnc2c1ccn2[C@@H]1O[C@H](COc2ccc3ccc(NCC4CC4)nc3c2)[C@H]2OC(C)(C)O[C@H]21] | a) Intermediate 32<br>b) Intermediate 274 |

TABLE 26-continued

| Int. | structure | Starting materials |
|---|---|---|
| 286 | 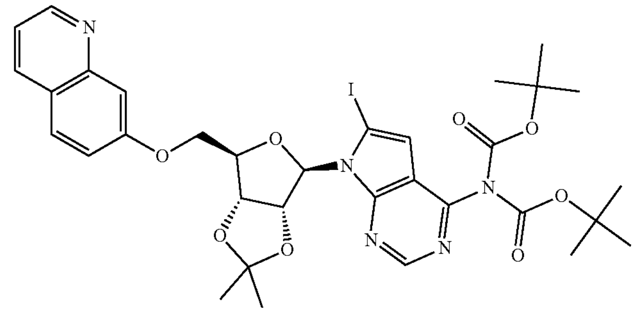 [SMILES: CC(C)(C)OC(=O)N(C(=O)OC(C)(C)C)c1ncnc2c1cc(I)n2[C@@H]1O[C@H](COc2ccc3cccnc3c2)[C@H]2OC(C)(C)O[C@H]21] | a) Intermediate285<br>b) 7-hydroxy quinoline |

Example A27

Preparation of Intermediate 90

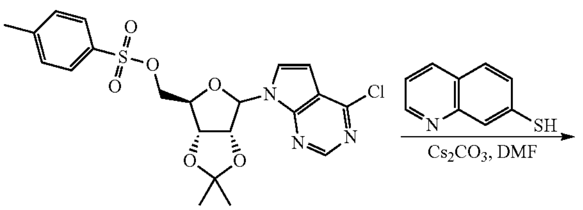

intermediate 15

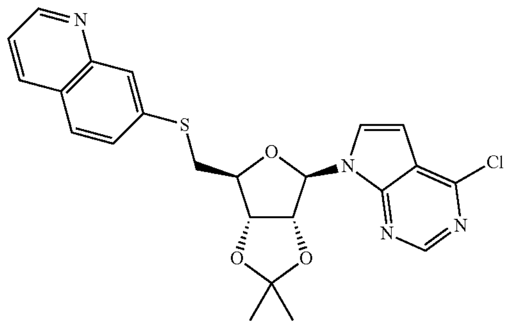

intermediate 90

A mixture of intermediate 15 (893 mg, ≈1.68 mmol), 7-quinolinethiol (1.6 g, 3.374 mmol, crude) and $Cs_2CO_3$ (1.21 g, 3.72 mmol) in DMF (20 mL) was stirred overnight at room temperature. The reaction was quenched with water (100 mL). The aqueous phase was extracted with ethyl acetate (200 mL×2). The combined organic layer was washed with brine (100 ml), dried over $Na_2SO_4$ and concentrated under reduced pressure. The residue was purified by flash column (gradient elution: Petroleum ether/ethyl acetate from 100/0 to 1/1) to give desired compound intermediate 90 (170 mg, 20% yield) as off-white solid.

Example A28

Preparation of Intermediate 91

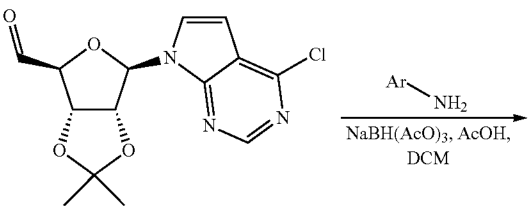

intermediate 33

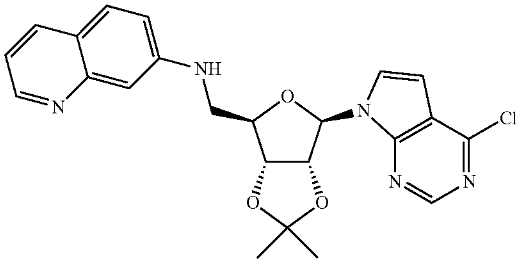

intermediate 91

7-aminoquinoline (Ar—$NH_2$ in scheme above) (700 mg, 4.85 mmol) was added to a solution of intermediate 33 (2.20 g, theoretically 6.80 mmol) in DCM (45 mL) and acetic acid (278 μL, 4.85 mmol). The solution was stirred for 10 min then sodium triacetoxyborohydride (2.98 g; 14.1 mmol) was added and the mixture was stirred at room temperature for 18 hours. A saturated aqueous solution of $NaHCO_3$ was added and the mixture was stirred for 30 minutes. The layers were separated and the aqueous layer was extracted with DCM. The combined organic layers were dried over $MgSO_4$, filtered off and evaporated in vacuo. The residues were purified by preparative LC (Irregular SiOH 15-40 μm, 80 g Grace, mobile phase gradient: from DCM 100% to DCM 95%, MeOH 5%) to give intermediate 91 as a yellow oil which crystallized on standing (1.22 g, 56% yield).

Below intermediates were prepared by an analogous reaction protocol as was used for the preparation of intermediate 91 using the appropriate starting materials (Table 15).

TABLE 15

| Int. | structure | Starting materials |
|---|---|---|
| 92 | 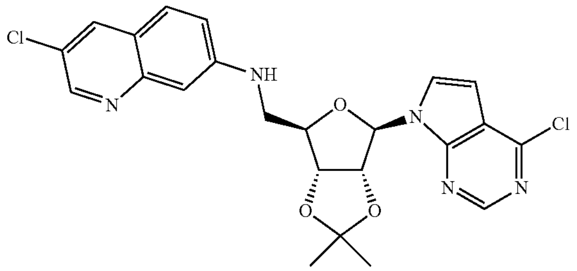 | a) Intermediate 33<br>b) 3-chloroquinlin-7-amine |
| 93 | 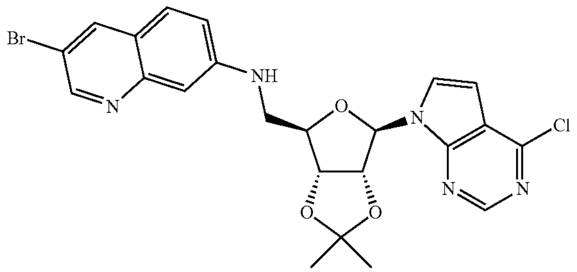 [SMILES: CC1(C)O[C@@H]2[C@H](O1)[C@@H](CNc1ccc3cc(Cl)cnc3c1)O[C@H]2n1ccc2c(Cl)ncnc21] | a) Intermediate 33<br>b) 3-bromoquinolin-7-amine |
| 94 | 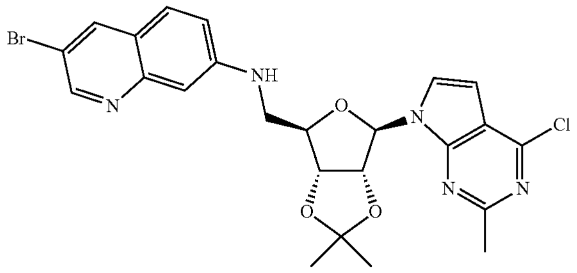 [SMILES: Cc1nc(Cl)c2ccn([C@@H]3O[C@H](CNc4ccc5cc(Br)cnc5c4)[C@H]4OC(C)(C)O[C@H]43)c2n1] | a) Intermediate 34<br>b) 3-bromoquinolin-7-amine |
| 95 | 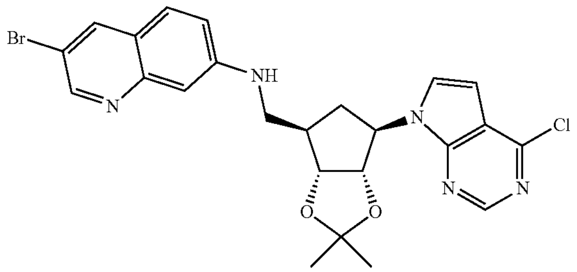 | a) Intermediate 35<br>b) 3-bromoquinolin-7-amine |

Example A29

Preparation of Intermediate 96

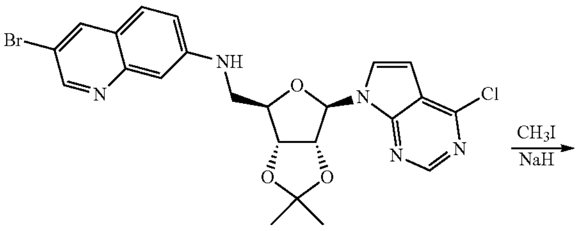

intermediate 93

-continued

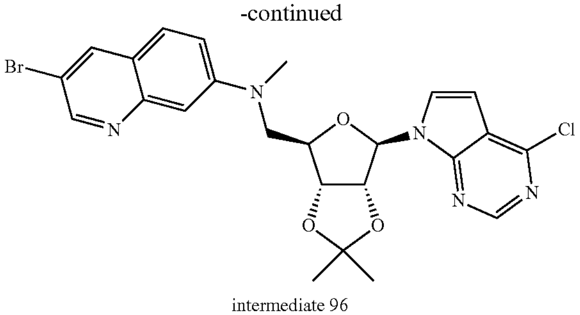

intermediate 96

To a stirred solution of intermediate 93 (1.0 g, 1.88 mmol) in DMF (20 mL) was added NaH (60% dispersion in mineral oil) (0.151 g, 3.77 mmol) at 0° C. under nitrogen atmosphere. Subsequently, the reaction mixture was stirred at room temperature for 30 minutes. Then $CH_3I$ (0.141 mL, 2.261 mmol) was added dropwise. The reaction mixture was stirred at room temperature for 4 hours. The reaction mixture was quenched by pouring it out into a beaker with ice and water under nitrogen atmosphere. The precipitate was filtered off yielding the precipitated int. 96. The remaining product was extracted from the water layer with ethylacetate. The separated organic layer was combined with the precipitated int. 96 and then dried with $MgSO_4$, filtered and the solvents of the filtrate evaporated. The residue was dissolved in ethylacetate and purified over a $SiO_2$ column, type Grace Reveleris SRC, 40 g, Si 40, on a Grace Reveleris X2 purification system using heptanes and ethylacetate as eluens in a gradient starting from 100% heptanes to 100% ethylacetate. The fractions containing product were combined and the solvents were evaporated yielding intermediate 96 (0.51 g, crude). This intermediate was used for next step reaction without further purification.

Below intermediates were also formed with the same reaction protocol as was used for the preparation of intermediate 96 (Table 27).

TABLE 27

| Int. | structure | Starting materials |
|---|---|---|
| 195 | 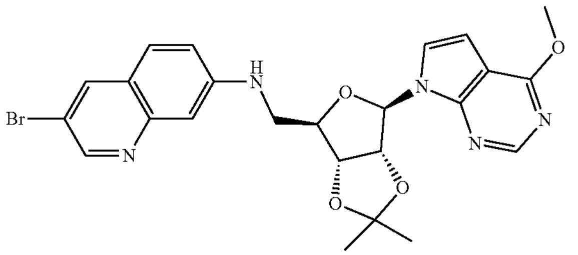 [SMILES: COc1ncnc2c1ccn2[C@@H]1O[C@H](CNc2ccc3cc(Br)cnc3c2)[C@H]2OC(C)(C)O[C@H]21] | intermediate 93 |
| 196 | 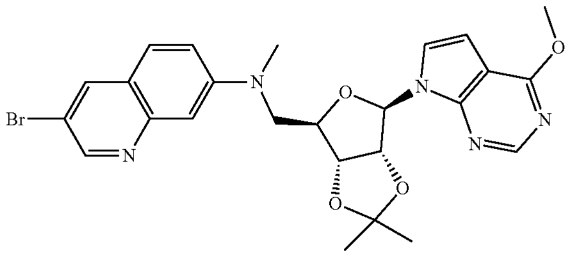 [SMILES: COc1ncnc2c1ccn2[C@@H]1O[C@H](CN(C)c2ccc3cc(Br)cnc3c2)[C@H]2OC(C)(C)O[C@H]21] | intermediate 93 |

Example A30

Preparation of Intermediate 97

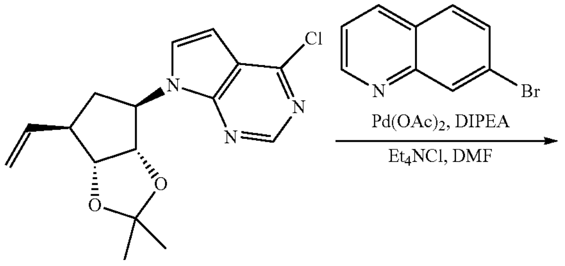

intermediate 38

-continued

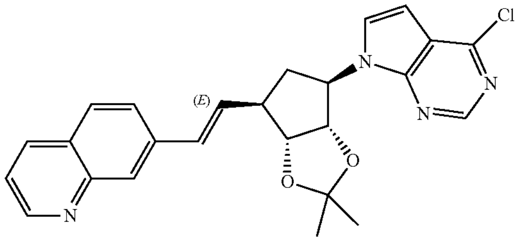

intermediate 97

A mixture of intermediate 38 (520 mg, 1.60 mmol), 7-bromoquinoline (390 mg, 1.87 mmol) and $Et_4NCl$ (261 mg, 1.79 mmol,) in DMF (15.00 mL) was degassed under vacuum and purged with $N_2$ for three times. DIEA (1.05 g, 8.15 mmol) and $Pd(OAc)_2$ (54.9 mg, 244 μmol,) were added to the reaction mixture. The mixture was stirred at 100° C. for 16 hours. The mixture was diluted with water (20 mL) and extracted with ethyl acetate (20 mL×3). The combined organic phase was dried with anhydrous $MgSO_4$, filtered and concentrated in vacuum. The residue was purified by silica gel chromatography (ISCO®; 12 g SepaFlash® Silica Flash Column, gradient elutionL from 100% of DCM to 25% Ethyl acetate in DCM), yielded Intermediate 97 as off-white solid. (670 mg, 91% yield; (E)).

The intermediates in Table 16 (all in the E configuration) were prepared by an analogous reaction protocol as was used for the preparation of intermediate 97 using the appropriate starting materials (Table 16).

TABLE 16

| Int. | Structure | Starting materials |
|---|---|---|
| 98 | 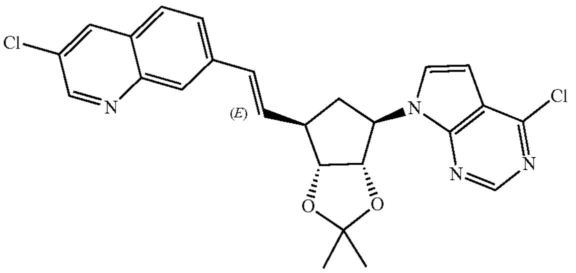 [SMILES: CC1(C)O[C@@H]2[C@H](O1)[C@@H](/C=C/c1ccc3cc(Cl)cnc3c1)C[C@H]2n1ccc2c(Cl)ncnc21] | a) Intermediate 38<br>b) 7-bromo-3-chloroquinoline |
| 99 | 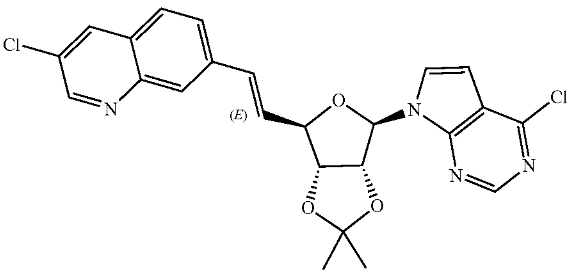 | a) Intermediate 39<br>b) 7-bromo-3-chloroquinoline |
| 100 | 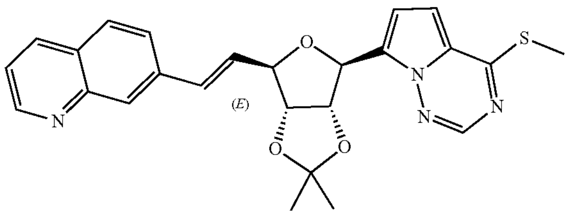 [SMILES: CSc1ncnn2c([C@@H]3O[C@H](/C=C/c4ccc5cccnc5c4)[C@H]4OC(C)(C)O[C@H]43)ccc12] | a) Intermediate 40<br>b) 7-bromoquinoline |

Example A31

Preparation of Intermediate 101

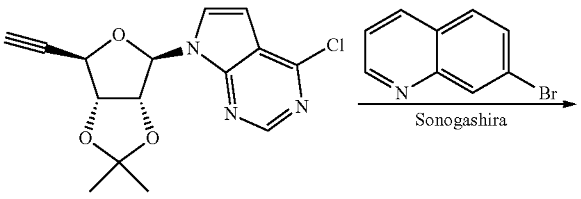

intermediate 41

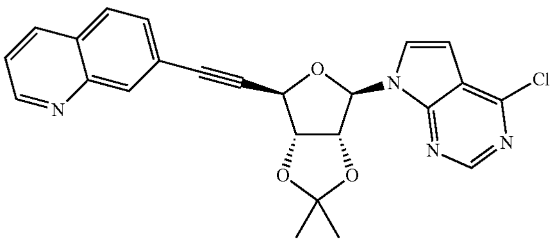

intermediate 101

In a sealed tube, bis(triphenylphosphine)palladium(II) dichloride (79.0 mg; 113 μmol) and copper(I) iodide (21.4 mg; 113 μmol) were added to a solution of 7-bromoquinoline (468 mg; 2.25 mmol) in 2-methyltetrahydrofuran (8 mL) previously degassed with $N_2$. The reaction mixture was degassed with $N_2$ and $Et_3N$ (1.25 mL; 9.01 mmol) was added, followed by adding intermediate 41 (1.08 g; 3.38 mmol) in (4 mL). The reaction mixture was degassed with $N_2$ then refluxed (80° C.) for 18 h. After cooling down to room temperature, the crude was partitioned between EtOAc and $H_2O$. The aqueous layer was separated and extracted with EtOAc. The combined organic layers were dried over $MgSO_4$, filtered off and evaporated in vacuo. The residues were purified by preparative LC (Irregular SiOH 15-40 μm, 50 g Merck, DCM loading, mobile phase gradient: from heptane 80%, EtOAc 20% to heptane 50%, EtOAc 50%) to give intermediate 101 as a pale yellow oil (304 mg, yield: 27%).

Example A32

Preparation of Intermediate 102

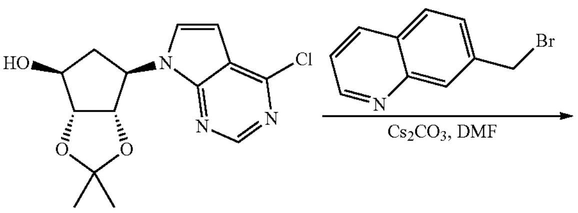

intermediate 43

-continued

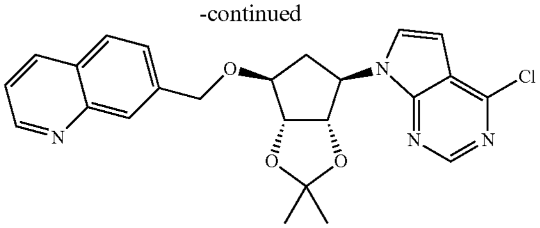

intermediate 102

To a solution of intermediate 43 (100 mg, 0.323 mmol) and 7-(bromomethyl)quinoline (117 mg, 0.387 mmol) in DMF (3 mL) was added NaH (117 mg, 80% purity in mineral oil, 1.615 mmol). The mixture was stirred at room temperature for 5 h. The reaction mixture was quenched with saturated aqueous $NH_4Cl$ (10 mL) and extracted with ethyl acetate (50 mL×3). The organic phase was washed with $H_2O$ (25 mL×3), dried with anhydrous $Na_2SO_4$ and concentrated under reduced pressure to give the crude product. The crude product was purified with Preparative-TLC (petroleum ether/ethyl acetate=3/2) to give intermediate 102 as a colourless oil (50 mg, 91% purity, 35% yield).

Below intermediates were prepared by an analogous reaction protocol as was used for the preparation of intermediate 102 using the appropriate starting materials (Table 17).

TABLE 17

| Int. | Structure | Starting materials |
| --- | --- | --- |
| 102a | 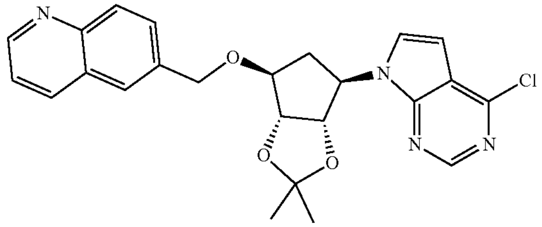 [SMILES: CC1(C)O[C@@H]2[C@H](O1)[C@@H](OCc1ccc3ncccc3c1)C[C@H]2n1ccc2c(Cl)ncnc21] | a) Intermediate 43<br>b) 6-(Bromomethyl)quinoline |
| 102b | 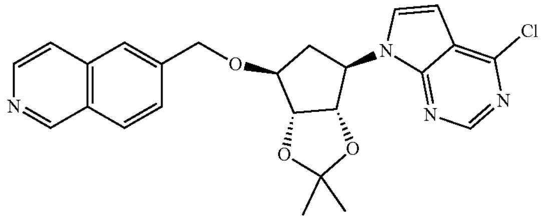 [SMILES: CC1(C)O[C@@H]2[C@H](O1)[C@@H](OCc1ccc3cnccc3c1)C[C@H]2n1ccc2c(Cl)ncnc21] | a) Intermediate 43<br>b) 6-(Bromomethyl)isoquinoline |
| 333 | 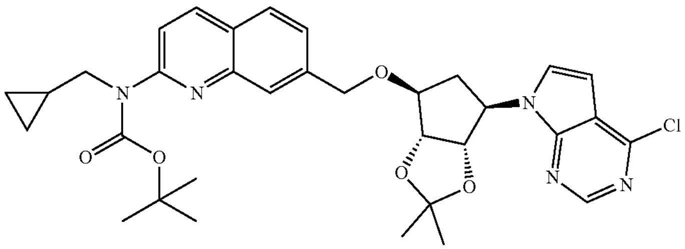 [SMILES: CC(C)(C)OC(=O)N(CC1CC1)c1ccc2ccc(CO[C@H]3C[C@@H](n4ccc5c(Cl)ncnc54)[C@@H]4OC(C)(C)O[C@@H]43)cc2n1] | a) Intermediate 43<br>b) intermediate 332 |

Example A33

Preparation of Intermediate 103

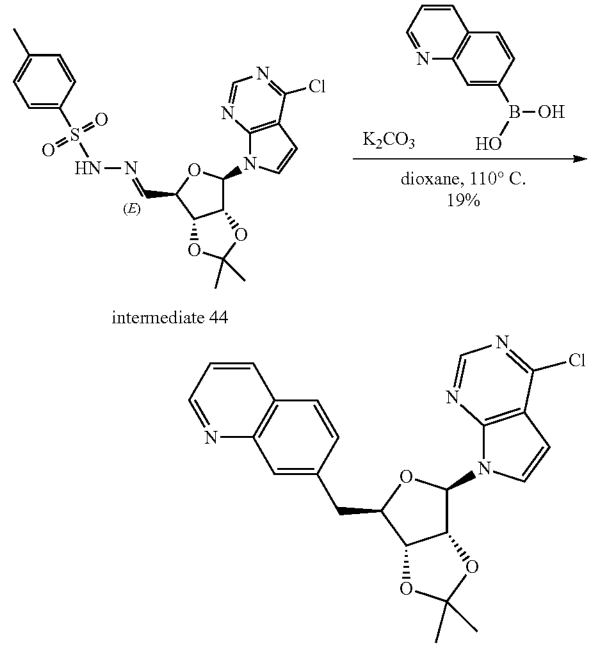

intermediate 44 intermediate 103

Potassium carbonate (507 mg, 3.67 mmol) was added in one portion to a solution of intermediate 44 (600 mg, 1.23 mmol) and quinolin-7-ylboronic acid (254 mg, 1.47 mmol) in dioxane (15 mL). The reaction mixture was stirred at 90° C. under $N_2$ for 2 hours, after which the mixture was allowed to cool to room temperature. Subsequently, ethyl acetate was added, the organic phase was washed with saturated $Na_2CO_3$ and brine, dried with anhydrous $MgSO_4$, filtered and concentrated under reduced pressure. The crude product was purified by silica gel column chromatography (gradient eluention: heptane/ethyl acetate from 100/0 to 40/60) to give intermediate 103 (100 mg, 19% yield).

Below intermediates were prepared by an analogous reaction protocol as was used for the preparation of intermediate 103 using the appropriate starting materials (Table 28).

TABLE 28

| Int. | structure | Starting material |
|---|---|---|
| 197 | 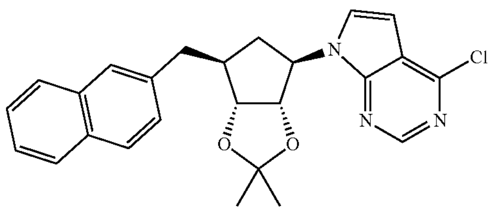 [SMILES: CC1(C)O[C@@H]2[C@@H](Cc3ccc4ccccc4c3)C[C@@H](n3ccc4c(Cl)ncnc43)[C@@H]2O1] | Intermediate 207 and 2-naphthaleneboronic acid |
| 208 | 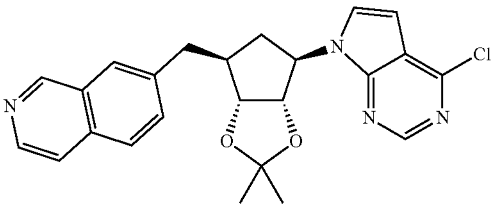 [SMILES: CC1(C)O[C@@H]2[C@@H](Cc3ccc4ccncc4c3)C[C@@H](n3ccc4c(Cl)ncnc43)[C@@H]2O1] | Intermediate 207 and isoquinoline-7-boronic acid |
| 225 | 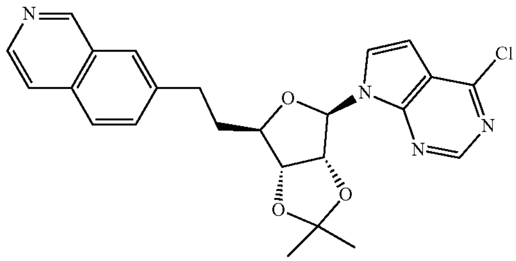 [SMILES: CC1(C)O[C@@H]2[C@H](O1)[C@@H](CCc1ccc3ccncc3c1)O[C@H]2n1ccc2c(Cl)ncnc21] | Intermediate 224 and isoquinoline-7-boronic acid |

Example A34

Preparation of Intermediate 104

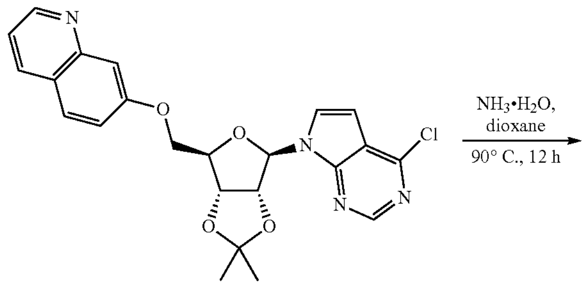

Intermediate 45

-continued

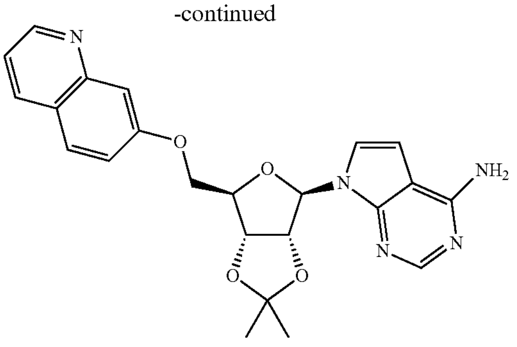

Intermediate 104

Intermediate 45 (350 mg, crude, ≈0.626 mmol) was dissolved in 5 mL of dioxane. Then 5 mL of $NH_3 \cdot H_2O$ was added. The mixture was heated in a sealed tube (autoclave) at 90° C. for 12 hours. The mixture was cooled to room temperature. The solvent was concentrated in vacuum to give the crude intermediate 104 (300 mg,) as a yellow oil.

Example A35

Preparation of Intermediate 105

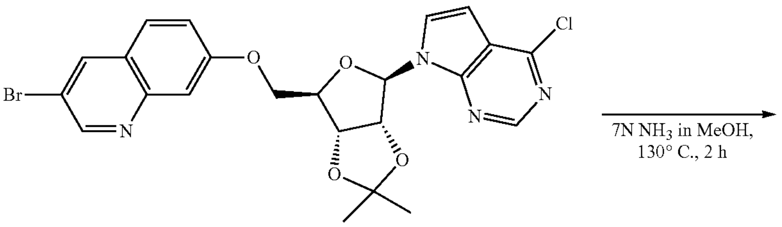

intermediate 59

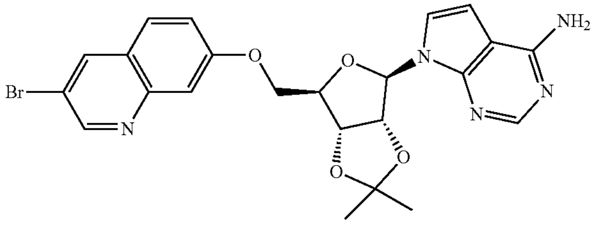

intermediate 105

The crude Intermediate 59 (q.s., theoretically 0.83 mmol) was dissolved in 7M $NH_3$ in MeOH (20 mL, 7 M, 140 mmol). The resulting solution was stirred and heated at 130° C. using microwave irradiation for 2 hour. The solvents were evaporated. The residue was dissolved in dichloromethane and purified over a $SiO_2$ column, type Grace Reveleris SRC, 12 g, Si 40, on a Grace Reveleris X2 purification system using dichloromethane and methanol as eluens in a gradient starting from 100% DCM for 20 column volumes to 20% MeOH and 80% DCM over 20 column volumes. The fractions containing the product were combined and the solvents were evaporated yielding crude Intermediate 105 (175 mg) used as such in the next reaction step.

The intermediates in Table 18 were prepared by an analogous reaction protocol as described in A34 or A35 using the appropriate starting materials (Table 18). Intermediates 136, 137 and 138 were obtained in the E-configuration.

TABLE 18

| Int. | structure | Ref | Starting material |
|---|---|---|---|
| 106 | 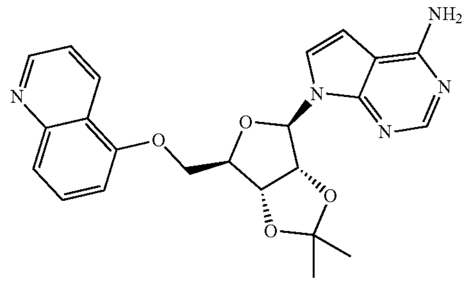 [SMILES: CC1(C)O[C@@H]2[C@H](O1)[C@@H](COc1cccc3ncccc13)O[C@H]2n1ccc2c(N)ncnc21] | A34 | Intermediate 62 |
| 107 | 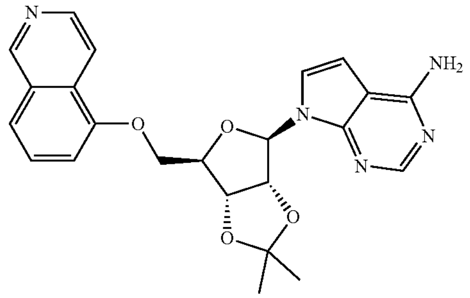 [SMILES: CC1(C)O[C@@H]2[C@H](O1)[C@@H](COc1cccc3cnccc13)O[C@H]2n1ccc2c(N)ncnc21] | A34 | Intermediate 63 |
| 108 | 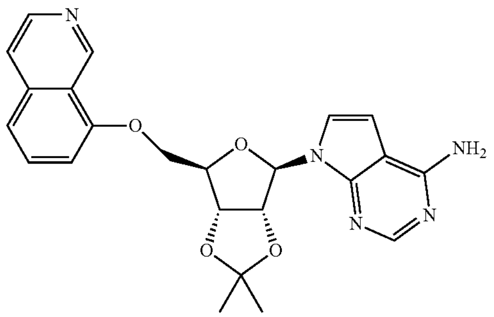 [SMILES: CC1(C)O[C@@H]2[C@H](O1)[C@@H](COc1cccc3ccncc13)O[C@H]2n1ccc2c(N)ncnc21] | A34 | Intermediate 49 |
| 109 | 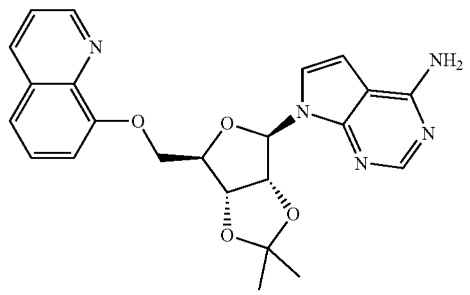 [SMILES: CC1(C)O[C@@H]2[C@H](O1)[C@@H](COc1cccc3cccnc13)O[C@H]2n1ccc2c(N)ncnc21] | A34 | Intermediate 64 |

TABLE 18-continued
| Int. | structure | Ref | Starting material |
| --- | --- | --- | --- |
| 110 | 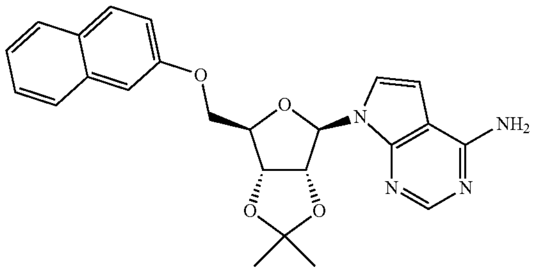 [SMILES: CC1(C)O[C@@H]2[C@H](O1)[C@@H](COc1ccc3ccccc3c1)O[C@H]2n1ccc2c(N)ncnc21] | A34 | Intermediate 71 |
| 111 | 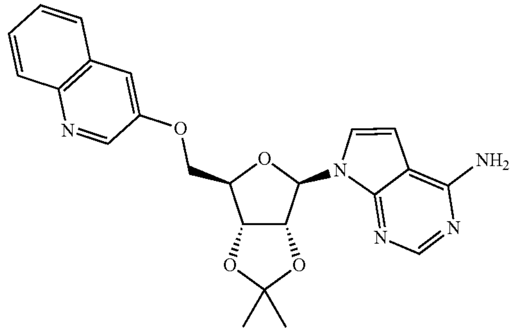 [SMILES: CC1(C)O[C@@H]2[C@H](O1)[C@@H](COc1cnc3ccccc3c1)O[C@H]2n1ccc2c(N)ncnc21] | A34 | Intermediate 48 |
| 112 | 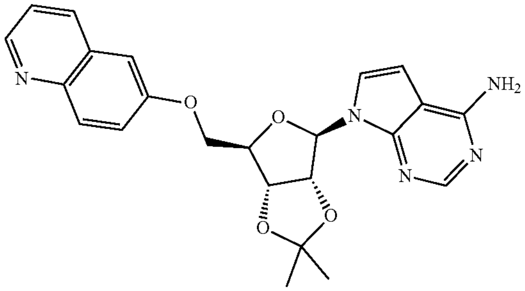 [SMILES: CC1(C)O[C@@H]2[C@H](O1)[C@@H](COc1ccc3ncccc3c1)O[C@H]2n1ccc2c(N)ncnc21] | A34 | Intermediate 47 |
| 113 | 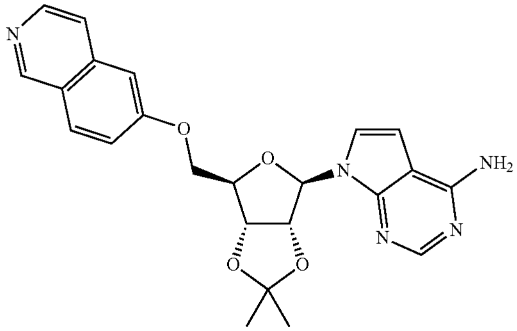 [SMILES: CC1(C)O[C@@H]2[C@H](O1)[C@@H](COc1ccc3cnccc3c1)O[C@H]2n1ccc2c(N)ncnc21] | A34 | Intermediate 65 |
| 114 | 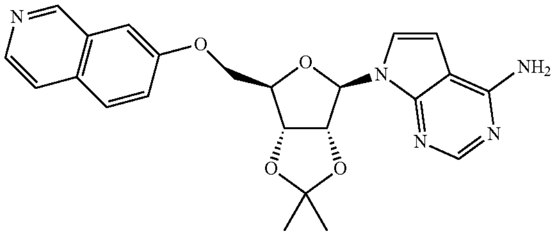 [SMILES: CC1(C)O[C@@H]2[C@H](O1)[C@@H](COc1ccc3ccncc3c1)O[C@H]2n1ccc2c(N)ncnc21] | A34 | Intermediate 46 |

TABLE 18-continued
| Int. | structure | Ref | Starting material |
|---|---|---|---|
| 115 | 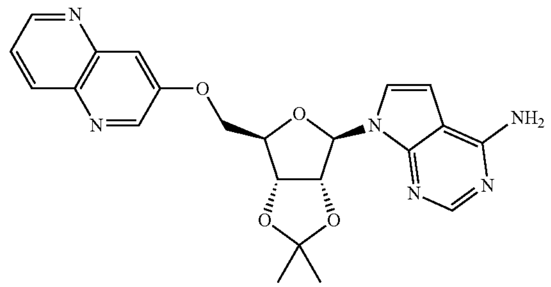 [SMILES: CC1(C)O[C@@H]2[C@H](O1)[C@@H](COc1cnc3cccnc3c1)O[C@H]2n1ccc2c(N)ncnc21] | A34 | Intermediate 50 |
| 116 | 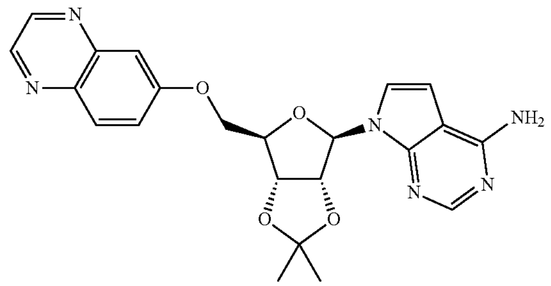 [SMILES: CC1(C)O[C@@H]2[C@H](O1)[C@@H](COc1ccc3nccnc3c1)O[C@H]2n1ccc2c(N)ncnc21] | A34 | Intermediate 51 |
| 117 | 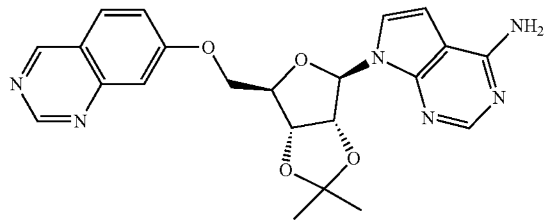 [SMILES: CC1(C)O[C@@H]2[C@H](O1)[C@@H](COc1ccc3cncnc3c1)O[C@H]2n1ccc2c(N)ncnc21] | A35 | Intermediate 52 |
| 118 | 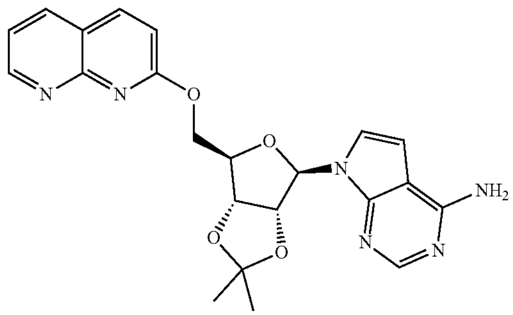 [SMILES: CC1(C)O[C@@H]2[C@H](O1)[C@@H](COc1ccc3cccnc3n1)O[C@H]2n1ccc2c(N)ncnc21] | A34 | Intermediate 66 |
| 119 | 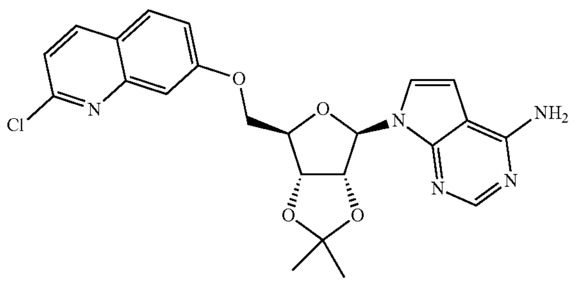 [SMILES: CC1(C)O[C@@H]2[C@H](O1)[C@@H](COc1ccc3ccc(Cl)nc3c1)O[C@H]2n1ccc2c(N)ncnc21] | A34 | Intermediate 67 |

TABLE 18-continued
| Int. | structure | Ref | Starting material |
|---|---|---|---|
| 120 | 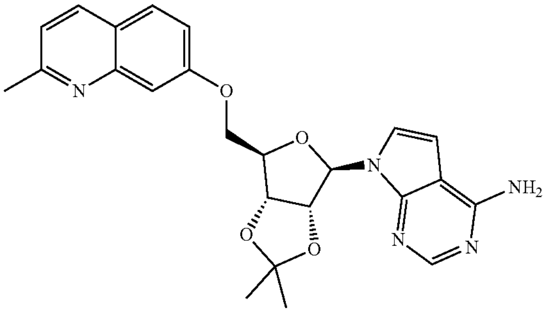 [SMILES: Cc1ccc2ccc(OC[C@H]3O[C@@H](n4ccc5c(N)ncnc54)[C@@H]4OC(C)(C)O[C@@H]43)cc2n1] | A34 | Intermediate 61 |
| 121 | 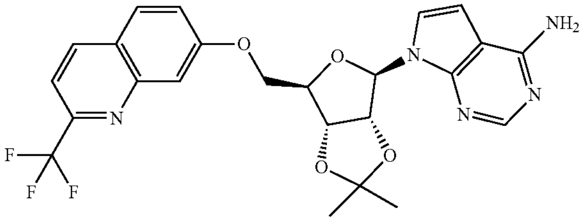 [SMILES: CC1(C)O[C@@H]2[C@H](O1)[C@@H](COc1ccc3ccc(C(F)(F)F)nc3c1)O[C@H]2n1ccc2c(N)ncnc21] | A35 | Intermediate 53 |
| 122 | 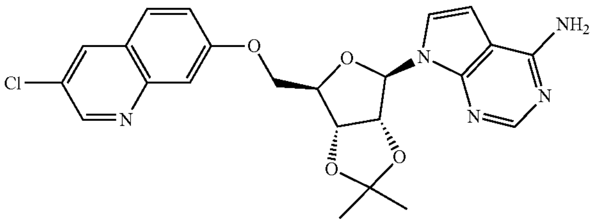 [SMILES: CC1(C)O[C@@H]2[C@H](O1)[C@@H](COc1ccc3cc(Cl)cnc3c1)O[C@H]2n1ccc2c(N)ncnc21] | A35 | Intermediate 55 |
| 123 | 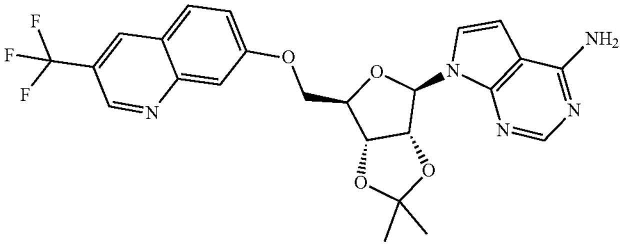 [SMILES: CC1(C)O[C@@H]2[C@H](O1)[C@@H](COc1ccc3cc(C(F)(F)F)cnc3c1)O[C@H]2n1ccc2c(N)ncnc21] | A34 | Intermediate 68 |
| 124 | 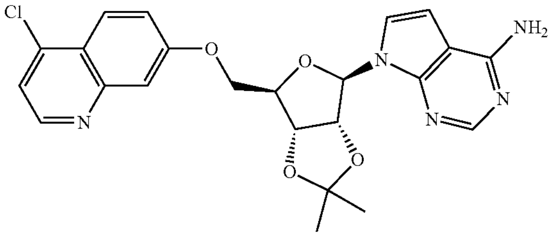 [SMILES: CC1(C)O[C@@H]2[C@H](O1)[C@@H](COc1ccc3c(Cl)ccnc3c1)O[C@H]2n1ccc2c(N)ncnc21] | A35 | Intermediate 54 |
| 125 | 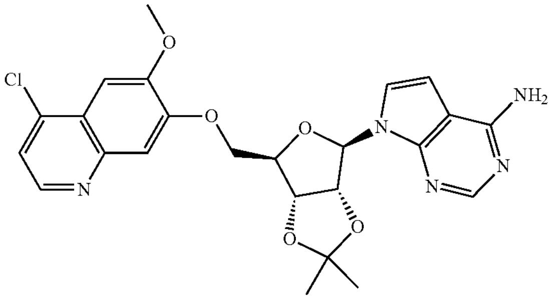 [SMILES: COc1cc2c(Cl)ccnc2cc1OC[C@H]1O[C@@H](n2ccc3c(N)ncnc32)[C@@H]2OC(C)(C)O[C@@H]21] | A35 | Intermediate 58 |

TABLE 18-continued
| Int. | structure | Ref | Starting material |
|---|---|---|---|
| 126 | 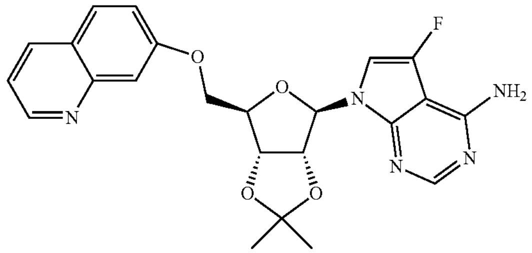 [SMILES: CC1(C)O[C@@H]2[C@H](O1)[C@@H](COc1ccc3cccnc3c1)O[C@H]2n1cc(F)c2c(N)ncnc21] | A34 | Intermediate 78 |
| 127 | 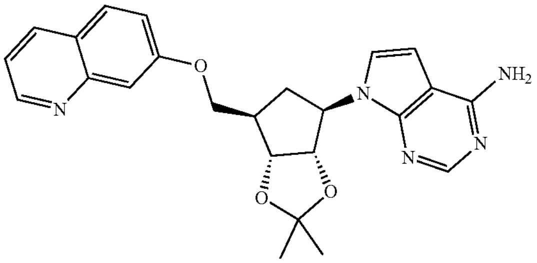 [SMILES: CC1(C)O[C@@H]2[C@@H](COc3ccc4cccnc4c3)C[C@@H](n3ccc4c(N)ncnc43)[C@@H]2O1] | A34 | Intermediate 69 |
| 128 | 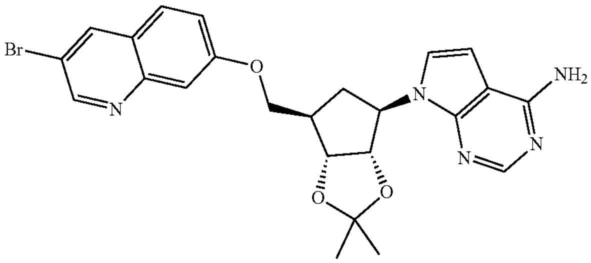 [SMILES: CC1(C)O[C@@H]2[C@@H](COc3ccc4cc(Br)cnc4c3)C[C@@H](n3ccc4c(N)ncnc43)[C@@H]2O1] | A34 | intermediate 77 |
| 129 | 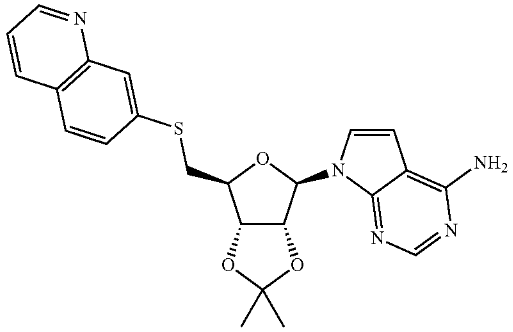 [SMILES: CC1(C)O[C@@H]2[C@H](O1)[C@@H](CSc1ccc3cccnc3c1)O[C@H]2n1ccc2c(N)ncnc21] | A34 | intermediate 90 |
| 130 | 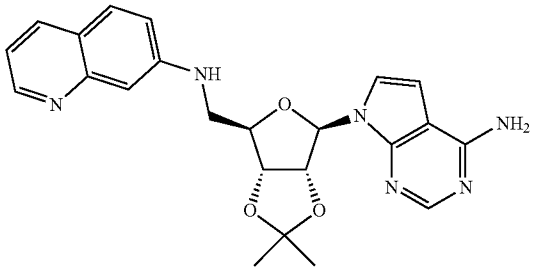 [SMILES: CC1(C)O[C@@H]2[C@H](O1)[C@@H](CNc1ccc3cccnc3c1)O[C@H]2n1ccc2c(N)ncnc21] | A34 | intermediate 91 |

TABLE 18-continued
| Int. | structure | Ref | Starting material |
|---|---|---|---|
| 131 | 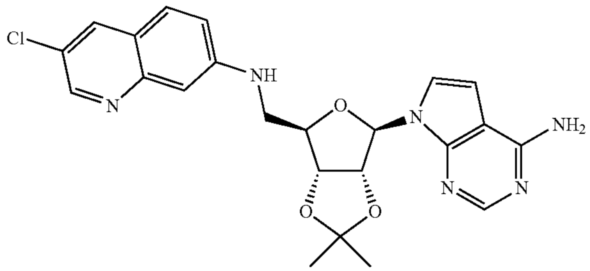 [SMILES: CC1(C)O[C@@H]2[C@H](O1)[C@@H](CNc1ccc3cc(Cl)cnc3c1)O[C@H]2n1ccc2c(N)ncnc21] | A34 | Intermediate 92 |
| 132 | 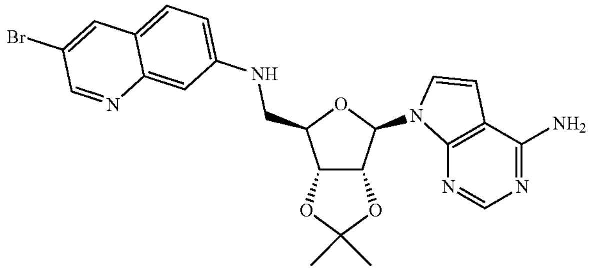 | A34 | Intermediate 93 |
| 133 | 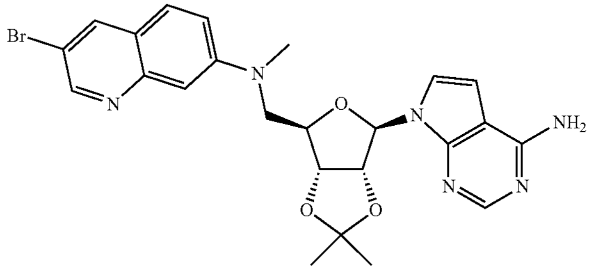 [SMILES: CN(C[C@H]1O[C@@H](n2ccc3c(N)ncnc32)[C@@H]2OC(C)(C)O[C@@H]21)c1ccc2cc(Br)cnc2c1] | A35 | Intermediate 96 |
| 134 | 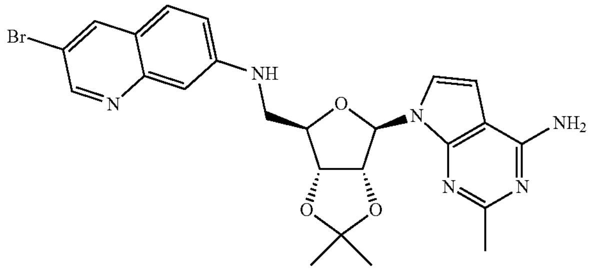 [SMILES: Cc1nc(N)c2ccn([C@@H]3O[C@H](CNc4ccc5cc(Br)cnc5c4)[C@H]4OC(C)(C)O[C@H]43)c2n1] | A34 | Intermediate 94 |
| 135 | 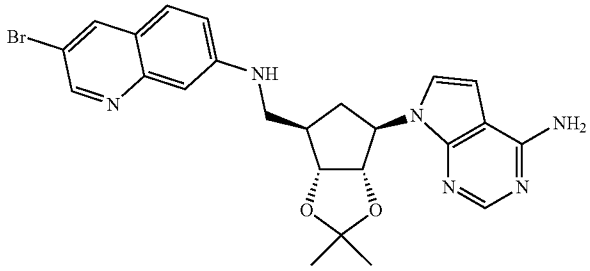 | A34 | Intermediate 95 |

TABLE 18-continued
| Int. | structure | Ref | Starting material |
|---|---|---|---|
| 136 | 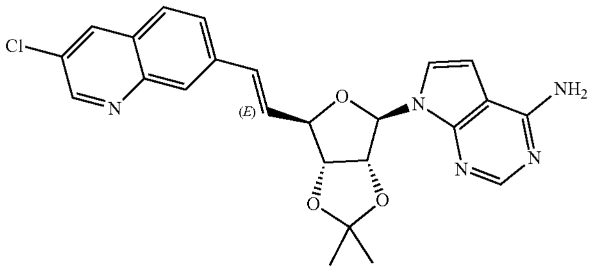 [SMILES: CC1(C)O[C@@H]2[C@H](O1)[C@@H](/C=C/c1ccc3cc(Cl)cnc3c1)O[C@H]2n1ccc2c(N)ncnc21] | A34 | Intermediate 99 |
| 137 | 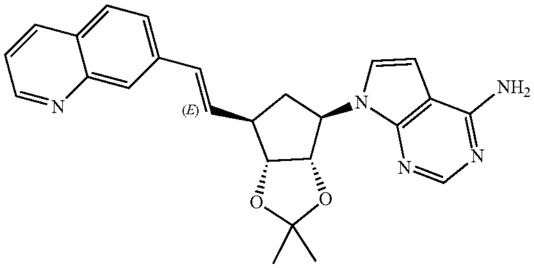 [SMILES: CC1(C)O[C@@H]2[C@H](O1)[C@@H](/C=C/c1ccc3cccnc3c1)C[C@H]2n1ccc2c(N)ncnc21] | A34 | intermediate 97 |
| 138 | 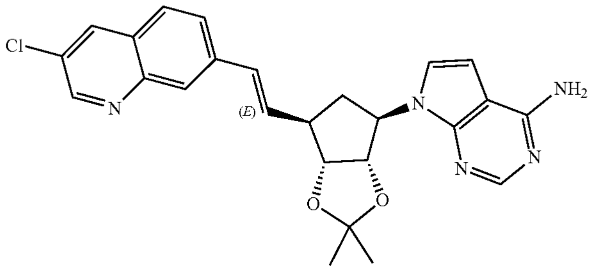 [SMILES: CC1(C)O[C@@H]2[C@H](O1)[C@@H](/C=C/c1ccc3cc(Cl)cnc3c1)C[C@H]2n1ccc2c(N)ncnc21] | A34 | Intermediate 98 |
| 139 | 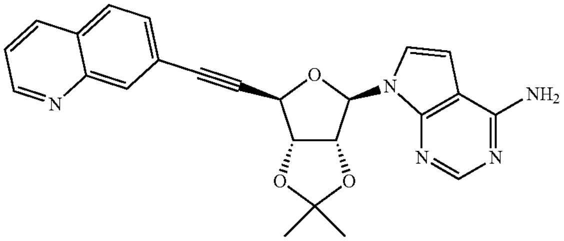 [SMILES: CC1(C)O[C@@H]2[C@H](O1)[C@@H](C#Cc1ccc3cccnc3c1)O[C@H]2n1ccc2c(N)ncnc21] | A35 | Intermediate 101 |
| 140 | 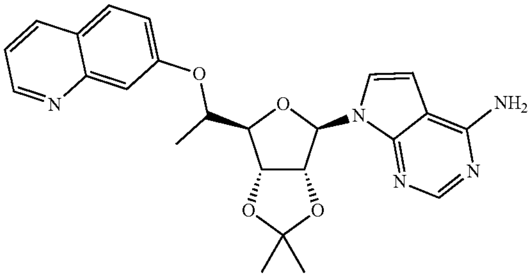 [SMILES: CC(Oc1ccc2cccnc2c1)[C@H]1O[C@@H](n2ccc3c(N)ncnc32)[C@@H]2OC(C)(C)O[C@@H]21] | A34 | Intermediate 60 |

TABLE 18-continued
| Int. | structure | Ref | Starting material |
|---|---|---|---|
| 141 | 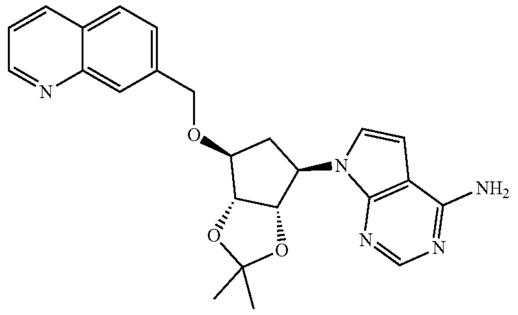 [SMILES: CC1(C)O[C@@H]2[C@H](O1)[C@@H](OCc1ccc3cccnc3c1)C[C@H]2n1ccc2c(N)ncnc21] | A34 | Intermediate 102 |
| 142 | 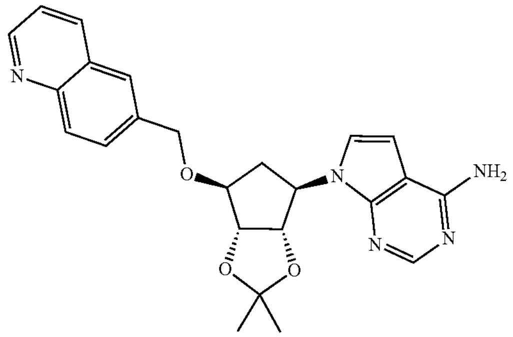 [SMILES: CC1(C)O[C@@H]2[C@H](O1)[C@@H](OCc1ccc3ncccc3c1)C[C@H]2n1ccc2c(N)ncnc21] | A34 | Intermediate 102a |
| 143 | 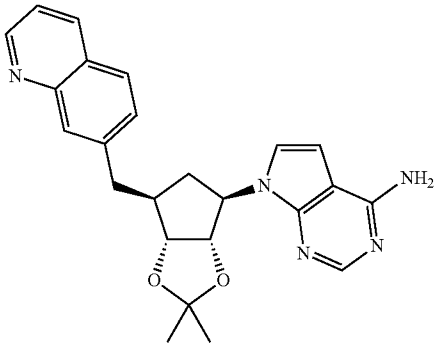 [SMILES: CC1(C)O[C@@H]2[C@@H](Cc3ccc4cccnc4c3)C[C@@H](n3ccc4c(N)ncnc43)[C@@H]2O1] | A35 | Intermediate 103 |
| 188 | 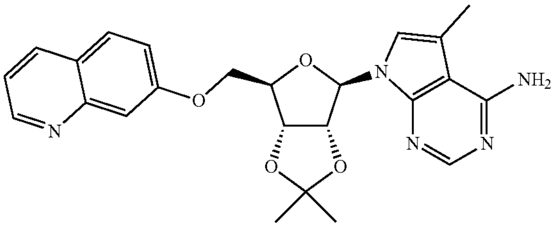 [SMILES: Cc1cn([C@@H]2O[C@H](COc3ccc4cccnc4c3)[C@H]3OC(C)(C)O[C@H]32)c2ncnc(N)c12] | A34 | Intermediate 187 |
| 192 | 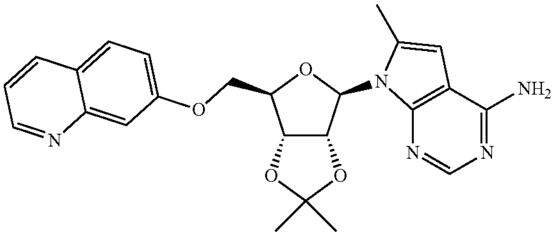 [SMILES: Cc1cc2c(N)ncnc2n1[C@@H]1O[C@H](COc2ccc3cccnc3c2)[C@H]2OC(C)(C)O[C@H]21] | A34 | Intermediate 191 |

TABLE 18-continued
| Int. | structure | Ref | Starting material |
| --- | --- | --- | --- |
| 194 | 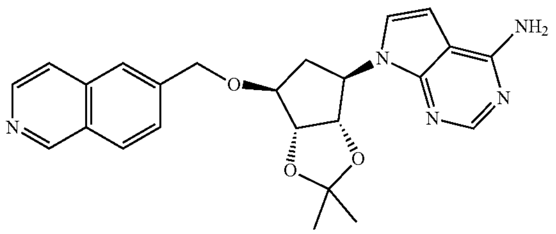 [SMILES: CC1(C)O[C@@H]2[C@H](O1)[C@@H](OCc1ccc3cnccc3c1)C[C@H]2n1ccc2c(N)ncnc21] | A34 | Intermediate 102b |
| 198 | 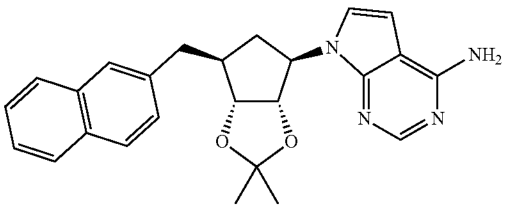 [SMILES: CC1(C)O[C@@H]2[C@@H](Cc3ccc4ccccc4c3)C[C@@H](n3ccc4c(N)ncnc43)[C@@H]2O1] | A35 | Intermediate 197 |
| 209 | 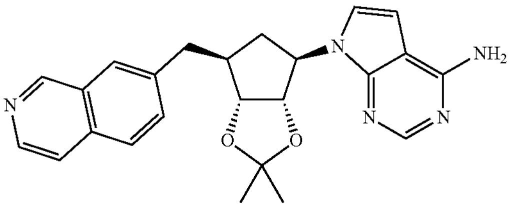 [SMILES: CC1(C)O[C@@H]2[C@@H](Cc3ccc4ccncc4c3)C[C@@H](n3ccc4c(N)ncnc43)[C@@H]2O1] | A34 | Intermediate 208 |
| 226 | 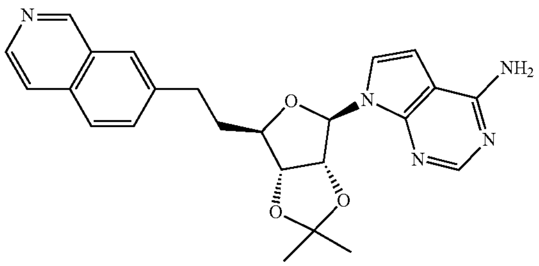 [SMILES: CC1(C)O[C@@H]2[C@H](O1)[C@@H](CCc1ccc3ccncc3c1)O[C@H]2n1ccc2c(N)ncnc21] | A34 | Intermediate 225 |
| 234 | 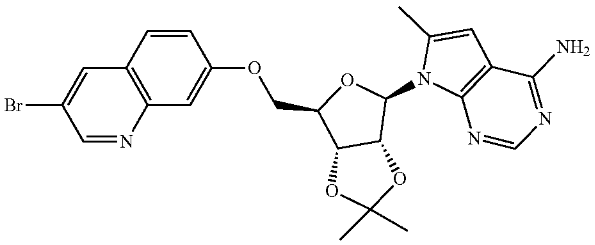 [SMILES: Cc1cc2c(N)ncnc2n1[C@@H]1O[C@H](COc2ccc3cc(Br)cnc3c2)[C@H]2OC(C)(C)O[C@H]21] | A35 | Intermediate 233 |
| 265 | 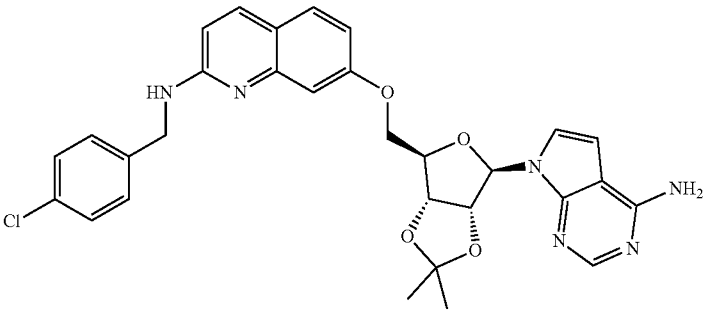 [SMILES: CC1(C)O[C@@H]2[C@H](O1)[C@@H](COc1ccc3ccc(NCc4ccc(Cl)cc4)nc3c1)O[C@H]2n1ccc2c(N)ncnc21] | A34 | Intermediate 264 |

TABLE 18-continued
| Int. | structure | Ref | Starting material |
|---|---|---|---|
| 334 | 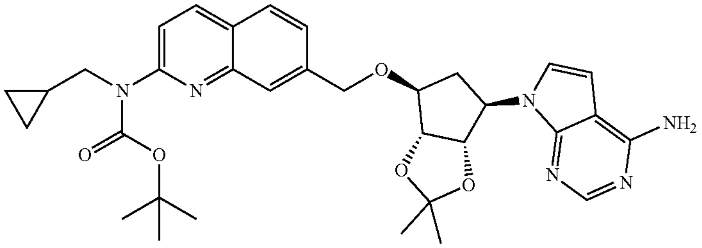 [SMILES: CC(C)(C)OC(=O)N(CC1CC1)c1ccc2ccc(CO[C@H]3C[C@@H](n4ccc5c(N)ncnc54)[C@@H]4OC(C)(C)O[C@@H]43)cc2n1] | A34 | Intermediate 333 |
| 462 | 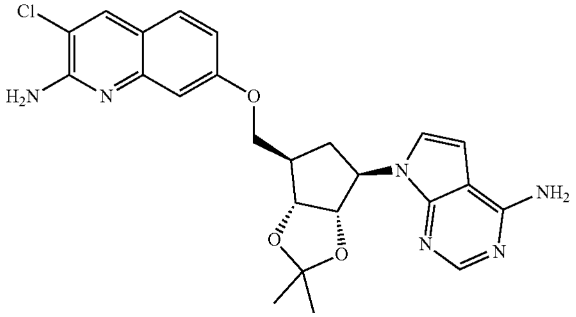 [SMILES: CC1(C)O[C@@H]2[C@@H](COc3ccc4cc(Cl)c(N)nc4c3)C[C@@H](n3ccc4c(N)ncnc43)[C@@H]2O1] | A34 | Intermediate 461 |
| 464 | 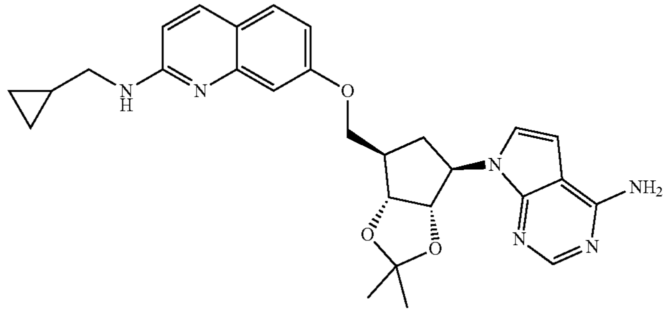 [SMILES: CC1(C)O[C@@H]2[C@@H](COc3ccc4ccc(NCC5CC5)nc4c3)C[C@@H](n3ccc4c(N)ncnc43)[C@@H]2O1] | A34 | Intermediate 463 |
| 485 | 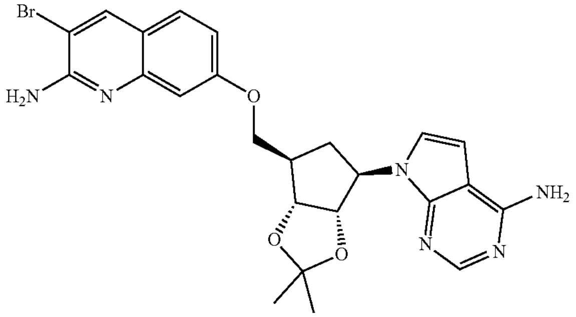 [SMILES: CC1(C)O[C@@H]2[C@@H](COc3ccc4cc(Br)c(N)nc4c3)C[C@@H](n3ccc4c(N)ncnc43)[C@@H]2O1] | A34 | Intermediate 484 |
| 496 | 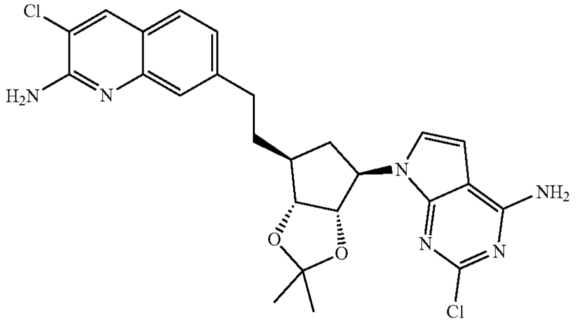 [SMILES: CC1(C)O[C@@H]2[C@@H](CCc3ccc4cc(Cl)c(N)nc4c3)C[C@@H](n3ccc4c(N)nc(Cl)nc43)[C@@H]2O1] | A34 | Intermediate 495 |

TABLE 18-continued
| Int. | structure | Ref | Starting material |
|---|---|---|---|
| 498 | 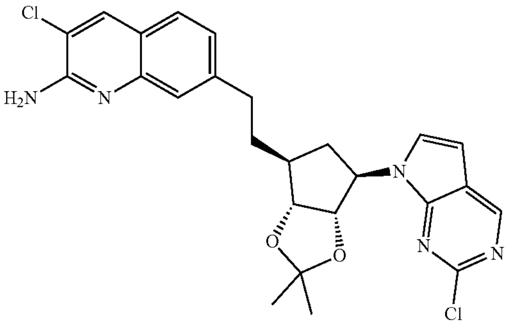 [SMILES: CC1(C)O[C@@H]2[C@@H](CCc3ccc4cc(Cl)c(N)nc4c3)C[C@@H](n3ccc4cnc(Cl)nc43)[C@@H]2O1] | A34 | Intermediate 497 |
| 500 | 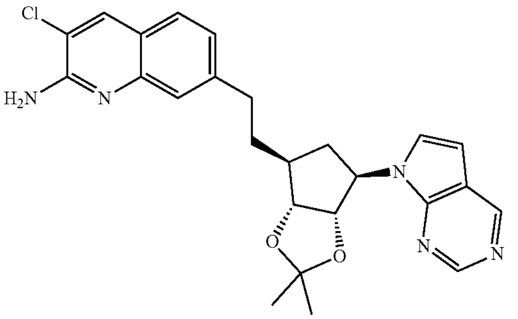 | A34 | Intermediate 499 |
| 501 | 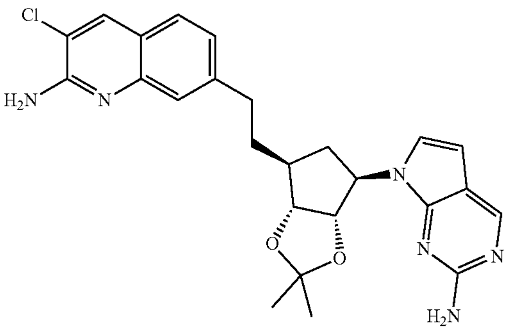 [SMILES: CC1(C)O[C@@H]2[C@@H](CCc3ccc4cc(Cl)c(N)nc4c3)C[C@@H](n3ccc4cnc(N)nc43)[C@@H]2O1] | A34 | Intermediate 497 |
| 516 | 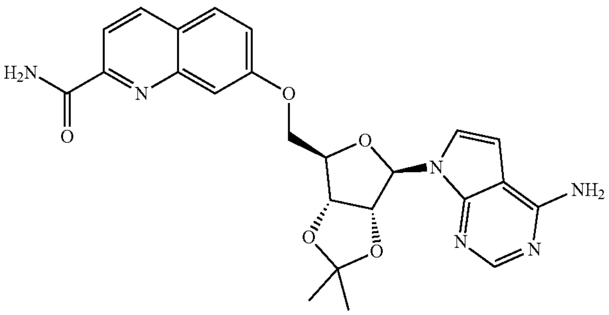 [SMILES: CC1(C)O[C@@H]2[C@H](O1)[C@@H](COc1ccc3ccc(C(N)=O)nc3c1)O[C@H]2n1ccc2c(N)ncnc21] | A34 | Intermediate 515 |

TABLE 18-continued
| Int. | structure | Ref | Starting material |
|---|---|---|---|
| 518 | 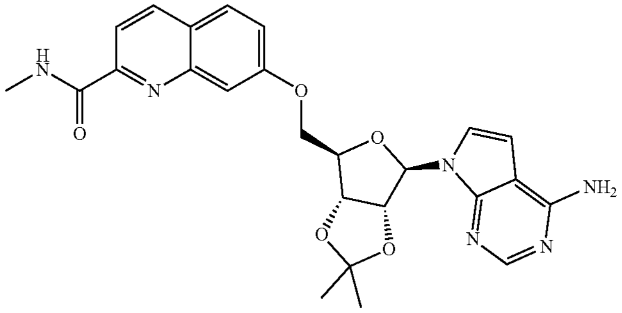 [SMILES: CNC(=O)c1ccc2ccc(OC[C@H]3O[C@@H](n4ccc5c(N)ncnc54)[C@@H]4OC(C)(C)O[C@@H]43)cc2n1] | A34 | Intermediate 517 |
| 520 | 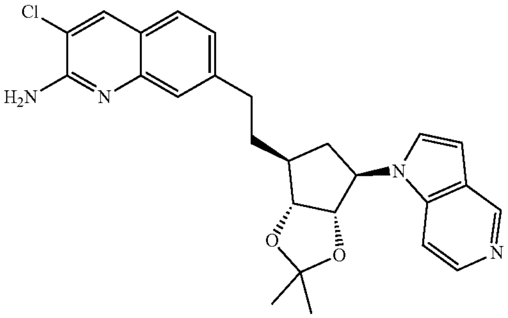 [SMILES: CC1(C)O[C@@H]2[C@@H](CCc3ccc4cc(Cl)c(N)nc4c3)C[C@@H](n3ccc4cnccc43)[C@@H]2O1] | A34 | Intermediate 519 |
| 522 | 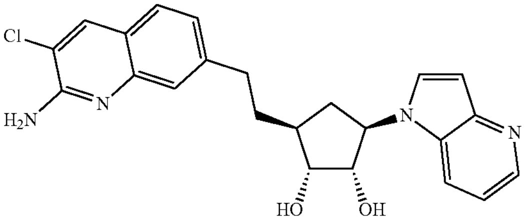 [SMILES: Nc1nc2cc(CC[C@H]3C[C@@H](n4ccc5ncccc54)[C@H](O)[C@@H]3O)ccc2cc1Cl] | A34 | Intermediate 521 |
| 524 | 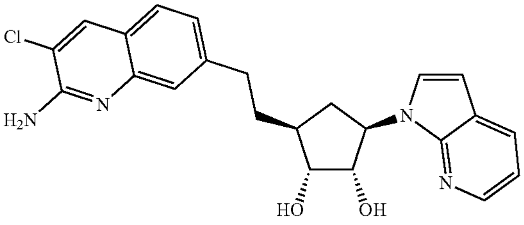 | A34 | Intermediate 523 |

Example A36

Preparation of Intermediate 144 and 144a

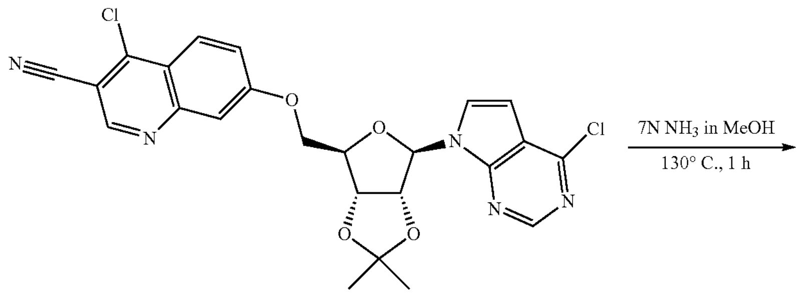

Intermediate 56

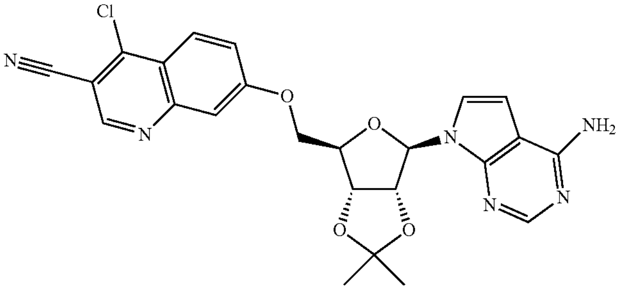

Intermediate 144

+

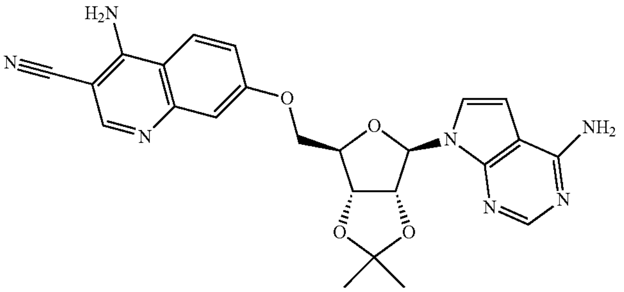

Intermediate 144a

A solution of Intermediate 56 (35.7 mg, ≈0.0662 mmol) in 7M $NH_3$ in MeOH (1 mL, 7 mmol) was stirred and heated at 130° C. using microwave irradiation for 1 hour. The solvents were evaporated. The residues were purified with Prep HPLC (Stationary phase: RP XBridge Prep C18 OBD-10 μm, 30×150 mm, Mobile phase: 0.25% $NH_4HCO_3$ solution in water, $CH_3CN$). The solvents of the purified fractions were evaporated and co-evaporated with MeOH yielding Intermediate 144 (12.9 mg, 37% yield) and Intermediate 144a (26.5 mg, 73%).

Example A37

Preparation of Intermediate 145 and 145a

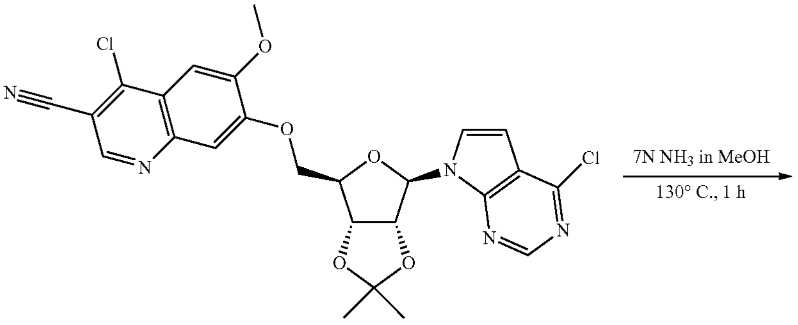

Intermediate 57

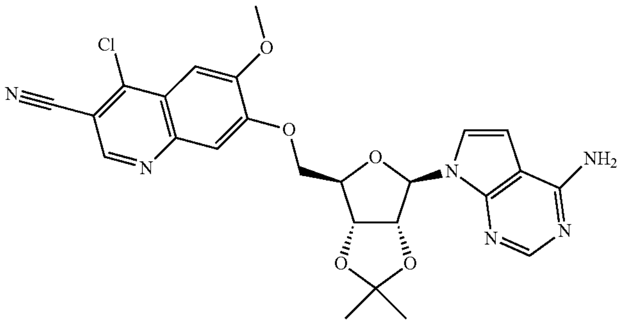

Intermediate 145

+

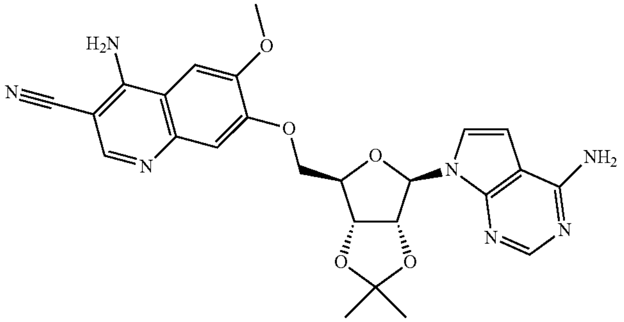

Intermediate 145a

A solution of crude Intermediate 57 (theoretically 2.36 mmol) in 7M $NH_3$ in MeOH (20 mL, 7 mmol) was stirred and heated at 130° C. using microwave irradiation for 2 hours. The solvents were evaporated. The residue was dissolved in DCM with MeOH and purified over a $SiO_2$ column, type Grace Reveleris SRC, 40 g, Si 40, on a Armen Spot II Ultimate purification system (gradient elution: DCM: MeOH from 100:0 to 20:80). The fractions containing product were combined and the solvents were removed, yielding crude Intermediate 145 (0.64 g) and crude Intermediate 145a (0.13 g). Both crude intermediates were used for the next reaction step reaction without further purification.

Example A38

Preparation of Intermediate 146

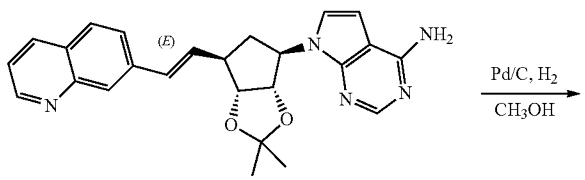

intermediate 137

-continued

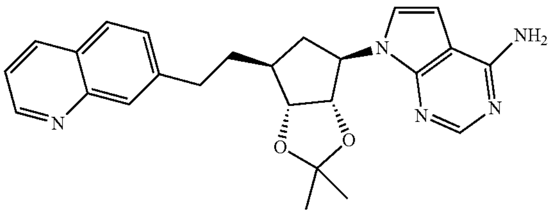

intermediate 146

To a mixture of Intermediate 137 (340 mg, theoretically 795 μmol) in MeOH (10.0 mL) was added Pd/C (100 mg, 10%) at 25° C. The suspension was degassed under vacuum and purged with $H_2$ (several times). The mixture was stirred under $H_2$ (15 psi) at 25° C. for 5 hours. The mixture was filtered and the filtrate was concentrated. The residue was purified by preparative-HPLC (Column: Diamonsil 150*20 mm, 5 μm, Mobile phase: from 15% MeCN in water (0.225% formic acid) to 45% MeCN in water (0.225% formic acid)

Flow Rate (ml/min): 25 ml/min), The fractions containing the desired product were combined and lyophilized. The residues were further purified by Chiral SFC (Column: OD (250 mm*30 mm, 10 μm), Mobile phase: Supercritical $CO_2$/EtOH+$NH_3 \cdot H_2O$ (0.1%)=50/50 Flow rate: 80 ml/min). Intermediate 146 (130 mg, 38% yield) was obtained as a white solid.

Below intermediates were prepared by an analogous reaction protocol as described for preparing intermediate 146 using the appropriate starting materials (Table 19).

TABLE 19

| Int. | structure | Starting material |
|---|---|---|
| 147 | 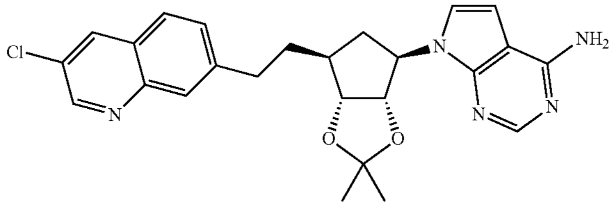 [SMILES: CC1(C)O[C@@H]2[C@@H](CCc3ccc4cc(Cl)cnc4c3)C[C@@H](n3ccc4c(N)ncnc43)[C@@H]2O1] | Intermediate 138 |
| 148 | 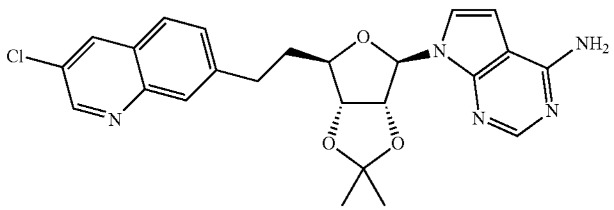 [SMILES: CC1(C)O[C@@H]2[C@H](O1)[C@@H](CCc1ccc3cc(Cl)cnc3c1)O[C@H]2n1ccc2c(N)ncnc21] | Intermediate 136 |

Example A39

Preparation of Intermediate 149

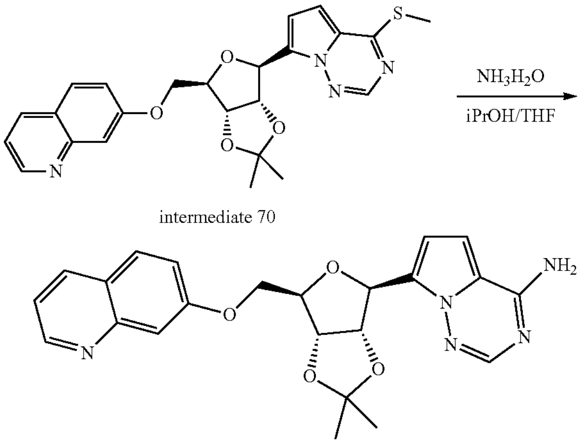

intermediate 70 intermediate 149

To a solution of Intermediate 70 (360 mg, ≈542 μmol) in THF (3.00 mL) was added iPrOH (3.00 mL) and ammonia (28% in water, 6.00 mL). The mixture was stirred at 85° C. for 72 hours in an autoclave. The solvent was removed and the residue was purified by flash column on silica gel (gradient elution: MeOH/DCM from 0/100 to 4/96), yielded Intermediate 149 as a white solid. (230 mg, 65% yield).

The intermediate in Table 20 was prepared by an analogous reaction protocol as was used for the preparation of intermediate 149 using the appropriate starting materials (Table 20). Intermediate 150 was obtained in the E-configuration.

TABLE 20

| Int. | structure | Starting material |
|---|---|---|
| 150 | 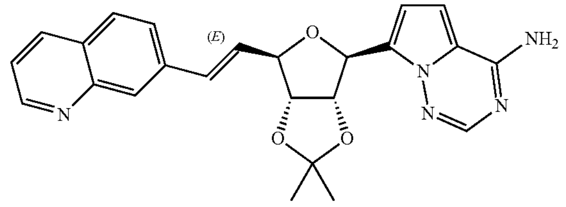 [SMILES: CC1(C)O[C@@H]2[C@H](O1)[C@@H](/C=C/c1ccc3cccnc3c1)O[C@H]2c1ccc2c(N)ncnn12] | Intermediate 100 |

Example A40

Preparation of Intermediate 151

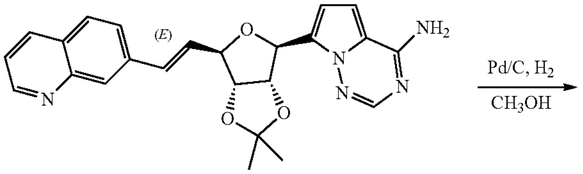

intermediate 150

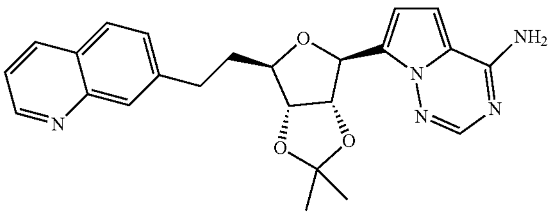

intermediate 151

A suspension of intermediate 150 (150 mg, 349 μmol) and Pd/C (80 mg, 10%) was stirred under an atmosphere of $H_2$ (15 Psi) for 7 hours at 15° C. The reaction mixture was filtered through Celite. The filtrate was concentrated under reduced pressure to afford intermediate 151 as a yellow solid (135 mg, 90% yield).

Example A41

Preparation of Intermediate 152

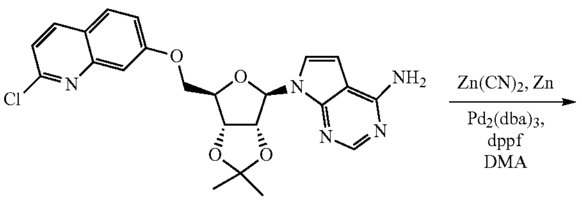

intermediate 119

-continued

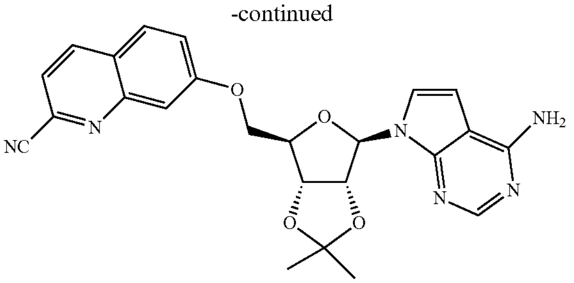

intermediate 152

To the solution of Intermediate 119 (550 mg, theoretically 1.18 mmol) in DMA (20 mL) were added Zinc cyanide (410 mg, 3.49 mmol), Zinc (55 mg, 0.86 mmol), Tris(dibenzylideneacetone)dipalladium (46 mg, 0.051 mmol), 1,1'-Bis (diphenylphosphino)ferrocene (92 mg, 0.17 mmol). The mixture was stirred at 100° C. for 12 hours under $N_2$. The catalyst was filtered and the solvent was evaporated. The residue was purified by flash column chromatography over silica gel (gradient eluent: EtOAc/Petroleum ether from 1/20 to 1/0). The solvent was evaporated to give the intermediate 152 as oil (450 mg, 70% yield).

Example A56

Preparation of Intermediate 214

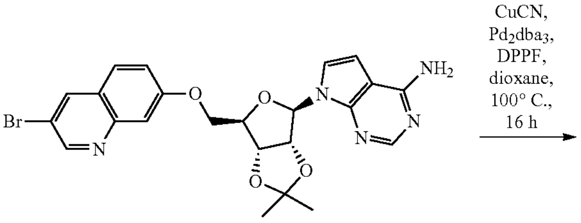

intermediate 105

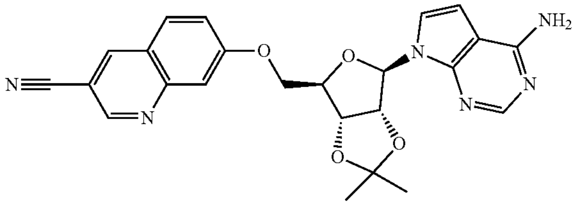

intermediate 214

A mixture of intermediate 105 (512. mg, 1 mmol), CuCN (358.2 mg, 4 mmol), $Pd_2dba_3$(92 mg, 0.1 mmol) and DPPF (221.7 mg, 0.4 mmol) in dioxane (6 ml) were stirred at 100° C. for 16 h. The reaction mixture was cooled, poured into water and extracted three times with ethylacetate. The organic layer was washed two times with water. The organic layer was dried and evaporated to dryness. The residue was purified by Prep HPLC (Stationary phase: RP XBridge Prep C18 OBD-10 μm, 50×150 mm, Mobile phase: 0.25% $NH_4HCO_3$ solution in water, $CH_3CN$) yielding intermediate 214 (363 mg, 79% yield).

Example A42

Preparation of Intermediate 153

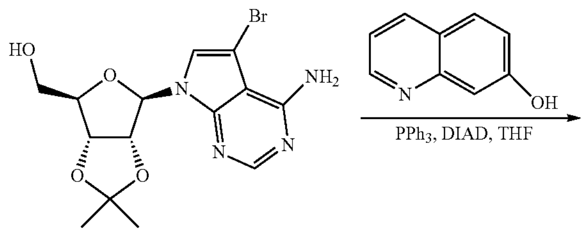

intermediate 23

-continued

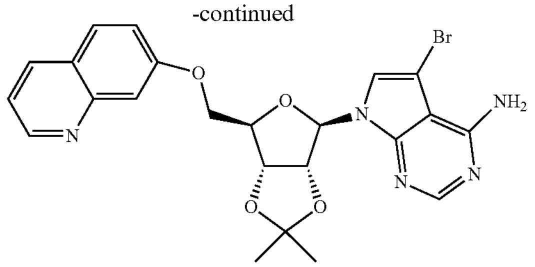

Intermediate 153

The mixture of intermediate 23 (50 mg, theoretically 0.13 mmol), 7-hydroxyquinoline (22 mg, 0.156 mmol) and $PPh_3$ (53 mg, 0.26 mmol) in dry THF (20 ml) was stirred at room temperature under $N_2$. DIAD (6.47 g, 32.037 mmol) was added dropwise. The reaction mixture was stirred at room temperature for 2 hours. The reaction mixture was concentrate to dryness, yielding crude intermediate 153.

Example A43

Preparation of Intermediate 154 and intermediate 154a

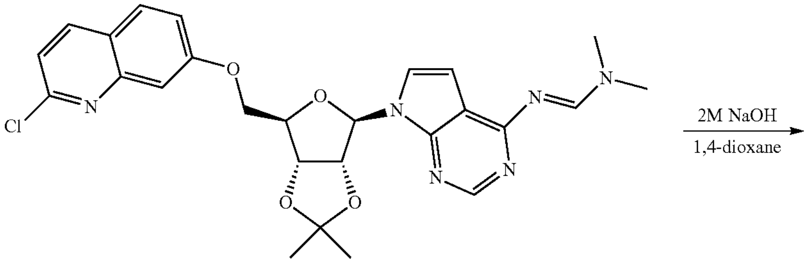

intermediate 72

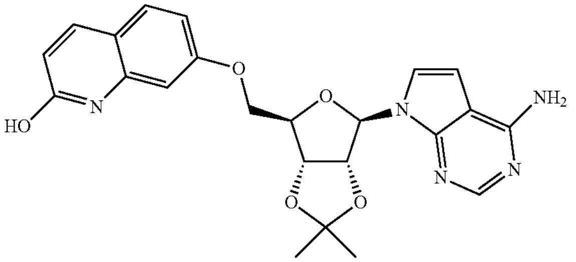

intermediate 154

+

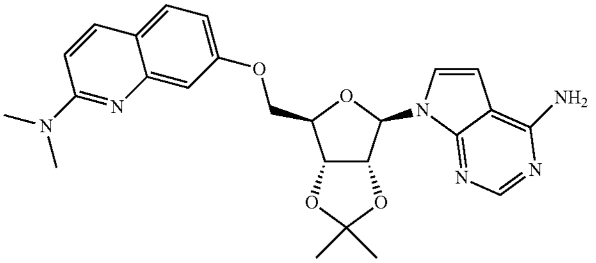

intermediate 154a

To a solution of intermediate 72 (1.0 g, 1.91 mmol) in 1,4-dioxane (10 mL) was added 2M NaOH (10 mL, 20 mmol). The reaction mixture was stirred at 150° C. for 1 hour under microwave condition. The mixture was diluted with water (15 mL), extracted with EtOAc (10 mL×3). The organic phase was washed with brine (15 mL), dried over $Na_2SO_4$, filtered and concentrated. The residue was purified by chromatography column (elution: EtOAc/MeOH 85/15). The desired fractions were collected and concentrated to give intermediate 154 (359 mg of a white solid, 41% yield) and intermediate 154a (300 mg, 32% yield).

Example A44

Preparation of Intermediate 155

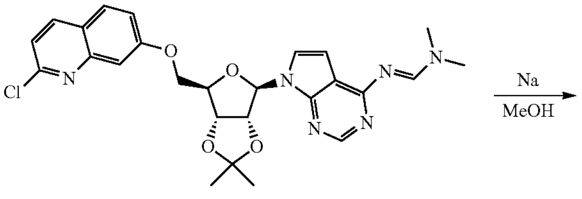

intermediate 72

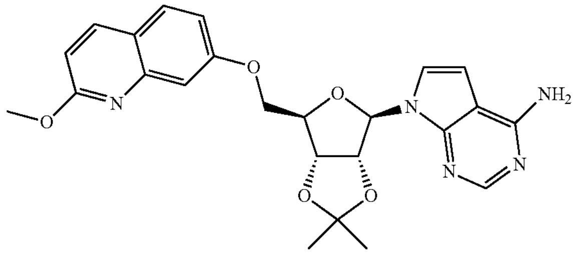

intermediate 155

Sodium (440 mg, 19.1 mmol) was stirred in MeOH (25 mL) at room temperature until sodium was dissolved completely. Then intermediate 72 (1.0 g, 1.91 mmol) was added into the reaction mixture and the reaction mixture was refluxed for 72 hours. The mixture was diluted with DCM (100 mL), washed with water (10 mL), brine (10 mL). The organic phase was dried over $Na_2SO_4$, filtered and concentrated to give crude intermediate 155 which was used as such for the next reaction step without further purification.

Example A45

Preparation of Intermediate 157

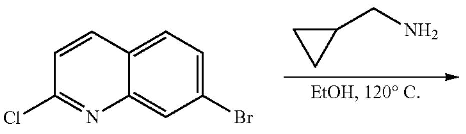

-continued

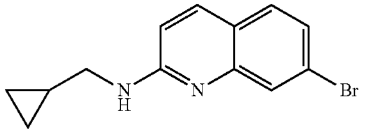

intermediate 157

7-bromo-2-chloro-quinoline (10.0 g, 41.2 mmol) and cyclopropylmethylamine (18 mL) in EtOH (80 mL) was stirred in a sealed tube at 120° C. overnight. The mixture was evaporated under vacuo to give intermediate 157 (15 g; crude) as a brown solid which used as such in the next reaction step without further purification.

Preparation of Intermediate 159

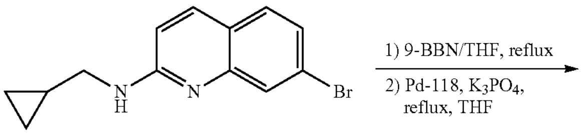

intermediate 157

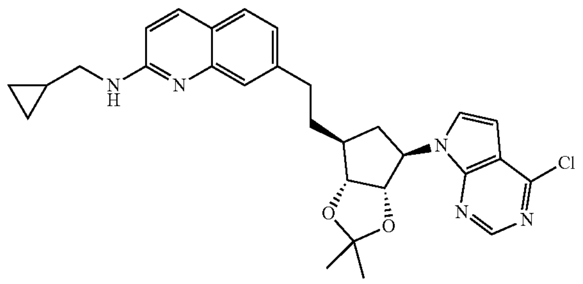

intermediate 159

Intermediate 38 (3.8 g, 11.9 mmol) in 9-BBN (0.5 M in THF, 95.1 mL, 47.5 mmol) was refluxed for 1 h under $N_2$. The mixture was cooled to room temperature, then $K_3PO_4$ (7.56 g, 35.6 mmol) in $H_2O$ (20 mL) was added, followed by THF (150 mL), intermediate 157 (4.4 g, ≈13 mmol) and Pd-118 (155 mg, 0.24 mmol). The resulting mixture was refluxed overnight. The mixture was diluted with $H_2O$ (100 mL), extracted with ethyl acetate (150 mL), the organic phase was dried by $Na_2SO_4$, then filtered and concentrated in vacuo to give the crude product. The crude product was purified by chromatography (ethyl acetate/petroleum ether 0/1 to 1/3) to give intermediate 159 (3.1 g, yield: 42.8%) as a yellow oil.

Below intermediates were prepared by an analogous reaction protocol as was used for the preparation of intermediate 159 using the appropriate starting materials (Table 29).

TABLE 29
| Int. | Structure | Starting materials |
| --- | --- | --- |
| 242 | 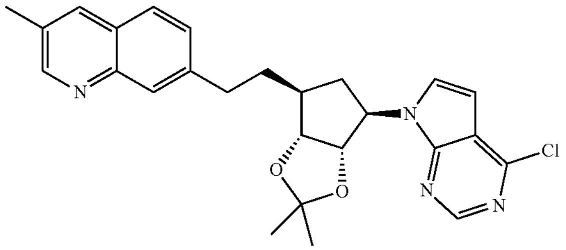 [SMILES: Cc1cnc2cc(CC[C@H]3C[C@@H](n4ccc5c(Cl)ncnc54)[C@@H]4OC(C)(C)O[C@H]34)ccc2c1] | a) Intermediate 38<br>b) 3-methyl-7-bromoquinoline |
| 245 | 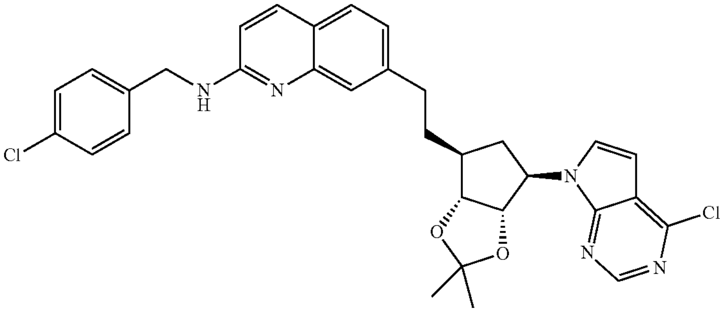 [SMILES: CC1(C)O[C@@H]2[C@@H](CCc3ccc4ccc(NCc5ccc(Cl)cc5)nc4c3)C[C@@H](n3ccc4c(Cl)ncnc43)[C@@H]2O1] | a) Intermediate 38<br>b) Intermediate 244 |
| 248 | 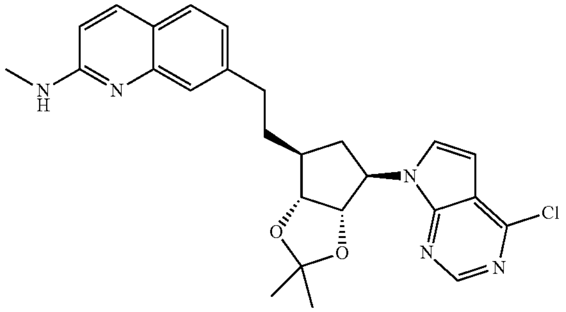 [SMILES: CNc1ccc2ccc(CC[C@H]3C[C@@H](n4ccc5c(Cl)ncnc54)[C@@H]4OC(C)(C)O[C@H]34)cc2n1] | a) Intermediate 38<br>b) 7-bromo-N-methyl-2-quinolinamine |
| 249 | 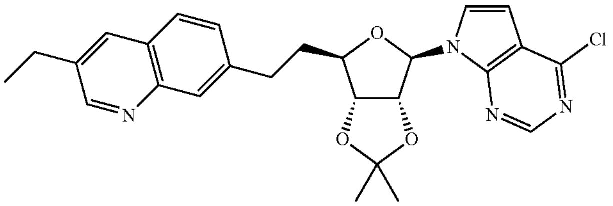 [SMILES: CCc1cnc2cc(CC[C@H]3O[C@@H](n4ccc5c(Cl)ncnc54)[C@@H]4OC(C)(C)O[C@@H]43)ccc2c1] | a) Intermediate 39<br>b) 7-bromo-3-ethyl-quinoline |
| 251 | 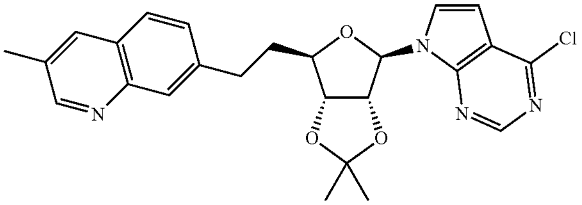 [SMILES: Cc1cnc2cc(CC[C@H]3O[C@@H](n4ccc5c(Cl)ncnc54)[C@@H]4OC(C)(C)O[C@@H]43)ccc2c1] | a) Intermediate 39<br>b) 7-bromo-3-methyl-quinoline |

TABLE 29-continued
| Int. | Structure | Starting materials |
|---|---|---|
| 254 | 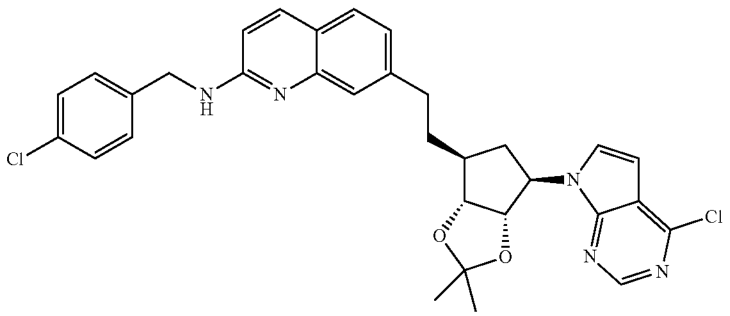 [SMILES: CC1(C)O[C@@H]2[C@@H](CCc3ccc4ccc(NCc5ccc(Cl)cc5)nc4c3)C[C@@H](n3ccc4c(Cl)ncnc43)[C@@H]2O1] | a) Intermediate 38<br>b) Intermediate 253 |
| 256 | 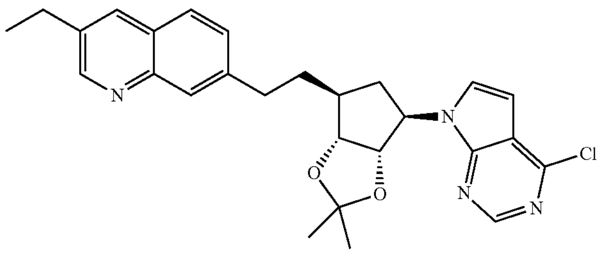 [SMILES: CCc1cnc2cc(CC[C@H]3C[C@@H](n4ccc5c(Cl)ncnc54)[C@@H]4OC(C)(C)O[C@H]34)ccc2c1] | a) Intermediate 38<br>b) 7-bromo-3-ethyl-quinoline |
| 259 | 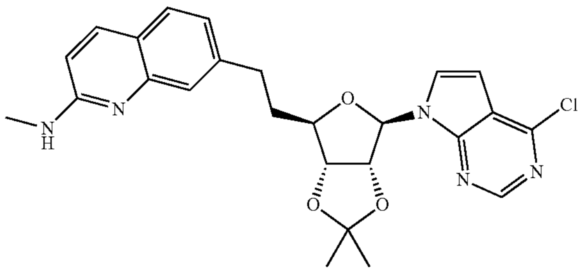 [SMILES: CNc1ccc2ccc(CC[C@H]3O[C@@H](n4ccc5c(Cl)ncnc54)[C@@H]4OC(C)(C)O[C@@H]43)cc2n1] | a) Intermediate 39<br>b) 7-bromo-N-methyl-2-quinolinamine |
| 266 | 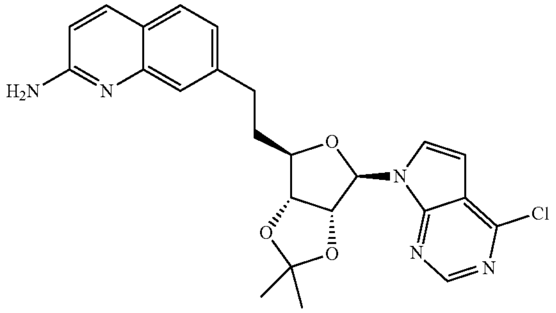 [SMILES: CC1(C)O[C@@H]2[C@H](O1)[C@@H](CCc1ccc3ccc(N)nc3c1)O[C@H]2n1ccc2c(Cl)ncnc21] | a) Intermediate 39<br>b) 7-bromo-2-Quinolinamine |
| 268 | 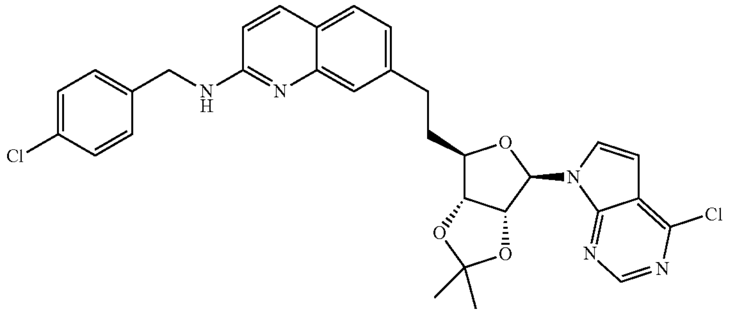 [SMILES: CC1(C)O[C@@H]2[C@H](O1)[C@@H](CCc1ccc3ccc(NCc4ccc(Cl)cc4)nc3c1)O[C@H]2n1ccc2c(Cl)ncnc21] | a) Intermediate 39<br>b) Intermediate 253 |

TABLE 29-continued
| Int. | Structure | Starting materials |
|---|---|---|
| 272 | 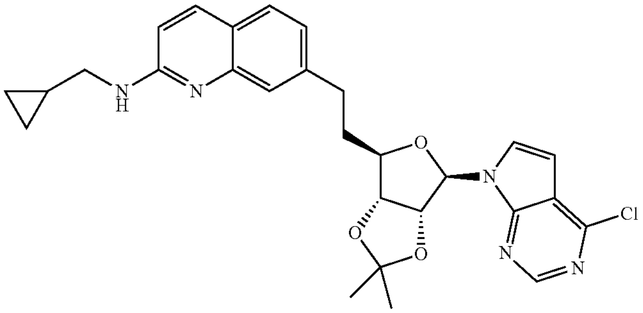 [SMILES: CC1(C)O[C@@H]2[C@H](O1)[C@@H](CCc1ccc3ccc(NCC4CC4)nc3c1)O[C@H]2n1ccc2c(Cl)ncnc21] | a) Intermediate 39<br>b) Intermediate 157 |
| 277 | 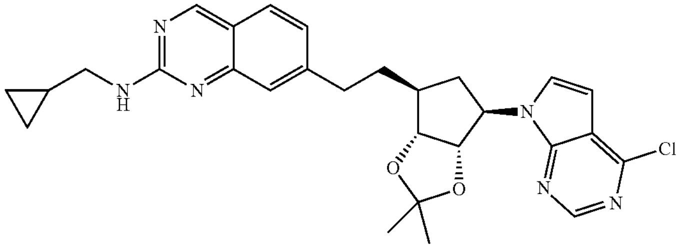 [SMILES: CC1(C)O[C@@H]2[C@@H](CCc3ccc4cnc(NCC5CC5)nc4c3)C[C@@H](n3ccc4c(Cl)ncnc43)[C@@H]2O1] | a) Intermediate 38<br>b) Intermediate 276 |
| 281 | 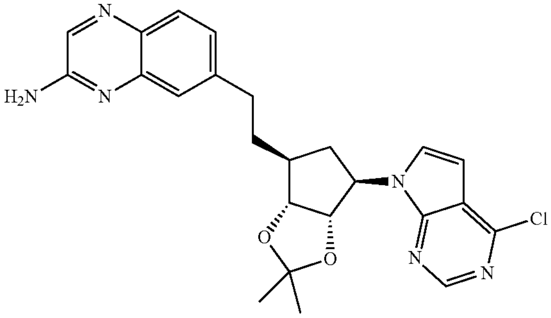 [SMILES: CC1(C)O[C@@H]2[C@@H](CCc3ccc4ncc(N)nc4c3)C[C@@H](n3ccc4c(Cl)ncnc43)[C@@H]2O1] | a) Intermediate 38<br>b) Intermediate 280 |
| 288 | 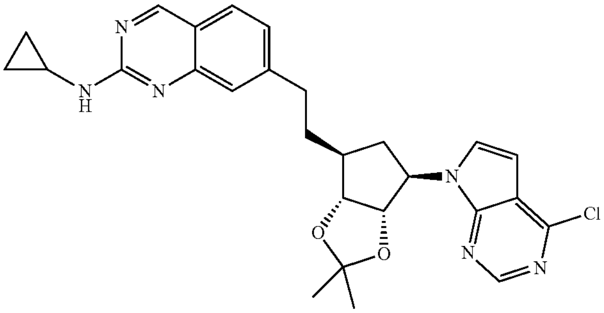 [SMILES: CC1(C)O[C@@H]2[C@@H](CCc3ccc4cnc(NC5CC5)nc4c3)C[C@@H](n3ccc4c(Cl)ncnc43)[C@@H]2O1] | a) Intermediate 38<br>b) Intermediate 287 |
| 291 | 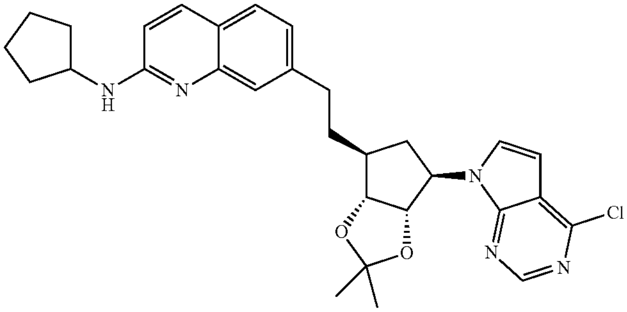 [SMILES: CC1(C)O[C@@H]2[C@@H](CCc3ccc4ccc(NC5CCCC5)nc4c3)C[C@@H](n3ccc4c(Cl)ncnc43)[C@@H]2O1] | a) Intermediate 38<br>b) Intermediate 290 |

TABLE 29-continued
| Int. | Structure | Starting materials |
| --- | --- | --- |
| 294 | 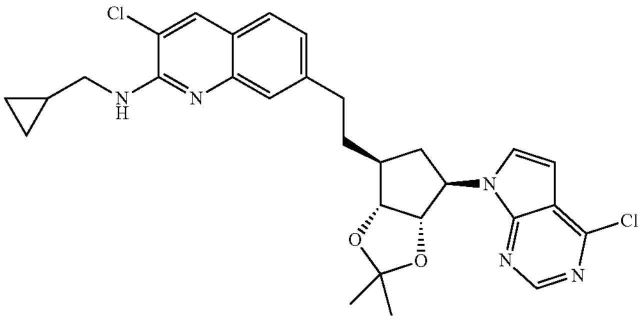 [SMILES: CC1(C)O[C@@H]2[C@@H](CCc3ccc4cc(Cl)c(NCC5CC5)nc4c3)C[C@@H](n3ccc4c(Cl)ncnc43)[C@@H]2O1] | a) Intermediate 38<br>b) Intermediate 293 |
| 297 | 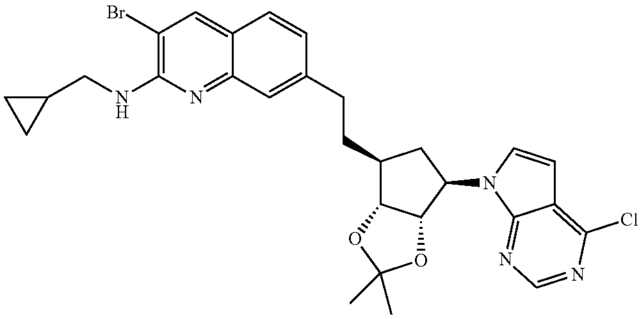 [SMILES: CC1(C)O[C@@H]2[C@@H](CCc3ccc4cc(Br)c(NCC5CC5)nc4c3)C[C@@H](n3ccc4c(Cl)ncnc43)[C@@H]2O1] | a) Intermediate 38<br>b) Intermediate 296 |
| 300 | 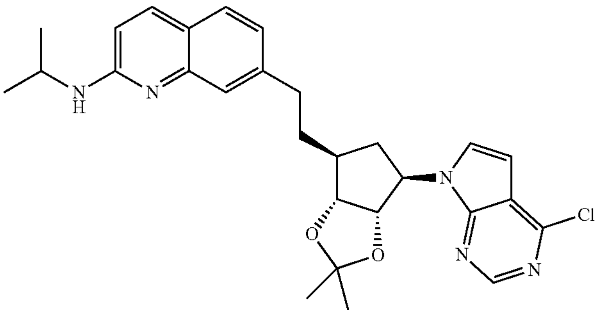 [SMILES: CC(C)Nc1ccc2ccc(CC[C@H]3C[C@@H](n4ccc5c(Cl)ncnc54)[C@@H]4OC(C)(C)O[C@H]34)cc2n1] | a) Intermediate 38<br>b) Intermediate 299 |
| 303 | 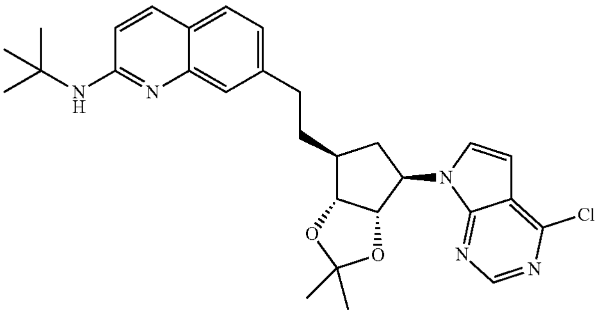 [SMILES: CC(C)(C)Nc1ccc2ccc(CC[C@H]3C[C@@H](n4ccc5c(Cl)ncnc54)[C@@H]4OC(C)(C)O[C@H]34)cc2n1] | a) Intermediate 38<br>b) Intermediate 302 |
| 306 | 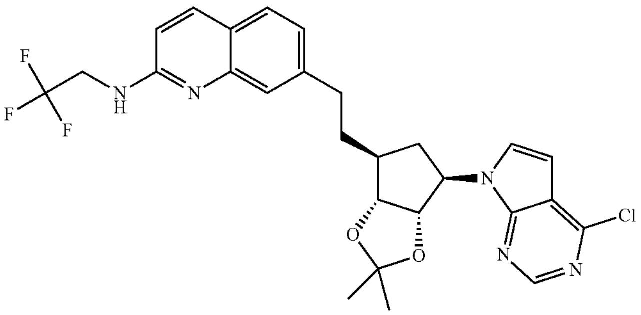 [SMILES: CC1(C)O[C@@H]2[C@@H](CCc3ccc4ccc(NCC(F)(F)F)nc4c3)C[C@@H](n3ccc4c(Cl)ncnc43)[C@@H]2O1] | a) Intermediate 38<br>b) Intermediate 305 |

TABLE 29-continued
| Int. | Structure | Starting materials |
| --- | --- | --- |
| 309 | 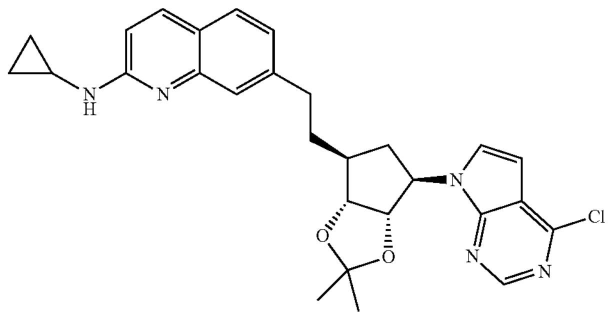 [SMILES: CC1(C)O[C@@H]2[C@@H](CCc3ccc4ccc(NC5CC5)nc4c3)C[C@@H](n3ccc4c(Cl)ncnc43)[C@@H]2O1] | a) Intermediate 38<br>b) Intermediate 308 |
| 312 | 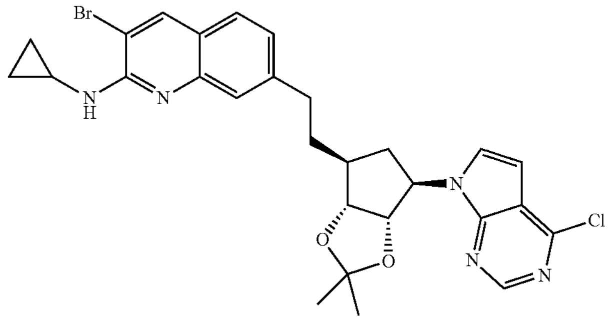 [SMILES: CC1(C)O[C@@H]2[C@@H](CCc3ccc4cc(Br)c(NC5CC5)nc4c3)C[C@@H](n3ccc4c(Cl)ncnc43)[C@@H]2O1] | a) Intermediate 38<br>b) Intermediate 311 |
| 315 | 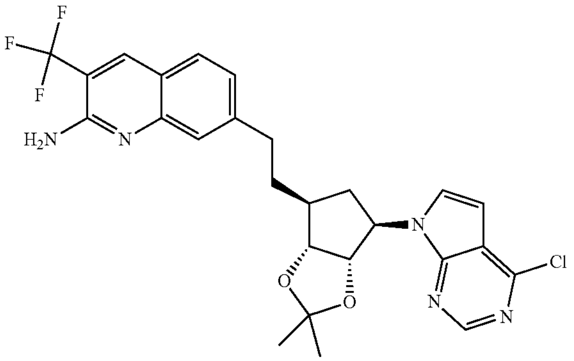 [SMILES: CC1(C)O[C@@H]2[C@@H](CCc3ccc4cc(C(F)(F)F)c(N)nc4c3)C[C@@H](n3ccc4c(Cl)ncnc43)[C@@H]2O1] | a) Intermediate 38<br>b) Intermediate 314 |
| 318 | 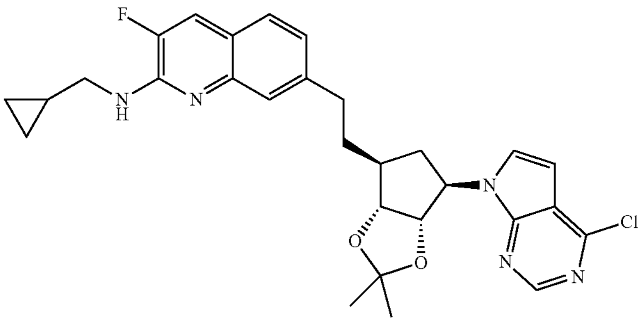 [SMILES: CC1(C)O[C@@H]2[C@@H](CCc3ccc4cc(F)c(NCC5CC5)nc4c3)C[C@@H](n3ccc4c(Cl)ncnc43)[C@@H]2O1] | a) Intermediate 38<br>b) Intermediate 317 |

TABLE 29-continued
| Int. | Structure | Starting materials |
|---|---|---|
| 321 | 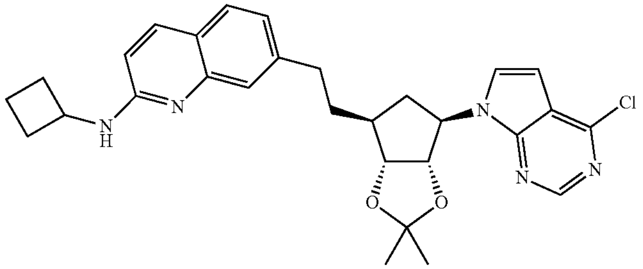 [SMILES: CC1(C)O[C@@H]2[C@@H](CCc3ccc4ccc(NC5CCC5)nc4c3)C[C@@H](n3ccc4c(Cl)ncnc43)[C@@H]2O1] | a) Intermediate 38<br>b) Intermediate 320 |
| 324 | 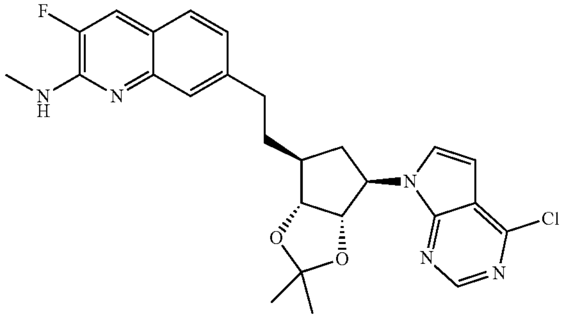 [SMILES: CNc1nc2cc(CC[C@H]3C[C@@H](n4ccc5c(Cl)ncnc54)[C@@H]4OC(C)(C)O[C@H]34)ccc2cc1F] | a) Intermediate 38<br>b) Intermediate 323 |
| 327 | 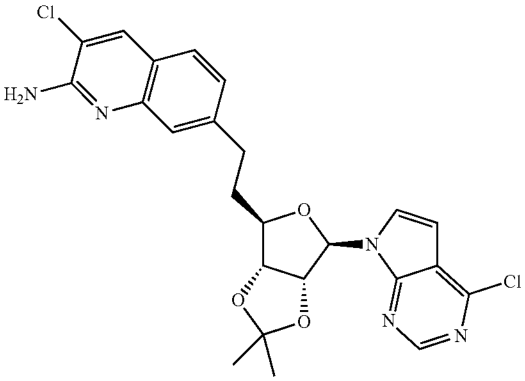 [SMILES: CC1(C)O[C@@H]2[C@H](O1)[C@@H](CCc1ccc3cc(Cl)c(N)nc3c1)O[C@H]2n1ccc2c(Cl)ncnc21] | a) Intermediate 39<br>b) Intermediate 326 |
| 330 | 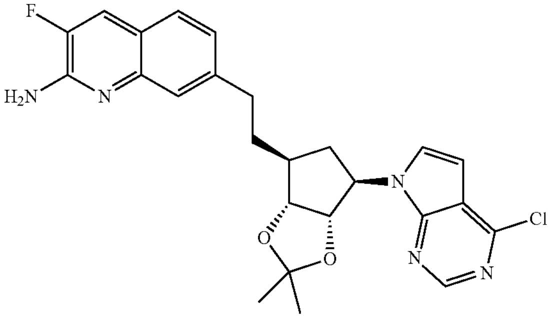 [SMILES: CC1(C)O[C@@H]2[C@@H](CCc3ccc4cc(F)c(N)nc4c3)C[C@@H](n3ccc4c(Cl)ncnc43)[C@@H]2O1] | a) Intermediate 38<br>b) Intermediate 329 |

TABLE 29-continued
| Int. | Structure | Starting materials |
| --- | --- | --- |
| 336 | 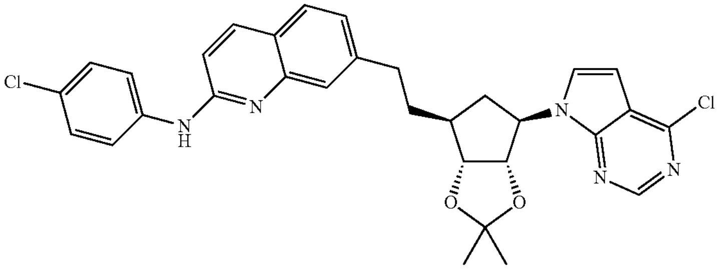 [SMILES: CC1(C)O[C@@H]2[C@@H](CCc3ccc4ccc(Nc5ccc(Cl)cc5)nc4c3)C[C@@H](n3ccc4c(Cl)ncnc43)[C@@H]2O1] | a) Intermediate 38<br>b) Intermediate 335 |
| 473 | 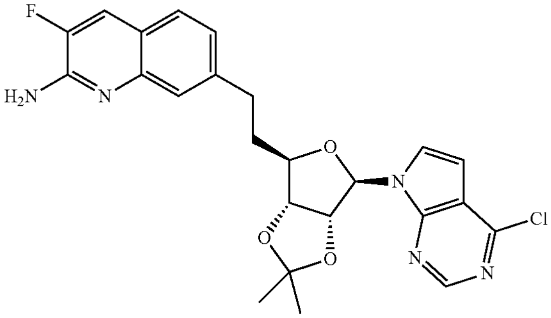 [SMILES: CC1(C)O[C@@H]2[C@H](O1)[C@@H](CCc1ccc3cc(F)c(N)nc3c1)O[C@H]2n1ccc2c(Cl)ncnc21] | a) Intermediate 39<br>b) Intermediate 329 |
Preparation of Intermediate 160
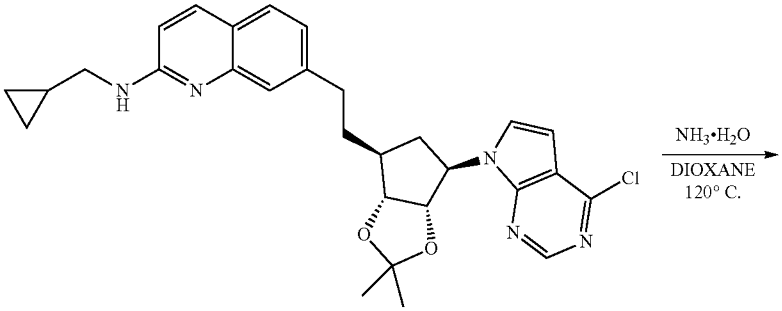
intermediate 159
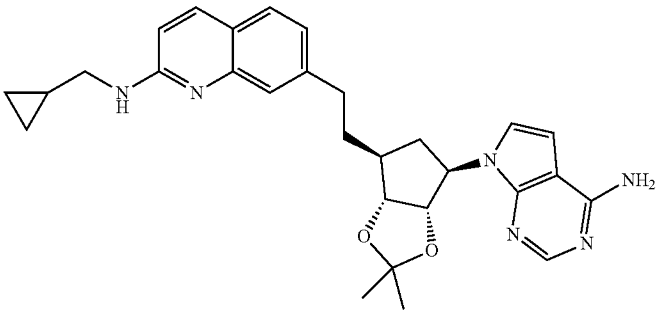
intermediate 160

Reaction performed in a sealed tube. Intermediate 159 (3.1 g, ≈5.1 mmol) was added to $NH_3 \cdot H_2O$ (30 mL) and dioxane (30 mL) and was stirred at 120° C. overnight. The mixture was concentrated in vacuo to give crude intermediate 160. This residue was purified by silica gel chromatography (ethylacetate 100% to ethyl acetate/MeOH 90/10) to give intermediate 160 (3.95 g, yield: 77%).

Example A46

Preparation of Intermediate 161

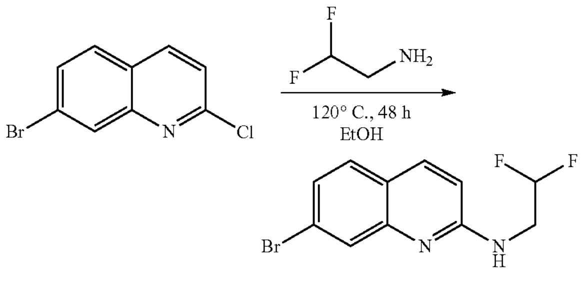

intermediate 161

7-Bromo-2-chloro-quinoline (1.5 g, 6.18 mmol) and 2,2-difluoroethylamine (0.552 g, 6.804 mmol) in EtOH (30 mL) were heated in a sealed tube at 120° C. overnight. The mixture was evaporated under vacuo to give intermediate 161 (1.8 g, yield: 88.1%) as a brown solid which used for next step without further purification.

Preparation of Intermediate 162

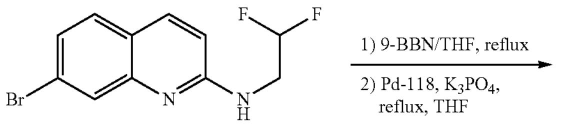

intermediate 161

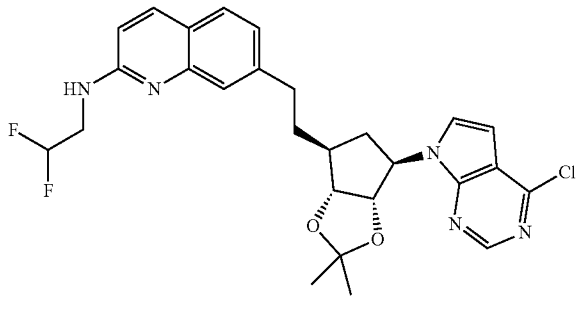

intermediate 162

Intermediate 38 (500 mg, 1.56 mmol) in 9-BBN (0.5M in THF, 15.6 mL, 7.8 mmol) was refluxed for 1 h under $N_2$. The mixture was cooled to room temperature, then $K_3PO_4$ (995.6 mg, 4.7 mmol) in $H_2O$ (2 mL) was added, followed by THF (20 mL), intermediate 161 (538.7 mg, ≈1.88 mmol) and Pd-118 (20.4 mg, 0.031 mmol). The resulting mixture was refluxed overnight. The mixture was diluted with $H_2O$ (60 mL), extracted with ethyl acetate (100 mL×2), the combined organic phases were dried by $Na_2SO_4$, then filtered and concentrated in vacuo to give the crude product. The crude product was purified by chromatography (ethyl acetate: petroleum ether ratio 1:10 to 1:5) to give intermediate 162 (650 mg, yield: 68.1%) as yellow oil.

Preparation of Intermediate 163

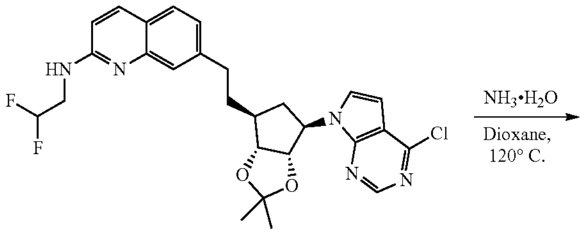

intermediate 162

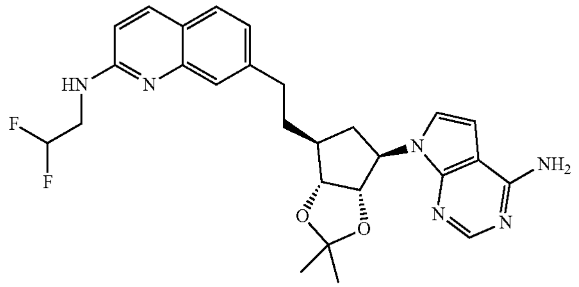

intermediate 163

Reaction performed in a sealed tube. Intermediate 162 (650 mg, ≈1.06 mmol) was added to $NH_3 \cdot H_2O$ (15 mL) and dioxane (10 mL) and was stirred at 120° C. overnight. The mixture was concentrated in vacuo to give intermediate 163 (680 mg, yield: 97.9%).

Example A47

Preparation of Intermediate 164

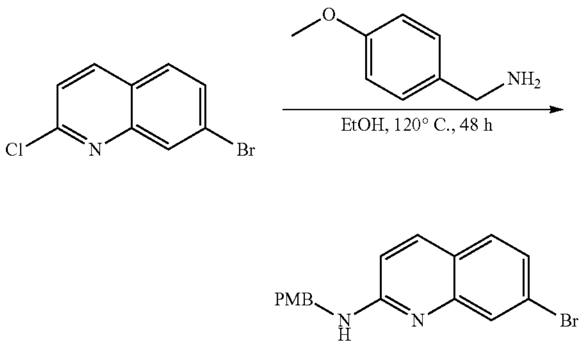

intermediate 164

A mixture of 7-bromo-2-chloroquinoline (10 g, 41.24 mmol) and 4-methoxybenzylamine (11.3 g, 82.5 mmol) in ethanol (40 ml) was heated in a sealed tube at 120° C. for 72 h. The mixture was evaporated under reduced pressure and purified by chromatography column (gradient eluent: $CH_2Cl_2$/petroleum ether from 1/10 to 1/0) to afford the desired product intermediate 164 (13 g, 82% yield) as a white solid.

Preparation of Intermediate 165

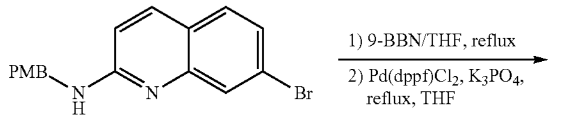

intermediate 164

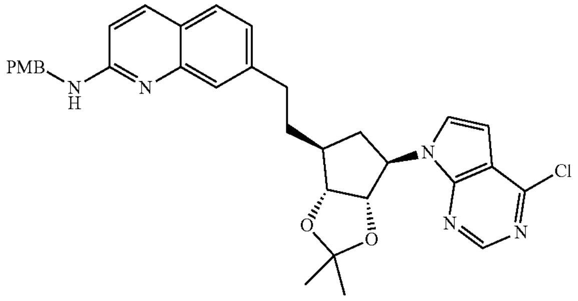

intermediate 165

A mixture of intermediate 38 (2 g, 5.0 mmol) in 9-BBN (50.0 ml, 25.0 mmol, 0.5M in THF) was refluxed for 1 h under $N_2$. The mixture was cooled to room temperature, then $K_3PO_4$ (3.18 mg, 15.0 mmol) in $H_2O$ (10 mL) was added, followed by THF (20 ml), intermediate 164 (2.58 mg, ≈7.50 mmol) and [1,1'-bis(diphenylphosphino)ferrocene]dichloropalladium(II) (163.0 mg, 0.25 mmol). The resulting mixture was refluxed for 3 h. The mixture was concentrated. The residue was dissolved in ethyl acetate (40 ml), washed with water (6 ml), brine (6 ml). The organic phase was dried over $Na_2SO_4$, filtered and concentrated to obtain the crude product. This was purified by chromatography column (gradient eluent: ethyl acetate/petroleum ether from 1/10 to 1/1). The desired fractions were collected and concentrated to give product intermediate 165 as a solid (2 g, 52.4% yield).

Below intermediates were prepared by an analogous reaction protocol as was used for the preparation of intermediate 165 using the appropriate starting materials (Table 30).

TABLE 30

| Int. | Structure | Starting materials |
|---|---|---|
| 237 | 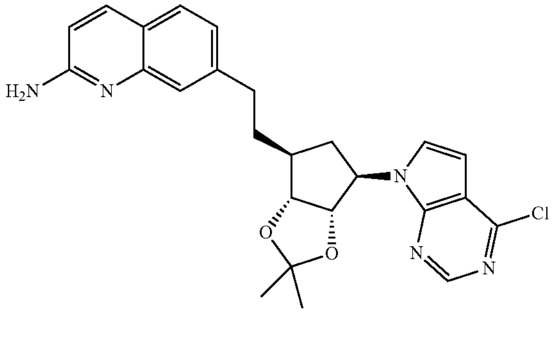 [SMILES: CC1(C)O[C@@H]2[C@@H](CCc3ccc4ccc(N)nc4c3)C[C@@H](n3ccc4c(Cl)ncnc43)[C@@H]2O1] | a) Intermediate 38<br>b) 2-amino-7-bromoquinoline |
| 238 | 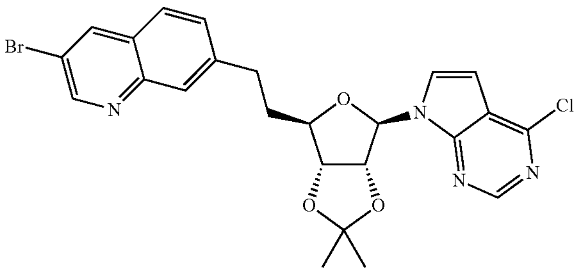 [SMILES: CC1(C)O[C@@H]2[C@H](O1)[C@@H](CCc1ccc3cc(Br)cnc3c1)O[C@H]2n1ccc2c(Cl)ncnc21] | a) Intermediate 39<br>b) 3-bromo-7-iodoquinoline |
| 260 | 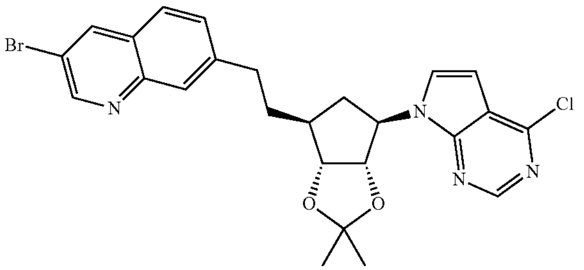 [SMILES: CC1(C)O[C@@H]2[C@@H](CCc3ccc4cc(Br)cnc4c3)C[C@@H](n3ccc4c(Cl)ncnc43)[C@@H]2O1] | a) Intermediate 38<br>b) 3-bromo-7-iodoquinoline |

TABLE 30-continued
| Int. | Structure | Starting materials |
|---|---|---|
| 482 | 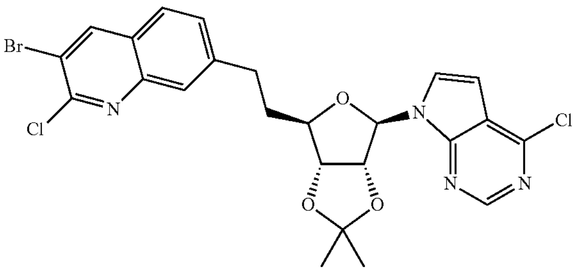 [SMILES: CC1(C)O[C@@H]2[C@H](O1)[C@@H](CCc1ccc3cc(Br)c(Cl)nc3c1)O[C@H]2n1ccc2c(Cl)ncnc21] | a) Intermediate 39<br>b) intermediate 175 |
| 488 | 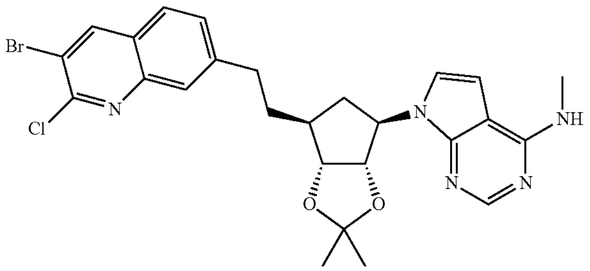 [SMILES: CNc1ncnc2c1ccn2[C@@H]1C[C@H](CCc2ccc3cc(Br)c(Cl)nc3c2)[C@H]2OC(C)(C)O[C@H]21] | a) Intermediate 487<br>b) intermediate 175 |
| 491 | 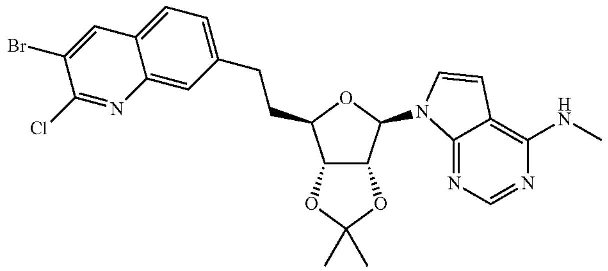 [SMILES: CNc1ncnc2c1ccn2[C@@H]1O[C@H](CCc2ccc3cc(Br)c(Cl)nc3c2)[C@H]2OC(C)(C)O[C@H]21] | a) Intermediate 490<br>b) intermediate 175 |
| 514 | 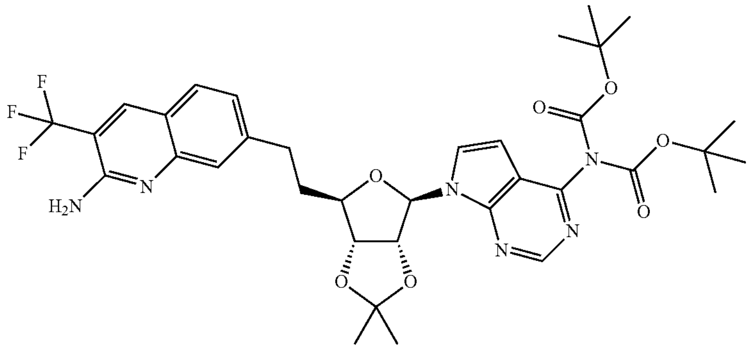 [SMILES: CC(C)(C)OC(=O)N(C(=O)OC(C)(C)C)c1ncnc2c1ccn2[C@@H]1O[C@H](CCc2ccc3cc(C(F)(F)F)c(N)nc3c2)[C@H]2OC(C)(C)O[C@H]21] | a) Intermediate 513<br>b) intermediate 314 |
Preparation of Intermediate 166
-continued
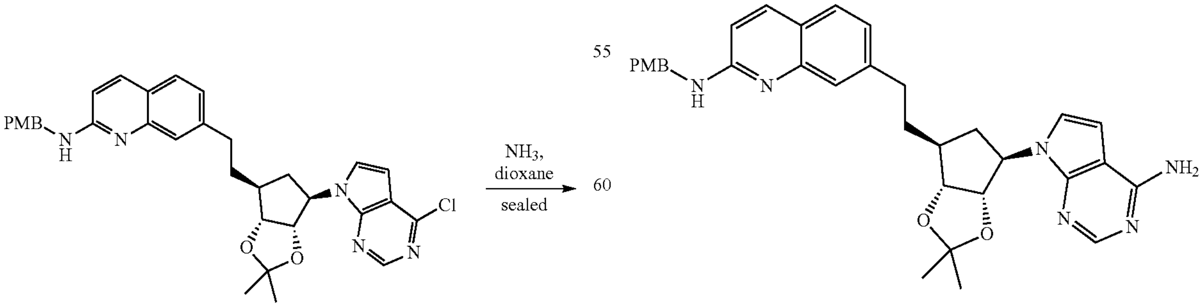
intermediate 165
intermediate 166

A mixture of intermediate 165 (500 mg, ≈0.655 mmol) and $NH_3{\cdot}H_2O$ (10 ml) in dioxane (10 ml) was heated in a sealed tube at 120° C. for 14 h. This reaction was evaporated under vacuo to obtain intermediate 166 (400 mg, 93.5% yield) as an oil.

Preparation of Intermediate 167

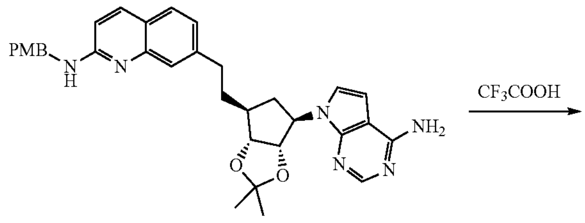

intermediate 166

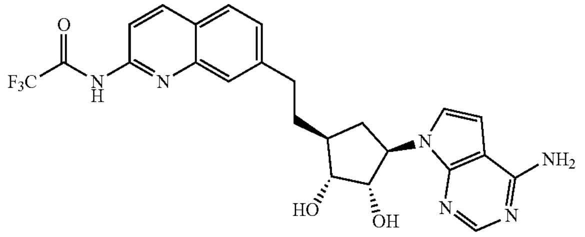

intermediate 167

The mixture of intermediate 166 (340 mg, ≈0.52 mmol) in $CF_3COOH$ (5 ml) was stirred at 60° C. for 1 h. The mixture was evaporated under vacuo to obtain intermediate 167 as a crude product (300 mg, 85.9% yield).

Example A48

Preparation of Intermediate 168

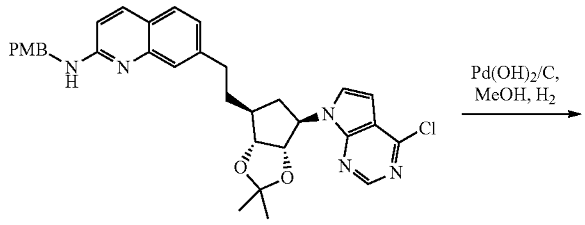

intermediate 165

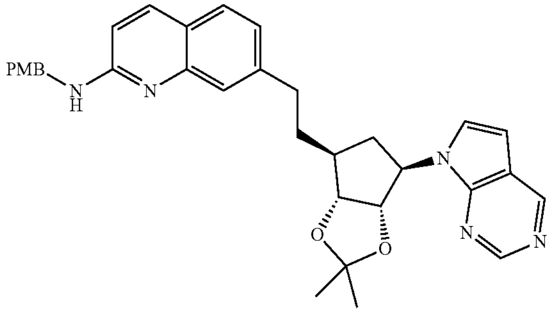

intermediate 168

Intermediate 165 (300 mg, ≈0.39 mmol) was dissolved in EtOH (20 ml) and ethyl acetate (4 ml) and hydrogenated under 1 atm of $H_2$ over $Pd(OH)_2/C$ (30 mg) for 7 hours. The mixture was filtered and evaporated under vacuo to obtain intermediate 168 as a crude product (200 mg, 70.6% yield).

Preparation of Intermediate 169

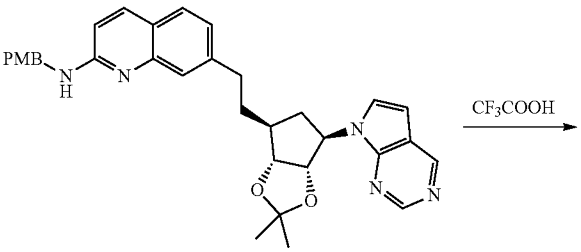

intermediate 168

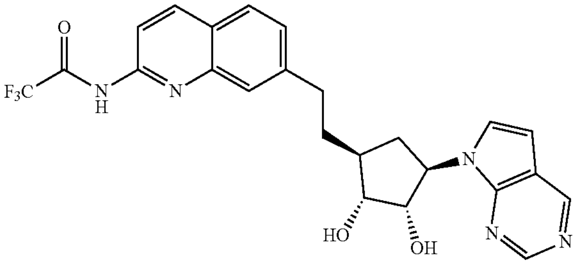

intermediate 169

The mixture of intermediate 168 (200 mg, ≈0.278 mmol) in $CF_3COOH$ (5 ml) was stirred at 60° C. for 1 h. The mixture was evaporated under vacuo to obtain intermediate 169 as a crude product (120 mg, 89.0% yield).

Example A49

Preparation of Intermediate 170

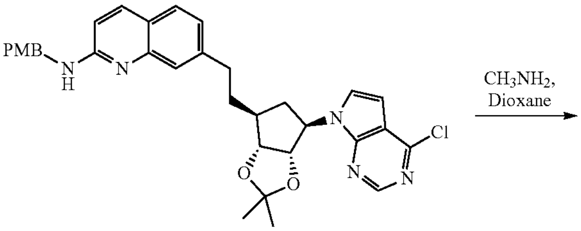

intermediate 165

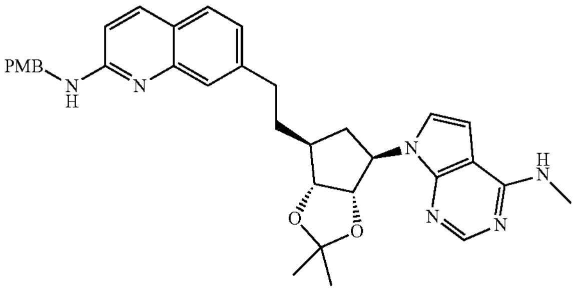

intermediate 170

A mixture of intermediate 165 (310 mg, ≈0.406 mmol) and $CH_3NH_2/H_2O$ (5 ml) in dioxane (5 ml) was stirred in a sealed tube at 120° C. for 14 h. This mixture was evaporated under vacuo to obtain intermediate 170 (200 mg, 80.1% yield) as a crude product.

Preparation of Intermediate 171

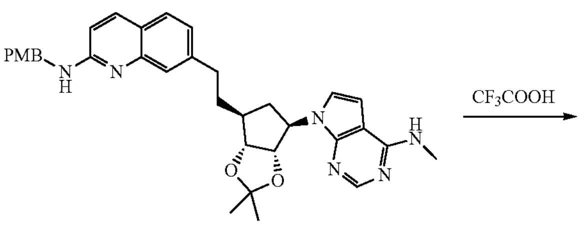

intermediate 170

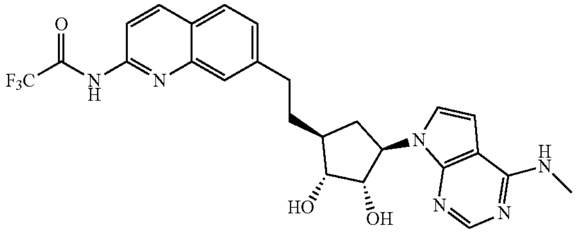

intermediate 171

The mixture of intermediate 170 (200 mg, ≈0.325 mmol) in $CF_3COOH$ (5 ml) was stirred at 50° C. for 1 h. The mixture was evaporated under vacuo to obtain intermediate 171 (160 mg, 84.0% yield) as a crude product.

Example A50

Preparation of Intermediate 172

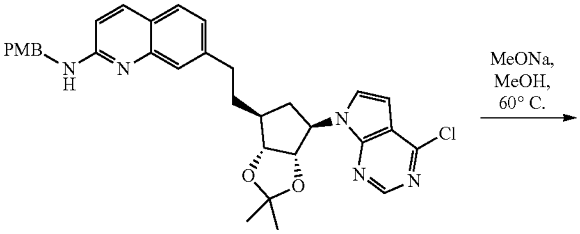

intermediate 165

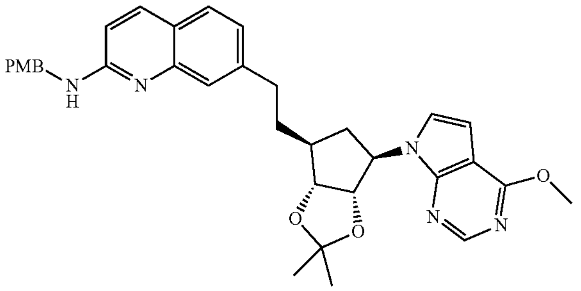

intermediate 172

A mixture of intermediate 165 (300 mg, 0.393 mmol) and sodium methoxide (63.7 mg, 1.18 mmol) in methanol (10 ml) was refluxed at 60° C. for 12 h. The mixture was evaporated under vacuo to give a crude product. Water (10 ml) was added, the mixture was extracted with ethyl acetate (10 ml×2), the organic layers were combined and evaporated under vacuo to obtain intermediate 172 (200 mg, 71.8% yield) as a crude product.

Preparation of Intermediate 173

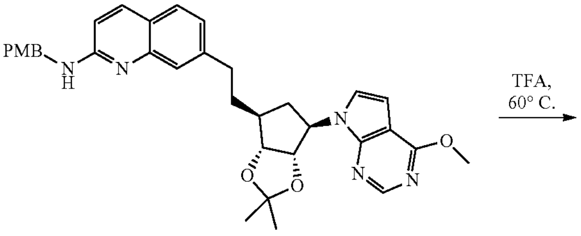

intermediate 172

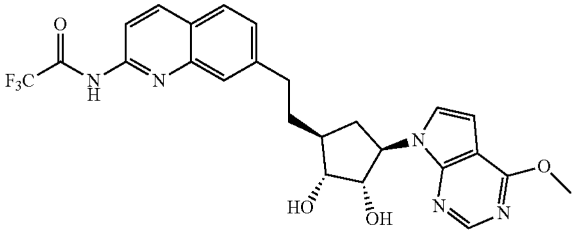

intermediate 173

The mixture of intermediate 172 (200 mg, ≈0.282 mmol) in TFA (5 ml) was stirred at 60° C. for 1 h. The mixture was evaporated under vacuo to obtain intermediate 173 (250 mg, 85.3% yield,) as the crude product.

Example A51

Preparation of Intermediate 174

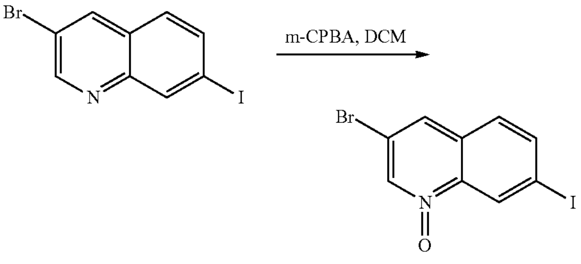

intermediate 174

3-Bromo-7-iodo-quinoline (5.99 g, 17.7 mmol) was dissolved in dichloromethane (60 mL), then m-CPBA (4.57 g, 26.5 mmol) was added in portions. The mixture was stirred at room temperature for 4 days. The mixture was quenched by a saturated $Na_2S_2O_3$ aqueous solution (40 mL) and a saturated $NaHCO_3$ aqueous solution (PH to 6-7), then extracted by dichloromethane (50 mL×3). The organic phase was washed with $H_2O$ (50 mL), dried with anhydrous $Na_2SO_4$ and evaporated under reduced pressure. The residue was purified by silica gel column (eluent: petroleum ether/ethyl acetate=10/1 to 1/1) to afford the desired product intermediate 174 (1.9 g, 14.1% yield) as a yellow solid.

Preparation of Intermediate 175

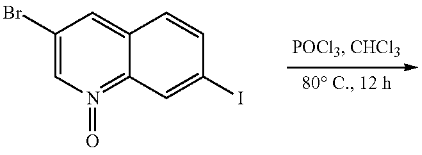

intermediate 174

-continued

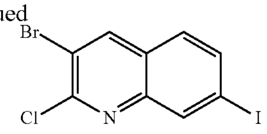

intermediate 175

To a solution of intermediate 174 (2.9 g, 8.29 mmol) in chloroform (60 mL) was added phosphoryl trichloride (8.3 g, 54.1 mmol). The mixture was stirred at 80° C. for 12 h. The mixture was evaporated under reduced pressure to obtain crude product. The crude product was purified by chromatography column (eluent: petroleum ether/ethyl acetate=10/1 to 1/1). The desired fractions were collected and concentrated to give product intermediate 175 (1.3 g, 41.5% yield) as a white solid.

Preparation of Intermediate 176

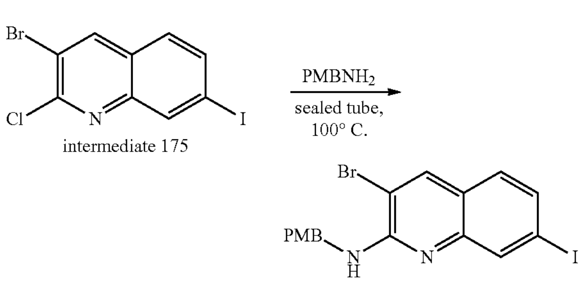

intermediate 175 intermediate 176

4-methoxybenzylamine (1.34 g, 9.78 mmol) was added into the mixture of intermediate 175 (0.8 g, 1.95 mmol) in ethanol (10 ml). The mixture was heated in a sealed tube at 100° C. for 12 h. The mixture was evaporated under vacuo to obtain the crude product. This was purified by chromatography column (gradient eluent: ethyl acetate/petroleum ether from 0/1 to 1/10). The desired fractions were collected and concentrated to give product intermediate 176 (600 mg, 51.6% yield) as an oil.

Preparation of Intermediate 177

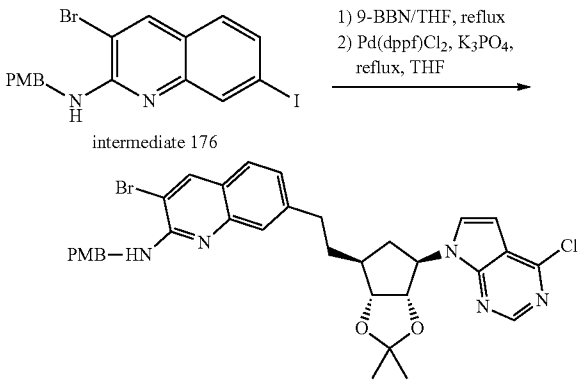

intermediate 176 intermediate 177

A mixture of intermediate 38 (44 mg, 0.138 mmol) in 9-BBN (1.3 ml, 0.69 mmol, 0.5M in THF) was refluxed for 1 h under $N_2$. The mixture was cooled to room temperature, then $K_3PO_4$ (87 mg, 0.413 mmol) in $H_2O$ (1 mL) was added, followed by THF (5 ml), intermediate 176 (122.727 mg, ≈0.206 mmol) and [1,1'-bis(diphenylphosphino)ferrocene] dichloropalladium(II) (4.48 mg, 0.007 mmol). The reaction mixture was refluxed for 3 hours. The mixture was concentrated. The residue was dissolved in ethyl acetate (40 ml), washed with water (6 ml), brine (6 ml). The organic phase was dried over $Na_2SO_4$, filtered and concentrated to give crude intermediate 177 fraction 1 (120 mg, 71.5% yield).

A mixture of intermediate 38 (233.7 mg, 0.73 mmol) in 9-BBN (7.31 ml, 3.65 mmol, 0.5M in THF) was refluxed for 1 h under $N_2$. The mixture was cooled to room temperature, then $K_3PO_4$ (87 mg, 0.413 mmol) in $H_2O$ (1 mL) was added, followed by THF (5 ml), intermediate 176 (478 mg, ≈0.80 mmol) and [1,1'-bis(diphenylphosphino)ferrocene]dichloropalladium(II) (23.8 mg, 0.037 mmol). The reaction mixture was refluxed for 3 hours. The mixture was concentrated. The residue was dissolved in ethyl acetate (40 ml), washed with water (6 ml), brine (6 ml). The organic phase was dried over $Na_2SO_4$, filtered and concentrated to with crude intermediate 177 fraction 2 (600 mg, 63.1% yield).

The two fractions were combined and purified by chromatography column (gradient eluent: ethyl acetate/petroleum ether from 1/10 to 1/1). The desired fractions were collected and concentrated to give intermediate 177 (300 mg, 61.0% yield) as a solid.

Preparation of Intermediate 178

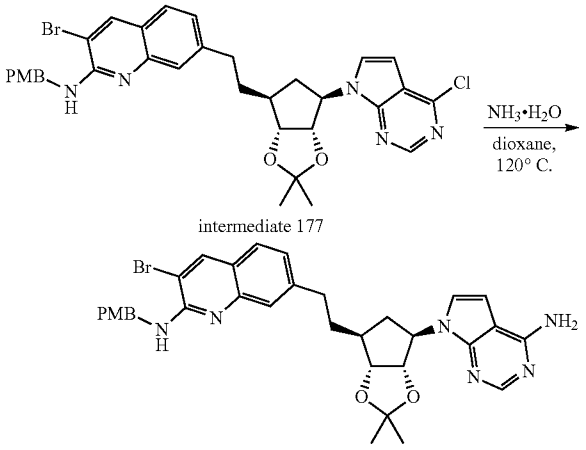

intermediate 177 intermediate 178

A mixture of intermediate 177 (300 mg, ≈0.446 mmol) and $NH_3 \cdot H_2O$ (10 ml) in dioxane (10 ml) was stirred in a sealed tube at 120° C. for 14 h. This reaction was evaporated under vacuo to obtain intermediate 178 (250 mg, 87.1% yield) as an oil.

Preparation of Intermediate 179

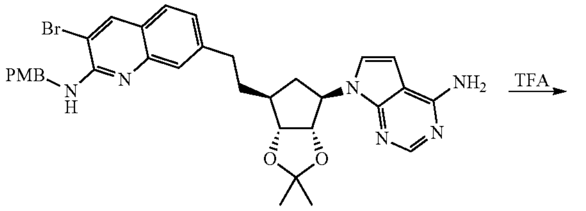

intermediate 178

-continued

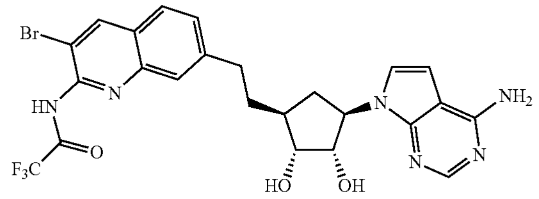

intermediate 179

The mixture of intermediate 178 (250 mg, ≈0.388 mmol) in TFA (5 ml) was stirred at 50° C. for 1 h. The mixture was evaporated under vacuo to obtain intermediate 179 (350 mg, 63.4% yield) as an oil.

Example A52

Preparation of Intermediate 180

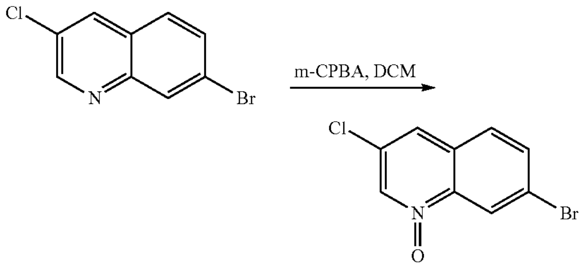

intermediate 180

3-Chloro-7-bromo-quinoline (10 g, 41.2 mmol) was dissolved in dichloromethane (150 mL). Then m-CPBA (7.83 g, 45.3 mmol) was added in portions. The mixture was stirred at 35° C. for 16 hours. The mixture was poured into a saturated $Na_2SO_3$ aqueous solution. The mixture was extracted by $CH_2Cl_2$. Then the mixture was washed by a saturated $Na_2SO_3$ aqueous solution (50 mL×2) and a saturated $NaHCO_3$ aqueous solution (50 mL×2). The organic was dried over anhydrous $Na_2SO_4$ and concentrated. The white solid was precipitated and filtered to give intermediate 180 (10 g, 78.8% yield) as a yellow solid.

Preparation of Intermediate 181

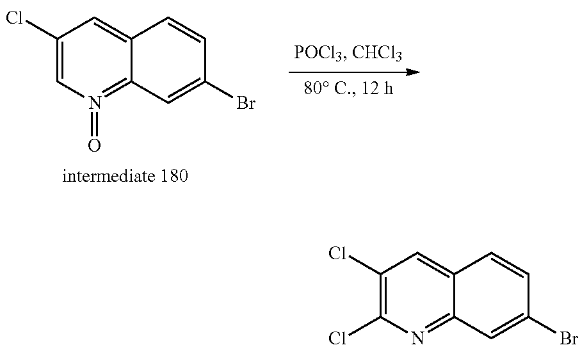

intermediate 180 intermediate 181

To a solution of intermediate 180 (6 g, 23.2 mmol) in chloroform (30 mL) was added phosphoryl trichloride (18.8 g, 122.5 mmol). The mixture was stirred at 80° C. for 1 h. The mixture was poured into water slowly. Then a saturated $NaHCO_3$ aqueous solution was added into the mixture to change the PH to approximately 7.

The mixture was extracted by $CH_2Cl_2$ (50 mL×2) and dried over anhydrous $Na_2SO_4$. The organic phase was concentrated. The crude product was purified by chromatography column (eluent: petroleum ether/ethyl acetate=1/0 to 4/1). The desired fractions were collected and concentrated to give intermediate 181 (5 g, 72.3% yield).

Preparation of Intermediate 182

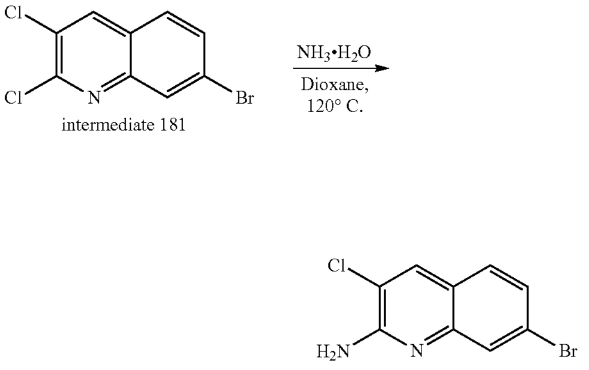

intermediate 181 intermediate 182

To $NH_3$ in $H_2O$ (10 ml) and dioxane (15 ml) was added intermediate 181 (1 g, 3.6 mmol). The mixture was heated in a sealed tube at 120° C. for 16 h. The mixture was extracted by EtOAc. The organic layer was dried by anhydrous $Na_2SO_4$ and concentrated. The residue was purified by chromatography column (gradient eluent: ethyl acetate/petrol ether from 0/1 to 1/3). The desired fractions were collected and concentrated to give product intermediate 182 (650 mg, 69.2% yield) as a pink solid.

Preparation of Intermediate 183

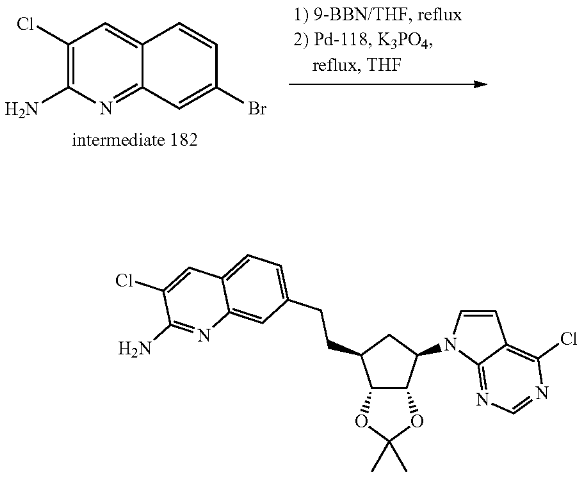

intermediate 182 intermediate 183

A mixture of intermediate 38 (100 mg, 0.313 mmol) in 9-BBN (2.19 ml, 1.09 mmol, 0.5M in THF) was refluxed for 1.5 h under $N_2$. The mixture was cooled to room temperature, then $K_3PO_4$ (199 mg, 0.938 mmol) in $H_2O$ (2 mL) was added, followed by THF (8 ml), intermediate 182 (88.6 mg, 0.344 mmol) and Pd-118 (26.48 mg, 0.407 mmol). The mixture was refluxed for 3 hours. The mixture was concentrated. The residue was dissolved in water, extracted with in ethyl acetate (20x2 ml) and washed with brine (10x2 ml). The organic phase was dried over $Na_2SO_4$, filtered and concentrated. The residue was purified by chromatography column (gradient eluent: ethyl acetate/petroleum ether from 0/1 to 1/3). The desired fractions were collected and concentrated to give intermediate 183 (100 mg, 55.4% yield).

Preparation of Intermediate 184

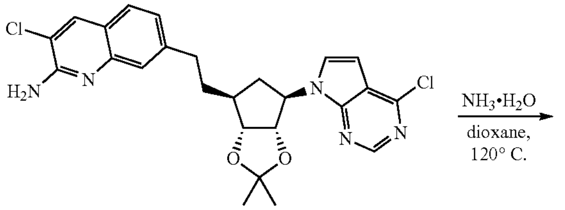

intermediate 183

-continued

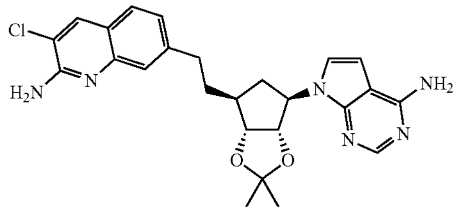

intermediate 184

A mixture of intermediate 183 (800 mg, ≈1.605 mmol) and $NH_3 \cdot H_2O$ (10 ml) in dioxane (10 ml) was heated in a sealed tube at 120° C. for 48 h. The mixture was extracted by EtOAc (30 mLx3). The organic phase was concentrated to obtain intermediate 184 (800 mg, 90% yield).

Below intermediates were prepared by an analogous reaction protocol as was used for the preparation of intermediate 184 using the appropriate starting materials (Table 31).

TABLE 31

| Int. | Structure | Starting materials |
|---|---|---|
| 239 | 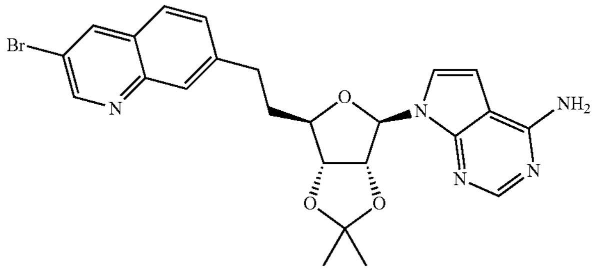 | Intermediate 238 |
| 243 | 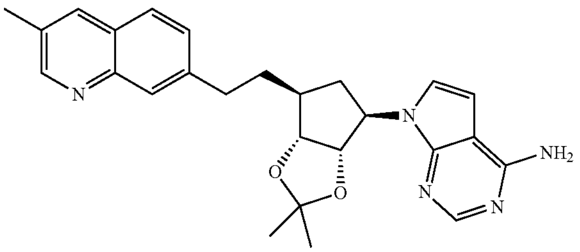 [SMILES: Cc1cnc2cc(CC[C@H]3C[C@@H](n4ccc5c(N)ncnc54)[C@@H]4OC(C)(C)O[C@H]34)ccc2c1] | Intermediate 242 |
| 250 | 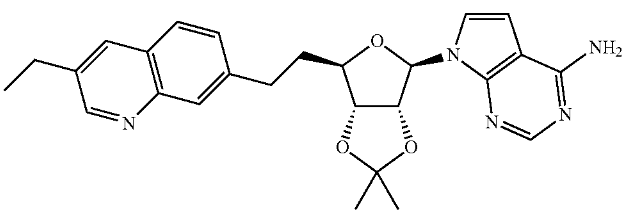 [SMILES: CCc1cnc2cc(CC[C@H]3O[C@@H](n4ccc5c(N)ncnc54)[C@@H]4OC(C)(C)O[C@@H]43)ccc2c1] | Intermediate 249 |

TABLE 31-continued
| Int. | Structure | Starting materials |
| --- | --- | --- |
| 252 | 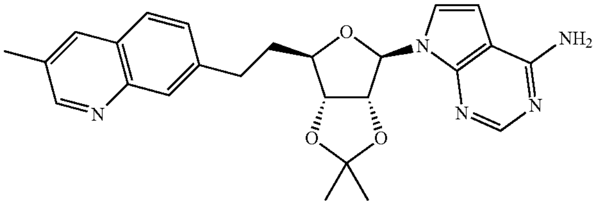 [SMILES: Cc1cnc2cc(CC[C@H]3O[C@@H](n4ccc5c(N)ncnc54)[C@@H]4OC(C)(C)O[C@@H]43)ccc2c1] | Intermediate 251 |
| 255 | 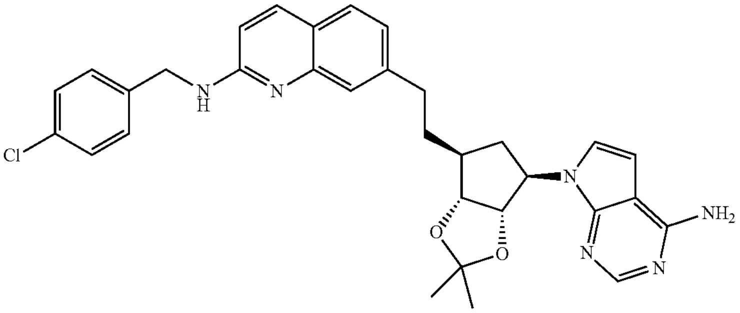 [SMILES: CC1(C)O[C@@H]2[C@@H](CCc3ccc4ccc(NCc5ccc(Cl)cc5)nc4c3)C[C@@H](n3ccc4c(N)ncnc43)[C@@H]2O1] | Intermediate 254 |
| 257 | 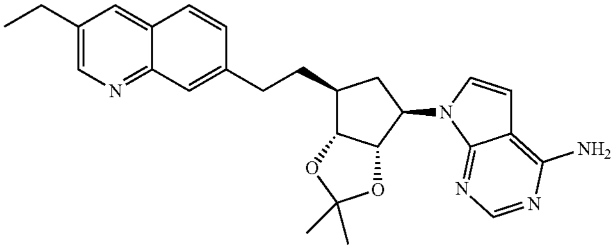 [SMILES: CCc1cnc2cc(CC[C@H]3C[C@@H](n4ccc5c(N)ncnc54)[C@@H]4OC(C)(C)O[C@H]34)ccc2c1] | Intermediate 256 |
| 258 | 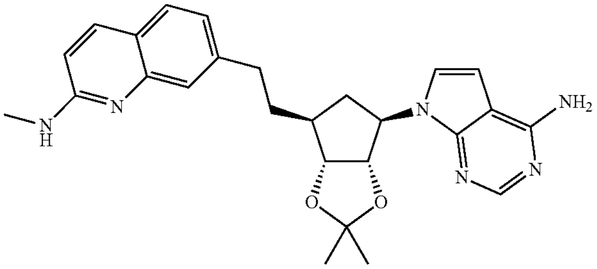 [SMILES: CNc1ccc2ccc(CC[C@H]3C[C@@H](n4ccc5c(N)ncnc54)[C@@H]4OC(C)(C)O[C@H]34)cc2n1] | Intermediate 248 |
| 261 | 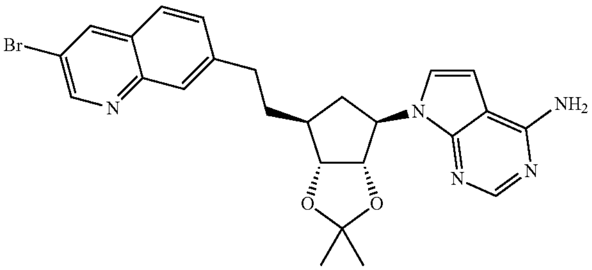 [SMILES: CC1(C)O[C@@H]2[C@@H](CCc3ccc4cc(Br)cnc4c3)C[C@@H](n3ccc4c(N)ncnc43)[C@@H]2O1] | Intermediate 260 |

TABLE 31-continued
| Int. | Structure | Starting materials |
| --- | --- | --- |
| 267 | 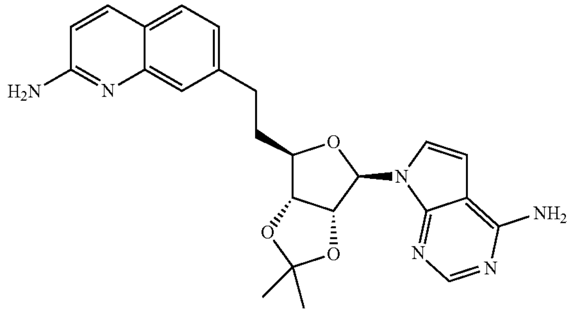 [SMILES: CC1(C)O[C@@H]2[C@H](O1)[C@@H](CCc1ccc3ccc(N)nc3c1)O[C@H]2n1ccc2c(N)ncnc21] | Intermediate 266 |
| 269 | 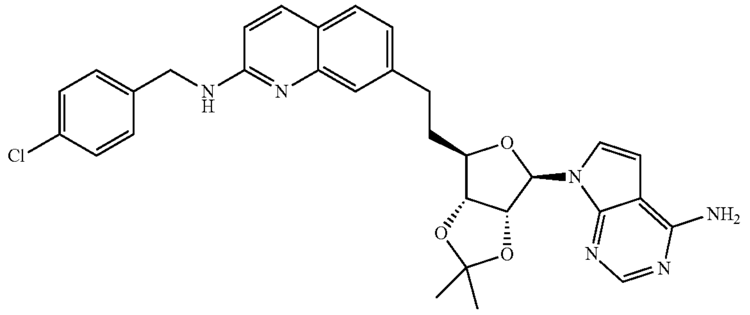 [SMILES: CC1(C)O[C@@H]2[C@H](O1)[C@@H](CCc1ccc3ccc(NCc4ccc(Cl)cc4)nc3c1)O[C@H]2n1ccc2c(N)ncnc21] | Intermediate 268 |
| 271 | 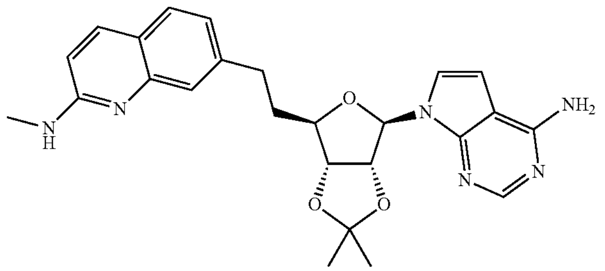 [SMILES: CNc1ccc2ccc(CC[C@H]3O[C@@H](n4ccc5c(N)ncnc54)[C@@H]4OC(C)(C)O[C@@H]43)cc2n1] | Intermediate 259 |
| 273 | 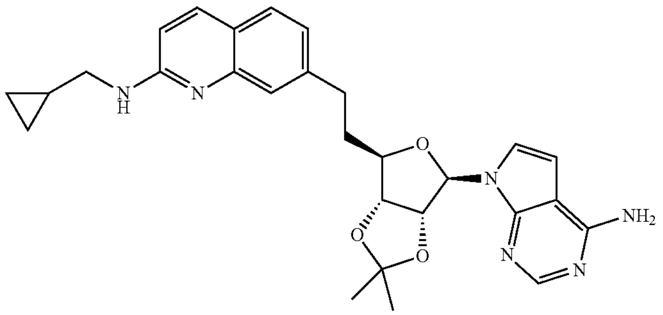 [SMILES: CC1(C)O[C@@H]2[C@H](O1)[C@@H](CCc1ccc3ccc(NCC4CC4)nc3c1)O[C@H]2n1ccc2c(N)ncnc21] | Intermediate 272 |
| 278 | 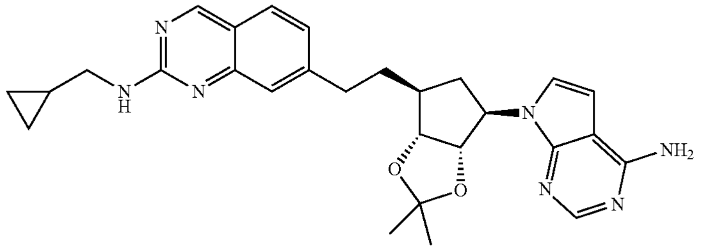 [SMILES: CC1(C)O[C@@H]2[C@@H](CCc3ccc4cnc(NCC5CC5)nc4c3)C[C@@H](n3ccc4c(N)ncnc43)[C@@H]2O1] | Intermediate 277 |

TABLE 31-continued
| Int. | Structure | Starting materials |
| --- | --- | --- |
| 289 | 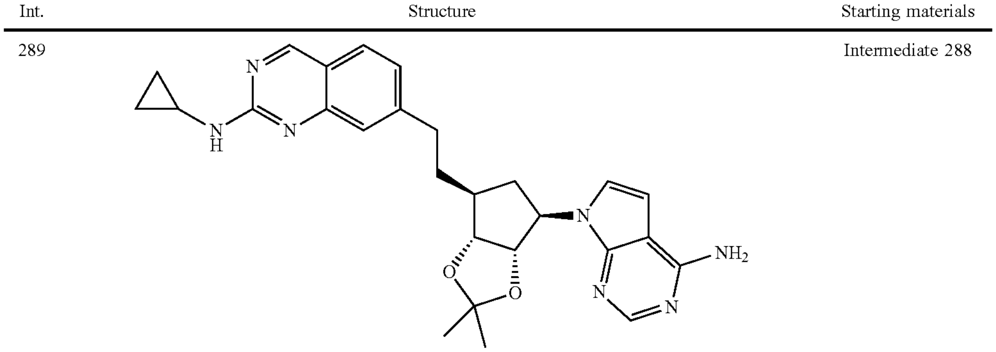 | Intermediate 288 |
| 292 | 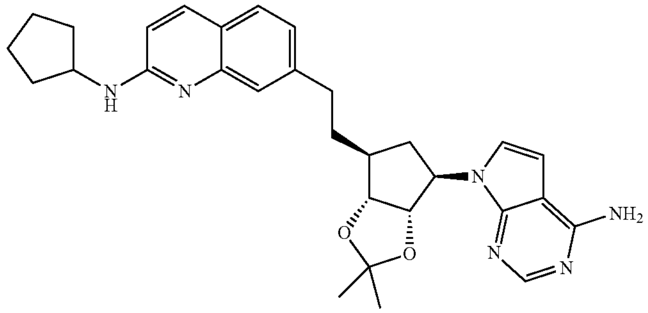 [SMILES: CC1(C)O[C@@H]2[C@@H](CCc3ccc4ccc(NC5CCCC5)nc4c3)C[C@@H](n3ccc4c(N)ncnc43)[C@@H]2O1] | Intermediate 291 |
| 295 | 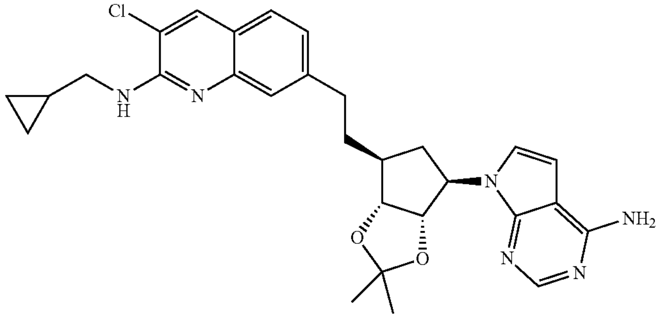 [SMILES: CC1(C)O[C@@H]2[C@@H](CCc3ccc4cc(Cl)c(NCC5CC5)nc4c3)C[C@@H](n3ccc4c(N)ncnc43)[C@@H]2O1] | Intermediate 294 |
| 298 | 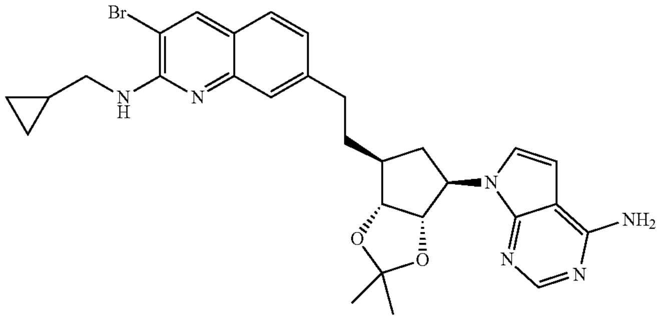 [SMILES: CC1(C)O[C@@H]2[C@@H](CCc3ccc4cc(Br)c(NCC5CC5)nc4c3)C[C@@H](n3ccc4c(N)ncnc43)[C@@H]2O1] | Intermediate 297 |
| 301 | 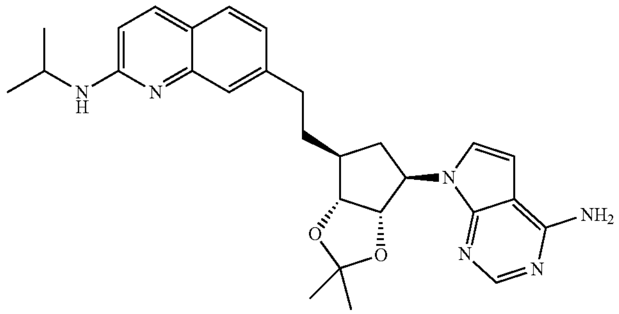 [SMILES: CC(C)Nc1ccc2ccc(CC[C@H]3C[C@@H](n4ccc5c(N)ncnc54)[C@@H]4OC(C)(C)O[C@H]34)cc2n1] | Intermediate 300 |

TABLE 31-continued
| Int. | Structure | Starting materials |
| --- | --- | --- |
| 304 | 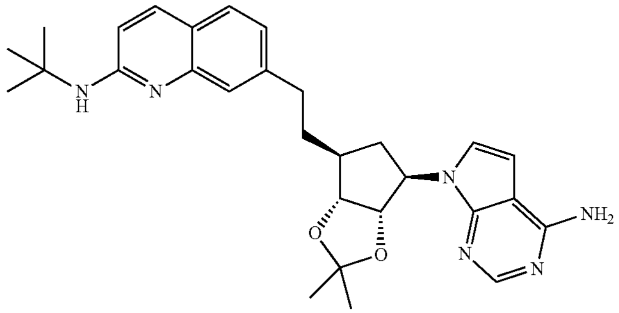 [SMILES: CC(C)(C)Nc1ccc2ccc(CC[C@H]3C[C@@H](n4ccc5c(N)ncnc54)[C@@H]4OC(C)(C)O[C@H]34)cc2n1] | Intermediate 303 |
| 307 | 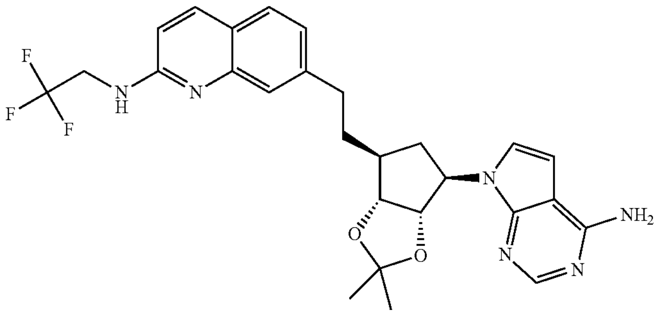 [SMILES: CC1(C)O[C@@H]2[C@@H](CCc3ccc4ccc(NCC(F)(F)F)nc4c3)C[C@@H](n3ccc4c(N)ncnc43)[C@@H]2O1] | Intermediate 306 |
| 310 | 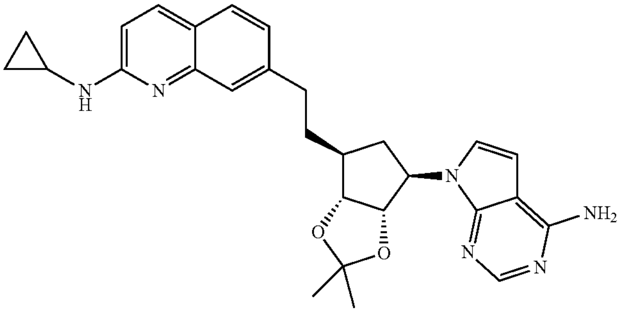 [SMILES: CC1(C)O[C@@H]2[C@@H](CCc3ccc4ccc(NC5CC5)nc4c3)C[C@@H](n3ccc4c(N)ncnc43)[C@@H]2O1] | Intermediate 309 |
| 313 | 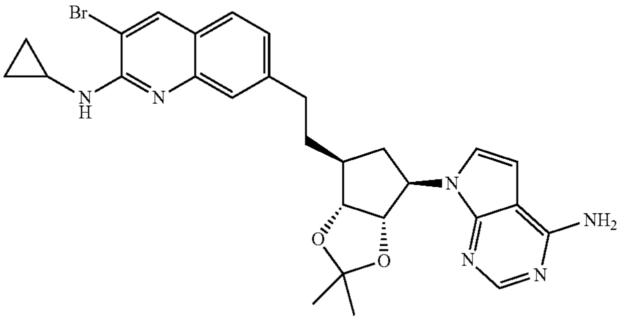 [SMILES: CC1(C)O[C@@H]2[C@@H](CCc3ccc4cc(Br)c(NC5CC5)nc4c3)C[C@@H](n3ccc4c(N)ncnc43)[C@@H]2O1] | Intermediate 312 |

TABLE 31-continued
| Int. | Structure | Starting materials |
| --- | --- | --- |
| 316 | 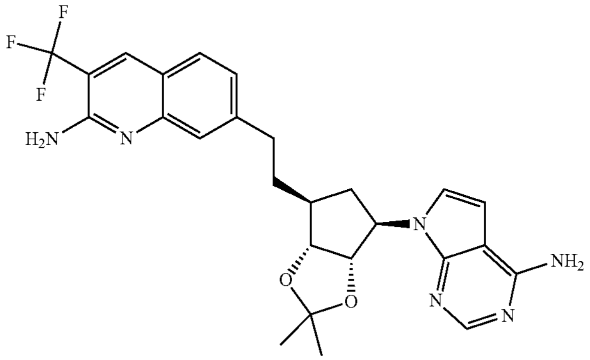 [SMILES: CC1(C)O[C@@H]2[C@@H](CCc3ccc4cc(C(F)(F)F)c(N)nc4c3)C[C@@H](n3ccc4c(N)ncnc43)[C@@H]2O1] | Intermediate 315 |
| 319 | 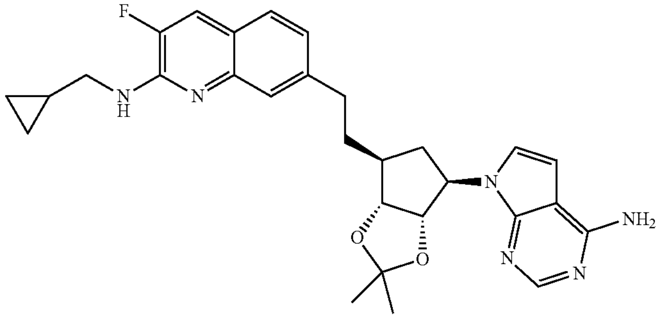 [SMILES: CC1(C)O[C@@H]2[C@@H](CCc3ccc4cc(F)c(NCC5CC5)nc4c3)C[C@@H](n3ccc4c(N)ncnc43)[C@@H]2O1] | Intermediate 318 |
| 322 | 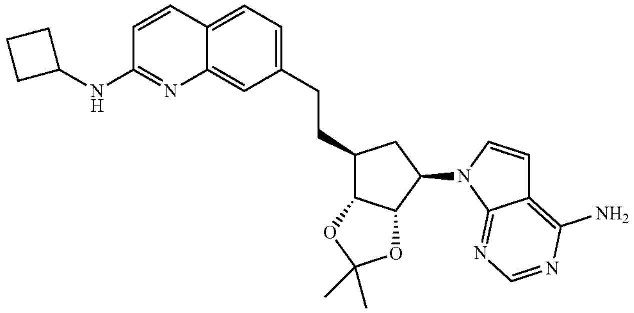 [SMILES: CC1(C)O[C@@H]2[C@@H](CCc3ccc4ccc(NC5CCC5)nc4c3)C[C@@H](n3ccc4c(N)ncnc43)[C@@H]2O1] | Intermediate 321 |
| 325 | 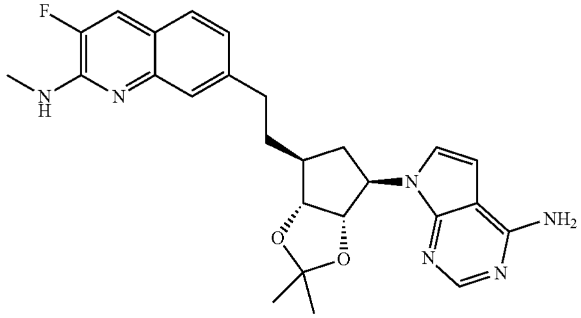 [SMILES: CNc1nc2cc(CC[C@H]3C[C@@H](n4ccc5c(N)ncnc54)[C@@H]4OC(C)(C)O[C@H]34)ccc2cc1F] | Intermediate 324 |

TABLE 31-continued
| Int. | Structure | Starting materials |
|---|---|---|
| 328 | 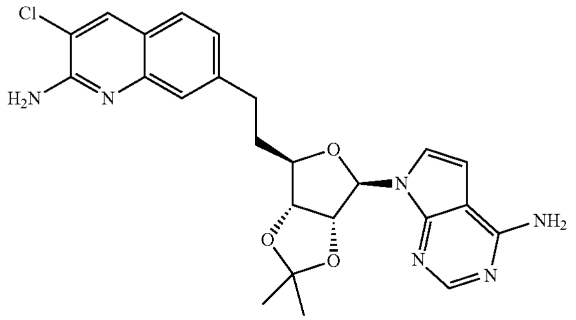 [SMILES: CC1(C)O[C@@H]2[C@H](O1)[C@@H](CCc1ccc3cc(Cl)c(N)nc3c1)O[C@H]2n1ccc2c(N)ncnc21] | Intermediate 327 |
| 331 | 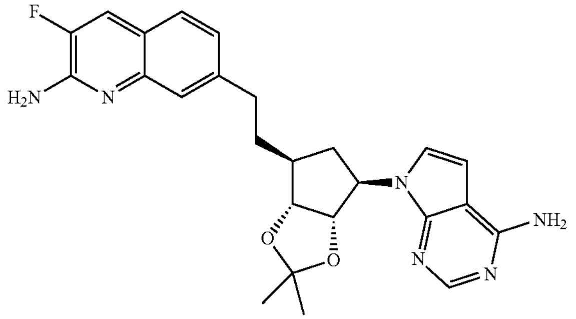 [SMILES: CC1(C)O[C@@H]2[C@@H](CCc3ccc4cc(F)c(N)nc4c3)C[C@@H](n3ccc4c(N)ncnc43)[C@@H]2O1] | Intermediate 330 |
| 337 | 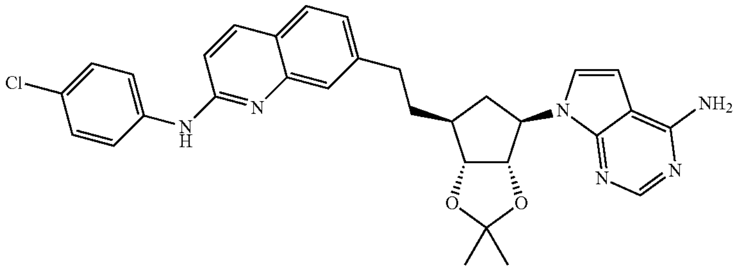 [SMILES: CC1(C)O[C@@H]2[C@@H](CCc3ccc4ccc(Nc5ccc(Cl)cc5)nc4c3)C[C@@H](n3ccc4c(N)ncnc43)[C@@H]2O1] | Intermediate 336 |
| 483 | 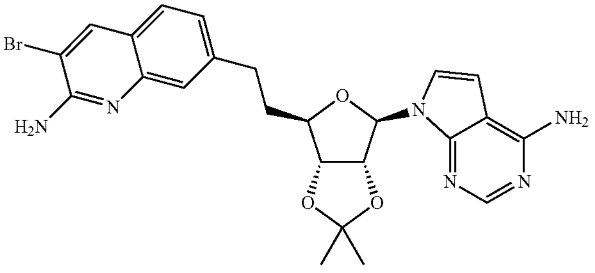 [SMILES: CC1(C)O[C@@H]2[C@H](O1)[C@@H](CCc1ccc3cc(Br)c(N)nc3c1)O[C@H]2n1ccc2c(N)ncnc21] | Intermediate 482 |

Example A57

Preparation of Intermediate 316

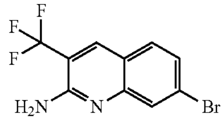

intermediate 314

+

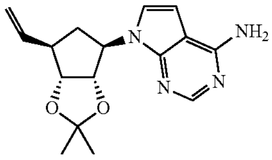

intermediate 433

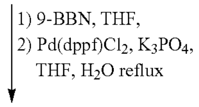

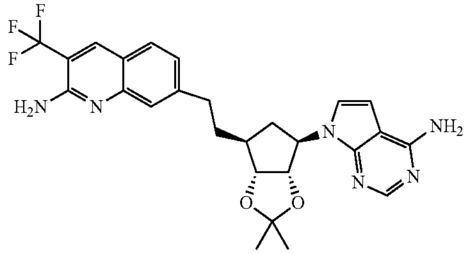

intermediate 316

Intermediate 433 (10.8 g, 35.96 mmol) was dissolved in 60 mL of THF and 9-BBN 0.5 M in THF (226.5 ml, 113.2 mmol)) was added and the reaction mixture was stirred for 2 hours. $K_3PO_4$ (38.1 g, 179.78 mmol) in 65 ml of water was added and the reaction mixture was vigorously stirred for 30 min. Intermediate 314 (10.46 g, 35. 96 mmol) and [1,1'-bis (diphenylphosphino)ferrocene]dichloropalladium(ii) were added, and the reaction mixture was degassed. The resulting mixture was stirred for 2 hours at 60° C. and allowed to cool to room temperature overnight. EtOAc was added to the reaction mixture, the organic layer was washed with water and brine, dried on $MgSO_4$ and concentrated under reduced pressure to give crude product. The residue was purified by normal phase HPLC (Stationary phase: silicagel type: 60A 25_40 μm (Merck), Mobile phase: Gradient from 95% Dichloromethane, 5% methanol to 90% Dichloromethane, 10% methanol). The desired fractions were collected and evaporated. The residue was re-purified by normal phase HPLC (Stationary phase: silicagel type 60A 25_40 um (Merck), Mobile phase: isocratic 95% Ethyl acetate and 5% ethanol yielding intermediate 316 (7.9 g, 43% yield).

Example A 99

Preparation of Intermediate 528

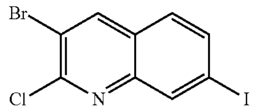

intermediate 175

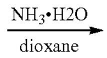

-continued

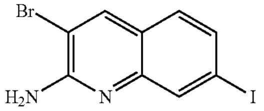

intermediate 528

Intermediate 175 (630 mg, 1.71 mmol) was dissolved in dioxane (10 ml). Then $NH_3 \cdot H_2O$ (10 ml) was added. The reaction mixture was stirred at 120° C. for 24 hours in a sealed tube. The reaction mixture was extracted with EtOAc (50 ml×3). The organic layers were combined, dried with $Na_2SO_4$, and the solvent was evaporated to give intermediate 528 (380 mg, 62% yield) as a solid.

Preparation of Intermediate 529

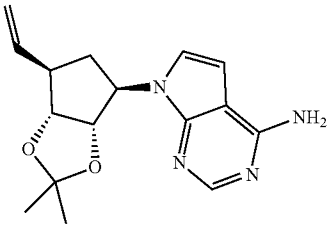

intermediate 433

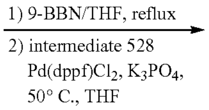

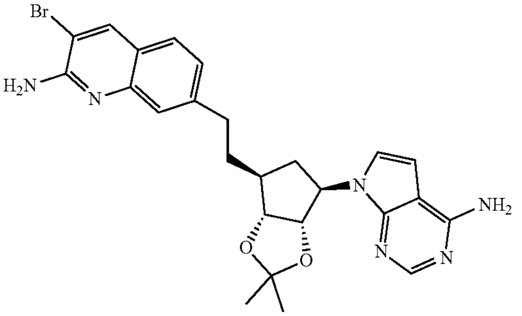

intermediate 529

A mixture of intermediate 433 (22 g, 72.7 mmol) in 9-BBN/THF (0.5M THF solution, 585 mL, 292.3 mmol) was stirred at 50° C. for 1 hour under $N_2$. The mixture was cooled to room temperature, and $K_3PO_4$ (77.6 g, 365.6 mmol) and $H_2O$ (80 mL) were added. The mixture stirred at room temperature for 0.5 hour, then THF (95 mL), intermediate 528 (22.9 g, 65.8 mmol) and $Pd(dppf)Cl_2$ (4.77 g, 7.30 mmol) were added under $N_2$. The resulting mixture was stirred at 50° C. for 3 hours. The mixture was concentrated. The residue was dissolved in ethyl acetate (120 ml). The organic layer was washed with water (10 mL) and brine (10 mL). The organic phase was dried over $Na_2SO_4$, filtered and concentrated. The residue was purified by column chromatography over silica gel (petroleum ether/ethyl acetate ratio 1/1 to petroleum ether/ethyl acetate ratio 0/1). The pure fractions were collected and the solvent was evaporated under vacuum to give 23.5 g of intermediate 529.

Example A53

Preparation of Intermediate 193

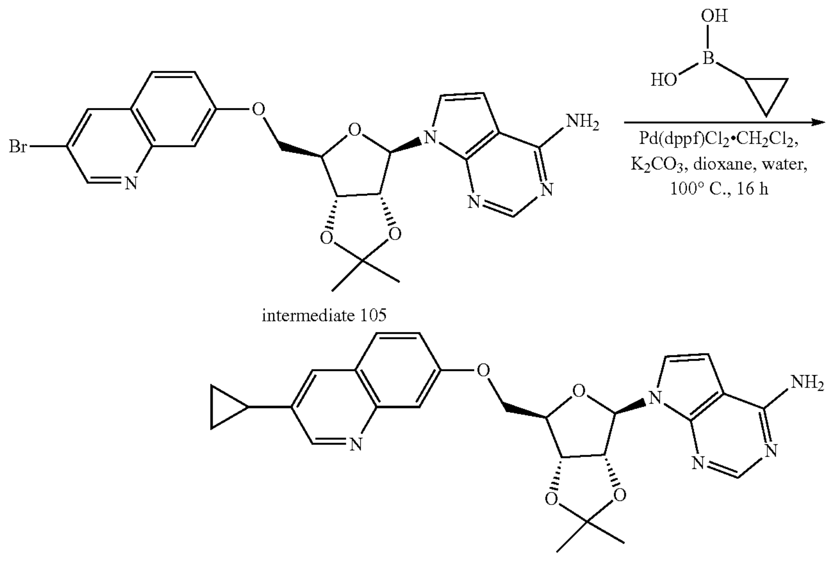

intermediate 105 intermediate 193

To a solution of intermediate 105 (256 mg, 0. 5 mmol) and cyclopropylboronic acid (107.5 mg, 1.25 mmol) in dioxane (3 ml) at r.t. was added. Pd(dppf)$Cl_2$·$CH_2Cl_2$ (41 mg, 0.05 mmol). Nitrogen was purged through reaction mixture for one minute followed by addition of $K_2CO_3$ (174 mg, 1.25 mmol) and water (0.2 ml) and again nitrogen was purged through reaction mixture for one minute. The reaction mixture was heated in a closed vessel up to 100° C. for 16 h. The reaction mixture was filtered over decalite and evaporated to dryness. The residue was purified via Prep HPLC (Stationary phase: RP XBridge Prep C18 OBD-10 μm, 50×150 mm, Mobile phase: 0.25% $NH_4HCO_3$ solution in water, $CH_3CN$ yielding intermediate 193 (110 mg, 46.5%)

Example A58

Step 1

Preparation of Intermediate 434

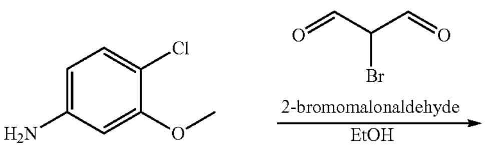

4-chloro-3-methoxyaniline

-continued

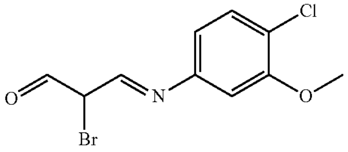

intermediate 434

2-bromomalonaldehyde (2.1 g, 13.96 mmol) was added in portions to a solution of 4-chloro-3-methoxyaniline (2.0 g, 12.69 mmol) in EtOH (100 mL) at 0° C. under $N_2$ atmosphere. After stirring at room temperature for 2 h, the mixture was concentrated to give intermediate 434 (4.0 g, 69.5% yield) which used in the next step without further purification.

Below intermediates were prepared by an analogous reaction protocol as was used for the preparation of intermediate 434 using the appropriate starting materials (Table 32).

TABLE 32

| Intermediates | Structure | Starting materials |
| --- | --- | --- |
| 435 | 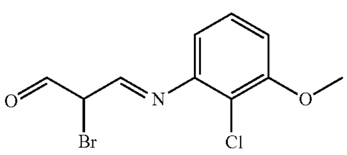 | a) 2-chloro-3-methoxyaniline<br>b) 2-bromomalonaldehyde |

TABLE 32-continued

| Intermediates | Structure | Starting materials |
| --- | --- | --- |
| 436 | 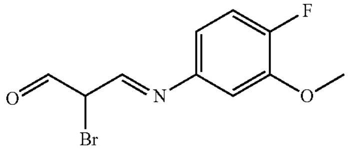 | a) 4-fluoro-3-methoxyaniline<br>b) 2-bromomalonaldehyde |

Step 2

Preparation of Intermediate 437

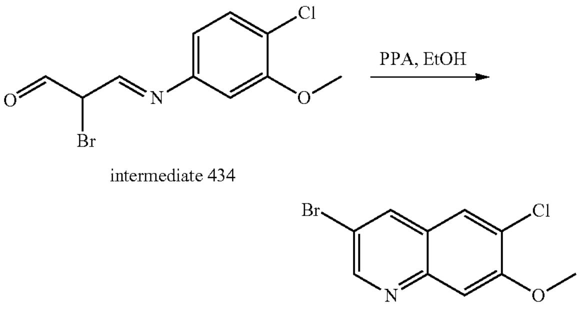

intermediate 434 intermediate 437

The reaction was executed twice.

A mixture of intermediate 434 (1.0 g, 3.44 mmol) and PPA (1.0 g) in EtOH (20 mL) was heated at 95° C. in a Microwave Tube for 1 h. The two reaction mixtures were combined and concentrated. The residue was diluted with water and extracted with $CH_2Cl_2$ (50 mL×5). The organic phase was washed with aq·$NaHCO_3$, brine, dried over $Na_2SO_4$, filtered and concentrated. The residue was purified by chromatography column (eluens: Petroleum ether/EtOAc 85/15). The desired fractions were collected and concentrated to give intermediate 437 (0.77 g, 41% yield) as a yellow solid.

Below intermediates were prepared by an analogous reaction protocol as was used for the preparation of intermediate 437 using the appropriate starting materials (Table 33).

TABLE 33

| Int. | Structure | Starting materials |
| --- | --- | --- |
| 438 | 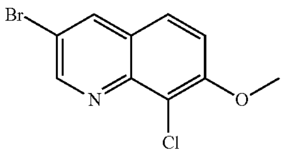 | intermediate 435 |
| 439 | 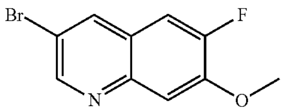 | intermediate 436 |

Step 3

Preparation of Intermediate 200

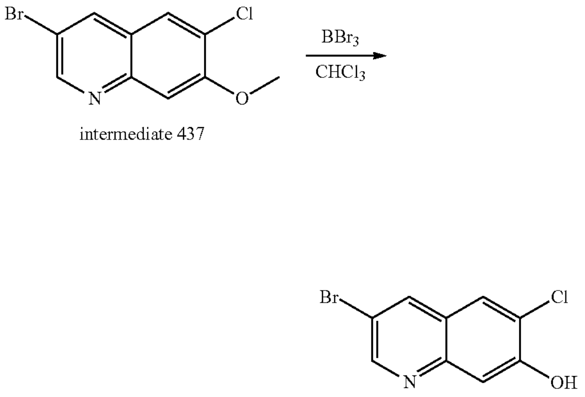

intermediate 437 intermediate 200

$BBr_3$ (1.6 mL, 16.60 mmol) was added to a solution of intermediate 437 (1.28 g, 4.70 mmol) in $CHCl_3$ (25 mL) at 0° C. The reaction mixture was refluxed for 48 hours. The reaction mixture was adjusted to pH 7 with a sat. sodium hydrogen carbonate solution. The mixture was concentrated until $CHCl_3$ was removed. The resulting mixture was filtered to give intermediate 200 (1.1 g, 91% yield) as a solid.

Below intermediates were prepared by an analogous reaction protocol as was used for the preparation of intermediate 200 using the appropriate starting materials (Table 34).

TABLE 34

| Int. | Structure | Starting materials |
| --- | --- | --- |
| 205 | 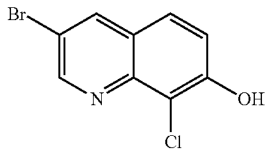 | intermediate 438 |
| 229 | 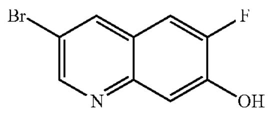 | intermediate 439 |

Example A59

Step 1

Preparation of Intermediate 440

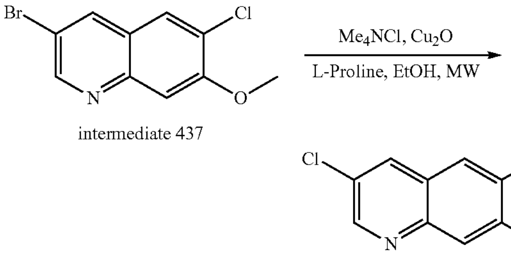

intermediate 437 intermediate 440

A mixture of intermediate 437 (720 mg, 2.64 mmol), Tetramethylammonium Chloride (2.90 g, 26.42 mmol), Copper(I) Oxide (378.0 mg, 2.64 mmol) and L-Proline (608.3 mg, 5.28 mmol) in EtOH (15 mL) was stirred at 110° C. in a microwave tube for 60 min. The mixture was filtered, and the filtrate was concentrated. The residue was purified by chromatography (eluens: Petroleum ether/EtOAc 3/1). The desired fractions were collected and concentrated to give intermediate 440 (290 mg, 48-% yield) as solid.

Step 2

Preparation of Intermediate 216

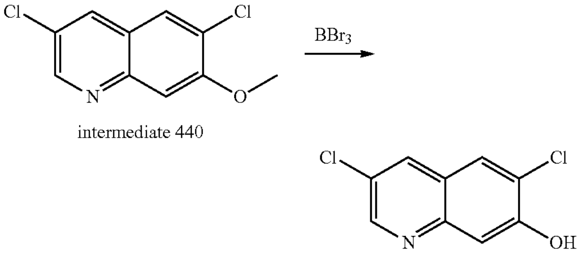

intermediate 440 intermediate 216

$BBr_3$ (2.34 mL, 24.5 mmol) was added to a solution of intermediate 440 (280 mg, 1.23 mmol) in $ClCH_2CH_2Cl$ (15 mL) at 0° C. The reaction mixture was refluxed overnight. The reaction mixture was adjusted to pH 7 with a sat. sodium hydrogen carbonate solution. The mixture was concentrated until $ClCH_2CH_2Cl$ was removed. The resulting solid was filtered to give intermediate 216 (250 mg, 87.5% yield).

Example A60

Step 1

Preparation of Intermediate 441

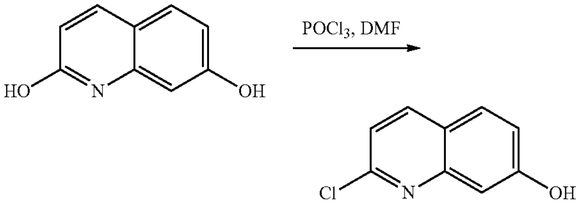

intermediate 441

The quinoline-2,7-diol (20 g, 124.1 mmol, 1.0 eq) was taken up into DMF (40 mL), $POCl_3$ (107.7 g, 702.5 mmol, 5.7 eq) was added at room temperature. The reaction mixture was stirred at 70° C. for 1 h. The solvent was removed under reduced pressure, the residue was poured slowly into water (300 mL) at 0° C. To the solution was added a saturation $Na_2CO_3$ aq. until pH=8. The mixture was extracted with ethyl acetate 1000 mL×2. The organic layer was washed with brine 1000 mL and concentrated under vacuum to afford the product intermediate 441 (20 g, 88% yield) as a solid.

Step 2

Preparation of Intermediate 442

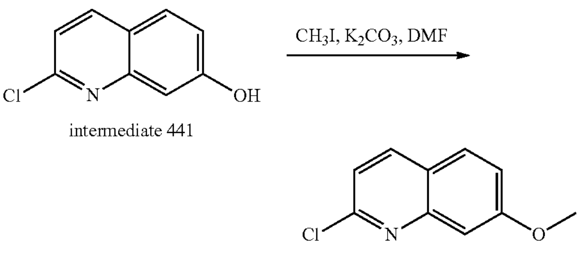

intermediate 441 intermediate 442

Intermediate 441 (2.5 g, 13.9 mmol, 1.0 eq) was dissolved in DMF (25 mL), $K_2CO_3$ (5.76 g, 41.76 mmol, 3 eq) and $CH_3I$ (5.2 g, 36.6 mmol, 2.63 eq) were added. The reaction mixture was stirred at 25° C. for 12 hr. The reaction mixture was poured into water (100 mL) and was extracted with EtOAc (150 mL). The organic layer was washed by water (80 mL×2), brine (800 mL) and dried over anhydrous $Na_2SO_4$. The solvent was removed under reduced pressure to give intermediate 442 (2.6 g, 96% yield) as a white solid.

Step 3

Preparation of Intermediate 443

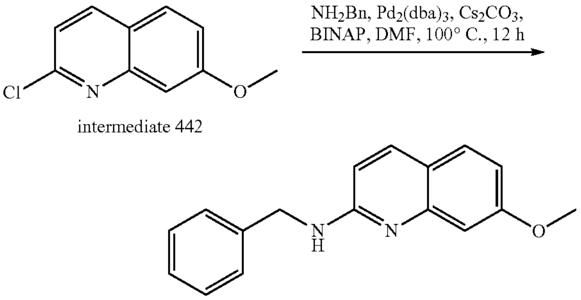

intermediate 442 intermediate 443

To a solution of intermediate 442 (900 mg, 4.5 mmol, 1.0 eq.), $NH_2Bn$ (0.578 g, 5.4 mmol, 1.2 eq) and $Cs_2CO_3$ (2.93 g, 9 mmol, 2.0 eq) in DMF (5 mL) were added $Pd_2(dba)_3$ (412 mg, 0.45 mmol, 0.1 eq) and BINAP (280 mg, 0.45 mmol, 0.1 eq). The resulted mixture was stirred at 100° C. under $N_2$ for 12 hr. The solvent was removed under reduced pressure, the residue was triturated with EtOAc (100 mL) and water (100 mL). The aqueous layer was extracted with EtOAc (100 mL). The combined organic layers were washed with brine (60 mL) and dried over anhydrous $Na_2SO_4$. The solvent was removed under reduced pressure, the residue was purified by column chromatography (eluent: EtOAc/ petroleum ether ratio 0/1 to 1/5) to afford intermediate 443 (450 mg, 37% yield) as a yellow solid.

Step 4

Preparation of Intermediate 231

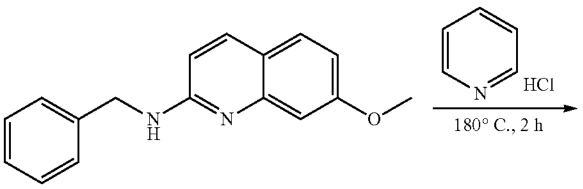

intermediate 443

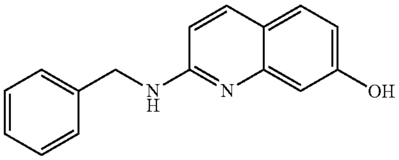

intermediate 231

Intermediate 443 (500 mg, 1.78 mmol, 1.0 eq.) and pyridine hydrochloride (3.2 g, 28 mmol, 16 eq) were placed in a tube. The reaction mixture was stirred at 180° C. for 2 hr. The reaction mixture was cooled to room temperature. The reaction mixture was dissolved in 25 ml of DCM and 25 ml of $H_2O$, and the pH was adjusted to around 8-9 by progressively adding solid $K_2CO_3$, and the layers were separated. The aqueous layer was extracted with DCM (20 mL×3). The combined organic layers were dried ($Na_2SO_4$), filtered and the solvent was concentrated in vacuum to give intermediate 231 (440 mg, 96% yield) as an oil which was used in the next step without further purification.

Example A61

Step 1

Preparation of Intermediate 444

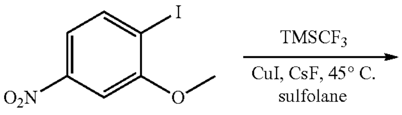

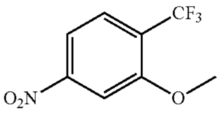

intermediate 444

A mixture of CO (6.80 g, 35.84 mmol), CsF (14.15 g, 93.18 mmol) 1-iodo-2-methoxy-4-nitrobenzene (10 g, 35.84 mmol.) and sulfolane (20 ml), was stirred rapidly at 45° C. To this mixture was added trimethyl(trifluoromethyl)silane (13.25 g, 93.18 mmol) dropwise over 4 hours using a syringe pump, and the resulting mixture was stirred at 45° C. for 18 hours. The mixture was diluted with ethyl acetate (500 mL) and stirred with Celite for 5 min. The reaction mixture was filtered through a pad of Celite, diluted with ethyl acetate (500 mL). The organic layer was washed with 10% $NH_4OH$, 1.0 N HCl, brine, dried over $Na_2SO_4$, filtered, and concentrated to give the crude product. The crude product was purified by chromatography (ethyl acetate/petroleum ether 0/1 to 1/4) to give intermediate 444 (8 g, 91% yield) as a white solid.

Step 2

Preparation of Intermediate 445

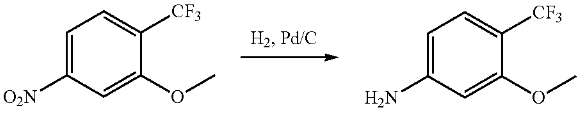

intermediate 444 intermediate 445

Intermediate 444 (7.1 g, 28.9 mmol) was taken up into methanol (100 mL and then 5% Pd/C (0.7 g,) was added. The mixture was hydrogenated at room temperature for 48 hours under $H_2$ (50 Psi) atmosphere. The mixture was filtered and the filtrate was evaporated under vacuum to obtain intermediate 445 (7 g) as a white solid.

Step 3

Preparation of Intermediate 446

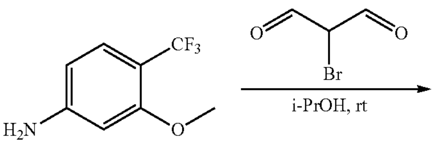

intermediate 445

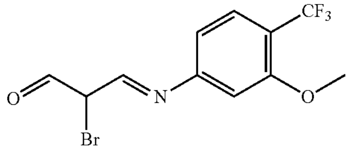

intermediate 446

A mixture of intermediate 445 (6.2 g, 32.4 mmol), 2-bromomalonaldehyde (5.38 g, 35.7 mmol) and i-PrOH (120 mL) was stirred at room temperature for 5 min. The mixture was filtered and the filtered cake was washed with i-prOH (1.0 mL). The filtered cake was dried under vacuum to obtain intermediate 446 (6 g, 51% yield) as a yellow solid.

Step 4

Preparation of Intermediate 447

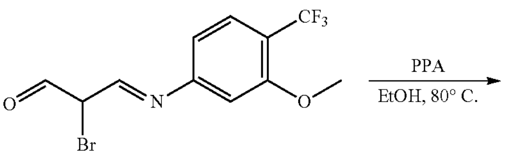

intermediate 446

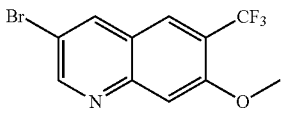

intermediate 447

A mixture of intermediate 446 (6 g, 18.5 mmol) and PPA (10 mL) in ethanol (150 mL) was stirred at 80° C. overnight. The mixture was evaporated under vacuum. Water (100 mL) was added to the mixture and the mixture was extracted with ethyl acetate (100 mL×3). The organic layers were combined and evaporated under vacuum to give the crude product. The crude product was purified by chromatography (ethyl acetate/petroleum ether 0/1 to 1/10) to give intermediate 447 (3.3 g, 54% yield) as a white solid.

Step 5

Preparation of Intermediate 210

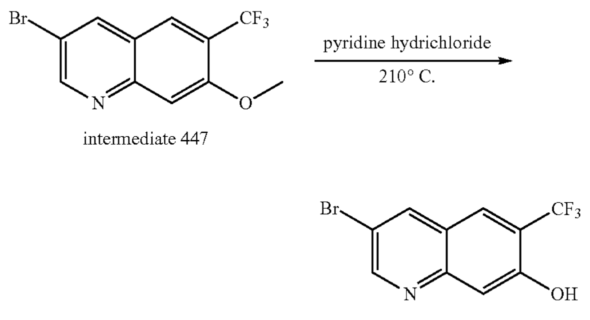

intermediate 447 intermediate 210

A mixture of intermediate 447 (1 g, 3.27 mmol) and pyridine hydrochloride (6 g, 51.9 mmol) was stirred at 210° C. for 2 hours. The reaction mixture was cooled to room temperature. Water (20 mL) was added into the mixture. The mixture was extracted with ethyl acetate (20 mL×3). The organic layers were combined and evaporated under vacuo to give the crude product. The crude product was purified by chromatography (ethyl acetate/petroleum ether 0/1 to 1/10) to obtain intermediate 210 (500 mg, 49% yield) as a white solid.

Example A62

Step 1

Preparation of Intermediate 448

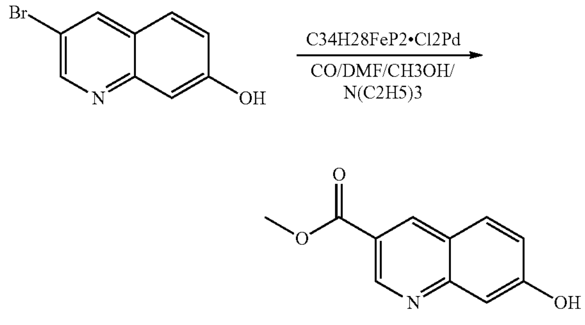

intermediate 448

3-bromo-7-hydroxyquinoline (5 g, 213 mmol) was dissolved in a mixture of DMF (50 mL) and $CH_3OH$ (50 mL). [1,1'-bis(diphenylphosphino)ferrocene] dichloropalladium (ii) (0.816 g, 1.12 mmol) and $N(C_2H_5)_3$ (6.76 g, 66.9 mmol) were added. The mixture was stirred at 140° C. overnight under a CO atmosphere (3 MPa). The mixture was evaporated under vacuum. Then residue was purified by column chromatography (eluent: petroleum ether/ethyl acetate: ratio 10/1 to 0/1). The product fractions were collected and the solvent was evaporated to afford intermediate 448 (2.5 g, yield: 45.1%) as a yellow solid.

Step 2

Preparation of Intermediate 449

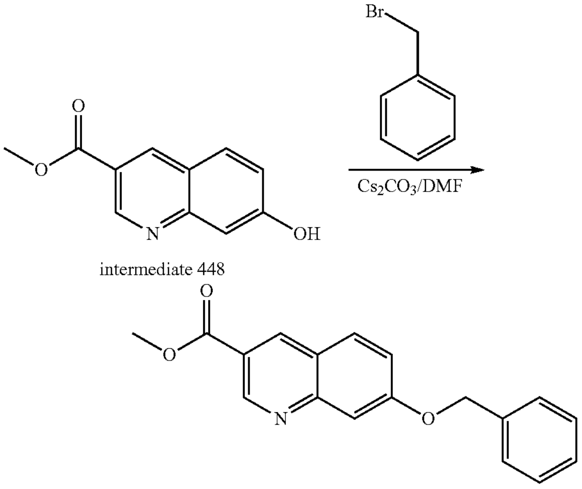

intermediate 448 intermediate 449

$Cs_2CO_3$ (15.76 g, 48.37 mmol) was added to the mixture of intermediate 448 (4 g, 16.1 mmol) and benzyl bromide (2.76 g, 16.1 mmol) in DMF (50 mL) under ice cooling. The mixture was stirred at room temperature for 12 h. The reaction mixture was filtered. The filtrate was concentrated under vacuo to give the crude product as brown solid. The crude product was purified by silica gel chromatography (eluent: petroleum ether/ethyl acetate: ratio 20/1 to 5/1) to give intermediate 449 (4.2 g, yield: 82%) as a yellow solid.

Step 3

Preparation of Intermediate 450

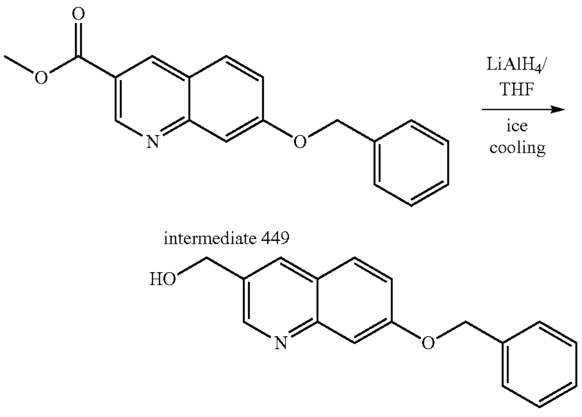

intermediate 449 intermediate 450

LiAlH4 (1.1 g, 28.3 mmol) was added to the mixture of intermediate 449 (3 g, 9.45 mmol) in THF (60 mL) under $N_2$ with ice cooling. The mixture was stirred at room temperature for 2 h. $H_2O$ (0.3 mL) and aq·NaOH (10%, 0.3 mL) were added to the mixture. The mixture was filtered. The filtrate was treated with $H_2O$ (20 mL) and extracted with EtOAc (40 mL×2). The organic layer was concentrated under vacuo to give crude product as solid. The product was purified by chromatography column (eluent: petroleum ether/EtOAc 1/2) to give the intermediate 450 (822 mg, yield: 32%) as a solid.

Step 4

Preparation of Intermediate 451

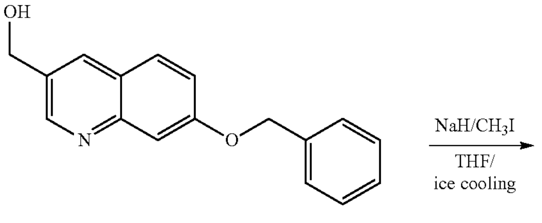

intermediate 450

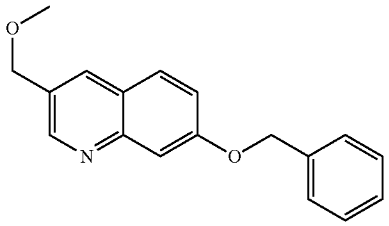

intermediate 451

NaH 60% (178 mg, 4.46 mmol,) was added to the mixture of intermediate 450 (600 mg, 2.23 mmol) in THF (30 mL) under $N_2$ with ice cooling. $CH_3I$ (316 mg, 2.23 mmol) was added and the reaction was stirred at room temperature overnight. EtOAc (40 mL) and water (20 mL) were added to the mixture. The organic phase was separated and dried over $Na_2SO_4$, filtered and concentrated to give crude product as a yellow oil. The crude product was purified by chromatography column (eluent: Petroleum ether/EtOAc 1/2) to give intermediate 451 (620 mg, yield: 98%) as an oil.

Step 5

Preparation of Intermediate 246

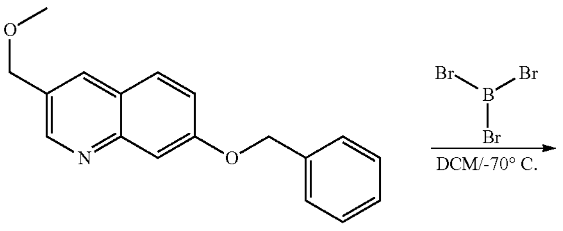

intermediate 451

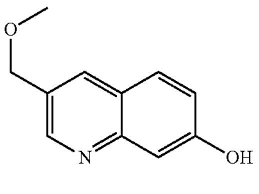

intermediate 246

$BBr_3$ (1 g, 4.29 mmol) was added to solution of intermediate 451 (600 mg, 2.15 mmol) in $CH_2Cl_2$ (60 mL) at −70° C. and the reaction was stirred for 30 min. MeOH (40 mL) was added to the reaction mixture at −70° C. The reaction mixture was stirred for 10 min. The mixture was concentrated under vacuum to give intermediate 246 (400 mg, yield: 95%) as yellow oil.

Example A63

Preparation of Intermediate 263

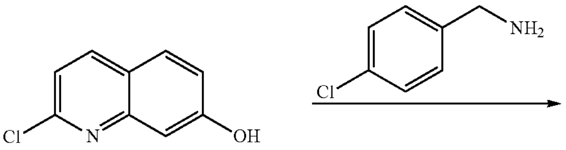

intermediate 441

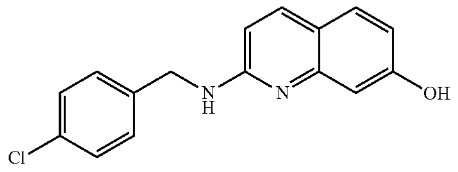

intermediate 263

Intermediate 441 (1.2 g, 6.68 mmol), 4-chlorobenzylamine (2.84 g, 20.0 mmol) and DIEA (1.73 g, 13.36 mmol) were dissolved in $CH_3CN$ (25 mL). The mixture was heated at 120° C. for 1.5 hours by microwave. The mixture was concentrated under reduced pressure to give the crude product as a brown oil. The crude product was purified by chromatography on silica gel (petroleum ether/ethyl acetate: ratio from 20/1 to 3/1) to give intermediate 263 (1.2 g, 35% yield) as a yellow solid.

Below intermediates were prepared by an analogous reaction protocol as was used for the preparation of intermediate 263 using the appropriate starting materials (Table 35).

TABLE 35

| Int. | Structure | Starting materials |
|---|---|---|
| 274 | 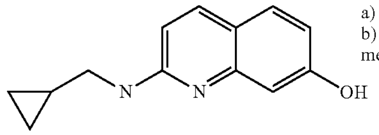 | a) Intermediate 441<br>b) cyclopropyl-methanamine |

Example A66

Step 1

Preparation of Intermediate 452

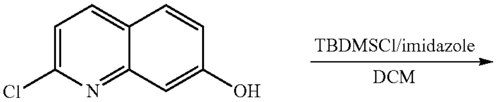

intermediate 441

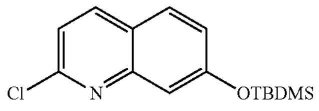

intermediate 452

To the solution of intermediate 441 (5 g, 27.84 mmol) and imidazole (2.27 g, 33.5 mmol) in $CH_2Cl_2$ (100 mL) was added TBDMSCl (5.04 g, 33.4 mmol) at 0° C. The reaction was stirred at room temperature for 4 hours. Water (100 ml) was added and the mixture was extracted with $CH_2Cl_2$ (80 mL×3). The organic phase was washed with brine (50 mL), dried over anhydrous $Na_2SO_4$, filtered and concentrated to give the crude product. The crude product was purified by column chromatography over silica gel (petroleum ether/ethyl acetate: ratio 10/1). The desired fractions were concentrated to give intermediate 452 (8.0 g, 98% yield) as an oil.

Step 2

Preparation of Intermediate 453

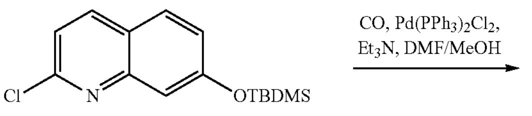

intermediate 452

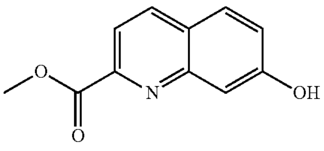

intermediate 453

A solution of intermediate 452 (5 g, 17.0 mmol), $Pd(PPh_3)_2Cl_2$ (1.19 g, 1.70 mmol) and $Et_3N$ (3.44 g, 34.0 mmol) in DMF (10 mL) and MeOH (60 mL) was stirred in an autoclave at room temperature under CO (50 psi) atmosphere. The solution was heated to 80° C. overnight. The reaction mixture was then filtered. The filtrate was concentrated to give the crude product. The crude product was purified by column chromatography on silica gel (petroleum ether/ethyl acetate, from 20/1 to 1/1) to afford intermediate 453 (3.4 g, 98% yield) as a light yellow solid.

Step 3

Preparation of Intermediate 454

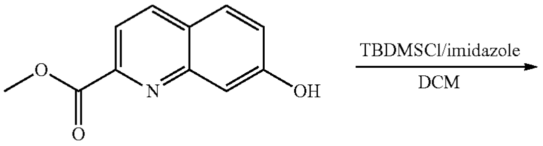

intermediate 453

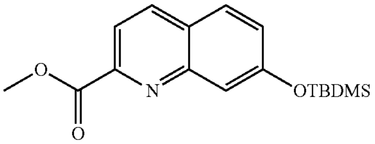

intermediate 454

To the solution of intermediate 453 (1.5 g, 7.38 mmol) and imidazole (0.60 g, 8.86 mmol) in $CH_2Cl_2$ (80 mL) was added TBDMSCl (1.34 g, 8.86 mmol) at 0° C. The reaction was stirred at room temperature for 2 hours. The reaction was poured into water and extracted with ethyl acetate (150 mL×3) and the organic phase was washed with brine (80 mL). The organic phase was dried over anhydrous $Na_2SO_4$, filtered and concentrated to give the crude product. The crude product was purified by column chromatography over silica gel (petroleum ether/ethyl acetate: ratio 5:1). The desired fractions were concentrated to give intermediate 454 (2.4 g, 97.5% yield) as a white oil.

Step 4

Preparation of Intermediate 455

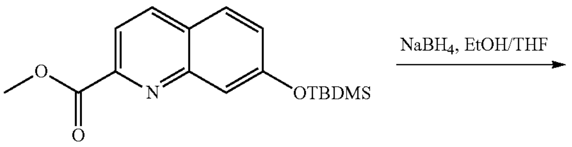

intermediate 454

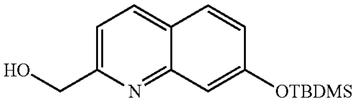

intermediate 455

To a solution of $NaBH_4$ (2.264 g, 59.85 mmol) in EtOH (20 mL) cooled to 0° C. was added dropwise a solution of intermediate 454 (1.9 g, 5.98 mmol) in THF (20 mL) over 5 min under $N_2$. The solution was allowed to warm to room temperature and was stirred for 2 hours. A saturated aqueous $NaHCO_3$ solution (20 mL) and water (50 mL) were added to the reaction. The mixture was extracted with EtOAc (80 ml×3). The combined organic layers were washed with brine (50 ml), dried with $Na_2SO_4$, filtered and concentrated to give the crude product intermediate 455 (1.2 g, 66.5% yield).

Step 5

Preparation of Intermediate 456

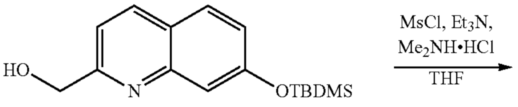

intermediate 455

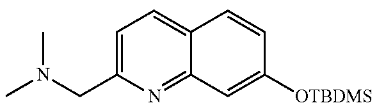

intermediate 456

To a solution of intermediate 455 (1.2 g, 4.15 mmol) and $Et_3N$ (1.26 g, 12.44 mmol) cooled in THF (20 mL) was added MsCl (569.9 mg, 4.98 mmol) dropwise under $N_2$. The reaction mixture was stirred at 0° C. under $N_2$ for 30 minutes. Dimethyl amine hydrochloride (1.69 g, 20.73 mmol, 5 eq) and $Et_3N$ (4.195 g, 10 eq) were added. The reaction mixture was stirred at room temperature for 2 days. Water (40 ml) was added and the mixture was extracted with ethyl acetate (50 ml×3). The organic layers were combined, dried over $Na_2SO_4$, filtered and concentrated to give the crude product as an oil. The crude product was purified by column chromatography over silica gel (petroleum ether/ethyl acetate: ratio 1/1). The desired fractions were concentrated to give intermediate 456 (550 mg) as an oil.

Step 6

Preparation of Intermediate 212

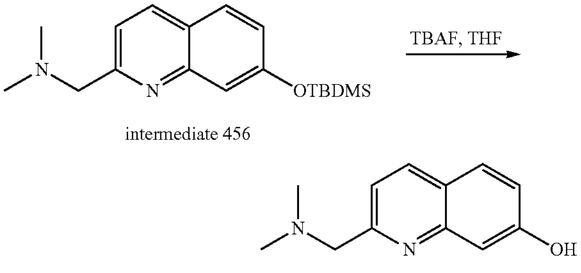

intermediate 456 intermediate 212

To a solution of intermediate 456 (500 mg, 1.58 mmol) in THF (20 mL) was added TBAF (1 M solution in THF, 1.58 mL, 1.58 mmol) dropwise at room temperature under $N_2$. The reaction mixture was stirred at room temperature for 30 minutes. The reaction mixture was poured into water (40 ml) and was extracted with EtOAc (50 ml×3). The organic layers were combined, dried over $Na_2SO_4$, filtered and evaporated to give the crude product. The crude product was purified by TLC ($CH_2Cl_2$/MeOH: ratio 5/1) to give intermediate 212 (80 mg, 22.5% yield) as a light yellow oil.

Example A67

Step 1

Preparation of Intermediate 457 and Intermediate 458

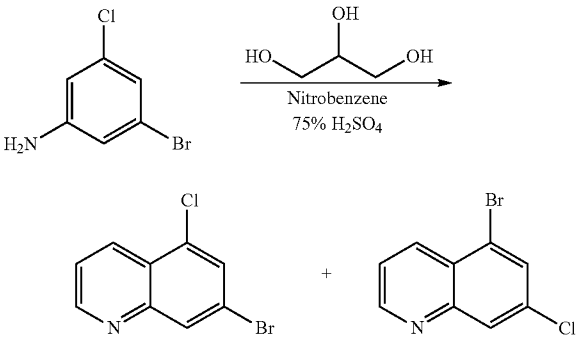

intermediate 457 intermediate 458

3-chloro-5-bromoaniline (1 g, 4.84 mmol) was dissolved in 75% $H_2SO_4$ (10 mL). Then glycerol (1.11 g, 12.1 mmol) and nitrobenzene (0.59 g, 4.84 mmol) were added. The reaction mixture was stirred at 150° C. for 3 hours under $N_2$. EtOAc (50 ml) was added and the mixture was adjusted to pH to 6-7 with a 30% solution of NaOH in water. The solid was filtered off over celite and the organic layer was separated and evaporated. The residue was purified by flash column chromatograph over silica gel (gradient eluent: petroleum ether/EtOAc from 20/1 to 5/1). The desired fractions were collected and the solvent was evaporated to give a mixture of intermediate 457 and intermediate 458 (750 mg) as a white solid.

Step 2

Preparation of Intermediate 459 and Intermediate 460

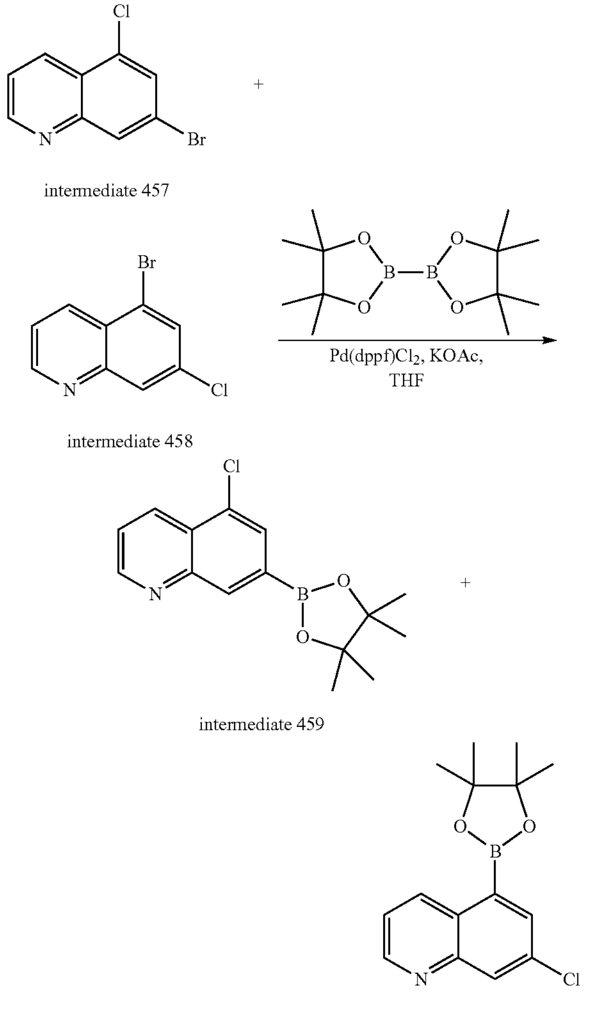

intermediate 457 intermediate 458 intermediate 459 intermediate 460

A mixture of intermediate 457 and intermediate 458 (750 mg), bis(pinacolato)diboron (942.5 mg, 3.7 mmol), Pd(dppf) $Cl_2$ (113.1 mg, 0.155 mmol) and KOAc (910.6 mg, 9.28 mmol) in TIE (20 mL) was stirred at 60° C. for 2 hours under $N_2$. Water (30 ml) was added and extracted with EtOAc (30 mL×3). The organic layers were combined, dried over $Na_2SO_4$, filtered and concentrated to give a mixture of intermediate 459 and intermediate 460 (1.0 g) as a yellow oil.

Step 3

Preparation of Intermediate 220a and Intermediate 220b

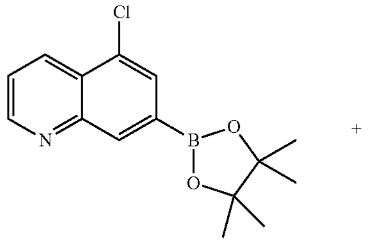

intermediate 459

-continued

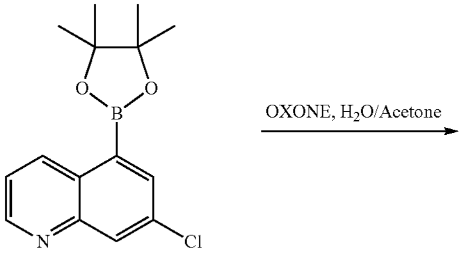

intermediate 460

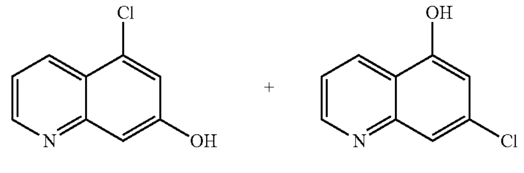

intermediate 220a intermediate 220b

To a mixture of intermediate 459 and intermediate 460 (1 g) in acetone (10 mL) was added a solution of oxone (1.25 g 2.03 mmol) in 1120 (10 mL) dropwise under $N_2$ at 0° C. The reaction mixture was stirred at 0° C. for 1 hour. Water (20 ml) was added and the mixture was extracted with EtOAc (3x30 ml). The organic layer was combined, dried over $Na_2SO_4$, filtered and concentrated. The residue was triturated under EtOAc/petroleum ether (1/10). The precipitate was filtered off and dried give a mixture of intermediate 220a and intermediate 220b (150 mg) as a yellow solid.

Example A68

Preparation of Intermediate 218

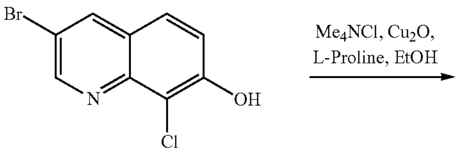

intermediate 205

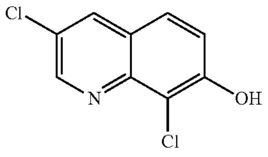

intermediate 218

A mixture of intermediate 205 (400 mg, 1.55 mmol), $Me_4NCl$ (1.36 g, 12.4 mmol), $Cu_2O$ (88.5 mg, 0.62 mmol) and L-Proline (142.5 mg, 1.24 mmol) in EtOH (10 mL) was stirred at 110° C. for 120 min using a single mode microwave. The reaction mixture was concentrated and purified by column chromatography (eluent: petroleum ether/ethyl acetate: ratio 1/0 to 1/1). The product fractions were collected and the solvent was evaporated to afford intermediate 218 (350 mg, 97%) as a yellow solid.

Example A69

Preparation of Intermediate 235

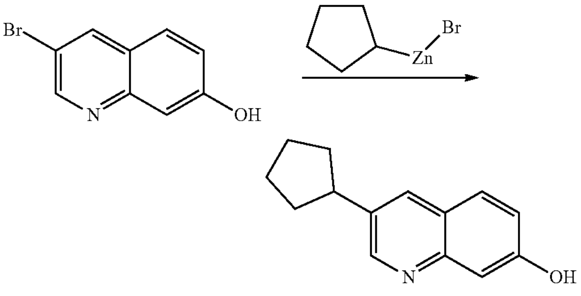

intermediate 235

The reaction was performed twice.

To a solution of 3 bromo-7 hydroxyquinoline (500 mg, 2.23 mmol) in THF (10 mL) was added cyclopentylzinc(II) bromide (0.5 M solution, 7.14 mL, 3.57 mmol), bis(tri-tert-butylphosphine)palladium(0) (114.0 mg, 0.223 mmol) and t-BuOK (250.4 mg, 2.23 mmol) under a $N_2$ atmosphere. The reaction mixture was heated to 100° C. for 45 min in a microwave. The reaction mixture was cooled to room temperature, filtered and concentrated under reduced pressure to give the crude product as a yellow oil. The two crude products were combined and purified on silica gel column (petroleum ether/ethyl acetate ratio: 5/1 to 1/1) to obtain intermediate 235 (300 mg) as a yellow solid.

Preparation of Intermediate 240

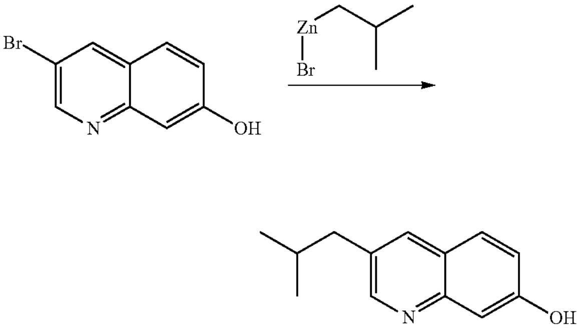

intermediate 240

The reaction was performed twice.

To a solution of 3 promo-7-hydroxyquinoline (700 mg 3.12 mmol) in THF (10 mL) was added isobutylzinc(II) bromide (0.5 M solution, 9.37 mL, 4.69 mmol), bis(tri-tert-butylphosphine)palladium(0) (319.3 mg 0.625 mmol) and t-BuOK (350.58 mg 3.12 mmol) under a $N_2$ atmosphere. The reaction mixture was heated at 100° C. for 45 min in a microwave. The reaction mixture was cooled to room temperature, filtered and concentrated under reduced pressure to give the crude product. The two crude products were combined and purified on silica gel column (petroleum ether/ethyl acetate: ratio 3/1 to 1/1) to obtain intermediate 240 (410 mg) as a yellow solid.

Example A98

Step 1:

Preparation of Intermediate 505

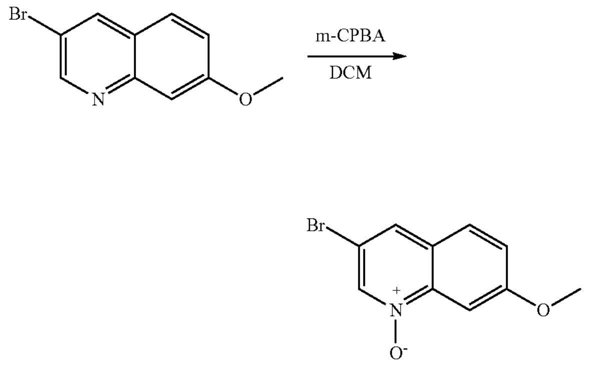

intermediate 505

3-bromo 7-methoxyquinoline (5 g, 21 mmol) was dissolved in dichloromethane (50 mL). Then 3-chloroperoxybenzoic acid (5.116 g, 25.2 mmol) was added into the mixture in fractions at 0° C. The resulting mixture was stirred at room temperature overnight. The mixture was poured into a sat·$Na_2SO_3$ aqueous solution (30 ml). The mixture was extracted by dichloromethane (50 mL×2). Then the organic phase was washed with a sat·$NaHCO_3$ aqueous solution (50 mL) and brine (50 mL). The organic layer was dried over anhydrous $Na_2SO_4$. A white solid precipitated which was filtered to obtain intermediate 505 (6.4 g, 87% yield).

Step 2:

Preparation of Intermediate 506

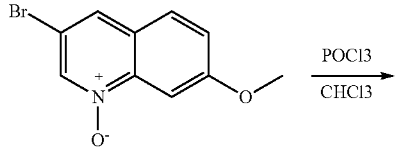

intermediate 505

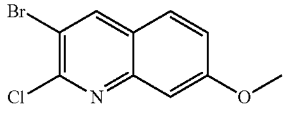

intermediate 506

Intermediate 505 (6.4 g, 18.25 mmol) was dissolved in chloroform (100 mL). Then phosphorus oxychloride (20 ml) was added and the reaction mixture was refluxed at 80° C. for 3 hours. The solvent was removed under reduced pressure to obtain intermediate 506 (5.8 g, 97% yield) as a white solid, which was used in the next step without further purification.

Step 3:

Preparation of Intermediate 507

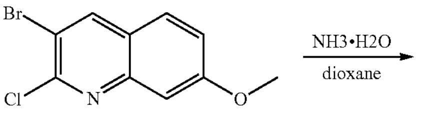

intermediate 506

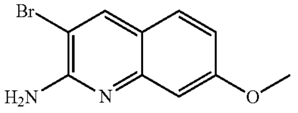

intermediate 507

A mixture of intermediate 506 (3 g, 11 mmol) and $NH_3 \cdot H_2O$ (20 ml) in dioxane (20 ml) was heated in a sealed tube at 120° C. for 72 h. The mixture was extracted with $CH_2Cl_2$ (50 mL×3). The organic phase was concentrated under vacuum to give the crude product. The crude product was purified by chromatography (ethyl acetate/petroleum ether 0/20 to 1/20) to obtain intermediate 507 (0.9 g, 32% yield) as a white solid.

Step 4:

Preparation of Intermediate 477

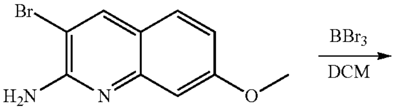

intermediate 507

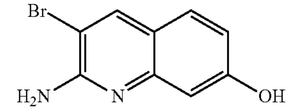

intermediate 477 intermediate 507 (1.2 g, 4.74 mmol) was dissolved in $CH_2Cl_2$ (12 ml). Then the yellow clear reaction was cooled to 0° C. and $BBr_3$ (23.75 g mmol) was added. The reaction mixture was stirred at room temperature for 16 hours. The reaction was quenched with MeOH slowly at 0° C. and stirred at 15° C. for 15 min. The red suspension was concentrated. The residue was adjusted to pH 8 with aqueous $NaHCO_3$. The precipitate was filtered and washed with $H_2O$ (10 mL). The filter cake was dried in vacuum to obtain intermediate 477 (1.1 g, 97% yield) as off-white solid.

Example A99

Step 1:

Preparation of Intermediate 508

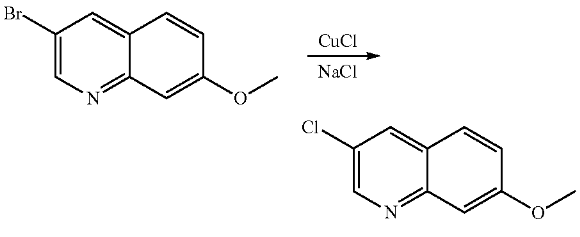

intermediate 508

A mixture of 3-bromo 7-methoxyquinoline (10 g, 42 mmol), CuCl (20 g, 204 mmol), NaCl (20 g, 345 mmol) and N-methylpyrrolidin-2-one (200 ml) was heated at 120° C. for 2 hours. Then the reaction mixture was stirred at 170° C. for 2 hours. The reaction was diluted with a saturated aqueous ammonium chloride solution, ethyl acetate was added and the mixture was stirred to dissolve the product. The mixture was filtered to remove the insoluble material and the organic phase was separated. The aqueous phase was extracted with ethyl acetate (200 mL×3) and the insoluble material was washed with warm ethyl acetate (200 mL×3). The ethyl acetate fractions were combined, washed with water, dried over $Na_2SO_4$ and evaporated under reduced pressure. The residue was purified by flash chromatography (gradient eluent: EtOAc/petrol ether from 1/20 to 1/5) to obtain intermediate 508 (2 g, 22% yield) as white solid.

Step 2:

Preparation of Intermediate 509

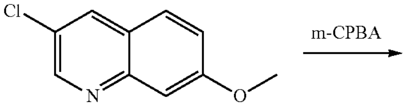

intermediate 508

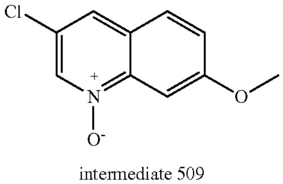

intermediate 509

Intermediate 508 (2 g, 10.3 mmol) was dissolved in dichloromethane (40 mL). Then 3-chloroperoxybenzoic acid (3.565 g, 20.65 mmol) was added into the mixture in fractions at 0° C. The resulting mixture was stirred at room temperature overnight. The mixture was poured into a sat. $Na_2SO_3$ aqueous solution (30 ml). The mixture was extracted by dichloromethane (50 mL×2). Then the organic phase was washed with a sat. $NaHCO_3$ aqueous solution (50 mL) and brine (50 mL). The organic layer was dried over anhydrous $Na_2SO_4$. A white solid precipitated and was filtered to obtain intermediate 509 (2 g, 83% yield).

Step 3:

Preparation of Intermediate 510

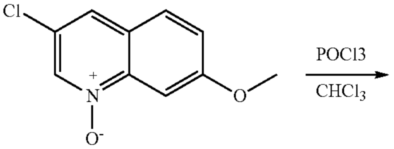

intermediate 509

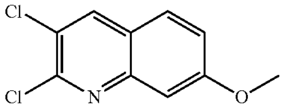

intermediate 510

Intermediate 509 (2.4 g, 18.25 mmol) was dissolved in chloroform (50 mL). Then phosphorus oxychloride (10.5 g, 68.69 mmol) was added and the reaction mixture was refluxed at 80° C. for 2 hours. The reaction mixture was slowly poured into water. Then a sat. $NaHCO_3$ aqueous solution was added into the mixture to change the pH to ~7. The reaction mixture was extracted with dichloromethane (200 mL×2) and the organic layer was dried over anhydrous $Na_2SO_4$. The organic phase was concentrated to obtain intermediate 510 (2.5 g, 93% yield) as a white solid.

Step 4:

Preparation of Intermediate 511

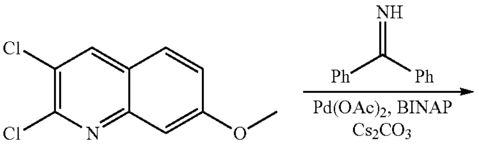

intermediate 510

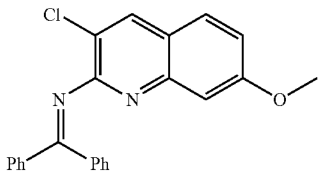

intermediate 511

A mixture of intermediate 510 (2.2 g, 9.64 mmol), benzophenone imine (1.78 g, 9.83 mmol), $Pd(OAc)_2$ (0.21 g, 0.96 mmol), BINAP (0.6 g, 0.96 mmol) $Cs_2CO_3$ (6.28 g, 19.29 mmol) and toluene (50 mL) was heated at 110° C. for 48 hours under $N_2$. The catalyst was filtered and the solvent was evaporated. The residue was purified by flash column chromatography over silica gel (gradient eluent: EtOAc/petrol ether from 1/15 to 1/1). The product fractions were collected and the solvent was evaporated to obtain intermediate 511 (2 g, 54% yield) as an oil.

Step 5:

Preparation of Intermediate 468

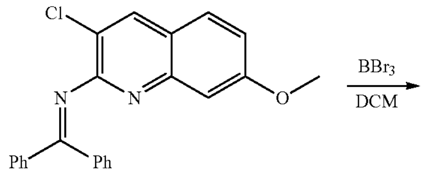

intermediate 511

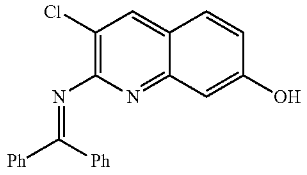

intermediate 468

Intermediate 511 (2 g, 5.2 mmol) was dissolved in $CH_2Cl_2$ (100 ml). Then the yellow clear reaction was cooled to 0° C. and $BBr_3$ (20 g, 79.84 mmol) was added. The reaction mixture was stirred at room temperature for 14 hours. The reaction mixture was adjusted to pH 7 with sat. sodium hydrogen carbonate solution and extracted with EtOAc (3×300 mL). The combined organic layers were separated, dried with $Na_2SO_4$, and the solvent was evaporated to obtain intermediate 468 (2 g, 69.5% yield) as white solid.

Example A70

Preparation of Intermediate 305

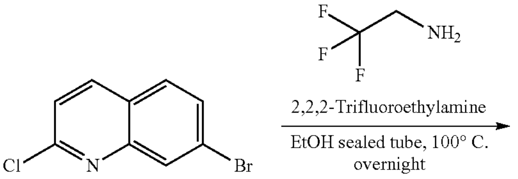

7-Bromo-2-Chloroquinoline

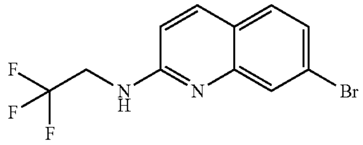

intermediate 305

A mixture of 7-Bromo-2-Chloroquinoline (2.45 g, 10.1 mmol) and 2,2,2-Trifluoroethylamine (5.0 g, 50.5 mol) in EtOH (60 mL) was stirred in a sealed tube at 120° C. overnight. The reaction mixture was treated with aq. NaCl (80 mL) and extracted with EtOAc (80 mL×2). The organic layers were combined and concentrated under vacuo to give crude product. The crude product was purified by silica gel chromatography (ethyl acetate/petroleum ether 0/1 to 3/7) to give intermediate 305 (2.5 g, 62.5% yield) as white solid.

Below intermediates were prepared by an analogous reaction protocol as was used for the preparation of intermediate 305 using the appropriate starting materials (Table 36).

TABLE 36

| Int. | Structure | Starting materials |
|---|---|---|
| 244 | 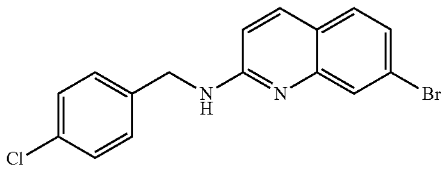 [SMILES: Clc1ccc(CNc2ccc3ccc(Br)cc3n2)cc1] | 7-bromo-2-chloroquinoline<br>(4-chlorophenyl)methanamine |
| 263 | 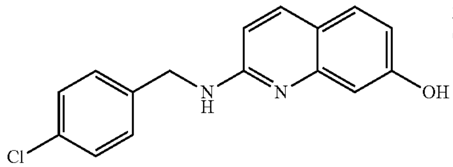 | 2-chloro-7-hydroxyquinoline<br>(4-chlorophenyl)methanamine |
| 274 | 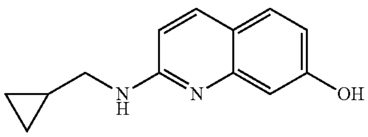 [SMILES: Oc1ccc2ccc(NCC3CC3)nc2c1] | 2-chloro-7-hydroxyquinoline<br>cyclopropylmethylamine |
| 299 | 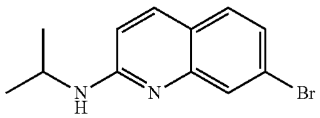 | propan-2-amine<br>7-bromo-2-chloroquinoline |

TABLE 36-continued

| Int. | Structure | Starting materials |
|---|---|---|
| 308 | 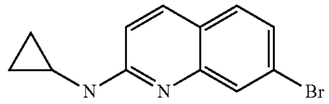 [SMILES: Brc1ccc2ccc(NC3CC3)nc2c1] | 7-bromo-2-chloroquinoline<br>Cyclopropyiamine |
| 320 | 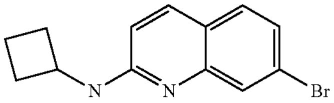 [SMILES: Brc1ccc2ccc(NC3CCC3)nc2c1] | 7-bromo-2-chloroquinoline<br>Cyclobutylamine |
| 302 | 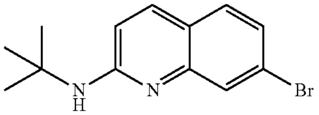 [SMILES: CC(C)(C)Nc1ccc2ccc(Br)cc2n1] | 7-bromo-2-chloroquinoline<br>Tert.-butylamine |
| 290 | 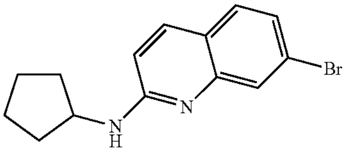 [SMILES: Brc1ccc2ccc(NC3CCCC3)nc2c1] | 7-bromo-2-chloroquinoline<br>Cyclopentylamine |
| 293 | 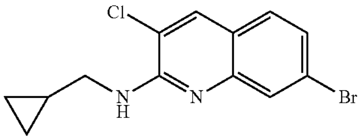 [SMILES: Clc1cc2ccc(Br)cc2nc1NCC1CC1] | intermediate 181<br>cyclopropylmethylamine |
| 296 | 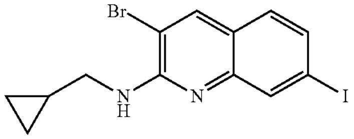 [SMILES: Brc1cc2ccc(I)cc2nc1NCC1CC1] | intermediate 175<br>cyclopropylmethylamine |
| 311 | 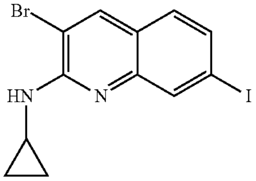 [SMILES: Brc1cc2ccc(I)cc2nc1NC1CC1] | intermediate 175<br>cyclopropylamine |
| 317 | 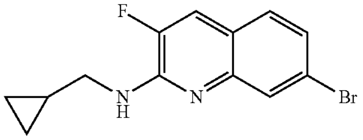 [SMILES: Fc1cc2ccc(Br)cc2nc1NCC1CC1] | Intermediate 400<br>cyclopropylmethylamine |

Example A71

Preparation of Intermediate 338

-continued

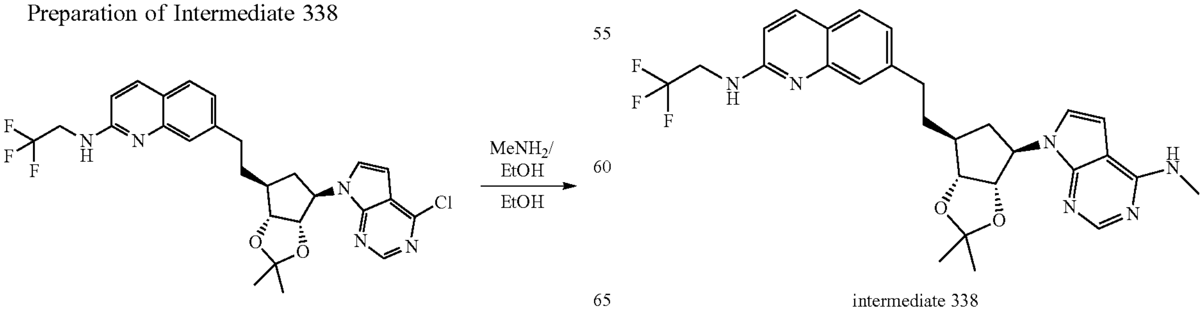

intermediate 306 intermediate 338

A mixture of intermediate 306 (520 mg, 0.95 mmol) and $CH_3NH_2$/EtOH (15 mL) in EtOH (15 mL) was stirred at 120° C. overnight in a sealed tube. The reaction was concentrated to give intermediate 338 (590 mg) which was used for next step without further purification.

Below intermediates were prepared by an analogous reaction protocol as was used for the preparation of intermediate 338 using the appropriate starting materials (Table 37).

TABLE 37

| Int. | Structure | Starting materials |
| --- | --- | --- |
| 339 | 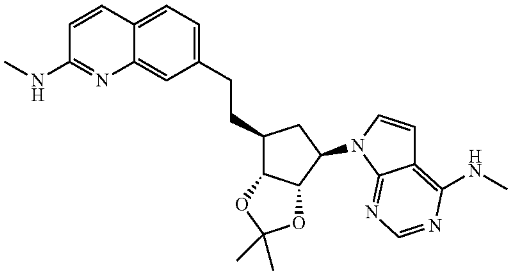 | Intermediate 248 methylamine |
| 340 | 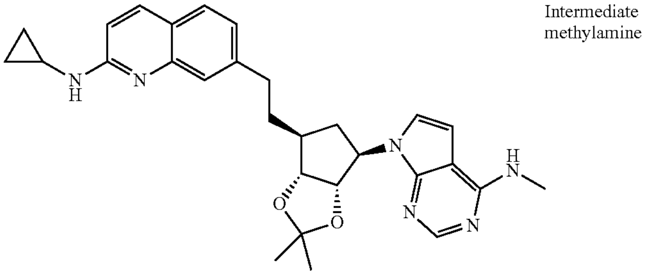 | Intermediate 309 methylamine |
| 341 | 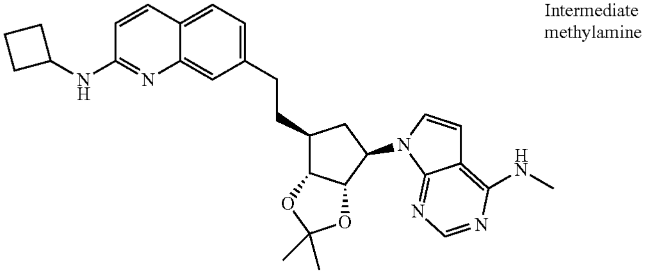 | Intermediate 321 methylamine |
| 342 | 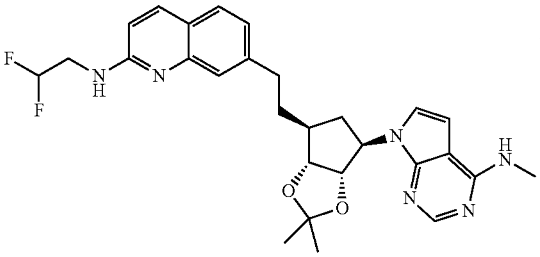 [SMILES: CNc1ncnc2c1ccn2[C@@H]1C[C@H](CCc2ccc3ccc(NCC(F)F)nc3c2)[C@H]2OC(C)(C)O[C@H]21] | Intermediate 162 methylamine |
| 343 | 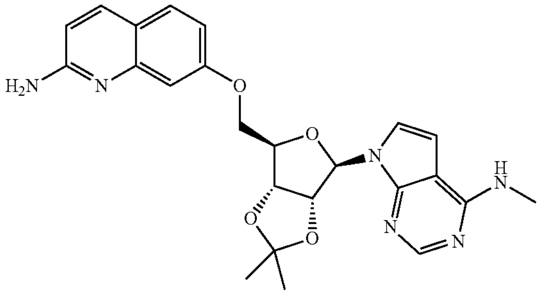 [SMILES: CNc1ncnc2c1ccn2[C@@H]1O[C@H](COc2ccc3ccc(N)nc3c2)[C@H]2OC(C)(C)O[C@H]21] | Intermediate 262 methylamine |

TABLE 37-continued
| Int. | Structure | Starting materials |
|---|---|---|
| 344 | 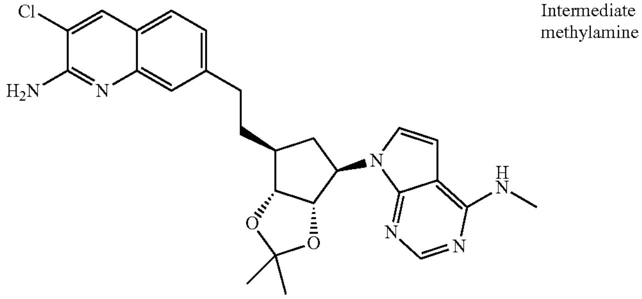 | Intermediate 183 methylamine |
| 345 | 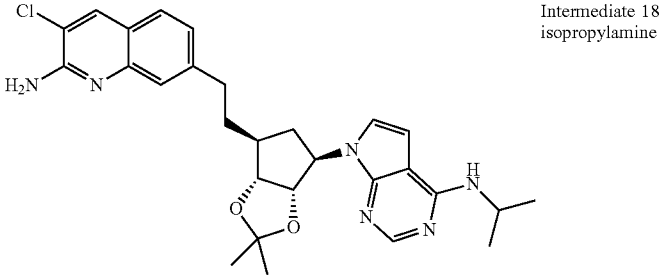 | Intermediate 183 isopropylamine |
| 346 | 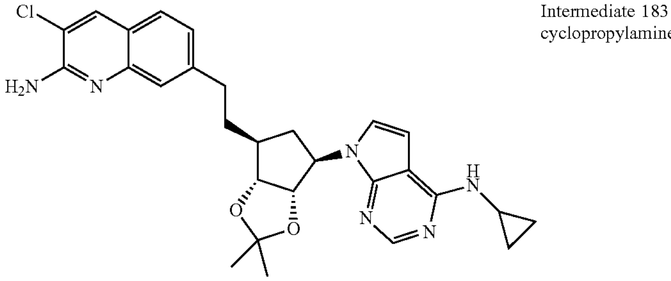 | Intermediate 183 cyclopropylamine |
| 347 | 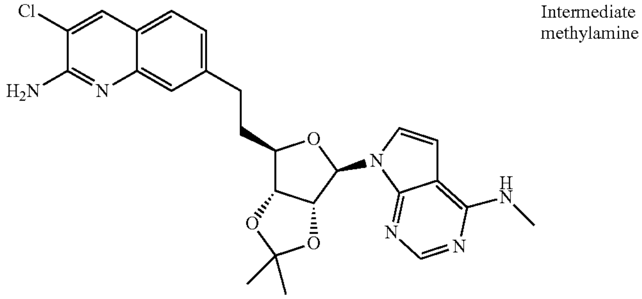 | Intermediate 327 methylamine |
| 348 | 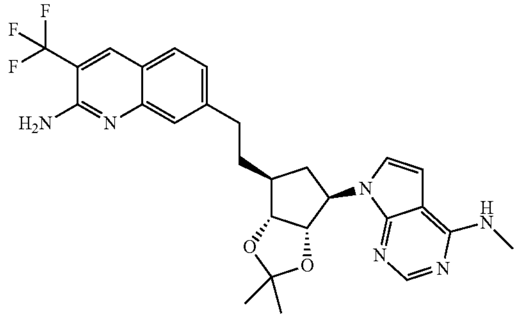 [SMILES: CNc1ncnc2c1ccn2[C@@H]1C[C@H](CCc2ccc3cc(C(F)(F)F)c(N)nc3c2)[C@H]2OC(C)(C)O[C@H]21] | Intermediate 315 methylamine |

TABLE 37-continued
| Int. | Structure | Starting materials |
|---|---|---|
| 349 | 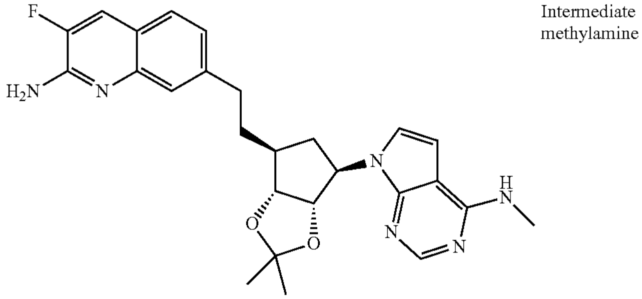 | Intermediate 330 methylamine |
| 350 | 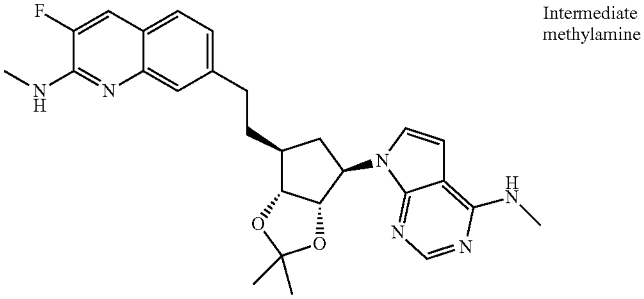 | Intermediate 324 methylamine |
| 351 | 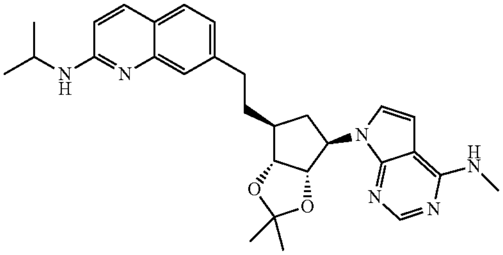 [SMILES: CNc1ncnc2c1ccn2[C@@H]1C[C@H](CCc2ccc3ccc(NC(C)C)nc3c2)[C@H]2OC(C)(C)O[C@H]21] | Intermediate 300 methylamine |
| 352 | 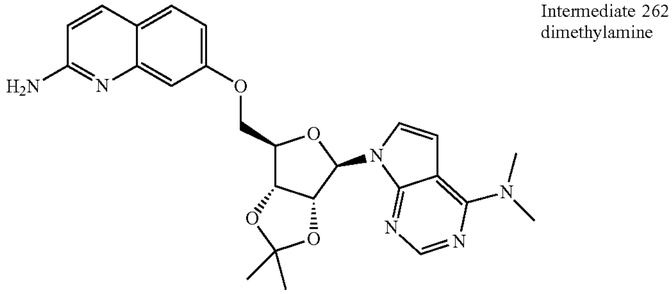 | Intermediate 262 dimethylamine |
| 405 | 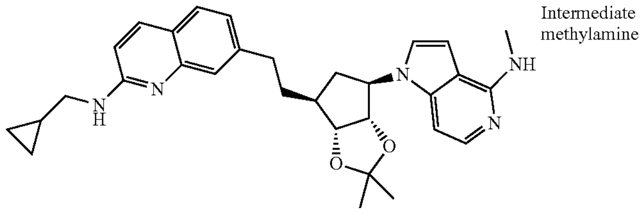 | Intermediate 159 methylamine |

TABLE 37-continued
| Int. | Structure | Starting materials |
|---|---|---|
| 465 | 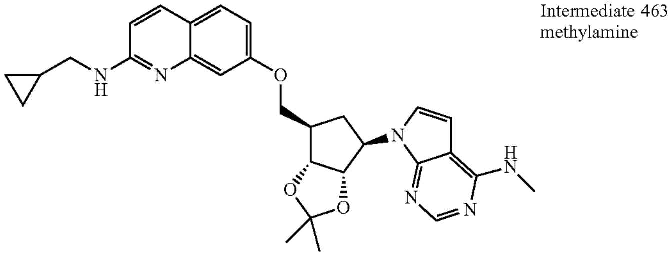 | Intermediate 463 methylamine |
| 467 | 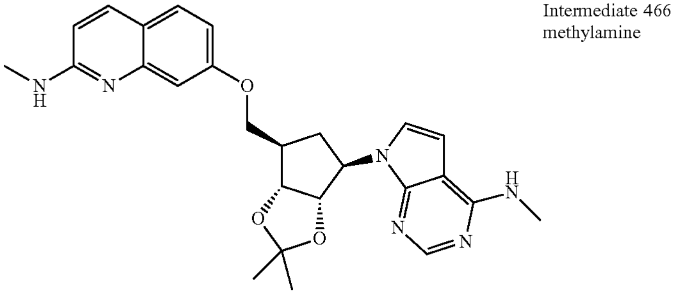 | Intermediate 466 methylamine |
| 470 | 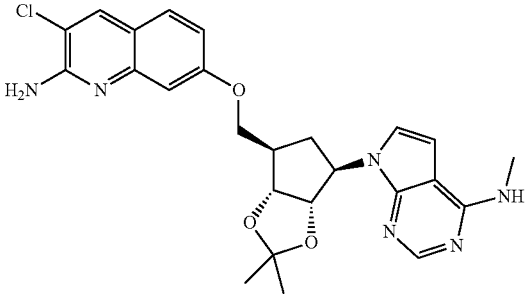 [SMILES: CNc1ncnc2c1ccn2[C@@H]1C[C@H](COc2ccc3cc(Cl)c(N)nc3c2)[C@H]2OC(C)(C)O[C@H]21] | Intermediate 469 methylamine |
| 474 | 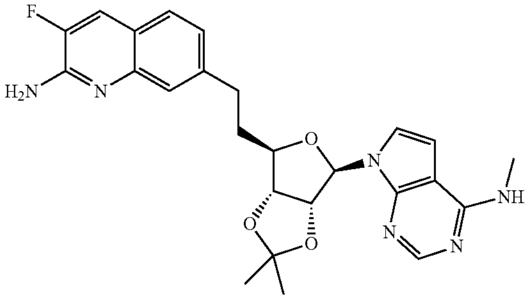 [SMILES: CNc1ncnc2c1ccn2[C@@H]1O[C@H](CCc2ccc3cc(F)c(N)nc3c2)[C@H]2OC(C)(C)O[C@H]21] | Intermediate 473 methylamine |
| 476 | 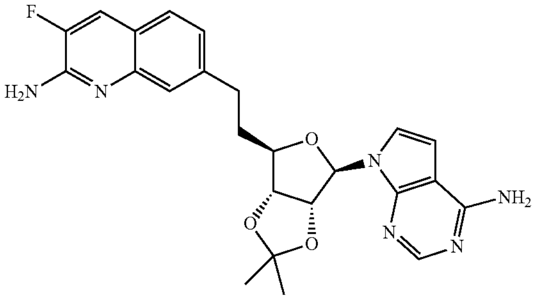 [SMILES: CC1(C)O[C@@H]2[C@H](O1)[C@@H](CCc1ccc3cc(F)c(N)nc3c1)O[C@H]2n1ccc2c(N)ncnc21] | Intermediate 473 $NH_4OH$ |

TABLE 37-continued
| Int. | Structure | Starting materials |
| --- | --- | --- |
| 479 | 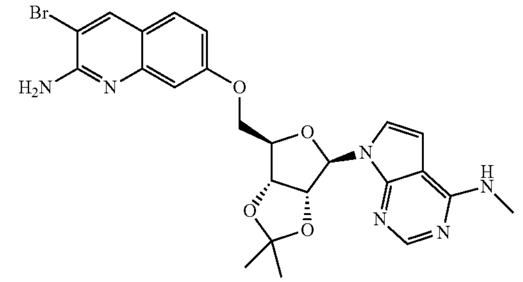 | Intermediate 478 methylamine |
| 480 | 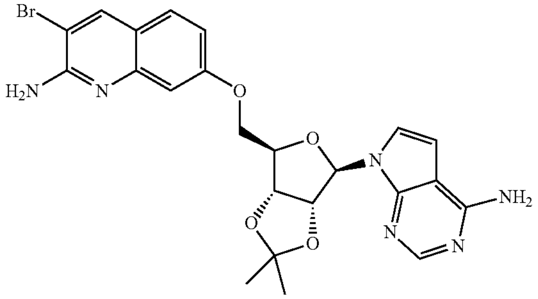 [SMILES: CC1(C)O[C@@H]2[C@H](O1)[C@@H](COc1ccc3cc(Br)c(N)nc3c1)O[C@H]2n1ccc2c(N)ncnc21] | Intermediate 478 $NH_4OH$ |
| 481 | 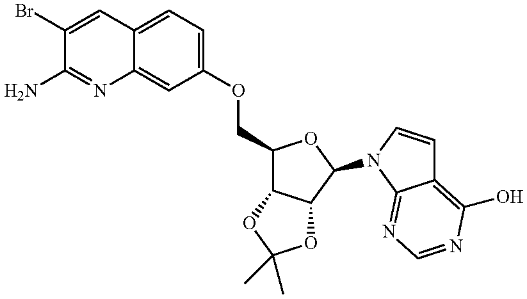 [SMILES: CC1(C)O[C@@H]2[C@H](O1)[C@@H](COc1ccc3cc(Br)c(N)nc3c1)O[C@H]2n1ccc2c(O)ncnc21] | Intermediate 478 $NH_4OH$ |
| 486 | 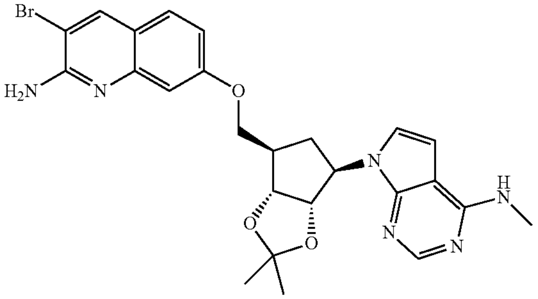 [SMILES: CNc1ncnc2c1ccn2[C@@H]1C[C@H](COc2ccc3cc(Br)c(N)nc3c2)[C@H]2OC(C)(C)O[C@H]21] | Intermediate 484 methylamine |
| 489 | 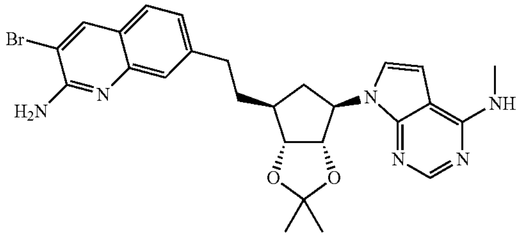 [SMILES: CNc1ncnc2c1ccn2[C@@H]1C[C@H](CCc2ccc3cc(Br)c(N)nc3c2)[C@H]2OC(C)(C)O[C@H]21] | Intermediate 488 $NH_4OH$ |

TABLE 37-continued

| Int. | Structure | Starting materials |
|---|---|---|
| 492 | 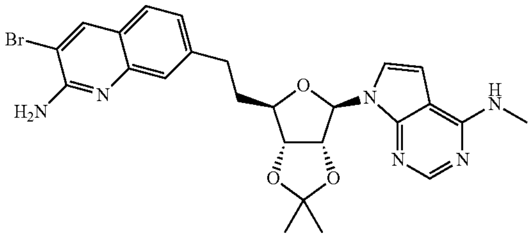 [SMILES: CNc1ncnc2c1ccn2[C@@H]1O[C@H](CCc2ccc3cc(Br)c(N)nc3c2)[C@H]2OC(C)(C)O[C@H]21] | Intermediate 491 methylamine |

Example A72

Preparation of Intermediate 353

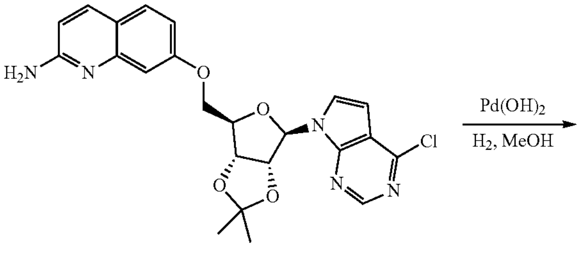

intermediate 262

-continued

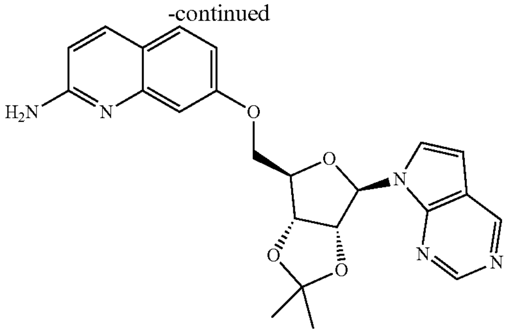

intermediate 353

A mixture of intermediate 262 (310 mg, 0.61 mmol) in MeOH (5 mL) was hydrogenated at room temperature ($H_2$, atmospheric pressure) with $Pd(OH)_2$ (20 mg) as catalyst over weekend. After uptake of $H_2$ (1 equiv), the mixture was filtered and the filtrate was evaporated to give intermediate 353 (260 mg, 81.3% yield) which was used in the next step without further purification.

Below intermediates were prepared by an analogous reaction protocol as was used for the preparation of intermediate 353 using the appropriate starting materials (Table 38).

TABLE 38

| Int. | Structure | Starting materials |
|---|---|---|
| 354 | 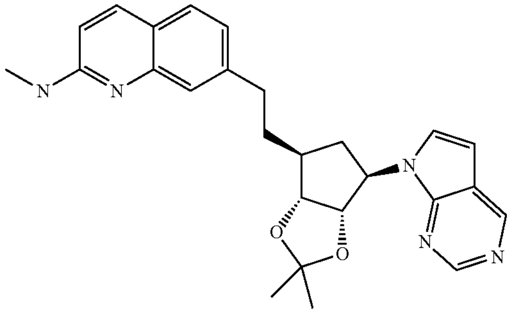 [SMILES: CNc1ccc2ccc(CC[C@H]3C[C@@H](n4ccc5cncnc54)[C@@H]4OC(C)(C)O[C@H]34)cc2n1] | Intermediate 248 |

TABLE 38-continued
| Int. | Structure | Starting materials |
| --- | --- | --- |
| 355 | 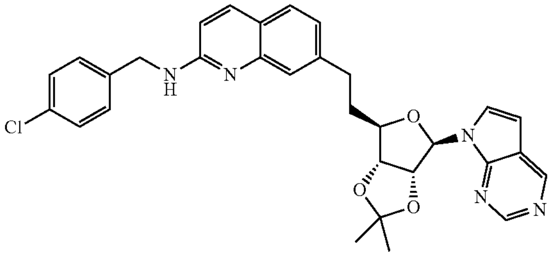 [SMILES: CC1(C)O[C@@H]2[C@H](O1)[C@@H](CCc1ccc3ccc(NCc4ccc(Cl)cc4)nc3c1)O[C@H]2n1ccc2cncnc21] | Intermediate 268 |
| 356 | 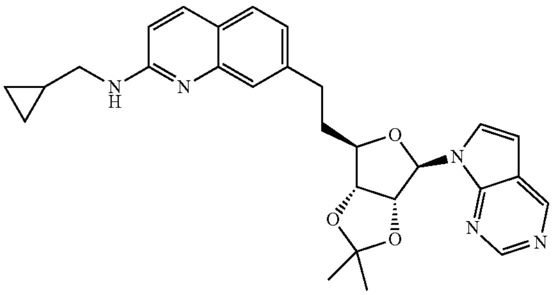 [SMILES: CC1(C)O[C@@H]2[C@H](O1)[C@@H](CCc1ccc3ccc(NCC4CC4)nc3c1)O[C@H]2n1ccc2cncnc21] | Intermediate 159 |
| 357 | 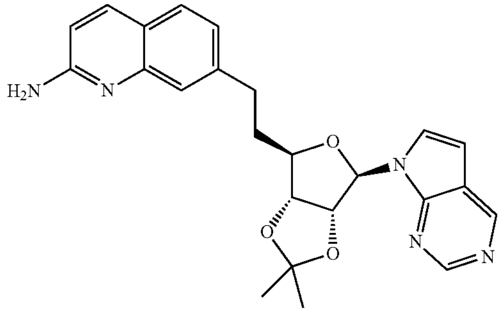 [SMILES: CC1(C)O[C@@H]2[C@H](O1)[C@@H](CCc1ccc3ccc(N)nc3c1)O[C@H]2n1ccc2cncnc21] | Intermediate 266 |
| 358 | 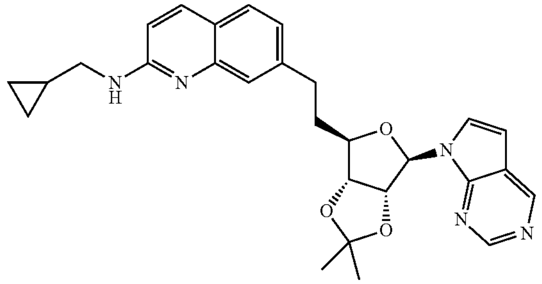 [SMILES: CC1(C)O[C@@H]2[C@H](O1)[C@@H](CCc1ccc3ccc(NCC4CC4)nc3c1)O[C@H]2n1ccc2cncnc21] | Intermediate 272 |
| 359 | 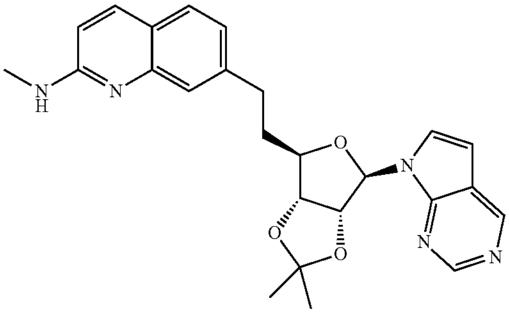 [SMILES: CNc1ccc2ccc(CC[C@H]3O[C@@H](n4ccc5cncnc54)[C@@H]4OC(C)(C)O[C@@H]43)cc2n1] | Intermediate 259 |

TABLE 38-continued
| Int. | Structure | Starting materials |
| --- | --- | --- |
| 360 | 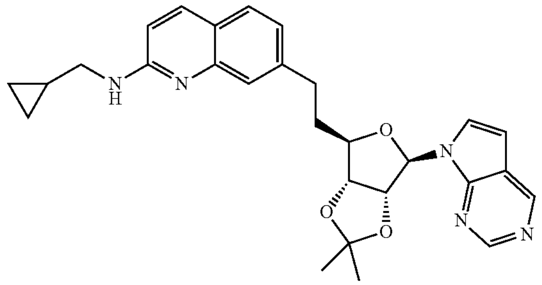 [SMILES: CC1(C)O[C@@H]2[C@H](O1)[C@@H](CCc1ccc3ccc(NCC4CC4)nc3c1)O[C@H]2n1ccc2cncnc21] | Intermediate 275 |
| 361 | 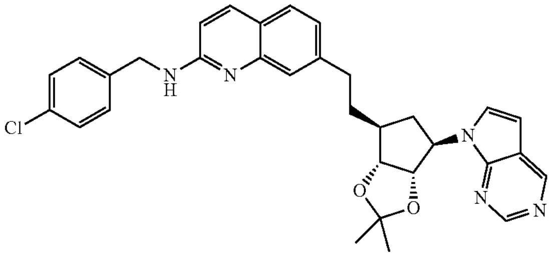 [SMILES: CC1(C)O[C@@H]2[C@@H](CCc3ccc4ccc(NCc5ccc(Cl)cc5)nc4c3)C[C@@H](n3ccc4cncnc43)[C@@H]2O1] | Intermediate 254 |
| 362 | 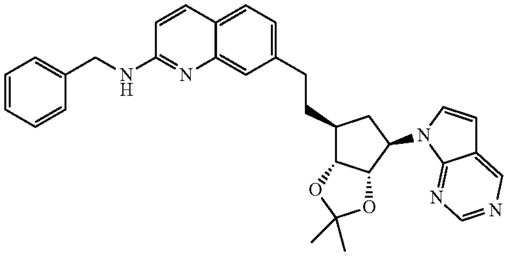 [SMILES: CC1(C)O[C@@H]2[C@@H](CCc3ccc4ccc(NCc5ccccc5)nc4c3)C[C@@H](n3ccc4cncnc43)[C@@H]2O1] | Intermediate 254 |
| 401 | 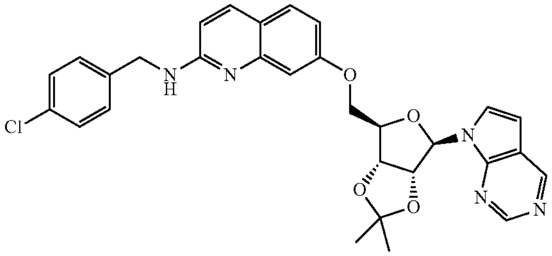 [SMILES: CC1(C)O[C@@H]2[C@H](O1)[C@@H](COc1ccc3ccc(NCc4ccc(Cl)cc4)nc3c1)O[C@H]2n1ccc2cncnc21] | Intermediate 264 |
| 402 | 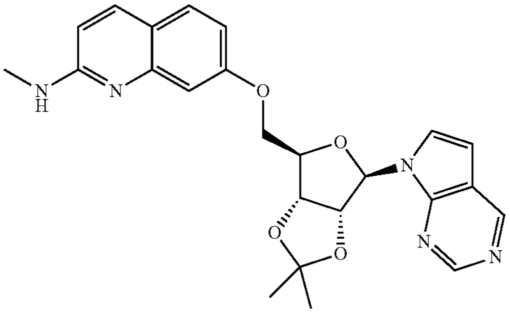 [SMILES: CNc1ccc2ccc(OC[C@H]3O[C@@H](n4ccc5cncnc54)[C@@H]4OC(C)(C)O[C@@H]43)cc2n1] | Intermediate 270 |

Example A73

Preparation of Intermediate 403

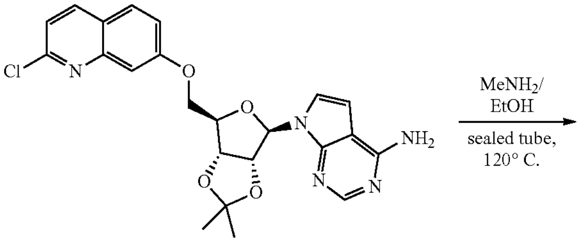

intermediate 119

-continued

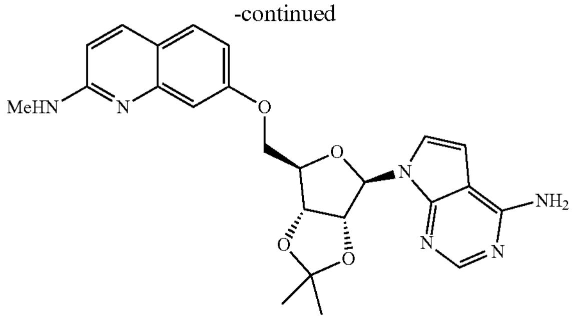

intermediate 403

A mixture of intermediate 119 (600 mg, 0.82 mmol) and $CH_3NH_2$/EtOH (5 mL) in EtOH (25 mL) were stirred at 120° C. overnight in a sealed tube. The reaction mixture was concentrated to give intermediate 403 (600 mg) which used in the next step without further purification.

Example A74

Preparation of Intermediate 404

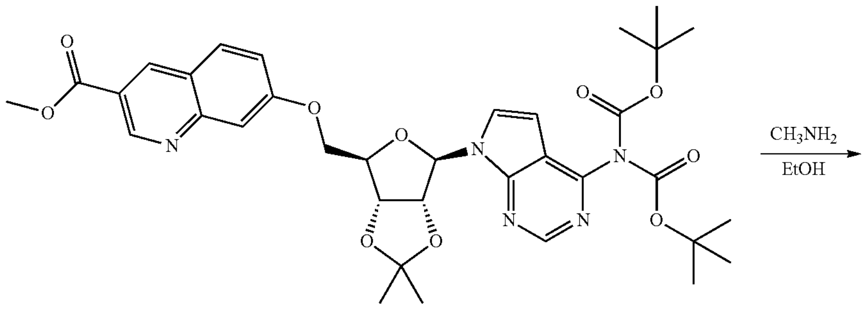

intermediate 228

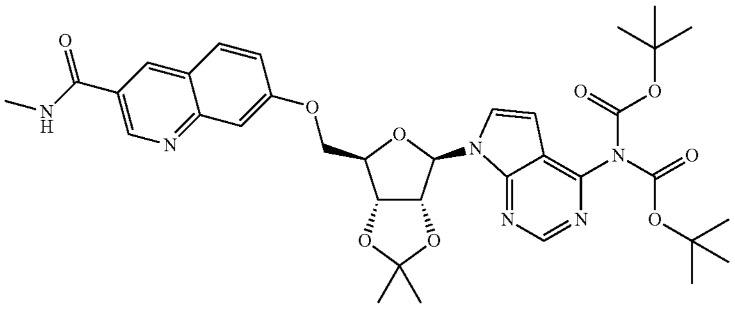

intermediate 404

Intermediate 228 (350 mg, 0.5 mmol) and methylamine (15 ml, 2 M) in EtOH were stirred at 120° C. for 1.5 hours in a microwave. The mixture was concentrated in vacuo to give intermediate 404 as yellow solid. The crude product was used in the next step directly without purification.

Example A75

Step 1

Preparation of Intermediate 363

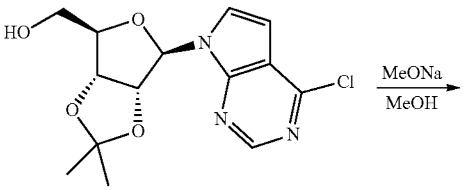

intermediate 1

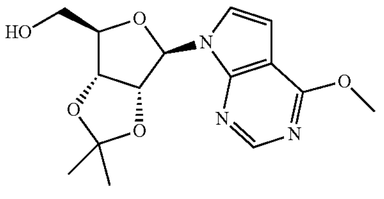

intermediate 363

A mixture of intermediate 1 (250 mg, 0.77 mmol) and MeONa (331.5 mg, 6.14 mmol) in MeOH was stirred at room temperature for 1 h. The mixture was diluted with water (20 mL), and was extracted with $CH_2Cl_2$ (50 mL×3). The organic phase was washed with brine (10 mL), dried over $Na_2SO_4$, filtered and concentrated to give intermediate 363 (250 mg, 96% yield) which was used for the next reaction step without further purification.

Step 2

Preparation of Intermediate 364

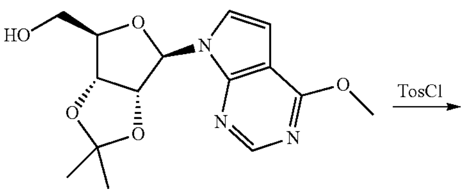

intermediate 363

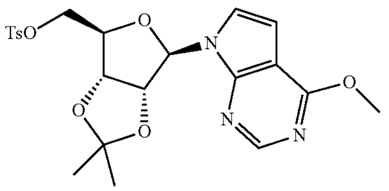

intermediate 364

TosCl (0.415 g, 2.18 mmol) was added dropwise into the mixture of intermediate 363 (0.35 g, 1.1 mmol), triethylamine (0.455 mL, 3.27 mmol) and 4-dimethylaminopyridine (67 mg, 0.545 mmol) in dichloromethane (5 mL) under ice cooling. The mixture was stirred at room temperature for 3 h. The mixture was quenched with water (10 mL) and extracted with $CH_2Cl_2$ (30 mL×3). The organic phase was washed with brine (10 mL), dried over $Na_2SO_4$, filtered and concentrated. Then residue was purified by column chromatography (eluent: Petroleum ether/ethyl acetate ratio 1/0 to 3/1). The product fractions were collected and the solvent was evaporated to afford intermediate 364 (446 mg, 86% yield) as an oil.

Step 3

Preparation of Intermediate 365

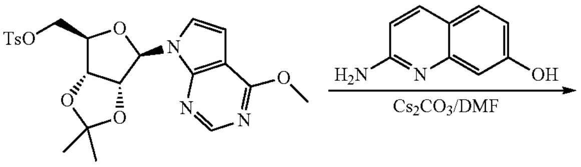

intermediate 364

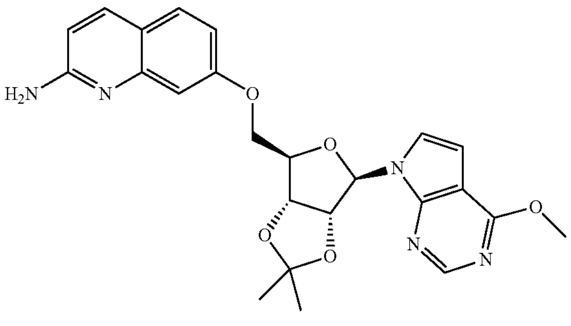

intermediate 365

A mixture of intermediate 364 (446 mg, 0.94 mmol), 2-amino-7-hydroxyquinoline (167 mg, 1.04 mmol) and $Cs_2CO_3$ (1.02 g, 3.13 mmol) in DMF (5 mL) was stirred at room temperature overnight. The mixture was filtered, and the solvent was evaporated. The residue was purified by column chromatography (eluent: ethyl acetate). The product fractions were collected and the solvent was evaporated to afford intermediate 365 (257.3 mg, 53.3% yield) as solid.

Example A76

Preparation of Intermediate 366

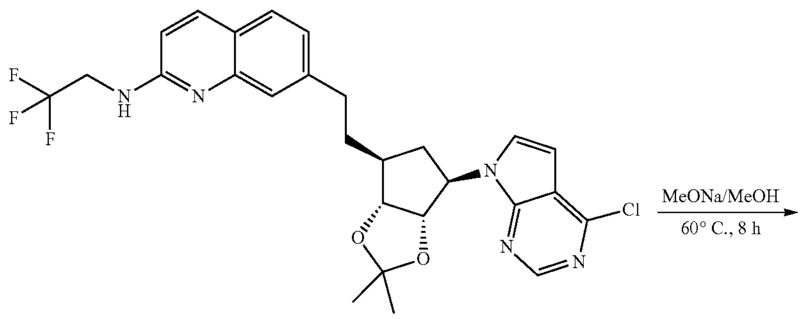

intermediate 306

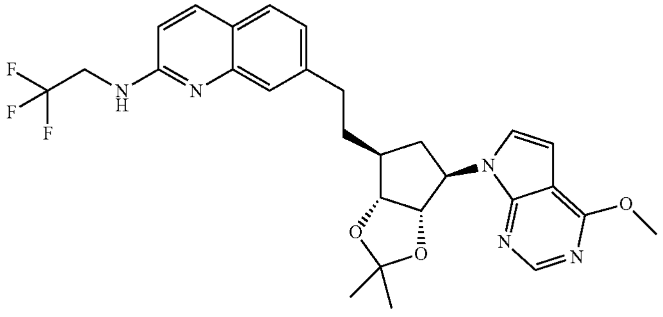

intermediate 366

A mixture of intermediate 306 (400 mg, 0.73 mmol) and MeONa (158.2 mg, 2.93 mmol) in MeOH (10 mL) was stirred at 60° C. for 10 h. The mixture was diluted with water (20 mL), extracted with $CH_2Cl_2$ (50 mL×3). The organic phase was washed with brine (10 mL), dried over $Na_2SO_4$, filtered and concentrated to give intermediate 366 which used in the next step without further purification.

Below intermediates were prepared by an analogous reaction protocol as was used for the preparation of intermediate 366 using the appropriate starting materials (Table 39).

TABLE 39

| Int. | Structure | Starting materials |
|---|---|---|
| 367 | 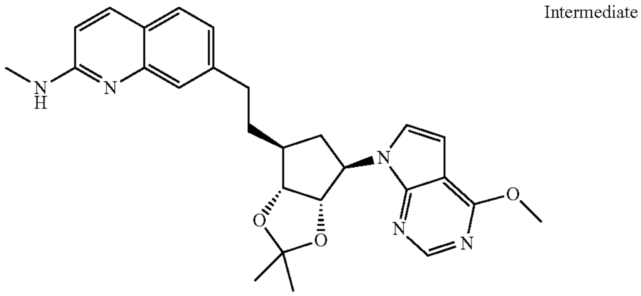 | Intermediate 248 |
| 368 | 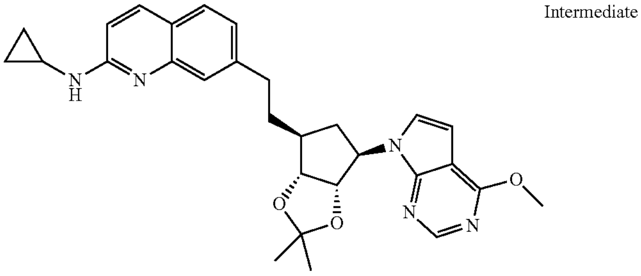 | Intermediate 309 |

TABLE 39-continued
| Int. | Structure | Starting materials |
| --- | --- | --- |
| 369 | 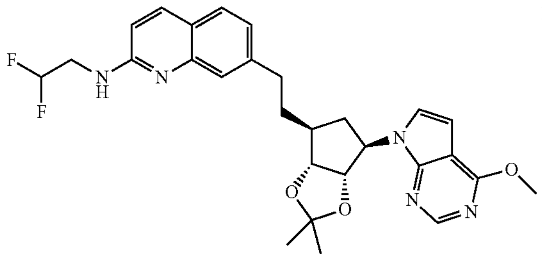 [SMILES: COc1ncnc2c1ccn2[C@@H]1C[C@H](CCc2ccc3ccc(NCC(F)F)nc3c2)[C@H]2OC(C)(C)O[C@H]21] | Intermediate 162 |
| 366 | 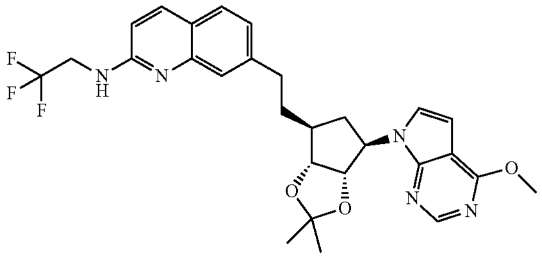 [SMILES: COc1ncnc2c1ccn2[C@@H]1C[C@H](CCc2ccc3ccc(NCC(F)(F)F)nc3c2)[C@H]2OC(C)(C)O[C@H]21] | Intermediate 306 |
| 371 | 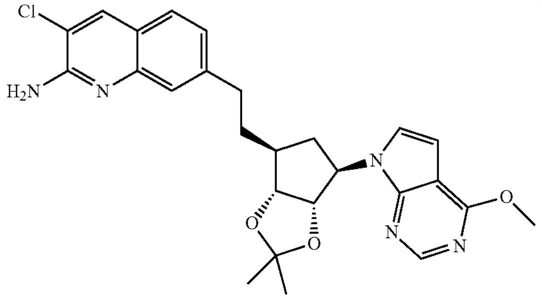 [SMILES: COc1ncnc2c1ccn2[C@@H]1C[C@H](CCc2ccc3cc(Cl)c(N)nc3c2)[C@H]2OC(C)(C)O[C@H]21] | Intermediate 183 |
| 372 | 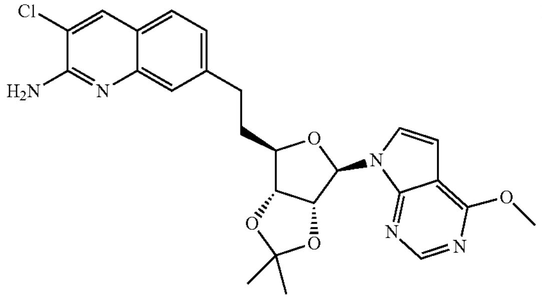 | Intermediate 327 |
| 373 | 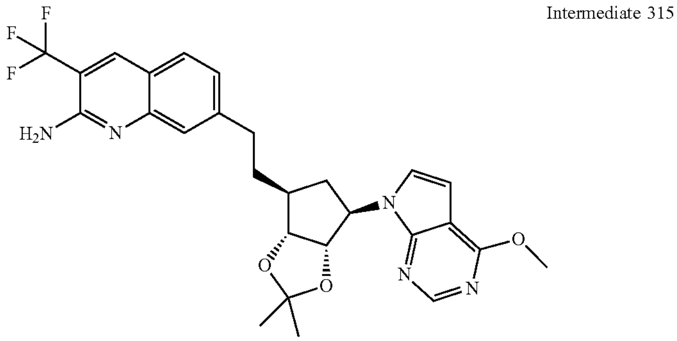 | Intermediate 315 |

TABLE 39-continued
| Int. | Structure | Starting materials |
|---|---|---|
| 374 | 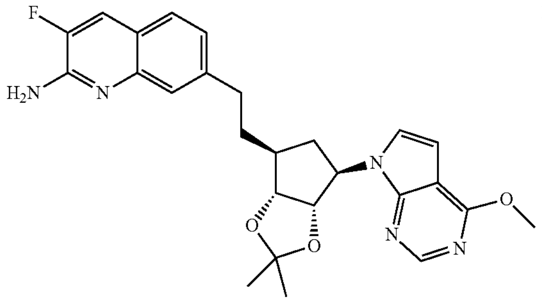 [SMILES: COc1ncnc2c1ccn2[C@@H]1C[C@H](CCc2ccc3cc(F)c(N)nc3c2)[C@H]2OC(C)(C)O[C@H]21] | Intermediate 330 |
| 375 | 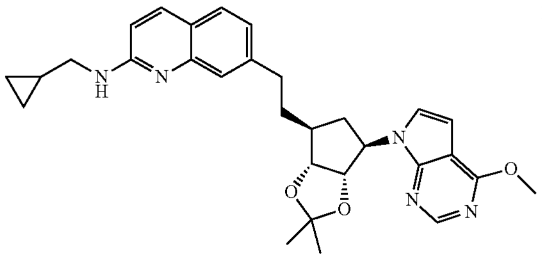 [SMILES: COc1ncnc2c1ccn2[C@@H]1C[C@H](CCc2ccc3ccc(NCC4CC4)nc3c2)[C@H]2OC(C)(C)O[C@H]21] | Intermediate 159 |
| 471 | 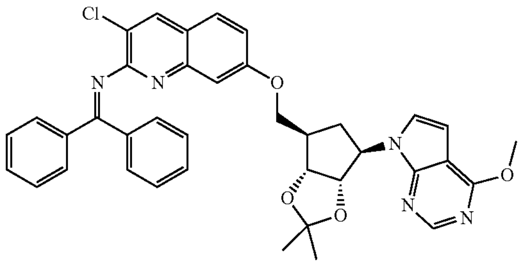 [SMILES: COc1ncnc2c1ccn2[C@@H]1C[C@H](COc2ccc3cc(Cl)c(N=C(c4ccccc4)c4ccccc4)nc3c2)[C@H]2OC(C)(C)O[C@H]21] | Intermediate 469 |
| 475 | 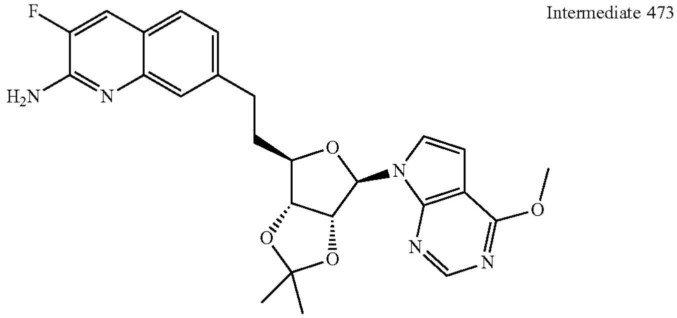 | Intermediate 473 |

Example A76

Preparation of Intermediate 472

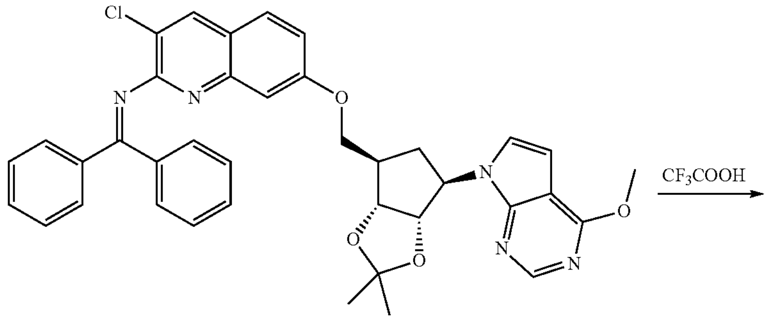

intermediate 471

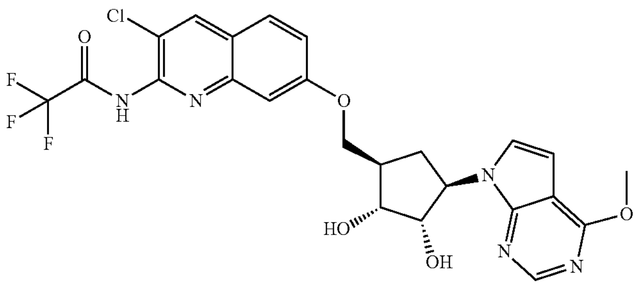

intermediate 472

Intermediate 471 (900 mg, 1.36 mmol) was dissolved in TFA (3 ml).

The reaction mixture was stirred at 50° C. for 7 hours.

The solvent was evaporated to give desired intermediate 472 as an oil.

Below intermediates were prepared by an analogous reaction protocol as was used for the preparation of intermediate 472 using the appropriate starting materials (Table 49).

TABLE 49

| Int. | Structure | Starting materials |
|---|---|---|
| 527 | 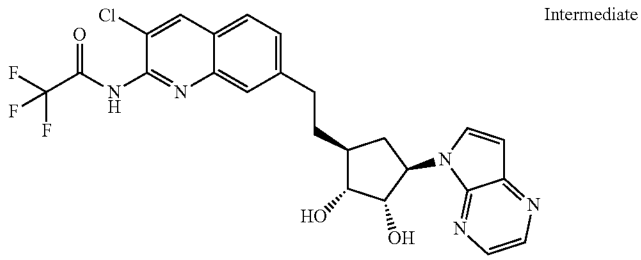 | Intermediate 526 |
| 535 | 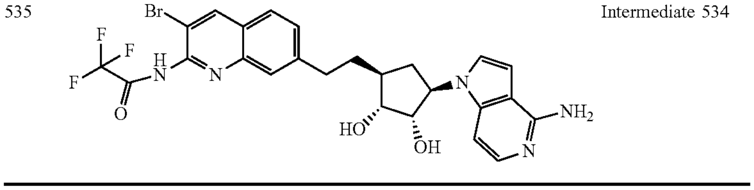 | Intermediate 534 |

Example A77

Preparation of Intermediate 376

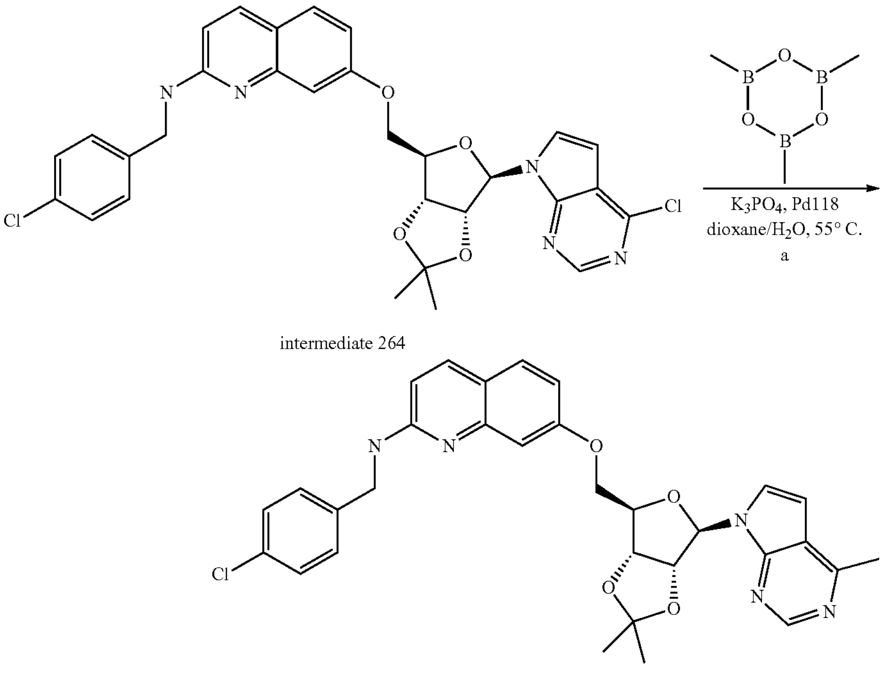

intermediate 264 intermediate 376

To intermediate 264 (330 mg, 0.44 mmol) and $C_3H_9B_3O_3$ (164 mg, 1.3 mmol) in dioxane/$H_2O$ (6 ml, dioxane/$H_2O$ ratio 5/1,) was added $K_3PO_4$ (277 mg, 1.3 mmol) and 1,1'-bis (di-tert-butylphosphino) ferrocene palladiumdichloride (28.3 mg, 0.04 mmol). The mixture was stirred at 80° C. overnight. The mixture was treated with water (30 mL) and extracted with ethyl acetate (40 mL×3), dried ($Na_2SO_4$), filtered and concentrated by vacuum to give the crude product as a brown oil. The crude product was purified by flash column chromatography (gradient eluent: petroleum ether: ethyl acetate from 20/1 to 3/1) to give intermediate 376 (170 mg, 69% yield) as a yellow oil.

Below intermediates were prepared by an analogous reaction protocol as was used for the preparation of intermediate 376 using the appropriate starting materials (Table 40).

TABLE 40

| Int. | Structure | Starting materials |
|---|---|---|
| 377 | 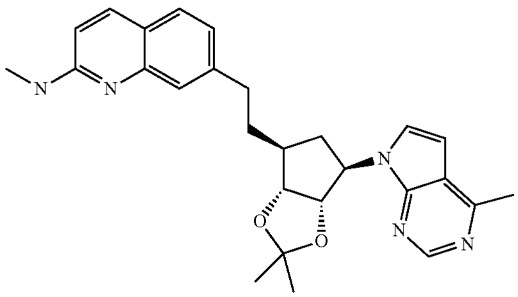 | Intermediate 248 |
| 378 | 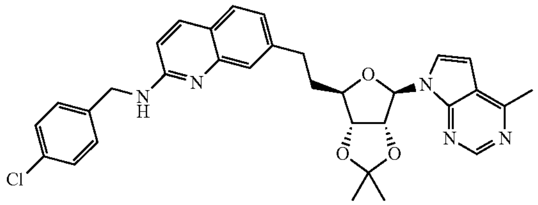 [SMILES: Cc1ncnc2c1ccn2[C@@H]1O[C@H](CCc2ccc3ccc(NCc4ccc(Cl)cc4)nc3c2)[C@H]2OC(C)(C)O[C@H]21] | Intermediate 268 |

TABLE 40-continued
| Int. | Structure | Starting materials |
|---|---|---|
| 379 | 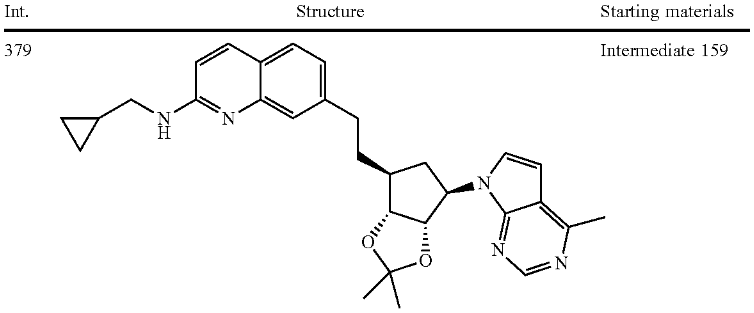 | Intermediate 159 |
| 380 | 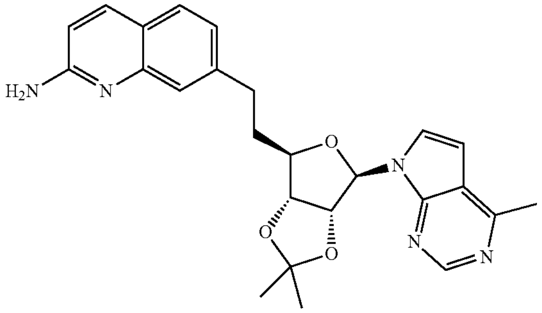 [SMILES: Cc1ncnc2c1ccn2[C@@H]1O[C@H](CCc2ccc3ccc(N)nc3c2)[C@H]2OC(C)(C)O[C@H]21] | Intermediate 266 |
| 381 | 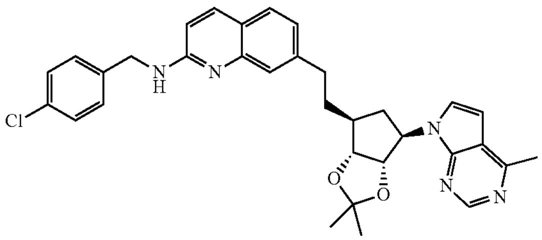 [SMILES: Cc1ncnc2c1ccn2[C@@H]1C[C@H](CCc2ccc3ccc(NCc4ccc(Cl)cc4)nc3c2)[C@H]2OC(C)(C)O[C@H]21] | Intermediate 245 |
Example A78
Step 1
Preparation of Intermediate 382
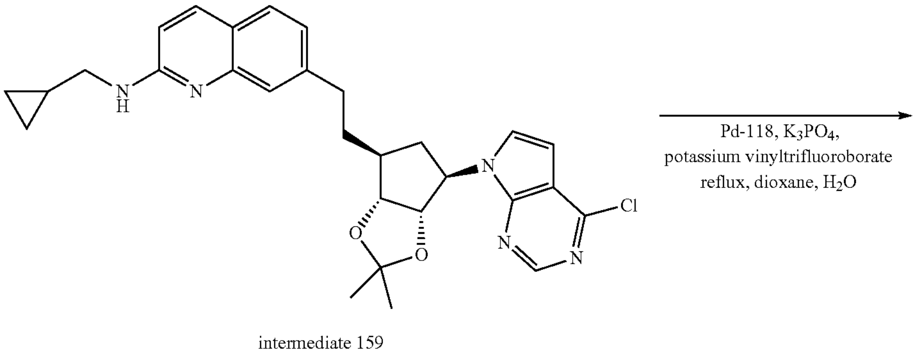
intermediate 159

-continued

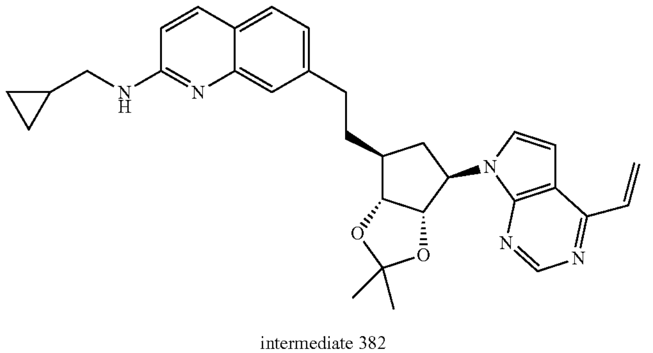

intermediate 382

To a solution of intermediate 159 (0.85 g, 1.28 mmol) in dioxane (20 ml) and $H_2O$ (5 ml) was added potassium vinyltrifluoroborate (223 mg, 1.67 mmol) and potassium phosphate tribasic (544 mg, 2.57 mmol) at room temperature. 1,1'-bis(di-tert-butylphosphino)ferrocene palladium dichloride (42 mg, 0.064 mmol) was added to the above solution under nitrogen atmosphere. The reaction mixture was stirred at 80° C. under nitrogen atmosphere overnight. The mixture was extracted with ethyl acetate (20 ml×2), the organic layers were combined and concentrated under vacuo The residue was purified by chromatography column (gradient eluent: ethyl acetate/petrol ether from 1/10 to 1/1). The desired fractions were collected and concentrated to give product intermediate 382 (400 mg, yield: 60%) as an oil.

Step 2

Preparation of Intermediate 383

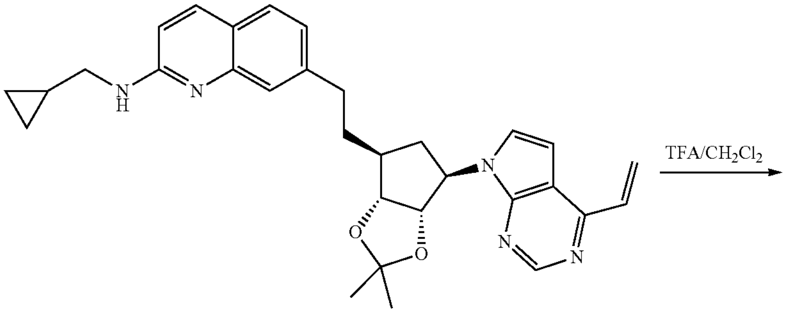

intermediate 382

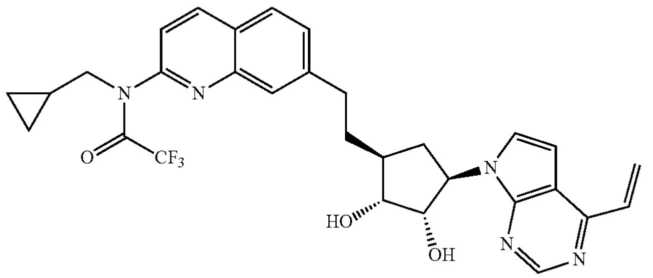

intermediate 383

Trifluroacetic acid (0.5 ml) was added to a solution of intermediate 382 (400 mg, 0.78 mmol) in $CH_2Cl_2$ (10 ml). The mixture was stirred at room temperature for 3 h. The mixture was evaporated under vacuo to give intermediate 383 (300 mg, yield: 48%).

Example A79

Preparation of Intermediates 384 and 385

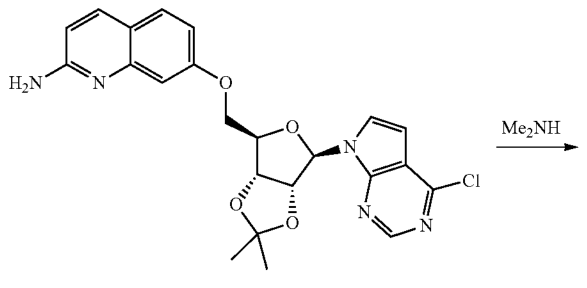

intermediate 262

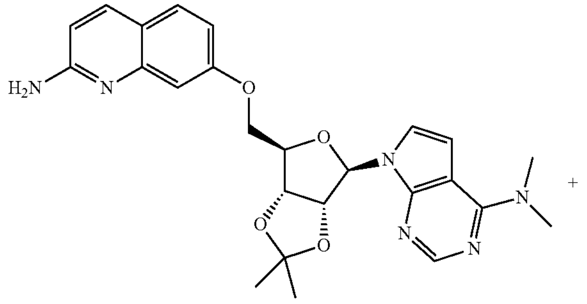

intermediate 384

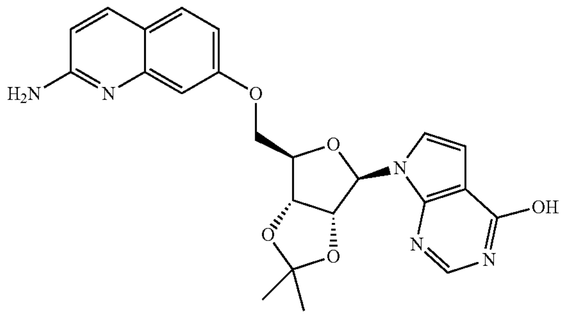

intermediate 385

$Me_2NH$ (20 mL) was added into the mixture of intermediate 262 (200 mg, 0.43 mmol) in dioxane (20 mL) and stirred in sealed tube at 110° C. overnight. The reaction mixture was concentrated to give a mixture of intermediate 384 and intermediate 385 (210 mg) as solid.

Example A80

Step 1

Preparation of Intermediate 412

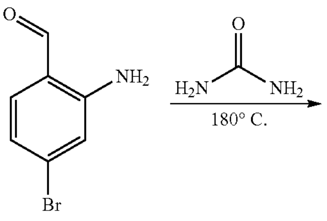

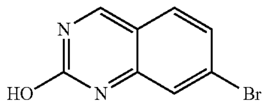

intermediate 412

A mixture of 2-amino-4-bromo-benzaldehyde (13 g, 65 mmol) and urea (54.6 g, 910 mmol) was heated to 180° C. in an oil bath for 2 hours. Then the reaction was cooled to room temperature and $H_2O$ (500 mL) was added. The reaction mixture was stirred at room temperature for 1 hour. The solid was collected by filtration to obtain intermediate 412 (16 g, 93% yield) as white solid.

Step 2

Preparation of Intermediate 413

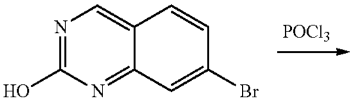

intermediate 412

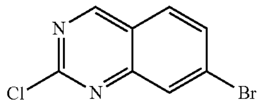

intermediate 413

A mixture of intermediate 412 (16 g, 71 mmol) and $POCl_3$ (280 g, 1.84 mol) was heated to 110° C. in an oil bath under $N_2$ for 3 hours. Then the reaction was cooled to room temperature and poured into ice/water (4000 g). The reaction mixture was stirred at room temperature for 1 hour and was extracted with ethyl acetate (2000 mL×2). The organic layer washed with brine and dried over anhydrous $Na_2SO_4$. The solvent was evaporated under vacuum to give the crude product. The crude product was purified by chromatography (ethyl acetate/petroleum ether 0/1 to 1/5) to obtain intermediate 413 (10 g, 53% yield) as white solid.

Step 3

Preparation of Intermediate 386

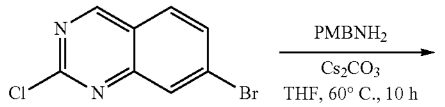

intermediate 413

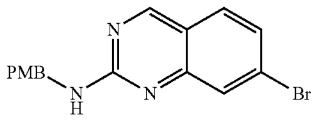

intermediate 386

A mixture of intermediate 413 (4 g, 16.5 mmol), 4-methoxybenzylamine (3.4 g, 24.6 mmol) and cesium carbonate (15 g, 49.3 mmol) in THF (100 mL) was stirred at room temperature for 12 hours. The reaction mixture was filtered and the filtrate was evaporated under vacuum to give the crude product. The crude product was purified by chromatography (ethyl acetate/petroleum ether 0/1 to 1/10) to obtain intermediate 386 (2.3 g, 29%) yield) as oil.

Below intermediates were prepared by an analogous reaction protocol as was used for the preparation of intermediate 386 using the appropriate starting materials (Table 42).

TABLE 42

| intermediates | Structure | Starting materials |
|---|---|---|
| 276 | 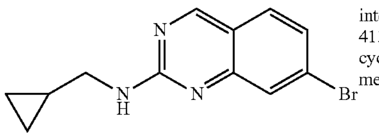 | intermediate 413 cyclopropylmethylamine |
| 287 | 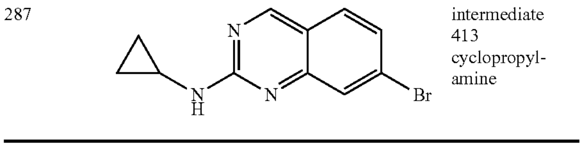 | intermediate 413 cyclopropylamine |

Step 4

Preparation of Intermediate 387

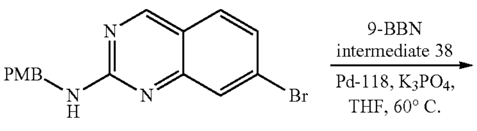

intermediate 386

-continued

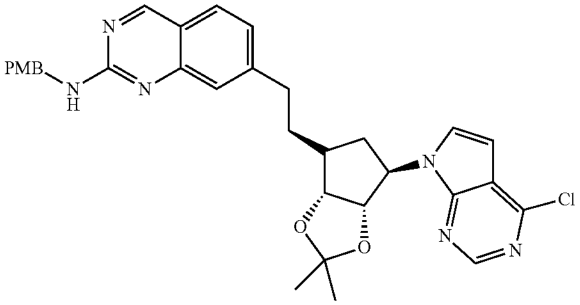

intermediate 387

Intermediate 38 (1.5 g, 4.69 mmol) in 9-BBN (0.5 M in THF, 56.3 mL, 28.1 mmol) was refluxed for 1 h under $N_2$. The mixture was cooled to room temperature, then $K_3PO_4$ (2.98 g, 14.1 mmol) in $H_2O$ (5 mL) was added, followed by THF (40 mL), intermediate 386 (2.1 g, 6.1 mmol) and Pd-118 (61.1 mg, 0.094 mmol). The resulting mixture was refluxed overnight. The mixture was diluted with $H_2O$ (50 mL), extracted with ethyl acetate (150 mL), the organic phase was dried by $Na_2SO_4$, then filtered and concentrated in vacuo to give the crude product. The crude product was purified by chromatography (ethyl acetate/petroleum ether 0/1 to 1/10) to give intermediate 387 (1.3 g, yield: 47%) as an oil.

Step 5

Preparation of Intermediate 388

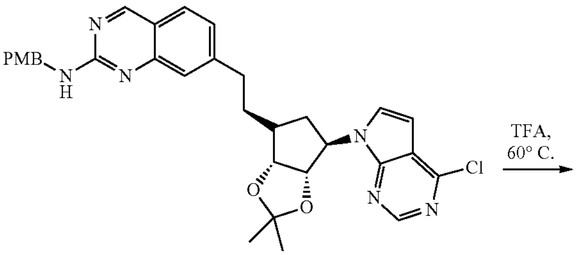

intermediate 387

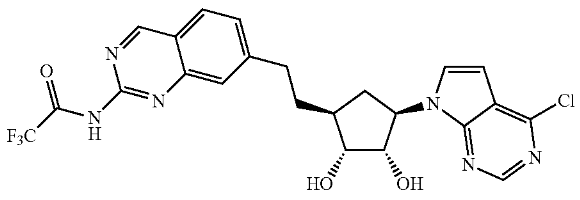

intermediate 388

Intermediate 387 (500 mg, 0.85 mmol) was dissolved in TFA (10 mL) and stirred at 60° C. for 1 hour. The mixture was concentrated to obtain crude intermediate 388 (1 g as a solid.

Example A81

Step 1

Preparation of Intermediate 389

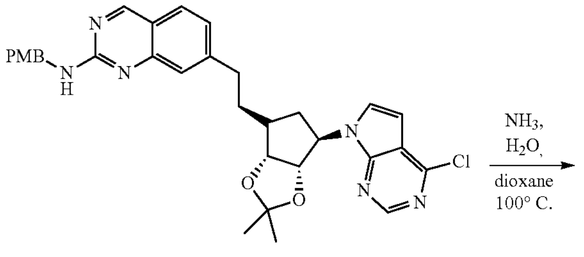

intermediate 387

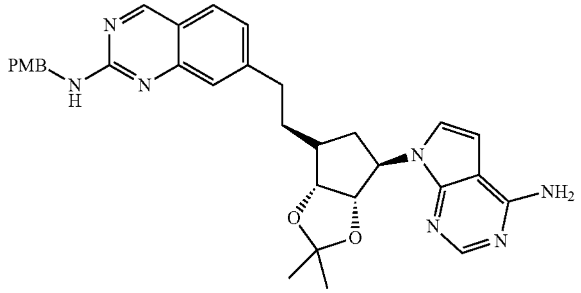

intermediate 389

A mixture of intermediate 387 (450 mg, 0.77 mmol) and $NH_3 \cdot H_2O$ (10 mL) in dioxane (10 mL) was heated to 80° C. for 24 hours in a sealed tube. The reaction mixture was extracted with ethyl acetate (50 ml×3). The organic layers were separated, dried with $Na_2SO_4$, and the solvent was evaporated to obtain intermediate 389 (290 mg, 66.6% yield) as oil.

Step 2

Preparation of Intermediate 390

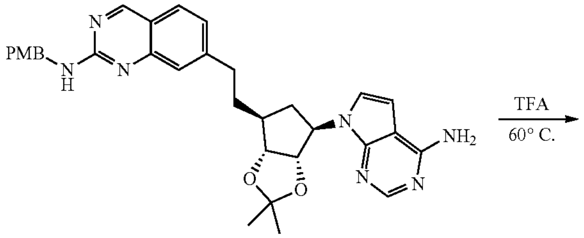

intermediate 389

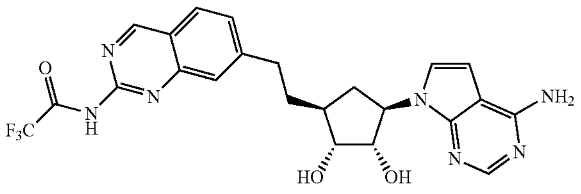

intermediate 390

Intermediate 389 (290 mg, 0.51 mmol) was dissolved in TEA (10 mL) and stirred at 60° C. for 1 hour. The mixture was concentrated to obtain crude intermediate 390 (300 mg) as an oil.

Example A82

Preparation of Intermediate 347

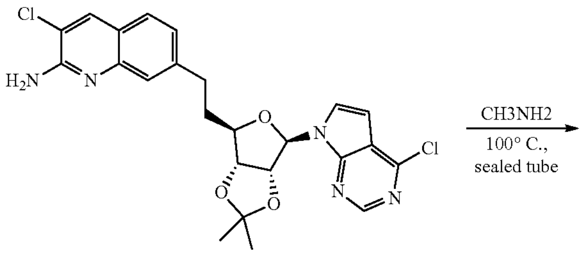

intermediate 327

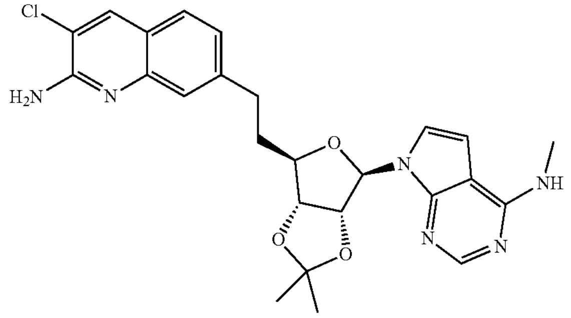

intermediate 347

A mixture of intermediate 327 (1100 mg, 2.20 mmol) in methylamine/ethanol (30 ml, 40%) was heated in a sealed tube at 80° C. for 24 h. The organic phase was concentrated to obtain intermediate 347 (1.2 g, 99% yield)

Example A83

Preparation of Intermediate 372

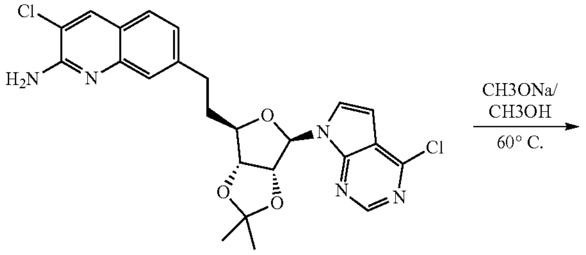

intermediate 327

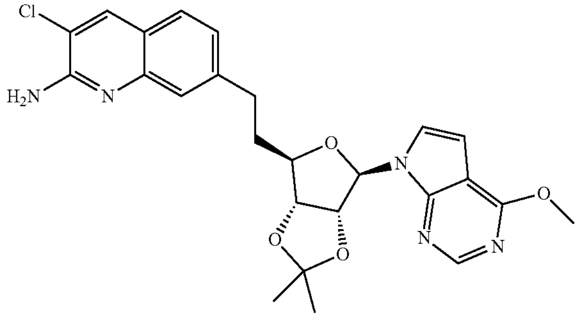

intermediate 372

A mixture of intermediate 327 (550 mg, 1.1 mmol), sodium methoxide (356.3 mg, 6.60 mmol) in methanol (10 ml) was refluxed at 60° C. for 12 h. The reaction mixture was evaporated under vacuum. Water (10 ml) was added and the mixture was extracted with ethyl acetate (10 mL×2), the organic layers were combined and evaporated under vacuum to obtain intermediate 372 (510 mg, 75% yield) as an oil.

Example A84

Step 1

Preparation of Intermediate 393

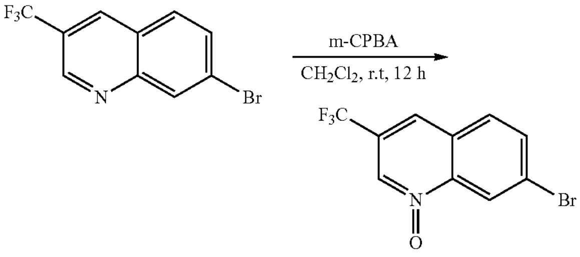

intermediate 393

7-bromo-3-(trifluoromethyl)quinoline) (1.0 g, 3.62 mmol) was dissolved in DCM (30 mL), m-CPBA (1.25 g, 7.25 mmol) was added into the mixture in portions. The resulting mixture was stirred at room temperature overnight. The reaction mixture was poured into a mixture of saturated $Na_2S_2O_3$ (50.0 mL) and 1N NaOH (50 mL) aqueous solution. The mixture was then extracted with DCM (200 mL×2), and the combined organic phases were washed with brine (100 mL), dried over anhydrous $Na_2SO_4$, filtered and concentrated to afford the product intermediate 393 (1.0 g, 80% yield) as a brown solid, which was used in the next step without further purification.

Step 2

Preparation of Intermediate 394

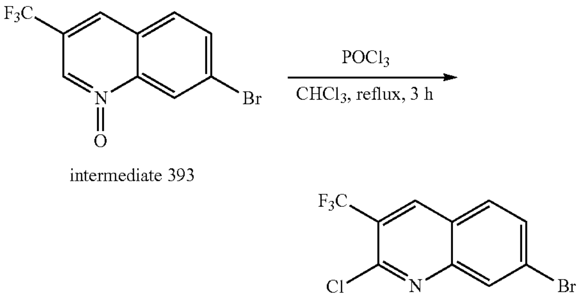

intermediate 393 intermediate 394

Intermediate 393 (200 mg, 0.685 mmol) was taken up into $CHCl_3$ (10 mL). $POCl_3$ (1.0 mL) was added at room temperature. The reaction mixture was stirred at 80° C. for 12 hours. The solvent was removed under reduced pressure, the residue was triturated with ethyl acetate (50 mL) and sat. $Na_2CO_3$ (50 mL), the organic layer was separated, the organic layer was washed with brine (50 mL) and dried over anhydrous $Na_2SO_4$. The solvent was removed under reduced pressure to give intermediate 394 (200 mg, 83%) as a brown oil.

Step 3

Preparation of Intermediate 314

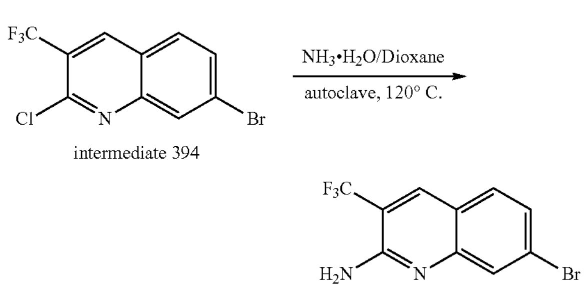

intermediate 394 intermediate 314

Intermediate 394 (2.2 g, 5.43 mmol) was dissolved in dioxane (30 mL) and $NH_3H_2O$ (30 mL) was added. The reaction mixture was stirred at 120° C. in an autoclave overnight. The solvent was removed under reduced pressure, the residue was purified by column chromatography (EtOAc/petroleum ether ratio: 0/10 to 1/10) to afford intermediate 314 (1.4 g, 88.6% yield) as a white solid.

Example A85

Preparation of Intermediate 348

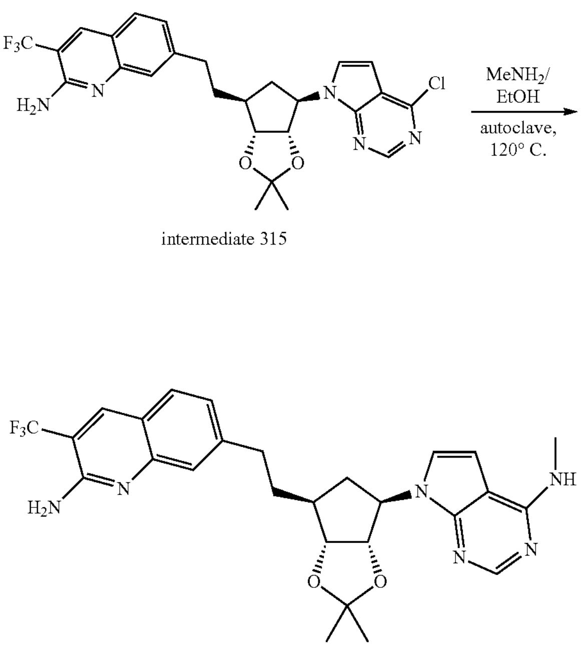

intermediate 315 intermediate 348

Intermediate 315 (420 mg, 0.79 mmol) was dissolved in an ethanol solution of $MeNH_2$ (30%, 30 mL) and EtOH (30 mL). The reaction mixture was stirred at 100° C. in an autoclave for 12 hours. The solvent was removed under reduced pressure to afford intermediate 348 (450 mg, crude) as a brown solid, which was used in the next step without further purification.

Example A86

Step 1

Preparation of Intermediate 373

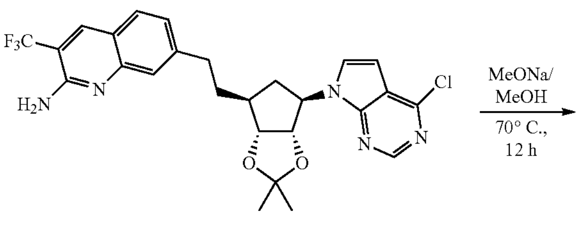

intermediate 315

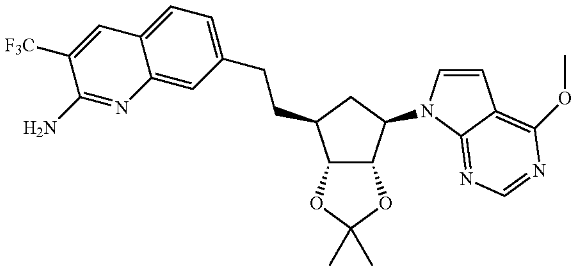

intermediate 373

Intermediate 315 (300 mg, 0.56 mmol) was dissolved in MeOH (20 ml), MeONa (483 mg, 4.46 mmol) was added. The reaction mixture was stirred at 70° C. for 12 hours. The solvent was removed under reduced pressure to afford intermediate 373 (340 mg, crude) as a brown solid, which was used in the next step without further purification.

Example A87

Step 1

Preparation of Intermediate 395

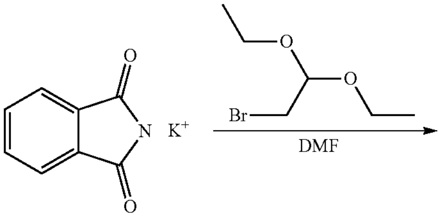

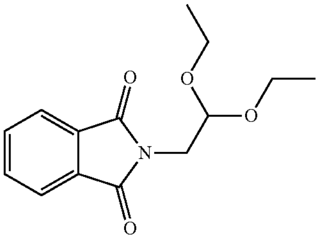

intermediate 395

1H-Isoindole-1,3(211)-dione, potassium salt (1:1) (50 g, 221.9 mmol) and 2-bromo-1,1-diethoxy-ethane (54.7 g, 277.4 mmol) in DMF were stirred at 150° C. for 4 hours. The DMF was removed under reduced pressure. The residue was purified by column chromatography (elution: petroleum ether/ethyl acetate ratio 5/1) to afford intermediate 395 (40 g, yield: 64%) as a white solid.

Step 2

Preparation of Intermediate 396

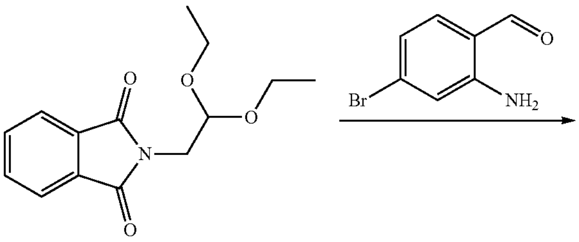

intermediate 395

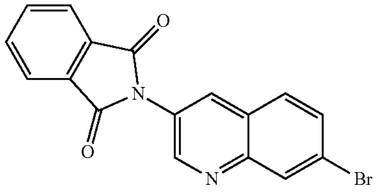

intermediate 396

A mixture of intermediate 395 (22.1 g, 84.0 mmol), 4-bromo-2-amino-benzaldehyde (14 g, 70.0 mmol) and p-$MeC_6H_4SO_3H \cdot H_2O$ (13.3 g, 70.0 mmol) in PhMe (200 mL) was refluxed for 4 hours. The mixture was cooled and filtered. The solid was washed with toluene to give the crude PTSA-salt of the product as a brown solid. The solid was stirred in saturated aq. sodium bicarbonate and extracted with dichloromethane The solvent was evaporated and the residual solid was slurried in ethanol and collected to obtain intermediate 396 (14.2 g, 56% yield).

Step 3

Preparation of Intermediate 397

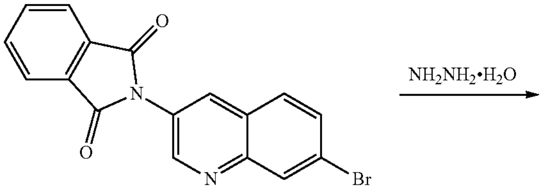

intermediate 396

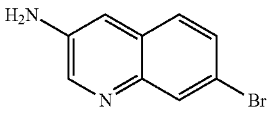

intermediate 397

A suspension of intermediate 396 (14 g, 38.5 mmol) in ethanol (150 mL) was treated with $NH_2NH_2 \cdot H_2O$ (4.5 g, 76.9 mmol) and was refluxed for 1 hour. The mixture was allowed to cool and filtered. The filtrate was collected and evaporated to obtain intermediate 397 (8.6 g, 94% yield).

Step 4

Preparation of Intermediate 398

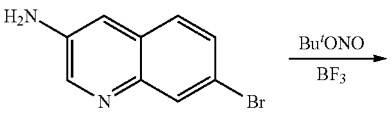

intermediate 397

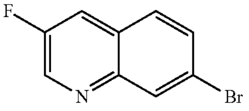

intermediate 398

Intermediate 397 (8 g, 35.86 mmol) was dissolved in PhCl (80 mL). Boron trifluoride diethyl etherate (4.45 mL) was added drop-wise over 10 mins. The mixture was heated to 60° C. Tert-butyl nitrite (6.1 mL) was added drop-wise over 20 mins at this temperature. The reaction solution was heated to 100° C. and stirred for 1 hour. The mixture was cooled and poured into an ice/aqueous sodium bicarbonate solution. The mixture was extracted with $CH_2Cl_2$ (500 mL×2). The combined organic layers were washed with brine, dried ($Na_2SO_4$) and concentrated by vacuum to give the crude product. The crude product was purified by column chromatography (gradient eluent: petroleum ether/ethyl acetate from 1/0 to 20/1) to obtain intermediate 398 (1.57 g, 19% yield).

Step 5

Preparation of Intermediate 399

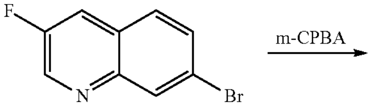

intermediate 398

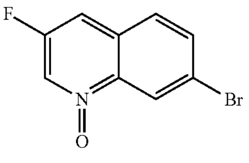

intermediate 399

A mixture of intermediate 398 (1.57 g, 6.95 mmol) and m-CPBA (2.1 g, 10.4 mmol) in $CHCl_3$ (30 mL) was stirred at 50° C. overnight. The reaction solution was quenched with a solution of $Na_2SO_3$ (50 mL) and basified with a solution of $NaHCO_3$ (50 mL). The mixture was extracted with $CH_2Cl_2$ (300 mL×3). The combined organic layers were washed with brine, dried ($Na_2SO_4$), filtered and concentrated by vacuum to obtain intermediate 399 (2 g, 97.2% yield) as a brown solid.

Step 6

Preparation of Intermediate 400

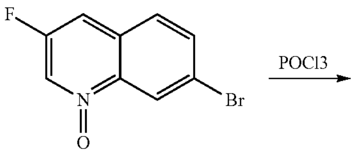

intermediate 399

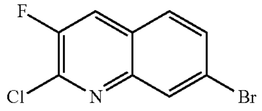

intermediate 400

The mixture of intermediate 399 (2 g, 6.75 mmol) and $POCl_3$ (10.6 g, 69 mmol) in $CHCl_3$ (40 mL) was refluxed for 3 hours. The reaction solution was poured into water (100 mL), basified with a solution of $NaHCO_3$ (80 mL) to pH>7 and stirred for 5 mins. The mixture was extracted with DCM (500 mL×3). The combined organic layers were washed with brine, dried ($Na_2SO_4$), filtered and concentrated in vacuum to give the crude product as yellow solid. The crude product was purified by column chromatography over silica gel (petroleum ether/ethyl acetate: ratio 1/0 to petroleum ether/ethyl acetate 10/1). The pure fractions were collected and the solvent was evaporated under vacuum to give intermediate 400 (1.4 g, 78% yield) as a white solid.

Step 7

Preparation of Intermediate 329

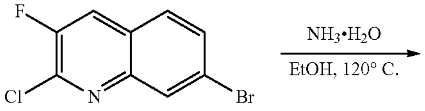

intermediate 400

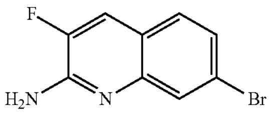

intermediate 329

A mixture of intermediate 400 (600 mg, 2.3 mmol) and $NH_3 \cdot H_2O$ (15 mL) in $CH_3CH_2OH$ (15 mL) was heated in a sealed tube at 120° C. overnight. The mixture was concentrated in vacuum. The residue was purified by column chromatography over silica gel (petroleum ether/ethyl acetate from 20/1 to petroleum ether/ethyl acetate 1/1). The pure fractions were collected and the solvent was evaporated under vacuum to give intermediate 329 (390 mg, 67% yield) as white solid.

Example A88

Step 1

Preparation of Intermediate 330

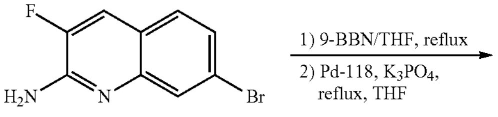

intermediate 329

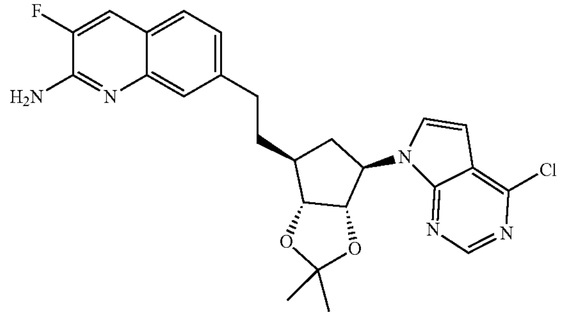

intermediate 330

Intermediate 38 (470 mg, 1.47 mmol) in 9-BBN (0.5 M in THF, 11.8 mL, 5.9 mmol) was refluxed for 1 h under $N_2$. The mixture was cooled to room temperature, then $K_3PO_4$ (936.6 mg, 4.41 mmol) in $H_2O$ (2 mL) was added, followed by THF (20 mL), intermediate 329 (390 mg, 1.62 mmol) and Pd-118 (19.2 mg, 0.029 mmol). The resulting mixture was refluxed overnight. The mixture was diluted with $H_2O$ (80 mL) and extracted with ethyl acetate (150 mL). The organic phase was dried by $Na_2SO_4$, then filtered and concentrated in vacuo to give the crude product. The crude product was purified by chromatography (ethyl acetate/petroleum ether from 0/1 to 1/3) to give intermediate 330 (460 mg, 55% yield) as a yellow oil.

Step 2

Preparation of Intermediate 374

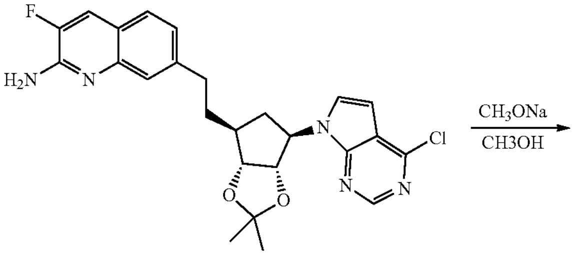

intermediate 330

-continued

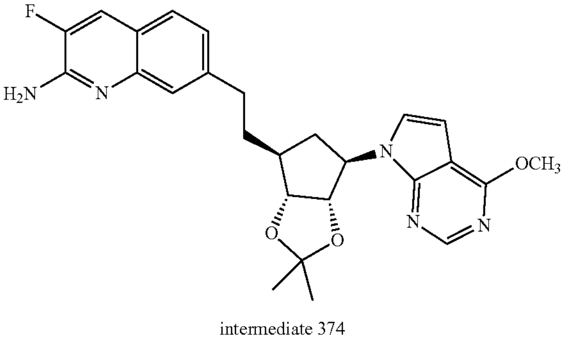

intermediate 374

A mixture of intermediate 330 (400 mg, 0.70 mmol) and $CH_3ONa$ (380.17 mg, 7.04 mmol) in $CH_3OH$ (15 mL) was refluxed overnight. The mixture was concentrated by vacuum. The residue was treated with water (60 mL) and extracted with EtOAc (100 mL×3). The combined organic layers were washed with brine, dried ($Na_2SO_4$), filtered and concentrated under reduced pressure to give intermediate 374 (350 mg, 87% yield) as a brown oil.

Example A89

Step 1

Preparation of Intermediate 323

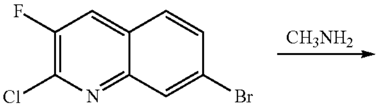

intermediate 400

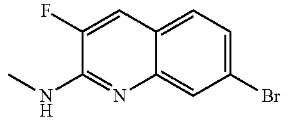

intermediate 323

A solution of intermediate 400 (400 mg, 1.54 mmol) in $CH_3NH_2$ (40% solution in 20 ml $CH_3CH_2OH$) was heated in sealed tube at 120° C. overnight. The mixture was concentrated in vacuum. The crude product was purified by column chromatography (gradient eluent: petroleum ether/ethylacetate from 20/1 to 5/1) to give intermediate 323 (350 mg, 89% yield) as yellow solid.

Step 2

Preparation of Intermediate 324

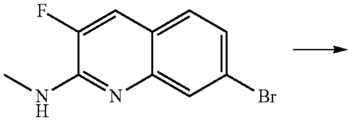

intermediate 323

-continued

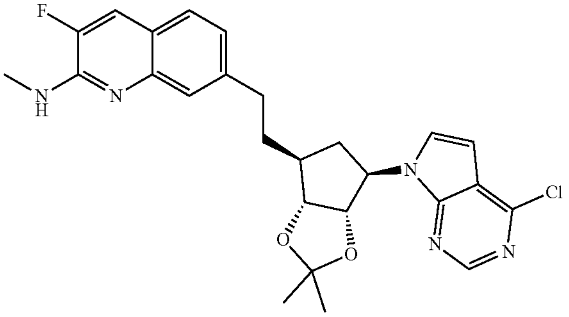

intermediate 324

Intermediate 38 (365 mg, 1.14 mmol) in 9-BBN (0.5 mol/L in THF, 11.4 mL, 5.72 mmol) was refluxed for 1 h under $N_2$. The mixture was cooled to room temperature, then $K_3PO_4$ (728 mg, 3.43 mmol) in $H_2O$ (2 mL) was added, followed by THF (20 mL), intermediate 323 (350 mg, 1.37 mmol) and Pd-118 (14.90 mg, 0.023 mmol). The resulting mixture was refluxed overnight. The mixture was diluted with $H_2O$ (80 mL) and extracted with ethyl acetate (100 mL). The organic phase was dried with $Na_2SO_4$, filtered and concentrated in vacuo to give the crude product. The crude product was purified by chromatography (ethyl acetate/petroleum ether from 1/10 to 1/5) to give intermediate 324 (350 mg, 61% yield) as a yellow oil.

Step 3

Preparation of Intermediate 350

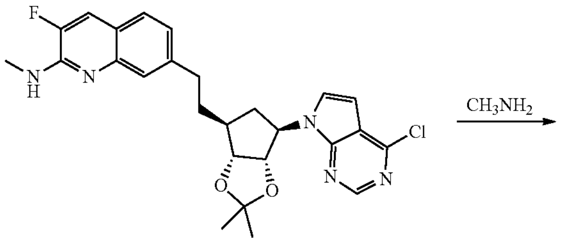

intermediate 324

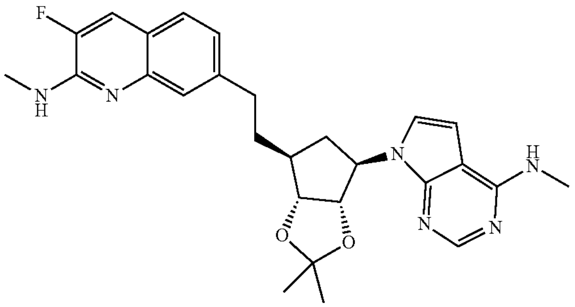

intermediate 350

A solution of intermediate 324 (350 mg, 0.71 mmol) in $CH_3NH_2$ (40% solution in 10 ml EtOH) was heated in sealed tube at 120° C. overnight. The mixture was concentrated by vacuum to give the intermediate 350 (350 mg, 97% yield).

Example A90

Preparation of Intermediate 349

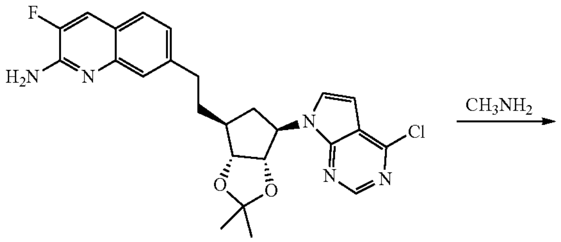

intermediate 330

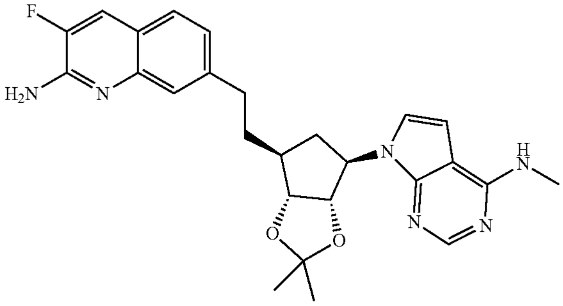

intermediate 349

A solution of intermediate 330 (350 mg, 0.726 mmol) in $CH_3NH_2$ (40% solution in 15 ml $CH_3CH_2OH$) was heated in sealed tube at 120° C. for overnight. The mixture was concentrated by vacuum to give the intermediate 349 (350 mg, 99.9% yield).

Example A91

Step 1

Preparation of Intermediate 414

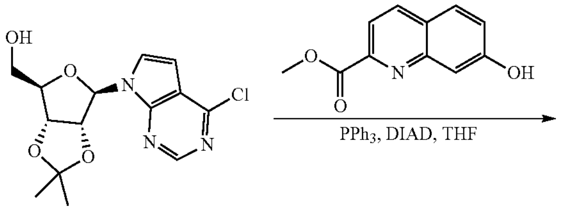

intermediate 1

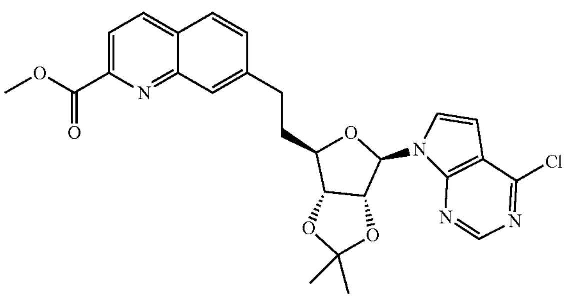

intermediate 414

To the solution of intermediate 1 (1.0 g, 4.9 mmol), 7-hydroxyquinoline-2-methylcarboxylate (1.36 g, 4.18 mmol) and $PPh_3$ (2.58 g, 9.84 mmol) in THF (10 mL) was added DIAD (1.99 g, 9.84 mmol) at 0° C. The mixture was stirred at room temperature overnight under $N_2$. Water (25 mL) was added and the mixture was extracted with ethyl acetate (100 mL×3). The combined organic layers were washed with brine (1000 mL). The organic phase was dried over anhydrous $Na_2SO_4$, filtered and concentrated to give the crude product as an oil. The crude product was purified by column chromatography over silica gel (elution: petroleum ether/ethyl acetate ratio 1/1). The desired fractions were collected and concentrated to give the product intermediate 414 (1.2 g, 31% yield) as a solid.

Step 2

Preparation of Intermediate 415

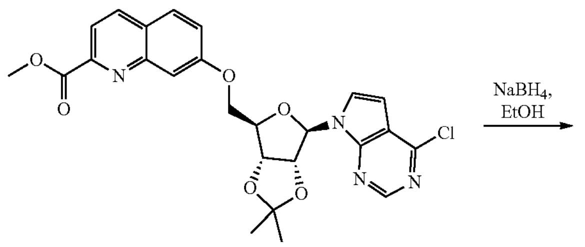

intermediate 414

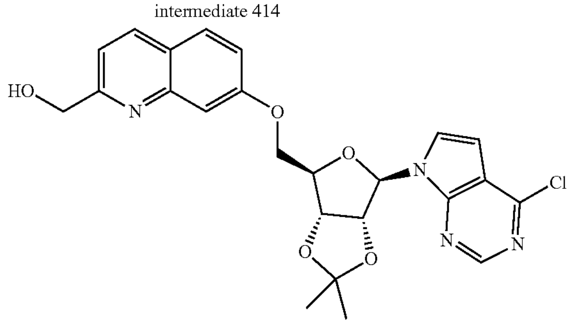

intermediate 415

To a solution of intermediate 414 (600 mg, 1.18 mmol) in EtOH (5 mL) was added $NaBH_4$ (0.132 g, 3.53 mmol) at room temperature under $N_2$. The reaction mixture was stirred at room temperature for 3 hours. Water (20 ml) was added and the mixture was extracted with $CH_2Cl_2$ (50 ml×3). The organic layers were combined, dried ($Na_2SO_4$), filtered and concentrated to give the desired product as an oil. The crude product was purified by column chromatography over silica gel (eluens: ethyl acetate). The desired fractions were concentrated to give the intermediate 415 (0.27 g, 54.3% yield) as a solid.

Step 3

Preparation of Intermediate 416

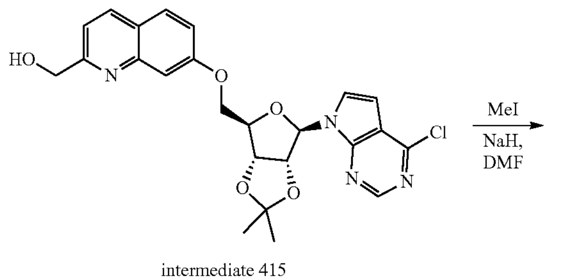

intermediate 415

-continued

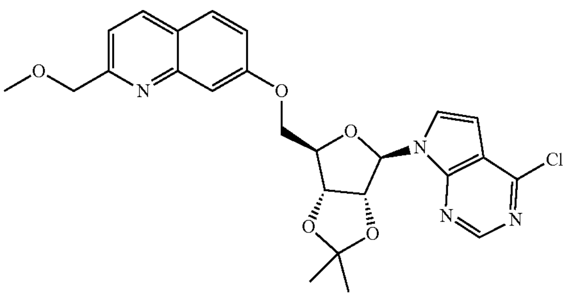

intermediate 416

To a solution of intermediate 415 (0.27 g, 0.56 mmol) in anhydrous DMF (5 mL) was added $NaH_{60\%}$ (33.5 mg, 0.83 mmol). The reaction mixture was stirred at room temperature for 20 min under argon. Then MeI (158 mg, 1.12 mmol) was added dropwise. The reaction mixture was stirred at room temperature for 1 h. The mixture was poured into ice-water (10 mL) and extracted with $CH_2Cl_2$ (40 mL×3). The combined extracts were washed with brine, dried over $Na_2SO_4$, filtered and evaporated to give the product as an oil. The crude product was purified by column (eluens: petroleum ether/ethyl acetate 20/1 to 1/1) to give the intermediate 416 (120 mg, 43% yield) as a solid.

Step 4

Preparation of Intermediate 417

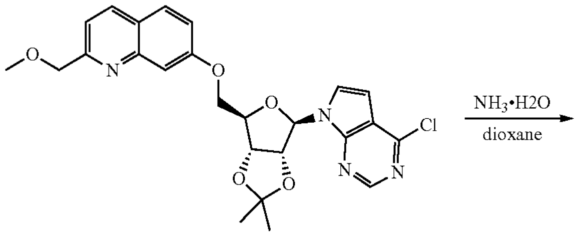

intermediate 416

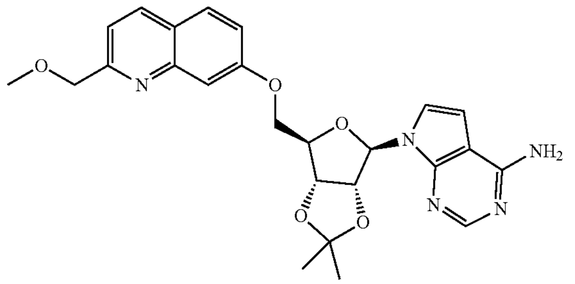

intermediate 417

A solution of intermediate 416 (120 mg, 0.24 mmol) in $NH_3 \cdot H_2O$ (5 mL) and dioxane (5 mL) was stirred in a sealed tube. The mixture was stirred at 90° C. overnight. The reaction was concentrated to give a crude product as an oil. The crude product was purified by prep-TLC (DCM/MeOH: ratio 10/1) to give intermediate 417 (70 mg, 44% yield) as a solid.

Example A92

Step 1

Preparation of Intermediate 418

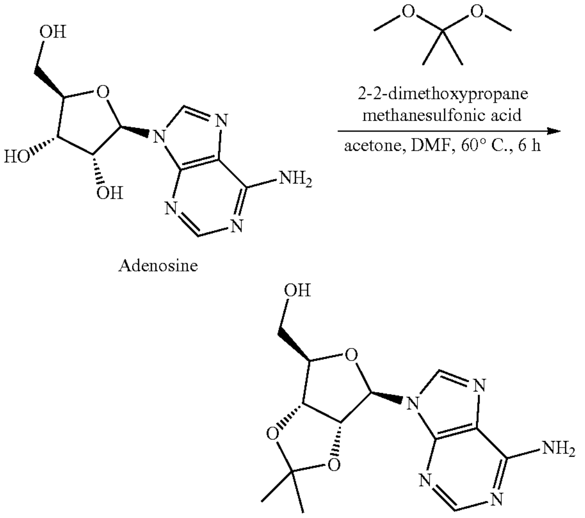

Adenosine intermediate 418

To a solution of Adenosine (75 g, 281 mmol) in acetone (1200 mL) and DMF (400 mL) was added 2,2-dimethoxy-propane (35.1 g, 336.8 mmol) and methanesulfonic acid (40.5 g, 421 mmol) under $N_2$. The reaction mixture was stirred at 60° C. for 6 h. The reaction mixture was treated with aqueous $NaHCO_3$ (PH to 7-8) and then concentrated under reduced pressure. The residue was diluted with $H_2O$ (1200 mL) and extracted with ethyl acetate (1500 ml×3). The organic layers were combined, washed with brine (500 mL), dried and concentrated under reduced pressure to give intermediate 418 (85 g, 96.3% yield) as a white solid.

Step 2

Preparation of Intermediate 419

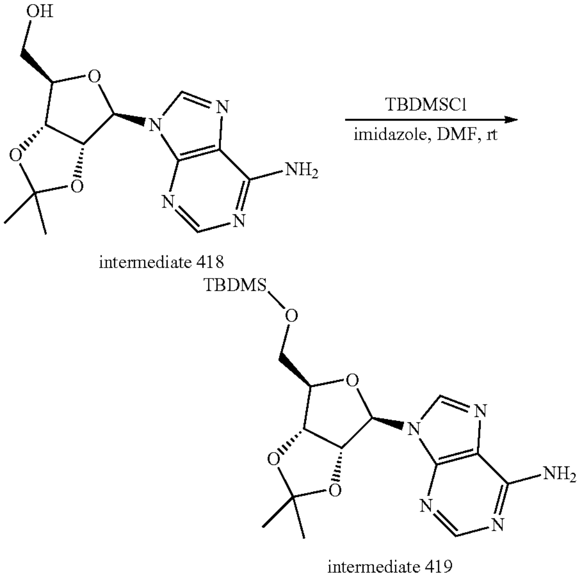

intermediate 418 intermediate 419

To a solution of intermediate 418 (87.8 g, 286 mmol) and imidazole (38.9 g, 571.4 mmol) in DMF (800 mL) was added TBDMSCl (51.67 g, 342.8 mmol) at room temperature under $N_2$. The reaction was stirred at room temperature for overnight. Water (1000 ml) was added at room temperature, then a white solid was formed and filtered off. The solid was collected and dissolved in ethyl acetate (1500 ml) and washed with brine (500 ml). The organic phase was dried over anhydrous $Na_2SO_4$, filtered and concentrated to give intermediate 419 (120 g, 99% yield) as a white solid.

Step 3

Preparation of Intermediate 420

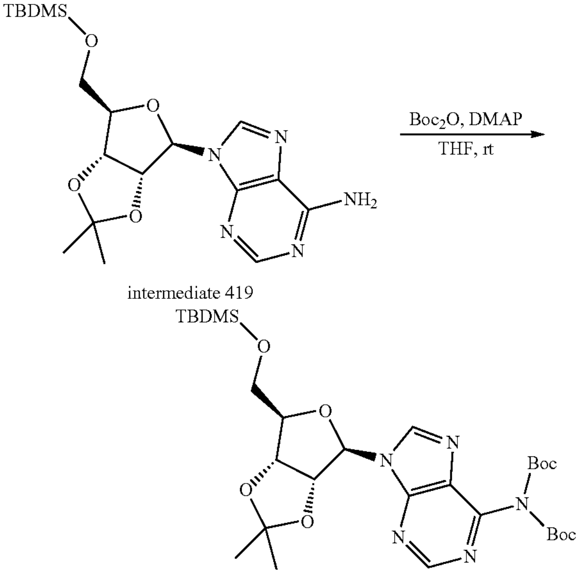

intermediate 419 intermediate 420

A mixture of intermediate 419 (116.3 g, 275.9 mmol), DMAP (3.37 g, 27.6 mmol) and THF (1500 mL) was stirred at room temperature. $Boc_2O$ (150.5 g, 689.7 mmol) was added dropwise. The mixture was stirred at room temperature for 2 hours. The mixture was evaporated under vacuum. The residue was dissolved in ethyl acetate (1500 ml) and washed with brine (1000 ml). The organic phases were combined, dried over anhydrous $Na_2SO_4$, filtered and concentrated to give intermediate 420 (170 g, 83% yield) as a white solid.

Step 4

Preparation of Intermediate 421

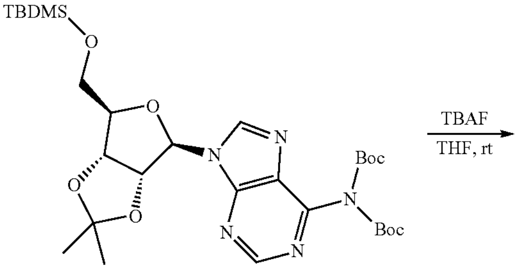

intermediate 420

-continued

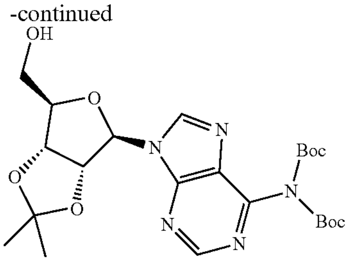

intermediate 421

To a solution of intermediate 420 (176 g, 238.8 mmol) in THF (2000 mL) was added TBAF (1 M in THF, 238.8 mL, 238.8 mmol) dropwise at room temperature under $N_2$. The reaction mixture was stirred at room temperature for 1 hour. The mixture was poured into water (2000 ml) and extracted with ethyl acetate (2000 ml×3). The combined organic layers were dried over $Na_2SO_4$, filtered and evaporated to give the crude product. This residue was purified by flash column chromatograph over silica gel (eluens: petroleum ether/ethyl acetate 10/1 to 1/1). The desired fractions were collected and the solvent was evaporated to give intermediate 421 (85 g, 72.5%) as a yellow oil.

Step 5

Preparation of Intermediate 422

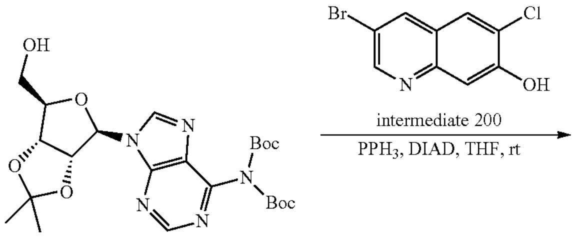

intermediate 421

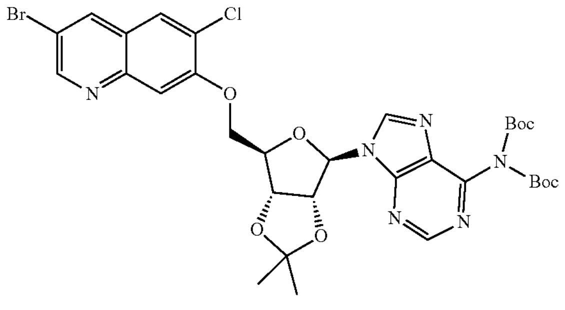

intermediate 422

To a solution of intermediate 421 (1 g, 1.97 mmol), intermediate 200 (509 mg, 1.97 mmol) and DIAD (1.19 g, 5.91 mmol) in THF (20 mL) was added $PPh_3$ (1.55 g, 5.91 mmol) at room temperature under $N_2$. The mixture was stirred at room temperature for 4 hours. Water (40 mL) was added and the mixture was extracted with ethyl acetate (3×50 mL). The organic layers were combined, dried over $Na_2SO_4$, filtered and concentrated under reduced pressure to give the chide product. This residue was purified by flash column chromatograph over silica gel (eluent: petroleum/ethyl acetate from 10/1 to 2/1.) The desired fractions were collected and the solvent was evaporated to give the product as a yellow oil. The oil was purified by HPLC column:

Phenomenex Gemini C18 250×50 mm×10 μm; Conditions: A: water (0.05% ammonia hydroxide v/v), B: MeCN; at the beginning: A (48%) and B (52%), at the end: A (18%) and B (82%); Gradient Time (min) 30; 100% B Hold Time (min) 5; Flow Rate (ml/min) 90) to give intermediate 422 (650 mg, 41% yield) as a white solid.

Example A93

Preparation of Intermediate 423

Step 1

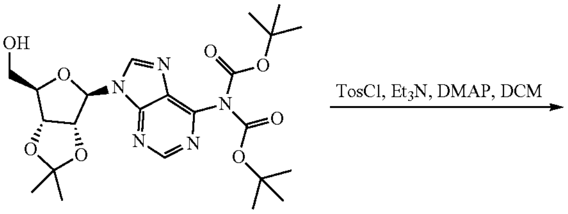

intermediate 421

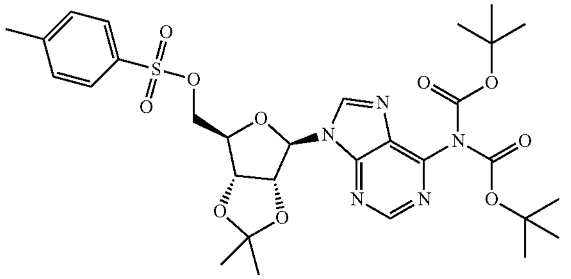

intermediate 423

A mixture of intermediate 421(2 g, 3.94 mmol), $Et_3N$ (0.797 g, 7.88 mmol) and DMAP (0.096 g, 0.788 mmol) was stirred in DCM (40 ml) at room temperature TosCl (1.127 g, 5.91 mmol) was added. The reaction mixture was stirred overnight. Then 50 ml of saturated. $NaHCO_3$ was added into the mixture and the layers were separated. The aqueous layer was extracted with DCM (50 mL×2). The combined organic layers were dried with $Na_2SO_4$, filtered and concentrated under vacuum to give crude product as an oil. The crude product was purified by column (eluent: petroleum ether/EtOAc ratio 10/1 to 3/1) to give intermediate 423 (1.25 g, yield 45%) as a white solid.

Step 2

Preparation of Intermediate 424

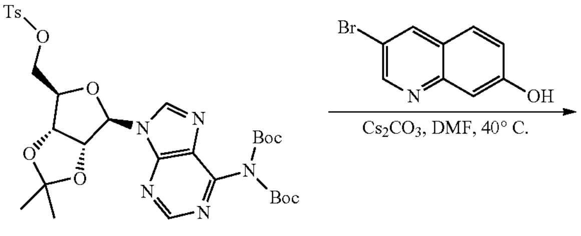

intermediate 423

-continued

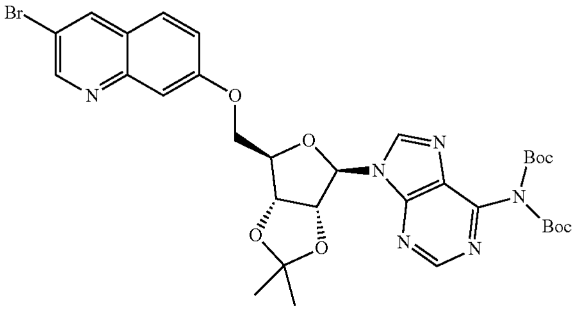

intermediate 424

To a solution of intermediate 423 (1.1 g, 1.66 mmol), 3-bromo-7-hydroxy quinoline (0.372 g, 1.66 mmol) and DMF (40 mL) was add $Cs_2CO_3$ (1.63 g, 4.98 mmol) at room temperature under $N_2$. The mixture was stirred at 40° C. for 6 hours. The reaction mixture was filtered and the filtrate was evaporated. The residue was purified by column over silica gel (eluens: petroleum ether/ethyl acetate: ratio 20/1 to 0/1) to give intermediate 424 (1.1 g, 87% yield) as a yellow oil.

Example A94

Step 1

Preparation of Intermediate 425

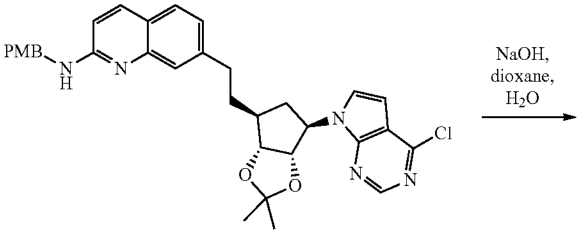

intermediate 165

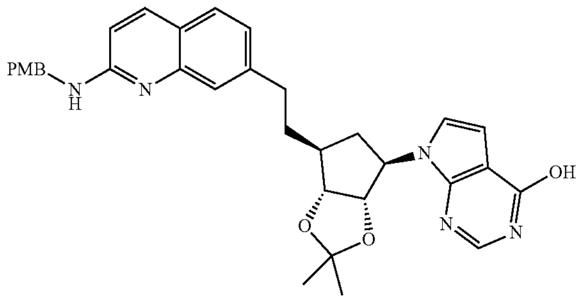

intermediate 425

A mixture of intermediate 165 (300 mg, 0.393 mmol,) and NaOH solution (19.2 ml, 38.5 mmol, 2M) in dioxane (5 ml) was refluxed at 60° C. for 48 h. The mixture was extracted with ethyl acetate (10 ml×3), the organic layers were combined and evaporated under vacuo to obtain intermediate 425 (300 mg, 42% yield) as a crude product.

Step 2

Preparation of Intermediate 426

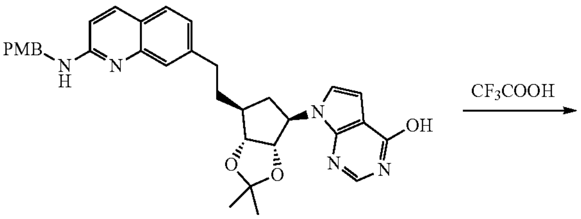

intermediate 425

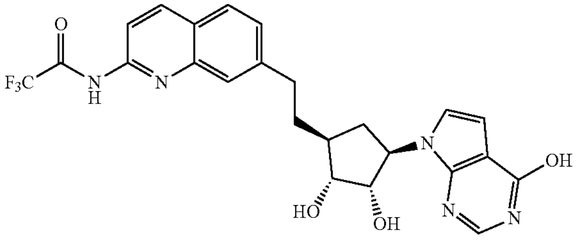

intermediate 426

The solution of intermediate 425 (300 mg, 0.164 mmol) in trifluroacetic acid (5 ml) was stirred at 50° C. for 1 h. The mixture was evaporated under vacuo to obtain intermediate 426 (150 mg, 75% yield) as a crude product.

Example A95

Step 1

Preparation of Intermediate 427

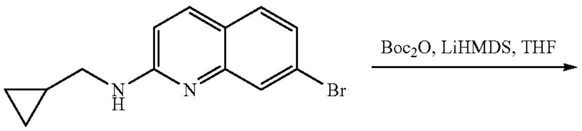

intermediate 157

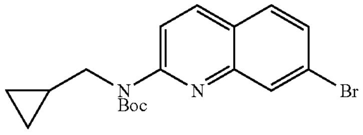 [SMILES: Brc1ccc2cnc(NCC3CC3)nc2c1]

intermediate 427

To a solution of intermediate 157 (4 g, 14.4 mmol) in THF (100 mL) was added LiHMDS (28.8 mL, 1 M). The reaction mixture was stirred at 0° C. for 15 min, then $Boc_2O$ (6.3 g, 28.8 mmol) was added. The reaction mixture was stirred at room temperature for another 30 min. The reaction mixture was quenched with saturated aq. $NH_4Cl$ (50 ml) and extracted with ethyl acetate (50 ml×2). The organic layers were combined and evaporated under vacuum to obtain intermediate 427 (5 g) as a crude product.

Step 2

Preparation of Intermediate 428

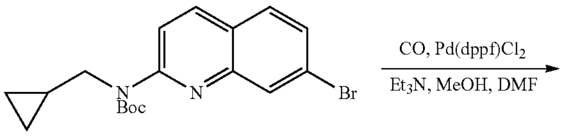

intermediate 427

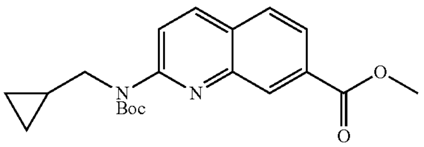

intermediate 428

To a solution of intermediate 427 (5.0 g, 13.25 mmol) in MeOH (25 mL) and DMF (25 mL) was added Pd(dppf)$Cl_2$ (0.970 g, 1.32 mmol) and $Et_3N$ (4.02 g, 39.76 mmol). The reaction mixture was degassed under vacuum and purged with CO— gas three times. The reaction was stirred overnight under CO atmosphere at 120° C. The reaction mixture was diluted with $H_2O$ (100 mL) and was then extracted with ethyl acetate (100 mL×3). The organic layer was washed with $H_2O$ (100 mL) and dried with anhydrous $Na_2SO_4$ and concentrated under reduced pressure. The crude product was purified by column chromatography over silica gel (petroleum ether/ethyl acetate: ratio 5/1 to petroleum ether/ethyl acetate 2/1). The pure fractions were collected and the solvent was evaporated under vacuum to obtain intermediate 428 (4.0 g, 85% yield).

Step 3

Preparation of Intermediate 429

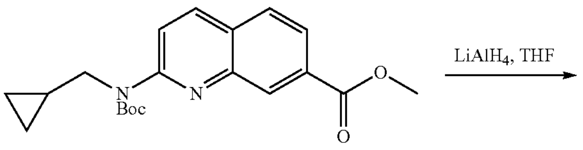

intermediate 428

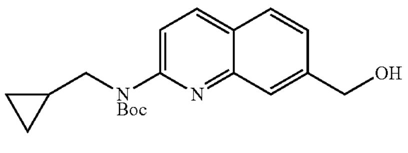

intermediate 429

To a solution of intermediate 428 (4.0 g, 11.2 mmol) in THF (20 mL) was added $LiAlH_4$ (0.426 mg, 11.2 mmol). The reaction mixture was stirred at room temperature for 3 hrs. The mixture was quenched with aq. 10% KOH (0.5 mL), filtered and the filtrate was concentrated under reduced pressure to give intermediate 429 (3.4 g, 90% yield) as an oil.

Step 4

Preparation of Intermediate 332

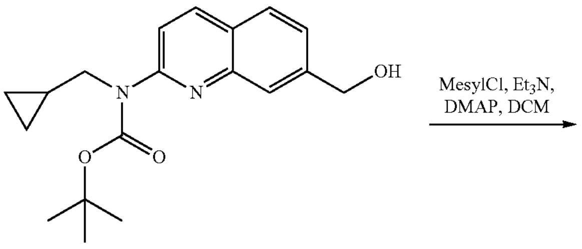

intermediate 429

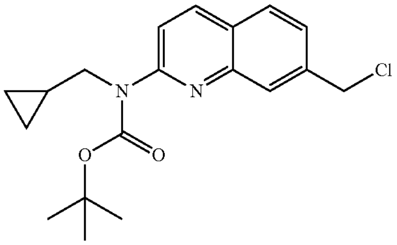

intermediate 332

To a solution of intermediate 429 (1.3 g, 3.96 mmol) in DCM (20 ml) was added mesyl chloride (0.907 g, 7.92 mmol), DMAP (96.7 mg, 0.792 mmol) and $Et_3N$ (1.2 g, 11.88 mmol). The reaction mixture was stirred overnight at room temperature. The reaction mixture was diluted with DCM (100 mL) and the organic phase was then washed with aq. $K_2CO_3$ (50 mL×3). The organic phase was dried with $Na_2SO_4$ and was then concentrated under reduced pressure to give intermediate 332 as a yellow oil which was used in the next step reaction without further purification.

Example A96

Step 1

Preparation of Intermediate 430

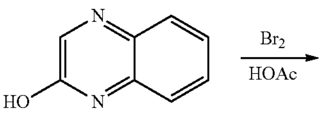

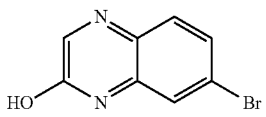

intermediate 430

$Br_2$(0.89 mL) was added to the solution of 2-Hydroxyquinoxaline (1.5 g, 10.2 mmol) in HOAc (15 mL) and the reaction was stirred at room temperature for 6 hours. The solid was filtered and washed with ethyl acetate to give intermediate 430 (2.2 g, yield: 95%) as a white solid.

Step 2

Preparation of Intermediate 431

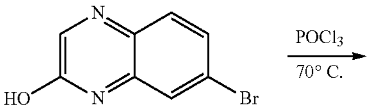

intermediate 430

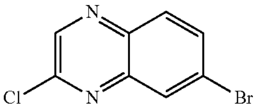

intermediate 431

$POCl_3$ (48.5 g, 316 mmol) was added to intermediate 430 (2.2 g, 9.7 mmol). The mixture was stirred at 70° C. for 2 hours. The mixture was poured slowly into water. aq. $NaHCO_3$ was added into the mixture until no more gas evolution occurred. The mixture was extracted with EtOAc. The organic phase was filtered and washed with brine. The organic phase was dried over $Na_2SO_4$ and concentrated to give intermediate 431 (2 g, yield: 81%)

Step 3

Preparation of Intermediate 432

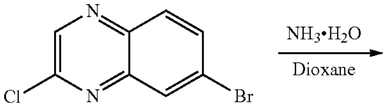

intermediate 431

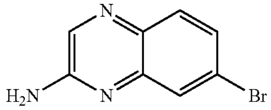

intermediate 432

A solution of intermediate 431 (100 mg, 0.41 mmol) in dioxane (4 mL) and $NH_3 \cdot H_2O$ (10 mL, 25%) was stirred in a sealed tube at 110° C. overnight. The mixture was concentrated to give the crude intermediate 432 (108 mg) as a yellow solid.

Example A97

Step 1

Preparation of Intermediate 493

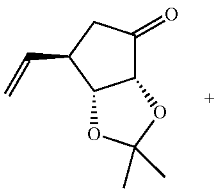

intermediate 408

-continued

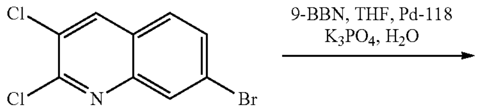

intermediate 181

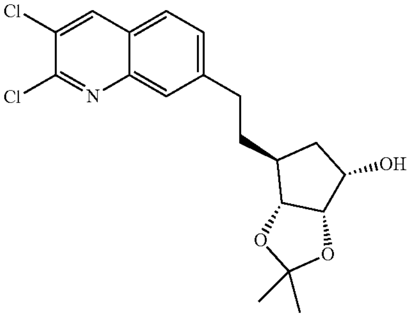

intermediate 493

A mixture of intermediate 408 (10 g, 54.88 mmol) in a 9-BBN 0.5 M solution in THF (439 ml, 219.5 mmol) was stirred at 50° C. for 1 h under $N_2$. The mixture was cooled to room temperature, then $K_3PO_4$ (34.9 g, 164.6 mmol) in $H_2O$ (20 mL) were added, followed by THF (110 ml), intermediate 181 (15.19 g, 54.88 mmol) and Pd-118 (1788 mg, 2.74 mmol). The resulting mixture was stirred at 50° C. for 0.5 h. The mixture was concentrated. The residue was dissolved in ethyl acetate (400 ml), washed with water (400 ml) and brine (400 ml). The organic phase was dried over $Na_2SO_4$, filtered and concentrated. The crude product was purified by column chromatography over silica gel (petroleum ether/ethyl acetate 10/1 to petroleum ether/ethyl acetate 1/1). The pure fractions were collected and the solvent was evaporated under vacuum to give intermediate 393 (19 g, 82% yield) as a solid.

Below intermediates were prepared by an analogous reaction protocol as was used for the preparation of intermediate 393 using the appropriate starting materials (Table 50).

TABLE 50

| intermediates | Structure | Starting materials |
| --- | --- | --- |
| 530 | 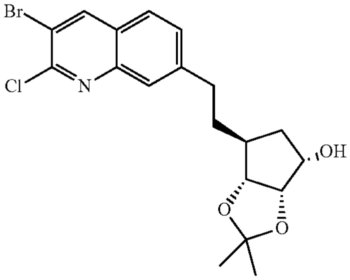 [SMILES: CC1(C)O[C@@H]2[C@@H](CCc3ccc4cc(Br)c(Cl)nc4c3)C[C@H](O)[C@@H]2O1] | intermediate 408 intermediate 175 |

Step 2

Preparation of Intermediate 494

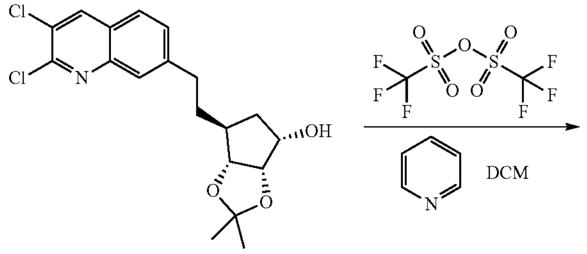

intermediate 493

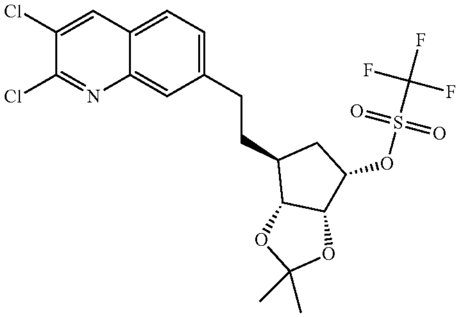

intermediate 494

Intermediate 493 (4 g, 10.46 mmol) and pyridine (2.48 g, 31.39 mmol) were dissolved in DCM (50 ml) under $N_2$. Triflic anhydride (5.9 g, 20.93 mmol) was added at 0° C. and the reaction mixture was stirred for 0.5 hour. Then the reaction mixture was stirred at 25° C. for 1 hour. The solvent was removed in vacuo The residue was purified by column chromatography over silica gel (petroleum ether/ethyl acetate ratio 10/0 to petroleum ether/ethyl acetate ratio 4/1). The pure fractions were collected and the solvent was evaporated under vacuum to give intermediate 494 (3.5 g, 65% yield) as a white solid.

Below intermediates were prepared by an analogous reaction protocol as was used for the preparation of intermediate 394 using the appropriate starting materials (Table 51).

TABLE 51

| intermediates | Structure | Starting materials |
|---|---|---|
| 531 | 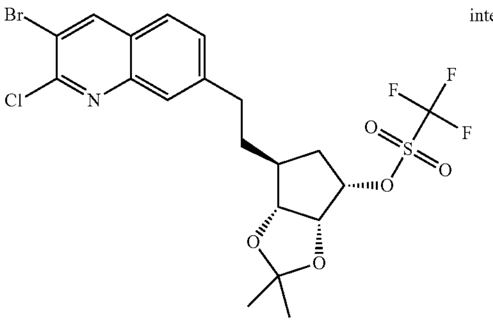 | intermediate 530 |

Step 3

Preparation of Intermediate 495

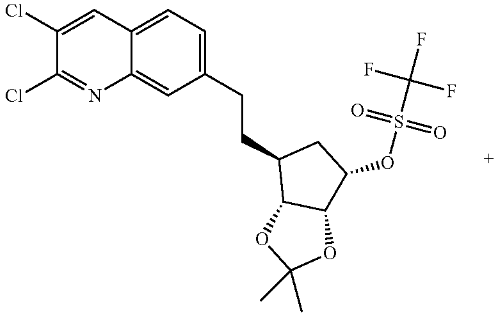

intermediate 494

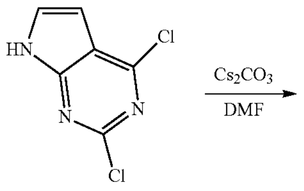

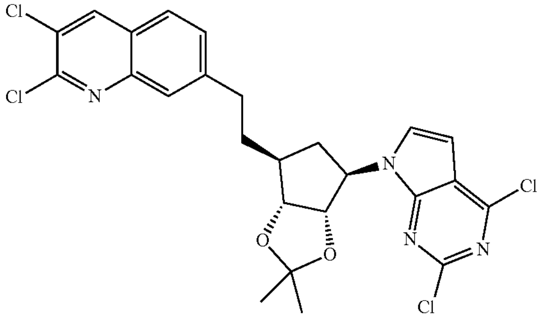

intermediate 495

7H-Pyrrolo[2,3-d]pyrimidine, 2,4-dichloro-(1.24 g, 6.61 mmol) and $Cs_2CO_3$ (3.23 g, 9.91 mmol) were dissolved in DMF (20 ml) under $N_2$. Then intermediate 494 was added.

The reaction mixture was stirred at 25° C. for 12 hours. To the mixture was added ethyl acetate (50 mL) and water (50 mL). The organic layer was separated, washed with $H_2O$, and dried ($Na_2SO_4$). The solvent was removed under reduced pressure. The crude product was purified by column chromatography over silica gel (petroleum ether/ethyl acetate ratio 10/1 to petroleum ether/ethyl acetate ratio 4/1). The pure fractions were collected and the solvent was evaporated under vacuum to give intermediate 495 (900 mg, 37% yield) as a yellow solid.

Below intermediates were prepared by an analogous reaction protocol as was used for the preparation of intermediate 495 using the appropriate starting materials (Table 43).

TABLE 43

| intermediates | Structure | Starting materials |
|---|---|---|
| 497 | 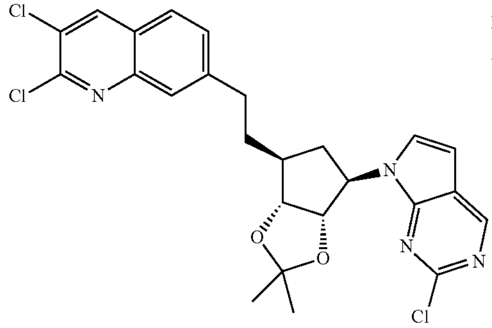 | intermediate 494<br>7H-Pyrrolo[2,3-d]pyrimidine, 2-chloro |
| 499 | 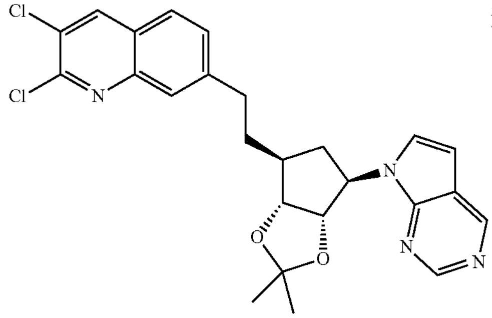 [SMILES: CC1(C)O[C@@H]2[C@@H](CCc3ccc4cc(Cl)c(Cl)nc4c3)C[C@@H](n3ccc4nccnc43)[C@@H]2O1] | intermediate 494<br>7H-Pyrrolo[2,3-d]pyrimidine |
| 519 | 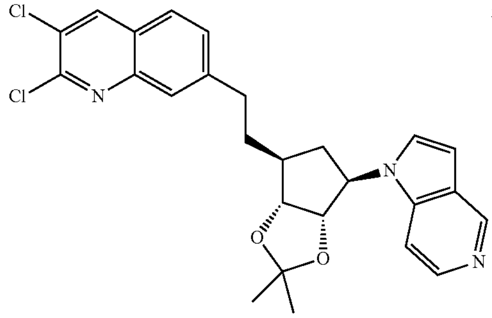 | intermediate 494<br>1H-Pyrrolo[3,2-c]pyridine |
| 521 | 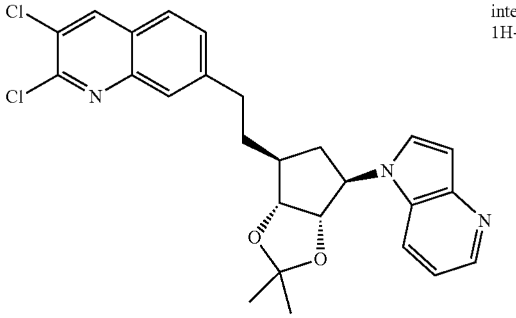 | intermediate 494<br>1H-Pyrrolo[3,2-b]pyridine |

TABLE 43-continued
| intermediates | Structure | Starting materials |
| --- | --- | --- |
| 523 | 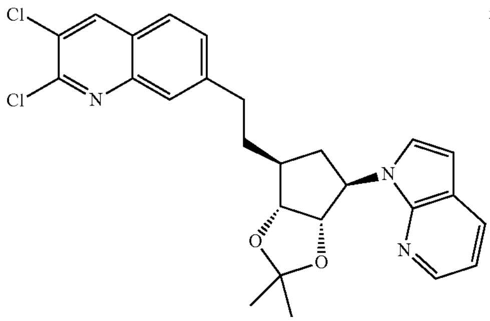 [SMILES: CC1(C)O[C@@H]2[C@@H](CCc3ccc4cc(Br)c(Cl)nc4c3)C[C@@H](n3ccc4ncccc43)[C@@H]2O1] | intermediate 494<br>1H-Pyrrolo[2,3-b]pyridine |
| 525 | 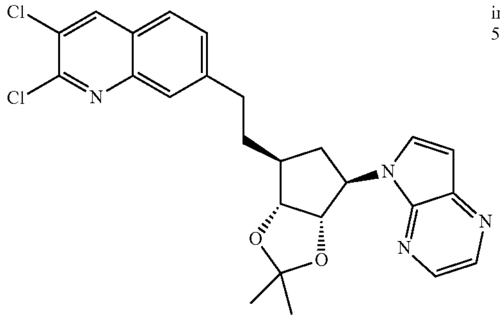 | intermediate 494<br>5H-Pyrrolo[2,3-b]pyrazine |
| 532 | 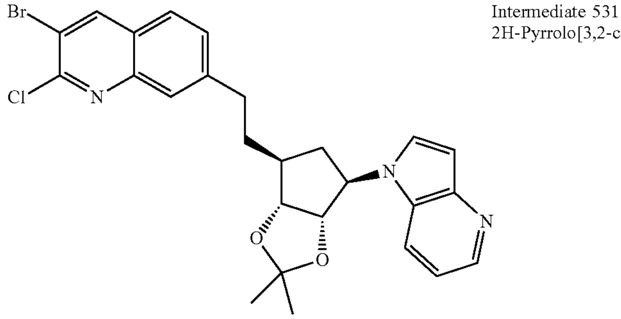 | Intermediate 531<br>2H-Pyrrolo[3,2-c]pyridine |
| 533 | 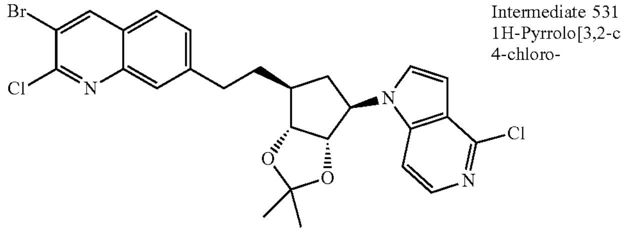 | Intermediate 531<br>1H-Pyrrolo[3,2-c]pyridine,<br>4-chloro- |

Example A100

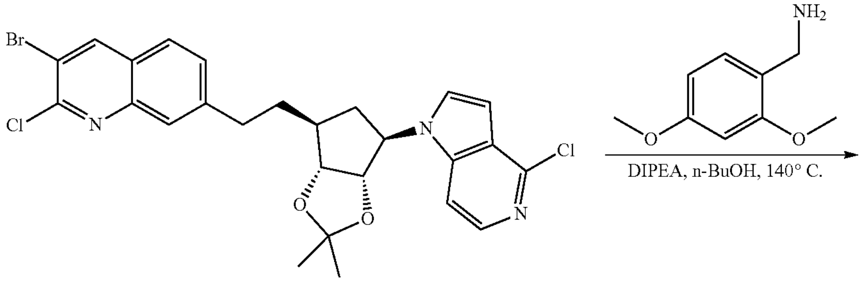

intermediate 533

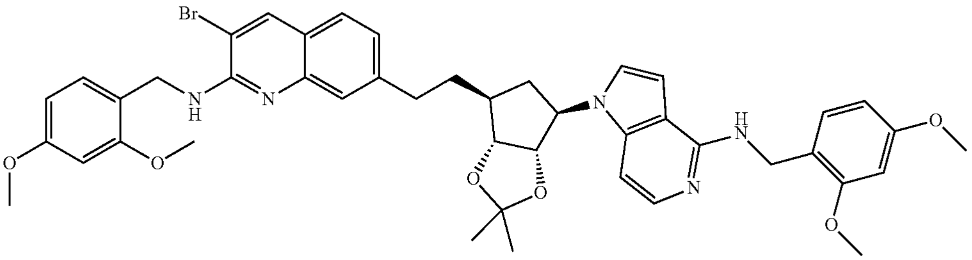

intermediate 534

A solution of intermediate 533 (1.75 g, 3.1 mmol), 2,4-dimethoxybenzylamine hydrochloride (2.6 g, 15.6 mmol) and DIPEA (1.2 g, 9.3 mmol) in n-BuOH (5 mL) was stirred at 140° C. for 3 days. The reaction mixture was diluted with $CH_2Cl_2$ (30 mL) and washed with $H_2O$ (20 mL×2). The organic phase was separated and dried with $Na_2SO_4$ and the solvent was removed under vacuo. The crude product was purified by column chromatography over silica gel (petroleum ether/ethyl acetate ratio 10/1 to petroleum ether/ethyl acetate ratio 1/2) to give intermediate 534 (1.1 g, yield 81%) as a yellow solid.

Example A98

Preparation of Intermediate 526

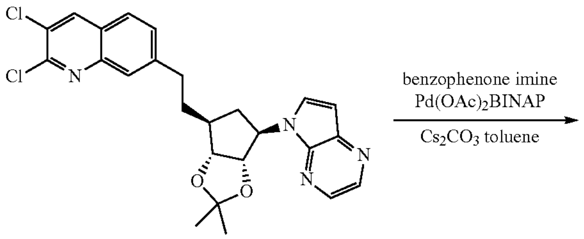

intermediate 525

-continued

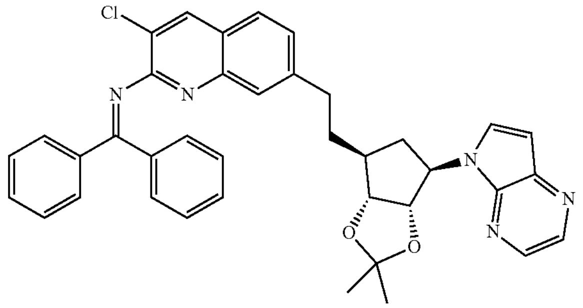

intermediate 526

Intermediate 525 (900 mg, 1.862 mmol), benzophenone imine (354.3 mg, 1.95 mmol) $Pd(OAc)_2$(41.8 mg, 0.186 mmol), BINAP (115.9 mg, 0.186 mmol) and $Cs_2CO_3$ (1213 mg, 3.72 mmol) were dissolved in toluene (20 ml). The mixture was stirred at 110° C. for 14 hours under $N_2$. The catalyst was filtered and the solvent was evaporated. The residue was purified by flash column chromatography over silica gel (gradient eluent: EtOAc/petrol ether from 1/15 to 1/1) The product fractions were collected and the solvent was evaporated to give intermediate 526 (660 mg, 51% yield) as a yellow solid.

B. Preparation of the Compounds

Example B1

Preparation of Compound 1

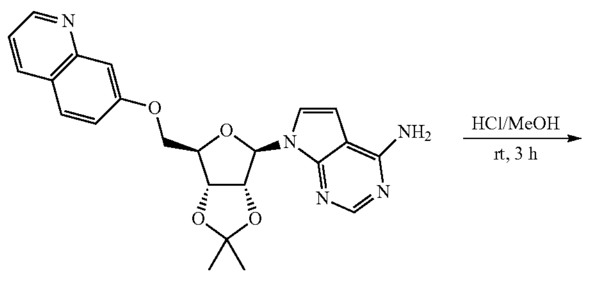

Intermediate 104

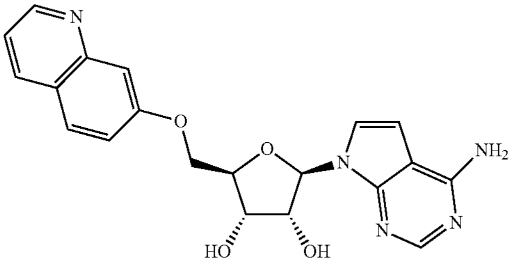

compound 1

Intermediate 104 (300 mg, crude, 0.568 mmol) was dissolved in 5 ml of 4M HCl/MeOH. The mixture was stirred at room temperature for 3 hours. The solvent was concentrated in vacuum. The residue was dissolved in 4 ml of MeOH and the pH was adjusted to around pH=9 with a saturated $Na_2CO_3$ solution. The solvent was purified by preparative-HPLC (HPLC condition: Column: Gemini 150*25 mm*5 μm; gradient elution: 0.05% ammonia/ $CH_3CN$, from 81/19 to 71/29) to give compound 1 (70 mg, 30% yield) as a white solid.

Example B2

Preparation of Compound 2

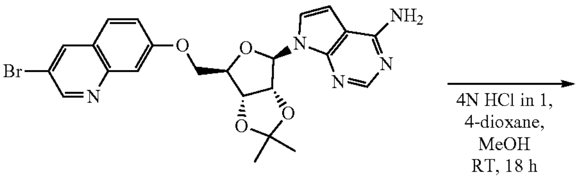

Intermediate 105

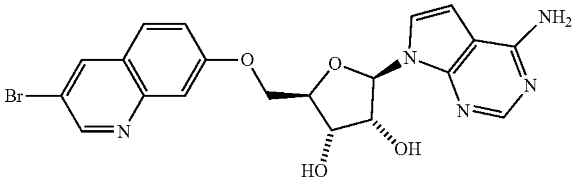

compound 2

4M HCl in dioxane (0.7 mL, 2.9 mmol) was added to a stirred solution of intermediate 105 (175.1 mg, crude, 0.29 mmol) in MeOH (10 mL) at room temperature. The reaction mixture was stirred at room temperature for 18 hours. The reaction was quenched by the addition of 1.5 mL of a 7 N solution of $NH_3$ in MeOH. The solvents were evaporated. The residue was dissolved in DCM. The precipitate was filtered off. The filtrate was purified over a $SiO_2$ column, type Grace Reveleris SRC, 12 g, Si 40, on an Armen Spot II Ultimate purification system using DCM and MeOH as eluens in a gradient starting from 100% DCM and ending with 40% MeOH and 60% DCM. The fractions containing the product were combined and the solvents were evaporated yielding 24.5 mg of compound 2.

Example B3

Preparation of Compound 2

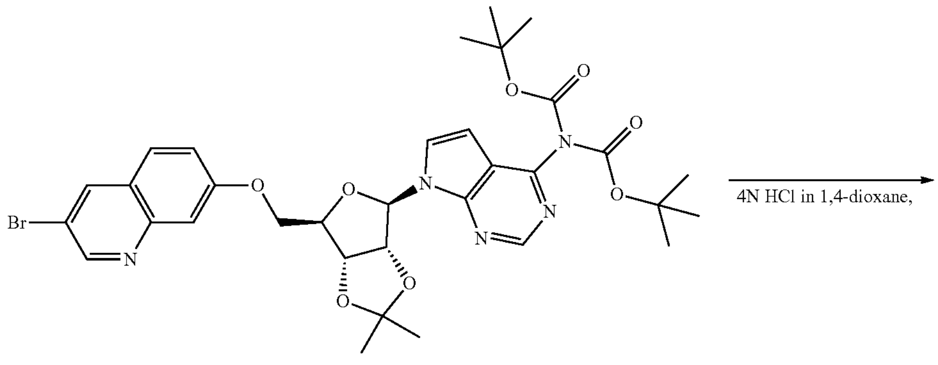

Intermediate 89

-continued

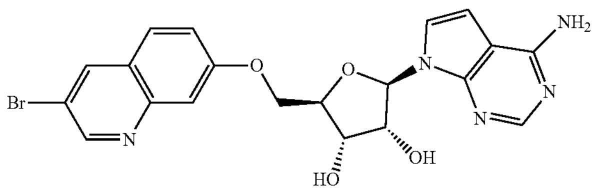

compound 2

Intermediate 89 (12.2 g, 15.751 mmol) was dissolved in HCl/MeOH (220 ml, 4M). The mixture was stirred at room temperature for 3 days. The solid was precipitate out after 18 hours reaction. The reaction mixture was combined with another batch of reaction mixture (1 g of intermediate 89). The resulting solid was filtered through a funnel collected. The residue was triturated with water, and the pH was adjusted to around 8 by progressively adding solid $K_2CO_3$. The resulting solid was filtered through a buchner funnel rinsed with water (100 mL*5) and collected, which was lyophilized to give the compound 2 (5.95 g, 73% yield) as a white solid.

Example B4

Preparation of Compound 3

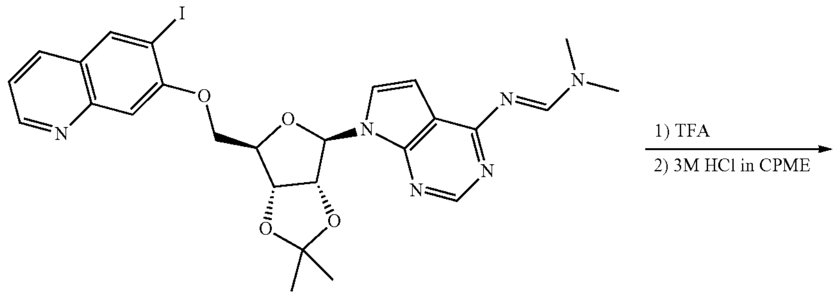

intermediate 74

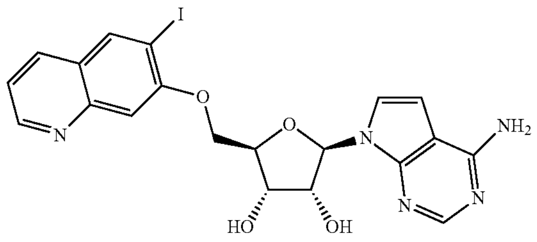

compound 3

To a solution of intermediate 74 (249 mg, 0.405 mmol) in DCM (3.5 mL) was added TFA (0.8 mL, 10.5 mmol) and the mixture was stirred at rt for 5 days. The mixture was evaporated in vacuo. The residue was solubilized in MeOH (6 mL) and HCl (3M in CPME) (1.5 mL, 4.5 mmol) was added and the mixture was stirred overnight at room temperature. The mixture was quenched with $NH_3$ in MeOH (7N) and evaporated in vacuo. The residue was taken-up in DCM/MeOH (1/1), filtered off and the filtrate was evaporated in vacuo. The residues were purified by preparative LC (irregular SiOH, 15-40 μm, 10 g, Merck, dry loading (Celite®), mobile phase gradient elution: from DCM: MeOH/aq. $NH_3$ (9:1) from 97.5:2.5 to 87.5:12.5) to give compound 3 as a white solid (156 mg, 73% yield).

Example B5

Preparation of Compound 4

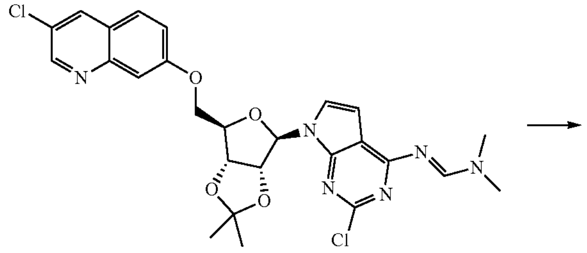

intermediate 86

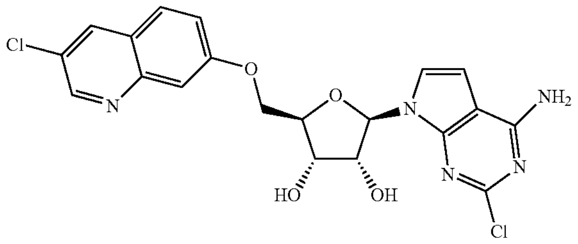

compound 4

To a solution of intermediate 86 (750 mg, ≈0.71 mmol) in MeOH (40 mL) was added 4M HCl in MeOH (20 mL) at rt. Subsequently the mixture was stirred at 50° C. for 12 hours. The solvent was concentrated in vacuo. The residues were dissolved in 10 ml MeOH and the pH was adjusted to around 8 with $NaHCO_3$. The mixture was filtered and the solvent was purified by preparative-HPLC (gradient elution: 0.05% $NH_3{\cdot}H_2O$ in MeOH/0.05% $NH_3{\cdot}H_2O$ in $H_2O$). The desired fractions were combined and the solvent was evaporated to give compound 4 as a white solid (207 mg, 61%).

Below compounds were prepared by an analogous reaction protocol as example B 1, B2, B3, B4, B5 or B20 (further in experimental part) using the appropriate starting materials (Table 21). Compounds 55, 57, 57a and 61 were obtained in the E-configuration.

TABLE 21

| Compound | Structure | Reaction protocol | Starting material |
|---|---|---|---|
| 5 | 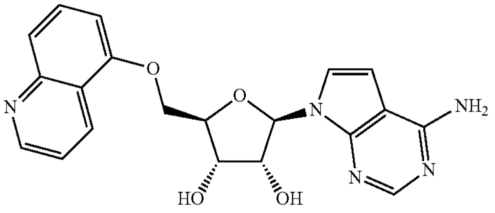 [SMILES: Nc1ncnc2c1ccn2[C@@H]1O[C@H](COc2cccc3ncccc23)[C@@H](O)[C@H]1O] | B1 | Intermediate 106 |
| 6 | 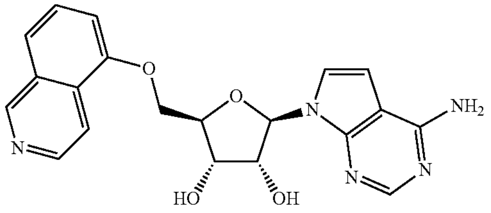 [SMILES: Nc1ncnc2c1ccn2[C@@H]1O[C@H](COc2cccc3cnccc23)[C@@H](O)[C@H]1O] | B1 | Intermediate 107 |
| 7 | 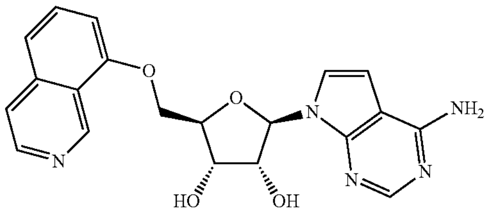 [SMILES: Nc1ncnc2c1ccn2[C@@H]1O[C@H](COc2cccc3ccncc23)[C@@H](O)[C@H]1O] | B1 | Intermediate 108 |
| 8 | 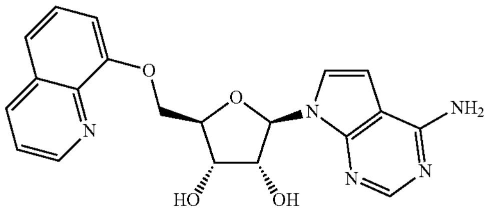 [SMILES: Nc1ncnc2c1ccn2[C@@H]1O[C@H](COc2cccc3cccnc23)[C@@H](O)[C@H]1O] | B1 | Intermediate 109 |

TABLE 21-continued
| Compound | Structure | Reaction protocol | Starting material |
|---|---|---|---|
| 9 | 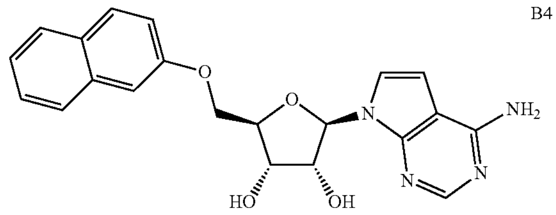 | B4 | Intermediate 110 |
| 10 | 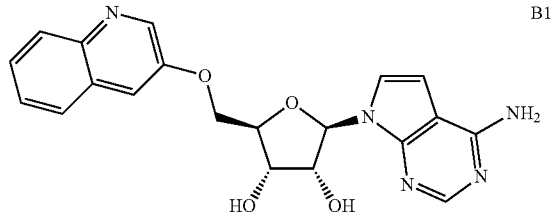 | B1 | Intermediate 111 |
| 11 | 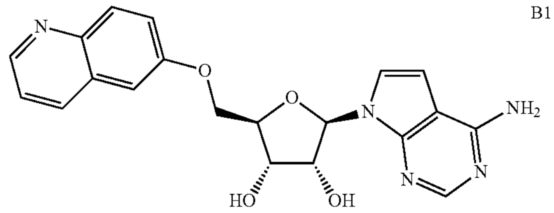 | B1 | Intermediate 112 |
| 12 | 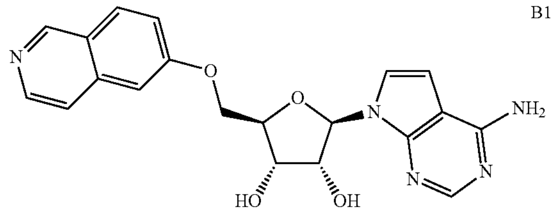 | B1 | Intermediate 113 |
| 13 | 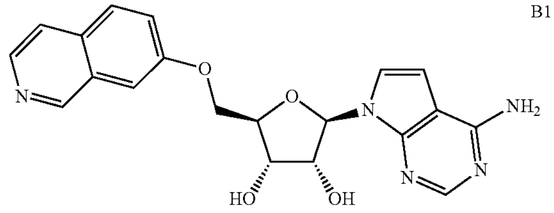 | B1 | Intermediate 114 |
| 14 | 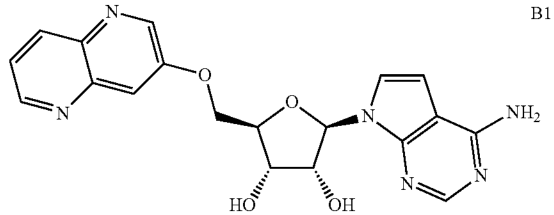 | B1 | Intermediate 115 |
| 15 | 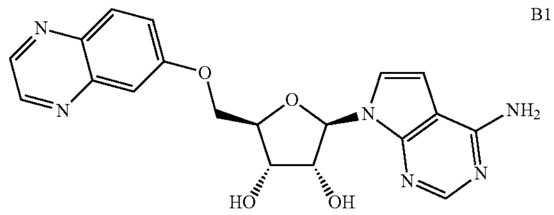 | B1 | Intermediate 116 |

TABLE 21-continued
| Compound | Structure | Reaction protocol | Starting material |
|---|---|---|---|
| 16 | 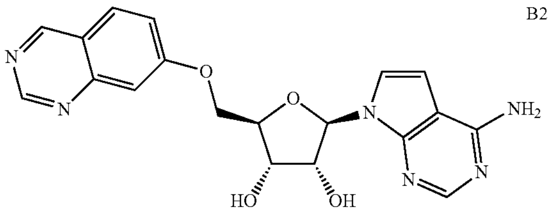 | B2 | Intermediate 117 |
| 17 | 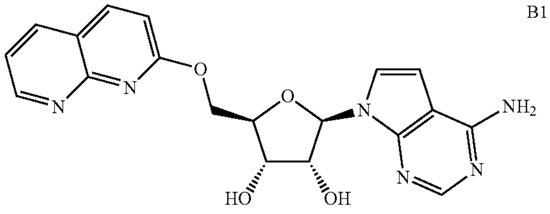 | B1 | Intermediate 118 |
| 18 | 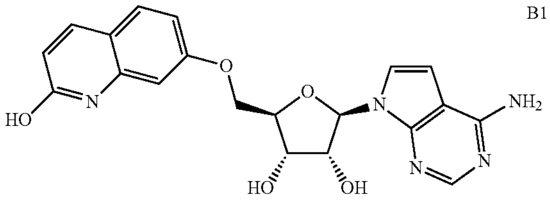 | B1 | Intermediate 154 |
| 19 | 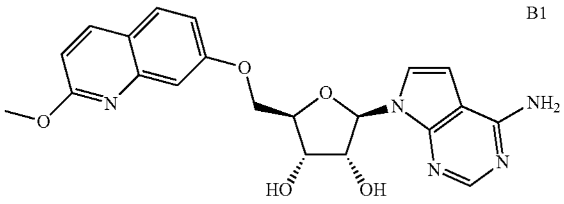 [SMILES: COc1ccc2ccc(OC[C@H]3O[C@@H](n4ccc5c(N)ncnc54)[C@H](O)[C@@H]3O)cc2n1] | B1 | Intermediate 155 |
| 20 | 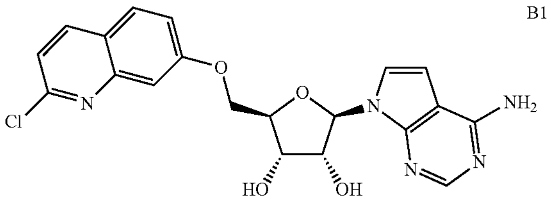 | B1 | Intermediate 119 |
| 21 | 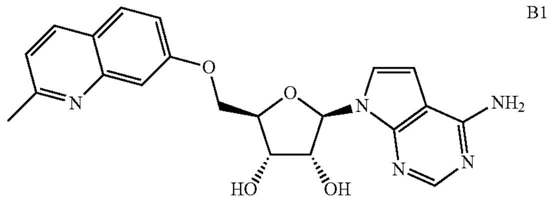 | B1 | Intermediate 120 |
| 22 | 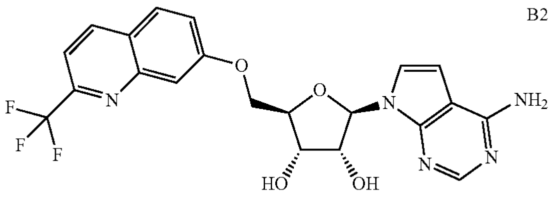 [SMILES: Nc1ncnc2c1ccn2[C@@H]1O[C@H](COc2ccc3ccc(C(F)(F)F)nc3c2)[C@@H](O)[C@H]1O] | B2 | Intermediate 121 |

TABLE 21-continued
| Compound | Structure | Reaction protocol | Starting material |
|---|---|---|---|
| 23 | 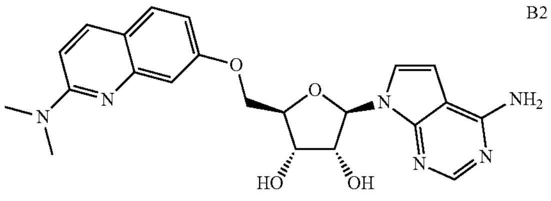 | B2 | Intermediate 154a |
| 24 | 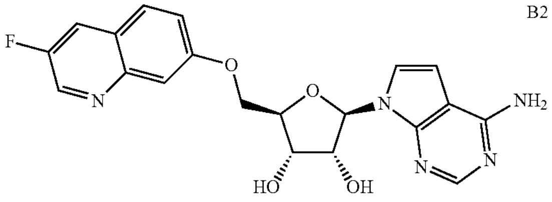 [SMILES: Nc1ncnc2c1ccn2[C@@H]1O[C@H](COc2ccc3cc(F)cnc3c2)[C@@H](O)[C@H]1O] | B2 | Intermediate 80 |
| 25 | 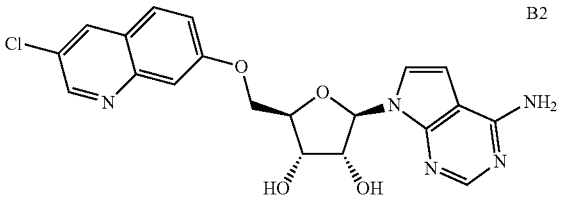 [SMILES: Nc1ncnc2c1ccn2[C@@H]1O[C@H](COc2ccc3cc(Cl)cnc3c2)[C@@H](O)[C@H]1O] | B2 | Intermediate 122 |
| 26 | 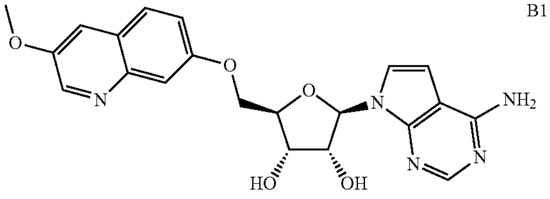 | B1 | Intermediate 79 |
| 27 | 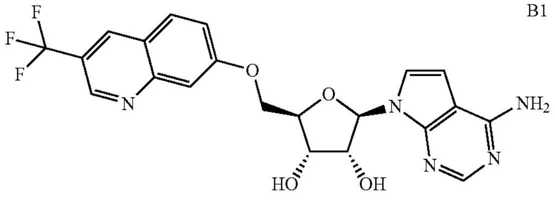 [SMILES: Nc1ncnc2c1ccn2[C@@H]1O[C@H](COc2ccc3cc(C(F)(F)F)cnc3c2)[C@@H](O)[C@H]1O] | B1 | Intermediate 123 |
| 28 | 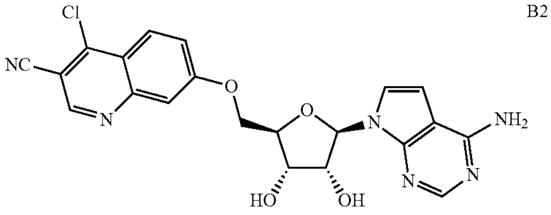 | B2 | Intermediate 144 |
| 29 | 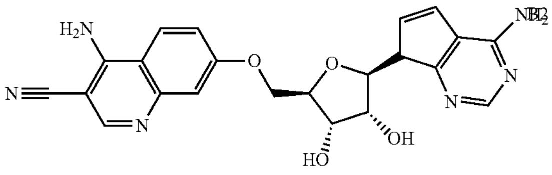 [SMILES: N#Cc1cnc2cc(OC[C@H]3O[C@@H](C4C=Cc5c(N)ncnc54)[C@H](O)[C@@H]3O)ccc2c1N] | B2 | Intermediate 144a |

TABLE 21-continued
| Compound | Structure | Reaction protocol | Starting material |
|---|---|---|---|
| 30 | 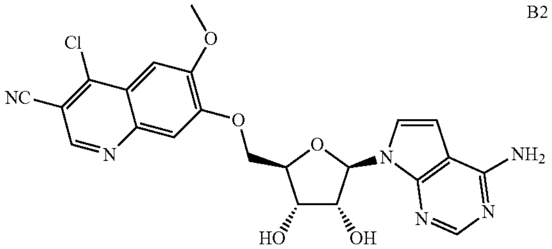 [SMILES: COc1cc2c(Cl)c(C#N)cnc2cc1OC[C@H]1O[C@@H](n2ccc3c(N)ncnc32)[C@H](O)[C@@H]1O] | B2 | Intermediate 145 |
| 31 | 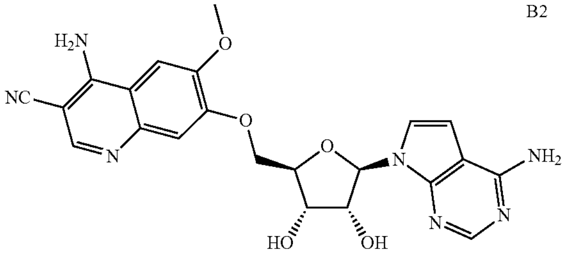 [SMILES: COc1cc2c(N)c(C#N)cnc2cc1OC[C@H]1O[C@@H](n2ccc3c(N)ncnc32)[C@H](O)[C@@H]1O] | B2 | Intermediate 145a |
| 32 | 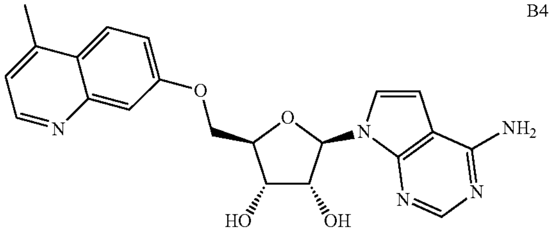 | B4 | Intermediate 73 |
| 33 | 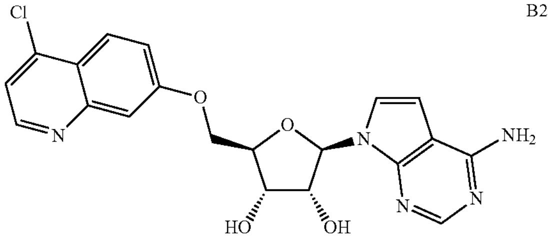 | B2 | Intermediate 124 |
| 34 | 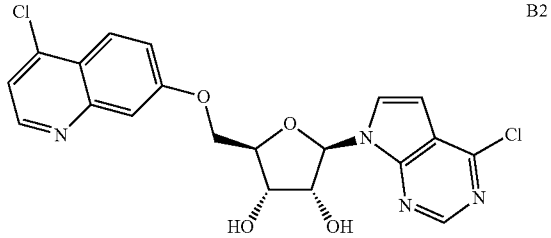 | B2 | Intermediate 54 |
| 35 | 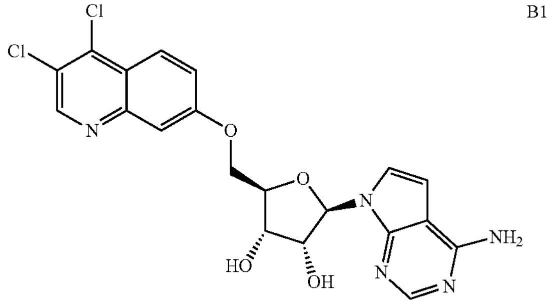 | B1 | Intermediate 84 |

TABLE 21-continued
| Compound | Structure | Reaction protocol | Starting material |
|---|---|---|---|
| 36 | 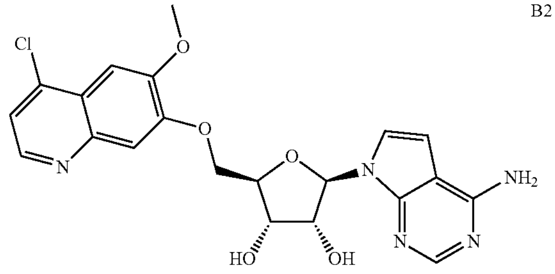 | B2 | Intermediate 125 |
| 37 | 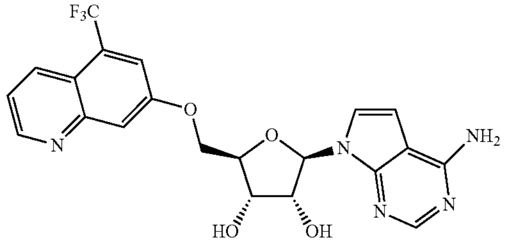 [SMILES: Nc1ncnc2c1ccn2[C@@H]1O[C@H](COc2cc(C(F)(F)F)c3cccnc3c2)[C@@H](O)[C@H]1O] | B5 | Intermediate 81 |
| 38 | 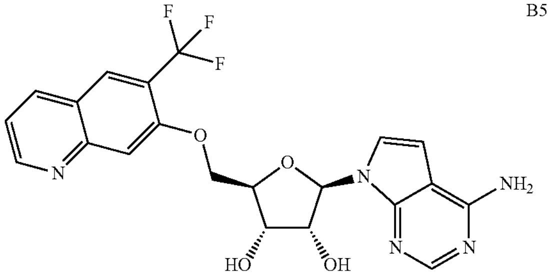 | B5 | Intermediate 82 |
| 39 | 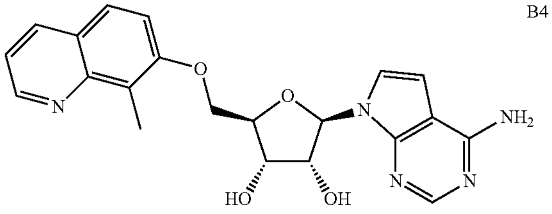 | B4 | Intermediate 75 |
| 40 | 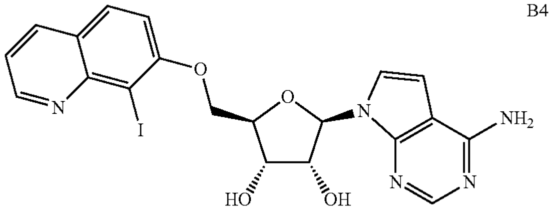 | B4 | Intermediate 76 |
| 41 | 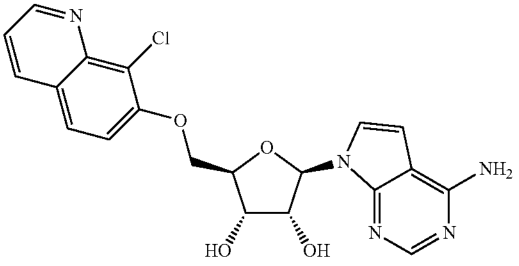 [SMILES: Nc1ncnc2c1ccn2[C@@H]1O[C@H](COc2ccc3cccnc3c2Cl)[C@@H](O)[C@H]1O] | B5 | Intermediate 83 |

TABLE 21-continued
| Compound | Structure | Reaction protocol | Starting material |
|---|---|---|---|
| 42 | 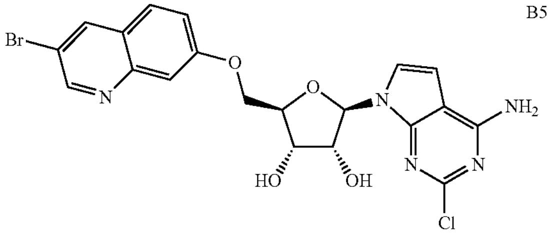 | B5 | Intermediate 87 |
| 43 | 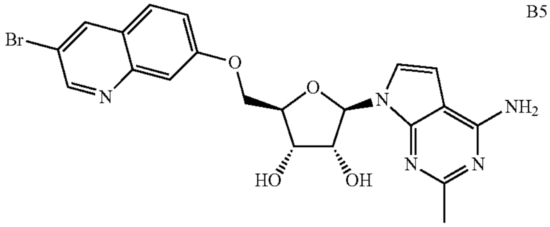 | B5 | Intermediate 88 |
| 44 | 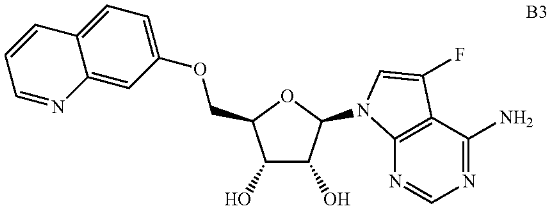 | B3 | Intermediate 126 |
| 45 | 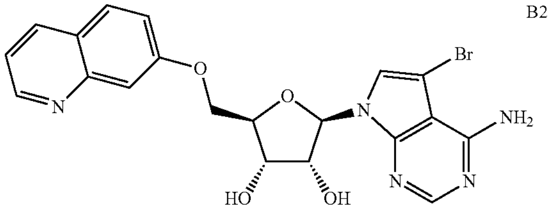 | B2 | Intermediate 153 |
| 46 | 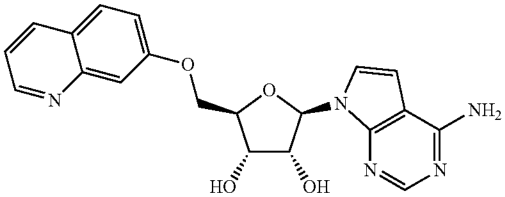 [SMILES: Nc1ncnc2c1ccn2[C@@H]1O[C@H](COc2ccc3cccnc3c2)[C@@H](O)[C@H]1O] | B1 | Intermediate 127 |
| 47 | 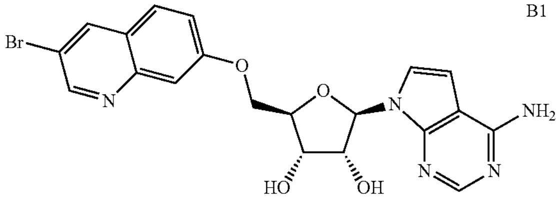 | B1 | Intermediate 128 |
| 48 | 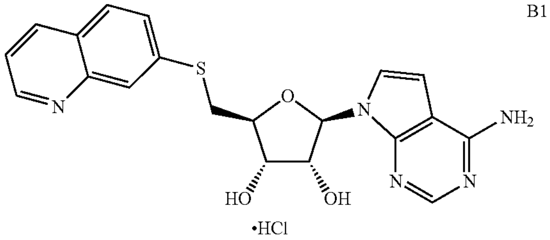 | B1 | Intermediate 129 |

TABLE 21-continued
| Compound | Structure | Reaction protocol | Starting material |
|---|---|---|---|
| 49 | 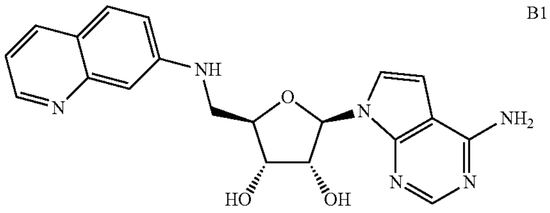 | B1 | Intermediate 130 |
| 50 | 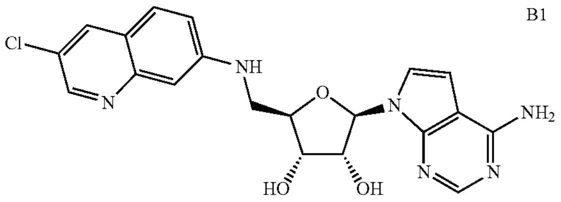 [SMILES: Nc1ncnc2c1ccn2[C@@H]1O[C@H](CNc2ccc3cc(Cl)cnc3c2)[C@@H](O)[C@H]1O] | B1 | Intermediate 131 |
| 51 | 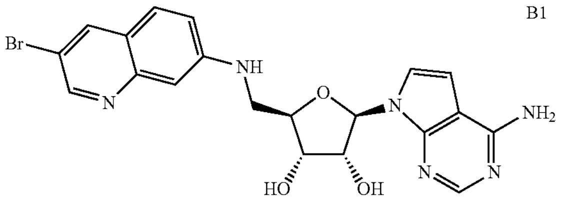 [SMILES: Nc1ncnc2c1ccn2[C@@H]1O[C@H](CNc2ccc3cc(Br)cnc3c2)[C@@H](O)[C@H]1O] | B1 | Intermediate 132 |
| 52 | 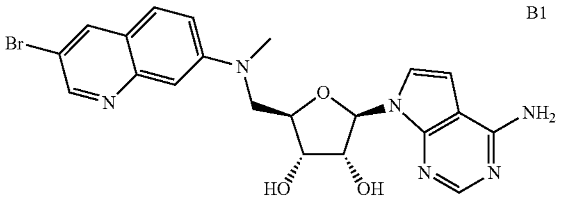 [SMILES: CN(C[C@H]1O[C@@H](n2ccc3c(N)ncnc32)[C@H](O)[C@@H]1O)c1ccc2cc(Br)cnc2c1] | B1 | Intermediate 133 |
| 53 | 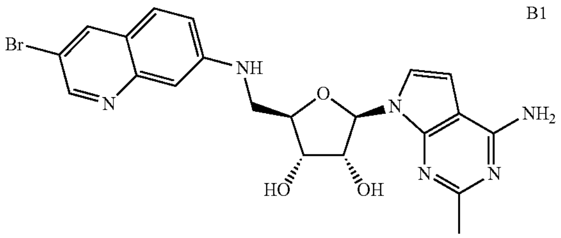 [SMILES: Cc1nc(N)c2ccn([C@@H]3O[C@H](CNc4ccc5cc(Br)cnc5c4)[C@@H](O)[C@H]3O)c2n1] | B1 | Intermediate 134 |
| 54 | 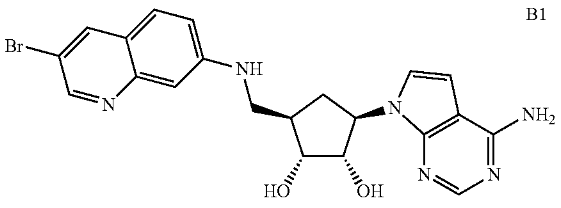 | B1 | Intermediate 135 |
| 54a | 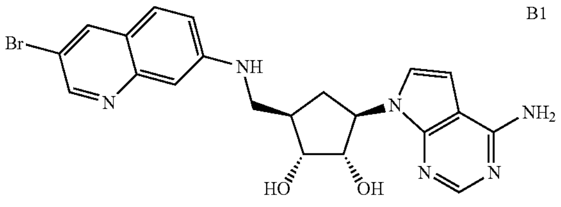 •2HCl | B1 | Intermediate 135 |

TABLE 21-continued
| Compound | Structure | Reaction protocol | Starting material |
|---|---|---|---|
| 55 | 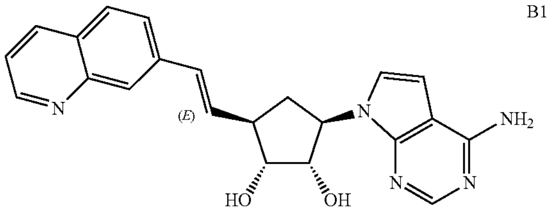 | B1 | Intermediate 137 |
| 56 | 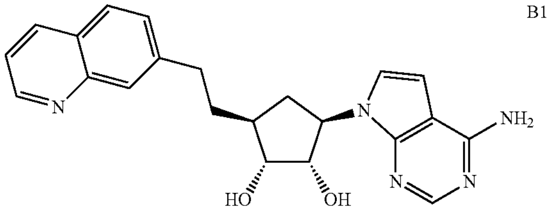 | B1 | Intermediate 146 |
| 57 | 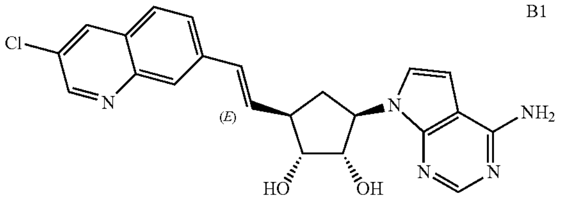 [SMILES: Nc1ncnc2c1ccn2[C@@H]1C[C@H](/C=C/c2ccc3cc(Cl)cnc3c2)[C@@H](O)[C@H]1O] | B1 | Intermediate 138 |
| 57a | 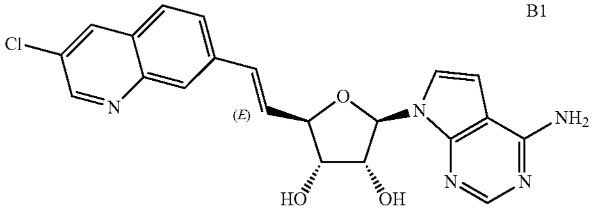 [SMILES: Nc1ncnc2c1ccn2[C@@H]1O[C@H](/C=C/c2ccc3cc(Cl)cnc3c2)[C@@H](O)[C@H]1O] | B1 | Intermediate 136 |
| 58 | 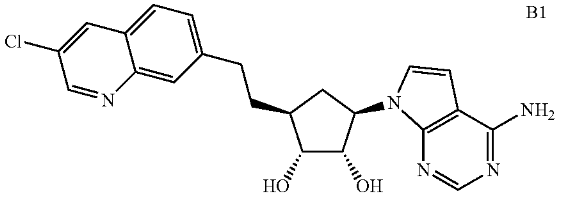 [SMILES: Nc1ncnc2c1ccn2[C@@H]1C[C@H](CCc2ccc3cc(Cl)cnc3c2)[C@@H](O)[C@H]1O] | B1 | Intermediate 147 |
| 59 | 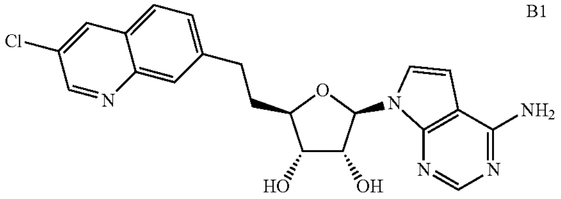 [SMILES: Nc1ncnc2c1ccn2[C@@H]1O[C@H](CCc2ccc3cc(Cl)cnc3c2)[C@@H](O)[C@H]1O] | B1 | Intermediate 148 |
| 60 | 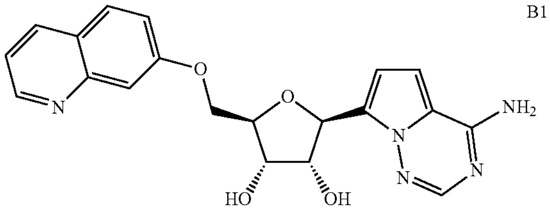 | B1 | Intermediate 149 |

TABLE 21-continued
| Compound | Structure | Reaction protocol | Starting material |
| --- | --- | --- | --- |
| 61 | 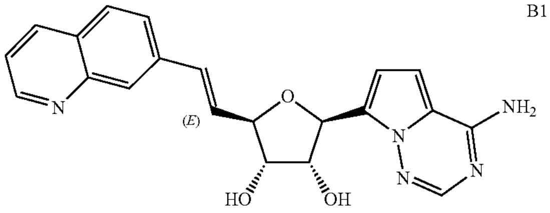 | B1 | Intermediate 150 |
| 62 | 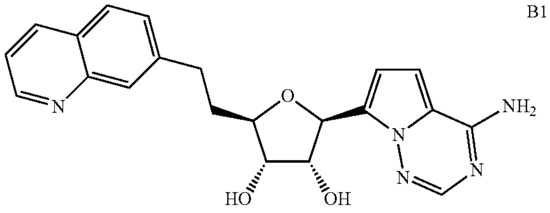 | B1 | Intermediate 150 |
| 63 | 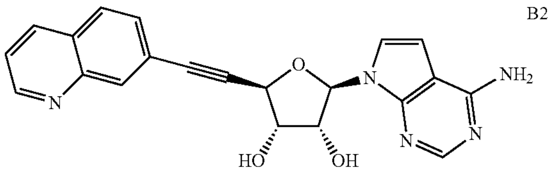 | B2 | Intermediate 139 |
| 64 | 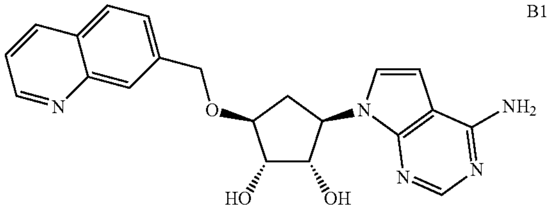 | B1 | Intermediate 141 |
| 65 | 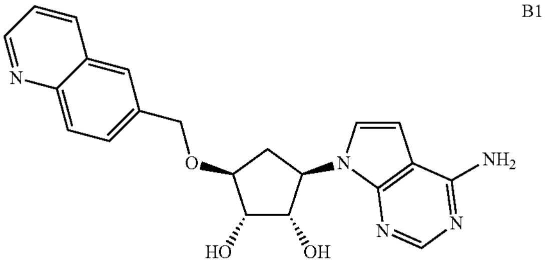 | B1 | Intermediate 142 |
| 66 | 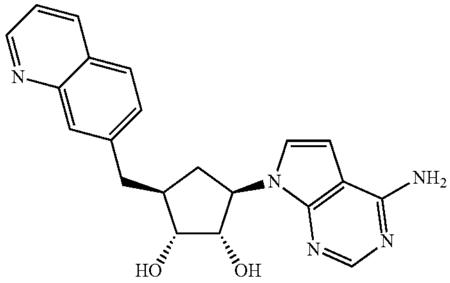 [SMILES: Nc1ncnc2c1ccn2[C@@H]1C[C@H](Cc2ccc3cccnc3c2)[C@@H](O)[C@H]1O] | B1 | Intermediate 143 |

TABLE 21-continued
| Compound | Structure | Reaction protocol | Starting material |
|---|---|---|---|
| 82 | 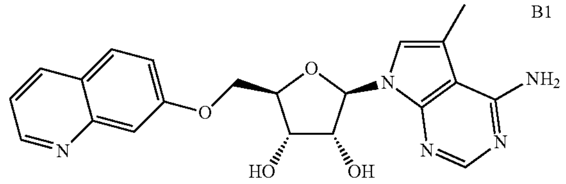 •2HCl | B1 | Intermediate 188 |
| 83 | 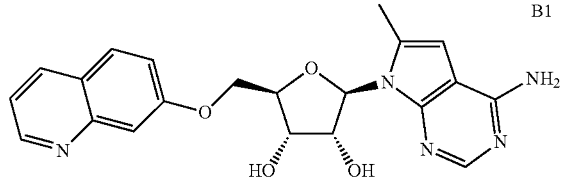 •2HCl | B1 | Intermediate 192 |
| 84 | 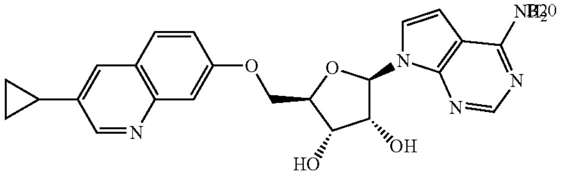 | B20 | Intermediate 193 |
| 85 | 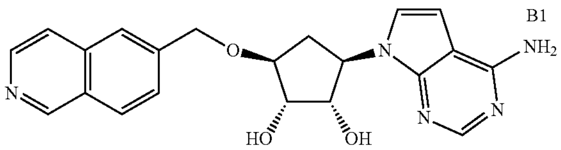 [SMILES: Nc1ncnc2c1ccn2[C@@H]1C[C@H](OCc2ccc3cnccc3c2)[C@@H](O)[C@H]1O] | B1 | Intermediate 194 |
| 86 | 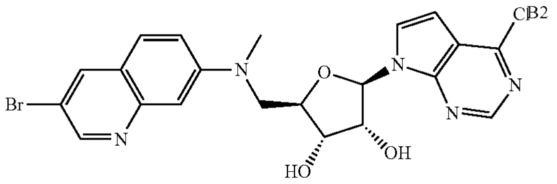 | B2 | Intermediate 96 |
| 87 | 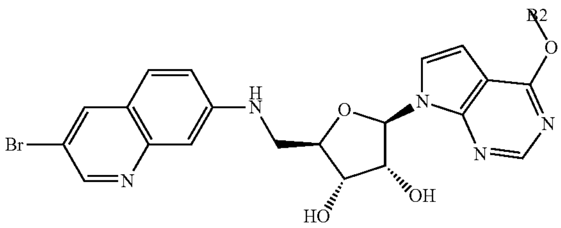 [SMILES: COc1ncnc2c1ccn2[C@@H]1O[C@H](CNc2ccc3cc(Br)cnc3c2)[C@@H](O)[C@H]1O] | B2 | Intermediate 195 |
| 88 | 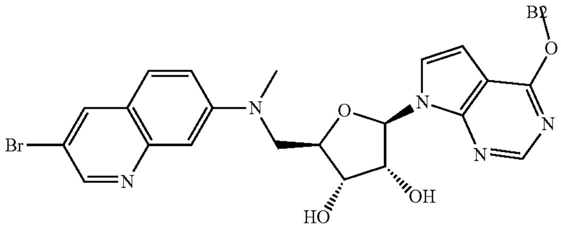 [SMILES: COc1ncnc2c1ccn2[C@@H]1O[C@H](CN(C)c2ccc3cc(Br)cnc3c2)[C@@H](O)[C@H]1O] | B2 | Intermediate 196 |

TABLE 21-continued
| Compound | Structure | Reaction protocol | Starting material |
| --- | --- | --- | --- |
| 90 | 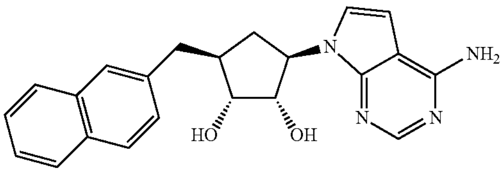 [SMILES: Nc1ncnc2c1ccn2[C@@H]1C[C@H](Cc2ccc3ccccc3c2)[C@@H](O)[C@H]1O] | B1 | Intermediate 198 |
| 91 | 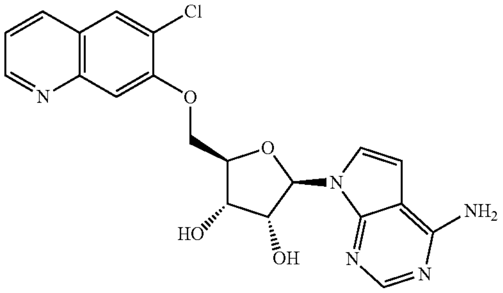 [SMILES: Nc1ncnc2c1ccn2[C@@H]1O[C@H](COc2cc3ncccc3cc2Cl)[C@@H](O)[C@H]1O] | B5 | Intermediate 199 |
| 92 | 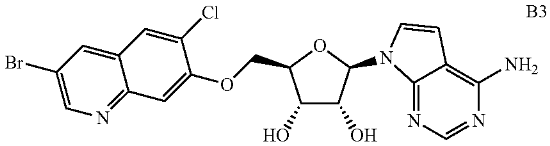 | B3 | Intermediate 201 |
| 94 | 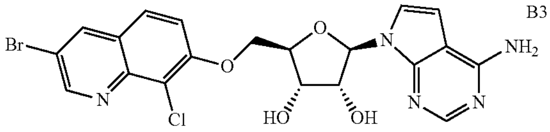 | B3 | Intermediate 206 |
| 95 | 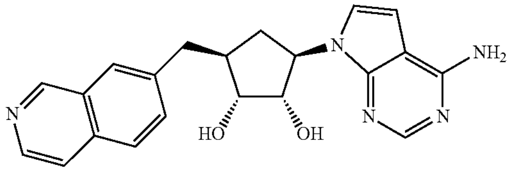 [SMILES: Nc1ncnc2c1ccn2[C@@H]1C[C@H](Cc2ccc3ccncc3c2)[C@@H](O)[C@H]1O] | B1 | Intermediate 209 |
| 96 | 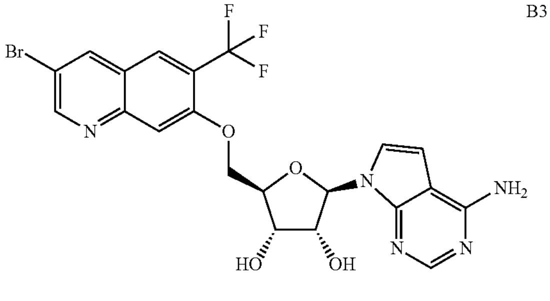 | B3 | Intermediate 211 |
| 97 | 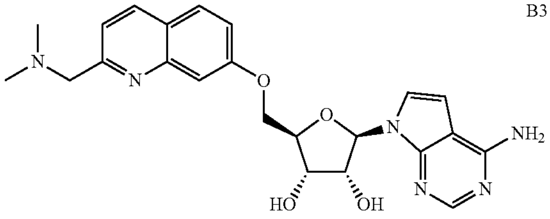 [SMILES: CN(C)Cc1ccc2ccc(OC[C@H]3O[C@@H](n4ccc5c(N)ncnc54)[C@H](O)[C@@H]3O)cc2n1] | B3 | Intermediate 213 |

TABLE 21-continued
| Compound | Structure | Reaction protocol | Starting material |
|---|---|---|---|
| 98 | 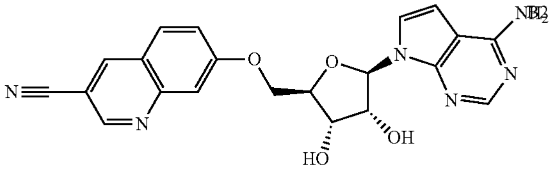 [SMILES: N#Cc1cnc2cc(OC[C@H]3O[C@@H](n4ccc5c(N)ncnc54)[C@H](O)[C@@H]3O)ccc2c1] | B2 | Intermediate 214 |
| 99 | 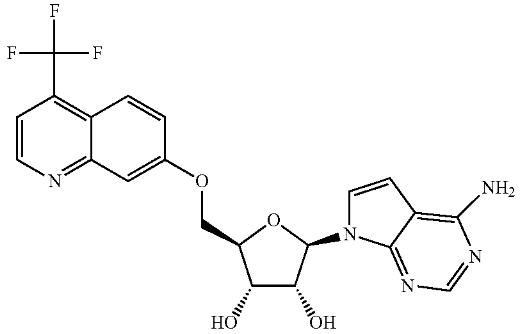 [SMILES: Nc1ncnc2c1ccn2[C@@H]1O[C@H](COc2ccc3c(C(F)(F)F)ccnc3c2)[C@@H](O)[C@H]1O] | B3 | Intermediate 215 |
| 100 | 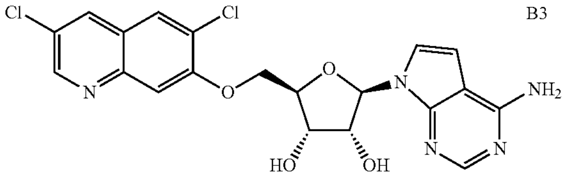 [SMILES: Nc1ncnc2c1ccn2[C@@H]1O[C@H](COc2cc3ncc(Cl)cc3cc2Cl)[C@@H](O)[C@H]1O] | B3 | Intermediate 217 |
| 101 | 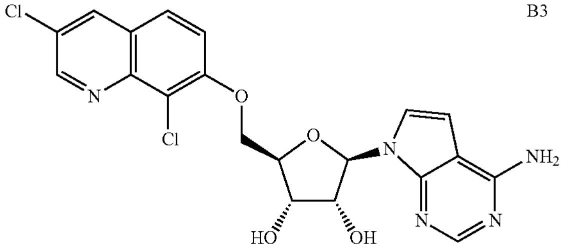 [SMILES: Nc1ncnc2c1ccn2[C@@H]1O[C@H](COc2ccc3cc(Cl)cnc3c2Cl)[C@@H](O)[C@H]1O] | B3 | Intermediate 219 |
| 102 | 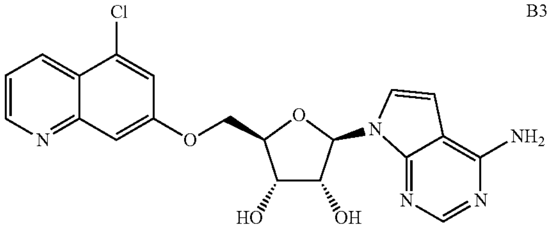 [SMILES: Nc1ncnc2c1ccn2[C@@H]1O[C@H](COc2cc(Cl)c3cccnc3c2)[C@@H](O)[C@H]1O] | B3 | Intermediate 221 |
| 103 | 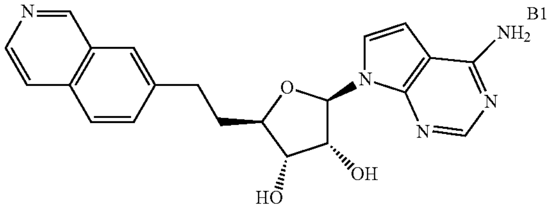 | B1 | Intermediate 226 |

TABLE 21-continued
| Compound | Structure | Reaction protocol | Starting material |
|---|---|---|---|
| 104 | 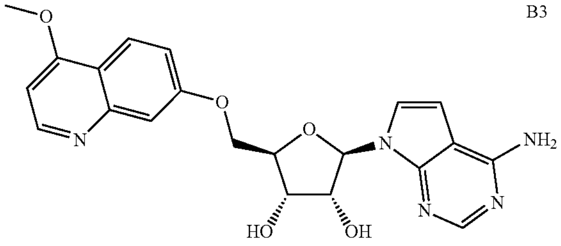 [SMILES: COc1ccnc2cc(OC[C@H]3O[C@@H](n4ccc5c(N)ncnc54)[C@H](O)[C@@H]3O)ccc12] | B3 | Intermediate 227 |
| 105 | 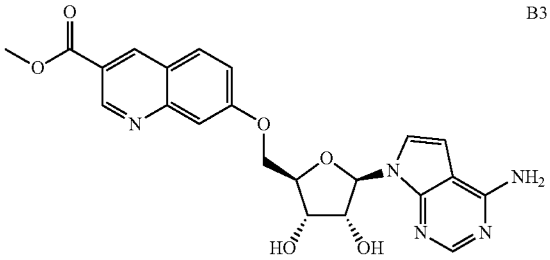 [SMILES: COC(=O)c1cnc2cc(OC[C@H]3O[C@@H](n4ccc5c(N)ncnc54)[C@H](O)[C@@H]3O)ccc2c1] | B3 | Intermediate 228 |
| 106 | 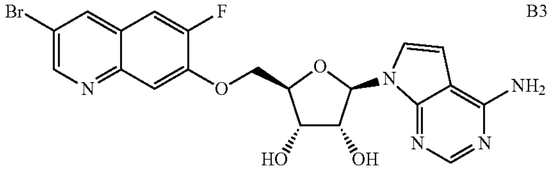 | B3 | Intermediate 230 |
| 107 | 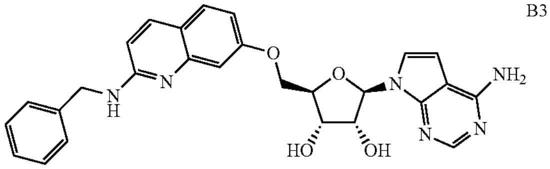 | B3 | Intermediate 232 |
| 108 | 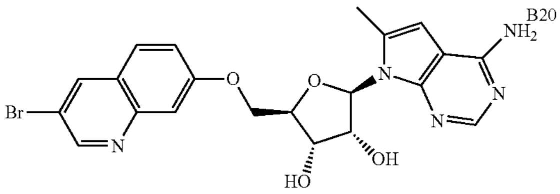 | B20 | Intermediate 234 |
| 109 | 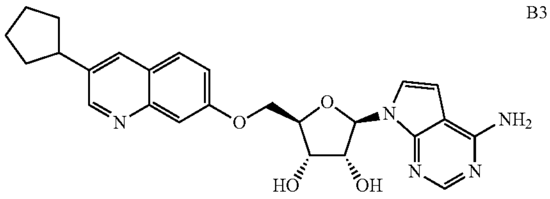 | B3 | Intermediate 236 |
| 110 | 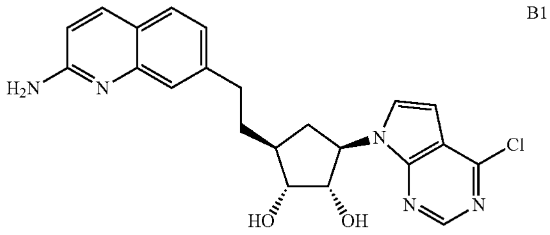 | B1 | Intermediate 237 |

TABLE 21-continued
| Compound | Structure | Reaction protocol | Starting material |
| --- | --- | --- | --- |
| 111 | 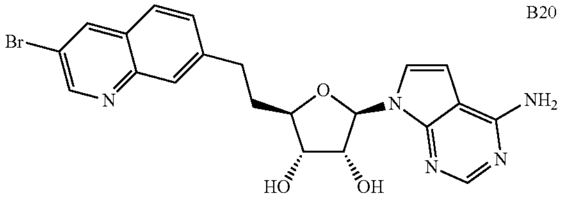 [SMILES: Nc1ncnc2c1ccn2[C@@H]1O[C@H](CCc2ccc3cc(Br)cnc3c2)[C@@H](O)[C@H]1O] | B20 | Intermediate 239 |
| 112 | 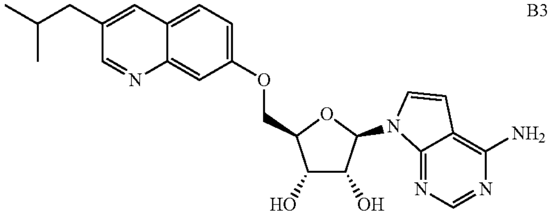 [SMILES: CC(C)Cc1cnc2cc(OC[C@H]3O[C@@H](n4ccc5c(N)ncnc54)[C@H](O)[C@@H]3O)ccc2c1] | B3 | Intermediate 241 |
| 113 | 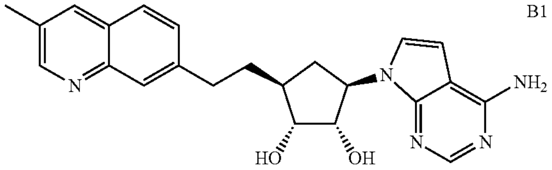 [SMILES: Cc1cnc2cc(CC[C@H]3C[C@@H](n4ccc5c(N)ncnc54)[C@H](O)[C@@H]3O)ccc2c1] | B1 | Intermediate 243 |
| 114 | 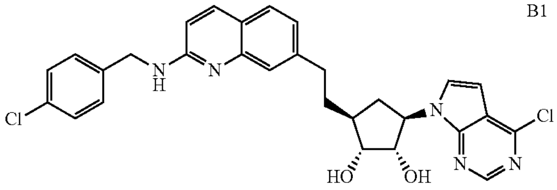 [SMILES: O[C@@H]1[C@@H](CCc2ccc3ccc(NCc4ccc(Cl)cc4)nc3c2)C[C@@H](n2ccc3c(Cl)ncnc32)[C@@H]1O] | B1 | Intermediate 245 |
| 115 | 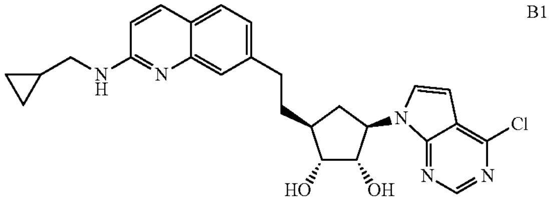 | B1 | Intermediate 159 |
| 120 | 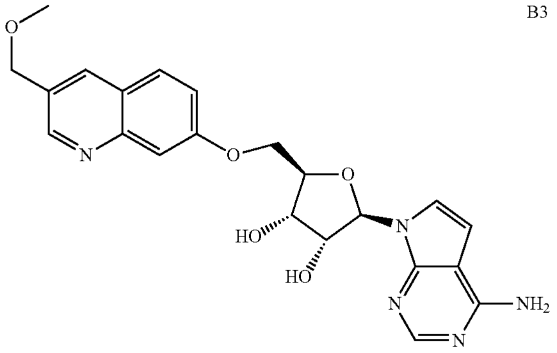 [SMILES: COCc1cnc2cc(OC[C@H]3O[C@@H](n4ccc5c(N)ncnc54)[C@H](O)[C@@H]3O)ccc2c1] | B3 | Intermediate 247 |

TABLE 21-continued
| Compound | Structure | Reaction protocol | Starting material |
|---|---|---|---|
| 121 | 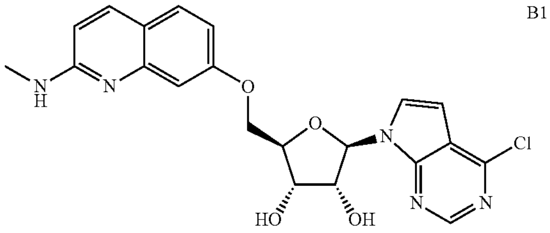 | B1 | Intermediate 248 |
| 122 | 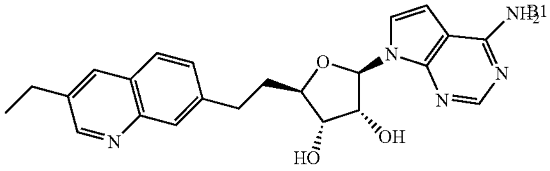 | B1 | Intermediate 250 |
| 123 | 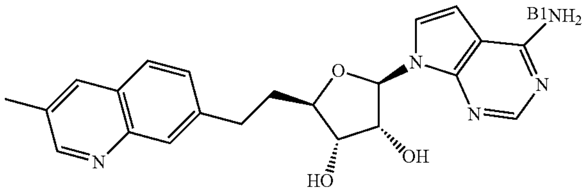 [SMILES: Cc1cnc2cc(CC[C@H]3O[C@@H](n4ccc5c(N)ncnc54)[C@H](O)[C@@H]3O)ccc2c1] | B1 | Intermediate 252 |
| 124 | 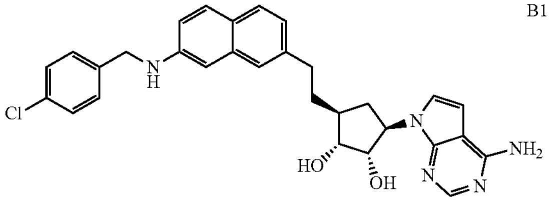 [SMILES: Nc1ncnc2c1ccn2[C@@H]1C[C@H](CCc2ccc3ccc(NCc4ccc(Cl)cc4)cc3c2)[C@@H](O)[C@H]1O] | B1 | Intermediate 255 |
| 125 | 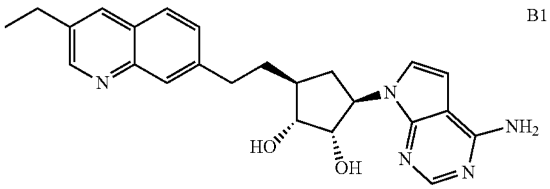 | B1 | Intermediate 257 |
| 126 | 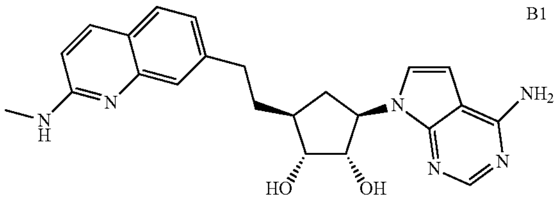 [SMILES: CNc1ccc2ccc(CC[C@H]3C[C@@H](n4ccc5c(N)ncnc54)[C@H](O)[C@@H]3O)cc2n1] | B1 | Intermediate 258 |
| 127 | 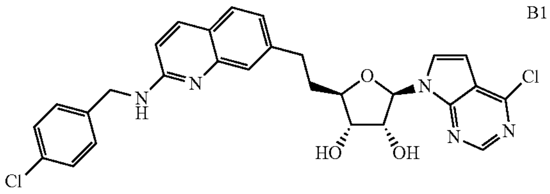 | B1 | Intermediate 254 |

TABLE 21-continued
| Compound | Structure | Reaction protocol | Starting material |
| --- | --- | --- | --- |
| 128 | 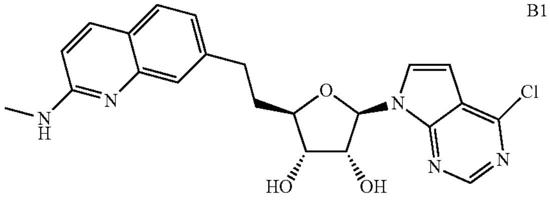 | B1 | Intermediate 259 |
| 129 | 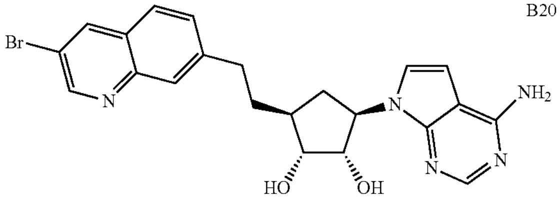 | B20 | Intermediate 261 |
| 130 | 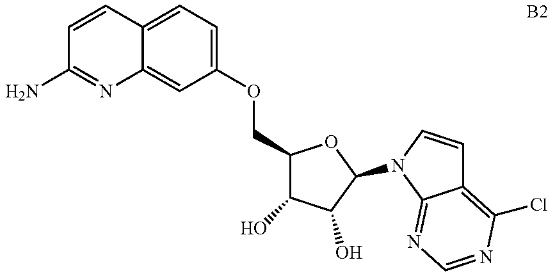 [SMILES: Nc1ccc2ccc(OC[C@H]3O[C@@H](n4ccc5c(Cl)ncnc54)[C@H](O)[C@@H]3O)cc2n1] | B2 | Intermediate 262 |
| 131 | 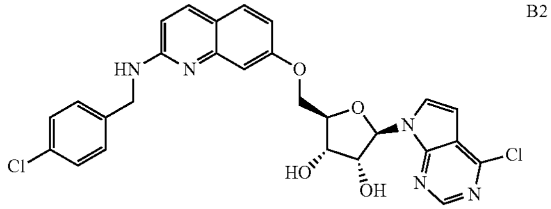 | B2 | Intermediate 264 |
| 132 | 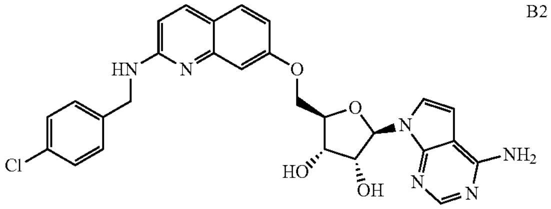 | B2 | Intermediate 265 |
| 133 | 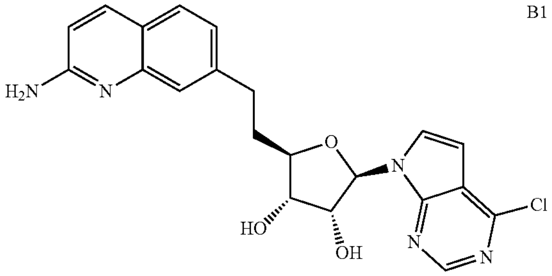 [SMILES: Nc1ccc2ccc(CC[C@H]3O[C@@H](n4ccc5c(Cl)ncnc54)[C@H](O)[C@@H]3O)cc2n1] | B1 | Intermediate 266 |

TABLE 21-continued
| Compound | Structure | Reaction protocol | Starting material |
|---|---|---|---|
| 134 | 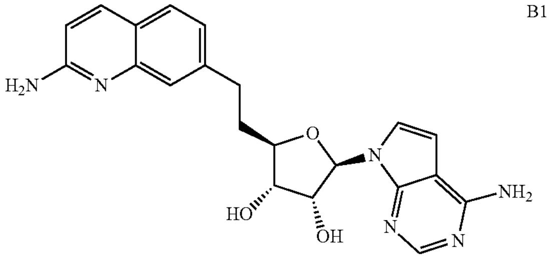 | B1 | Intermediate 267 |
| 135 | 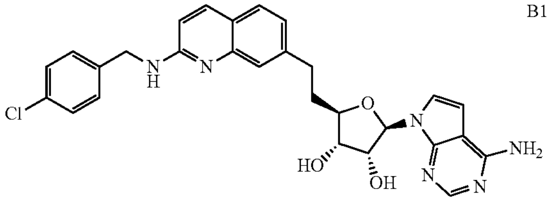 | B1 | Intermediate 269 |
| 136 | 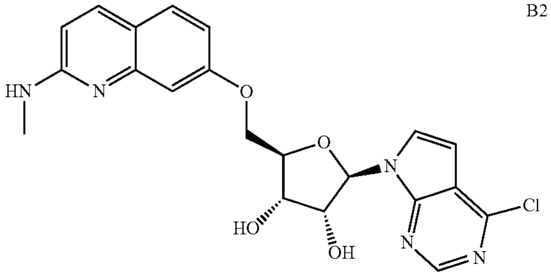 | B2 | Intermediate 270 |
| 137 | 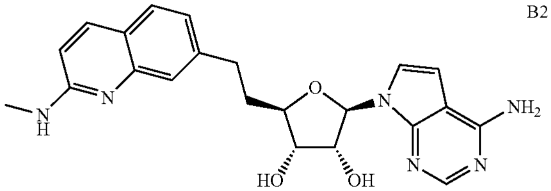 | B2 | Intermediate 271 |
| 138 | 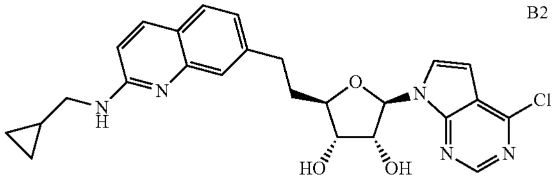 [SMILES: O[C@@H]1[C@H](O)[C@@H](CCc2ccc3ccc(NCC4CC4)nc3c2)O[C@H]1n1ccc2c(Cl)ncnc21] | B2 | Intermediate 272 |
| 139 | 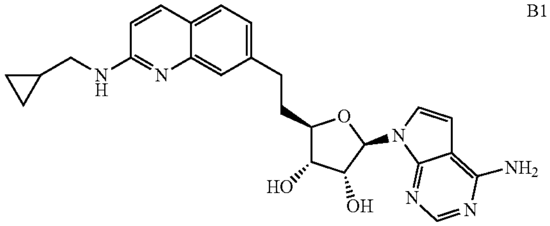 | B1 | Intermediate 273 |

TABLE 21-continued
| Compound | Structure | Reaction protocol | Starting material |
|---|---|---|---|
| 140 | 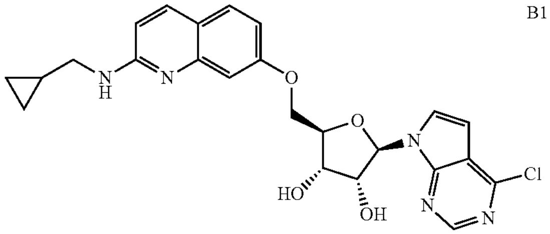 | B1 | Intermediate 275 |
| 141 | 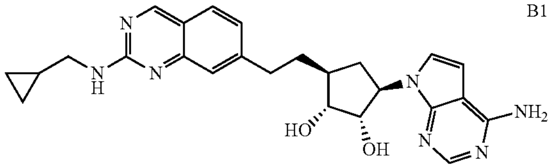 [SMILES: Nc1ncnc2c1ccn2[C@@H]1C[C@H](CCc2ccc3cnc(NCC4CC4)nc3c2)[C@@H](O)[C@H]1O] | B1 | Intermediate 278 |
| 142 | 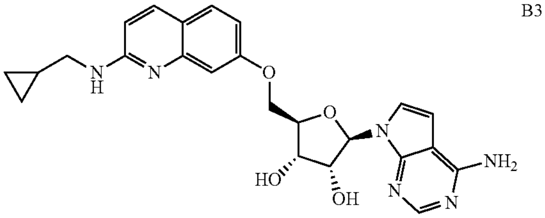 | B3 | Intermediate 279 |
| 143 | 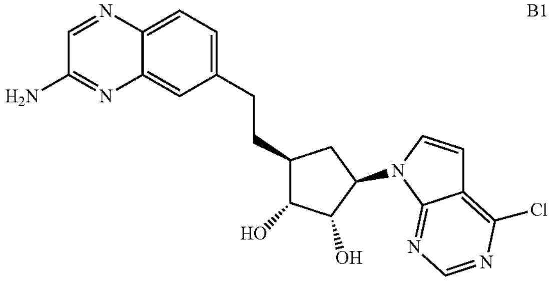 [SMILES: Nc1cnc2ccc(CC[C@H]3C[C@@H](n4ccc5c(Cl)ncnc54)[C@H](O)[C@@H]3O)cc2n1] | B1 | Intermediate 281 |
| 144 | 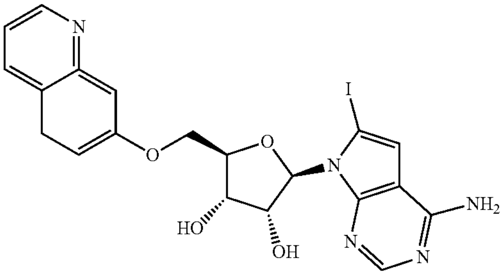 | B20 | Intermediate 286 |
| 145 | 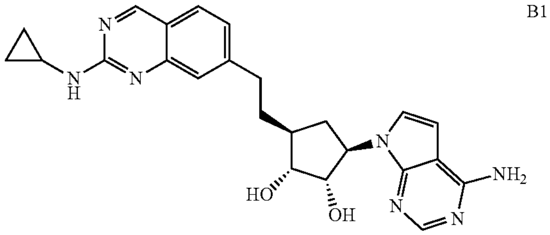 | B1 | Intermediate 289 |

TABLE 21-continued
| Compound | Structure | Reaction protocol | Starting material |
| --- | --- | --- | --- |
| 146 | 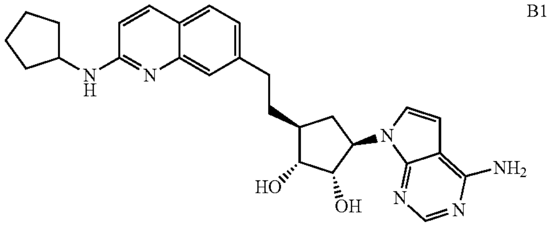 | B1 | Intermediate 292 |
| 147 | 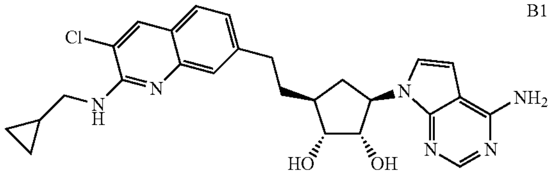 [SMILES: Nc1ncnc2c1ccn2[C@@H]1C[C@H](CCc2ccc3cc(Cl)c(NCC4CC4)nc3c2)[C@@H](O)[C@H]1O] | B1 | Intermediate 295 |
| 148 | 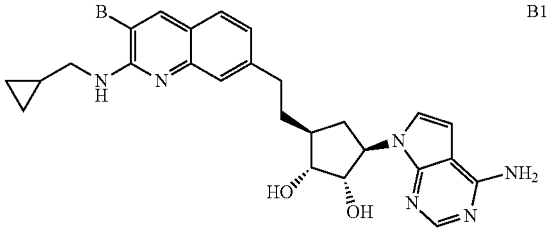 | B1 | Intermediate 298 |
| 149 | 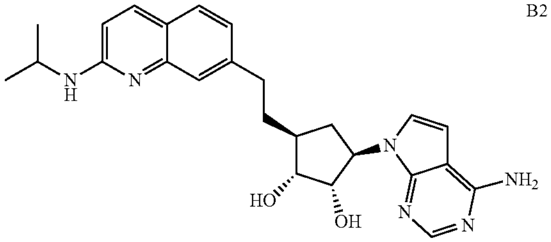 | B2 | Intermediate 301 |
| 150 | 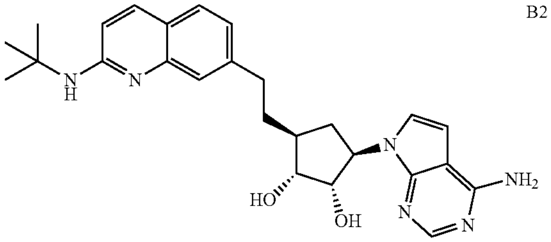 | B2 | Intermediate 304 |
| 151 | 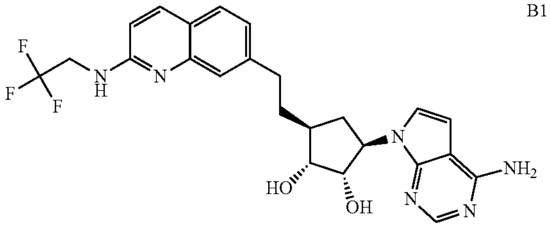 | B1 | Intermediate 307 |

TABLE 21-continued
| Compound | Structure | Reaction protocol | Starting material |
| --- | --- | --- | --- |
| 152 | 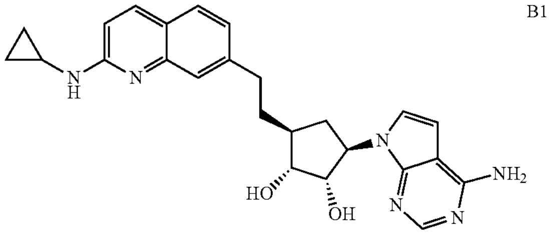 | B1 | Intermediate 310 |
| 153 | 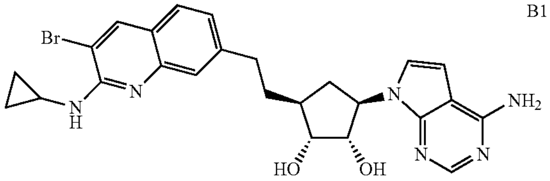 | B1 | Intermediate 313 |
| 154 | 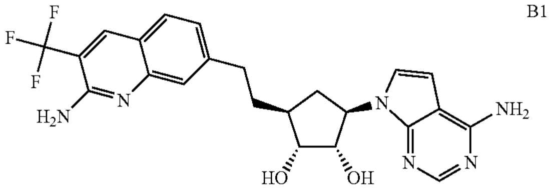 | B1 | Intermediate 316 |
| 155 | 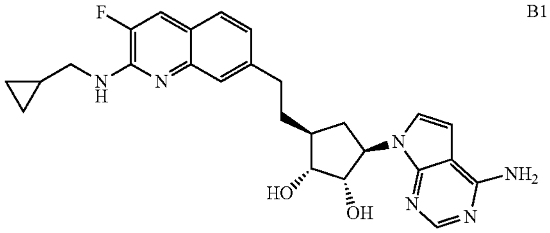 | B1 | Intermediate 319 |
| 156 | 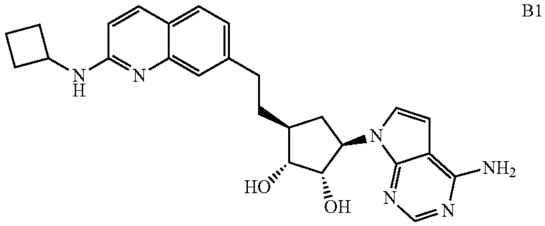 | B1 | Intermediate 322 |
| 157 | 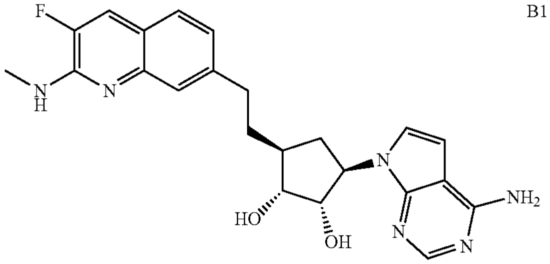 | B1 | Intermediate 325 |

TABLE 21-continued
| Compound | Structure | Reaction protocol | Starting material |
|---|---|---|---|
| 158 | 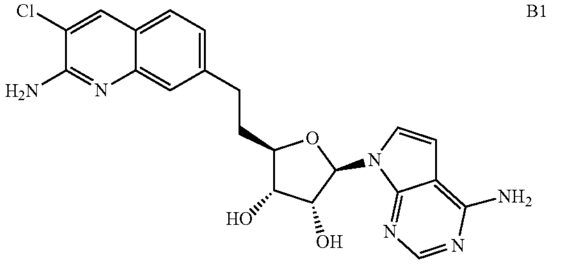 | B1 | Intermediate 328 |
| 159 | 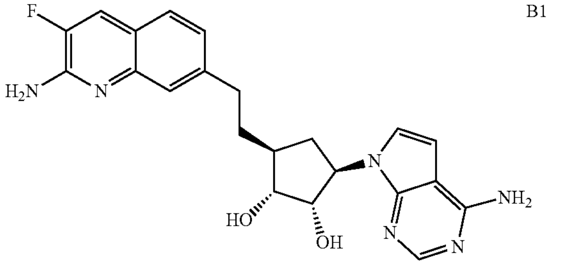 | B1 | Intermediate 331 |
| 160 | 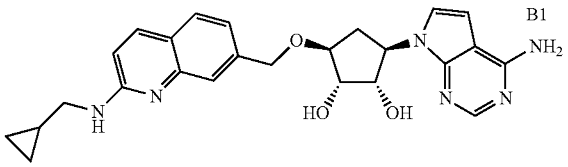 [SMILES: Nc1ncnc2c1ccn2[C@@H]1C[C@H](OCc2ccc3ccc(NCC4CC4)nc3c2)[C@@H](O)[C@H]1O] | B1 | Intermediate 334 |
| 161 | 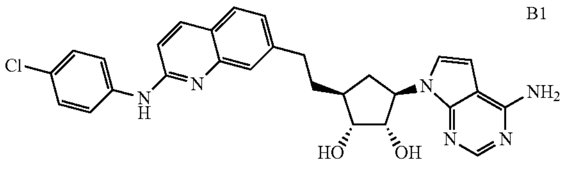 [SMILES: Nc1ncnc2c1ccn2[C@@H]1C[C@H](CCc2ccc3ccc(Nc4ccc(Cl)cc4)nc3c2)[C@@H](O)[C@H]1O] | B1 | Intermediate 337 |
| 222 | 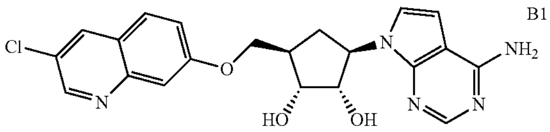 | B1 | Intermediate 504 |
| 223 | 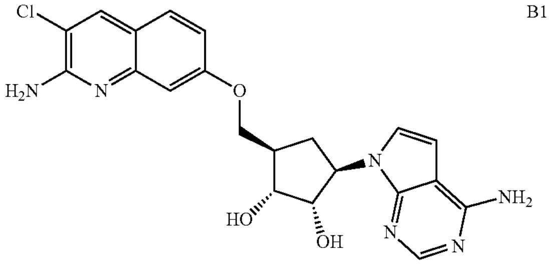 | B1 | Intermediate 462 |
| 224 | 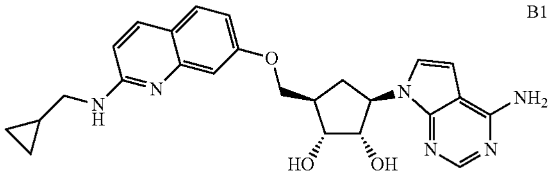 [SMILES: Nc1ncnc2c1ccn2[C@@H]1C[C@H](COc2ccc3ccc(NCC4CC4)nc3c2)[C@@H](O)[C@H]1O] | B1 | Intermediate 464 |

TABLE 21-continued
| Compound | Structure | Reaction protocol | Starting material |
|---|---|---|---|
| 236 | 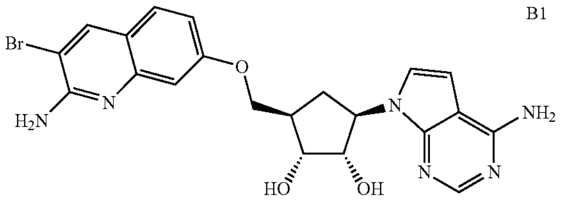 [SMILES: Nc1nc2cc(OC[C@H]3C[C@@H](n4ccc5c(N)ncnc54)[C@H](O)[C@@H]3O)ccc2cc1Br] | B1 | Intermediate 484 |
| 240 | 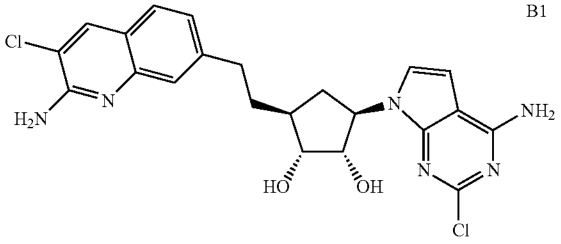 [SMILES: Nc1nc2cc(CC[C@H]3C[C@@H](n4ccc5c(N)nc(Cl)nc54)[C@H](O)[C@@H]3O)ccc2cc1Cl] | B1 | Intermediate 496 |
| 241 | 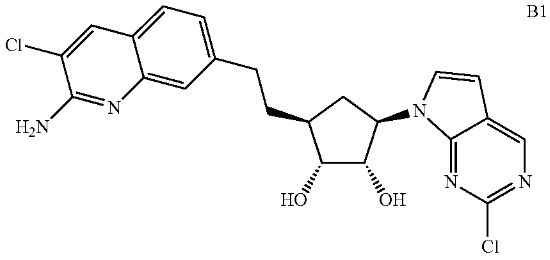 | B1 | Intermediate 498 |
| 242 | 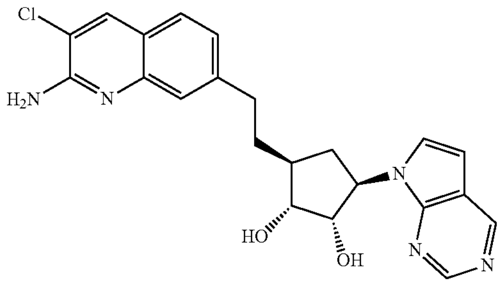 [SMILES: Nc1nc2cc(CC[C@H]3C[C@@H](n4ccc5cncnc54)[C@H](O)[C@@H]3O)ccc2cc1Cl] | B1 | Intermediate 500 |
| 243 | 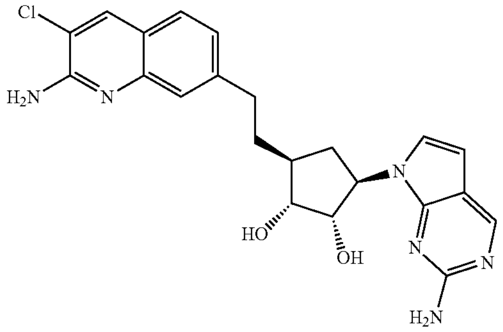 [SMILES: Nc1ncc2ccn([C@@H]3C[C@H](CCc4ccc5cc(Cl)c(N)nc5c4)[C@@H](O)[C@H]3O)c2n1] | B1 | Intermediate 501 |
| 244 | 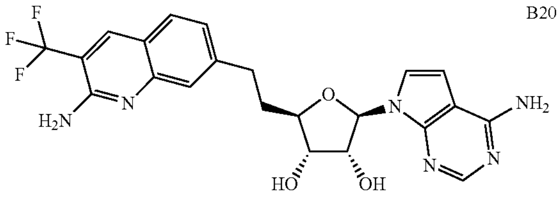 | B20 | Intermediate 514 |

TABLE 21-continued
| Compound | Structure | Reaction protocol | Starting material |
|---|---|---|---|
| 245 | 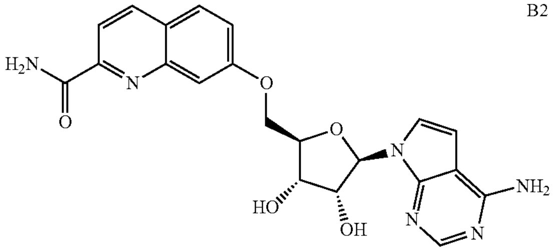 [SMILES: NC(=O)c1ccc2ccc(OC[C@H]3O[C@@H](n4ccc5c(N)ncnc54)[C@H](O)[C@@H]3O)cc2n1] | B2 | Intermediate 516 |
| 246 | 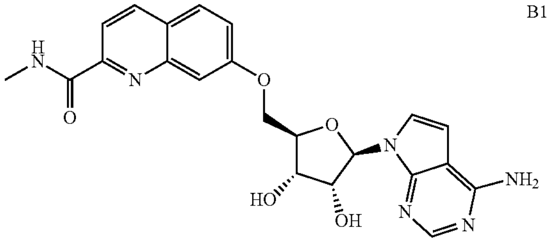 | B1 | Intermediate 518 |
| 247 | 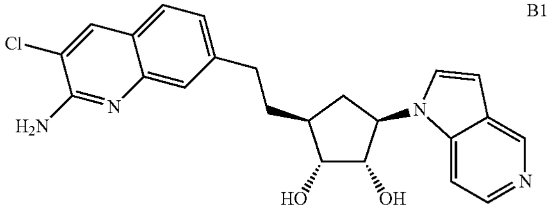 | B1 | Intermediate 520 |
| 248 | 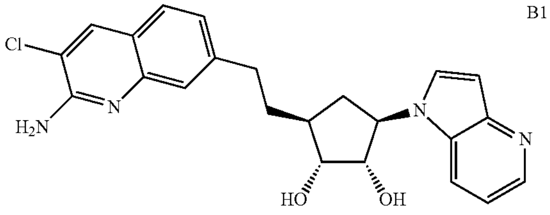 | B1 | Intermediate 522 |
| 249 | 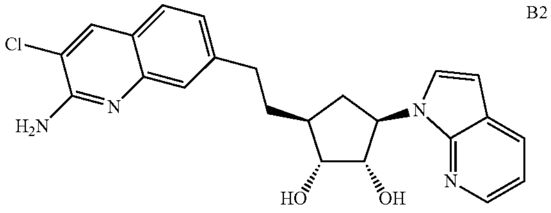 | B2 | Intermediate 524 |
| 251 | 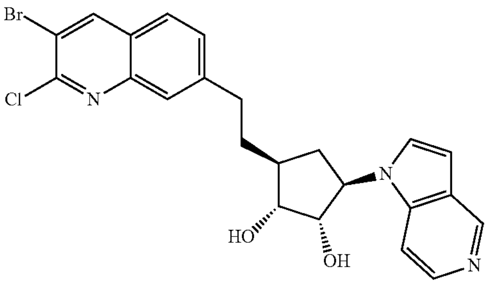 [SMILES: O[C@@H]1[C@@H](CCc2ccc3cc(Br)c(Cl)nc3c2)C[C@@H](n2ccc3cnccc32)[C@@H]1O] | B2 | Intermediate 532 |

Example B6

Preparation of Compound 67 and Compound 68

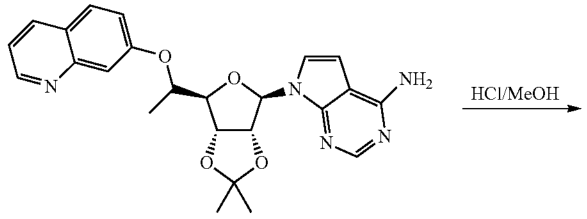

Intermediate 140

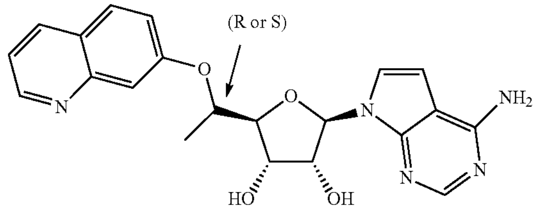

Compound 67

+

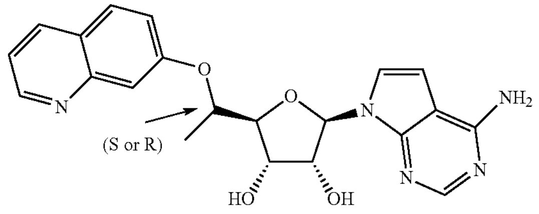

Compound 68

Intermediate 140 (210 mg, crude, 0.399 mmol) was dissolved in 5 ml of HCl/MeOH. The mixture was stirred at room temperature for 7 hours. The reaction was quenched by addition of $NH_3$/MeOH to adjust the pH to around 8 at 0° C. The resulting solid was then removed by filtration and washed with $CH_2Cl_2$ (10 ml) and the combined organic filtrate was concentrated under reduced pressure to give the crude product. The residue was purified by preparative-HPLC (HPLC condition: Columns: Phenomenex Gemini 150*25 mm*10 um; mobile phase gradient elution with 21% Water in ACN;) to yield compound 67 (40 mg) and compound 68 (52 mg) as a white solid.

Example B7

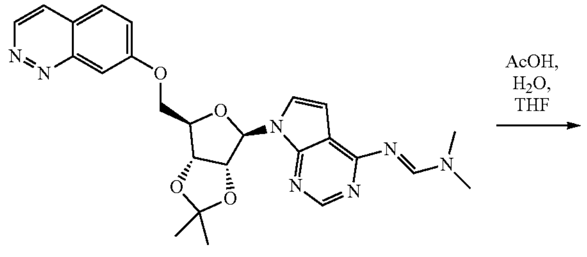

intermediate 85

-continued

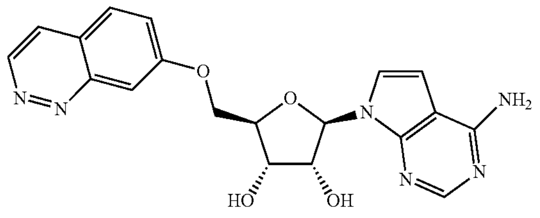

Compound 69

The reaction mixture of intermediate 85 (150 mg, 0.233 mmol) in 5 mL of mixed solvent AcOH, water and THF with ration as 13:7:3) was stirred overnight at 60° C. Then the mixture was stirred at 80° C. for 1 days. The solvent was concentrated in vacuum. The residue was dissolved in 4 ml of MeOH and the pH was adjusted to around 9 with $Na_2CO_3$ solid. The solvent was purified by preparative-HPLC (HPLC condition: Columns: Gemini 150*25 mm*5 μM; gradient elution with water (0.05% ammonia hydroxide v/v):ACN from 97:3 to 67:33) to give compound 69 as a white solid. (13 mg, 14% yield).

Example B8

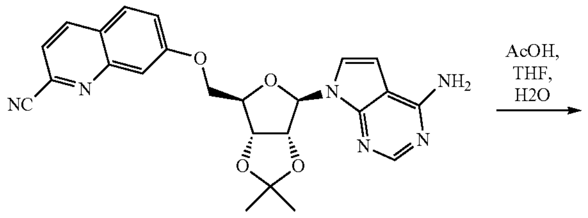

Intermediate 152

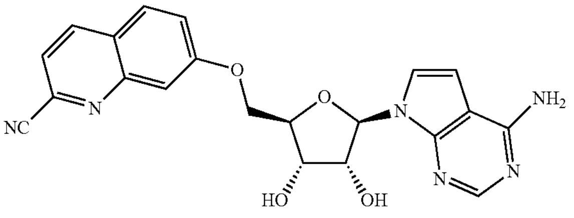

Compound 70

Intermediate 152 (425 mg, 0.927 mmol) was dissolved in the mixed solution of AcOH (22 mL), THF (5 mL) and $H_2O$ (12 mL). The mixture was stirred at 50° C. for 12 hours. The solvent was concentrated in vacuum. The crude product was purified by preparative-HPLC (gradient elution: 0.05% $NH_3{\cdot}H_2O$ in MeOH/0.05% $NH_3{\cdot}H_2O$ in $H_2O$). The combined solvent was evaporated to give the desired compound 70 as a solid (69.3 mg, 18% yield).

Example B9

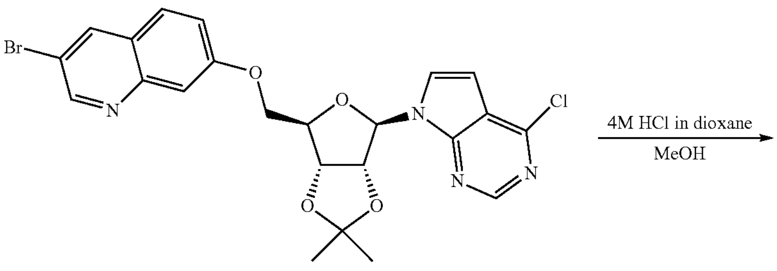

intermediate 59

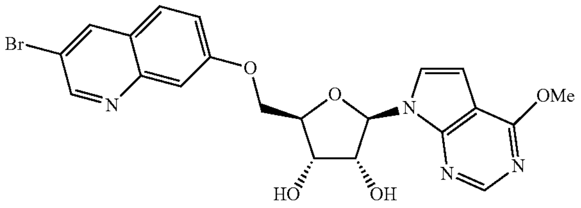

compound 71

To a solution of intermediate 59 (187 mg, ≈0.18 mmol) in 1,4-dioxane (5 mL) was added 4M HCl in dioxane (0.46 mL, 1.8 mmol). The reaction mixture was stirred at room temperature for 18 hours. The reaction was quenched by the addition of 1.5 mL 7N solution of $NH_3$ in MeOH. The solvents were evaporated. The residue was dissolved in dichloromethane with methanol (q.s.) and then purified over a $SiO_2$ column, type Grace Reveleris SRC, 12 g, Si 40, on a Armen Spot II Ultimate purification system using dichloromethane and methanol as eluens in a gradient starting from 100% DCM for 5 column volumes and ending with 40% MeOH and 60% DCM over 25 column volumes. The fractions containing product were combined and the solvents were evaporated yielding 62 mg crude product mixture. The crude product mixture was purified by Prep HPLC (Stationary phase: RP XBridge Prep C18 OBD-10 μm, 30×150 mm, Mobile phase: 0.25% $NH_4HCO_3$ solution in water, $CH_3CN$), yielding compound 71 (5.5 mg, 6% yield).

Example B10

Preparation of Compound 1a

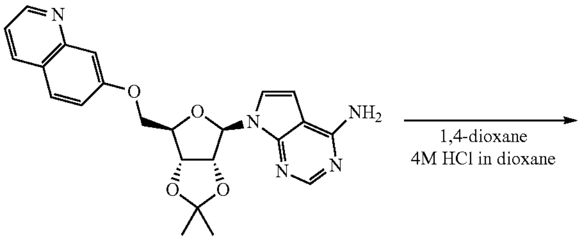

Intermediate 100

-continued

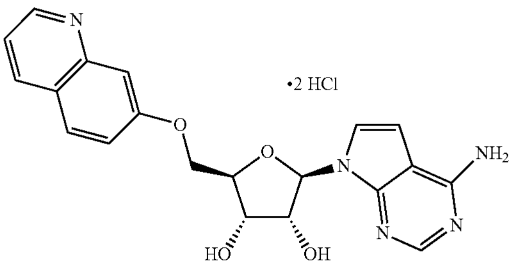

compound 1a

To a solution of intermediate 100 (9.26 g, 17.5 mmol) in 1,4-dioxane (300 mL) was added 4M HCl in 1,4-dioxane (43.8 mL, 175 mmol). The reaction mixture was stirred at room temperature for 4 hours. The reaction mixture was poured out into a beaker with DIPE (1 L). The suspension was stirred for 20 minutes and then the solvents were decantated off. The remaining precipitate was recrystallized in EtOH. The precipitate was filtered off, washed with DIPE and then dried in vacuo at 50° C. yielding compound 1a as salt with 2 equivalent of HCl (8.33 g, quantitive yield).

Example B11

Preparation of Compound 72 (via Intermediate 156)

Step a:

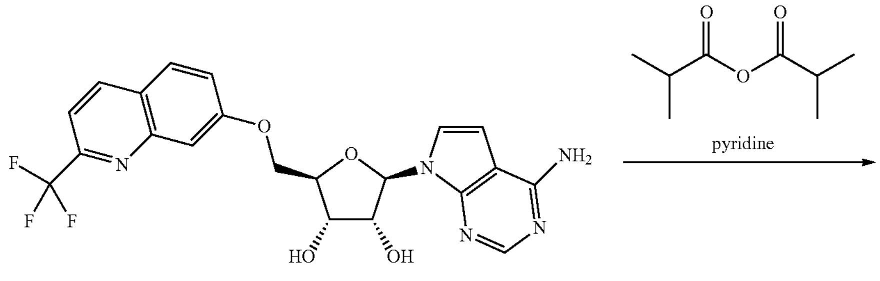

Compound 22

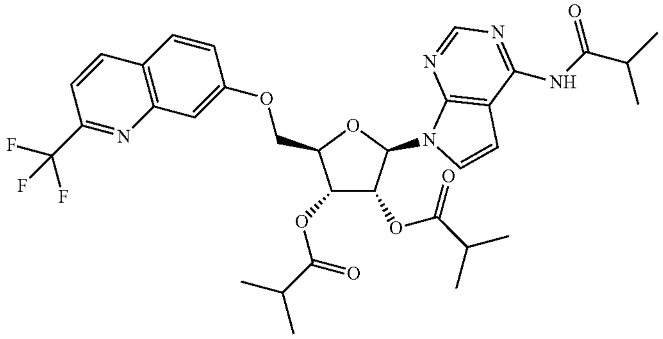

Intermediate 156

Isobutyric anhydride (2.36 mL, 14.2 mmol) was added to a stirred solution of compound 22 (688.3 mg, 1.418 mmol) in pyridine (25 mL, 310.361 mmol) at rt. After addition the reaction mixture was stirred at 50° C. for 18 hours. The solvents were evaporated. The residue was co-evaporated with toluene. The residue was dissolved in DCM and purified over a $SiO_2$ column, type Grace Reveleris SRC, 40 g, Si 40, on a Armen Spot II Ultimate purification system using DCM and MeOH as eluens in a gradient starting from 100% DCM for 5 column volumes and ending with 40% MeOH and 60% DCM over 30 column volumes. The desired fractions were combined and the solvents were evaporated yielding 0.94 g of intermediate 156.

Step b:

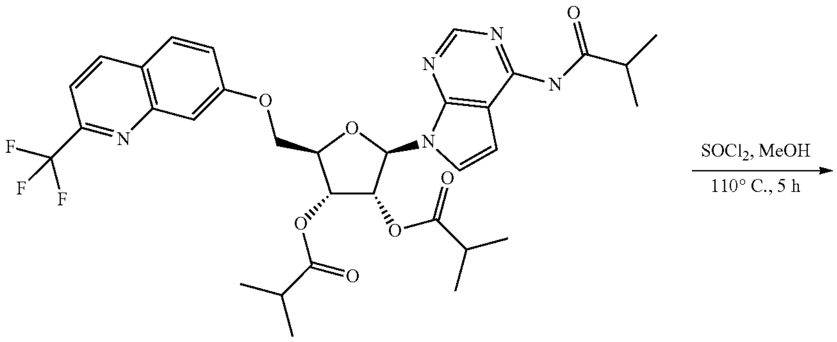

Intermediate 156

-continued

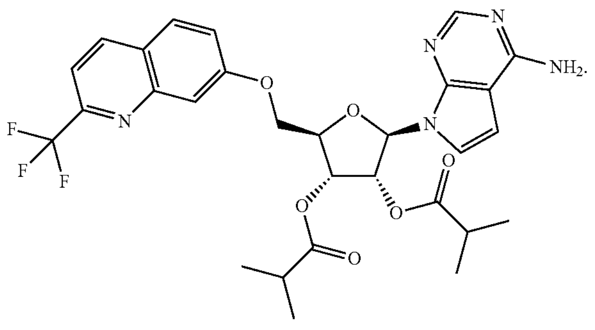

Compound 72
•HCl

A solution of intermediate 156 (0.94 g, 1.372 mmol) and $SOCl_2$ (99.493 μL, 1.372 mmol) in MeOH (20 mL, 0.791 g/mL, 493.725 mmol) was stirred and heated at 110° C. using microwave irradiation for 5 hours. The solvents were evaporated. The residue was dissolved in DCM and purified over a $SiO_2$ column, type Grace Reveleris SRC, 12 g, Si 40, on a Armen Spot II Ultimate purification system using DCM and MeOH as eluens in a gradient starting from 100% DCM for 10 column volumes and ending with 20% MeOH and 80% DCM over 30 column volumes. The fractions containing product were combined and the solvents were evaporated yielding compound 72 (·HCl) (0.66 g, 74% yield).

Below compound was prepared by an analogous reaction protocol of example B11 using the appropriate starting materials (Table 22).

TABLE 22

| Compound | Structure | Starting material |
|---|---|---|
| 73 | 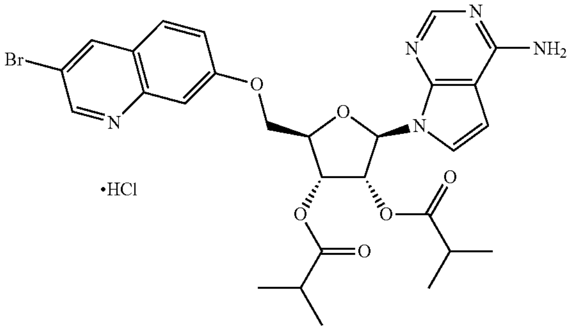 [SMILES: CC(C)C(=O)O[C@@H]1[C@H](OC(=O)C(C)C)[C@@H](COc2ccc3cc(Br)cnc3c2)O[C@H]1n1ccc2c(N)ncnc21 ; Cl] •HCl | Compound 2 |
| 89 | 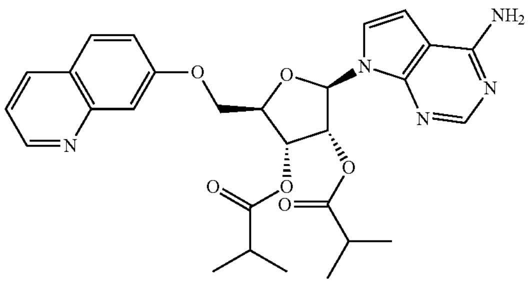 [SMILES: CC(C)C(=O)O[C@@H]1[C@H](OC(=O)C(C)C)[C@@H](COc2ccc3cccnc3c2)O[C@H]1n1ccc2c(N)ncnc21] | Compound 1 |

Example B12

Preparation of Compound 74

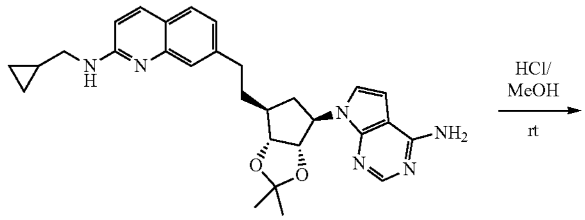

intermediate 160

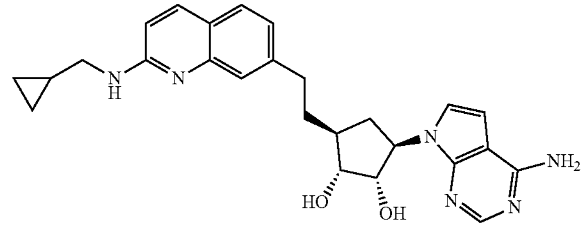

Compound 74

To a solution of intermediate 160 (3.45 g, 6.9 mmol) in MeOH (10 mL) was added HCl/MeOH (4N, 10 mL), and the mixture was stirred at room temperature for 1 hour. The mixture was lyophilized to give crude Compound 74 fraction 1 which was purified by prep-HPLC (Column: Phenomenex Synergi Max-RP 250*80 mm 10 μm, Condition: water (0.05% ammonia hydroxide v/v)-ACN, Start B: 30%, End B: 60, Gradient Time (min): 22, FlowRate (ml/min): 120). The desired fractions were collected and lyophilized to give crude Compound 74 fraction 2 which was further purified by prep-HPLC (Column Phenomenex Gemini 150*25 mm*10 μm, Condition: gradient water (0.05% ammonia hydroxide v/v)-ACN. The desired fractions were collected and lyophilized to give Compound 74 (1383 mg, yield: 43.1%) as solid.

Salt forms of Compound 74 were prepared according to state of the art procedures, known to the skilled person (Table 44).

TABLE 44

| Compound | Structure | Starting material |
|---|---|---|
| 116 | 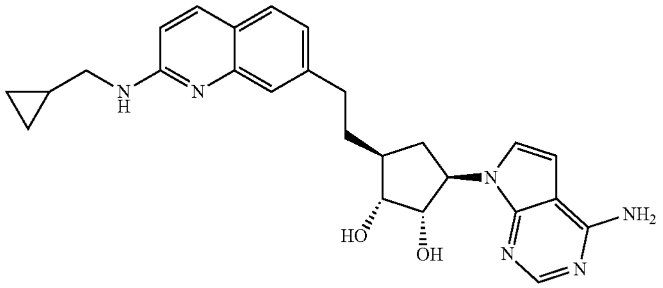 •HCl | Compound 74 |
| 117 | 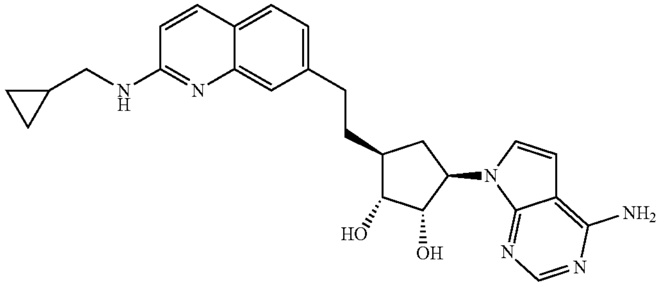 •HCOOH | Compound 74 |
| 118 | 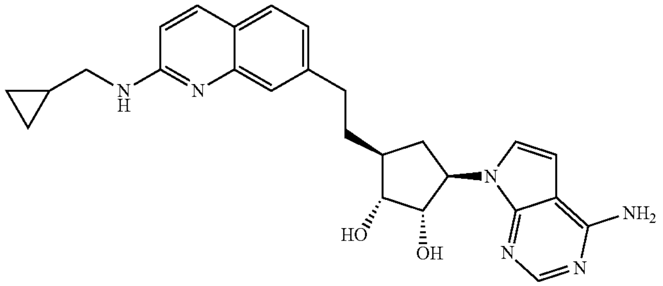 •$C_6H_8O_7$ (citric acid) | Compound 74 |

TABLE 44-continued

| Compound | Structure | Starting material |
|---|---|---|
| 119 | 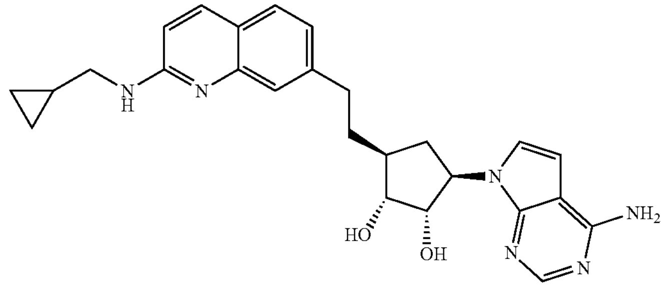 •$C_4H_4O_4$ trans | Compound 74 |

Example B13

Preparation of Compound 75

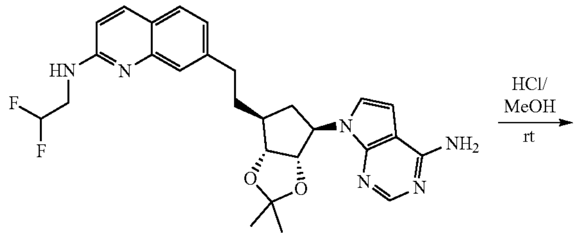

Intermediate 163

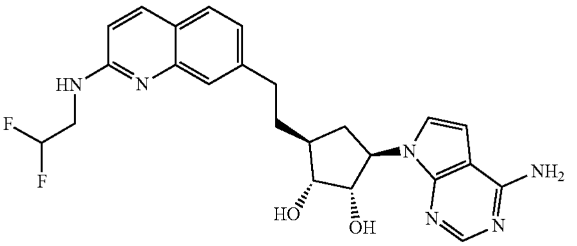

Compound 75

A solution of intermediate 163 (680 mg, ≈1.04 mmol) in MeOH (q.s.) was dissolved in HCl/MeOH (4M, 15 mL), stirred at room temperature for 2 hours. The mixture was basified with $NH_3 \cdot H_2O$ to pH>7. The solution was washed with $H_2O$ (100 mL), extracted with ethyl acetate (150 mL×3). The combined organic layers were dried ($Na_2SO_4$), filtered and concentrated in vacuo to give the crude product as brown solid. The crude product was purified by prep-HPLC (Column:Waters Xbridge Prep OBD C18 150×30 mm, 5 μm; Condition: gradient water (0.05% ammonia hydroxide v/v)-MeOH). The desired fractions were collected and lyophilized to give Compound 75 (129.8 mg, yield: 26.4%) as white solid.

Example B14

Preparation of Compound 76

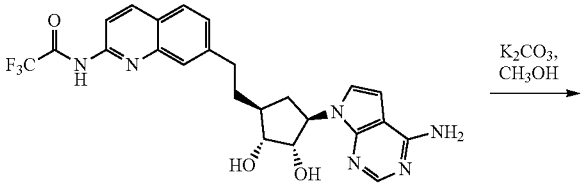

intermediate 167

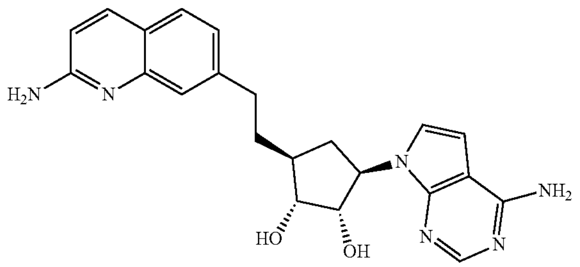

Compound 76

The mixture of intermediate 167 (250 mg) and $K_2CO_3$ (185.3 mg, 1.34 mmol) in MeOH (3 ml) was stirred at 60° C. for 1 h. The mixture was filtered and evaporated under vacuo to obtain the crude product. This was purified by preparative-HPLC (Column: Waters Xbridge Prep OBD C18 150×30 mm, 5 μm, Condition: gradient water (0.05% ammonia hydroxide v/v)-MeOH). The desired fractions were collected and the solvent was evaporated to give Compound 76 as a white solid (82.2 mg, 45.3% yield).

Example B15

Preparation of Compound 77

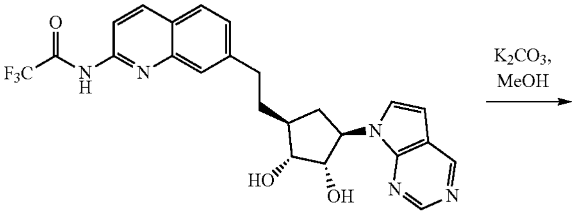

intermediate 169

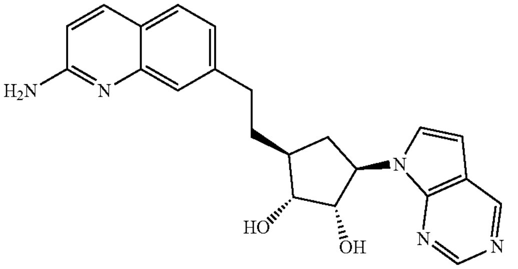

Compound 77

The mixture of intermediate 169 (120 mg, 0.185 mmol) and $K_2CO_3$ (76.40 mg, 0.554 mmol) in methanol (3 ml) was stirred at 60° C. for 1 h. The mixture was filtered and evaporated under vacuo to obtain a crude product. The crude product was purified by prep-HPLC (Column: Waters Xbridge Prep OBD C18 150×30 mm, 5 μm, Condition: gradient water (0.05% ammonia hydroxide v/v)-MeOH). The desired fractions were collected and the solvent was evaporated to give Compound 77 as a white solid (21.4 mg, 29.4% yield).

Below Compounds were prepared by an analogous reaction protocol as was used for the preparation of compound 77 using the appropriate starting materials (Table 48).

TABLE 48

| compound | Structure | Starting materials |
| --- | --- | --- |
| 250 | 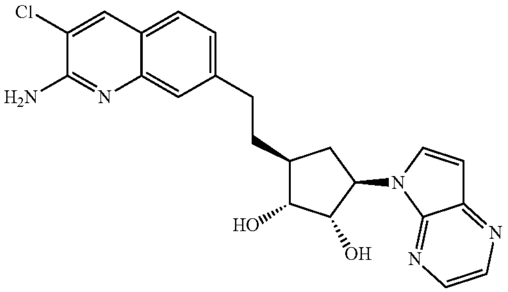 [SMILES: Nc1nc2cc(CC[C@H]3C[C@@H](n4ccc5nccnc54)[C@H](O)[C@@H]3O)ccc2cc1Cl] | intermediate 527 |
| 252 | 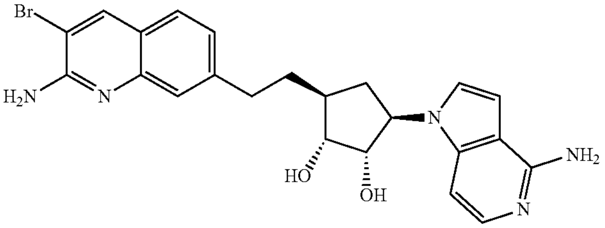 [SMILES: Nc1nc2cc(CC[C@H]3C[C@@H](n4ccc5c(N)nccc54)[C@H](O)[C@@H]3O)ccc2cc1Br] | intermediate 535 |

Example B16

Preparation of Compound 78

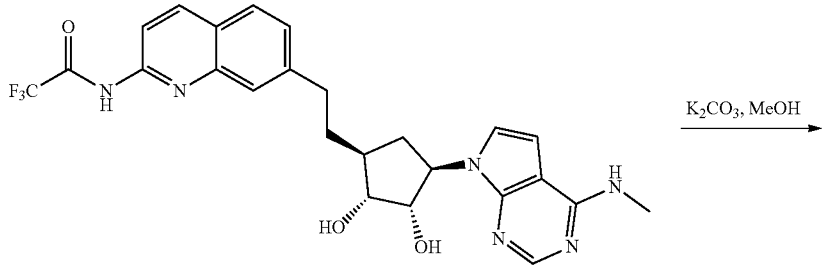

intermediate 171

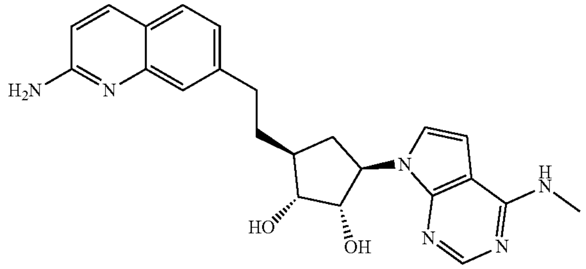

Compound 78

The mixture of intermediate 171 (160 mg, 0.273 mmol) and $K_2CO_3$ (113.073 mg, 0.819 mmol) in methanol (3 ml) was stirred at 50° C. for 1 h. The mixture was filtered and evaporated under vacuo to obtain the crude product. This was purified by prep-HPLC (Column: Waters Xbridge Prep OBD C18 150×30 mm, 5 μm, Condition: gradient water (0.05% ammonia hydroxide v/v)-MeOH). The desired fractions were collected and the solvent was evaporated to give Compound 78 (87.2 mg, 75.3% yield) as a white solid.

Example B17

Preparation of Compound 79

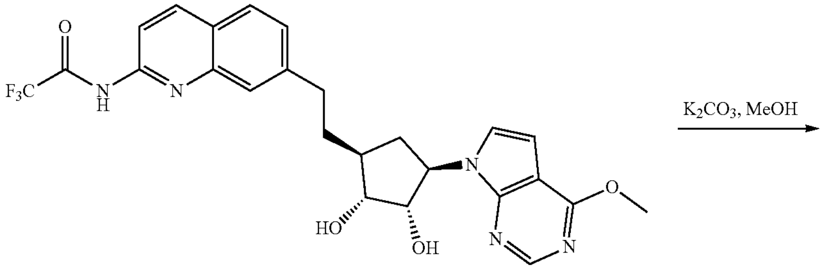

intermediate 173

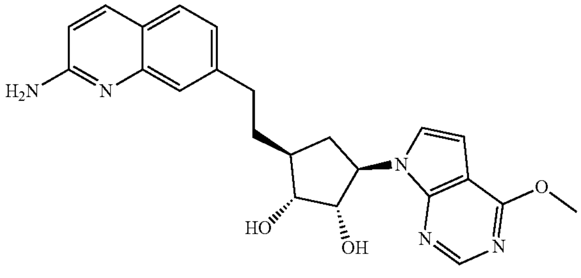

Compound 79

The mixture of intermediate 173 (250 mg, 0.241 mmol) and $K_2CO_3$ (99.6 mg, 0.72 mmol) in methanol (3 ml) was stirred at 50° C. for 1 h. The mixture was filtered and evaporated under vacuo to obtain the crude product. This was purified by preparative-HPLC (Column: Waters Xbridge Prep OBD C18 150×30 mm, 5 μm, Condition: gradient water (0.05% ammonia hydroxide v/v)-MeOH). The desired fractions were collected and the solvent was evaporated to give Compound 79 (96.1 mg, 94.5% yield) as a white solid.

Below compound was prepared by an analogous reaction protocol of Compound 79 using the appropriate starting materials (Table 45).

The mixture of intermediate 179 (350 mg) and $K_2CO_3$ (102 mg, 0.74 mmol) in methanol (3 mL) was stirred at 60° C. for 1 h. The mixture was filtered and evaporated under vacuo to obtain a crude product. The crude product was purified by prep-HPLC (Column: Waters Xbridge Prep OBD C18 150×30 mm, 5 μm, Condition: gradient water (0.05% ammonia hydroxide v/v)-ACN). The desired fractions were collected and the solvent was evaporated to give Compound 80 (113.3 mg, 94.9% yield) as a white solid.

TABLE 45

| Compound | Structure | Starting material |
|---|---|---|
| 228 | 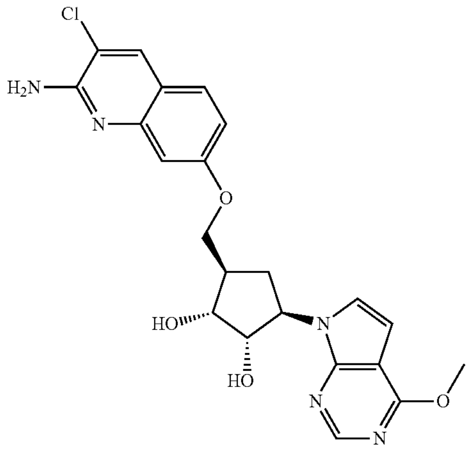 [SMILES: COc1ncnc2c1ccn2[C@@H]1C[C@H](COc2ccc3cc(Cl)c(N)nc3c2)[C@@H](O)[C@H]1O] | Intermediate 472 |

Example B18

Preparation of Compound 80

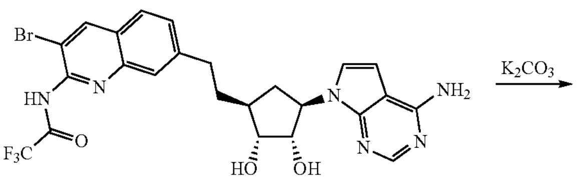

intermediate 179

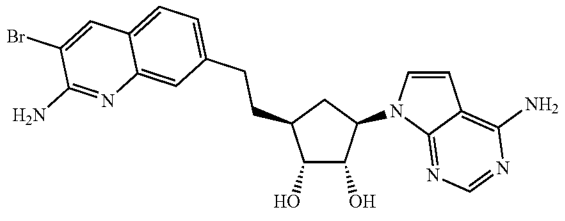

Compound 80

Alternative Preparation of Compound 80

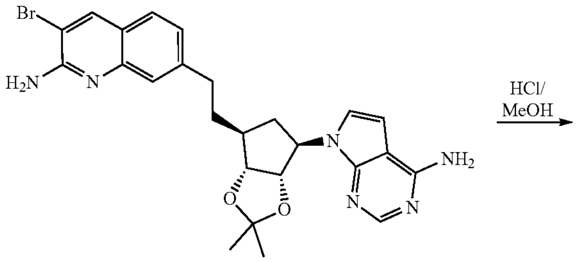

intermediate 529

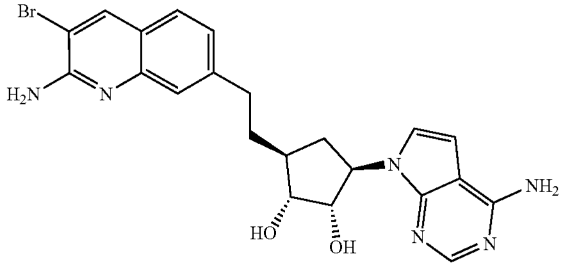

compound 80

Intermediate 529 (21 g, 40.12 mmol) was dissolved in HCl/MeOH (250 mL). The mixture was stirred at room temperature for 2 hours. The solvent was concentrated in vacuum. Then $H_2O$ (100 mL) was added. The pH was adjusted to around 9 by progressively adding aq. $Na_2CO_3$ (800 mL). The precipitate was filtered off to give crude product. The crude product was recrystallized from EtOH (250 mL) to give 11.4 g of Compound 80 as a white solid. The filtrate of the recrystallization was concentrated in vacuum. This residue was added to EtOH (50 mL) and refluxed for 3 hours. The reaction was cooled and the precipitate was filtered off to give product 2.2 g of Compound 80. The filtrate of the second recrystallization was concentrated in vacuum to give another 2.2 g of Compound 80.

Example B19

Preparation of Compound 81

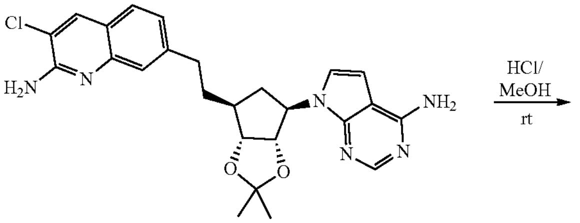

intermediate 184

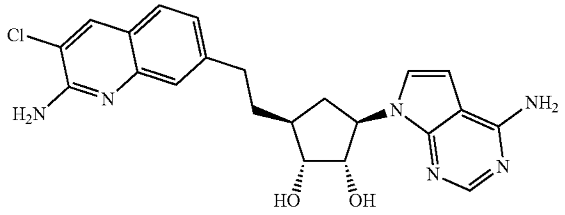

Compound 81

The mixture of intermediate 184 (800 mg, 1.67 mmol) and HCl in methanol (15 ml) was stirred at r.t. for 2 h. The mixture was neutralized with $NH_4OH$. The mixture was extracted by EtOAc (20 mL×3). The organic phase was evaporated and the crude product was purified by Prep-HPLC (gradient: water (10 mM $NH_4HCO_3$)-ACN). The combined solvent was evaporated to give Compound 81 (280 mg, 38% yield) as a white solid.

Example B20

Preparation of Compound 84

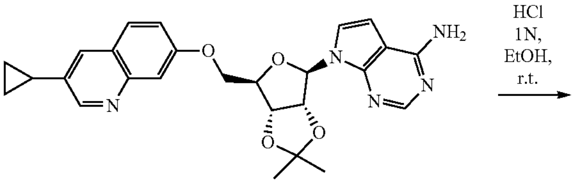

intermediate 193

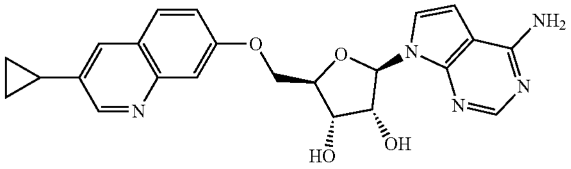

compound 84

Intermediate 193 (110 mg, 0.23 mmol) in EtOH (3.5 ml) was stirred at r.t. HCl 1N (2.3 ml, 2.3 mmol) was added dropwise. Stirring was continued for 72 h. Then the reaction mixture was treated with $NH_3$ 28% in water (0.235 ml, 3.5 mmol). The product started to precipitate. The precipitate was filtered off and was washed with EtOH/$H_2O$ ratio 9 to 1 and dried yielding compound 84 (90 mg, 89% yield)

Example B21

Preparation of Compound 162

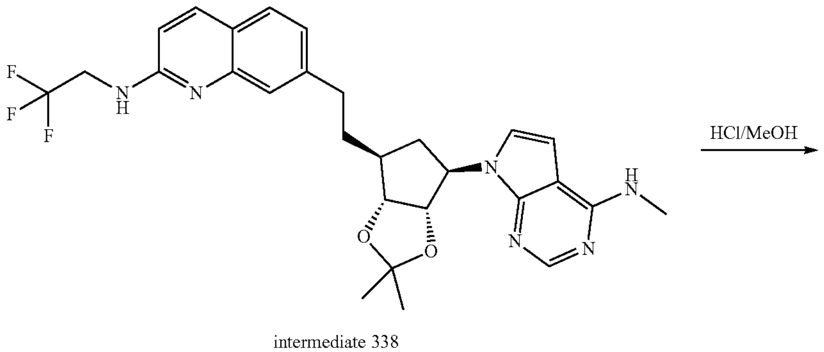

intermediate 338

-continued

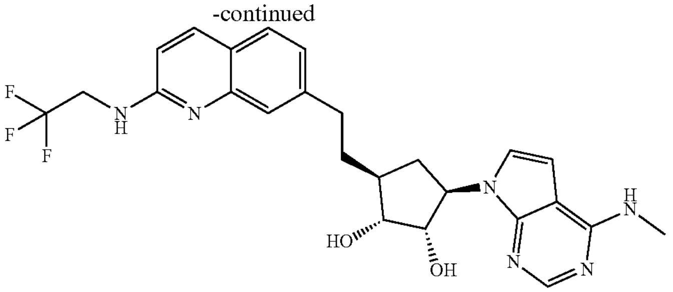

compound 162

A solution of intermediate 338 (520 mg, 0.96 mmol) in HCl/MeOH (4N, 7 mL) and MeOH (2 mL) was stirred at room temperature for 1 h. The reaction was concentrated. The residue was dissolved in $H_2O$ (3 mL) and basified by aq·$NH_3$·$H_2O$. A precipitate was formed and collected. The solid was purified by prep-HPLC: conditions; A: (water (0.05% ammonia hydroxide v/v)-B: ACN, Begin B 30% End B 60%). The desired fractions were collected and lyophilized to give the product (250 mg). The product was further purified by prep-SFC (Column OD (250 mm×30 mm, 10 μm); Conditions A: 0.1% ammonia hydroxide v/v), B: EtOH; Begin B 35%, End B 35%; flow rate (ml/min) 60). The desired fractions were collected and lyophilized to give compound 162 (206 mg, 43% yield) as a solid.

Below compounds were prepared by an analogous reaction protocol as was used for the preparation of compound 162 using the appropriate starting materials (Table 46).

TABLE 46

| Compound | Structure | Starting materials |
|---|---|---|
| 163 | 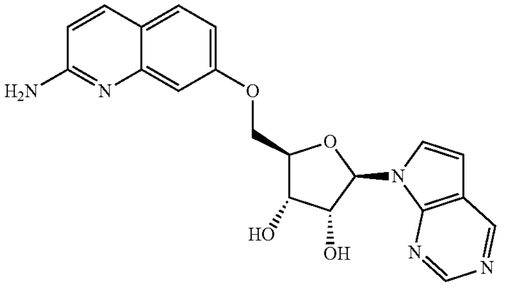 [SMILES: Nc1ccc2ccc(OC[C@H]3O[C@@H](n4ccc5cncnc54)[C@H](O)[C@@H]3O)cc2n1] | Intermediate 353 |
| 164 | 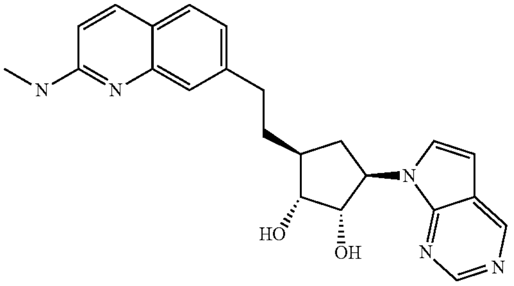 [SMILES: CNc1ccc2ccc(CC[C@H]3C[C@@H](n4ccc5cncnc54)[C@H](O)[C@@H]3O)cc2n1] | Intermediate 354 |
| 165 | 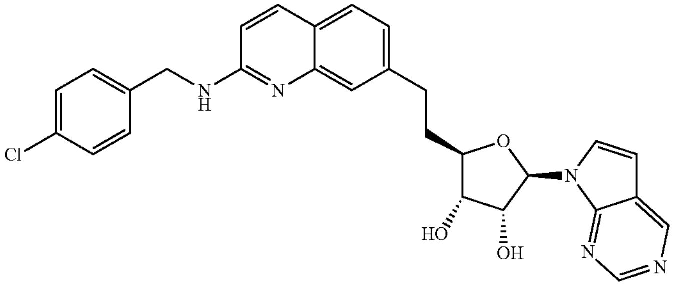 [SMILES: O[C@@H]1[C@H](O)[C@@H](CCc2ccc3ccc(NCc4ccc(Cl)cc4)nc3c2)O[C@H]1n1ccc2cncnc21] | Intermediate 355 |

TABLE 46-continued
| Compound | Structure | Starting materials |
| --- | --- | --- |
| 166 | 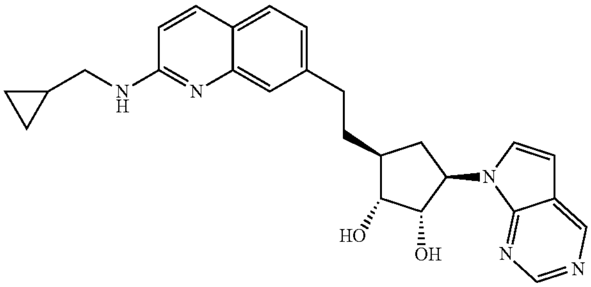 [SMILES: O[C@@H]1[C@@H](CCc2ccc3ccc(NCC4CC4)nc3c2)C[C@@H](n2ccc3cncnc32)[C@@H]1O] | Intermediate 356 |
| 167 | 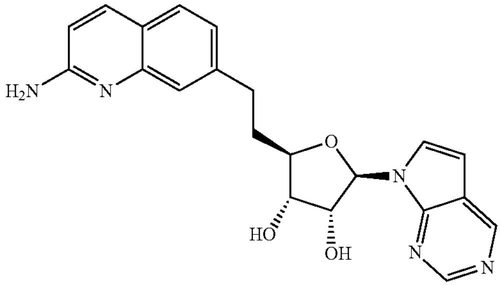 [SMILES: Nc1ccc2ccc(CC[C@H]3O[C@@H](n4ccc5cncnc54)[C@H](O)[C@@H]3O)cc2n1] | Intermediate 357 |
| 168 | 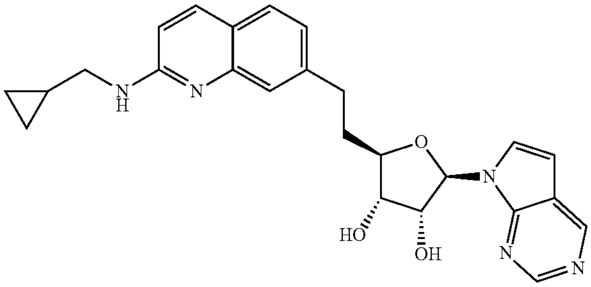 [SMILES: O[C@@H]1[C@H](O)[C@@H](CCc2ccc3ccc(NCC4CC4)nc3c2)O[C@H]1n1ccc2cncnc21] | Intermediate 358 |
| 169 | 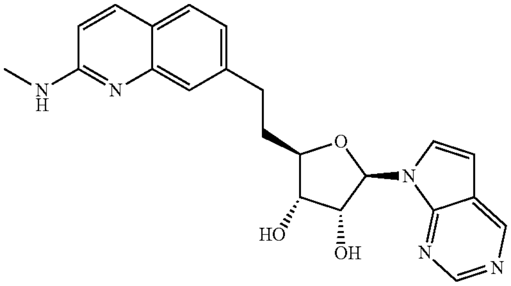 [SMILES: CNc1ccc2ccc(CC[C@H]3O[C@@H](n4ccc5cncnc54)[C@H](O)[C@@H]3O)cc2n1] | Intermediate 359 |
| 170 | 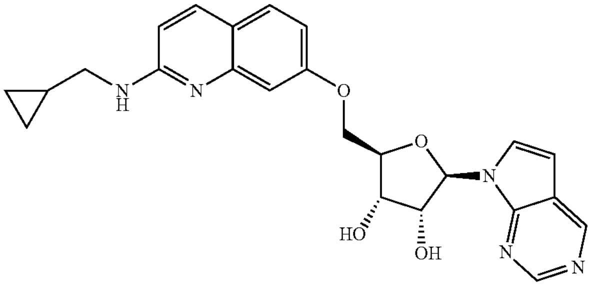 [SMILES: O[C@@H]1[C@H](O)[C@@H](COc2ccc3ccc(NCC4CC4)nc3c2)O[C@H]1n1ccc2cncnc21] | Intermediate 360 |

TABLE 46-continued
| Compound | Structure | Starting materials |
| --- | --- | --- |
| 171 | 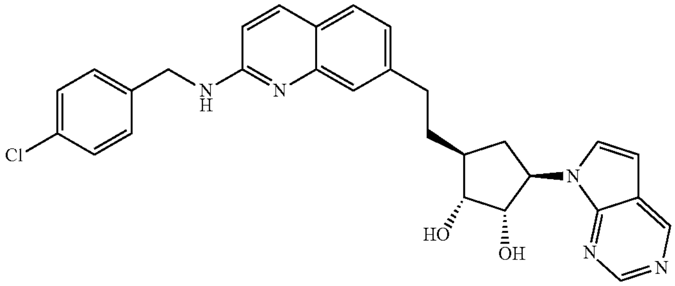 [SMILES: O[C@@H]1[C@@H](CCc2ccc3ccc(NCc4ccc(Cl)cc4)nc3c2)C[C@@H](n2ccc3cncnc32)[C@@H]1O] | Intermediate 361 |
| 172 | 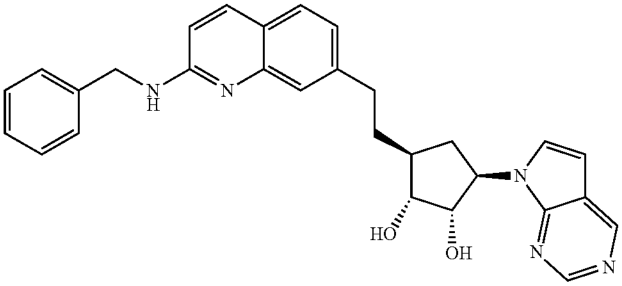 [SMILES: O[C@@H]1[C@@H](CCc2ccc3ccc(NCc4ccccc4)nc3c2)C[C@@H](n2ccc3cncnc32)[C@@H]1O] | Intermediate 362 |
| 173 | 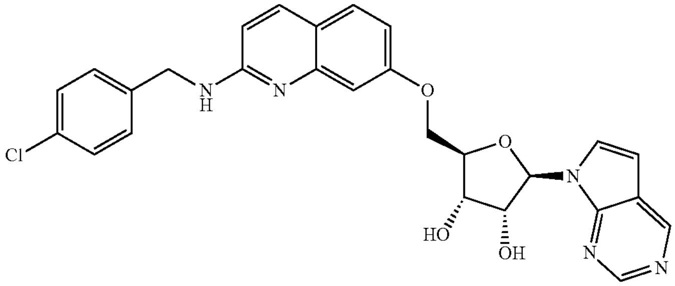 [SMILES: O[C@@H]1[C@H](O)[C@@H](COc2ccc3ccc(NCc4ccc(Cl)cc4)nc3c2)O[C@H]1n1ccc2cncnc21] | Intermediate 401 |
| 174 | 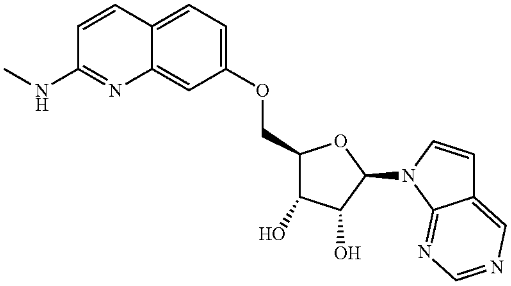 [SMILES: CNc1ccc2ccc(OC[C@H]3O[C@@H](n4ccc5cncnc54)[C@H](O)[C@@H]3O)cc2n1] | Intermediate 402 |
| 175 | 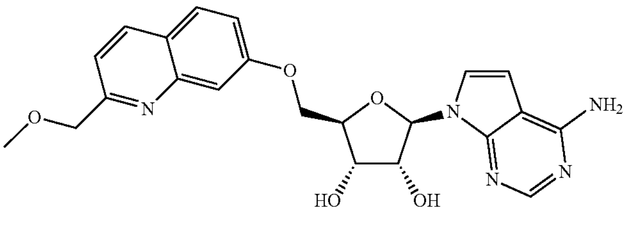 [SMILES: COCc1ccc2ccc(OC[C@H]3O[C@@H](n4ccc5c(N)ncnc54)[C@H](O)[C@@H]3O)cc2n1] | Intermediate 417 |

TABLE 46-continued
| Compound | Structure | Starting materials |
| --- | --- | --- |
| 176 | 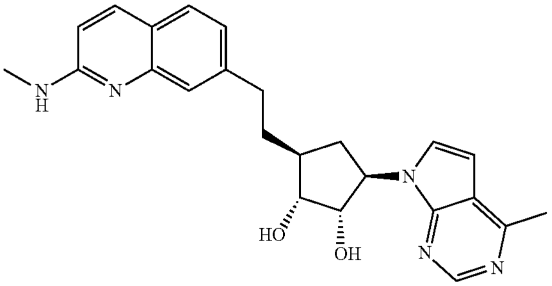 | Intermediate 377 |
| 177 | 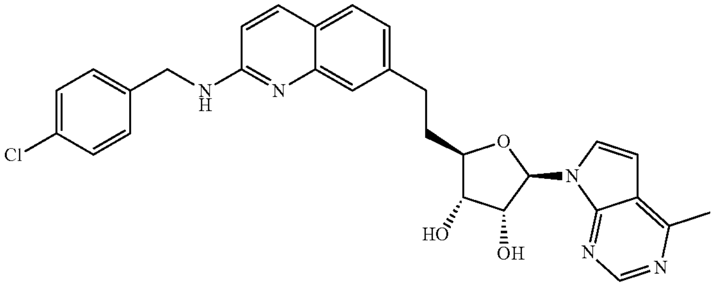 | Intermediate 378 |
| 178 | 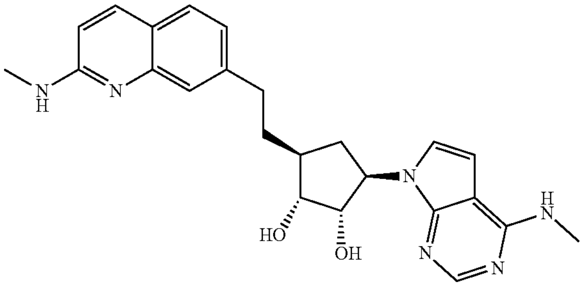 | Intermediate 339 |
| 179 | 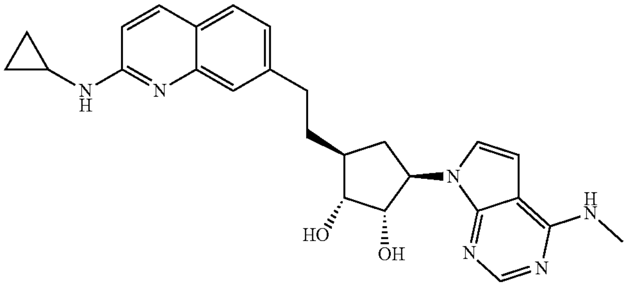 [SMILES: CNc1ncnc2c1ccn2[C@@H]1C[C@H](CCc2ccc3ccc(NC4CC4)nc3c2)[C@@H](O)[C@H]1O] | Intermediate 340 |
| 180 | 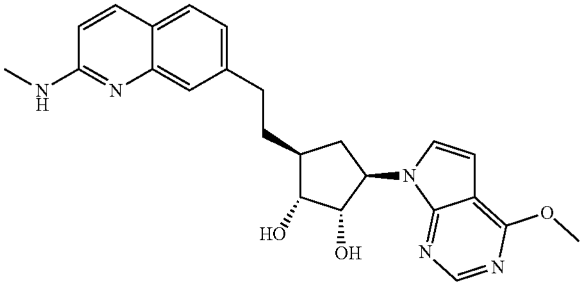 | Intermediate 367 |

TABLE 46-continued
| Compound | Structure | Starting materials |
|---|---|---|
| 181 | 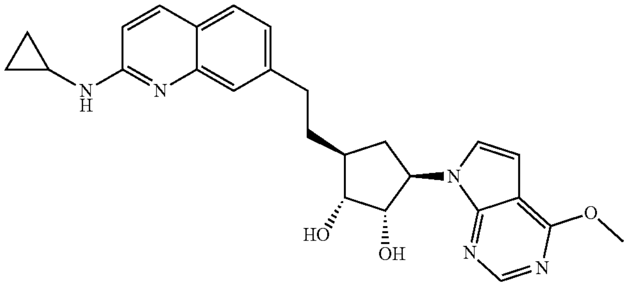 [SMILES: COc1ncnc2c1ccn2[C@@H]1C[C@H](CCc2ccc3ccc(NC4CC4)nc3c2)[C@@H](O)[C@H]1O] | Intermediate 368 |
| 182 | 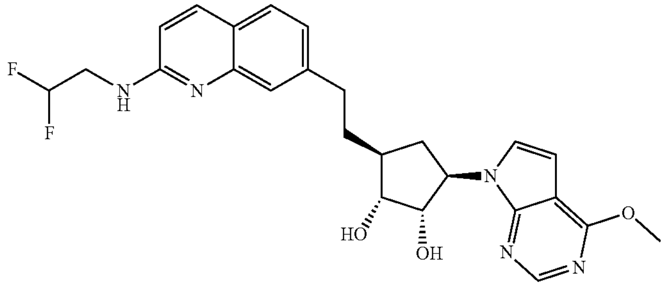 [SMILES: COc1ncnc2c1ccn2[C@@H]1C[C@H](CCc2ccc3ccc(NCC(F)F)nc3c2)[C@@H](O)[C@H]1O] | Intermediate 369 |
| 183 | 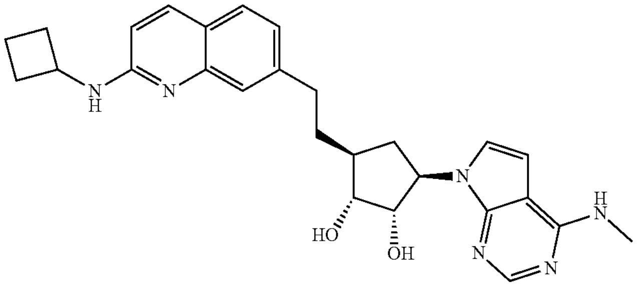 [SMILES: CNc1ncnc2c1ccn2[C@@H]1C[C@H](CCc2ccc3ccc(NC4CCC4)nc3c2)[C@@H](O)[C@H]1O] | Intermediate 341 |
| 184 | 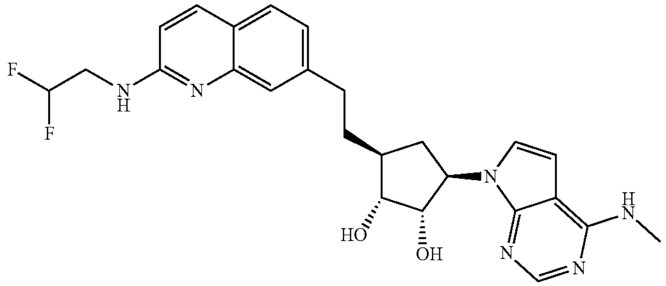 [SMILES: CNc1ncnc2c1ccn2[C@@H]1C[C@H](CCc2ccc3ccc(NCC(F)F)nc3c2)[C@@H](O)[C@H]1O] | Intermediate 342 |
| 185 | 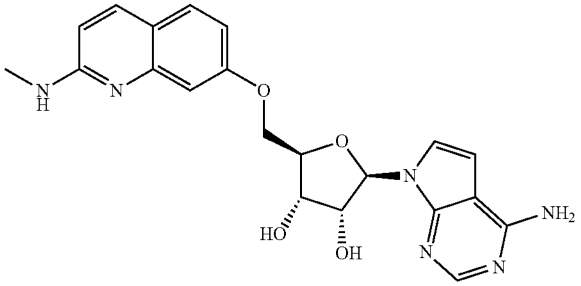 [SMILES: CNc1ccc2ccc(OC[C@H]3O[C@@H](n4ccc5c(N)ncnc54)[C@H](O)[C@@H]3O)cc2n1] | Intermediate 403 |

TABLE 46-continued
| Compound | Structure | Starting materials |
| --- | --- | --- |
| 186 | 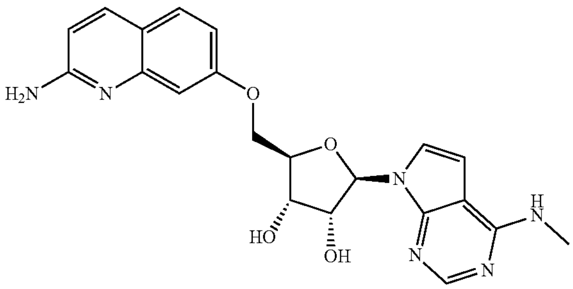 [SMILES: CNc1ncnc2c1ccn2[C@@H]1O[C@H](COc2ccc3ccc(N)nc3c2)[C@@H](O)[C@H]1O] | Intermediate 343 |
| 187 | 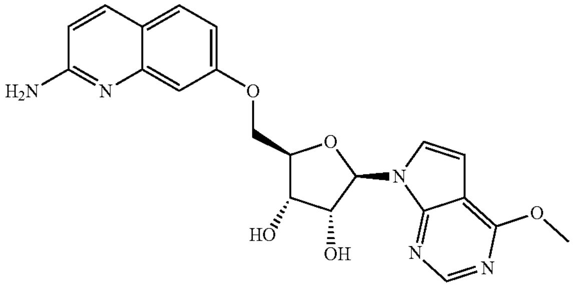 [SMILES: COc1ncnc2c1ccn2[C@@H]1O[C@H](COc2ccc3ccc(N)nc3c2)[C@@H](O)[C@H]1O] | Intermediate 365 |
| 188 | 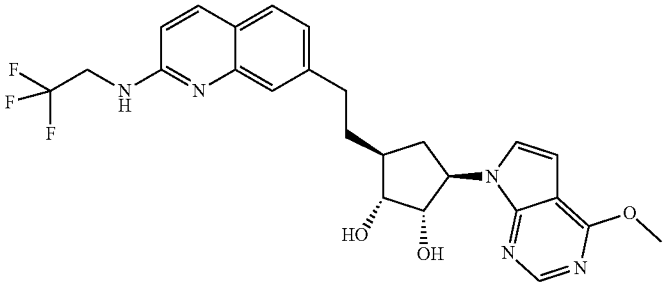 [SMILES: COc1ncnc2c1ccn2[C@@H]1C[C@H](CCc2ccc3ccc(NCC(F)(F)F)nc3c2)[C@@H](O)[C@H]1O] | Intermediate 366 |
| 189 | 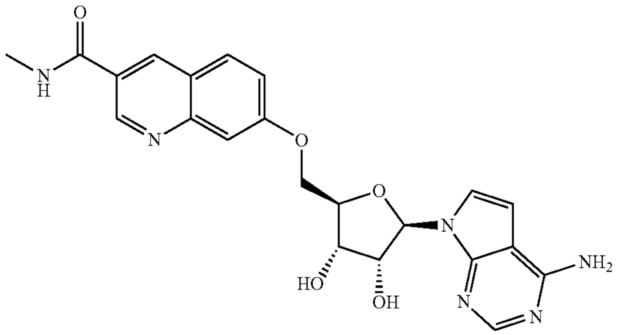 [SMILES: CNC(=O)c1cnc2cc(OC[C@H]3O[C@@H](n4ccc5c(N)ncnc54)[C@H](O)[C@@H]3O)ccc2c1] | Intermediate 404 |
| 190 | 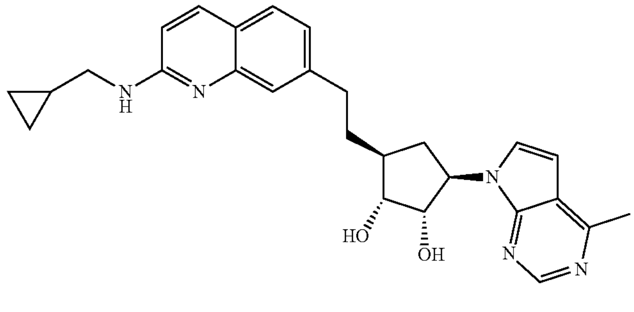 [SMILES: Cc1ncnc2c1ccn2[C@@H]1C[C@H](CCc2ccc3ccc(NCC4CC4)nc3c2)[C@@H](O)[C@H]1O] | Intermediate 379 |

TABLE 46-continued
| Compound | Structure | Starting materials |
| --- | --- | --- |
| 191 | 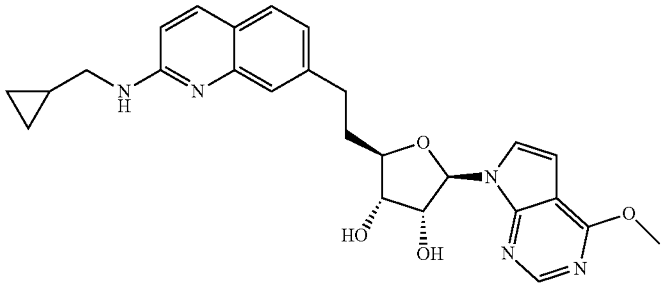 [SMILES: COc1ncnc2c1ccn2[C@@H]1O[C@H](CCc2ccc3ccc(NCC4CC4)nc3c2)[C@@H](O)[C@H]1O] | Intermediate 375 |
| 192 | 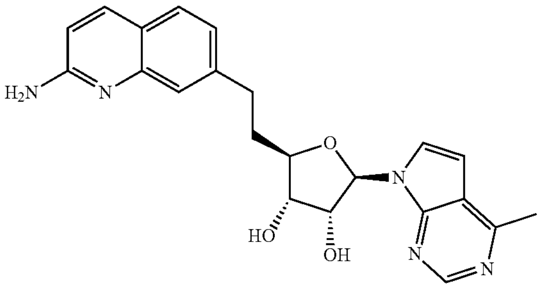 [SMILES: Cc1ncnc2c1ccn2[C@@H]1O[C@H](CCc2ccc3ccc(N)nc3c2)[C@@H](O)[C@H]1O] | Intermediate 380 |
| 193 | 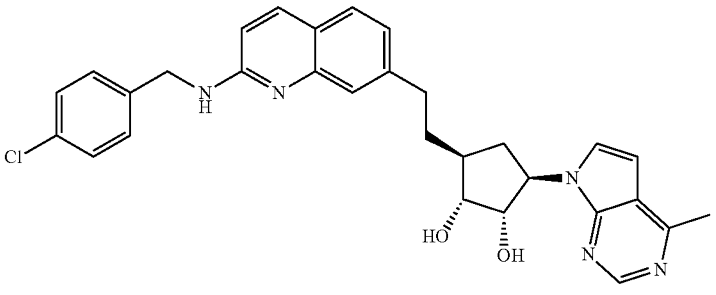 [SMILES: Cc1ncnc2c1ccn2[C@@H]1C[C@H](CCc2ccc3ccc(NCc4ccc(Cl)cc4)nc3c2)[C@@H](O)[C@H]1O] | Intermediate 381 |
| 194 | 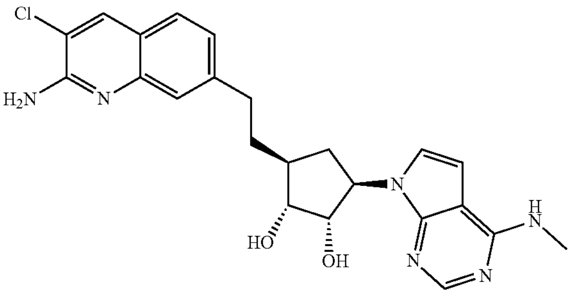 [SMILES: CNc1ncnc2c1ccn2[C@@H]1C[C@H](CCc2ccc3cc(Cl)c(N)nc3c2)[C@@H](O)[C@H]1O] | Intermediate 344 |
| 195 | 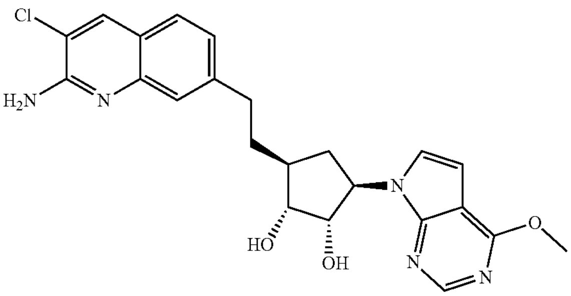 | Intermediate 371 |

TABLE 46-continued
| Compound | Structure | Starting materials |
| --- | --- | --- |
| 196 | 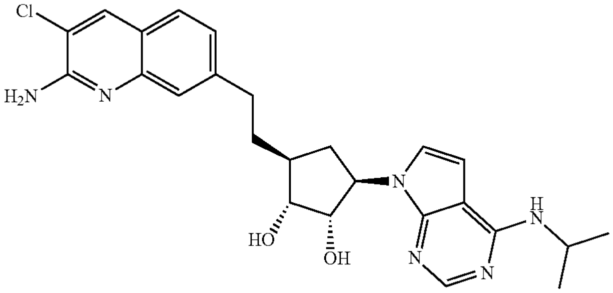 [SMILES: CC(C)Nc1ncnc2c1ccn2[C@@H]1C[C@H](CCc2ccc3cc(Cl)c(N)nc3c2)[C@@H](O)[C@H]1O] | Intermediate 345 |
| 197 | 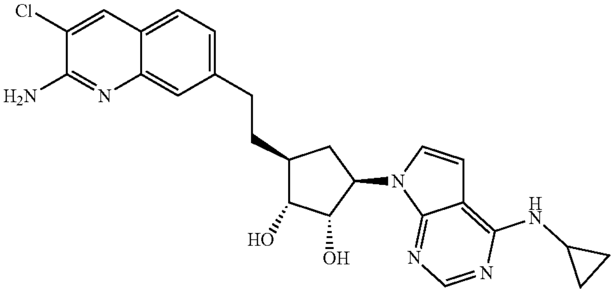 [SMILES: Nc1nc2cc(CC[C@H]3C[C@@H](n4ccc5c(NC6CC6)ncnc54)[C@H](O)[C@@H]3O)ccc2cc1Cl] | Intermediate 346 |
| 198 | 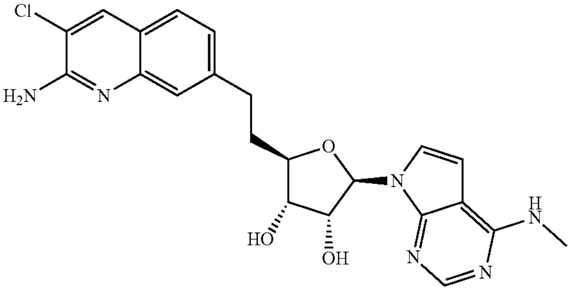 | Intermediate 347 |
| 199 | 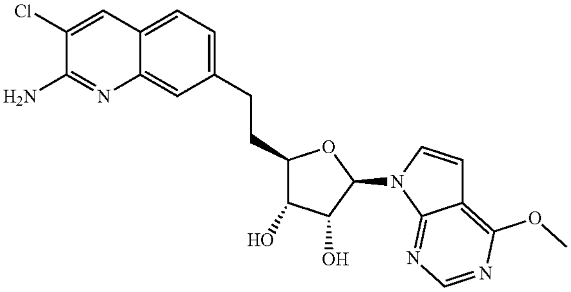 | Intermediate 372 |
| 200 | 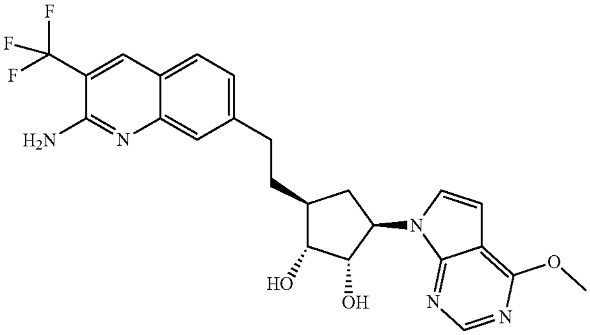 [SMILES: COc1ncnc2c1ccn2[C@@H]1C[C@H](CCc2ccc3cc(C(F)(F)F)c(N)nc3c2)[C@@H](O)[C@H]1O] | Intermediate 373 |

TABLE 46-continued
| Compound | Structure | Starting materials |
|---|---|---|
| 201 | 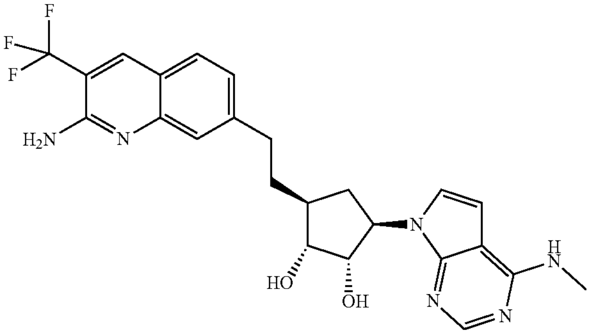 [SMILES: CNc1ncnc2c1ccn2[C@@H]1C[C@H](CCc2ccc3cc(C(F)(F)F)c(N)nc3c2)[C@@H](O)[C@H]1O] | Intermediate 348 |
| 202 | 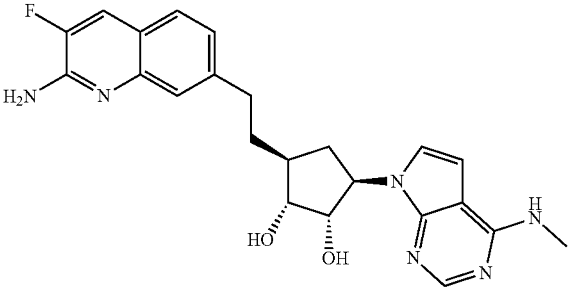 | Intermediate 349 |
| 203 | 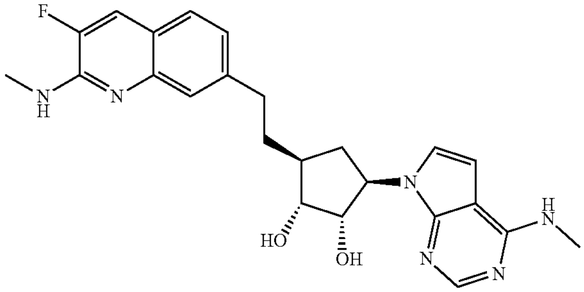 | Intermediate 350 |
| 204 | 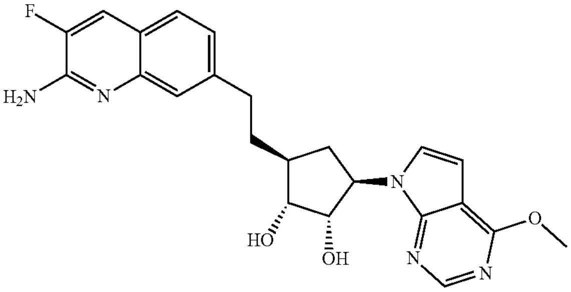 | Intermediate 374 |
| 205 | 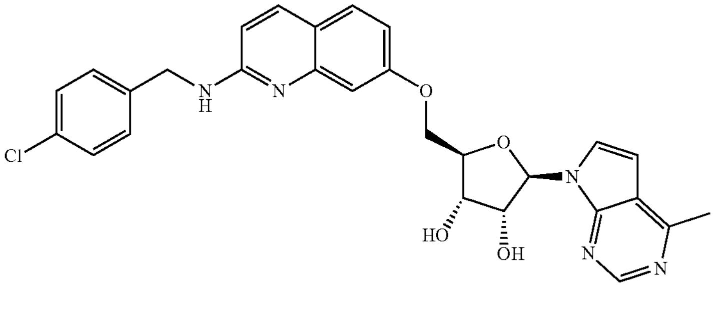 [SMILES: Cc1ncnc2c1ccn2[C@@H]1O[C@H](COc2ccc3ccc(NCc4ccc(Cl)cc4)nc3c2)[C@@H](O)[C@H]1O] | Intermediate 376 |

TABLE 46-continued
| Compound | Structure | Starting materials |
|---|---|---|
| 206 | 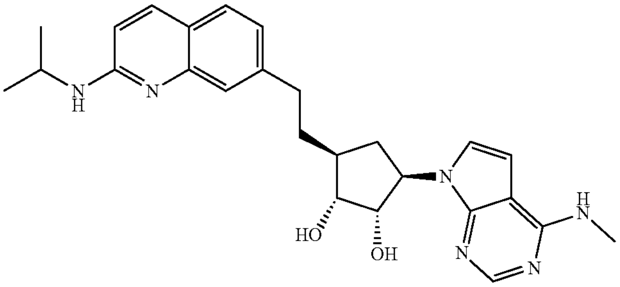 [SMILES: CNc1ncnc2c1ccn2[C@@H]1C[C@H](CCc2ccc3ccc(NC(C)C)nc3c2)[C@@H](O)[C@H]1O] | Intermediate 351 |
| 208 | 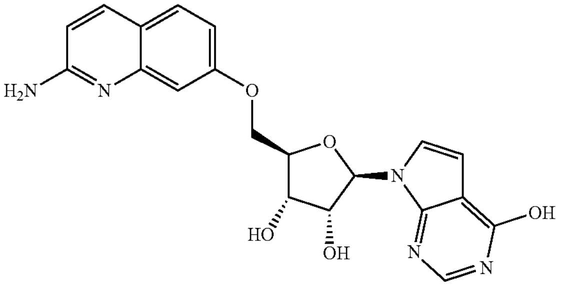 [SMILES: Nc1ccc2ccc(OC[C@H]3O[C@@H](n4ccc5c(O)ncnc54)[C@H](O)[C@@H]3O)cc2n1] | Intermediate 385 |
| 209 | 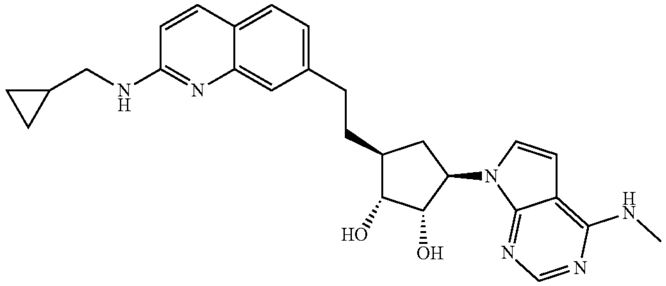 [SMILES: CNc1ncnc2c1ccn2[C@@H]1C[C@H](CCc2ccc3ccc(NCC4CC4)nc3c2)[C@@H](O)[C@H]1O] | Intermediate 405 |
| 210 | 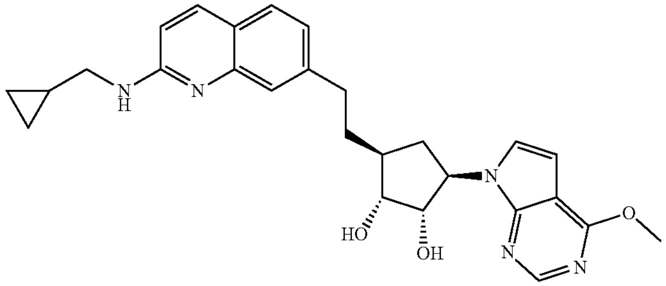 [SMILES: COc1ncnc2c1ccn2[C@@H]1C[C@H](CCc2ccc3ccc(NCC4CC4)nc3c2)[C@@H](O)[C@H]1O] | Intermediate 375 |
| 225 | 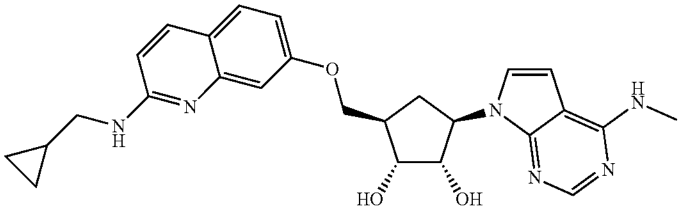 [SMILES: CNc1ncnc2c1ccn2[C@@H]1C[C@H](COc2ccc3ccc(NCC4CC4)nc3c2)[C@@H](O)[C@H]1O] | Intermediate 465 |

TABLE 46-continued
| Compound | Structure | Starting materials |
| --- | --- | --- |
| 226 | 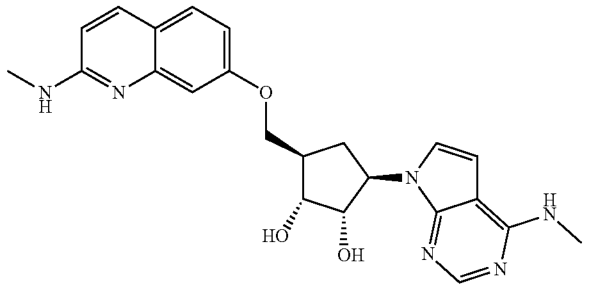 | Intermediate 467 |
| 227 | 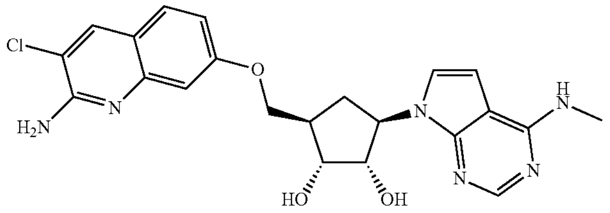 [SMILES: CNc1ncnc2c1ccn2[C@@H]1C[C@H](COc2ccc3cc(Cl)c(N)nc3c2)[C@@H](O)[C@H]1O] | Intermediate 470 |
| 229 | 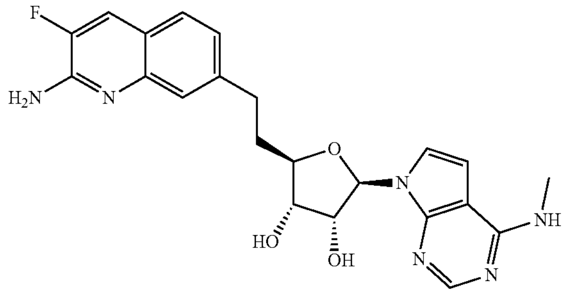 [SMILES: CNc1ncnc2c1ccn2[C@@H]1O[C@H](CCc2ccc3cc(F)c(N)nc3c2)[C@@H](O)[C@H]1O] | Intermediate 474 |
| 230 | 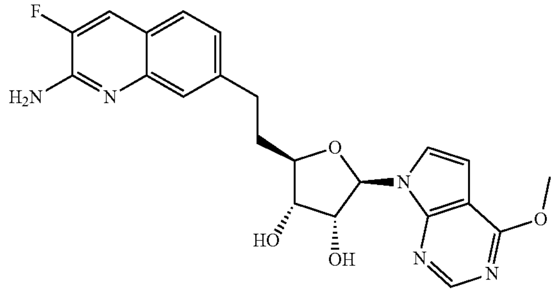 [SMILES: COc1ncnc2c1ccn2[C@@H]1O[C@H](CCc2ccc3cc(F)c(N)nc3c2)[C@@H](O)[C@H]1O] | Intermediate 475 |
| 231 | 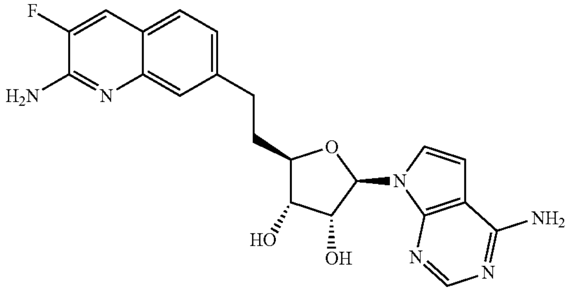 [SMILES: Nc1nc2cc(CC[C@H]3O[C@@H](n4ccc5c(N)ncnc54)[C@H](O)[C@@H]3O)ccc2cc1F] | Intermediate 476 |

TABLE 46-continued
| Compound | Structure | Starting materials |
|---|---|---|
| 232 | 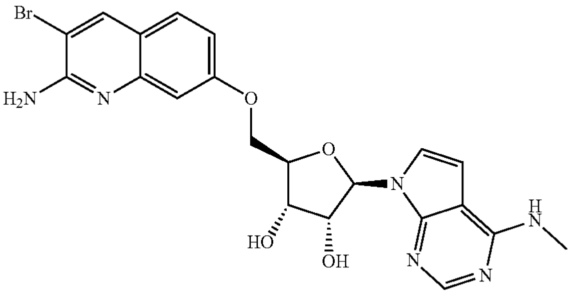 | Intermediate 479 |
| 233 | 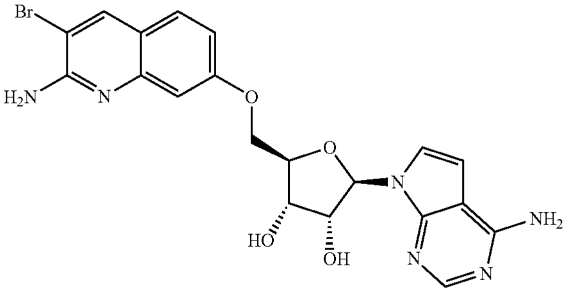 [SMILES: Nc1nc2cc(OC[C@H]3O[C@@H](n4ccc5c(N)ncnc54)[C@H](O)[C@@H]3O)ccc2cc1Br] | Intermediate 480 |
| 234 | 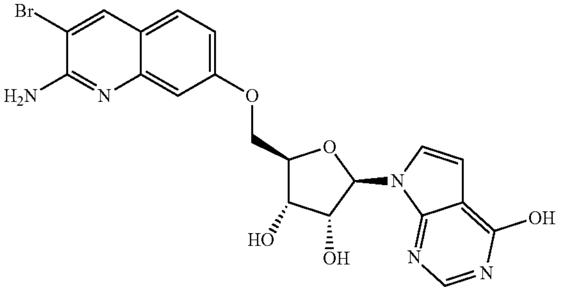 [SMILES: Nc1nc2cc(OC[C@H]3O[C@@H](n4ccc5c(O)ncnc54)[C@H](O)[C@@H]3O)ccc2cc1Br] | Intermediate 481 |
| 235 | 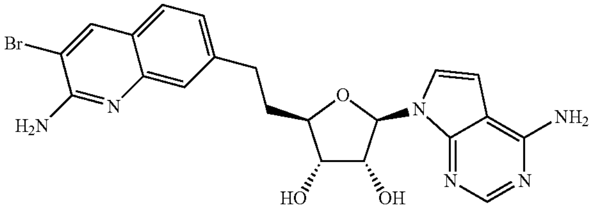 [SMILES: Nc1nc2cc(CC[C@H]3O[C@@H](n4ccc5c(N)ncnc54)[C@H](O)[C@@H]3O)ccc2cc1Br] | Intermediate 483 |
| 237 | 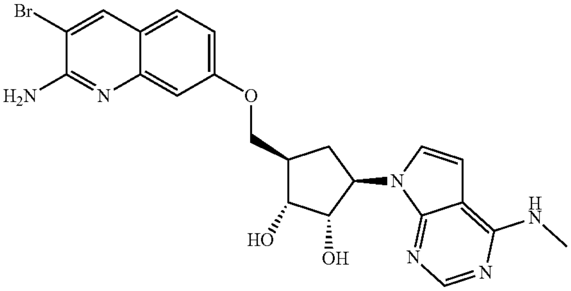 [SMILES: CNc1ncnc2c1ccn2[C@@H]1C[C@H](COc2ccc3cc(Br)c(N)nc3c2)[C@@H](O)[C@H]1O] | Intermediate 486 |

TABLE 46-continued

| Compound | Structure | Starting materials |
|---|---|---|
| 238 | 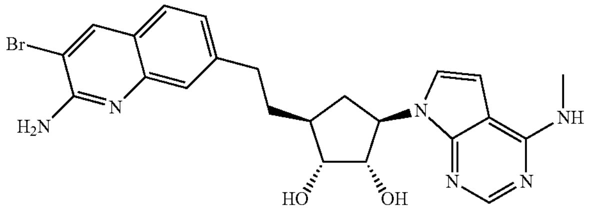 [SMILES: CNc1ncnc2c1ccn2[C@@H]1C[C@H](CCc2ccc3cc(Br)c(N)nc3c2)[C@@H](O)[C@H]1O] | Intermediate 489 |
| 239 | 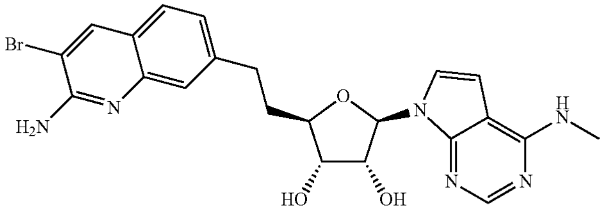 [SMILES: CNc1ncnc2c1ccn2[C@@H]1O[C@H](CCc2ccc3cc(Br)c(N)nc3c2)[C@@H](O)[C@H]1O] | Intermediate 492 |

Example B22

Preparation of Compound 163

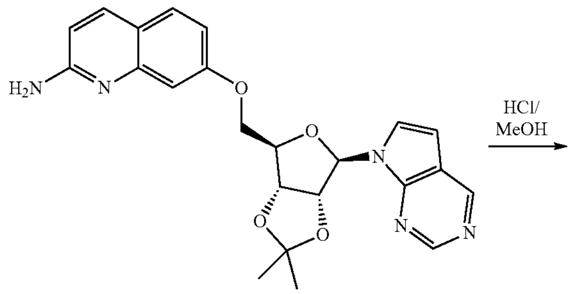

intermediate 353

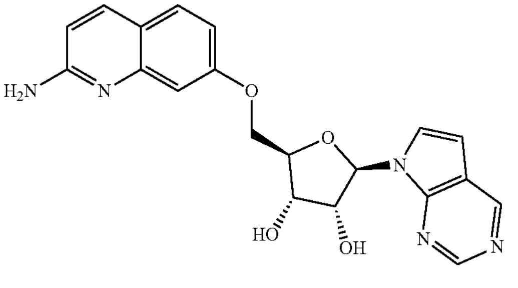

compound 163

A mixture of intermediate 353 (260 mg, 0.49 mmol) in HCl/MeOH (4N, 1 mL) and MeOH (1 mL) was stirred at room temperature for 1 h. The reaction was concentrated. The residue was basified by $NH_3 \cdot H_2O$ to pH>8. The residue was purified by HPLC: Column: Gemini 150×25 mm 5 μm; conditions: A: water (0.05% ammonia hydroxide v/v), B: MeCN; at the beginning: A (89%) and B (11%), at the end: A (59%) and B (41%), Gradient Time (min) 10; 100% B Hold Time (min) 2; Flow Rate (ml/min) 25. The desired fractions were collected and concentrated. The residue was lyophilized to give compound 163 (93.4 mg, 48.6% yield) as solid.

Example B23

Preparation of Compound 185

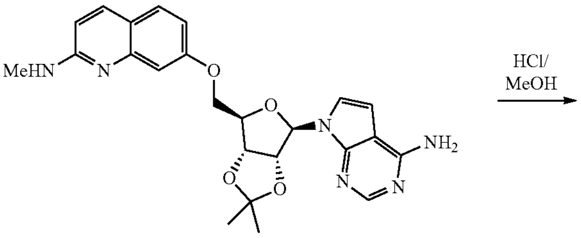

intermediate 403

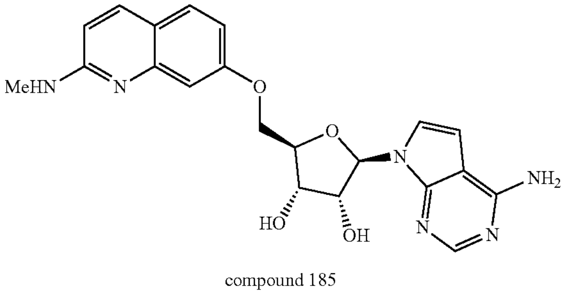

compound 185

A solution of intermediate 403 (600 mg, 1.28 mmol) in HCl/MeOH (4N, 2.7 mL) and MeOH (1 mL) was stirred at room temperature for 4 h. The reaction was concentrated. The residue was basified by $NH_3 \cdot H_2O$ to pH>8. A precipitate was formed and collected by filtration. The precipitate was washed with water and MTBE. The precipitate was lyophilized to give compound 185 (345 mg, 61% yield) as solid.

Example B24

Preparation of Compound 187

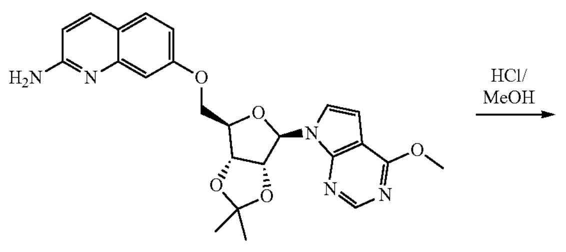

intermediate 365

-continued

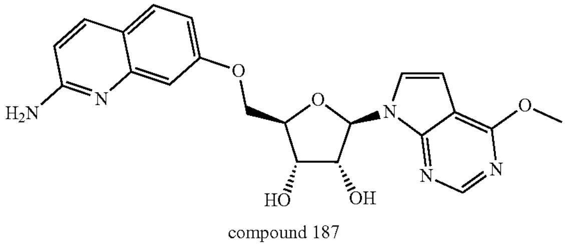

compound 187

A solution of intermediate 365 (250 mg, 0.54 mmol) in HCl/MeOH (4N, 1.52 mL) and MeOH (1 mL) was stirred at room temperature for 1 h. The reaction was concentrated. The residue was basified by $NH_3{\cdot}H_2O$ to pH>8 and concentrated. The residue was purified by HPLC: column: Gemini 150×25 mm, 5 μm; conditions: A: water (0.05% ammonia hydroxide v/v), B: ACN); at the beginning: A (89%) and B (11%), at the end: A (59%) and B (41%); gradient time (min) 10; 100% B hold time (min) 2; flow rate (ml/min) 25. The desired fractions were collected and concentrated. The residue was lyophilized to give compound 187 (29.4 mg, 13% yield) as a solid.

Example B 25

Preparation of Compound 188

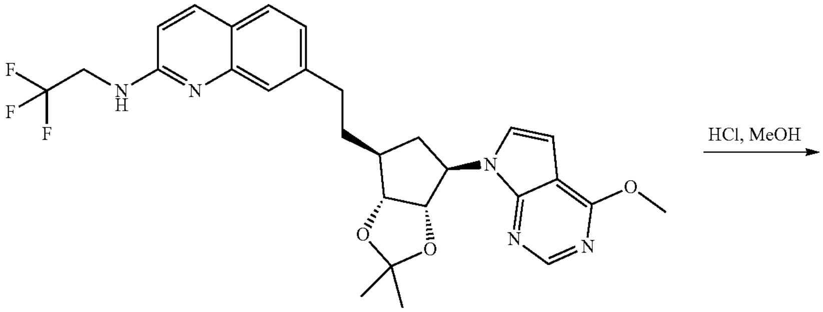

intermediate 366

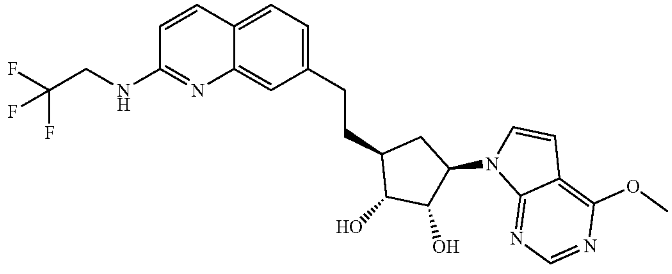

compound 188

A solution of intermediate 366 (410 mg, 0.76 mmol) in HCl/MeOH (4N, 7 mL) and MeOH (2 mL) was stirred at room temperature for 1 h. The reaction was concentrated. The residue was dissolved in $H_2O$ (3 mL) and basified by aq·$NH_3{\cdot}H_2O$. A precipitate was formed and collected. The solid was purified by prep-HPLC (Phenomenex Gemini 150×25 mm, 10 μm; conditions: A: water (0.05% ammonia hydroxide v/v), B:ACN); at the beginning: A (70%) and B (30%), at the end: A (40%) and B (60%); gradient time (min) 10; 100% B hold time (min) 3; flow rate (ml/min) 25. The desired fractions were collected and lyophilized to give compound 188 (131.3 mg, 34.5%) as solid.

Example B26

Preparation of Compound 211

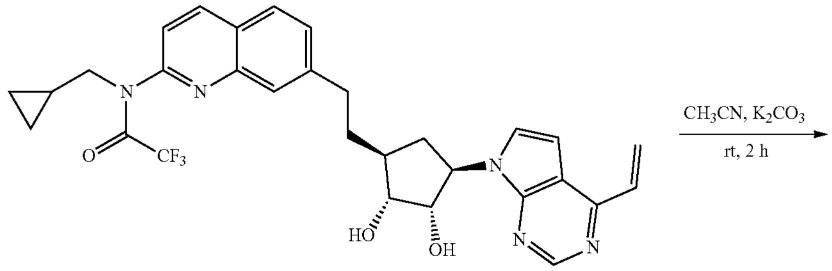

intermediate 383

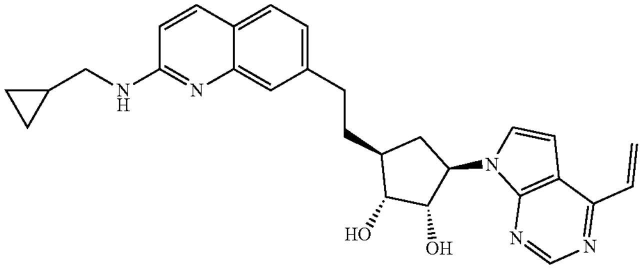

compound 211

Potassium carbonate (155 mg, 1.1 mmol) was added to intermediate 383 (0.3 g, 0.376 mmol) in $CH_3CN$ (10 ml). The mixture was stirred at room temperature for 3 h. The mixture was evaporated under vacuo. The residue was purified by preparative-HPLC (Column: Waters Xbridge Prep OBD C18 150×30 mm 5 μm; Condition: water (0.05% ammonia hydroxide v/v)-ACN, Begin: B 35%, End: B 65%, Gradient Time (min): 10, 100% B Hold Time (min): 3, FlowRate (ml/min): 25). The combined solvent was evaporated to give the product as a white solid. The product was purified by SFC separation (Column: OJ (250 mm×30 mm, 10 um), Condition; A: (0.1% ammonia hydroxide v/v)-B: EtOH, Begin: B 50%, End: B 50%, Flow Rate (ml/min): 80). The combined solvent was evaporated to give compound 211 (76 mg, yield:39%) as a white solid.

Example B27

Preparation of Compound 253

Compound 253 was prepared by an analogous reaction protocol as was used for the preparation of intermediate 382 described in A78 (Step 1) using the appropriate starting materials (Table 41).

TABLE 41

| Compound | Structure | Starting materials |
| --- | --- | --- |
| 253 | 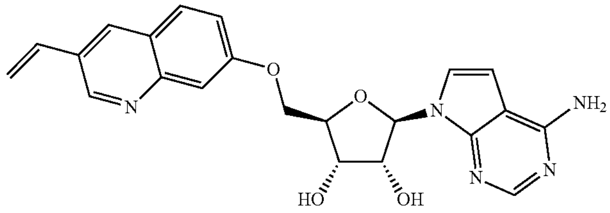 [SMILES: C=Cc1cnc2cc(OC[C@H]3O[C@@H](n4ccc5c(N)ncnc54)[C@H](O)[C@@H]3O)ccc2c1] | Compound 2 |

Example B28

Preparation of Compounds 207 and 208

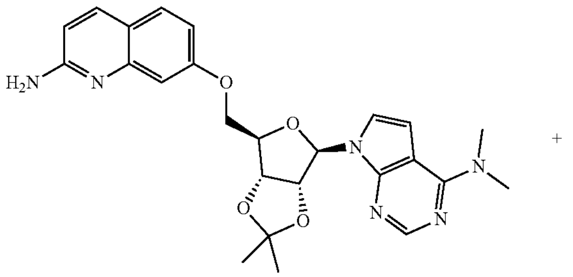

intermediare 384

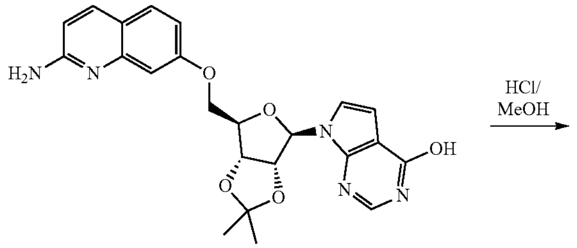

intermediare 385

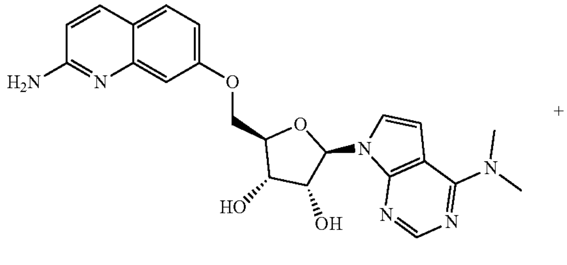

compound 207

-continued

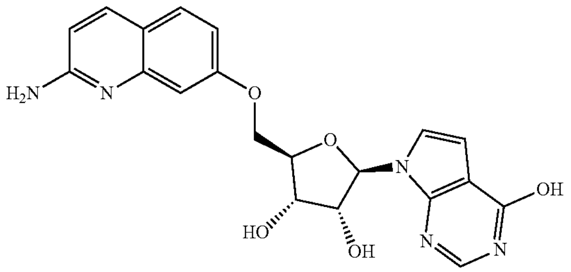

compound 208

HCl/MeOH (1 mL, 4 mol/L) was added into the mixture of intermediate 384 and intermediate 385 (200 mg) in MeOH (1 mL) and stirred at room temperature for 30 min. The reaction mixture was added dropwise into aq. $NH_3 \cdot H_2O$ (2 mL) and concentrated under vacuo to dryness to give the crude product. The crude product was purified by preparative high-performance liquid chromatography over Column: Phenomenex Gemin 150x25 mm 10 μm; Condition: A: water (0.05% ammonia hydroxide v/v), B: MeCN; at the beginning: A (85%) and B (15%), at the end: A: (55%) and B (45%). The pure fractions were collected and the solvent was evaporated under vacuum. The residues were lyophilized to give compound 207 (32 mg) and compound 208 (41 mg) as white solids.

Example B29

Preparation of Compound 215

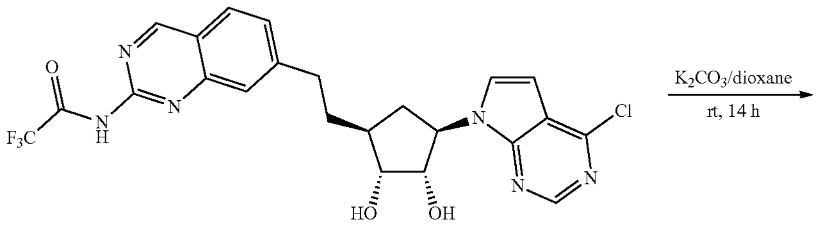

intermediate 388

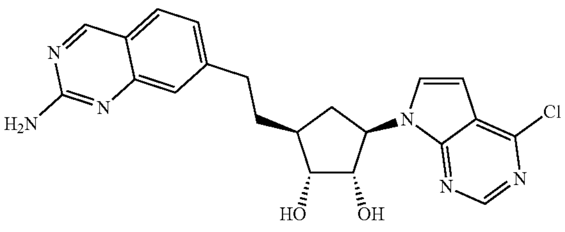

compound 215

A mixture of intermediate 388 (1 g, 0.67 mmol) and $K_2CO_3$ (1 g, 7.25 mmol) in $CH_2Cl_2$ (10 mL) and dioxane (10 mL) was stirred at 50° C. for 2 hours. The mixture was filtered and the filtrate was concentrated to give the crude product. The crude product was purified by preparative-HPLC (gradient elution: 0.05% $NH_3{\cdot}H_2O$ in $CH_3OH$/0.05% $NH_3{\cdot}H_2O$ in $H_2O$; Column: Kromasil 150×25 mm, 10 μm) to obtain compound 215 (102 mg, 34% yield) as a white solid.

Example B30

Preparation of Compound 216

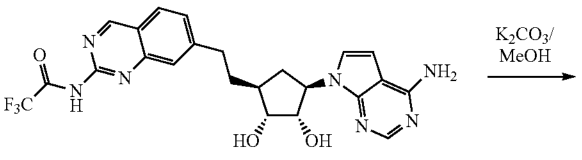

intermediate 390

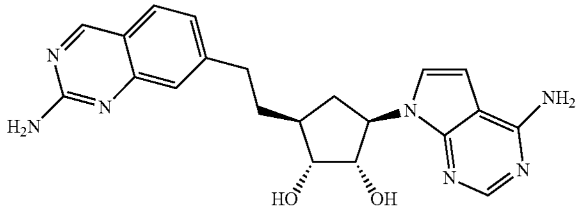

compound 216

A mixture of intermediate 390 (300 mg, 0.60 mmol) and $K_2CO_3$ (0.25 g, 1.80 mmol) in methanol (10 mL) was stirred at 50° C. for 2 hours. The mixture was filtered and concentrated to give the crude product. The crude product was purified by preparative-HPLC (gradient elution: 0.05% $NH_3{\cdot}H_2O$ in $CH_3OH$/0.05% $NH_3{\cdot}H_2O$ in $H_2O$; column: Kromasil 150×25 mm, 10 μm) to obtain compound 216 (37.9 mg, 15.5% yield) as a white solid.

Example B31

Preparation of Compound 198

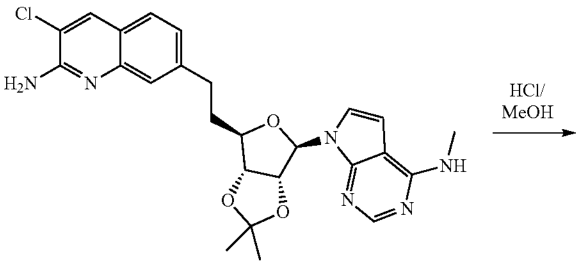

intermediate 347

-continued

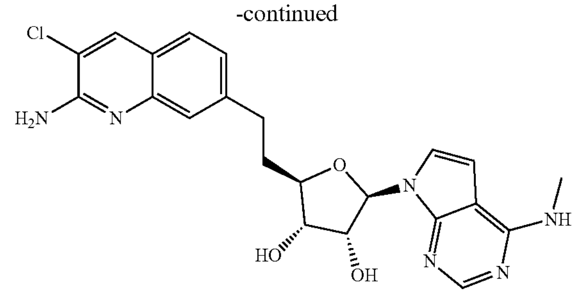

compound 198

A mixture of intermediate 347 (1.2 g, 2.42 mmol) in HCl/MeOH (20 mL, 4M) was stirred at room temperature for 2 hours. The solvent was concentrated in vacuum. Then $H_2O$ (50 ml) was added and the pH was adjusted to 9 by progressively adding solid $NaHCO_3$. The solid was filtered and washed with $H_2O$ (100 mL×6), methanol (100 mL×2) and diisopropylether (100 mL×2). The filtered cake was dried under vacuum to give compound 198 (273.7 mg, 24% yield) as white solid.

Example B32

Preparation of Compound 199

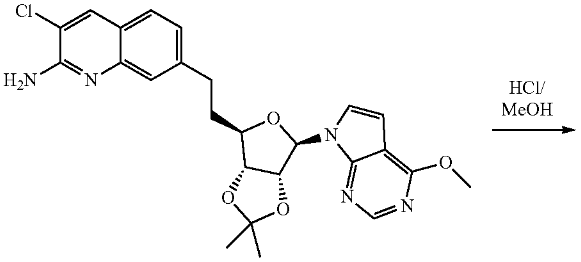

intermediate 372

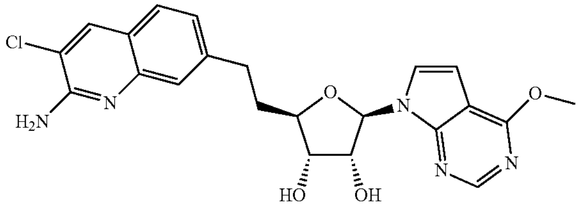

compound 199

A mixture of intermediate 372 (510 mg, 0.824 mmol) in HCl/MeOH (10 mL, 4M) was stirred at room temperature for 2 hours. The solvent was concentrated in vacuum. Then $H_2O$ (50 ml) was added and the pH was adjusted to 9 by progressively adding solid $NaHCO_3$. Then ethyl acetate (50 mL) was added. The organic layer was separated and the aqueous phase was extracted with ethyl acetate (50 mL×2). The combined organic phase was dried with anhydrous $Na_2SO_4$, filtered and concentrated in vacuum to give crude product. The crude product was purified by preparative-HPLC (Column: Waters Xbridge Prep OBD C18 150×30 mm, 5 μm, Conditions: A: water (0.05% ammonia hydroxide v/v)-B:ACN, Begin: B 13%, End: B 43%, Gradient Time (min): 10, 100% B Hold Time (min): 3, FlowRate (ml/min): 25) to obtain compound 199 (84.7 mg, 22% yield) as a white solid.

Example B33

Preparation of Compound 218

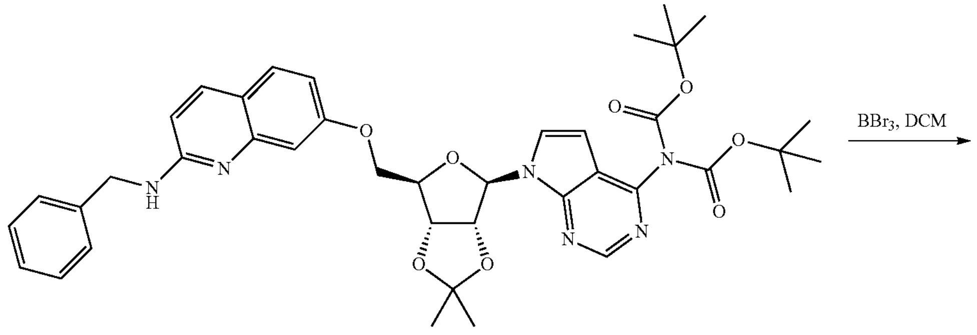

intermediate 232

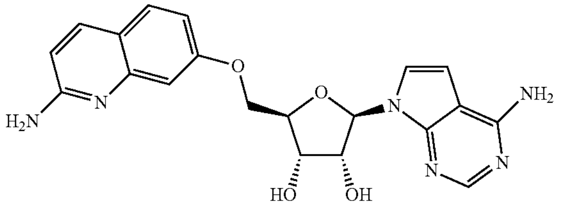

compound 218

To a solution of intermediate 232 (500 mg, 0.677 mmol, 1.0 eq) in DCM (15 mL) was added $BBr_3$ (0.64 mL, 6.77 mmol, 10.0 eq) at −78° C. under $N_2$. The resulted mixture was stirred overnight at 20° C. The solid was filtered, rinsed with $CH_2Cl_2$ and collected to give the crude product. The residue was triturated with water, and the pH was adjusted to around 8 by progressively added solid $K_2CO_3$. The resulting solid was filtered through a funnel rinsed with water (20 mL×5) and collected. The residue was purified by preparative-HPLC. (HPLC condition; A: water (0.05% ammonia hydroxide v/v)-B: ACN; Columns: Gemini 150×25 mm, 5 μm; Begin B: 9%, End B: 39%) to afford the product compound 218 (79 mg, 0.193 mmol, 29% yield,) as a white solid.

Example B34

Preparation of Compound 201

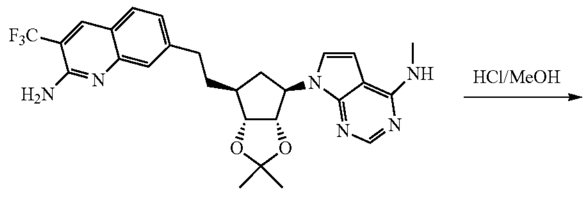

intermediate 348

-continued

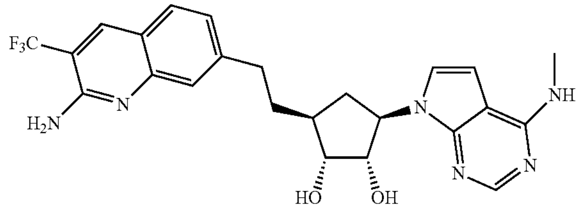

compound 201

Intermediate 348 (450 mg, 0.855 mmol) was dissolved in MeOH (15 mL), HCl/MeOH (4N, 15 mL) was added. The reaction mixture was stirred at room temperature for 2 hours. The solvent was removed by evaporation. The residue was triturated with EtOAc (100 mL) and saturated $Na_2CO_3$ (30 mL). The organic layer was separated and washed by brine (30 mL), dried over anhydrous $Na_2SO_4$, filtered and concentrated. The residue was purified by prep. HPLC (Waters Xbridge Prep OBD C18 150×30 mm 5 μm, conditions: A: water (0.05% $NH_4OH$ v/v)-B: ACN, FlowRate: 25 ml/min, gradient from B 35% to B 65%) to afford compound 201 (148 mg, 35% yield) as a white solid.

Example B35

Preparation of Compound 200

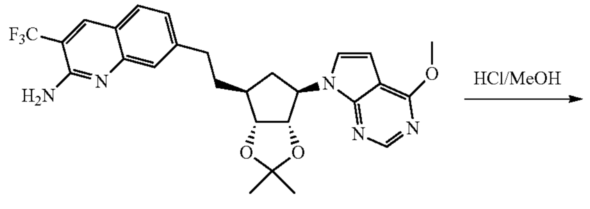

intermediate 373

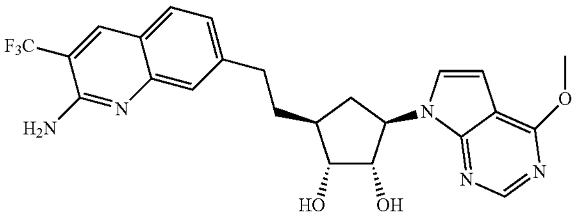

compound 200

Intermediate 373 (340 mg, 0.595 mmol) was dissolved in MeOH (50 mL) and 4N HCl/MeOH (10 mL) was added. The reaction mixture was stirred at room temperature for 2 hours. The solvent was removed by evaporation. The residue was triturated with EtOAc (100 mL) and saturated $Na_2CO_3$ (30 mL), the separated organic layer was washed by brine (30 mL), dried over anhydrous $Na_2SO_4$, filtered and concentrated. The residue was purified by prep. HPLC (Waters Xbridge Prep OBD C18 150×30 mm 5 μm, conditions; A: water (0.05% $NH_4OH$ v/v)-B: ACN, FlowRate: 25 ml/min, gradient from B 35% to B 65%) to afford the compound 200 (135 mg, 46% yield) as a white solid.

Example B36

Preparation of Compound 204

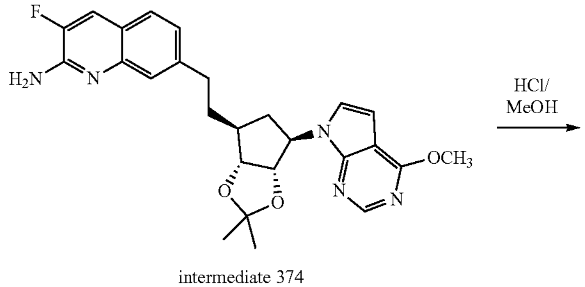

intermediate 374

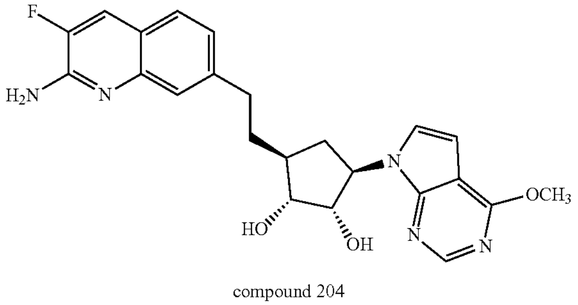

compound 204

A solution of intermediate 374 (350 mg, 0.73 mmol) in HCl/MeOH (4 M, 10 mL) was stirred at room temperature for 2 hours. The mixture was basified with $NH_3 \cdot H_2O$ (20 mL) to pH>7. The solution was washed with water (60 mL) and extracted with EtOAc (80 mL×3). The combined organic layers were washed with brine (80 mL), dried ($Na_2SO_4$), filtered and concentrated by vacuum to give the crude product as brown solid. The crude product was purified by HPLC (Column: Waters Xbridge Prep OBD C18 150×30 mm 5 μm; Conditions; A: water (0.05% ammonia hydroxide v/v)-B: ACN; Begin B: 25%; End B: 55%; Gradient Time (min): 10; 100% B Hold Time (min): 3; FlowRate (ml/min): 25) to give compound 204 (102.9 mg, 32% yield) as white solid.

Example B37

Preparation of Compound 203

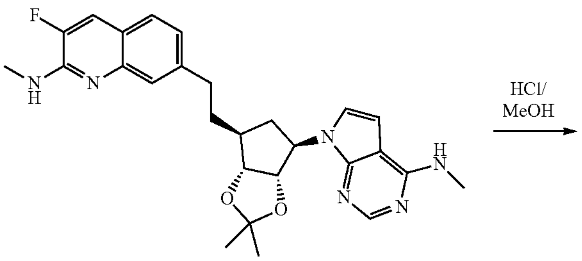

intermediate 350

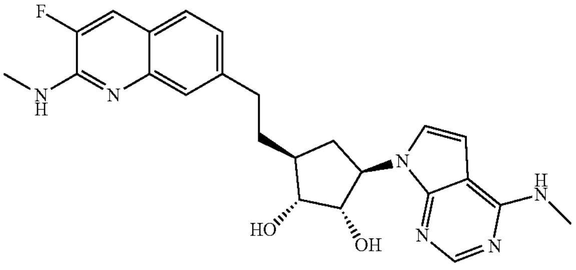

compound 203

A solution of intermediate 350 (300 mg, 0.61 mmol) in $HCl/CH_3OH$ (4 mol/L, 10 mL) was stirred at room temperature for 2 hours. The mixture was basified with $NH_3 \cdot H_2O$ (8 mL) to pH>7. The solution was treated with water (100 mL) and extracted with ethyl acetate (150 mL×3). The combined organic layers were washed with brine (100 mL), dried ($Na_2SO_4$), filtered and concentrated by vacuum to give the crude product as a brown solid. The crude product was purified by HPLC (Column: Waters Xbridge Prep OBD C18 150×30 mm, 5 μm; Condition; A: water (0.05% ammonia hydroxide v/v)-B: ACN; Begin B: 25%; End 9:55%; Gradient Time (min): 10; 100% B Hold Time (min): 3; FlowRate (ml/min): 25) to give compound 203 (129.8 mg, 47% yield) as a white solid.

Example B38

Preparation of Compound 202

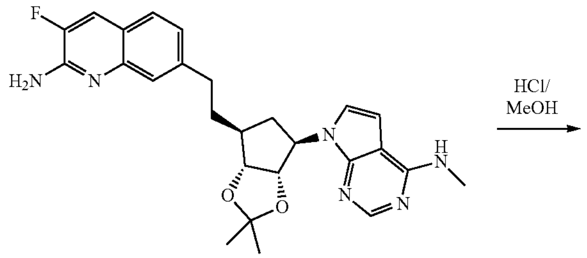

intermediate 349

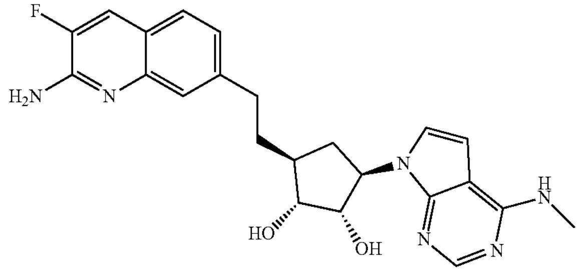

compound 202

A solution of intermediate 349 (350 mg, 0.734 mmol) in $HCl/CH_3OH$ (4 M, 10 mL) was stirred at room temperature for 2 hours. The mixture was basified with $NH_3 \cdot H_2O$ (10 mL) to pH>7. The solution was washed with water (100 mL) and extracted with ethyl acetate (150 mL×3). The combined organic layers were washed with brine (100 mL), dried ($Na_2SO_4$), filtered and concentrated by vacuum to give the crude product as a brown solid. The crude product was purified by HPLC to give compound 202 (149 mg, 46% yield) as white solid.

Example B39

Preparation of Compound 219

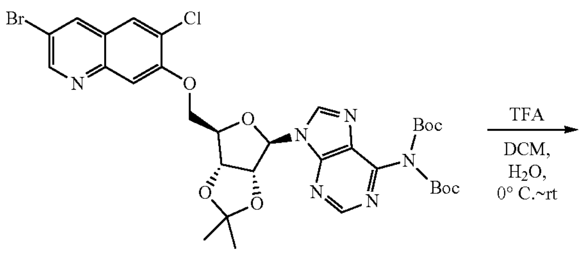

intermediate 422

-continued

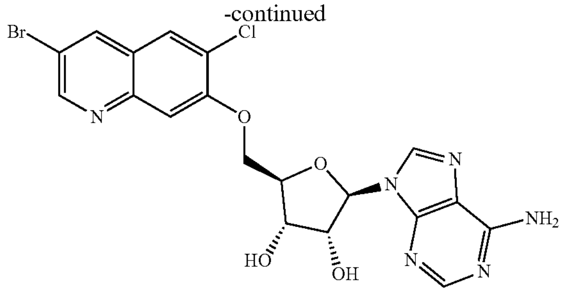

compound 219

To a solution of intermediate 422 (600 mg, 0.80 mmol) in DCM (11 mL) was added TFA (12 mL, 163 mmol) dropwise under $N_2$ at 0° C. The reaction mixture was stirred at 0° C. for 30 minutes, then $H_2O$ (3 mL) was added. The reaction mixture was stirred at room temperature overnight. The solvent was removed under vacuum. The residue was dissolved in water (30 ml) and the pH was adjusted to 8 and was then filtered. The solid was collected, dried under vacuum to give compound 219 (326 mg, 86.5% yield) as a white solid.

Example B40

Preparation of Compound 220

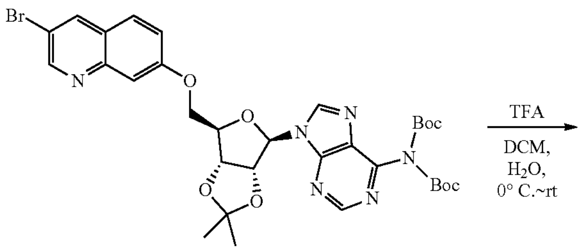

intermediate 424

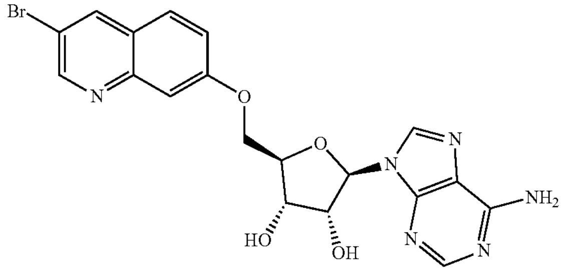

compound 220

To a solution of intermediate 424 (1 g, 1.20 mmol) in DCM (10 mL) was added TFA (10 mL, 135 mmol) dropwise under $N_2$ at 0° C. The reaction mixture was stirred at 0° C. for 30 minutes, then $H_2O$ (3 mL) was added. The reaction mixture was stirred at room temperature for 4 hours. The solvent was removed under vacuum. The residue was dissolved in MeOH (10 ml) and adjusted pH to 8, then filtered and the filtrate was concentrated to give the crude product. The crude product was purified by HPLC Column: DuraShell 150×25 mm, 5 μm; Conditions: A: water (0.05% $NH_4OH$ v/v), B: MeOH; at the beginning: A (60%) and B (40%), at the end: A (30%) and B (70%); Gradient Time (min) 10; 100% B Hold Time (min) 3; Flow Rate (ml/min) 25 to give compound 220 (106 mg, 19% yield) as a white solid.

Example B42

Preparation of Compound 221

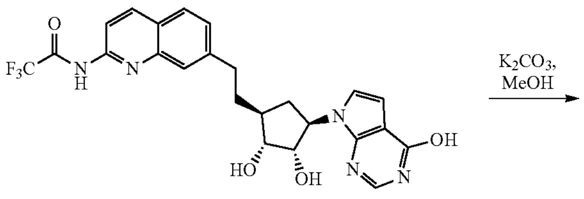

intermediate 426

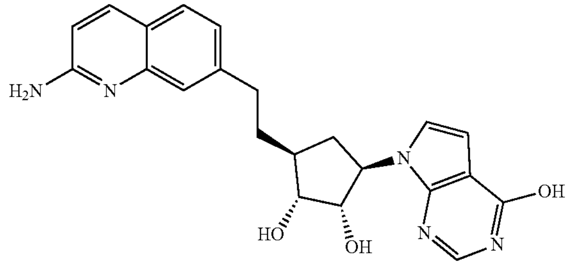

compound 211

The mixture of intermediate 426 (150 mg, 0.123 mmol,) and potassium carbonate (51 mg, 0.369 mmol) in methanol (3 ml) was stirred at 60° C. for 1 h. The mixture was filtered and the filtrate was evaporated under vacuo to obtain the crude product as a solid. This residue was purified by preparative-HPLC (Column: Waters Xbridge Prep OBD C18 150×30 mm, 5 μm, Condition; A: water (0.05% ammonia hydroxide v/v) B: ACN, Begin: B 13%, End: B 43%, Gradient Time (min): 10, 100% B Hold Time (min): 3, FlowRate (ml/min): 25). The combined solvents were evaporated to give compound 221 (39 mg) as a white solid.

C. Conversions of Compounds

Example C1

Preparation of Compound 217

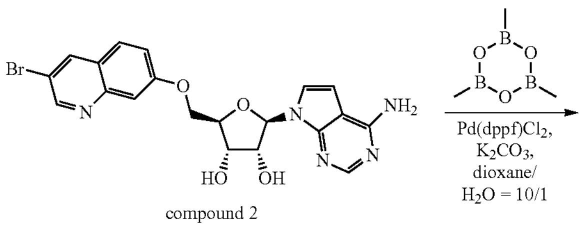

compound 2

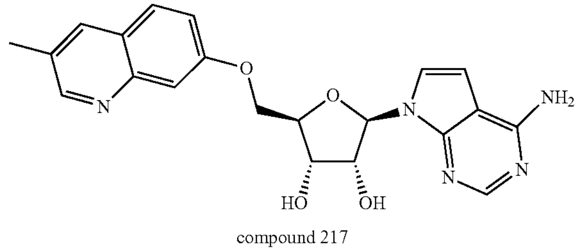

compound 217

To a solution of compound 2 (1.6 g, 2.88 mmol, 1.0 eq,), 2,4,6-trimethyl-1,3,5,2,4,6-trioxatriborinane (0.72 g, 5.76 mmol, 2.0 eq) and $K_2CO_3$ (0.796 g, 5.76 mmol, 2.0 eq) in dioxane/$H_2O$ ratio 10/1 (30 mL) was added. $Pd(dppf)Cl_2$ (210 mg, 0.288 mmol, 0.1 eq). The resulting mixture was stirred at 90° C. under $N_2$ for 16 hours. The resulting solid was filtered off. The filtrate was concentrated. The residue was triturated with water (30 ml), and DCM (30 ml) was added. A solid precipitated out of the reaction. The resulting solid was filtered to give the crude product. The residue was purified by column chromatography (gradient: petroleum ether/ethyl acetate/MeOH ratio 20/1/0 to 0/20/1). The product fractions were collected and the solvent was evaporated to give the product as solid. The product was purified by preparative-HPLC (HPLC condition: A: water (0.05% ammonia hydroxide v/v)-B: ACN; Column: Gemini 150×25 mm, 5 μm; Begin B: 15%, End B: 45%) and to afford compound 217 (300 mg, 0.73 mmol, 25% yield,) as a white solid.

Example C2

Preparation of Compound 212

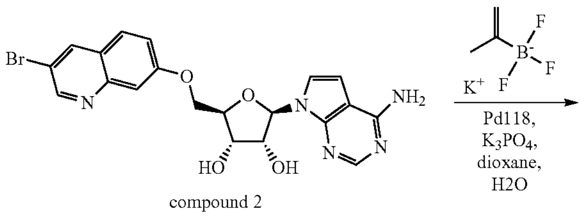

compound 2

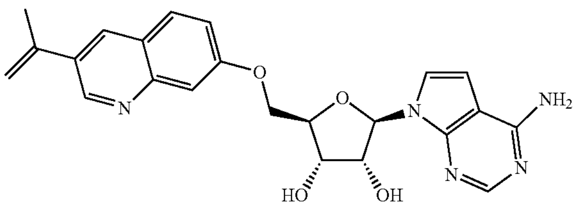

compound 212

To a solution of compound 2 (1 g, 1.8 mmol) in dioxane (40 ml) and $H_2O$ (10 ml) was added potassium isopropenyltrifluoroborate (319 mg, 2.16 mmol) and $K_3PO_4$ (764 mg, 3.6 mmol) at room temperature. 1,1'-bis(di-tert-butylphosphino)ferrocene palladium dichloride (58 mg, 0.09 mmol) was added to the above solution under nitrogen atmosphere. The reaction mixture was stirred at 80° C. under nitrogen atmosphere overnight. The mixture was extracted with ethylacetate, the organic layers were combined and concentrated under vacuo to give the crude product.

This crude product was purified by preparative-HPLC (gradient elution: 0.05% $NH_3 \cdot H_2O$ in $CH_3CN$/0.05% $NH_3 \cdot H_2O$ in $H_2O$; Column: DuraShell 150×25 mm, 5 μm). The combined solvent was evaporated to give the desired product as a white solid of the product (300 mg, yield 35%). 100 mg of the product was purified by SFC separation (AD (250 mm×30 mm, 10 μm)). The combined solvents were evaporated under vacuo to give the desired product as a white solid of compound 212 (71.9 mg).

Example C3

Preparation of Compound 213

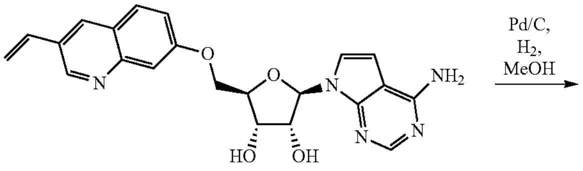

compound 253

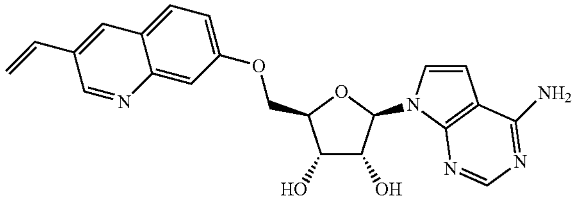

compound 213

Pd/C (20 mg) was added into the mixture of compound 253 (200 mg, 0.429 mmol) in MeOH (20 ml). The mixture was hydrogenated at 25° C. for 24 h under $H_2$ atmosphere. The mixture was filtered and evaporated under vacuo to obtain a crude product. It was purified by preparative-HPLC (gradient elution: 0.05% $NH_3 \cdot H_2O$ in $CH_3CN$/0.05% $NH_3 \cdot H_2O$ in $H_2O$; Column: Waters Xbridge Prep OBD C18 150×30 mm, 5 mm). The combined solvent was evaporated to give compound 213 as a white solid (132 mg, yield 73%).

Below compounds were prepared by an analogous reaction protocol as was used for the preparation of compound 213 using the appropriate starting materials (Table 47).

TABLE 47

| compounds | Structure | Starting materials |
|---|---|---|
| 214 | 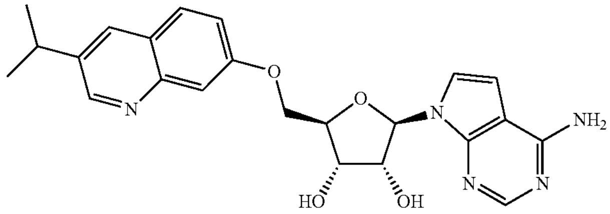 [SMILES: CC(C)c1cnc2cc(OC[C@H]3O[C@@H](n4ccc5c(N)ncnc54)[C@H](O)[C@@H]3O)ccc2c1] | Compound 212 |

Analytical Part

NMR

For a number of compounds, $^1$H NMR spectra were recorded on a Bruker DPX-360 operating at 360 MHz, on a Bruker Avance 600 operating at 600 MHz, on a Bruker Avance 400 operating at 400 MHz, or on a Varian 400MR spectrometer operating at 400 MHz. As solvents CHLOROFORM-d (deuterated chloroform, $CDCl_3$), Methanol-$d_4$ or DMSO-$d_6$ (deuterated DMSO, dimethyl-$d_6$ sulfoxide) were used. Chemical shifts (δ) are reported in parts per million (ppm) relative to tetramethylsilane (TMS), which was used as internal standard.

Co. 217: $^1$H NMR (400 MHz, DMSO-$d_6$) δ ppm 2.44 (s, 3H) 4.21-4.34 (m, 3H) 4.34-4.43 (m, 1H) 4.50 (q, J=5.7 Hz, 1H) 5.37 (d, J=5.0 Hz, 1H) 5.44 (d, J=6.3 Hz, 1H) 6.17 (d, J=5.5 Hz, 1H) 6.61 (d, J=3.8 Hz, 1H) 7.01 (br s, 2H) 7.27 (dd, J=8.8, 2.5 Hz, 1H) 7.37 (d, J=3.8 Hz, 1H) 7.41 (d, J=2.3 Hz, 1H) 7.81 (d, J=9.0 Hz, 1H) 8.05 (br s, 1H) 8.07 (s, 1H) 8.70 (d, J=2.0 Hz, 1H).

Co. 218: $^1$H NMR (400 MHz, DMSO-$d_6$) δ ppm 4.14-4.34 (m, 4H) 4.48 (q, J=5.7 Hz, 1H) 5.36 (d, J=5.0 Hz, 1H) 5.44 (d, J=6.3 Hz, 1H) 6.15 (d, J=5.5 Hz, 1H) 6.33 (br s, 2H) 6.58 (d, J=8.8 Hz, 1H) 6.61 (d, J=3.8 Hz, 1H) 6.83 (dd, J=8.7, 2.4 Hz, 1H) 6.91 (d, J=2.3 Hz, 1H) 7.02 (br s, 2H) 7.35 (d, J=3.8 Hz, 1H) 7.53 (d, J=8.8 Hz, 1H) 7.79 (d, J=8.8 Hz, 1H) 8.07 (s, 1H).

Co. 74: $^1$H NMR (600 MHz, DMSO-$d_6$) δ ppm 0.24-0.27 (m, 2H) 0.45-0.48 (m, 2H) 1.08-1.14 (m, 1H) 1.52 (dt, J=12.4, 10.3 Hz, 1H) 1.67-1.74 (m, 1H) 1.84-1.92 (m, 1H) 1.96 (ddt, J=13.0, 9.3, 6.4, 6.4 Hz, 1H) 2.25 (dt, J=12.7, 7.9 Hz, 1H) 2.65-2.72 (m, 1H) 2.72-2.79 (m, 1H) 3.26 (dd, J=6.5, 5.6 Hz, 2H) 3.75 (q, J=4.9 Hz, 1H) 4.21 (dt, J=7.6, 6.2 Hz, 1H) 4.63 (d, J=4.8 Hz, 1H) 4.77 (d, J=6.3 Hz, 1H) 4.81 (dt, J=10.5, 8.0 Hz, 1H) 6.55 (d, J=3.5 Hz, 1H) 6.72 (d, J=8.9 Hz, 1H) 6.91 (br s, 2H) 6.99-7.03 (m, 2H) 7.26 (d, J=3.5 Hz, 1H) 7.33 (s, 1H) 7.50 (d, J=8.1 Hz, 1H) 7.76 (d, J=8.8 Hz, 1H) 8.04 (s, 1H).

Co. 129: $^1$H NMR (360 MHz, DMSO-$d_6$) δ ppm 1.53 (dt, J=12.3, 10.2 Hz, 1H) 1.69-1.81 (m, 1H) 1.82-1.93 (m, 1H) 1.95-2.05 (m, 1H) 2.25 (dt, J=12.4, 7.9 Hz, 1H) 2.78-2.93 (m, 2H) 3.76 (q, J=5.0 Hz, 1H) 4.21 (q, J=5.9 Hz, 1H) 4.66 (d, J=4.8 Hz, 1H) 4.73-4.86 (m, 2H) 6.55 (d, J=3.3 Hz, 1H) 6.95 (br s, 2H) 7.27 (d, J=3.7 Hz, 1H) 7.59 (dd, J=8.4, 1.8 Hz, 1H) 7.87 (s, 1H) 7.91 (d, J=8.4 Hz, 1H) 8.03 (s, 1H) 8.68 (d, J=2.2 Hz, 1H) 8.91 (d, J=2.6 Hz, 1H).

Co. 130: $^1$H NMR (400 MHz, DMSO-$d_6$) δ ppm 4.22-4.39 (m, 3H) 4.59 (q, J=5.0 Hz, 1H) 5.49 (br d, J=4.5 Hz, 1H) 5.60 (d, J=6.0 Hz, 1H) 6.29 (d, J=5.5 Hz, 1H) 6.64 (m, J=9.0 Hz, 2H) 6.78 (d, J=3.8 Hz, 1H) 6.90 (dd, J=8.7, 1.9 Hz, 1H) 6.97 (d, J=1.5 Hz, 1H) 7.58 (d, J=8.5 Hz, 1H) 7.87 (d, J=9.0 Hz, 1H) 7.97 (d, J=4.0 Hz, 1H) 8.69 (s, 1H).

Co. 176: $^1$H NMR (400 MHz, Methanol-$d_4$) δ ppm 2.32-2.45 (m, 1H) 2.48-2.62 (m, 1H) 2.65-2.83 (m, 2H) 3.01-3.12 (m, 1H) 3.45 (s, 3H) 3.49-3.63 (m, 2H) 3.69 (d, J=4.8 Hz, 3H) 4.53-4.61 (m, 1H) 5.05-5.11 (m, 1H) 5.51 (d, J=4.8 Hz, 1H) 5.60 (d, J=6.3 Hz, 1H) 5.70-5.81 (m, 1H) 7.47 (d, J=8.8 Hz, 1H) 7.50 (d, J=3.8 Hz, 1H) 7.73 (br q, J=5.0 Hz, 1H) 7.84 (dd, 1.5 Hz, 1H) 8.17 (br s, 1H) 8.32 (d, J=8.0 Hz, 1H) 8.53 (d, J=3.5 Hz, 1H) 8.58 (d, J=8.8 Hz, 1H) 9.43 (s, 1H).

Co. 80: $^1$H NMR (600 MHz, DMSO-$d_6$) δ ppm 1.50-1.56 (m, 1H) 1.68-1.75 (m, 1H) 1.85-1.92 (m, 1H) 1.96 (ddt, J=13.0, 9.0, 6.5, 6.5 Hz, 1H) 2.25 (dt, J=12.7, 7.9 Hz, 1H) 2.69-2.80 (m, 2H) 3.76 (br t, J=4.7 Hz, 1H) 4.21 (dd, J=7.6, 6.0 Hz, 1H) 4.57 (br s, 1H) 4.72 (br s, 1H) 4.80 (dt, J=10.5, 7.9 Hz, 1H) 6.50 (br s, 2H) 6.59 (d, J=3.5 Hz, 1H) 7.07 (br s, 2H) 7.12 (dd, J=8.2, 1.6 Hz, 1H) 7.29 (d, J=3.6 Hz, 1H) 7.34 (s, 1H) 7.58 (d, J=8.1 Hz, 1H) 8.07 (s, 1H) 8.31 (s, 1H).

Co. 185: $^1$H NMR (400 MHz, DMSO-$d_6$) δ ppm 2.96 (br d, J=3.5 Hz, 3H) 4.16-4.36 (m, 4H) 4.44-4.55 (m, 1H) 5.38 (br d, J=5.3 Hz, 1H) 5.47 (br d, J=6.2 Hz, 1H) 6.16 (d, J=5.7 Hz, 1H) 6.63 (d, J=4.0 Hz, 1H) 6.70 (br d, J=9.3 Hz, 1H) 6.89-6.97 (m, 1H) 7.05-7.23 (m, 3H) 7.37 (d, J=3.5 Hz, 1H) 7.63 (br d, J=9.3 Hz, 1H) 7.84-7.95 (m, 1H) 8.09 (s, 1H).

Co. 75: $^1$H NMR (400 MHz, DMSO-$d_6$) δ ppm 1.45-1.59 (m, 1H) 1.65-1.77 (m, 1H) 1.83-2.02 (m, 2H) 2.25 (dt, J=12.5, 7.9 Hz, 1H) 2.63-2.83 (m, 2H) 3.72-3.89 (m, 3H) 4.16-4.24 (m, 1H) 4.64 (d, J=4.8 Hz, 1H) 4.77 (d, J=6.3 Hz, 1H) 4.79-4.84 (m, 1H) 6.22 (tt, J=56.7, 4.1 Hz, 1H) 6.54 (d, J=3.5 Hz, 1H) 6.78 (d, J=8.8 Hz, 1H) 6.91 (br s, 2H) 7.09 (dd, J=8.2, 1.6 Hz, 1H) 7.26 (d, J=3.5 Hz, 1H) 7.36 (t, J=6.0 Hz, 1H) 7.40 (br s, 1H) 7.57 (d, J=8.0 Hz, 1H) 7.87 (d, J=8.8 Hz, 1H) 8.03 (s, 1H).

Co. 81: $^1$H NMR (400 MHz, DMSO-$d_6$) δ ppm 1.42-1.60 (m, 1H) 1.62-1.77 (m, 1H) 1.81-2.00 (m, 2H) 2.24 (dt, J=12.7, 7.8 Hz, 1H) 2.64-2.83 (m, 2H) 3.70-3.79 (m, 1H) 4.16-4.25 (m, 1H) 4.62 (br d, J=4.9 Hz, 1H) 4.71-4.87 (m, 2H) 6.54 (d, J=3.5 Hz, 1H) 6.65 (br s, 2H) 6.90 (br s, 2H) 7.12 (br d, J=7.5 Hz, 1H) 7.25 (d, J=3.5 Hz, 1H) 7.34 (s, 1H) 7.58 (d, J=8.4 Hz, 1H) 8.03 (s, 1H) 8.14 (s, 1H).

Co. 151: $^1$H NMR (400 MHz, DMSO-$d_6$) δ ppm 1.45-1.57 (m, 1H) 1.62-1.77 (m, 1H) 1.82-2.01 (m, 2H) 2.25 (dt, J=12.4, 7.9 Hz, 1H) 2.65-2.82 (m, 2H) 3.75 (q, J=4.8 Hz, 1H) 4.20 (dt, J=7.6, 6.2 Hz, 1H) 4.26-4.39 (m, 2H) 4.64 (d, J=4.8 Hz, 1H) 4.73-4.87 (m, 2H) 6.54 (d, J=3.5 Hz, 1H) 6.82 (d, J=8.8 Hz, 1H) 6.91 (br s, 2H) 7.12 (dd, J=8.0, 1.5 Hz, 1H) 7.26 (d, J=3.5 Hz, 1H) 7.42 (s, 1H) 7.54 (br t, J=6.4 Hz, 1H) 7.59 (d, J=8.0 Hz, 1H) 7.91 (d, J=8.9 Hz, 1H) 8.03 (s, 1H).

Co. 152: $^1$H NMR (400 MHz, DMSO-$d_6$) δ ppm 0.39-0.62 (m, 2H) 0.67-0.84 (m, 2H) 1.46-1.62 (m, 1H) 1.64-1.78 (m, 1H) 1.82-2.02 (m, 2H) 2.25 (dt, J=12.6, 8.0 Hz, 1H) 2.63-2.83 (m, 3H) 3.70-3.79 (m, 1H) 4.15-4.25 (m, 1H) 4.63 (d, J=4.9 Hz, 1H) 4.73-4.86 (m, 2H) 6.54 (d, J=3.5 Hz, 1H) 6.75 (br d, J=8.8 Hz, 1H) 6.90 (br s, 2H) 7.05 (dd, 1.5 Hz, 1H) 7.13 (br d, J=2.6 Hz, 1H) 7.26 (d, J=3.5 Hz, 1H) 7.37 (br s, 1H) 7.54 (d, J=7.9 Hz, 1H) 7.84 (d, J=8.8 Hz, 1H) 8.03 (s, 1H).

Co. 146: $^1$H NMR (400 MHz, DMSO-$d_6$) δ ppm 1.38-1.63 (m, 5H) 1.65-1.75 (m, 3H) 1.82-2.04 (m, 4H) 2.25 (dt, J=12.5, 7.9 Hz, 1H) 2.63-2.80 (m, 2H) 3.71-3.78 (m, 1H) 4.14-4.25 (m, 1H) 4.33 (dq, J=13.6, 6.7 Hz, 1H) 4.63 (d, J=4.9 Hz, 1H) 4.73-4.86 (m, 2H) 6.54 (d, J=3.1 Hz, 1H) 6.66 (d, J=8.8 Hz, 1H) 6.76-6.97 (m, 3H) 7.01 (dd, J=7.9, 1.3 Hz, 1H) 7.26 (d, J=3.5 Hz, 1H) 7.32 (s, 1H) 7.49 (d, J=8.4 Hz, 1H) 7.74 (d, J=8.8 Hz, 1H) 8.03 (s, 1H).

Co. 76: $^1$H NMR (400 MHz, DMSO-$d_6$) δ ppm 1.43-1.57 (m, 1H) 1.62-1.76 (m, 1H) 1.79-2.01 (m, 2H) 2.18-2.29 (m, 1H) 2.65-2.79 (m, 2H) 3.70-3.78 (m, 1H) 4.14-4.25 (m, 1H) 4.63 (br d, J=4.9 Hz, 1H) 4.73-4.86 (m, 2H) 6.42 (br s, 2H) 6.54 (br d, J=3.5 Hz, 1H) 6.69 (br d, J=8.8 Hz, 1H) 6.92 (br s, 2H) 7.05 (br d, J=8.4 Hz, 1H) 7.26 (br d, J=3.5 Hz, 1H) 7.28 (br s, 1H) 7.54 (br d, J=7.9 Hz, 1H) 7.84 (br d, J=8.8 Hz, 1H) 8.02 (s, 1H).

Co. 121: $^1$H NMR (400 MHz, DMSO-$d_6$) δ ppm 1.56-1.68 (m, 1H) 1.69-1.82 (m, 1H) 1.84-2.05 (m, 2H) 2.24-2.37 (m, 1H) 2.63-2.81 (m, 2H) 2.88 (d, J=4.4 Hz, 3H) 3.73-3.81 (m, 1H) 4.25-4.35 (m, 1H) 4.73 (d, J=4.4 Hz, 1H) 4.86 (d, J=6.6 Hz, 1H) 4.93-5.04 (m, 1H) 6.66 (d, J=8.8 Hz, 1H) 6.69 (d, J=3.5 Hz, 1H) 6.87-6.94 (m, 1H) 7.03 (br dd, J=7.9, 1.3 Hz, 1H) 7.37 (s, 1H) 7.51 (d, J=8.4 Hz, 1H) 7.77 (br d, J=8.8 Hz, 1H) 7.95 (d, J=4.0 Hz, 1H) 8.63 (s, 1H).

Co. 113: $^1$H NMR (400 MHz, DMSO-$d_6$) δ ppm 1.48-1.58 (m, 1H) 1.70-1.80 (m, 1H) 1.82-1.94 (m, 1H) 1.95-2.04 (m, 1H) 2.25 (dt, J=12.5, 8.1 Hz, 1H) 2.46 (s, 3H) 2.75-2.90 (m, 2H) 3.71-3.80 (m, 1H) 4.20 (br dd, J=14.1, 6.2 Hz, 1H) 4.65 (d, J=5.3 Hz, 1H) 4.73-4.86 (m, 2H) 6.54 (d, J=3.5 Hz, 1H) 6.92 (br s, 2H) 7.26 (d, J=3.5 Hz, 1H) 7.47 (dd, J=8.4, 1.8 Hz, 1H) 7.76-7.85 (m, 2H) 8.02 (s, 1H) 8.07 (br s, 1H) 8.72 (d, J=2.2 Hz, 1H).

OR (Optical Rotation)

Optical rotations were measured on a Perkin-Elmer 341 polarimeter with a sodium lamp (wavelength of light used is 589 nm (the sodium D line)). ('T' means temperature).

TABLE

Optical rotation values for enantiomerically pure compounds

| Co. Nr. | $\alpha_D$ (°) | Wavelength (nm) | Concentration (w/v %) | Solvent | T (° C) |
|---|---|---|---|---|---|
| 129 | −8.6 | 589 | 0.3835 | DMF | 20 |
| 130 | −84.95 | 589 | 0.3555 | DMF | 20 |
| 151 | −11.15 | 589 | 0.5380 | DMF | 20 |
| 113 | −8 | 589 | 0.5125 | DMF | 20 |
| 176 | −20.63 | 589 | 0.2715 | DMF | 20 |
| 74 | −9.7 | 589 | 0.3610 | DMF | 20 |
| 75 | −11.97 | 589 | 0.5345 | DMF | 20 |
| 146 | −10.19 | 589 | 0.5005 | DMF | 20 |
| 217 | −92.69 | 589 | 0.5265 | DMF | 20 |
| 185 | −88.93 | 589 | 0.5195 | DMF | 20 |
| 80 | −1.88 | 589 | 0.5315 | DMF | 20 |
| 121 | −18.82 | 589 | 0.3560 | DMF | 20 |
| 76 | −3.37 | 589 | 0.2670 | DMF | 20 |
| 218 | −79.03 | 589 | 0.3505 | DMF | 20 |
| 152 | −8.19 | 589 | 0.5370 | DMF | 20 |
| 81 | −2.48 | 589 | 0.3625 | DMF | 20 |

LCMS (Liquid Chromatography/Mass Spectrometry)

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica., "Q-Tof" Quadrupole Time-of-flight mass spectrometers, "CLND", ChemiLuminescent Nitrogen Detector, "ELSD" Evaporative Light Scanning Detector,

TABLE

LCMS Method codes (Flow expressed in mL/min; column temperature (T) in ° C.; Run time in minutes).

| Method code | Instrument | Column | Mobile phase | Gradient | Flow / Col T | Run time |
|---|---|---|---|---|---|---|
| 1 | Waters: Acquity ® UPLC ® DAD and SQD | Waters: BEH C18 (1.7 μm, 2.1 * 50 mm) | A: 10 mM $CH_3COONH_4$ in 90% $H_2O$ + 10% $CH_3CN$ B: MeOH | From 95% A to 5% A in 1.3 min, held for 0.2 min, to 95% A in 0.2 min held for 0.1 min. | 0.7 / 70 | 1.8 |
| 2 | Waters: Acquity ® UPLC ® DAD and SQD | Waters: BEH C18 (1.7 μm, 2.1 * 50 mm) | A: 10 mM $CH_3COONH_4$ in 95% $H_2O$ + 5% $CH_3CN$ B: $CH_3CN$ | From 95% A to 5% A in 1.3 min, held for 0.7 min. | 0.8 / 55 | 2 |
| 3 | Waters: Acquity ® UPLC ®-DAD and SQD | Waters: HSS T3 (1.8 μm, 2.1 * 100 mm) | A: 10 mM $CH_3COONH_4$ in in 95% $H_2O$ + 5% $CH_3CN$ B: $CH_3CN$ | From 100% A to 5% A in 2.10 min, to 0% A in 0.90 min to 5% A 0.5 min | 0.7 / 55 | 3.5 |
| 4 | Waters: Acquity ® UPLC ®-DAD and SQD | Waters: HSS T3 (1.8 μm, 2.1 * 100 mm) | A: 10 mM $CH_3COONH_4$ in in 95% $H_2O$ + 5% $CH_3CN$ B: $CH_3CN$ | From 100% A to 5% A in 2.10 min, to 0% A in 0.90 min to 5% A 0.5 min | 0.7 / 55 | 3.5 |
| 5 | Waters: Acquity UPLC ®-DAD and Quattro Micro ™ | Waters: BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% AB in 0.73 min, held for 0.73 min. | 0.343 / 40 | 6.2 |
| 6 | Agilent: 1100/1200-DAD and MSD | Waters: XBridge ™ Shield RP18 (5 μm, 2.1 × 50 mm) | A: $NH_4OH$ 0.05% in water, B: $CH_3CN$ | 100% A for 1 min, to 40% A in 4 min, held for 2.5 min, back to 100% A in 2 min. | 0.8 / 40 | 10.5 |
| 7 | Agilent: 1200-DAD and MSD6110 | Phenomenex: Luna-C18 (5 μm, 2 × 50 mm) | A: $CF_3COOH$ 0.1% in water, B: $CF_3COOH$ 0.05% in $CH_3CN$ | 100% A for 1 min, to 40% A in 4 min, to 15% A in 2.5 min, back to 100% A in 2 min. | 0.8 / 50 | 10 |
| 8 | Waters: Acquity ® UPLC ®-DAD and SQD | Waters: HSS T3 (1.8 μm, 2.1 * 100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.7 / 55 | 3.5 |
| 9 | Agilent: 1100/1200-DAD and MSD | Agilent: TC-C18 (5 μm, 2.1 × 50 mm) | A: $CF_3COOH$ 0.1% in water, B: $CF_3COOH$ 0.05% in $CH_3CN$ | 100% A for 1 min, to 40% A in 4 min, to 15% A in 2.5 min, back to 100% A in 2 min. | 0.8 / 50 | 10.5 |
| 10 | Agilent: 1100/1200-DAD and MSD | Agilent: TC-C18 (5 μm, 2.1 × 50 mm) | A: $CF_3COOH$ 0.1% in water, B: $CF_3COOH$ 0.05% in $CH_3CN$ | 90% A for 0.8 min, to 20% A in 3.7 min, held for 3 min, back to 90% A in 2 min. | 0.8 / 50 | 10.5 |
| 11 | Agilent: 1200-DAD and MSD6110 | Phenomenex: Luna-C18 (5 μm, 2 × 50 mm) | A: $CF_3COOH$ 0.1% in water, B: $CF_3COOH$ 0.05% in $CH_3CN$ | 90% A for 0.8 min, to 20% A in 3.7 min, held for 3 min, back to 90% A in 2 min. | 0.8 / 50 | 10 |
| 12 | Waters: Acqutty ® UPLC ®-DAD and SQD | Waters: BEH C18 (1.7 μm, 2.1 * 50 mm) | A: 10 mM $CH_3COONH_4$ in 95% $H_2O$ + 5% $CH_3CN$ B: $CH_3CN$ | From 95% A to 5% A in 1.3 min, held for 0.2 min, to 95% A in 0.2 min held for 0.1 min | 0.7 / 70 | 1.8 |

TABLE

| Co. No. means compound number; Retention time ($R_t$) in min; n.d. means not determined. | | | |
|---|---|---|---|
| Co. No. | $R_t$ | $[M + H]^+$ | LCMS Method |
| 1 | 0.71 | 394 | 1 |
| 1a | 0.60 | 394 | 2 |
| 2 | 1.41 | 472 | 4 |
| 3 | 2.00 | 520 | 5 |
| 4 | 0.98 | 462 | 1 |
| 5 | 0.66 | 394 | 1 |
| 6 | 0.70 | 394 | 1 |
| 7 | 0.76 | 394 | 1 |
| 8 | 0.77 | 394 | 1 |
| 9 | 2.31 | 393 | 5 |
| 10 | 0.74 | 394 | 1 |
| 11 | 0.65 | 394 | 1 |
| 12 | 0.62 | 394 | 1 |
| 13 | 0.66 | 394 | 1 |
| 14 | 0.96 | 395 | 4 |
| 15 | 1.02 | 395 | 4 |
| 16 | 0.44 | 395 | 2 |
| 17 | 0.58 | 395 | 1 |
| 18 | 0.55 | 410 | 1 |
| 19 | 0.91 | 424 | 1 |
| 20 | 0.89 | 428 | 1 |
| 21 | 0.83 | 408 | 1 |
| 22 | 1.51 | 462 | 4 |
| 23 | 0.88 | 437 | 1 |
| 24 | 0.80 | 412 | 1 |
| 25 | 1.39 | 428 | 4 |
| 26 | 0.79 | 424 | 1 |
| 27 | 0.97 | 462 | 1 |
| 28 | 0.66 | 453 | 2 |
| 29 | 0.47 | 434 | 2 |
| 30 | 0.69 | 483 | 2 |
| 31 | 0.50 | 464 | 2 |
| 32 | 1.91 | 408 | 5 |
| 33 | 1.36 | 428 | 3 |
| 34 | 0.91 | 447 | 2 |
| 35 | 1.11 | 462 | 1 |
| 36 | 0.69 | 458 | 2 |
| 37 | 0.96 | 462 | 1 |
| 38 | 0.86 | 462 | 1 |
| 39 | 2.00 | 408 | 5 |
| 40 | 1.90 | 520 | 5 |
| 41 | 0.70 | 428 | 1 |
| 42 | 1.01 | 506 | 1 |
| 43 | 0.98 | 486 | 1 |
| 44 | 1.24 | 412 | 4 |
| 45 | 0.97 | 472 | 1 |
| 46 | 0.84 | 392 | 1 |
| 47 | 1.49 | 470 | 4 |
| 48 | 0.79 | 410 | 1 |
| 49 | 1.61 | 393 | 5 |
| 50 | 1.36 | 427 | 4 |
| 51 | 1.39 | 471 | 3 |
| 52 | 1.43 | 485 | 4 |
| 53 | 0.99 | 485 | 1 |
| 54 | 1.04 | 469 | 1 |
| 55 | 1.29 | 388 | 4 |
| 56 | 0.91 | 390 | 1 |
| 57 | 1.12 | 422 | 1 |
| 57a | 1.44 | 424 | 4 |
| 58 | 1.77 | 424 | 6 |
| 59 | 1.45 | 426 | 4 |
| 60 | 0.69 | 394 | 1 |
| 61 | 0.76 | 390 | 1 |
| 62 | 0.81 | 392 | 1 |
| 63 | 1.97 | 388 | 5 |
| 64 | 0.82 | 392 | 1 |
| 65 | 0.76 | 392 | 1 |
| 66 | 1.24 | 376 | 3 |
| 67 | 0.79 | 408 | 1 |
| 68 | 0.82 | 408 | 1 |
| 69 | 0.50 | 395 | 1 |
| 70 | 0.74 | 419 | 1 |
| 71 | 0.95 | 487 | 2 |
| 72 | 1.22 | 602 | 2 |

TABLE-continued

| Co. No. means compound number; Retention time ($R_t$) in min; n.d. means not determined. | | | |
|---|---|---|---|
| Co. No. | $R_t$ | $[M + H]^+$ | LCMS Method |
| 73 | 1.17 | 612 | 2 |
| 74 | 0.80 | 459 | 2 |
| 75 | 4.23 | 469 | 6 |
| 76 | 3.65 | 405 | 6 |
| 77 | 0.90 | 390 | 1 |
| 78 | 2.77 | 419 | 7 |
| 79 | 3.59 | 420 | 7 |
| 80 | 2.99 | 483 | 7 |
| 81 | 3.08 | 439 | 7 |
| 245 | 3.06 | 437 | 9 |
| 246 | 3.41 | 451 | 6 |
| 85 | 3.50 | 392 | 6 |
| 175 | 3.52 | 438 | 6 |
| 82 | 1.24 | 408 | 4 |
| 83 | 1.26 | 408 | 4 |
| 54a | 1.43 | 469 | 4 |
| 91 | 2.80 | 428 | 9 |
| 86 | 1.84 | 504 | 4 |
| 87 | 0.89 | 486 | 2 |
| 88 | 0.94 | 500 | 2 |
| 84 | 1.38 | 434 | 4 |
| 89 | 1.02 | 534 | 2 |
| 90 | 1.57 | 375 | 4 |
| 92 | 1.52 | 506 | 8 |
| 94 | 1.43 | 506 | 8 |
| 217 | 0.87 | 408 | 1 |
| 222 | 3.64 | 426 | 9 |
| 95 | 1.21 | 376 | 3 |
| 96 | 3.98 | 540 | 9 |
| 97 | 3.51 | 451 | 6 |
| 98 | 1.16 | 419 | 4 |
| 99 | 3.68 | 462 | 9 |
| 100 | 1.49 | 462 | 8 |
| 219 | 1.43 | 507 | 8 |
| 213 | 2.82 | 422 | 9 |
| 101 | 1.40 | 462 | 8 |
| 220 | 1.34 | 473 | 8 |
| 102 | 1.35 | 428 | 8 |
| 212 | 4.04 | 434 | 6 |
| 214 | 2.99 | 436 | 9 |
| 103 | 1.21 | 392 | 4 |
| 104 | 2.89 | 424 | 6 |
| 105 | 3.65 | 452 | 6 |
| 218 | 3.39 | 409 | 6 |
| 106 | 1.45 | 490 | 8 |
| 107 | 3.25 | 499 | 7 |
| 108 | 1.49 | 486 | 4 |
| 109 | 3.24 | 462 | 7 |
| 110 | 3.72 | 424 | 7 |
| 185 | 3.60 | 423 | 6 |
| 111 | 1.49 | 470 | 4 |
| 112 | 3.19 | 450 | 7 |
| 113 | 2.92 | 404 | 7 |
| 114 | 2.17 | 548 | 8 |
| 115 | 2.90 | 478 | 11 |
| 116 | 0.79 | 459 | 2 |
| 117 | 1.60 | 459 | 8 |
| 118 | 1.60 | 459 | 8 |
| 119 | 1.60 | 459 | 8 |
| 120 | 2.75 | 438 | 7 |
| 121 | 1.71 | 438 | 8 |
| 122 | 2.97 | 420 | 7 |
| 123 | 3.82 | 406 | 6 |
| 124 | 2.53 | 529 | 11 |
| 189 | 3.16 | 451 | 6 |
| 166 | 3.01 | 444 | 7 |
| 125 | 3.10 | 418 | 7 |
| 126 | 2.98 | 419 | 7 |
| 127 | 3.14 | 550 | 11 |
| 128 | 3.55 | 440 | 7 |
| 171 | 2.55 | 514 | 11 |
| 164 | 2.93 | 404 | 7 |
| 129 | 1.58 | 468 | 4 |
| 130 | 3.13 | 428 | 7 |

TABLE-continued

Co. No. means compound number; Retention time ($R_t$) in min; n.d. means not determined.

| Co. No. | $R_t$ | $[M + H]^+$ | LCMS Method |
|---|---|---|---|
| 131 | 2.01 | 552 | 8 |
| 132 | 3.44 | 533 | 7 |
| 176 | 3.01 | 418 | 7 |
| 190 | 3.02 | 458 | 7 |
| 172 | 3.42 | 480 | 7 |
| 193 | 2.35 | 528 | 11 |
| 133 | 3.29 | 426 | 7 |
| 134 | 2.58 | 407 | 7 |
| 167 | 2.87 | 392 | 7 |
| 135 | 1.74 | 531 | 8 |
| 136 | 3.20 | 442 | 7 |
| 187 | 1.36 | 424 | 8 |
| 137 | 2.89 | 421 | 7 |
| 169 | 3.83 | 406 | 6 |
| 138 | 3.82 | 480 | 7 |
| 191 | 3.79 | 476 | 7 |
| 139 | 3.13 | 461 | 7 |
| 165 | 2.55 | 516 | 11 |
| 140 | 1.81 | 482 | 8 |
| 192 | 3.77 | 406 | 6 |
| 168 | 3.20 | 446 | 7 |
| 186 | 2.78 | 423 | 7 |
| 163 | 3.48 | 394 | 6 |
| 177 | 2.54 | 530 | 11 |
| 141 | 3.24 | 460 | 7 |
| 142 | 3.06 | 463 | 7 |
| 205 | 2.48 | 532 | 11 |
| 208 | 1.03 | 410 | 8 |
| 143 | 3.74 | 425 | 7 |
| 174 | 3.71 | 408 | 6 |
| 170 | 3.09 | 448 | 7 |
| 173 | 4.76 | 518 | 6 |
| 144 | 1.34 | 520 | 4 |
| 215 | 3.96 | 425 | 6 |
| 216 | 4.67 | 406 | 6 |
| 145 | 3.85 | 446 | 6 |
| 146 | 3.38 | 473 | 7 |
| 147 | 2.26 | 493 | 11 |
| 148 | 1.96 | 537 | 8 |
| 149 | 3.22 | 447 | 7 |
| 150 | 3.36 | 461 | 7 |
| 221 | 3.14 | 406 | 7 |
| 151 | 3.07 | 487 | 7 |
| 152 | 3.17 | 445 | 7 |
| 153 | 4.75 | 523 | 6 |
| 154 | 1.54 | 473 | 8 |
| 155 | 1.75 | 477 | 8 |
| 178 | 3.06 | 433 | 7 |
| 179 | 3.20 | 459 | 7 |
| 194 | 3.09 | 453 | 7 |
| 156 | 3.28 | 459 | 7 |
| 211 | 4.80 | 470 | 6 |
| 180 | 3.72 | 434 | 7 |
| 181 | 3.89 | 460 | 7 |
| 188 | 5.10 | 502 | 6 |
| 182 | 4.91 | 484 | 6 |
| 195 | 4.61 | 454 | 6 |
| 196 | 2.30 | 481 | 11 |
| 157 | 3.03 | 437 | 7 |
| 183 | 2.32 | 473 | 11 |
| 209 | 2.30 | 473 | 11 |
| 184 | 3.16 | 483 | 7 |
| 197 | 4.45 | 479 | 6 |
| 210 | 2.91 | 474 | 11 |
| 158 | 3.90 | 441 | 6 |
| 198 | 4.03 | 455 | 6 |
| 200 | 4.67 | 488 | 6 |
| 161 | 1.85 | 515 | 8 |
| 202 | 4.01 | 437 | 6 |
| 203 | 4.24 | 451 | 6 |
| 162 | 4.66 | 501 | 6 |
| 206 | 4.55 | 461 | 6 |
| 201 | 4.34 | 487 | 6 |
| 159 | 3.80 | 423 | 6 |

TABLE-continued

Co. No. means compound number; Retention time ($R_t$) in min; n.d. means not determined.

| Co. No. | $R_t$ | $[M + H]^+$ | LCMS Method |
|---|---|---|---|
| 204 | 4.31 | 438 | 6 |
| 199 | 3.66 | 456 | 7 |
| 160 | 4.27 | 461 | 6 |
| 223 | 3.03 | 441 | 7 |
| 224 | 3.18 | 461 | 7 |
| 225 | 3.30 | 475 | 7 |
| 226 | 3.00 | 435 | 7 |
| 227 | 1.47 | 455 | 8 |
| 228 | 1.69 | 456 | 8 |
| 229 | 1.35 | 439 | 8 |
| 230 | 1.56 | 440 | 8 |
| 231 | 1.24 | 425 | 8 |
| 232 | 3.99 | 501 | 6 |
| 233 | 2.88 | 487 | 7 |
| 234 | 0.87 | 488 | 1 |
| 235 | 2.98 | 485 | 7 |
| 236 | 3.06 | 485 | 7 |
| 237 | 3.11 | 499 | 7 |
| 238 | 1.57 | 497 | 8 |
| 239 | 1.48 | 499 | 8 |
| 249 | 3.59 | 423 | 7 |
| 240 | 3.59 | 473 | 7 |
| 250 | 3.49 | 424 | 7 |
| 241 | 3.79 | 458 | 7 |
| 242 | 3.07 | 424 | 7 |
| 248 | 3.10 | 423 | 7 |
| 243 | 3.14 | 439 | 7 |
| 244 | 1.47 | 475 | 8 |
| 247 | 3.13 | 423 | 7 |
| 251 | 3.09 | 467 | 7 |
| 252 | 1.48 | 482 | 4 |
| 253 | 3.80 | 420 | 6 |

Experimental Procedures In Vitro Assay (Assay 1a and 1b)

Reagents. PRMT5-MEP50 enzyme was purchased from Charles River (Argenta). The enzyme complex was produced in insect cells (Sf9) infected simultaneously with two baculoviruses. One virus expresses full length human PRMT5 with Flag-tag at N-terminus, the second virus expresses full length MEP50 with His6-TEV cleavage at N-terminus. The protein was affinity purified using anti-Flag (M2) beads eluted with 3×FLAG peptide, followed by His-Select eluted with 0.5M imidazole. Eluted protein was then dialysed against tris-buffered saline (TBS) (pH 8.0) containing 20% glycerol and 3 mM dithiothreitol (DTT).

Full-length untagged human recombinant histone H2A (residues 1-130, Genbank Accession #NM_021052, MW=14.1 kDa) expressed in *E. coli* was purchased from Reaction Biology Corporation, Cat #HMT-11-146. Reagents used for making reaction buffer or stopping reaction were purchased including Tris base (Sigma Cat #T-1503), NaCl (Sigma Cat #RGF-3270), $MgCl_2$ (Sigma Cat #M0250), DTT (Invitrogen Cat #15508-013) and Formic Acid (Riedel deHaen, Cat #33015)

High Throughput Mass Spectrometer Assay PRMT5 catalyzes the sequential methylations of the terminal nitrogen atoms on the guanidine groups of arginine residues within proteins using co-substrate S-adenosyl-L-methionine (AdoMet, SAM), forming mono-methyl (MMA), symmetric-dimethyl arginine (sDMA) and S-adenosyl-L-homocysteine (AdoHcy, SAH). The enzyme activity was determined by following the product SAH formation using high throughput mass spectrometry (Agilent Rapidfire 300 System coupled to a Sciex 4000 series QTrap® triple-quad MS/MS). The reaction buffer was 20 mM Tris-HCl, pH 8.5, 50 mM NaCl, 5 mM $MgCl_2$ and 1 mM DTT. The reaction activity was stopped using 1% formic acid (final concentration).

Inhibition Studies. The $IC_{50}$ Studies were performed using eleven point dosing series made for each compound by serially diluted 1:2 in dimethyl sulfoxide (DMSO), with point 12 being a DMSO control. Compounds were first spotted to plates, and followed by addition of 2 μM SAM and 0.6 μM H2A (histone H2A) solution mixture. The same volume of enzyme solution was added to initiate the enzymatic reactions. The final concentrations of the reaction are at 1 μM SAM, 0.3 μM H2A and 10 nM enzyme (assay 1a) or 1.25 nM enzyme (assay 1b). The reaction was incubated at 30° C. for 60 minutes (min) when 10 nM enzyme was used and for 120 min when 1.25 nM enzyme was used. Subsequently, the reaction was quenched by addition of formic acid to a final concentration of 1%. The inhibitions of SAH formation in the presence of compounds were calculated as a percentage of the control relative to the uninhibited reaction as a function of inhibitor concentration. The data were fit as follows:

$$Y = \text{Bottom} + (\text{Top} - \text{Bottom})/(1 + 10^{\wedge}((\log IC_{50} - X)^{*}h))$$

where $IC_{50}$ is the inhibitor concentration (same unit as X) at 50% inhibition and h is the Hill slope. Y is percent of inhibition, X is log of compound concentration. Bottom and Top are the plateaus in same units as Y.

Experimental Procedure PD Assay (Assay 2)

Reagents

A549 cells (ATCC, Cat #CCL-185) were cultured in Dulbecco's Modified Eagle's Medium (DMEM) (Sigma, Cat #D5796), supplemented with 10% Fetal Calf Serum (FCS) (HyClone™, Cat #SV30160.03), 100 mM Sodium Pyruvate (Sigma, Cat #S8636), 200 mM L-Glutamine (Sigma, Cat #G7513) and 50 mg/mL Gentamycing (Gibco, Cat #15750-037).

Reagents used for buffers were purchased: Dulbecco's phosphate buffered saline (DPBS) without Ca/Mg (Sigma, Cat #D8537), phosphate buffered saline (PBS) 10× (Roche, Cat #11 666 789 001), Formalin solution 10% (Sigma, HT50-1-128-4L), Methanol 100% (Sigma, Cat #32213-2.5L), Triton X-100 (Acros, Cat #215680010), Bovine Serum Albumin (BSA) (Sigma, Cat #A2153), Alexa fluor 488 goat anti-rabbit antibody (Life Technologies, Cat #A11034), HCS CellMask Deep Red Stain (Life Technologies, Cat #H32721), Hoechst Stain (Life Technologies, Cat #33258), Anti-dimethyl-Arginine, sym (SYM10) antibody (Millipore, 07-412).

Immunohistochemistry Procedure

Cells were plated at 400 cells/40 μL/well in 384 well black μplates clear bottom (Perkin Elmer) and overnight incubated at 37° C., 5% $CO_2$. The $IC_{50}$ Studies were performed using nine point dosing series ranging from 10 μM to 1 pM for each compound. 80 nL of the respective dilution of the compounds was added using the Labcyte POD 810 (Labcyte) reaching a final DMSO concentration of 0.2% in cell culture. After an incubation period of 48 h at 37° C. and 5% $CO_2$, cells were fixed in 10% formalin solution for 15 min at room temperature and 20 min in ice-cold methanol, after which they were washed 3× in DPBS. Subsequently, the cells were blocked for 1 h in blocking buffer (PBS+1% BSA and 0.5% Triton X-100) and incubated overnight at 4° C. with the SYM10 antibody diluted 1/2000 in blocking buffer. The cells were washed 3× with washing buffer (PBS+0.1% Triton X-100) and incubated with the Alexa fluor 488 goat anti-rabbit antibody diluted 1/200 in blocking buffer for 1 h at room temperature. Subsequently, they were washed 3× with washing buffer and incubated for 30 min at room temperature with PBS containing a 1/5000 dilution of Hoechst Stain and a 1/5000 dilution of the HCS CellMask Deep Red Stain. After a final wash with PBS, the plates were imaged using the 10×W lens of the Opera® system (Perkin Elmer Life Sciences) using following settings (values in nm):

| laser | Filter camera | Primary dichrome | Detect dichrome |
|---|---|---|---|
| 488 | 540/75 | 405/488/561/635 | 510 |
| 405 | 450/50 | 405/488/561/635 | 510 |
| 635 | 690/50 | 405/488/561/635 | 510 |

Analyses:

The inhibition of nuclear symmetric Arginine dimethylation in the presence of compounds (% effect) was calculated as the "median nuclear SYM10 intensity"/"median cytoplasmic SYM10 intensity", normalized by below equation:

$$\text{normalized} = 100 - \frac{\text{raw} - lowMedian}{highMedian - lowMedian} * 100$$

In the above equations, the following variable names are used:

| | |
|---|---|
| normalized | The normalized feature value |
| raw | The raw feature value |
| lowMedian | The median of the raw values of the low control wells |
| highMedian | The median of the raw values of the high control wells |

In the above equations, the following controls were used for normalization:

Low control: minimum level of symmetrically dimethylated Arginines (cells treated with reference compound at 10 μM).

High control: maximum level of symmetrically dimethylated Arginines (DMSO treated cells).

$IC_{50}$ and $pIC_{50}$ ($-\log IC_{50}$) values were calculated using the appropriate software.

The $pIC_{50}$ values in the Table below are averaged values (Co. No. means compound number; n.d. means not determined).

| Co. No. | $pIC_{50}$ Assay 1a | $pIC_{50}$ Assay 1b | $pIC_{50}$ Assay 2 |
|---|---|---|---|
| 5 | 5.7 | 5.3 | <5 |
| 1 | 7.8 | 7.9 | 7.1 |
| 1a | n.d. | n.d. | n.d. |
| 10 | 5.5 | 5.4 | ~5.15 |
| 6 | 5.5 | 5.3 | <5 |
| 11 | 5.5 | 5.1 | <5 |
| 12 | 5.8 | 5.4 | <5 |
| 8 | 5.2 | 4.9 | <5 |
| 7 | 5.9 | 5.6 | ~4.76 |
| 13 | 6.1 | 5.7 | 4.8 |
| 14 | 5.9 | 5.6 | <4.7 |
| 33 | 6.8 | 6.1 | 6.3 |
| 22 | 5.2 | 4.6 | ~4.75 |
| 2 | 8.1 | 7.6 | 7.4 |
| 15 | 6.0 | n.d. | <5.4 |
| 66 | 5.7 | 5.3 | <4.7 |
| 45 | 6.6 | n.d. | 6.2 |
| 44 | 7.2 | 6.9 | 6.6 |
| 25 | 7.9 | 7.4 | 6.9 |

-continued

| Co. No. | pIC$_{50}$ Assay 1a | pIC$_{50}$ Assay 1b | pIC$_{50}$ Assay 2 |
|---|---|---|---|
| 9 | 5.5 | n.d. | <4.7 |
| 60 | 6.6 | 6.4 | 5.9 |
| 46 | 7.7 | 7.2 | 6.9 |
| 48 | 7.0 | n.d. | 6.4 |
| 68 | 5.6 | <4 | ~5.14 |
| 67 | 7.0 | n.d. | 6.5 |
| 17 | 6.0 | 5.8 | 5.1 |
| 245 | 5.7 | 5.5 | <4.7 |
| 49 | 8.4 | 8.0 | 8.0 |
| 16 | 6.6 | 5.9 | 5.3 |
| 61 | 6.4 | 6.0 | ~5.88 |
| 55 | 8.1 | 7.5 | ~7.29 |
| 246 | 5.5 | n.d. | <4.7 |
| 71 | 5.5 | 5.7 | 5.0 |
| 3 | 7.4 | 6.8 | 6.2 |
| 32 | 7.4 | 6.9 | 6.3 |
| 21 | 5.9 | 5.8 | 5.3 |
| 20 | 5.7 | 5.6 | 5.2 |
| 64 | 6.9 | 6.1 | ~5.97 |
| 39 | 5.6 | 5.6 | 5.7 |
| 40 | 5.6 | 5.8 | ~4.92 |
| 27 | 6.4 | 6.1 | ~5.94 |
| 19 | 5.8 | 5.5 | <4.7 |
| 65 | 5.5 | 6.0 | 4.8 |
| 85 | <5 | 5.1 | 4.9 |
| 63 | 7.6 | 6.9 | 6.7 |
| 56 | 8.2 | 7.8 | 8.1 |
| 28 | <5 | 5.1 | <4.7 |
| 31 | 5.5 | 5.4 | <4.7 |
| 30 | <5 | 4.4 | <5 |
| 36 | 5.1 | 5.6 | <4.7 |
| 34 | 5.1 | <4 | <4.7 |
| 29 | 6.3 | 5.9 | 4.8 |
| 62 | 6.2 | 6.1 | 5.8 |
| 69 | 6.2 | 5.5 | <4.7 |
| 35 | 6.4 | 6.1 | 6.4 |
| 23 | 6.3 | 6.5 | 6.4 |
| 24 | 7.4 | 6.9 | 6.1 |
| 18 | 7.1 | 6.5 | ~5 |
| 175 | <5 | 5.5 | <5 |
| 51 | 8.0 | 7.8 | ~7.81 |
| 26 | 7.2 | 6.7 | ~6.6 |
| 70 | 6.2 | 5.8 | 5.2 |
| 4 | 7.2 | 6.7 | ~6.21 |
| 42 | 7.3 | 6.9 | 6.5 |
| 41 | 5.2 | 5.0 | <5 |
| 43 | 7.1 | 6.7 | 6.5 |
| 37 | 6.0 | 6.2 | 5.3 |
| 82 | 6.7 | 6.3 | 5.9 |
| 83 | 7.4 | 6.9 | 6.7 |
| 54 | 7.8 | 7.8 | 7.5 |
| 54a | 8.1 | 7.8 | 7.4 |
| 91 | 6.9 | 6.3 | 6.4 |
| 57a | 7.5 | 7.3 | 7.2 |
| 47 | 7.6 | 7.2 | 7.3 |
| 86 | 5.6 | 6.0 | 5.3 |
| 72 | <5 | <4 | <5 |
| 50 | 8.0 | 8.1 | 7.6 |
| 38 | 6.7 | 6.4 | 6.1 |
| 52 | 7.2 | 6.8 | 6.4 |
| 87 | 6.3 | 6.0 | 5.8 |
| 88 | <5 | 5.1 | <5 |
| 53 | 7.4 | 7.3 | 7.3 |
| 73 | <5 | <4 | 7.0 |
| 84 | 7.8 | 7.1 | 6.7 |
| 89 | <5 | 4.5 | 7.2 |
| 90 | 7.0 | 6.2 | <5 |
| 57 | 7.5 | n.d. | ~6.82 |
| 92 | 7.2 | n.d. | 6.1 |
| 94 | 6.0 | n.d. | ~6 |
| 217 | 8.3 | 7.7 | 7.4 |
| 222 | 7.5 | 7.2 | ~6.76 |
| 95 | 6.5 | 6.3 | <5 |
| 59 | 7.6 | 7.1 | 6.9 |
| 96 | 6.7 | 6.3 | 6.7 |
| 97 | <5 | 4.8 | <5 |

-continued

| Co. No. | pIC$_{50}$ Assay 1a | pIC$_{50}$ Assay 1b | pIC$_{50}$ Assay 2 |
|---|---|---|---|
| 58 | 7.9 | 7.7 | 7.4 |
| 98 | 6.2 | 5.8 | 5.0 |
| 99 | <5 | <4 | <5 |
| 100 | 6.9 | 6.7 | 6.1 |
| 219 | 5.4 | <4 | 5.1 |
| 213 | 8.1 | 7.8 | 7.2 |
| 101 | 6.0 | 6.1 | 5.7 |
| 220 | 6.5 | 6.3 | 5.6 |
| 102 | 7.0 | 6.3 | <5 |
| 212 | 7.7 | 7.3 | 6.7 |
| 214 | 7.5 | 7.0 | 6.4 |
| 103 | 6.4 | 5.9 | 5.1 |
| 104 | 5.3 | 4.8 | <5 |
| 105 | 6.8 | 6.0 | 5.6 |
| 218 | 8.6 | 8.3 | 8.3 |
| 106 | 7.2 | 6.8 | 6.4 |
| 107 | 8.9 | 8.4 | 8.4 |
| 108 | 7.4 | 7.0 | 7.2 |
| 109 | 6.9 | 6.7 | 6.0 |
| 110 | 8.7 | 8.8 | 9.3 |
| 185 | 8.4 | 8.1 | 7.3 |
| 111 | 7.9 | 7.4 | 7.2 |
| 112 | 7.3 | 6.7 | 6.4 |
| 113 | 8.3 | 8.0 | 8.3 |
| 114 | 7.8 | 7.6 | 7.9 |
| 115 | 8.0 | 8.3 | ~8.26 |
| 74 | 9.1 | 9.9 | 9.4 |
| 116 | n.d. | n.d. | n.d. |
| 117 | n.d. | n.d. | n.d. |
| 118 | n.d. | n.d. | n.d. |
| 119 | n.d. | n.d. | n.d. |
| 120 | 7.1 | 6.5 | 6.5 |
| 121 | 8.4 | 8.4 | 7.7 |
| 122 | 7.9 | 7.3 | 7.1 |
| 123 | 8.3 | 7.4 | 7.5 |
| 124 | 8.7 | 8.3 | 9.2 |
| 189 | 6.5 | 6.0 | 6.6 |
| 166 | 9.0 | 8.3 | 9.0 |
| 125 | 8.4 | 7.6 | 7.7 |
| 126 | 9.3 | 8.6 | 9.5 |
| 127 | 7.9 | 7.0 | 6.9 |
| 128 | 8.1 | 7.2 | 6.7 |
| 171 | 9.1 | 8.2 | 8.5 |
| 164 | 9.4 | 8.0 | >8.93 |
| 129 | 8.6 | 7.8 | 7.9 |
| 130 | 9.2 | 8.1 | 7.9 |
| 131 | 8.1 | 7.2 | ~7.18 |
| 132 | 9.1 | 8.6 | 8.6 |
| 76 | 9.6 | n.d. | 9.8 |
| 176 | 9.3 | 8.4 | 8.5 |
| 190 | 9.3 | 8.3 | ~8.73 |
| 172 | 9.3 | 8.4 | >8.93 |
| 193 | 9.0 | 8.1 | 8.5 |
| 133 | 9.2 | 8.2 | 8.2 |
| 134 | 9.4 | 8.5 | 8.8 |
| 167 | 9.1 | 8.3 | 8.5 |
| 135 | 9.0 | 8.2 | ~8.55 |
| 136 | 8.1 | 7.3 | 6.3 |
| 187 | 8.0 | 7.1 | 7.6 |
| 137 | 8.8 | 7.7 | 8.2 |
| 169 | 8.0 | 7.2 | 7.3 |
| 138 | 8.1 | 7.1 | 6.9 |
| 191 | 6.7 | 6.2 | 5.9 |
| 139 | 8.9 | 8.0 | 8.2 |
| 165 | 8.4 | 7.5 | 7.7 |
| 140 | 8.2 | 7.3 | 6.1 |
| 192 | 9.2 | 8.0 | 8.5 |
| 168 | 8.4 | 7.3 | 6.9 |
| 186 | 8.7 | 7.8 | 7.1 |
| 163 | 9.3 | 8.3 | 8.2 |
| 177 | 8.0 | 7.5 | 7.2 |
| 141 | 8.1 | 7.3 | 7.2 |
| 142 | 8.9 | 8.1 | 7.8 |
| 205 | 8.5 | 7.6 | 7.3 |
| 208 | 5.6 | 5.9 | <5 |
| 143 | 8.0 | 7.3 | 5.6 |

-continued

| Co. No. | $pIC_{50}$ Assay 1a | $pIC_{50}$ Assay 1b | $pIC_{50}$ Assay 2 |
|---|---|---|---|
| 174 | 8.0 | 7.3 | 6.9 |
| 170 | 8.2 | 7.2 | 7.1 |
| 173 | 8.7 | 7.8 | 7.4 |
| 77 | 9.3 | n.d. | >8.93 |
| 78 | 8.9 | n.d. | 9.5 |
| 144 | n.d. | n.d. | n.d. |
| 79 | 9.4 | n.d. | >8.93 |
| 215 | 8.1 | 7.4 | 5.9 |
| 216 | 9.0 | 8.1 | 8.0 |
| 145 | 7.8 | 7.1 | 7.1 |
| 146 | 9.6 | 8.6 | >8.93 |
| 147 | 6.6 | 6.6 | 7.5 |
| 80 | 9.9 | 9.7 | 9.6 |
| 148 | 6.4 | 6.1 | 6.7 |
| 75 | 9.6 | 9.3 | 8.8 |
| 149 | 9.5 | 8.3 | 9.0 |
| 150 | 9.0 | 7.8 | 7.5 |
| 221 | 7.6 | 6.8 | 7.3 |
| 81 | 9.6 | n.d. | 9.7 |
| 151 | 9.1 | 7.8 | 8.3 |
| 152 | 9.3 | 8.4 | >8.93 |
| 153 | n.d. | 6.7 | 7.5 |
| 154 | n.d. | 9.5 | 8.6 |
| 155 | n.d. | 6.8 | 6.6 |
| 178 | n.d. | 9.1 | 8.0 |
| 179 | n.d. | 9.2 | 8.3 |
| 194 | n.d. | 9.2 | 8.8 |
| 156 | n.d. | 9.5 | >8.93 |
| 211 | n.d. | 8.5 | ~5.59 |
| 180 | n.d. | 8.9 | 7.4 |
| 181 | n.d. | 8.9 | 7.4 |
| 188 | n.d. | 7.4 | 6.2 |
| 182 | n.d. | 8.2 | 6.5 |
| 195 | n.d. | 9.3 | 7.6 |
| 196 | n.d. | 8.7 | 7.0 |
| 157 | n.d. | 6.2 | 6.3 |
| 183 | n.d. | 9.3 | 8.2 |
| 209 | n.d. | 9.5 | 7.8 |
| 184 | n.d. | 8.7 | 7.2 |
| 197 | n.d. | 9.2 | 7.5 |
| 210 | n.d. | 8.6 | 6.9 |
| 158 | n.d. | 9.9 | 8.5 |
| 198 | n.d. | 8.4 | 7.2 |
| 200 | n.d. | 8.2 | 6.0 |
| 161 | n.d. | 8.8 | 7.4 |
| 202 | n.d. | 8.8 | 7.8 |
| 203 | n.d. | <5.6 | 5.2 |
| 162 | n.d. | 8.1 | 6.8 |
| 206 | n.d. | 8.8 | 7.6 |
| 201 | n.d. | 8.8 | 7.4 |
| 159 | n.d. | 9.9 | >8.93 |
| 204 | n.d. | 8.4 | 7.2 |
| 199 | n.d. | 7.4 | 6.6 |
| 160 | n.d. | 9.1 | 7.8 |
| 223 | nd. | 9.7 | 8.9 |
| 224 | nd. | >9.7 | nd. |
| 225 | n.d. | 8.2 | n.d. |
| 226 | n.d. | 8.2 | 7.0 |
| 227 | nd. | 8.9 | n.d. |
| 228 | n.d. | 8.3 | n.d. |
| 229 | n.d. | 7.4 | n.d. |
| 230 | n.d. | 6.2 | n.d. |
| 231 | n.d. | 9.2 | n.d. |
| 232 | n.d. | 8.4 | n.d. |
| 233 | n.d. | >9.7 | n.d. |
| 234 | n.d. | 6.1 | n.d. |
| 235 | n.d. | 9.7 | n.d. |
| 236 | nd. | >9.7 | n.d. |
| 237 | n.d. | 8.8 | 8.2 |
| 238 | n.d. | 9.1 | 8.9 |
| 239 | n.d. | 8.0 | 7.6 |
| 249 | nd. | 7.7 | 6.3 |
| 240 | n.d. | >9.7 | >8.93 |
| 250 | n.d. | 7.5 | 6.7 |
| 241 | n.d. | 8.6 | >8.93 |
| 242 | n.d. | 9.0 | >8.93 |

-continued

| Co. No. | $pIC_{50}$ Assay 1a | $pIC_{50}$ Assay 1b | $pIC_{50}$ Assay 2 |
|---|---|---|---|
| 248 | n.d. | 7.3 | 6.8 |
| 243 | n.d. | 9.1 | >8.93 |
| 244 | n.d. | 8.5 | n.d. |
| 247 | n.d. | 9.1 | n.d. |
| 251 | n.d. | 10.4 | n.d. |
| 252 | n.d. | 9.2 | n.d. |
| 253 | 7.7 | n.d. | n.d. |

Composition Examples

"Active ingredient" (a.i.) as used throughout these examples relates to compounds of Formula (I), and pharmaceutically acceptable addition salts, and solvates thereof; in particular to any one of the exemplified compounds.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:

1. A compound of Formula (I)

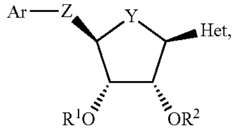

(I)

wherein $R^1$ represents hydrogen or —C(=O)—$C_{1-4}$alkyl;

$R^2$ represents hydrogen or —C(=O)—$C_{1-4}$alkyl;

Y represents —O—, —$CH_2$— or —$CF_2$—;

Z represents —$CH_2$—, —X—$CR^{5a}R^{5b}$—, —$CR^{5c}$═$CR^{5d}$—, —$CR^{5e}R^{5g}$—$CR^{5f}R^{5h}$—, or —C≡C—;

and when Y represents —$CH_2$— or —$CF_2$—, then Z can also represent —O— or —$CR^{5a}R^{5b}$—X;

$R^{5a}R^{5b}$, $R^{5c}$, $R^{5d}$, $R^{5e}$, $R^{5f}$, $R^{5g}$, and $R^{5h}$ each independently represent hydrogen or $C_{1-4}$alkyl;

X represents —O—, —S—, or —$NR^{11}$—;

$R^{11}$ represents hydrogen, $C_{1-4}$alkyl, or $C_{1-4}$alkyl substituted with one substituent selected from the group consisting of —OH, —O—$C_{1-4}$alkyl, $R^{12}$, —$NH_2$, —NH—$C_{1-4}$alkyl, and —N($C_{1-4}$alkyl)$_2$;

$R^{12}$ represents a 4-, 5-, 6- or 7-membered heterocyclic ring containing one nitrogen atom and optionally one oxygen atom; said 4-, 5-, 6- or 7-membered heterocyclic ring being attached to the remainder of the molecule via a ring nitrogen atom;

Ar represents a 10-membered bicyclic aromatic ring system consisting of two fused 6-membered rings,

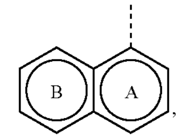, 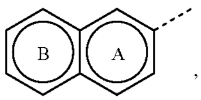, 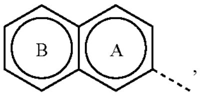, or 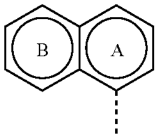

wherein at least 1 ring carbon atom of ring B is replaced by a nitrogen atom;

wherein optionally 1 additional ring carbon atom of ring A or ring B is replaced by a nitrogen atom; provided that when a nitrogen atom replaces one of the two fused carbon atoms, a carbonyl group is present in said bicyclic aromatic ring system;

Ar is optionally substituted with one, two, three or four substituents each independently selected from the group consisting of halo, —OH, —$NH_2$, —NH—$C_{1-4}$alkyl, —N($C_{1-4}$alkyl)$_2$, —$NHR^{10d}$, —$NR^{10c}R^{10d}$, cyano, —$CF_3$, —C(═O)—$NH_2$, —C(═O)—NH—$C_{1-4}$alkyl, —C(═O)—$C_{1-4}$alkyl, $C_{1-4}$alkyloxy, —C(═O)—O—$C_{1-4}$alkyl, $C_{3-6}$cycloalkyl, —O—$C_{3-6}$cycloalkyl, —NH—$C_{3-6}$cycloalkyl, —N($C_{3-6}$cycloalkyl)$_2$, $C_{2-6}$alkenyl, $C_{1-4}$alkyl substituted with one $C_{1-4}$alkyloxy, and $C_{1-4}$alkyl optionally substituted with one —$NR^{10a}R^{10b}$;

$R^{10a}$ and $R^{10b}$ each independently represent hydrogen or $C_{1-4}$alkyl;

$R^{10c}$ and $R^{10d}$ each independently represent $C_{3-6}$cycloalkyl; $R^{13}$; $R^{14}$; $C_{3-6}$cycloalkyl substituted with one, two or three substituents each independently selected from the group consisting of halo, —OH and —O—$C_{1-4}$alkyl; $C_{1-4}$alkyl substituted with one, two or three substituents each independently selected from the group consisting of halo, —OH and —O—$C_{1-4}$alkyl; or $C_{1-4}$alkyl substituted with one substituent selected from the group consisting of $C_{3-6}$cycloalkyl, $R^{13}$ and $R^{14}$;

$R^{13}$ represents a 4- to 7-membered monocyclic aromatic ring containing one, two or three heteroatoms each independently selected from O, S, S(═O)$_p$ and N; or a 6- to 11-membered bicyclic fused aromatic ring containing one, two or three heteroatoms each independently selected from O, S, S(═O)$_p$ and N;

said 4- to 7-membered monocyclic aromatic ring or 6- to 11-membered bicyclic fused aromatic ring is optionally substituted with one or two substituents selected from the group consisting of $C_{1-4}$alkyl;

p represents 1 or 2;

$R^{14}$ represents phenyl optionally substituted with one, two or three substituents each independently selected from the group consisting of halo;

Het represents a bicyclic aromatic heterocyclic ring system selected from the group consisting of (a-1), (a-2), (a-3), (a-4) and (a-5):

(a-1)

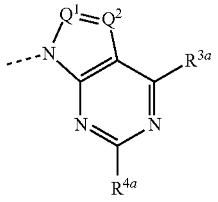

(a-2)

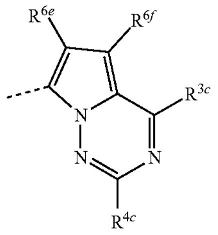

(a-3)

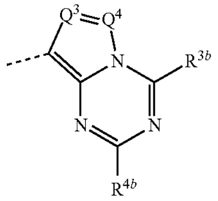

(a-4)

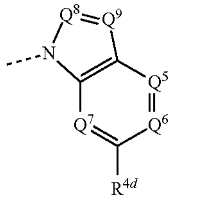

(a-5)

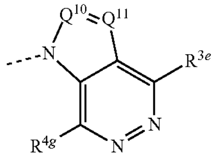

$R^{3a}$, $R^{3b}$, $R^{3c}$, $R^{3d}$ and $R^{3e}$ each independently represent hydrogen, halo, —$NR^{7a}R^{7b}$, $C_{1-4}$alkyl, $C_{2-4}$alkenyl, $C_{3-6}$cycloalkyl, —OH, or —O—$C_{1-4}$alkyl;

$R^{7a}$ represents hydrogen;

$R^{7b}$ represents hydrogen, $C_{3-6}$Cycloalkyl, or $C_{1-4}$alkyl;

$R^{4a}$, $R^{4b}$, $R^{4c}$, $R^{4d}$, $R^{4e}$, $R^{4f}$ and $R^{4g}$ each independently represent hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents N or $CR^{6a}$;

$Q^2$ represents N or $CR^{6b}$;

$Q^3$ represents N or $CR^{6c}$;

$Q^4$ represents N or $CR^{6d}$;

provided that maximum one of $Q^3$ and $Q^4$ represents N;

$Q^8$ represents N or $CR^{6g}$;

$Q^9$ represents N or $CR^{6h}$;

$Q^{10}$ represents N or $CR^{6i}$;

$Q^{11}$ represents N or $CR^{6j}$;

$Q^5$ represents $CR^{3d}$; $Q^6$ represents N; and $Q^7$ represents $CR^{4f}$; or $Q^5$ represents $CR^{3d}$; $Q^6$ represents $CR^{4e}$; and $Q^7$ represents N; or $Q^5$ represents N; $Q^6$ represents $CR^{4e}$; and $Q^7$ represents $CR^{4f}$; or $Q^5$ represents N; $Q^6$ represents $CR^{4e}$; and $Q^7$ represents N; or $Q^5$ represents N; $Q^6$ represents N; and $Q^7$ represents $CR^{4f}$; or $Q^5$ represents N; $Q^6$ represents N; and $Q^7$ represents N;

$R^{6a}$, $R^{6b}$, $R^{6c}$, $R^{6d}$, $R^{6e}$, $R^{6f}$, $R^{6g}$, $R^{6h}$, $R^{6i}$ and $R^{6j}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1s-4}$alkyl;

or a pharmaceutically acceptable addition salt or a solvate thereof.

2. The compound according to claim 1, wherein

Ar is optionally substituted with one, two, three or four substituents each independently selected from the group consisting of halo, —OH, —$NH_2$, —NH—$C_{1-4}$alkyl, —$N(C_{1-4}alkyl)_2$, cyano, —$CF_3$, —C(=O)—NH—$C_{1-4}$alkyl, —C(=O)—$C_{1-4}$alkyl, $C_{1-4}$alkyloxy, and $C_{1-4}$alkyl optionally substituted with one —$NR^{10a}R^{10b}$;

Het represents a bicyclic aromatic heterocyclic ring system selected from the group consisting of (a-1), (a-2) and (a-3):

(a-1)

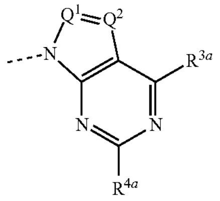

(a-2)

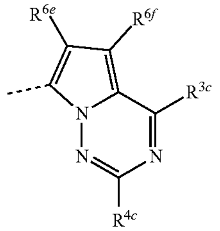

(a-3)

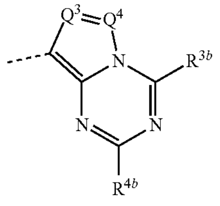

$R^{3a}$, $R^{3b}$ and $R^{3c}$ each independently represent hydrogen, halo, —$NR^{7a}R^{7b}$, or —O—$C_{1-4}$alkyl;

$R^{7b}$ represents hydrogen or $C_{1-4}$alkyl;

$R^{4a}$, $R^{4b}$ and $R^{4c}$ each independently represent hydrogen, halo, —$NR^{8a}R^{8b}$, or $C_{1-4}$alkyl;

$Q^1$ represents N or $CR^{6a}$;

$Q^2$ represents N or $CR^{6b}$;

$Q^3$ represents N or $CR^{6c}$;

$Q^4$ represents N or $CR^{6d}$;

provided that maximum one of $Q^3$ and $Q^4$ represents N;

$R^{6a}$, $R^{6b}$, $R^{6c}$, $R^{6d}$, $R^{6e}$ and $R^{6f}$ each independently represent hydrogen, halogen, $C_{1-4}$alkyl, —$NR^{9a}R^{9b}$, or $C_{1-4}$alkyl substituted with one, two or three halo atoms.

3. The compound according to claim 1, wherein $R^1$ represents hydrogen or —C(=O)—$C_{1-4}$alkyl;

$R^2$ represents hydrogen or —C(=O)—$C_{1-4}$alkyl;

Y represents —O—; Z represents —X—$CR^{5a}R^{5b}$—;

$R^{5a}$ and $R^{5b}$ each independently represent hydrogen or $C_{1-4}$alkyl;

X represents —O—, —S—, or —$NR^{11}$—; $R^{11}$ represents hydrogen;

Ar represents

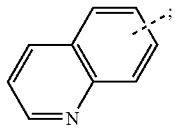

Ar is optionally substituted with one or two substituents each independently selected from the group consisting of halo, —OH, —$NH_2$, —NH—$C_{1-4}$alkyl, —N($C_{1-4}$alkyl)$_2$, cyano, —$CF_3$, —C(=O)—NH—$C_{1-4}$alkyl, —C(=O)—$C_{1-4}$alkyl, $C_{1-4}$alkyloxy, and $C_{1-4}$alkyl optionally substituted with one —$NR^{10a}R^{10b}$;

$R^{10a}$ and $R^{10b}$ each independently represent hydrogen or $C_{1-4}$alkyl;

Het represents a bicyclic aromatic heterocyclic ring system selected from the group consisting of (a-1);

$R^{3a}$ represents hydrogen, halo, —$NR^{7a}R^{7b}$ or —O—$C_{1-4}$alkyl;

$R^{7a}$ represents hydrogen;

$R^{7b}$ represents hydrogen;

$R^{4a}$ represents hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents $CR^{6a}$;

$Q^2$ represents $CR^{6b}$;

$R^{6a}$ and $R^{6b}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl.

4. The compound according to claim 1, wherein $R^1$ represents hydrogen;

$R^2$ represents hydrogen;

Y represents —O— or —$CH_2$—;

Z represents —X—$CR^{5a}R^{5b}$— or —$CR^{5e}R^{5g}$—$CR^{5f}R^{5h}$—;

and when Y represents —$CH_2$—, then Z can also represent —$CR^{5a}R^{5b}$—X—;

$R^{5a}$, $R^{5b}$, $R^{5e}$, $R^{5f}$, $R^{5g}$, and $R^{5h}$ represent hydrogen;

X represents —O—;

Ar represents

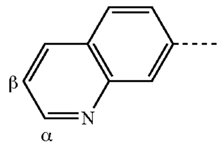

wherein Ar is optionally substituted in the position indicated by a with a substituent selected from the group consisting of —$NH_2$, —NH—$C_{1-4}$alkyl, and —$NHR^{10d}$; and wherein Ar is optionally substituted in the position indicated by β with a substituent selected from the group consisting of halo and $CF_3$;

provided however that Ar is substituted in at least one of the positions indicated by α or β;

$R^{10d}$ represents $C_{3-6}$cycloalkyl; $C_{1-4}$alkyl substituted with one, two or three halo substituents; or $C_{1-4}$alkyl substituted with one $C_{3-6}$cycloalkyl substituent;

Het represents a bicyclic aromatic heterocyclic ring system selected from the group consisting of (a-1) and (a-4);

$R^{3a}$ and $R^{3d}$ each independently represent hydrogen, halo, —$NR^{7a}R^{7b}$, $C_{1-4}$alkyl, or —O—$C_{1-4}$alkyl;

$R^{7a}$ represents hydrogen;

$R^{7b}$ represents hydrogen or $C_{1-4}$alkyl;

$R^{4a}$, $R^{4d}$ and $R^{4f}$ each independently represent hydrogen or halo;

$Q^1$ represents $CR^{6a}$;

$Q^2$ represents $CR^{6b}$;

$Q^8$ represents $CR^{6g}$;

$Q^9$ represents $CR^{6h}$;

$Q^5$ represents $CR^{3d}$; $Q^6$ represents N; and $Q^7$ represents $CR^{4f}$;

$R^{6a}$, $R^{6b}$, $R^{6g}$, and $R^{6h}$ represent hydrogen.

5. The compound according to claim 1, wherein $R^1$ and $R^2$ represent hydrogen.

6. The compound according to claim 1, wherein Y represents —O—.

7. The compound according claim 1, wherein Het represents a bicyclic aromatic heterocyclic ring system of Formula (a-1).

8. The compound according to claim 7, wherein $R^{3a}$ represents —$NR^{7a}R^{7b}$; and $R^{7a}$ and $R^{7b}$ represent hydrogen.

9. The compound according to claim 1, wherein Ar represents

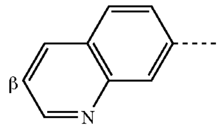

wherein Ar is substituted in the position indicated by β with a halo substituent.

10. A pharmaceutical composition comprising a pharmaceutically acceptable carrier and, as active ingredient, a therapeutically effective amount of a compound according to claim 1.

11. A method for treating a disease or condition selected from a blood disorder, metabolic disorders, autoimmune disorders, cancer, inflammatory diseases, cardiovascular diseases, neurodegenerative diseases, pancreatitis, multiorgan failure, kidney diseases, platelet aggregation, sperm motility, transplantation rejection, graft rejection, and lung injuries, comprising administering a compound as defined in claim 1.

12. The method according to claim 11 wherein the disease or condition is an autoimmune disorder, cancer, inflammatory disease, or a neurodegenerative disease.

13. The method according to claim 12 wherein the disease or condition is cancer.

14. The compound according to claim 1, wherein

Y represents —$CH_2$—;

Ar is optionally substituted with one, two, three or four substituents each independently selected from the group consisting of halo, —OH, —$NH_2$, —NH—$C_{1-4}$alkyl, —N($C_{1-4}$alkyl)$_2$, cyano, —$CF_3$, —C(=O)—NH—$C_{1-4}$alkyl, —C(=O)—$C_{1-4}$alkyl, $C_{1-4}$alkyloxy, and $C_{1-4}$alkyl optionally substituted with one —$NR^{10a}R^{10b}$;

Het represents a bicyclic aromatic heterocyclic ring system selected from the group consisting of (a-1);

$R^{3a}$ represents hydrogen, halo, —$NR^{7a}R^{7b}$, or —O—$C_{1-4}$alkyl;

$R^{7a}$ represents hydrogen;

$R^{7b}$ represents hydrogen or $C_{1-4}$alkyl;

$R^{4a}$ represents hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents N or $CR^{6a}$;

$Q^2$ represents N or $CR^{6b}$;

$R^{6a}$ and $R^{6b}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl.

15. The compound according to claim 14, wherein $Q^1$ and $Q^2$ represent CH.

16. The compound according to claim 1, wherein $R^1$ represents hydrogen;

$R^2$ represents hydrogen;

Y represents —$CH_2$—;

Z represents —X—$CR^{5a}R^{5b}$— or —$CH_2CH_2$—

$R^{5a}$ and $R^{5b}$ each independently represent hydrogen or $C_{1-4}$alkyl;

X represents —O—, —S—, or —$NR^1$—;

$R^{11}$ represents hydrogen;

Ar represents

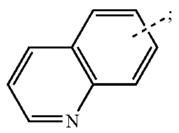

Ar is optionally substituted with one or two substituents each independently selected from the group consisting of halo, —OH, —$NH_2$, —NH—$C_{1-4}$alkyl, —N($C_{1-4}$alkyl)$_2$, cyano, —$CF_3$, —C(=O)—NH—$C_{1-4}$alkyl, —C(═O)—$C_{1-4}$alkyl, $C_{1-4}$alkyloxy, and $C_{1-4}$alkyl optionally substituted with one —$NR^{10a}R^{10b}$;

Het represents a bicyclic aromatic heterocyclic ring system selected from the group consisting of (a-1);

$R^{3a}$ represents hydrogen, halo, —$NR^{7a}R^{7b}$, or —O—$C_{1-4}$alkyl;

$R^{7a}$ represents hydrogen;

$R^{7b}$ represents hydrogen;

$R^{4a}$ represents hydrogen, halo, —$NR^{8a}R^{8b}$, or $C_{1-4}$alkyl;

$R^{8a}$ and $R^{8b}$ each independently represent hydrogen or $C_{1-4}$alkyl;

$Q^1$ represents $CR^{6a}$;

$Q^2$ represents $CR^{6b}$;

$R^{6a}$ and $R^{6b}$ each independently represent hydrogen, halogen, $C_{1-4}$alkyl, —$NR^{9a}R^{9b}$, or $C_{1-4}$alkyl substituted with one, two or three halo atoms;

$R^{9a}$ and $R^{9b}$ each independently represent hydrogen or $C_{1-4}$alkyl.

17. The compound according to claim 16, wherein Ar represents

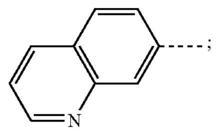

Ar is optionally substituted with one or two substituents each independently selected from the group consisting of halo, —OH, —$NH_2$, —NH—$C_{1-4}$alkyl, —N($C_{1-4}$alkyl)$_2$, cyano, —$CF_3$, —C(═O)—NH—$C_{1-4}$alkyl, —C(═O)—$C_{1-4}$alkyl, $C_{1-4}$alkyloxy, and $C_{1-4}$alkyl optionally substituted with one —$NR^{10a}R^{10b}$.

18. The compound according to any one of claim 1 and claims 14-17, wherein X represents —O— or —$NR^{11}$—.

19. The compound according to claim 18 wherein X represents —$NR^{11}$—.

* * * * *